(12) United States Patent
Zhang et al.

(10) Patent No.: US 11,746,093 B2
(45) Date of Patent: Sep. 5, 2023

(54) NITROGEN-CONTAINING COMPOUND, ELECTRONIC ELEMENT, AND ELECTRONIC DEVICE

(71) Applicant: Shaanxi Lighte Optoelectronics Material Co., Ltd., Xi'an (CN)

(72) Inventors: Kongyan Zhang, Xi'an (CN); Tiantian Ma, Xi'an (CN); Jiamei Cao, Xi'an (CN)

(73) Assignee: SHAANXI LIGHTE OPTOELECTRONICS MATERIAL CO., LTD., Shaanxi (CN)

( * ) Notice: Subject to any disclaimer, the term of this patent is extended or adjusted under 35 U.S.C. 154(b) by 0 days.

(21) Appl. No.: 18/010,241

(22) PCT Filed: Apr. 2, 2021

(86) PCT No.: PCT/CN2021/085415
§ 371 (c)(1),
(2) Date: Dec. 14, 2022

(87) PCT Pub. No.: WO2022/027992
PCT Pub. Date: Feb. 10, 2022

(65) Prior Publication Data
US 2023/0192627 A1  Jun. 22, 2023

(30) Foreign Application Priority Data

Aug. 7, 2020 (CN) .......................... 202010789251.8
Sep. 11, 2020 (CN) .......................... 202010956344.5

(51) Int. Cl.
*C07D 239/26* (2006.01)
*H10K 30/85* (2023.01)
(Continued)

(52) U.S. Cl.
CPC ......... *C07D 239/26* (2013.01); *C07D 251/24* (2013.01); *C07D 401/04* (2013.01);
(Continued)

(58) Field of Classification Search
CPC ... C07D 239/26; C07D 251/24; C07D 401/04
See application file for complete search history.

(56) References Cited

U.S. PATENT DOCUMENTS

2016/0372678 A1   12/2016   Arai

FOREIGN PATENT DOCUMENTS

| CN | 105308026 A | 2/2016 |
|---|---|---|
| CN | 109285957 A | 1/2019 |

(Continued)

OTHER PUBLICATIONS

International Search Report from corresponding International Application No. PCT/CN2021/085415, dated Jun. 30, 2021, 4 pages including translation.

*Primary Examiner* — Anthony Ho
(74) *Attorney, Agent, or Firm* — Tucker Ellis LLP

(57) ABSTRACT

The present disclosure provides a nitrogen-containing compound, an electronic element, and an electronic device, and belongs to the technical field of organic materials. In the nitrogen-containing compound, 1-adamantyl and a cyano group are connected on a nitrogen-containing heteroaryl core structure by a linking group, so that the molecule has a high dipole moment as a whole, organic materials with a high electron mobility can be obtained, and the electron transport properties of the electronic element can be improved, and when the nitrogen-containing compound is used as an electron transport layer of an organic electroluminescent device, the luminous efficiency and service life of the device can be improved, and the operating voltage can be reduced.

10 Claims, 2 Drawing Sheets

(51) Int. Cl.
    *H10K 85/60*     (2023.01)
    *C07D 251/24*    (2006.01)
    *C07D 405/04*    (2006.01)
    *C07D 405/14*    (2006.01)
    *C07D 405/10*    (2006.01)
    *C07D 401/04*    (2006.01)
    *C07D 409/04*    (2006.01)
    *C07D 403/04*    (2006.01)
    *C07D 403/14*    (2006.01)
    *C07D 409/14*    (2006.01)
    *C07D 409/10*    (2006.01)
    *C07D 401/10*    (2006.01)
    *C07D 403/10*    (2006.01)
    *C07D 491/048*   (2006.01)
    *H10K 50/16*     (2023.01)

(52) U.S. Cl.
    CPC ......... *C07D 401/10* (2013.01); *C07D 403/04* (2013.01); *C07D 403/10* (2013.01); *C07D 403/14* (2013.01); *C07D 405/04* (2013.01); *C07D 405/10* (2013.01); *C07D 405/14* (2013.01); *C07D 409/04* (2013.01); *C07D 409/10* (2013.01); *C07D 409/14* (2013.01); *C07D 491/048* (2013.01); *H10K 30/85* (2023.02); *H10K 50/16* (2023.02); *H10K 85/621* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *C07B 2200/05* (2013.01)

(56) References Cited

FOREIGN PATENT DOCUMENTS

| | | |
|---|---|---|
| CN | 110944988 A | 3/2020 |
| CN | 111018797 A | 4/2020 |
| CN | 111039881 A | 4/2020 |
| CN | 111039882 A | 4/2020 |
| CN | 111187228 A | 5/2020 |
| CN | 111377853 A | 7/2020 |
| CN | 112159348 A | 1/2021 |
| CN | 112812119 A | 5/2021 |
| CN | 112876462 A | 6/2021 |
| EP | 3636641 A1 | 4/2020 |
| WO | 2017179809 A1 | 10/2017 |
| WO | 2020050372 A1 | 3/2020 |

NITROGEN-CONTAINING COMPOUND, ELECTRONIC ELEMENT, AND ELECTRONIC DEVICE

CROSS REFERENCE TO RELATED APPLICATIONS

The present application claims the priority of Chinese Patent Application No. CN202010789251.8, filed on Aug. 7, 2020, the contents of which are incorporated herein by reference in its entirety a part of the present application. The present application claims the priority of Chinese Patent Application No. CN202010956344.5, filed on Sep. 11, 2020, the contents of which are incorporated herein by reference in its entirety a part of the present application.

TECHNICAL FIELD

The present disclosure relates to the technical field of organic materials, in particular to a nitrogen-containing compound, an electronic element and an electronic device.

BACKGROUND

As a new generation of display technology, organic electroluminescent device (OLED) have the advantages of ultrathinness, self-luminescence, wide viewing angle, fast response, high luminous efficiency, good temperature adaptability, simple production process, low driving voltage, low energy consumption, and the like, and have been widely used in industries such as flat panel displays, flexible displays, solid state lighting, and vehicle displays.

An organic luminescence phenomenon refers to a phenomenon in which an organic material is used to convert an electric energy into a luminous energy. An organic luminescence device using the organic luminescence phenomenon generally has a structure including an anode, a cathode, and an organic material layer between the anode and the cathode. In an organic luminescence device structure, when a voltage is applied between the anode and the cathode, holes and electrons are injected into the organic material layer from the anode and the cathode respectively, excitons are formed when the injected holes and electrons meet, and light is emitted when these excitons return to a ground state.

In the existing organic electroluminescent device, the most important problems are service life and efficiency, and with the area of the displays becoming larger, the driving voltage increases accordingly, leading to a decrease in luminous efficiency and power efficiency, and a decrease in service life. Thus, organic materials have to solve these efficiency or service life problems, and there is a need to continuously develop new materials for organic luminescence devices with high efficiency, long service life, and suitability for mass production.

It should be noted that the information disclosed in the background is merely used to enhance an understanding of the background of the present disclosure, and thus may include information that does not constitute the prior art known to those of ordinary skill in the art.

SUMMARY

The present disclosure aims to provide a nitrogen-containing compound, an electronic element and an electronic device to improve the performance of the electronic element and the electronic device.

In order to achieve the above-mentioned objective of the disclosure, the present disclosure adopts the following technical solutions:

According to one aspect of the present disclosure, a nitrogen-containing compound is provided, having a structure as shown in a formula 1:

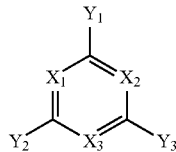

formula 1 where $X_1$, $X_2$, and $X_3$ are the same or different, and are each independently selected from $C(R_0)$ or N, and at least one of $X_1$, $X_2$, and $X_3$ is N;

$Y^1$ is

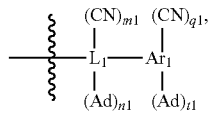

$Y_2$ is

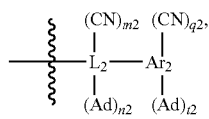

and $Y^3$ is

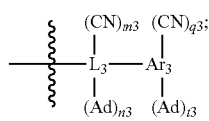

$L_1$, $L_2$, and $L_3$ are the same as or different from each other, and are each independently a single bond, substituted or unsubstituted arylene with 6 to 30 carbon atoms, or substituted or unsubstituted heteroarylene with 3 to 30 carbon atoms;

$Ar_1$, $Ar_2$, and $Ar_3$ are the same as or different from each other, and are each independently selected from substituted or unsubstituted aryl with 6 to 30 carbon atoms, and substituted or unsubstituted heteroaryl with 3 to 30 carbon atoms;

Ad is 1-adamantyl;

$m_1$ to $m_3$ is represented by $m_i$, $n_1$ to $n_3$ is represented by $n_i$, $q_1$ to $q_3$ is represented by $q_i$, and $t_1$ to $t_3$ is represented by $t_i$; and i is a variable, and is selected from 1, 2 or 3;

$m_i$ represents the number of cyano on $L_i$, $n_i$ represents the number of Ad on $L_i$, $q_i$ represents the number of cyano on $Ar_i$, and $t_i$ represents the number of Ad on $Ar_i$;

$m_i$ is independently selected from 0, 1, 2 or 3, and when $m_i$ is greater than 1, any two $m_1$ are the same or different;

$n_i$ is independently selected from 0, 1, 2 or 3, and when $n_i$ is greater than 1, any two $n_1$ are the same or different;

$q_i$ is independently selected from 0, 1, 2 or 3, and when $q_i$ is greater than 1, any two $q_1$ are the same or different;

$t_i$ is independently selected from 0, 1, 2 or 3, and when $t_i$ is greater than 1, any two $t_i$ are the same or different;

$m_1+m_2+m_3+q_1+q_2+q_3 \geq 1$, and $n_1+n_2+n_3+t_1+t_2+t_3 \geq 1$;

each $R_0$ is the same as or different from each other, and is independently selected from hydrogen, deuterium, alkyl with 1 to 10 carbon atoms, substituted or unsubstituted heteroaryl with 3 to 20 carbon atoms, or substituted or unsubstituted aryl with 6 to 20 carbon atoms; and substituents in $R_0$, $L_1$ to $L_3$ and $Ar_1$ to $Ar_3$ are the same or different, and are each independently selected from deuterium, a halogen group, cyano, a group A, alkyl with 1 to 10 carbon atoms, haloalkyl with 1 to 10 carbon atoms, alkenyl with 2 to 10 carbon atoms, cycloalkyl with 3 to 10 carbon atoms, heterocycloalkyl with 2 to 10 carbon atoms, cycloalkenyl with 5 to 10 carbon atoms, heterocycloalkenyl with 4 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, arylsilyl with 6 to 18 carbon atoms, or alkylsilyl with 3 to 12 carbon atoms; the group A is selected from substituted or unsubstituted heteroaryl with 3 to 20 carbon atoms, or substituted or unsubstituted aryl with 6 to 20 carbon atoms; and substituents in the group A are selected from deuterium, a halogen group, cyano, alkyl with 1 to 4 carbon atoms, or haloalkyl with 1 to 4 carbon atoms; and optionally, any two adjacent substituents form a ring.

In the nitrogen-containing compound of the present disclosure, nitrogen-containing heteroaryl is used as a core structure, adamantyl and a cyano group are connected on the nitrogen-containing heteroaryl core structure by using aryl or heteroaryl as a linking group, and the presence of cyano makes this part of the structure have a large dipole moment, thus improving the polarity of the material. Cyano and a heteroaryl group are combined, so that organic materials with a high electron mobility can be obtained. When the nitrogen-containing compound is used as an electron transport layer of an electronic element, the efficiency and service life of a device can be improved, and the operating voltage can be reduced. As a rigid and bulky polycyclic alkane structure, adamantyl itself can avoid the stacking of conjugated planes to form π aggregation, so that the film-forming properties of the material can be improved, the molecular weight and asymmetry of the compound are simultaneously enhanced at the same time, the thermal stability of the molecule is improved, the crystallinity of the material is also improved to a certain extent, and the stability of the compound can be improved when the compound is used in the electronic element, making the electronic element easier to be mass-production.

According to a second aspect of the present disclosure, an electronic element is provided, including an anode and a cathode which are oppositely disposed, and a functional layer disposed between the anode and the cathode; and the functional layer includes the nitrogen-containing compound described above.

According to a third aspect of the present disclosure, an electronic device is provided, including the electronic element described above.

It should be understood that the above general description and the following detailed description are only exemplary and explanatory, and are not intended to limit the present disclosure.

BRIEF DESCRIPTION OF THE DRAWINGS

The accompanying drawings here, which are incorporated in and constitute a part of this description, illustrate embodiments consistent with the present disclosure, and serve to explain the principles of the present disclosure together with the description. Obviously, the accompanying drawings in the following description are merely some embodiments of the present disclosure, and other drawings can be obtained according to these drawings without inventive labor for those of ordinary skill in the art.

The above and other features and advantages of the present disclosure will become more apparent by describing the embodiments in detail with reference to the accompanying drawings.

DESCRIPTION OF REFERENCE SIGNS

Figure 1:
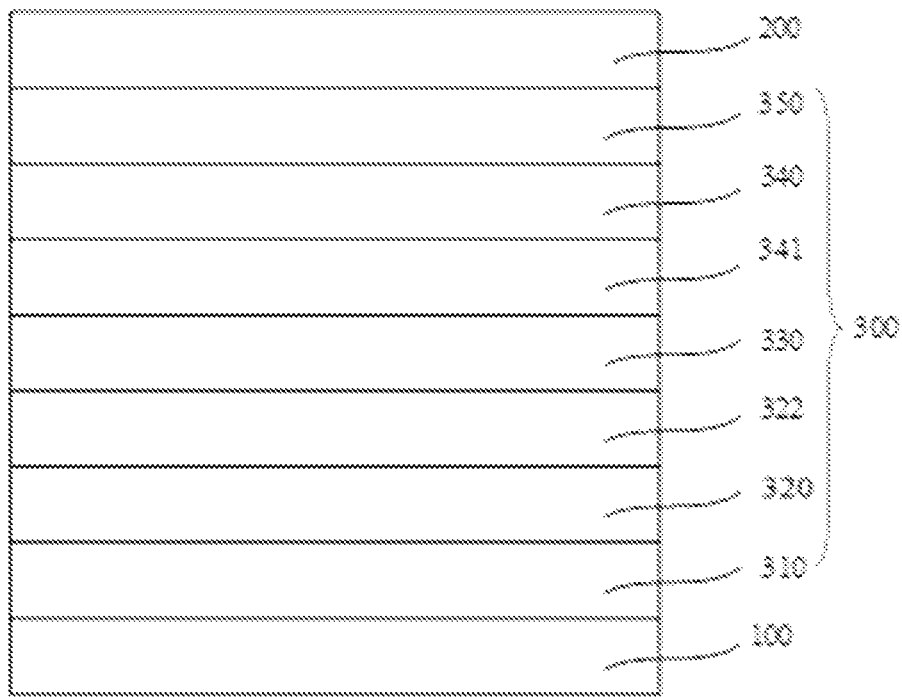
FIG. 1 is a structural schematic diagram of an organic electroluminescent device according to a embodiment of the present disclosure.

100, anode; 200, cathode; 300, functional layer; 310, hole injection layer; 320, hole transport layer; 322, electron blocking layer; 330, organic luminescence layer; 340, electron transport layer; 341, hole blocking layer; 350, electron injection layer; 360, photoelectric conversion layer; 400, first electronic device; and 500, second electronic device.

DETAILED DESCRIPTION

Embodiments will now be described more fully with reference to the accompanying drawings. However, the embodiments can be implemented in various forms and should not be construed as limited to the embodiments set forth here; and on the contrary, these embodiments are provided so that the present disclosure will be thorough and complete, and the concept of the embodiments is fully conveyed to those skilled in the art. The described features, structures, or characteristics may be combined in any suitable manner in one or more embodiments. In the following description, many specific details are provided to provide a thorough understanding of the embodiments of the present disclosure.

In the drawings, the thickness of regions and layers may be exaggerated for clarity. The same reference signs denote the same or similar structures in the drawings, and thus their detailed description will be omitted.

A nitrogen-containing compound in the embodiments of the present disclosure has a structural formula as shown in a formula 1:

formula 1

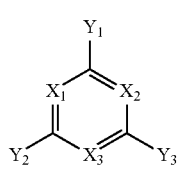

where $X_1$, $X_2$, and $X_3$ are the same or different, and are each independently selected from $C(R_0)$ or N, and at least one of $X_1$, $X_2$, and $X_3$ is N;

$Y_1$ is

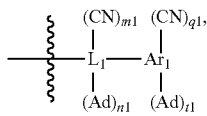

$Y_2$ is

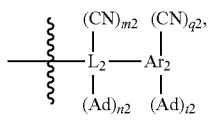

and $Y_3$ is

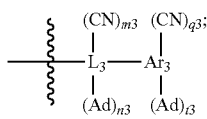

$L_1$, $L_2$, and $L_3$ are the same as or different from each other, and are each independently a single bond, substituted or unsubstituted arylene with 6 to 30 carbon atoms, or substituted or unsubstituted heteroarylene with 3 to 30 carbon atoms;

$Ar_1$, $Ar_2$, and $Ar_3$ are the same as or different from each other, and are each independently selected from substituted or unsubstituted aryl with 6 to 30 carbon atoms, or substituted or unsubstituted heteroaryl with 3 to 30 carbon atoms;

Ad is 1-adamantyl;

$m_1$ to $m_3$ is represented by $m_i$, $n_1$ to $n_3$ is represented by $n_i$, $q_1$ to $q_3$ is represented by $q_i$, and $t_1$ to $t_3$ is represented by $t_i$; and i is a variable, and is selected from 1, 2 or 3;

$m_i$ represents the number of cyano on $L_i$, $n_i$ represents the number of Ad on $L_i$, $q_i$ represents the number of cyano on $Ar_i$, and $t_i$ represents the number of Ad on $Ar_i$;

$m_i$ is independently selected from 0, 1, 2 or 3, and when $m_i$ is greater than 1, any two $m_i$ are the same or different;

$n_i$ is independently selected from 0, 1, 2 or 3, and when $n_i$ is greater than 1, any two $n_i$ are the same or different;

$q_i$ is independently selected from 0, 1, 2 or 3, and when $q_i$ is greater than 1, any two $q_i$ are the same or different;

$t_i$ is independently selected from 0, 1, 2 or 3, and when $t_1$ is greater than 1, any two $t_i$ are the same or different;

$m_1+m_2+m_3+q_1+q_2+q_3 \geq 1$, and $n_1+n_2+n_3+t_1+t_2+t_3 \geq 1$;

each $R_0$ is the same as or different from each other, and is independently selected from hydrogen, deuterium, alkyl with 1 to 10 carbon atoms, substituted or unsubstituted heteroaryl with 3 to 20 carbon atoms, or substituted or unsubstituted aryl with 6 to 20 carbon atoms; and substituents in $R_0$, $L_1$ to $L_3$ and $Ar_1$ to $Ar_3$ are the same or different, and are each independently selected from deuterium, a halogen group, cyano, a group A, alkyl with 1 to 10 carbon atoms, haloalkyl with 1 to 10 carbon atoms, alkenyl with 2 to 10 carbon atoms, cycloalkyl with 3 to 10 carbon atoms, heterocycloalkyl with 2 to 10 carbon atoms, cycloalkenyl with 5 to 10 carbon atoms, heterocycloalkenyl with 4 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, arylsilyl with 6 to 18 carbon atoms, or alkylsilyl with 3 to 12 carbon atoms; the group A is selected from substituted or unsubstituted heteroaryl with 3 to 20 carbon atoms, or substituted or unsubstituted aryl with 6 to 20 carbon atoms; and substituents in the group A are selected from deuterium, a halogen group, cyano, alkyl with 1 to 4 carbon atoms, or haloalkyl with 1 to 4 carbon atoms; and optionally, any two adjacent substituents form a ring.

In the nitrogen-containing compound of the present disclosure, nitrogen-containing heteroaryl is used as a core structure, 1-adamantyl and a cyano group are connected on the nitrogen-containing heteroaryl core structure by a linking group, and the presence of cyano makes this part of the structure have a large dipole moment, thus improving the polarity of the material. Cyano and a heteroaryl group are combined, so that organic materials with a high electron mobility can be obtained. When the nitrogen-containing compound is used as an electron transport layer of an electronic element, the efficiency and service life of a device can be improved, and the operating voltage can be reduced. As a rigid and bulky polycyclic alkane structure, adamantyl itself can avoid the direct stacking of conjugated planes to form π aggregation, so that the film-forming properties of the material can be improved, the molecular weight and asymmetry of the compounds are simultaneously enhanced at the same time, the thermal stability of the molecule is improved, the crystallinity of the material is also improved to a certain extent. Therefore, the stability of the compounds can be improved when applied to the electronic element, making the electronic element easier to be mass-production. In addition, compared with connection type of 2-adamantyl, connection type of 1-adamantyl has the advantages that the molecular polarity of the compounds can be improved, and the stability of the compounds is better.

In the present disclosure,

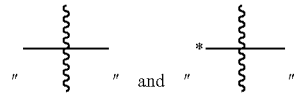

have a same meaning, and refer to a position of bonding to other substituents or connection positions.

In the present disclosure, the number of carbon atoms when $L_1$ to $L_3$, and $Ar_1$ to $Ar_3$ are selected from substituted aryl or substituted heteroaryl refers to the total number of carbon atoms of the aryl or heteroaryl and substituents on the aryl or heteroaryl. For example, substituted aryl with 18 carbon atoms means that the total number of carbon atoms of the aryl and substituents is 18. For example, if $Ar_1$ is 9-methyl-9-phenyl-fluorenyl, it belongs to substituted aryl with 20 carbon atoms.

When any one of $L_1$ to $L_3$ or $Ar_1$ to $Ar_3$ is selected from "substituted aryl(ene)", the aryl and all substituents on the aryl are taken as a whole as any one of $L_1$ to $L_3$ or $Ar_1$ to $Ar_3$.

In the present disclosure, $Y_1$ is

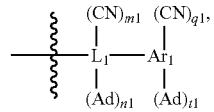

which means that $m_1$ cyano (CN) substituents and $n_1$ adamantyl (Ad) substituents are connected to $L_1$, and $q_1$ cyano (CN) substituents and $t_1$ adamantyl (Ad) substituents are connected to $Ar_1$. It can be understood that when $L_1$ is a substituted aryl, cyano and adamantyl can be connected to either the aryl or substituents of the aryl; and likewise, cyano connected to $Ar_1$ and adamantyl connected to $Ar_1$ have a same meaning. When $Ar_1$ to $Ar_3$ are substituted aryl or heteroaryl, cyano and adamantyl can be connected to either the aryl or heteroaryl or substituents of the aryl or heteroaryl. For example, $Ar_1$ is selected from naphthyl substituted by phenyl, where cyano can be connected to either phenyl or naphthyl. Similarly, when $L_1$ to $L_3$ are substituted arylene or heteroarylene, cyano and adamantyl can be connected to either the arylene or heteroarylene or substituents of the arylene or heteroarylene. For example, $L_1$ is selected from phenylene substituted by methyl, where cyano can be connected to either methyl or phenylene.

In the present disclosure, cyano and adamantyl can be located on a same linking group $Y_i$ or different linking groups $Y_i$ (i=1, 2 or 3). For example, in some embodiments, $Y_3$ includes both cyano and adamantyl; and in other embodiments, $Y_1$ includes cyano, and $Y_3$ includes adamantyl. On the other hand, cyano and adamantyl may both be connected to $L_i$ or may both be connected to $Ar_i$ or one of cyano and adamantyl is connected to $L_i$, and the other is connected to $Ar_i$. For example, in some embodiments, $L_1$ is connected to one cyano in $Y_1$, and $Ar_2$ is connected to one adamantyl in $Y_2$. In a word, in the chemical formula 1, there is at least one cyano and one adamantyl. When the compound contains a plurality of cyano, the plurality of cyano may be connected to the same Ar or the same L, or may be connected to different Ar or different L. For example, in some embodiments, a total of two cyano are included, where one cyano is connected to $Ar_1$, and the other cyano is connected to $Ar_2$. In other embodiments, a total of two cyano are included, and both cyano are connected to $Ar_1$. For another example, in some embodiments, a total of two cyano are included, where one cyano is connected to $L_1$, and the other cyano is connected to $L_2$. In other embodiments, a total of two cyano are included, and both cyano are connected to $L_1$. Similarly, when a plurality of adamantyl are included in substituents, the plurality of adamantyl may be connected to the same Ar or the same L, or may be connected to different Ar or the same L.

In the present disclosure, adamantyl is 1-adamantyl

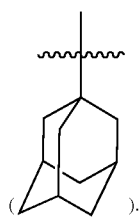

Optionally, in some embodiments, adamantyl is

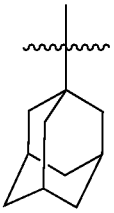

In the present disclosure,

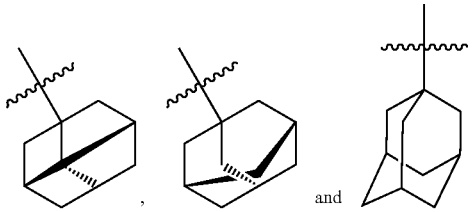

represent a same structure.

In the present disclosure, $C(R_0)$ indicates that a group $R_0$ is connected to a carbon atom.

In the present disclosure, when a specific definition is not otherwise provided, "hetero" means that at least one heteroatom selected from B, N, O, S, Se, Si or P is included in one functional group.

In the present disclosure, the case of sequential prefix nomenclature means that substituents are listed in the order in which they are written. For example, aralkoxy means alkoxy substituted with aryl, alkoxycarbonyl means carbonyl substituted with alkoxy, arylcarbonylalkenyl means alkenyl substituted with arylcarbonyl, and aryloxy means hydroxy substituted with aryl.

In the present disclosure, "aryl" refers to an optional functional group or substituent derived from an aromatic carbocyclic ring. The aryl can be monocyclic aryl or polycyclic aryl. In other words, the aryl can be monocyclic aryl, fused aryl, two or more monocyclic aryl conjugatedly linked by carbon-carbon bonds, two or more monocyclic aryl and fused aryl which are conjugatedly linked by a carbon-carbon bond, and two or more fused aryl conjugatedly linked by carbon-carbon bonds. The fused aryl refers to two or more rings in which two carbon atoms in a ring system are shared by two adjacent rings, where at least one of the rings is aromatic, e.g., the other rings can be cycloalkyl, cycloalkenyl, or aryl. Examples of the aryl in the present disclosure can include, but are not limited to, phenyl, naphthyl, anthryl, phenanthryl, biphenyl, terphenyl, tetraphenyl, pentaphenyl, benzo[9,10]phenanthryl, pyrenyl, benzofluoranthrenyl, chrysenyl, perylenyl, fluorenyl, triphenylene, naphthacenyl, triphenylenyl, and the like. In the present disclosure, fluorenyl may be substituted, and two substituents may be bonded to each other to form a spirocyclic structure. In the situation where the above fluorenyl is substituted, it may be:

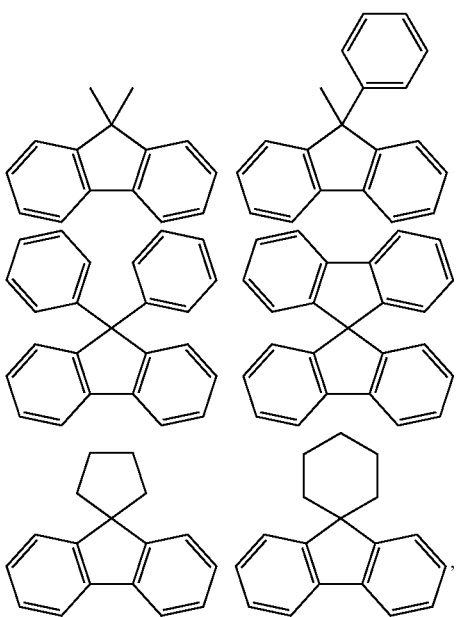

etc., but is not limited to this.

In the present disclosure, substituted aryl can be that one or two or more hydrogen atoms in the aryl are substituted by groups such as deuterium atom, a halogen group, cyano, aryl, heteroaryl, alkylsilyl, arylsilyl, alkyl, haloalkyl, cycloalkyl, alkoxy, alkylthio, and the like. For example, specific examples of aryl substituted by heteroaryl include, but are not limited to, phenyl substituted by dibenzofuranyl, phenyl substituted by dibenzothienyl, phenyl substituted by carbazolyl, phenyl substituted by pyridyl, and the like. It should be understood that the number of carbon atoms of the substituted aryl refers to the total number of carbon atoms of the aryl and substituents on the aryl, for example substituted aryl with 18 carbon atoms means that the total number of carbon atoms of the aryl and substituents is 18.

In the present disclosure, examples of aryl as a substituent may include, but are not limited to, phenyl, naphthyl, anthryl, phenanthryl, biphenyl, terphenyl, fluorenyl, dimethylfluorenyl, pyrenyl, and perylenyl.

In the present disclosure, in some embodiments, the number of carbon atoms of the aryl can be selected from 6, 10, 12, 13, 14, 15, 16, 17, 18, 20, 25, or 30. In some embodiments, the aryl is aryl with 6 to 30 carbon atoms; in other embodiments, the aryl is aryl with 6 to 25 carbon atoms; in other embodiments, the aryl is aryl with 6 to 20 carbon atoms; in other embodiments, the aryl is aryl with 6 to 18 carbon atoms; in other embodiments, the aryl is aryl with 6 to 15 carbon atoms; in other embodiments, the aryl is aryl with 6 to 13 carbon atoms; and in other embodiments, the aryl is aryl with 6 to 12 carbon atoms.

In the present disclosure, arylene is a divalent group, and in addition, the above description for aryl may apply to the arylene.

In the present disclosure, heteroaryl refers to a monocyclic or polycyclic system that contains at least one heteroatom independently selected from O, N, P, Si, Se, B, or S in the ring, and at least one ring system is aromatic. Each ring system in the heteroaryl contains a ring composed of 5 to 7 ring atoms, and has one or more points of connection to the remaining part of a molecule. The heteroaryl may be monocyclic heteroaryl or polycyclic heteroaryl, in other words, the heteroaryl may be a single aromatic ring system or a plurality of aromatic ring systems conjugatedly linked via carbon-carbon bonds, and any one aromatic ring system is one aromatic monocyclic ring or one aromatic fused ring. Fused heteroaryl refers to two or more rings in which two atoms in a ring system are shared by two adjacent rings, where at least one of the rings is aromatic, e.g., the other rings may be cycloalkyl, heterocyclyl, cycloalkenyl, or aryl.

For example, heteroaryl may include thienyl, furyl, pyrrolyl, imidazolyl, thiazolyl, oxazolyl, isothiazolyl, oxadiazolyl, triazolyl, azolyl, furazanyl, pyridyl, bipyridyl, phenanthridinyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, silafluorenyl, dibenzofuranyl, as well as N-arylcarbazolyl (e.g., N-phenylcarbazolyl), N-heteroarylcarbazolyl (e.g., N-pyridylcarbazolyl), N-alkylcarbazolyl (e.g., N-methylcarbazolyl), and the like, but is not limited to this. Thienyl, furyl, phenanthrolinyl, etc. are heteroaryl of the single aromatic ring system, and N-arylcarbazolyl, and N-heteroarylcarbazolyl are heteroaryl of the plurality of aromatic ring systems conjugatedly linked via carbon-carbon bonds.

In the present disclosure, substituted heteroaryl may be that one or two or more hydrogen atoms in the heteroaryl are substituted by groups such as deuterium atom, a halogen group, cyano, aryl, heteroaryl, trialkylsilyl, alkyl, cycloalkyl, alkoxy, alkylthio, and the like. For example, specific examples of aryl-substituted heteroaryl include, but are not limited to, dibenzofuranyl substituted by phenyl, dibenzothienyl substituted by phenyl, carbazolyl substituted by phenyl, pyridyl substituted by phenyl, and the like. It should be understood that the number of carbon atoms of the substituted heteroaryl refers to the total number of carbon atoms of the heteroaryl and substituents on the heteroaryl. For example, substituted heteroaryl with 14 carbon atoms means that the total number of carbon atoms of the heteroaryl and substituents is 14.

In the present disclosure, examples of heteroaryl as a substituent may include, but are not limited to, dibenzothienyl, dibenzofuranyl, carbazolyl, N-phenylcarbazolyl, pyridyl, bipyridyl, pyrimidinyl, triazinyl, quinolyl, isoquinolyl, quinazolinyl, benzimidazolyl, indolyl, and phenanthrolinyl.

In the present disclosure, in some embodiments, the number of carbon atoms of the heteroaryl can be selected from 3, 4, 5, 6, 7, 8, 9, 10, 11, 12, 13, 14, 15, 16, 17, 18, 20, 21, 22, 23, 24, 25, 26, 27, 28, 29, or 30. In some embodiments, the heteroaryl is heteroaryl with 3 to 12 carbon atoms, in other embodiments, the heteroaryl is heteroaryl with 3 to 15 carbon atoms, in other embodiments, the heteroaryl is heteroaryl with 5 to 12 carbon atoms, and in other embodiments, the heteroaryl is heteroaryl with 5 to 18 carbon atoms.

In the present disclosure, heteroarylene is a divalent group, and in addition, the above description for heteroaryl may apply to the heteroarylene.

In the present disclosure, the halogen group as a substituent may be fluorine, chlorine, bromine or iodine.

In the present disclosure, "alkyl" includes saturated linear or branched, monovalent or multivalent alkyl with 1 to 10 carbon atoms, where the alkyl may be independently optionally substituted by one or more substituents described in the present disclosure. In some embodiments, an alkyl group contains 1 to 10 carbon atoms; in other embodiments, the alkyl group contains 1 to 8 carbon atoms; in other embodiments, the alkyl group contains 1 to 6 carbon atoms; in other embodiments, the alkyl group contains 1 to 4 carbon atoms; and in other embodiments, the alkyl group contains 1 to 3 carbon atoms. Examples of alkyl groups with 1 to 4 carbon atoms as a substituent include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_3$), 2-methylpropyl or isobutyl (i-Bu, —$CH_2CH(CH_3)_2$), 1-methylpropyl, sec-butyl (s-Bu, —$CH(CH_3)CH_2CH_3$), tert-butyl (t-Bu, —$C(CH_3)_3$), and the like.

In the present disclosure, "alkenyl" refers to linear or branched, monovalent or multivalent hydrocarbyl containing 2 to 10 carbon atoms, with at least one site of unsaturation, i.e., one carbon-carbon $sp^2$ double bond, and the alkenyl group may be optionally substituted with one or more substituents as described in the present disclosure, including the positionings of "cis" and "trans", or the positionings of "E" and "Z". In some embodiments, the number of carbon atoms of the alkenyl is 2 to 6. As non-limiting examples, the alkenyl includes vinyl, allyl, isopropenyl, 2-butenyl, 3-butenyl, 1-pentenyl, 2-pentenyl, 3-pentenyl, 3-methyl-1-butenyl, 1,3-butadienyl, allyl, 1-phenylethen-1-yl, 2-phenylethen-1-yl, 2,2-stilben-1-yl, 2-phenyl-2-(naphthalen-1-yl)ethen-1-yl, 2,2-bis(diphen-1-yl)ethen-1-yl, styryl, and the like.

In the present disclosure, "alkoxy" means that an alkyl group is connected to the remaining part of a molecule via an oxygen atom, where the alkyl group has the meaning as described in the present disclosure. Examples of alkoxy as a substituent include, but are not limited to, methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), and the like.

In the present disclosure, "alkylthio" means that an alkyl group is connected to the remaining part of a molecule via a sulfur atom, where the alkyl group has the meaning as described in the present disclosure. Examples of alkylthio groups as a substituent include, but are not limited to, methylthio (MeS, —$SCH_3$), ethylthio (EtS, —$SCH_2CH_3$), 1-propylthio (n-PrS, n-propylthio, —$SCH_2CH_2CH_3$), 2-propylthio (i-PrS, i-propylthio, —$SCH(CH_3)_2$), and the like.

In the present disclosure, alkylsilyl refers to

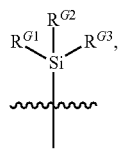

wherein $R^{G1}$, $R^{G2}$, and $R^{G3}$ are each independently alkyl; and specific examples of alkylsilyl include, but are not limited to, trimethylsilyl, triethylsilyl, tert-butyldimethylsilyl, and propyldimethylsilyl; and In the present disclosure, arylsilyl refers to

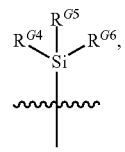

wherein $R^{G4}$, $R^{G5}$, and $R^{G6}$ are each independently aryl, and specific examples of arylsilyl include, but are not limited to, triphenylsilyl, diphenylsilyl, phenylsilyl, and the like, but are not limited to these.

In the present disclosure, "haloalkyl" means that an alkyl group is substituted by one or more halogen atoms, where the alkyl group has the meaning as described in the present disclosure. In one embodiment, haloalkyl with 1 to 4 carbon atoms includes fluorine-substituted alkyl with 1 to 4 carbon atoms, and such examples include, but are not limited to, trifluoromethyl, difluoromethyl, 1-fluoro-2-chloroethyl, and the like.

In the present disclosure, cycloalkyl refers to a group obtained by removing a hydrogen atom from monocyclic or polycyclic saturated cyclic hydrocarbon, and "cycloalkyl" may have one or more points of connection to the remaining part of a molecule. In some embodiments, the cycloalkyl is in a ring system containing 3 to 10 ring carbon atoms; in other embodiments, the cycloalkyl is cycloalkyl containing 5 to 10 ring carbon atoms; in other embodiments, the cycloalkyl is cycloalkyl containing 5 to 7 ring carbon atoms; and in other embodiments, the cycloalkyl is cycloalkyl containing 3 to 6 ring carbon atoms. The cycloalkyl group may be independently unsubstituted or substituted by one or more substituents described in the present disclosure. As non-limiting examples, the cycloalkyl includes cyclopropyl, cyclobutyl, cyclopentyl, cyclohexyl, norbornyl, adamantyl, and the like.

In the present disclosure, cycloalkenyl refers to a group obtained by removing a hydrogen atom from monocyclic or polycyclic unsaturated cyclic olefin, and "cycloalkenyl" may have one or more points of connection to the remaining part of a molecule. In some embodiments, the cycloalkenyl is cycloalkenyl containing 2 to 10 ring carbon atoms; and in other embodiments, the cycloalkenyl is cycloalkenyl containing 5 to 10 ring carbon atoms. The cycloalkenyl group may be independently unsubstituted or substituted with one or more substituents described in the present disclosure, for example cyclohexenyl.

A "ring" in the present disclosure includes a saturated ring, i.e. cycloalkyl, and heterocycloalkyl; and an unsaturated ring, i.e. cycloalkenyl, heterocycloalkenyl, aryl and heteroaryl.

In the present disclosure, n ring atoms form a ring system, i.e. a n-membered ring. For example, phenyl is 6-membered aryl. A 5- to 10-membered aromatic ring refers to aryl or heteroaryl containing 5 to 10 ring atoms; and a 5- to 10-membered aliphatic ring refers to cycloalkyl or cycloalkenyl containing 5 to 10 ring atoms.

In the present disclosure, "5- to 13-membered aliphatic rings" include, but are not limited to, cyclopentane, cyclohexane, cycloheptane, adamantane, camphorane, and the like; "5- to 10-membered aliphatic rings" include, but are not limited to, cyclopentane, cyclohexane, cycloheptane, and adamantane; a "5- to 6-membered aliphatic ring" is, for example cyclopentane or cyclohexane; and a "5- to 13-membered aromatic ring" in the present disclosure includes, but is not limited to, a pyrrole ring, furan, thiophene, benzene, naphthalene, pyridine, quinoline, quinoxaline, fluorene, and the like, where fluorene is a 13-membered aromatic ring.

In the present disclosure, any two adjacent substituents on $L_1$ to $L_3$ and $Ar_1$ to $Ar_3$ form a ring, which means that two substituents connected to a same atom form spiro cycloalkyl, or substituents connected to adjacent atoms are connected to each other to form a fused aryl ring.

The term "optional" or "optionally" means that the subsequently described event or circumstance may occur but not have to occur, and that the description includes circumstances where the event or situation occurs or does not occur. For example, "optionally, any two adjacent substituents form a ring", which means that the two adjacent substituents may but not have to form a ring, and this solution includes a circumstance where the two substituents are connected to each other to form a ring and a circumstance where the two substituents are present independently of each other. For example, two adjacent substituents may be present to form a saturated or unsaturated ring, or may be present independently of each other. Where two adjacent substituents connected to a same atom form a ring, the formed ring is spiro-connected to the remaining part of a molecule. Where two adjacent substituents connected to adjacent atoms form a ring, the formed ring is fused to the remaining part of a molecule.

An unpositioned connecting bond in the present disclosure refers to a single bond

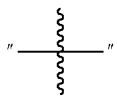

extending from a ring system, which means that one end of the connecting bond can be connected with any position in the ring system through which the bond penetrates, and the other end of the connecting bond is connected with the remaining part of a compound molecule.

For example, as shown in the following formula (f), naphthyl represented by the formula (f) is connected to other positions of a molecule through two unpositioned connecting bonds penetrating a dicyclic ring, and its meaning includes any one possible connecting mode represented by formulae (f-1) to (f-10).

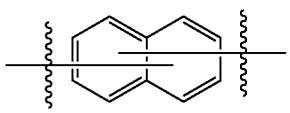

Formula (f)

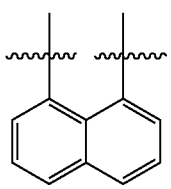

Formula (f-1)

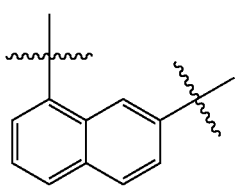

Formula (f-2)

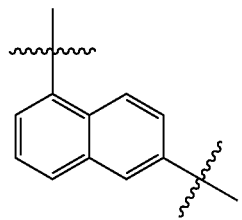

Formula (f-3)

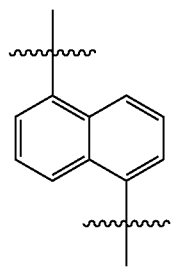

Formula (f-4)

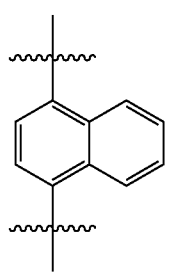

Formula (f-5)

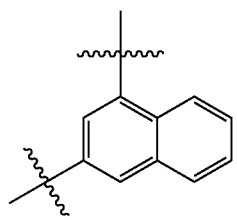

Formula (f-6)

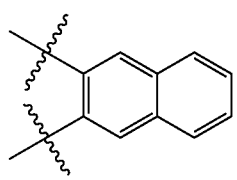

Formula (f-7)

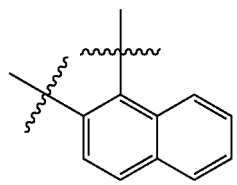

Formula (f-8)

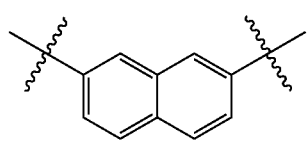

Formula (f-9)

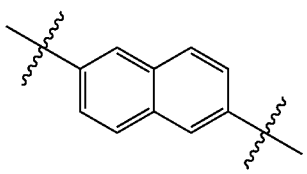

Formula (f-10)

For another example, as shown in the following formula (X'), phenanthryl represented by the formula (X') is connected with other positions of a molecule through one unpositioned connecting bond extending from the center of a benzene ring on one side, and its meaning includes any possible connecting mode represented by formulae (X'-1) to (X'-4).

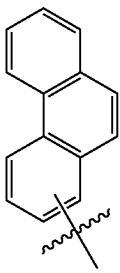

(X')

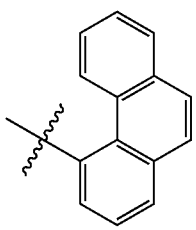

(X'-1)

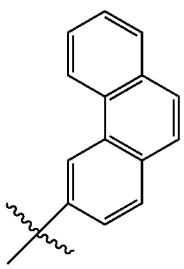

(X'-2)

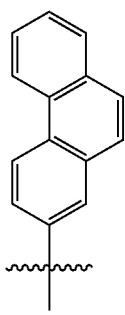

(X'-3)

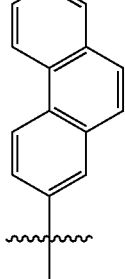

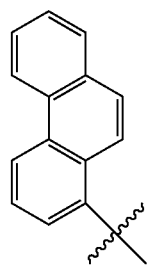

(X'-4)

An unpositioned substituent in the present disclosure refers to a substituent connected through a single bond extending from the center of a ring system, which means that the substituent can be connected to any possible position in the ring system. For example, as shown in the following formula (Y), a substituent R represented by the formula (Y) is connected with a quinoline ring through one unpositioned connecting bond, and its meaning includes any one possible connecting mode represented by formulae (Y-1) to (Y-7).

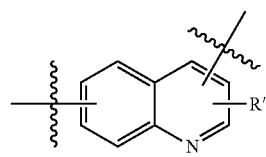

Formula (Y)

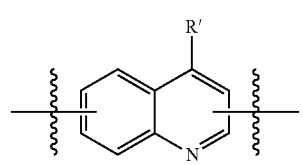

Formula (Y-1)

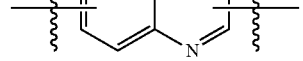

Formula (Y-2)

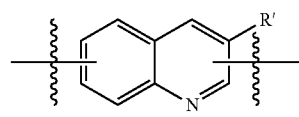

Formula (Y-3)

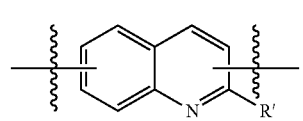

Formula (Y-4)

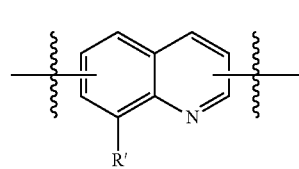

Formula (Y-5)

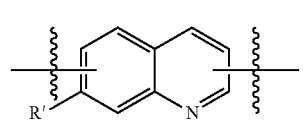

Formula (Y-6)

Formula (Y-7)

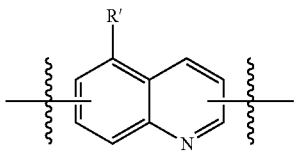

In the following, the meaning for unpositioned connection or unpositioned substitution is the same as that here, which will not be repeated later.

Optionally, in some embodiments, at least one of $X_1$, $X_2$, and $X_3$ in the compounds of the present disclosure is N. The meaning is that any one of $X_1$, $X_2$, and $X_3$ may be N, and the other two are optionally selected from $C(R_0)$ or N. Three situations that: $X_1$ is N, and $X_2$ and $X_3$ are each independently $C(R_0)$ or N; $X_2$ is N, and $X_1$ and $X_3$ are each independently $C(R_0)$ or N; and $X_3$ is N, and $X_1$ and $X_2$ are each independently $C(R_0)$ or N are included.

Optionally, in some embodiments, at least two of $X_1$, $X_2$, and $X_3$ in the compounds of the present disclosure are N. Its meaning is that any two of $X_1$, $X_2$, and $X_3$ can be N, and the other is $C(R_0)$; and specifically, four situations that: $X_1$ and $X_2$ are N, and $X_3$ is $C(R_0)$; $X_2$ and $X_3$ are N, and $X_1$ is $C(R_0)$; $X_1$ and $X_3$ are N, and $X_2$ is $C(R_0)$; and $X_1$, $X_2$, and $X_3$ are all N are included.

Optionally, in some embodiments, in the compounds of the present disclosure, $m_1+m_2+m_3+q_1+q_2+q_3$ is 1, 2, or 3, and $n_1+n_2+n_3+t_1+t_2+t_3$ is 1 or 2. The number of cyano and the number of adamantyl may or may not be equal. In some embodiments, the total number of cyano substituents in the compounds of the present disclosure is selected from 1, 2, or 3, and optionally, the total number of the cyano substituents in the compounds of the present disclosure is selected from 1 or 2. In some embodiments, the total number of adamantyl substituents in the compounds of the present disclosure is selected from 1 or 2. Optionally, the total number of the adamantyl substituents in the compounds of the present disclosure is 1.

Optionally, in some embodiments, the $Ar_1$, the $Ar_2$, and the $Ar_3$ are the same or different, and are each independently selected from substituted or unsubstituted aryl with 6 to 25 carbon atoms, or substituted or unsubstituted heteroaryl with 5 to 20 carbon atoms. In some embodiments, substituents in the $Ar_1$ to $Ar_3$ are the same or different, and are each independently selected from deuterium, a halogen group, cyano, a group A, trialkylsilyl with 3 to 8 carbon atoms, triphenylsilyl, alkyl with 1 to 4 carbon atoms, haloalkyl with 1 to 4 carbon atoms, cycloalkyl with 5 to 10 carbon atoms, alkoxy with 1 to 4 carbon atoms, alkylthio with 1 to 4 carbon atoms, aryloxy with 6 to 15 carbon atoms, or arylthio with 6 to 15 carbon atoms; the group A is selected from substituted or unsubstituted heteroaryl with 5 to 18 carbon atoms or substituted or unsubstituted aryl with 6 to 20 carbon atoms; and substituents in the group A are selected from deuterium, a halogen group, cyano, alkyl with 1 to 4 carbon atoms, or haloalkyl with 1 to 4 carbon atoms; and optionally, any two adjacent substituents form a 5- to 10-membered aliphatic ring or a 5- to 13-membered aromatic ring.

It can be understood that any two adjacent substituents are connected to each other to form an aliphatic ring, which means that two adjacent substituents connected to a same atom are connected to each other to form a spirocyclic ring; and any two adjacent substituents are connected to each other to form an aromatic ring, which means that two adjacent substituents connected to adjacent atoms are connected to each other to form a fused ring.

In some more specific embodiments, the substituents in the $Ar_1$ to $Ar_3$ are the same or different, and are each independently selected from deuterium, fluorine, cyano, methyl, ethyl, isopropyl, n-propyl, tert-butyl, trifluoromethyl, trimethylsilyl, methoxy, ethoxy, isopropoxy, methylthio, cyclopentyl, cyclohexyl, phenyl, biphenyl, terphenyl, naphthyl, fluorenyl, 9,9-dimethylfluorenyl, pyridyl, quinolyl, isoquinolyl, pyrimidinyl, carbazolyl, dibenzofuranyl, or dibenzothienyl; and optionally, any two adjacent substituents form a 5- to 6-membered aliphatic ring or a 6- to 13-membered aromatic ring.

Optionally, in some embodiments, the $Ar_1$, the $Ar_2$, and the $Ar_3$ are the same or different, and are each independently selected from the group consisting of groups represented by the following formulae i-1 to i-15:

i-1

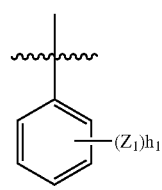

i-2

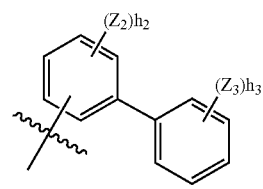

i-3

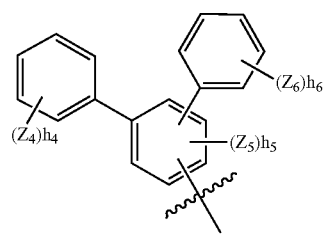

i-4

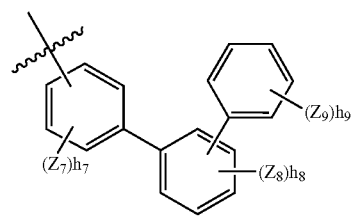

i-5

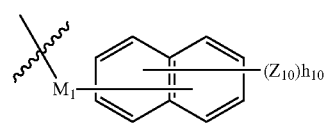

i-6

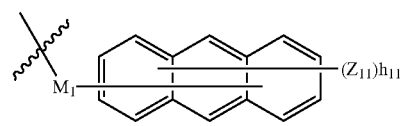

-continued i-7 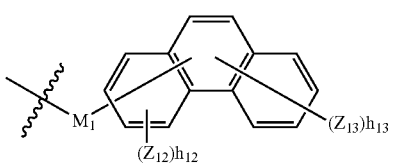

i-8 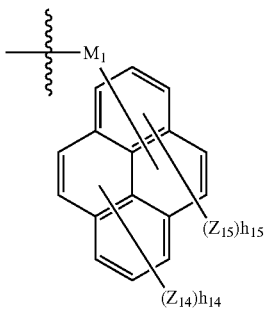

i-9 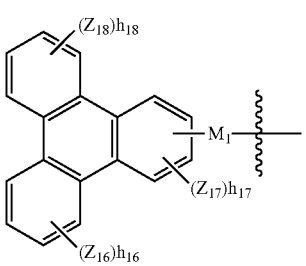

i-10 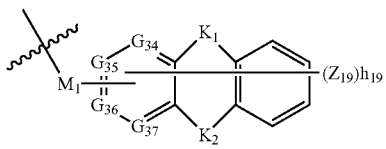

i-11 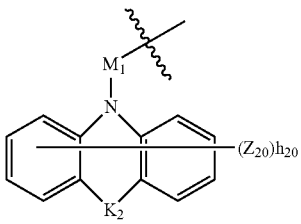

i-12 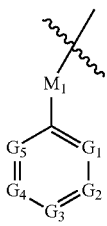

i-13 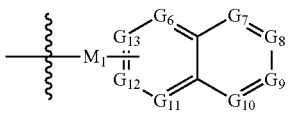

i-14 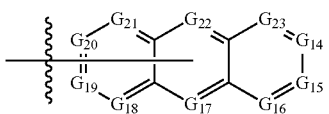

i-15 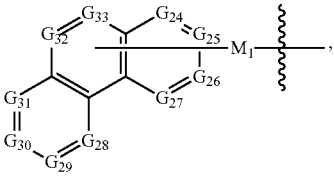

where $M_1$ is selected from a single bond or

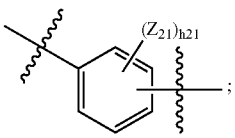

$G_1$ to $G_5$ are each independently selected from N or $C(J_1)$, and at least one of $G_1$ to $G_5$ is selected from N; and when two or more of $G_1$ to $G_5$ are selected from $C(J_1)$, any two $J_1$ are the same or different;

$G_6$ to $G_{13}$ are each independently selected from N or $C(J_2)$, and at least one of $G_6$ to $G_{13}$ is selected from N; and when two or more of $G_6$ to $G_{13}$ are selected from $C(J_2)$, any two $J_2$ are the same or different;

$G_{14}$ to $G_{23}$ are each independently selected from N or $C(J_3)$, and at least one of $G_{14}$ to $G_{23}$ is selected from N; and when two or more of $G_{14}$ to $G_{23}$ are selected from $C(J_3)$, any two $J_3$ are the same or different;

$G_{24}$ to $G_{33}$ are each independently selected from N or $C(J_4)$, and at least one of $G_{24}$ to $G_{33}$ is selected from N; and when two or more of $G_{24}$ to $G_{33}$ are selected from $C(J_4)$, any two $J_4$ are the same or different;

$G_{34}$ to $G_{37}$ are each independently selected from N or $C(J_5)$, and when two or more of $G_{34}$ to $G_{37}$ are selected from $C(J_5)$, any two $J_5$ are the same or different;

$Z_1$ is selected from hydrogen, deuterium, a halogen group, cyano, alkylsilyl with 3 to 8 carbon atoms, alkyl with 1 to 6 carbon atoms, haloalkyl with 1 to 6 carbon atoms, cycloalkyl with 5 to 10 carbon atoms, alkoxy with 1 to 6 carbon atoms, alkylthio with 1 to 6 carbon atoms, or triphenylsilyl;

$Z_2$ to $Z_9$, and $Z_{21}$ are each independently selected from hydrogen, deuterium, a halogen group, cyano, alkylsilyl with 3 to 8 carbon atoms, alkyl with 1 to 6 carbon atoms, haloalkyl with 1 to 6 carbon atoms, cycloalkyl with 5 to 10 carbon atoms, alkoxy with 1 to 6 carbon atoms, alkylthio with 1 to 6 carbon atoms, triphenylsilyl, or heteroaryl with 3 to 18 carbon atoms;

$Z_{10}$ to $Z_{20}$, and $J_1$ to $J_5$ are each independently selected from hydrogen, deuterium, a halogen group, cyano, alkylsilyl with 3 to 8 carbon atoms, alkyl with 1 to 6 carbon atoms, haloalkyl with 1 to 6 carbon atoms, cycloalkyl with 5 to 10 carbon atoms, alkoxy with 1 to 6 carbon atoms, alkylthio with 1 to 6 carbon atoms, triphenylsilyl, aryl with 6 to 18 carbon atoms, or heteroaryl with 3 to 18 carbon atoms; optionally, two adjacent $Z_{19}$ are connected to each other to form a 5- to 10-membered aromatic ring or a 5- to 10-membered heteroaromatic ring; and optionally, two adjacent $Z_{20}$ are connected to each other to form a 5- to 10-membered aromatic ring or a 5- to 10-membered heteroaromatic ring;

$h_1$ to $h_{21}$ are represented by $h_k$, $Z_1$ to $Z_{21}$ are represented by $Z_k$, k is a variable, and represents any integer from 1 to 21, and $h_k$ represents the number of a substituent $Z_k$; when k is selected from 5 or 17, $h_k$ is selected from 1, 2 or 3; when k is selected from 2, 7, 8, 12, 15, 16, 18 or 21, $h_k$ is selected from 1, 2, 3 or 4; when k is selected from 1, 3, 4, 6, 9 or 14, $h_k$ is selected from 1, 2, 3, 4 or 5; when k is 13, $h_k$ is selected from 1, 2, 3, 4, 5, or 6; when k is selected from 10 or 19, $h_k$ is selected from 1, 2, 3, 4, 5, 6 or 7; when k is 20, $h_k$ is selected from 1, 2, 3, 4, 5, 6, 7, or 8; when k is 11, $h_k$ is selected from 1, 2, 3, 4, 5, 6, 7, 8 or 9; and when $h_k$ is greater than 1, any two $Z_k$ are the same or different;

$K_1$ is selected from O, S, $N(Z_{22})$, $C(Z_{23}Z_{24})$, or $Si(Z_{23}Z_{24})$; where $Z_{22}$, $Z_{23}$, and $Z_{24}$ are each independently selected from aryl with 6 to 18 carbon atoms, heteroaryl with 3 to 18 carbon atoms, alkyl with 1 to 6 carbon atoms or cycloalkyl with 5 to 10 carbon atoms; or the $Z_{23}$ and the $Z_{24}$ are connected to each other to form a saturated or unsaturated ring with 5 to 13 carbon atoms together with the atoms to which they are jointly connected; and $K_2$ is selected from a single bond, O, S, $N(Z_{25})$, $C(Z_{26}Z_{27})$, or $Si(Z_{26}Z_{27})$; where $Z_{25}$, $Z_{26}$, and $Z_{27}$ are each independently selected from aryl with 6 to 18 carbon atoms, heteroaryl with 3 to 18 carbon atoms, alkyl with 1 to 6 carbon atoms, or cycloalkyl with 5 to 10 carbon atoms, or the $Z_{26}$ and the $Z_{27}$ are connected to each other to form a saturated or unsaturated ring with 5 to 13 carbon atoms together with the atoms to which they are jointly connected.

For example, in

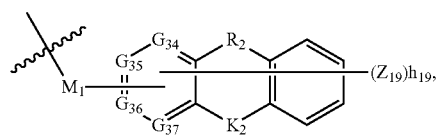

i-10 when $K_2$ is a single bond, $M_1$ is a single bond, $G_{34}$ to $G_{37}$ are C(H), $Z_{19}$ is hydrogen, and $K_1$ is selected from $C(Z_{23}Z_{24})$, and when $Z_{23}$ and $Z_{24}$ form a ring, the ring can be a 5-membered ring, for example

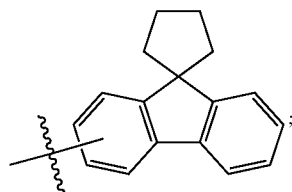

the ring can also be a 6-membered ring, for example

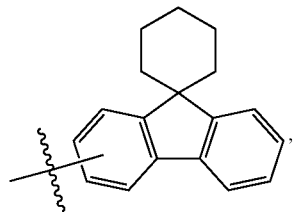

and the ring can also be a 13-membered ring, for example

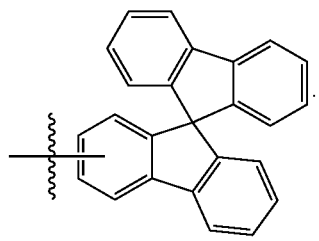

Of course, the number of carbon atoms on the ring formed by connecting the two substituents $Z_{23}$ and $Z_{24}$ to each other can also be other values, which will not be listed here.

The ring formed by connecting $Z_{26}$ and $Z_{27}$ to each other is similar to that of the $Z_{23}$ and the $Z_{24}$, which will not be repeated here.

Optionally, in some embodiments, $Ar_1$, $Ar_2$, and $Ar_3$ are the same or different, and are each independently selected from a substituted or unsubstituted group V, and the unsubstituted group V is selected from the group consisting of:

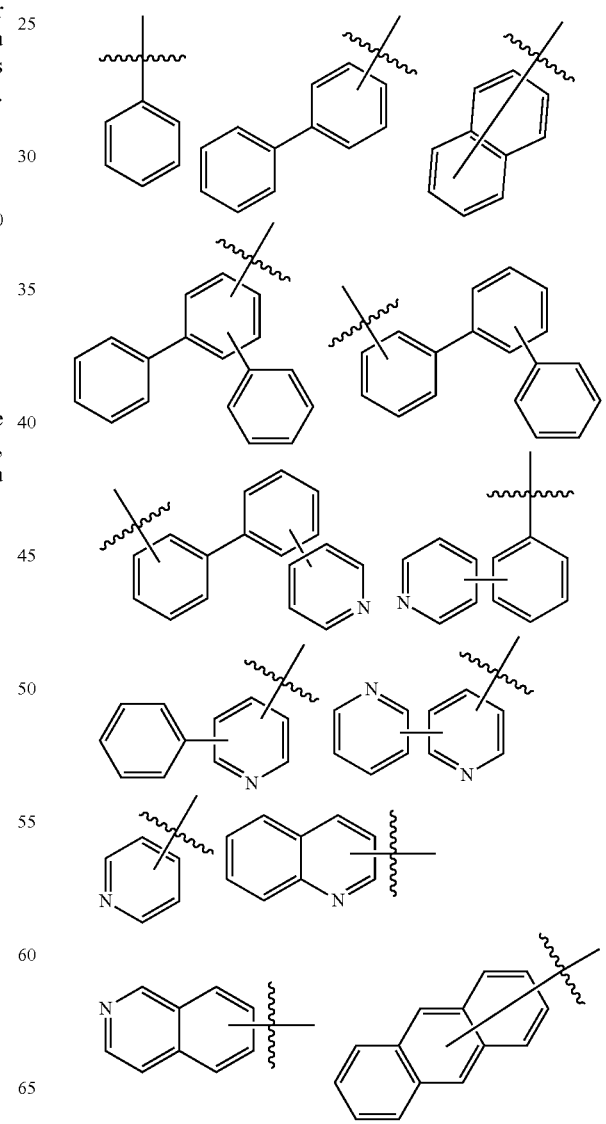

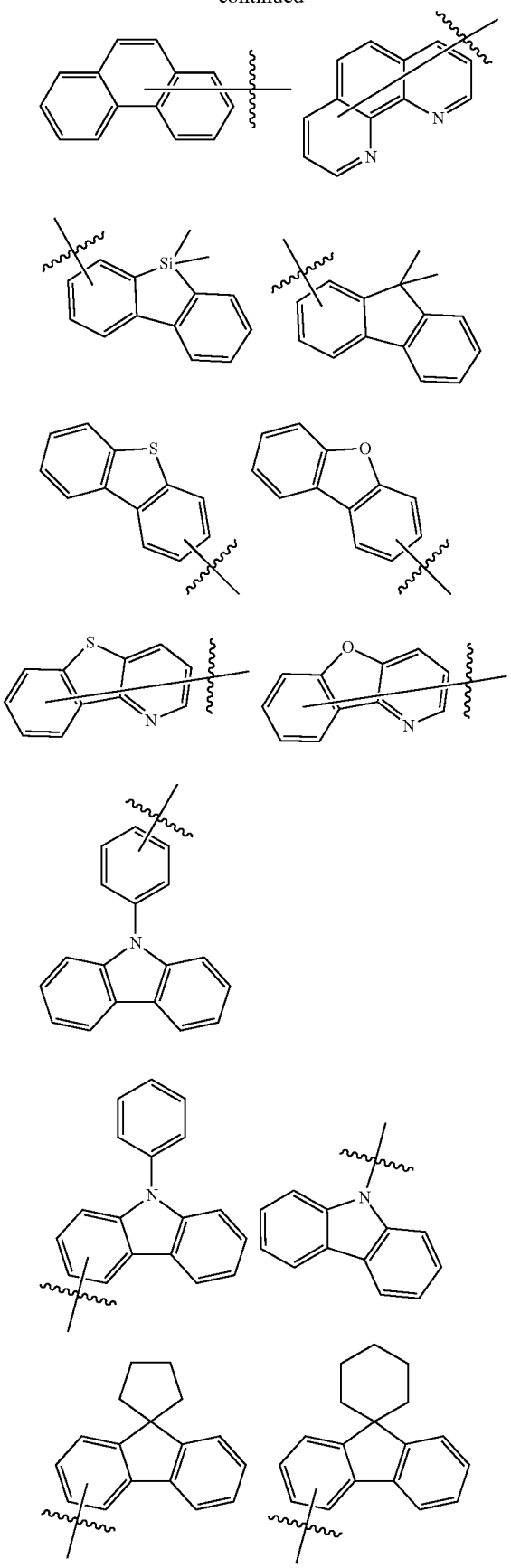
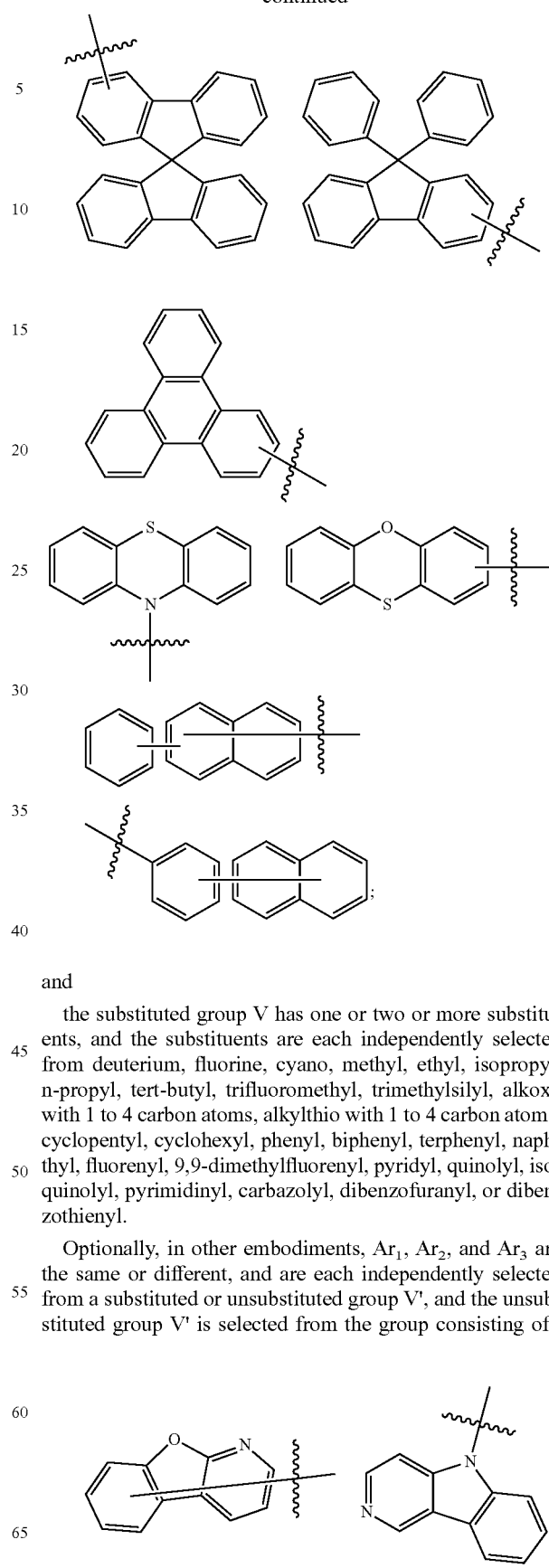

and the substituted group V has one or two or more substituents, and the substituents are each independently selected from deuterium, fluorine, cyano, methyl, ethyl, isopropyl, n-propyl, tert-butyl, trifluoromethyl, trimethylsilyl, alkoxy with 1 to 4 carbon atoms, alkylthio with 1 to 4 carbon atoms, cyclopentyl, cyclohexyl, phenyl, biphenyl, terphenyl, naphthyl, fluorenyl, 9,9-dimethylfluorenyl, pyridyl, quinolyl, isoquinolyl, pyrimidinyl, carbazolyl, dibenzofuranyl, or dibenzothienyl.

Optionally, in other embodiments, $Ar_1$, $Ar_2$, and $Ar_3$ are the same or different, and are each independently selected from a substituted or unsubstituted group V', and the unsubstituted group V' is selected from the group consisting of:

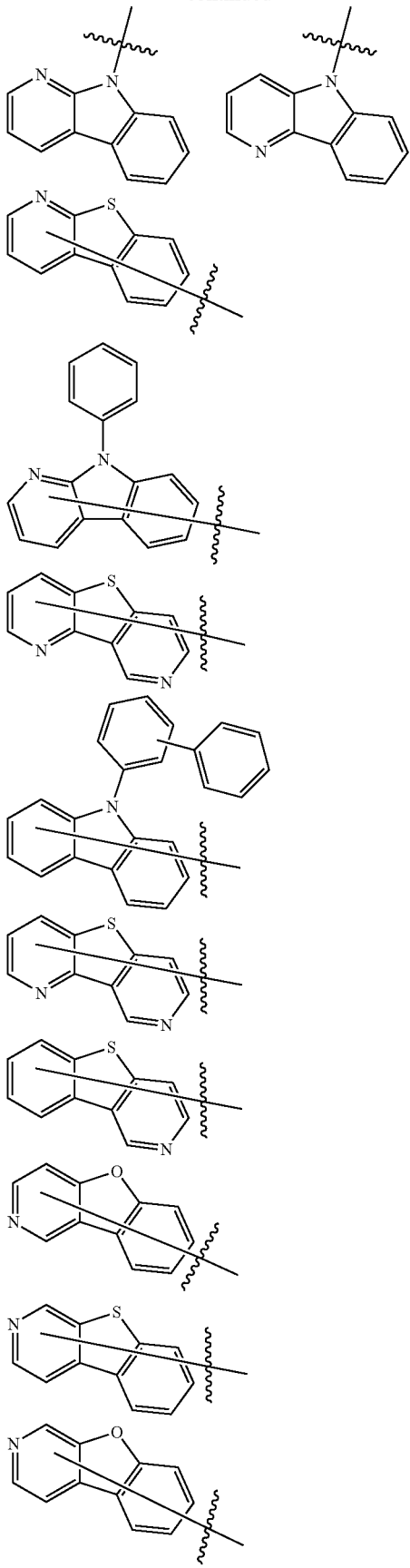
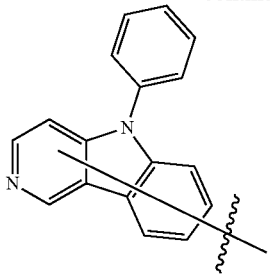
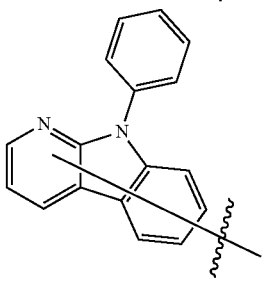
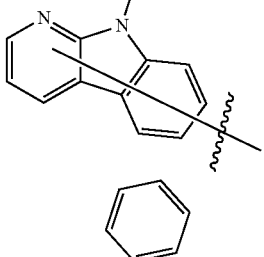
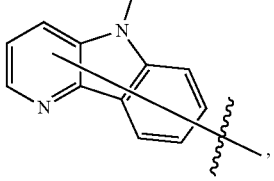

and the substituted group V' has one or two or more substituents, and the substituents are each independently selected from deuterium, fluorine, cyano, methyl, ethyl, isopropyl, n-propyl, tert-butyl, trifluoromethyl, trimethylsilyl, alkoxy with 1 to 4 carbon atoms, alkylthio with 1 to 4 carbon atoms, cyclopentyl, cyclohexyl, phenyl, biphenyl, terphenyl, naphthyl, fluorenyl, 9,9-dimethylfluorenyl, pyridyl, quinolyl, isoquinolyl, pyrimidinyl, carbazolyl, dibenzofuranyl, or dibenzothienyl.

Optionally, in some embodiments, the $Ar_1$, the $Ar_2$, and the $Ar_3$ are each independently selected from substituted or unsubstituted phenyl, substituted or unsubstituted biphenyl, substituted or unsubstituted terphenyl, substituted or unsubstituted naphthyl, substituted or unsubstituted fluorenyl, substituted or unsubstituted quinolyl, substituted or unsubstituted isoquinolyl, substituted or unsubstituted carbazolyl, substituted or unsubstituted dibenzothienyl, substituted or unsubstituted dibenzofuranyl, substituted or unsubstituted azadibenzothienyl, substituted or unsubstituted azadibenzofuranyl, substituted or unsubstituted azacarbazolyl, substituted or unsubstituted phenanthryl, substituted or unsubstituted anthryl, substituted or unsubstituted spirobifluorenyl, substituted or unsubstituted benzofuro[3,2-b]pyridyl, substituted or unsubstituted phenoxytheophyllinyl, substituted or unsubstituted phenothiazinyl, substituted or unsubstituted phenoxazinyl, substituted or unsubstituted spiro[cyclopentane-1,9'-fluorenyl], substituted or unsubstituted spiro[cyclohexane-1,9'-fluorenyl], substituted or unsubstituted 9H-9-silafluorenyl, or a group formed by linking two or three of the above groups by a single bond; and substituents in $Ar_1$, $Ar_2$, and $Ar_3$ are the same as or different from each other, and are each independently selected from the group consisting of deuterium, fluorine, chlorine, cyano, methyl, ethyl, isopropyl, n-propyl, tert-butyl, methoxy, ethoxy, trifluoromethyl, trimethylsilyl, phenyl, biphenyl, naphthyl, pyridyl, carbazolyl, dibenzofuranyl, and dibenzothienyl.

Optionally, in some embodiments, the $Ar_1$, the $Ar_2$, and the $Ar_3$ are the same or different, and are each independently selected from the group consisting of:

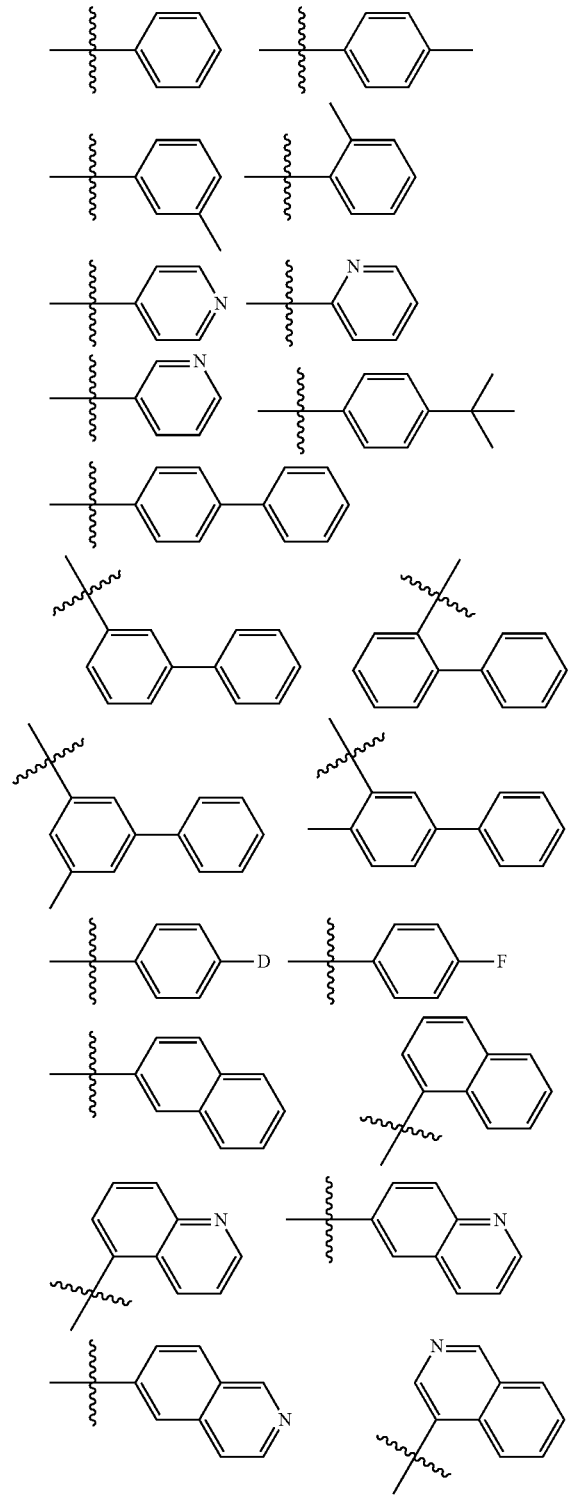

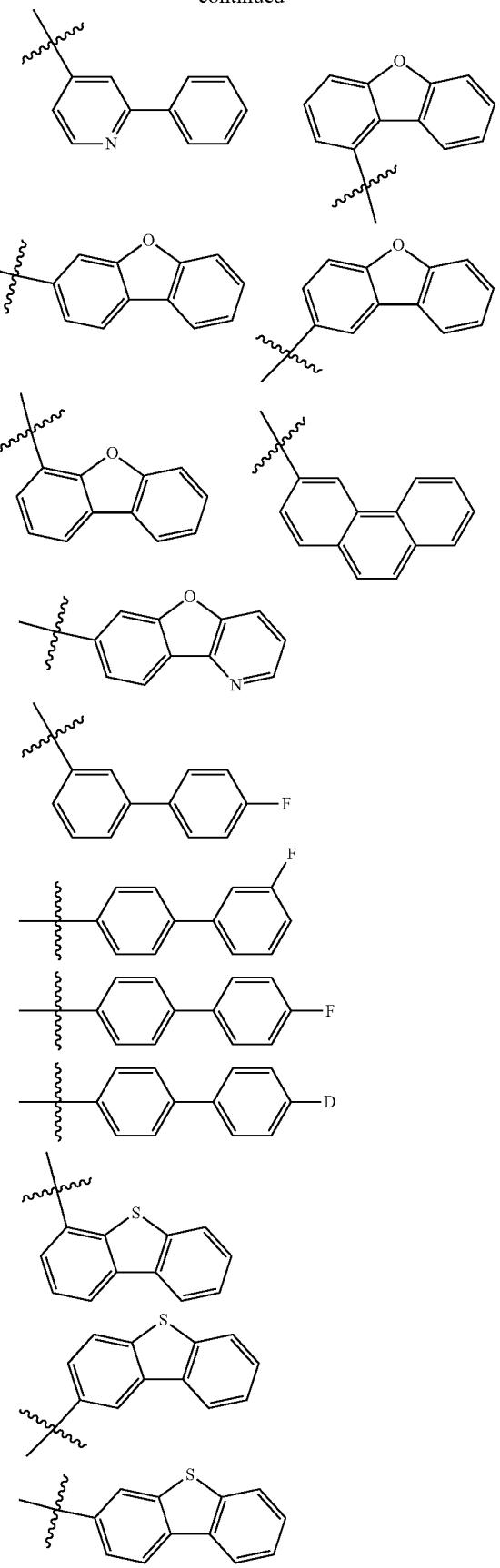

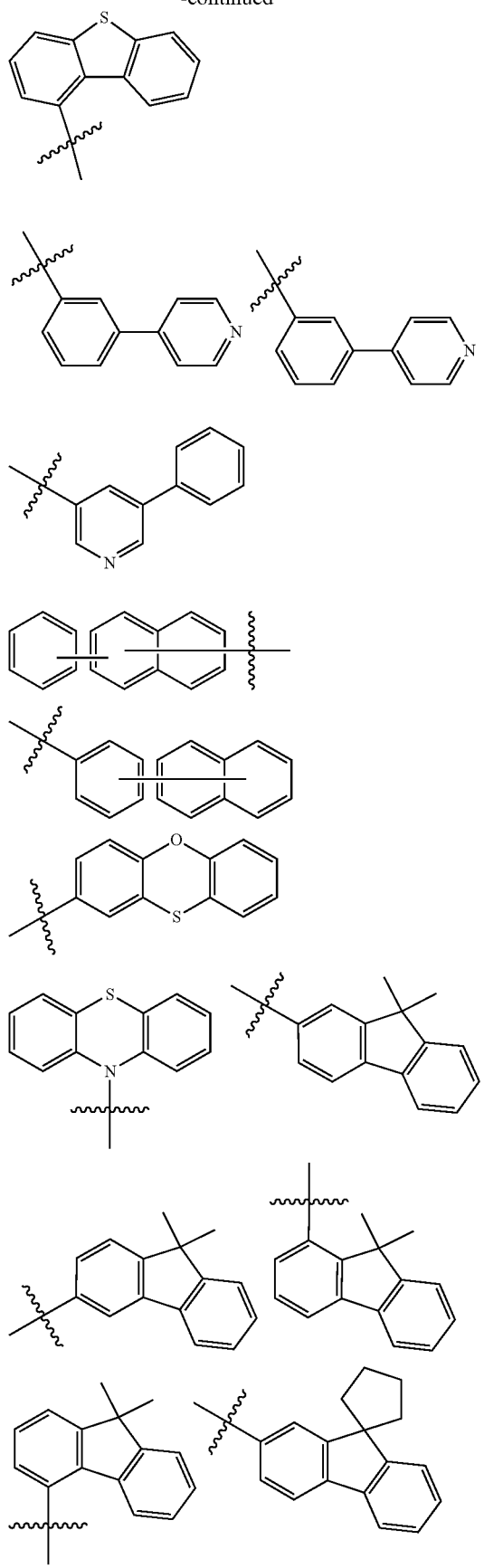
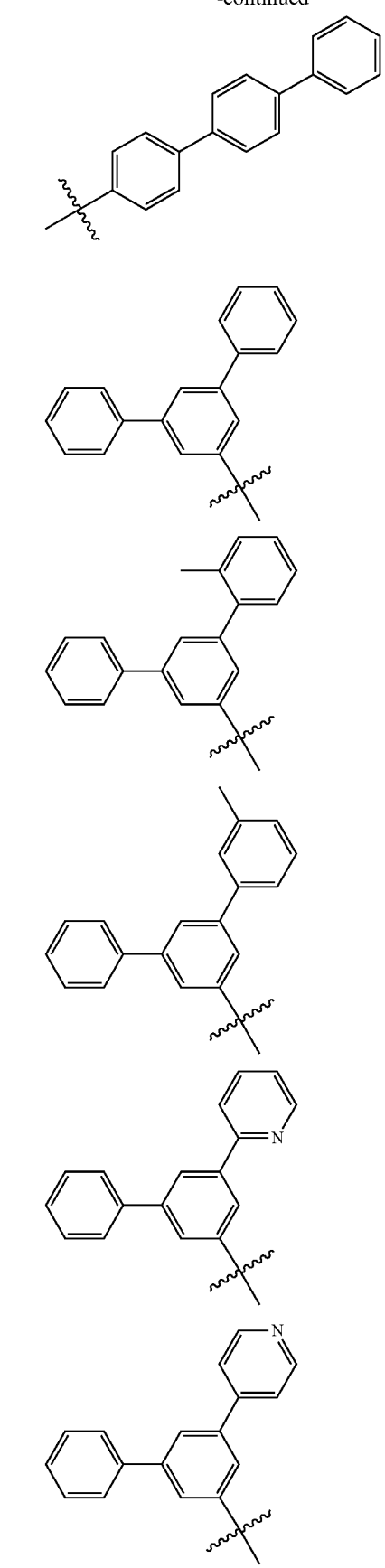

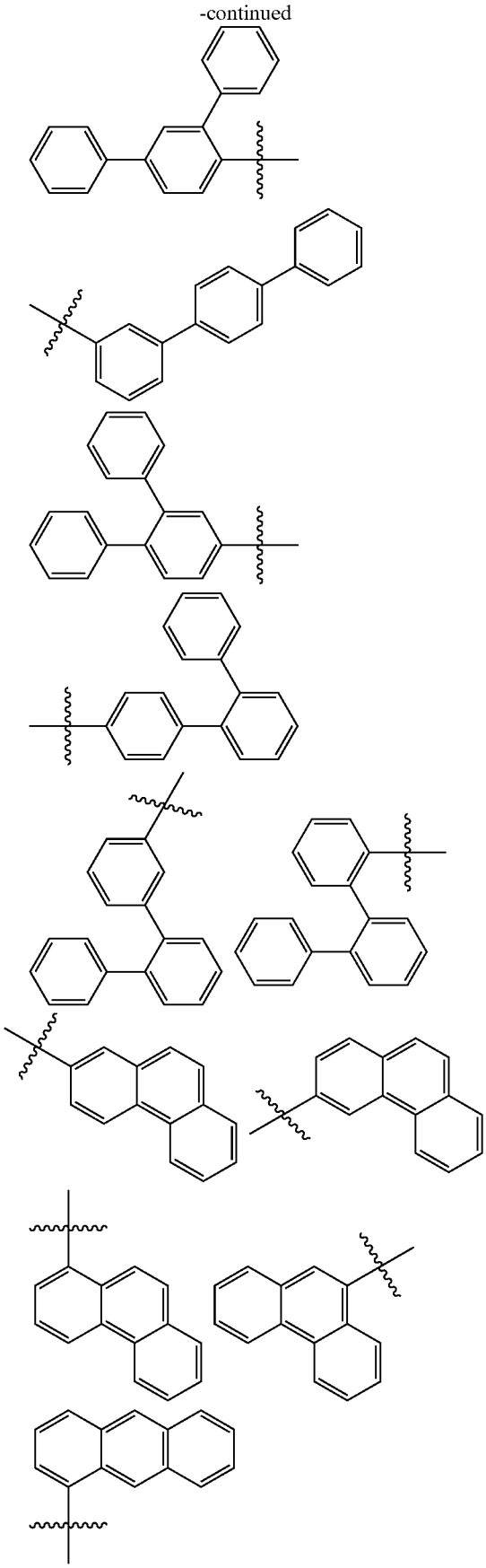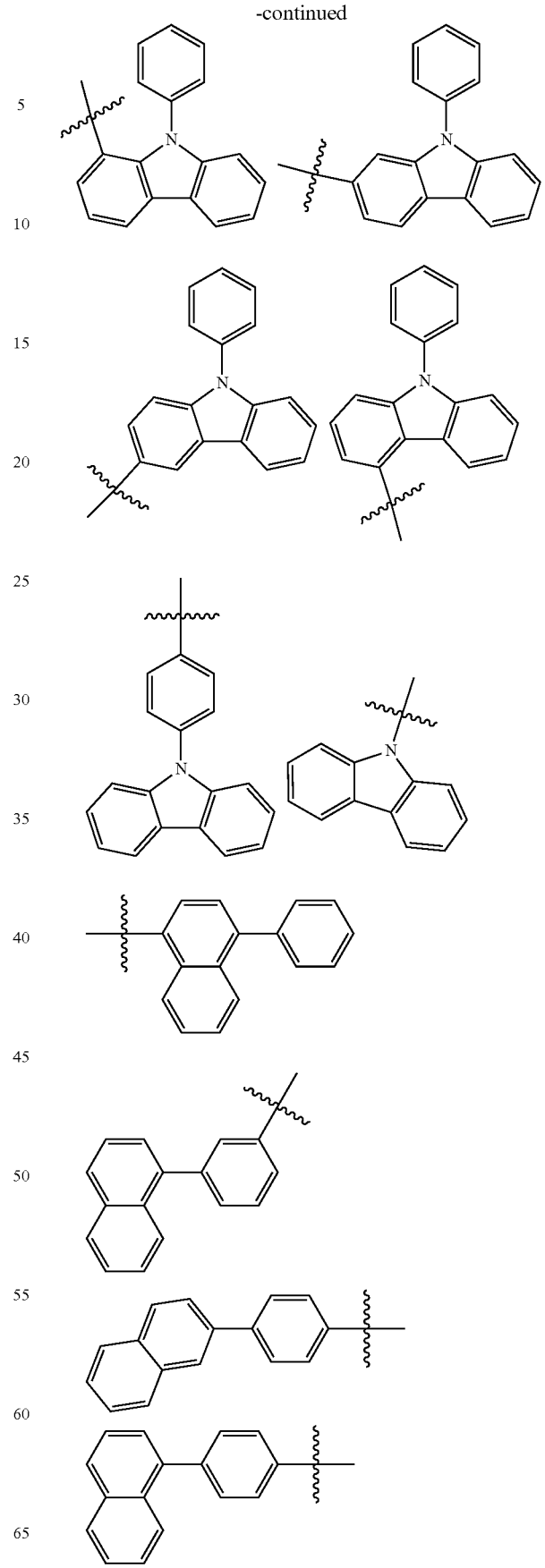

-continued
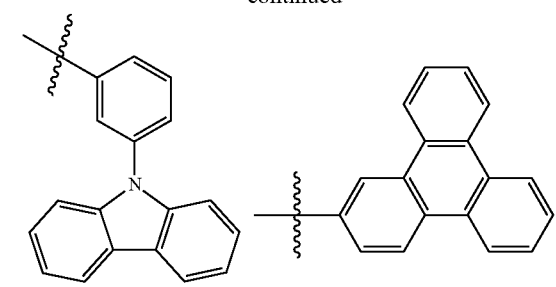
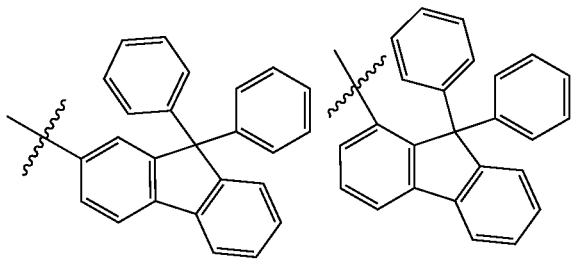
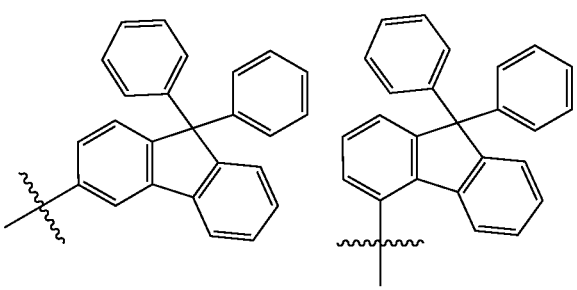
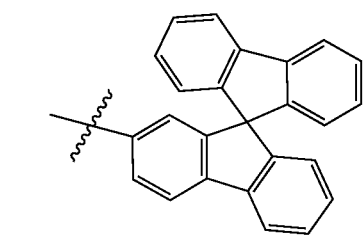
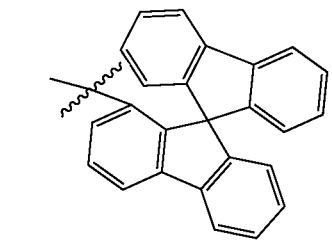
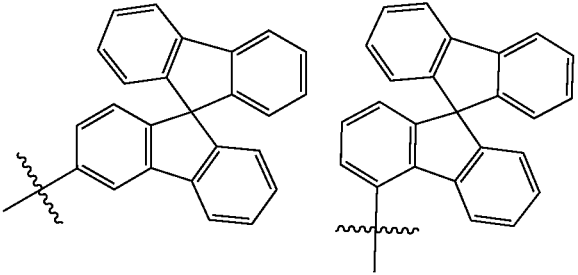
-continued
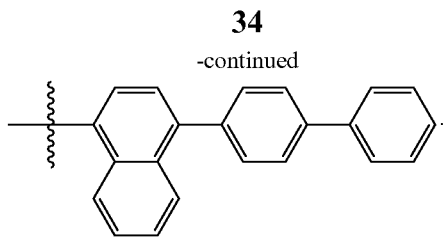
Optionally, in other embodiments, the $Ar_1$, the $Ar_2$, and the $Ar_3$ are the same or different, and are each independently selected from the group consisting of:
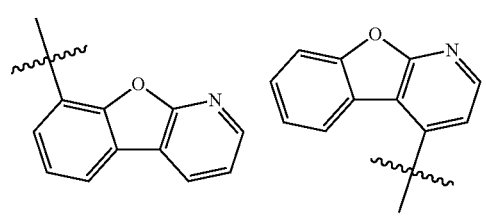
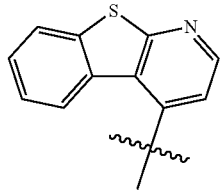
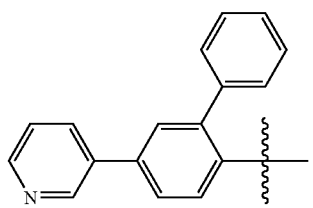
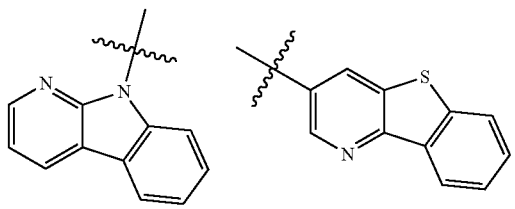
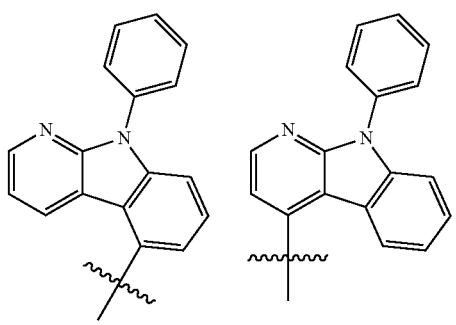

-continued
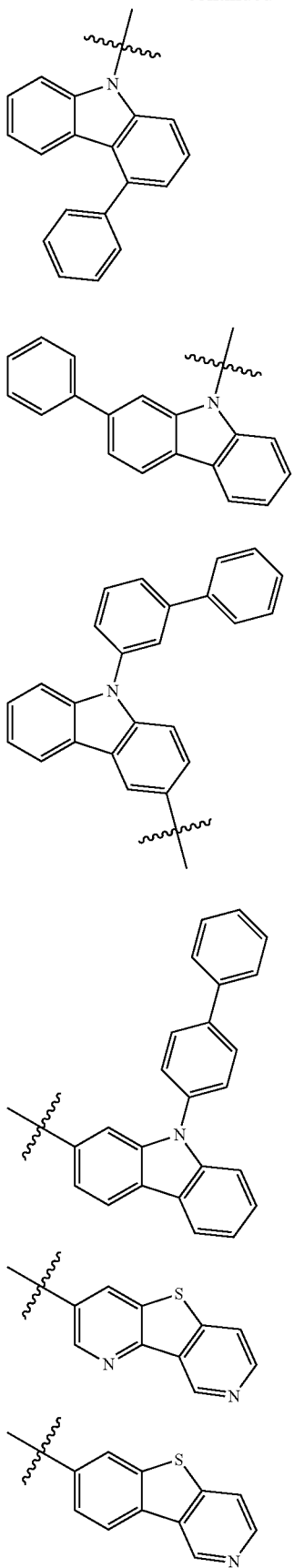
-continued
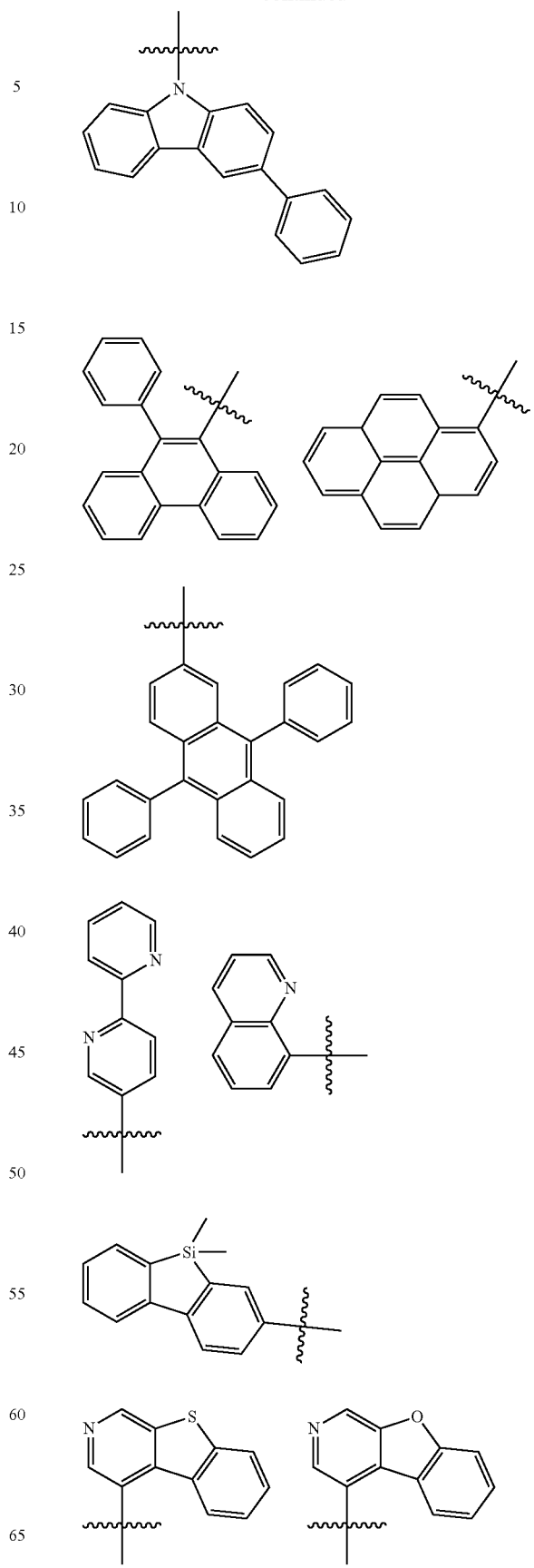

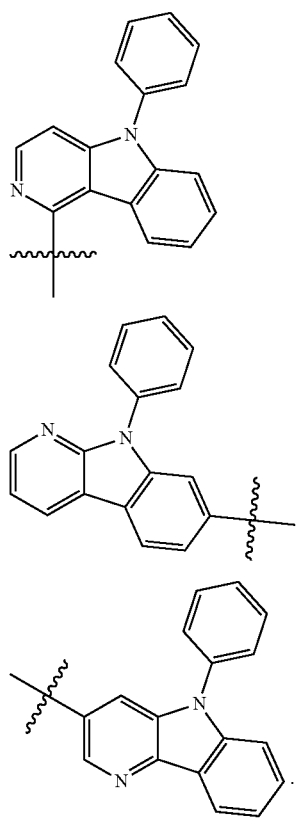
Optionally, in some embodiments, the $L_1$, the $L_2$, and the $L_3$ are the same or different, and are each independently selected from a single bond or selected from the group consisting of groups represented by formulae j-1 to j-14:
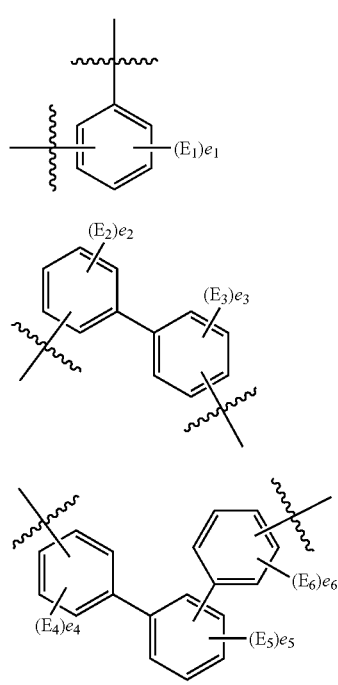
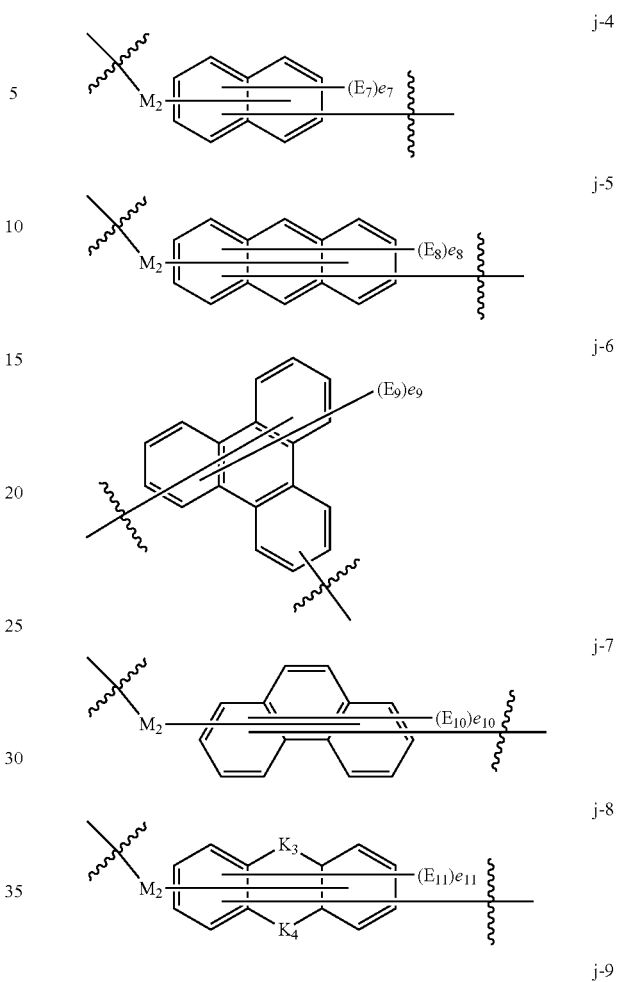
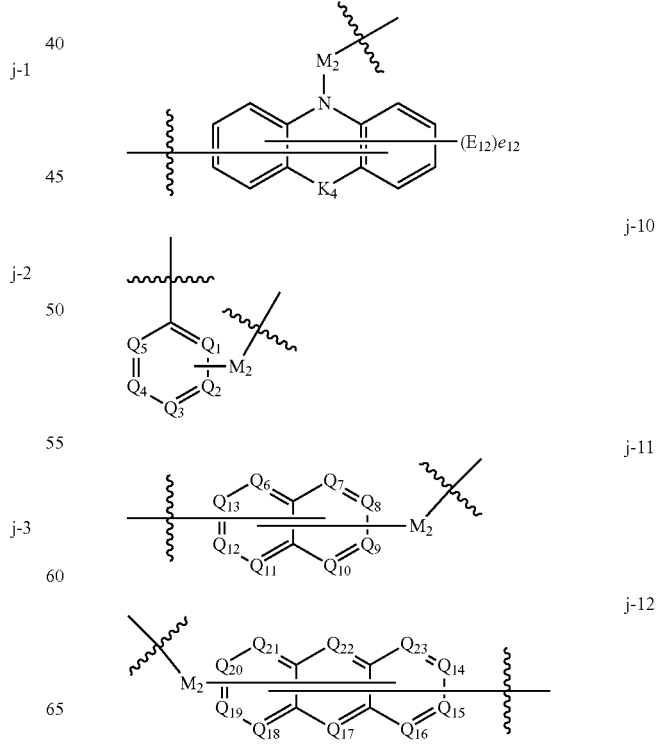

-continued

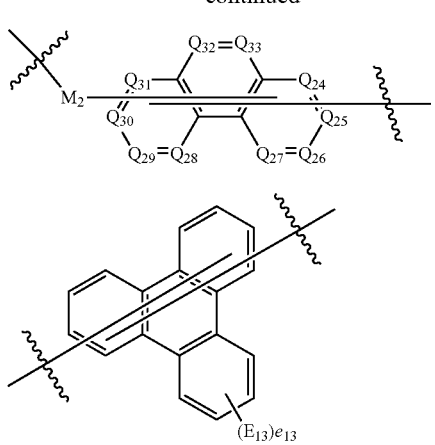

j-13 j-14 where M₂ is selected from a single bond or

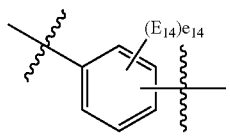

Q₁ to Q₅ are each independently selected from N or C(J₅), and at least one of Q₁ to Q₅ is selected from N; and when two or more of Q₁ to Q₅ are selected from C(J₅), any two J₅ are the same or different;

Q₆ to Q₁₃ are each independently selected from N or C(J₆), and at least one of Q₆ to Q₁₃ is selected from N; and when two or more of Q₆ to Q₁₃ are selected from C(J₆), any two J₆ are the same or different;

Q₁₄ to Q₂₃ are each independently selected from N, C or C(J₇), and at least one of Q₁₄ to Q₂₃ is selected from N; and when two or more of Q₁₄ to Q₂₃ are selected from C(J₇), any two J₇ are the same or different;

Q₂₄ to Q₃₃ are each independently selected from N, C or C(J₈), and at least one of Q₂₄-Q₃₃ is selected from N; and when two or more of Q₂₄ to Q₃₃ are selected from C(J₈), any two J₈ are the same or different;

$E_1$ to $E_{14}$, and $J_5$ to $J_8$ are each independently selected from: hydrogen, deuterium, a halogen group, cyano, heteroaryl with 3 to 20 carbon atoms, aryl with 6 to 20 carbon atoms, alkylsilyl with 3 to 8 carbon atoms, triphenylsilyl, alkyl with 1 to 6 carbon atoms, haloalkyl with 1 to 6 carbon atoms, alkenyl with 2 to 6 carbon atoms, cycloalkyl with 5 to 10 carbon atoms, heterocycloalkyl with 2 to 6 carbon atoms, alkoxy with 1 to 6 carbon atoms, alkylthio with 1 to 6 carbon atoms, aryloxy with 6 to 18 carbon atoms, or arylthio with 6 to 18 carbon atoms;

$e_1$ to $e_{14}$ are represented by $e_r$, $E_1$ to $E_{14}$ are represented by $E_r$, r is a variable, and represents any integer from 1 to 14, and $e_r$ represents the number of a substituent $E_r$; when r is selected from 1, 2, 3, 4, 5, 6, 13 or 14, $e_r$ is selected from 1, 2, 3 or 4; when r is selected from 7 or 11, $e_r$ is selected from 1, 2, 3, 4, 5 or 6; when r is 9 or 12, $e_r$ is selected from 1, 2, 3, 4, 5, 6, or 7; when r is selected from 8 or 10, $e_r$ is selected from 1, 2, 3, 4, 5, 6, 7, or 8; and when $e_r$ is greater than 1, any two $E_r$ are the same or different;

$K_3$ is selected from O, S, Se, $N(E_{15})$, $C(E_{16}E_{17})$, or $Si(E_{18}E_{19})$; where $E_{15}$, $E_{16}$, $E_{17}$, $E_{18}$, and $E_{19}$ are each independently selected from hydrogen, aryl with 6 to 20 carbon atoms, heteroaryl with 3 to 20 carbon atoms, alkyl with 1 to 6 carbon atoms, alkenyl with 2 to 6 carbon atoms, cycloalkyl with 5 to 10 carbon atoms, or heterocycloalkyl with 2 to 6 carbon atoms;

or, optionally, the $E_{16}$ and the $E_{17}$ are connected to each other to form a 5- to 13-membered aliphatic ring or a 5- to 13-membered aromatic ring together with the atoms to which they are jointly connected;

or, optionally, the $E_{18}$ and the $E_{19}$ are connected to each other to form a 5- to 13-membered aliphatic ring or a 5- to 13-membered aromatic ring together with the atoms to which they are jointly connected;

each $K_4$ is independently selected from a single bond, O, S, Se, $N(E_{20})$, $C(E_{21}E_{22})$, or $Si(E_{23}E_{24})$; where $E_{20}$, $E_{21}$, $E_{22}$, $E_{23}$, and $E_{24}$ are each independently selected from hydrogen, aryl with 6 to 20 carbon atoms, heteroaryl with 3 to 20 carbon atoms, alkyl with 1 to 6 carbon atoms, alkenyl with 2 to 6 carbon atoms, cycloalkyl with 5 to 10 carbon atoms, or heterocycloalkyl with 2 to 10 carbon atoms;

or, optionally, the $E_{21}$ and the $E_{22}$ are connected to each other to form a 5- to 13-membered aliphatic ring or a 5- to 13-membered aromatic ring together with the atoms to which they are jointly connected;

or, optionally, the $E_{23}$ and the $E_{24}$ are connected to each other to form a 5- to 13-membered aliphatic ring or a 5- to 13-membered aromatic ring together with the atoms to which they are jointly connected.

Optionally, in some embodiments, the $L_1$, the $L_2$, and the $L_3$ are the same or different, and are each independently selected from a single bond, substituted or unsubstituted arylene with 6 to 20 carbon atoms, or substituted or unsubstituted heteroarylene with 5 to 18 carbon atoms. In some embodiments, substituents in $L_1$, $L_2$, and $L_3$ are the same or different, and are each independently selected from deuterium, a halogen group, cyano, a group A, trialkylsilyl with 3 to 8 carbon atoms, triphenylsilyl, alkyl with 1 to 4 carbon atoms, haloalkyl with 1 to 4 carbon atoms, cycloalkyl with 5 to 10 carbon atoms, alkoxy with 1 to 4 carbon atoms, alkylthio with 1 to 4 carbon atoms, aryloxy with 6 to 15 carbon atoms, or arylthio with 6 to 15 carbon atoms; the group A is selected from substituted or unsubstituted heteroaryl with 5 to 12 carbon atoms or substituted or unsubstituted aryl with 6 to 15 carbon atoms, and substituents in the group A are selected from deuterium, a halogen group, cyano, alkyl with 1 to 4 carbon atoms, or haloalkyl with 1 to 4 carbon atoms; and optionally, any two adjacent substituents form a 5- to 10-membered aliphatic ring or a 5- to 13-membered aromatic ring.

In some more specific embodiments, the substituents in the $L_1$, the $L_2$, and the $L_3$ are the same or different, and are each independently selected from deuterium, fluorine, cyano, methyl, ethyl, isopropyl, n-propyl, tert-butyl, trifluoromethyl, trimethylsilyl, methoxy, ethoxy, isopropoxy, methylthio, cyclopentyl, cyclohexyl, phenyl, biphenyl, terphenyl, naphthyl, fluorenyl, 9,9-dimethylfluorenyl, pyridyl, quinolyl, isoquinolyl, pyrimidinyl, carbazolyl, dibenzofuranyl, or dibenzothienyl; and optionally, any two adjacent substituents form a 5- to 6-membered aliphatic ring or a 6- to 13-membered aromatic ring.

Optionally, in some embodiments, $L_1$, $L_2$, and $L_3$ are the same or different, and are each independently selected from a single bond, and a substituted or unsubstituted group W, and the unsubstituted group W is selected from the group consisting of:

-continued
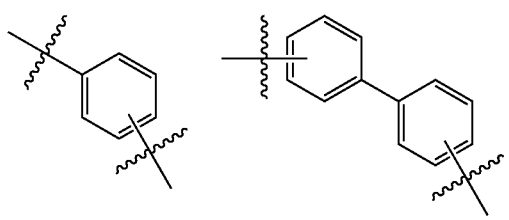
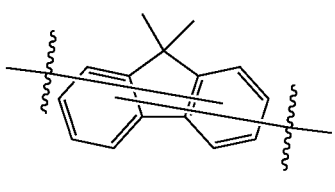
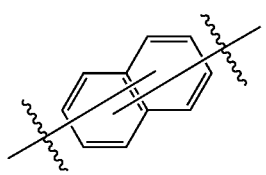
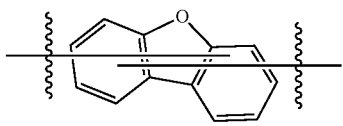
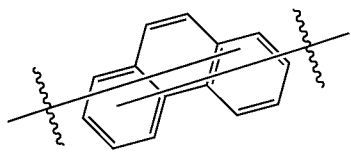
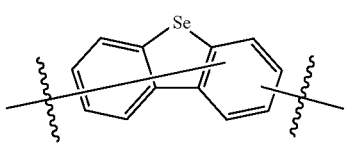
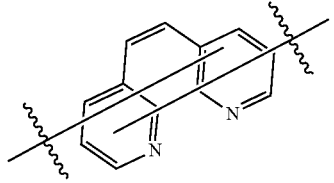
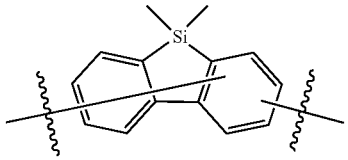
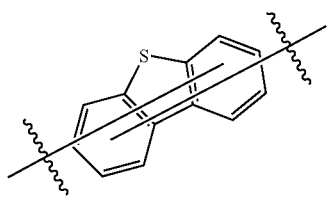
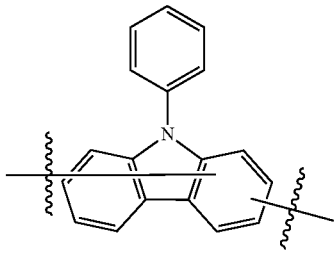
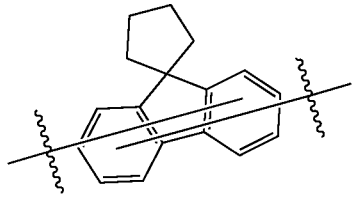
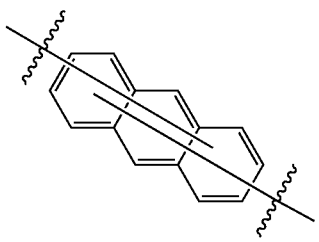
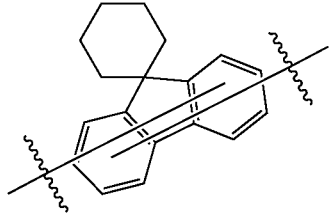
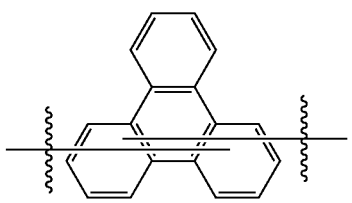
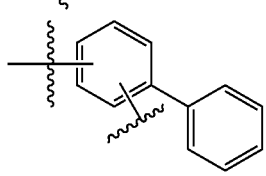
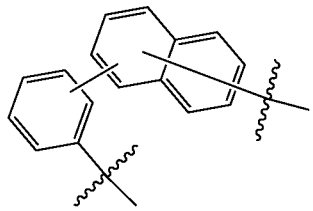
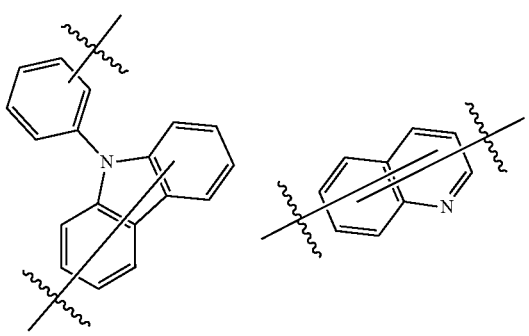

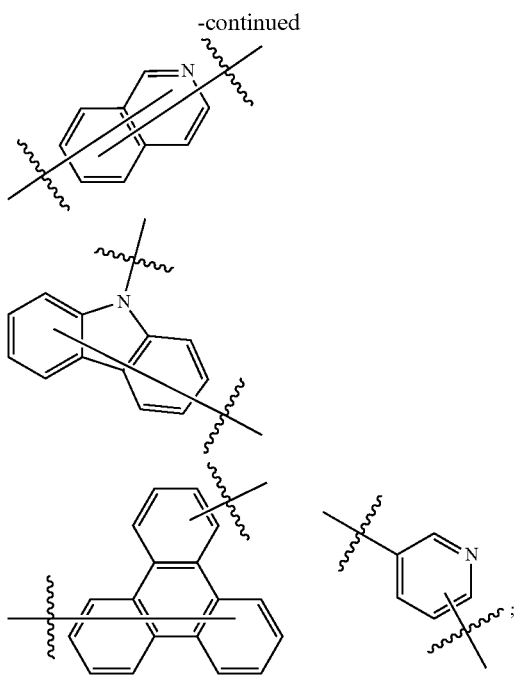

and when the group W is substituted with one or more substituents, the substituents in the group W are each independently selected from the group consisting of deuterium, fluorine, chlorine, cyano, methyl, ethyl, isopropyl, n-propyl, tert-butyl, alkoxy with 1 to 4 carbon atoms, trifluoromethyl, trimethylsilyl, cyclopentyl, cyclohexyl, phenyl, biphenyl, naphthyl, fluorenyl, 9,9-dimethylfluorenyl, pyridyl, quinolyl, isoquinolyl, pyrimidinyl, dibenzofuranyl, dibenzothienyl, and carbazolyl; and when the number of the substituents in the group W is more than 1, the substituents are the same or different.

Optionally, in some embodiments, the $L_1$, the $L_2$, and the $L_3$ are the same or different, and are each independently selected from a single bond, substituted or unsubstituted phenylene, substituted or unsubstituted biphenylene, substituted or unsubstituted terphenylene, substituted or unsubstituted naphthylene, substituted or unsubstituted fluorenylene, substituted or unsubstituted spiro[cyclopentane-1,9'-fluorenylene], substituted or unsubstituted spiro[cyclohexane-1,9'-fluorenylene], substituted or unsubstituted phenanthrolinylene, substituted or unsubstituted quinolylene, substituted or unsubstituted pyridylene, substituted or unsubstituted isoquinolylene, substituted or unsubstituted carbazolylene, substituted or unsubstituted dibenzothienylene, substituted or unsubstituted dibenzofurylene, substituted or unsubstituted phenanthrylene, substituted or unsubstituted anthrylene, or substituted or unsubstituted benzophenanthrylene, or is a group formed by connecting two or three of the above subunit groups by a single bond; and substituents in $L_1$, $L_2$, and $L_3$ are the same as or different from each other, and are each independently selected from the group consisting of deuterium, fluorine, chlorine, cyano, methyl, ethyl, isopropyl, n-propyl, tert-butyl, methoxy, ethoxy, trifluoromethyl, trimethylsilyl, phenyl, biphenyl, naphthyl, pyridyl, carbazolyl, dibenzofuranyl, and dibenzothienyl.

Optionally, in some embodiments, $L_1$ and $L_2$ are the same or different, and are each independently selected from a single bond or from the group consisting of:

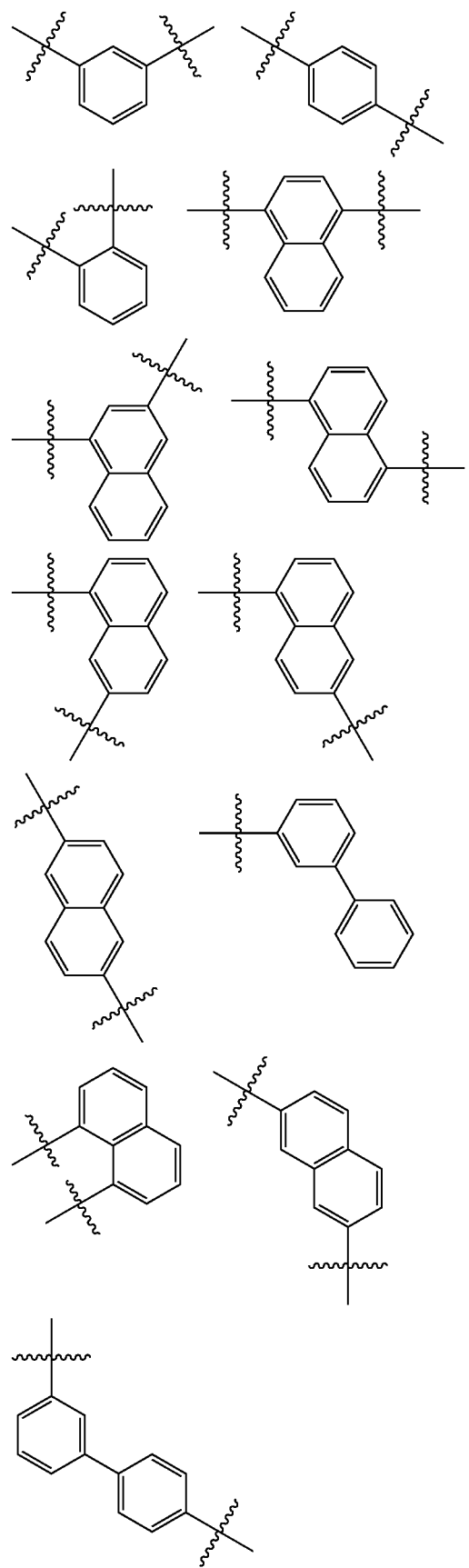

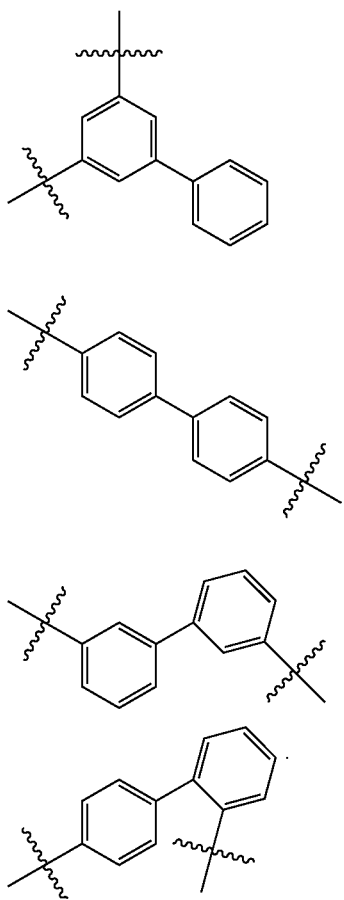
Optionally, in some embodiments, L₃ is selected from a single bond or the group consisting of:
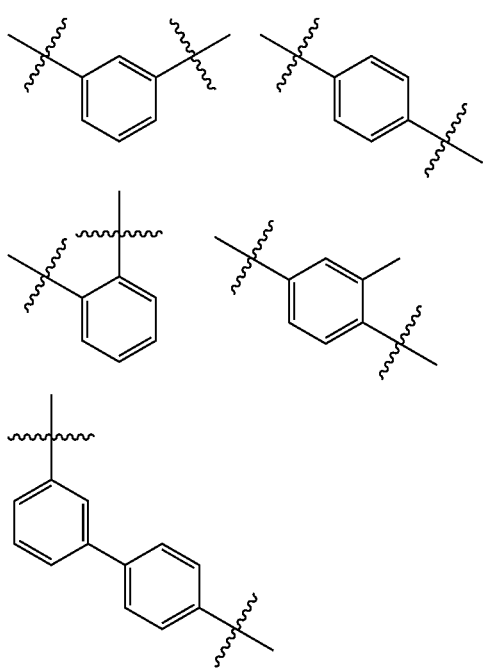
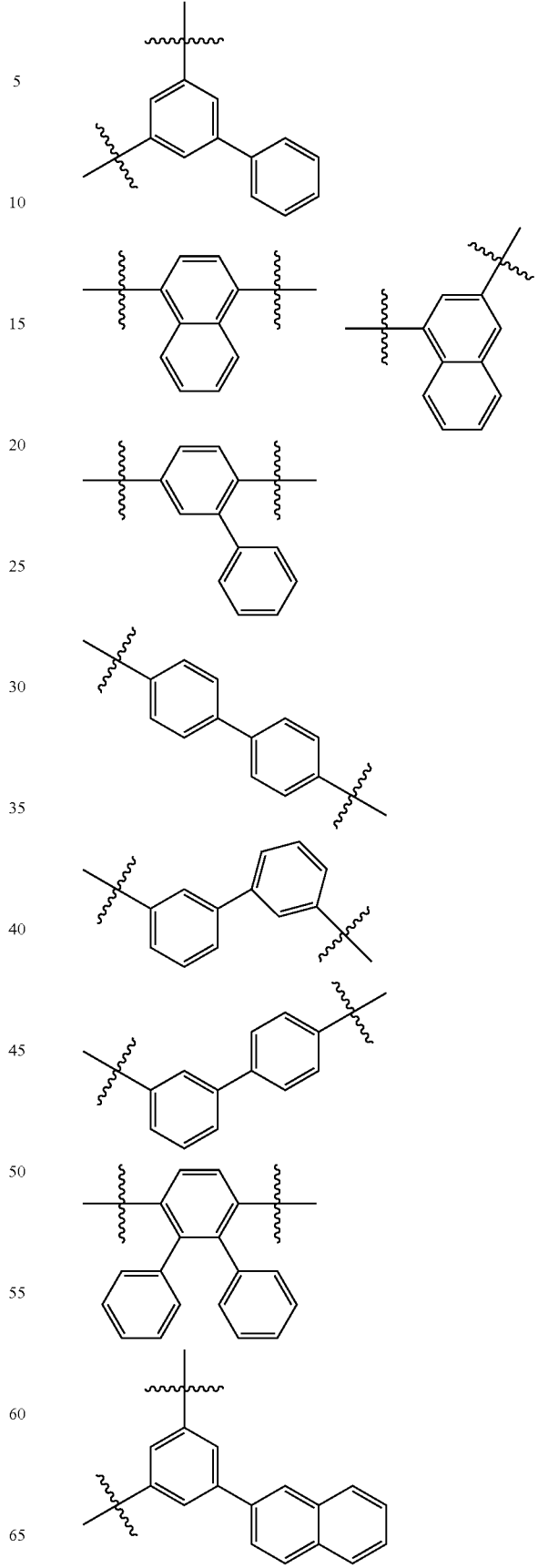

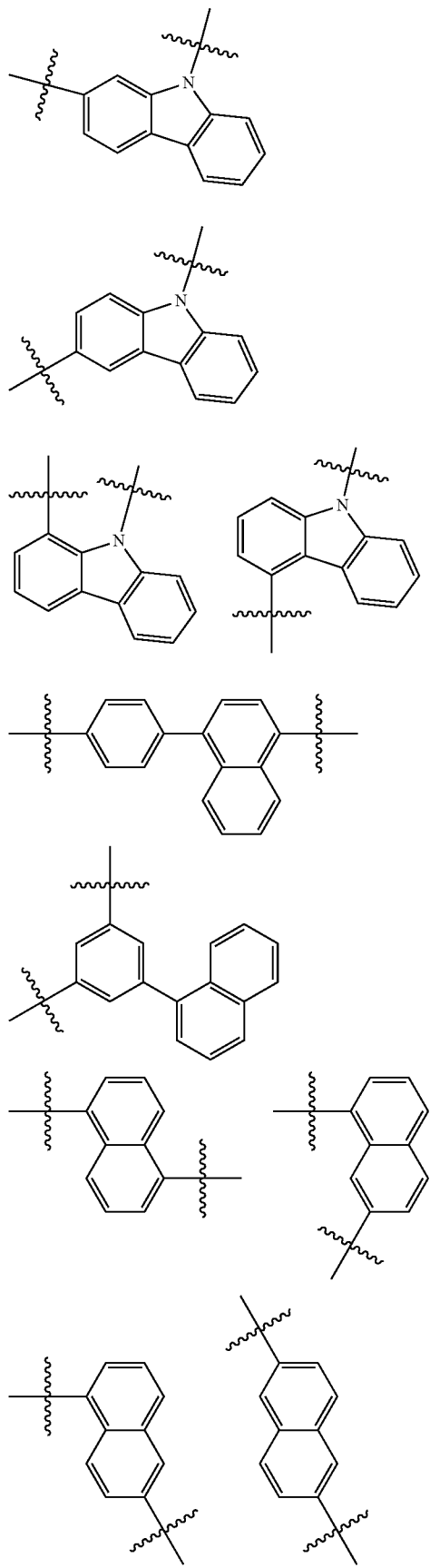

-continued
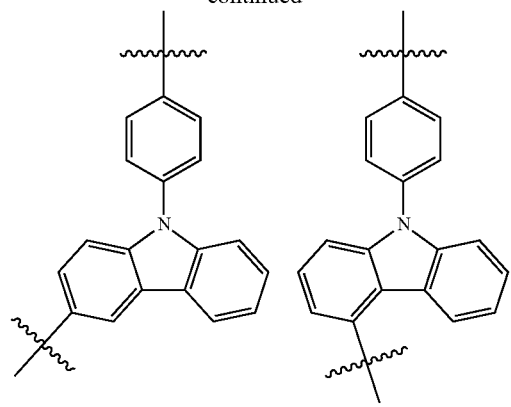
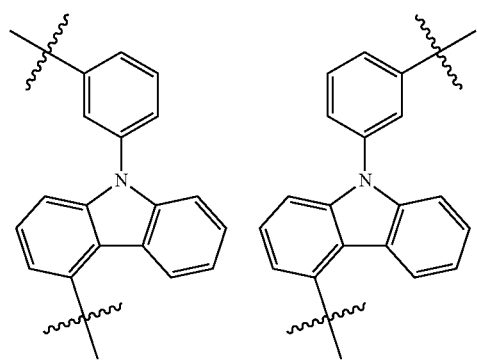
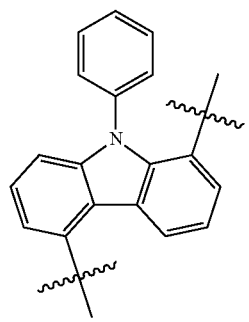
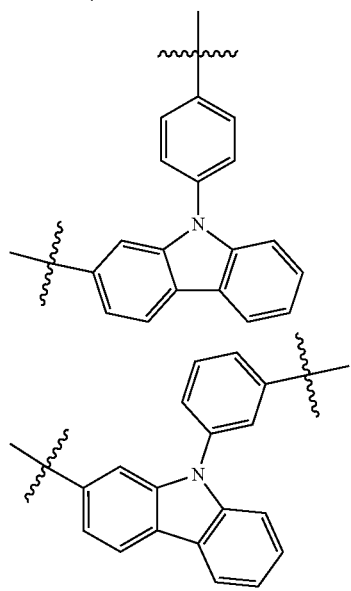
-continued
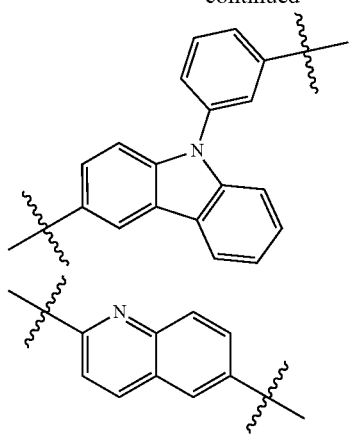
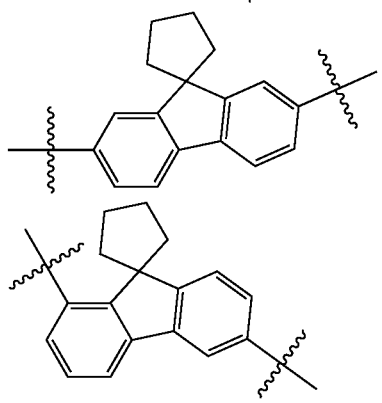
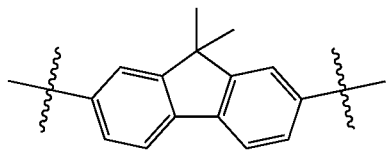
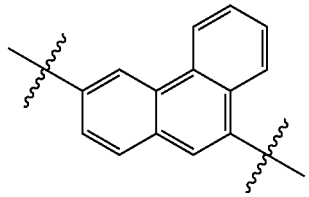
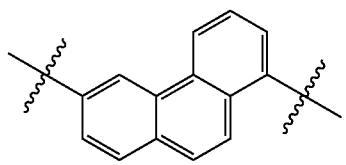
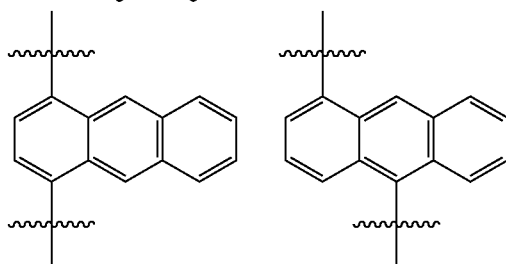
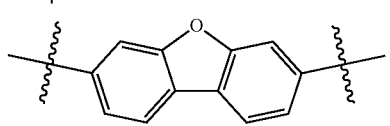

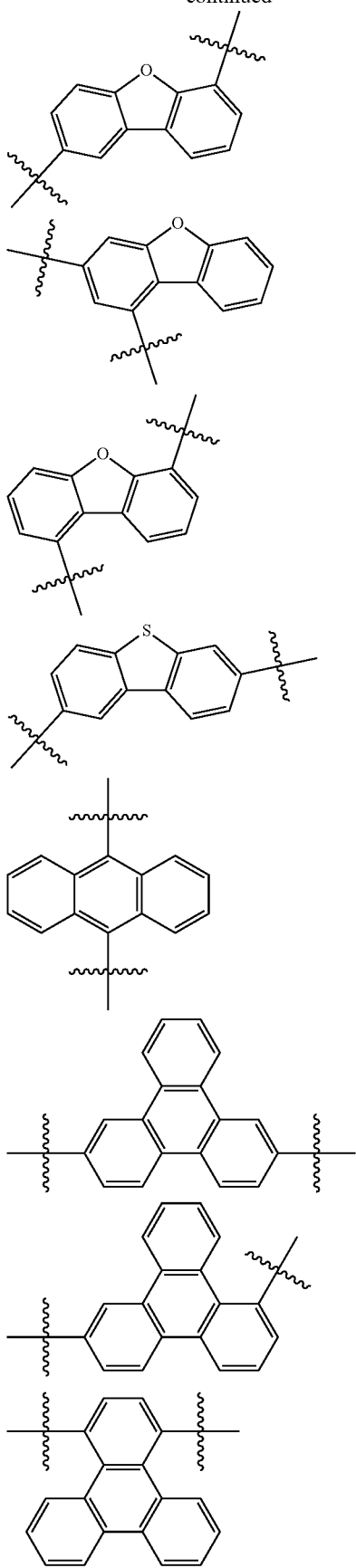
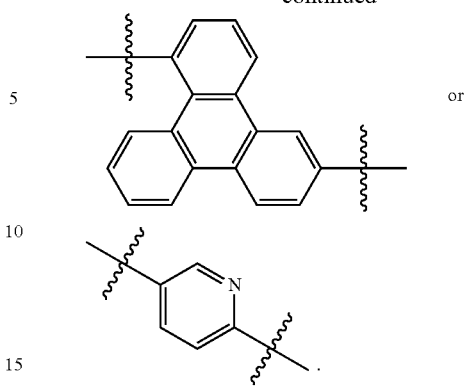
Optionally, in some embodiments, at least two of $X_1$, $X_2$, and $X_3$ are N, and at least one cyano and at least one adamantyl are connected to $Y_1$, $Y_2$, and $Y_3$ in total.
Optionally, in some more specific embodiments, $Y_1$ and $Y_2$ are each independently selected from the group consisting of:
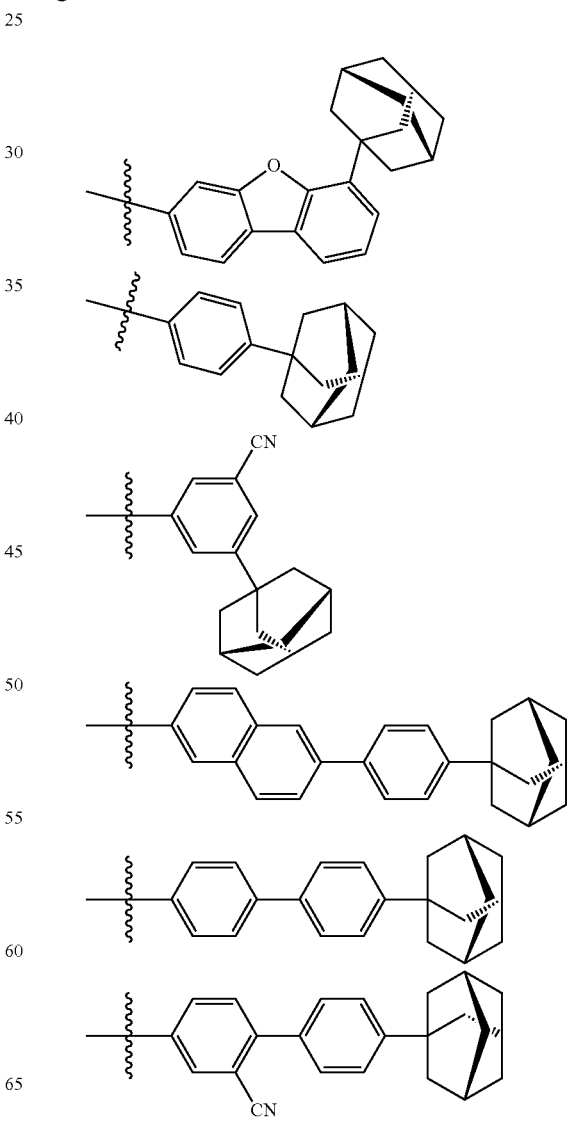

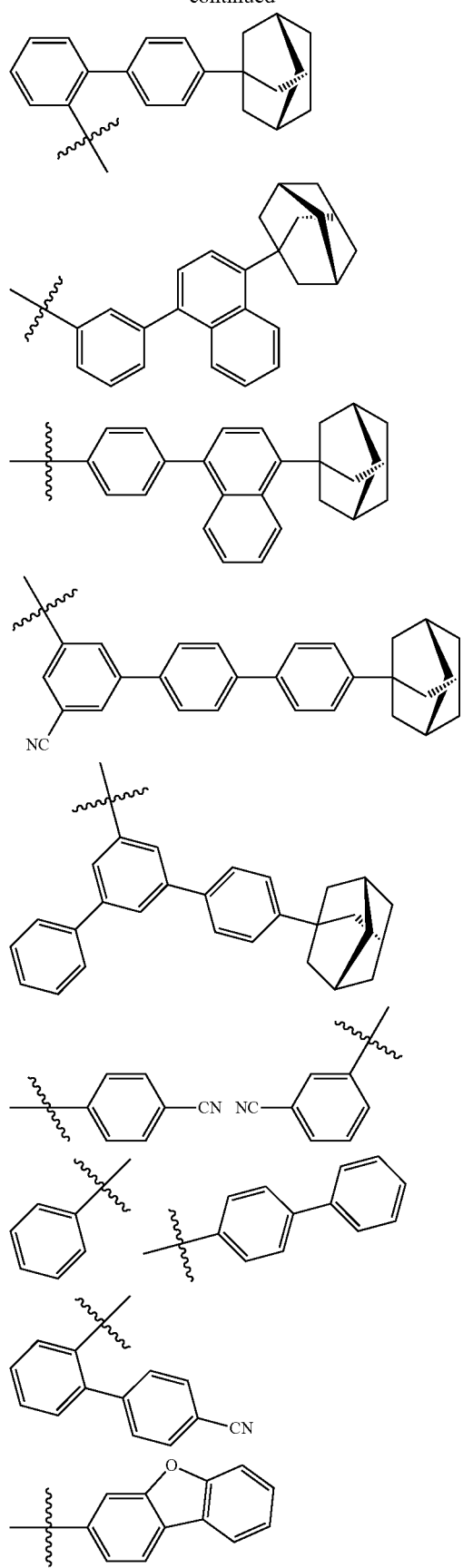
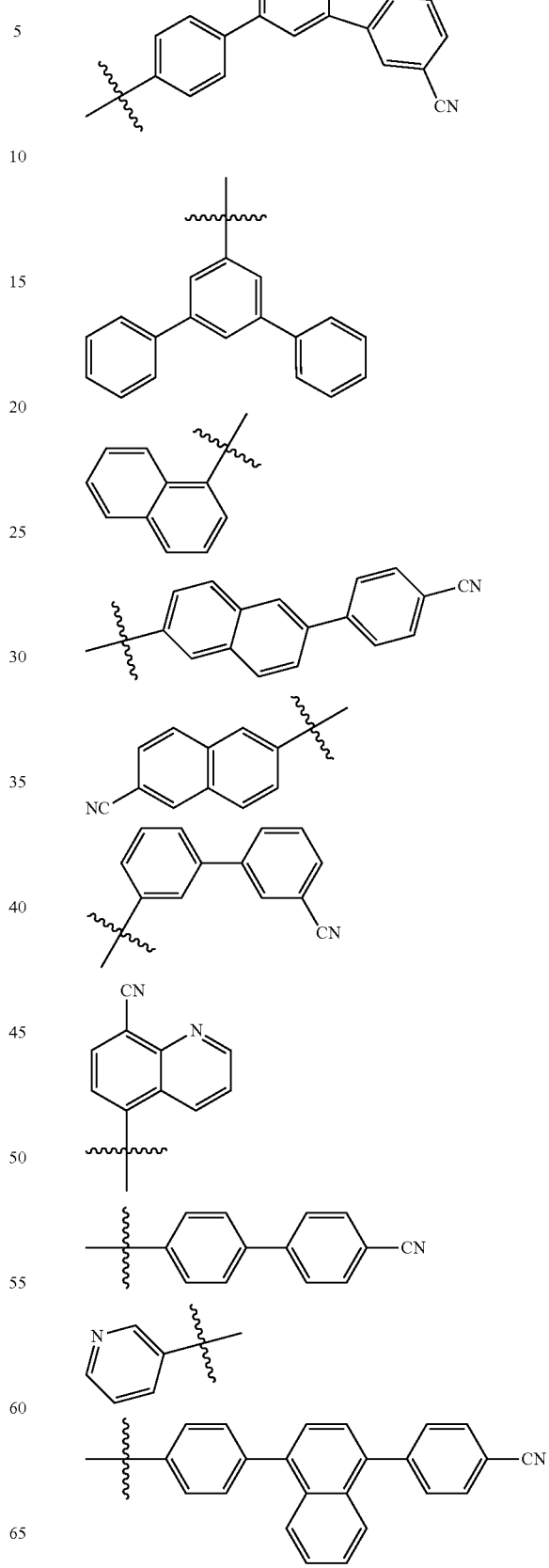

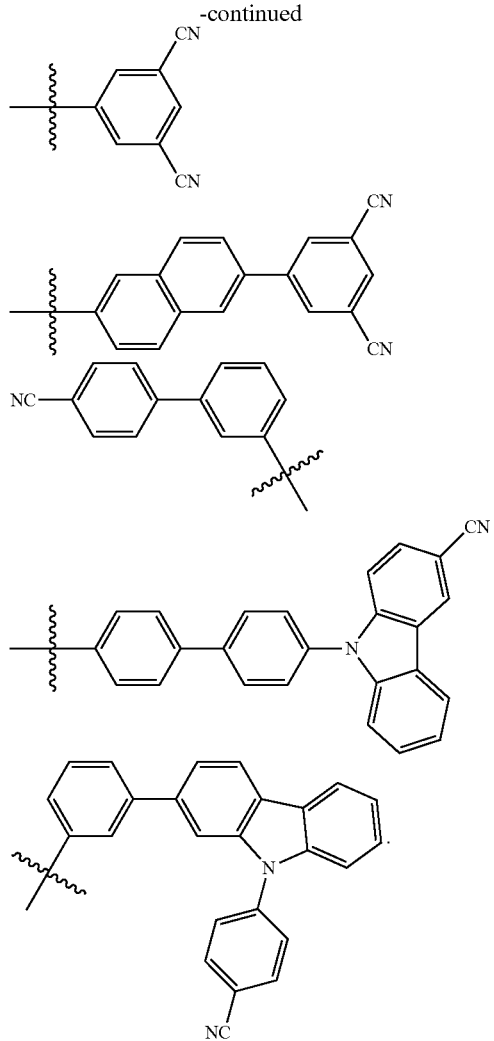
Optionally, in some more specific embodiments, $Y_3$ is selected from the group consisting of:
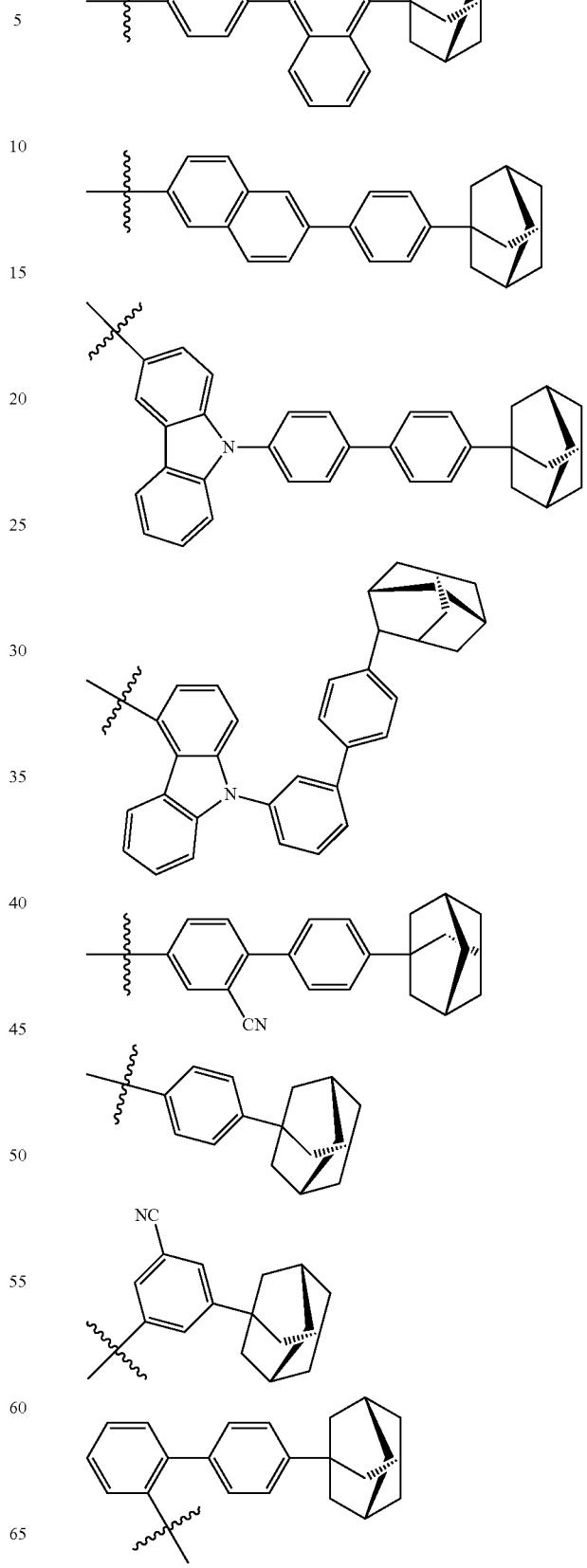

57
-continued
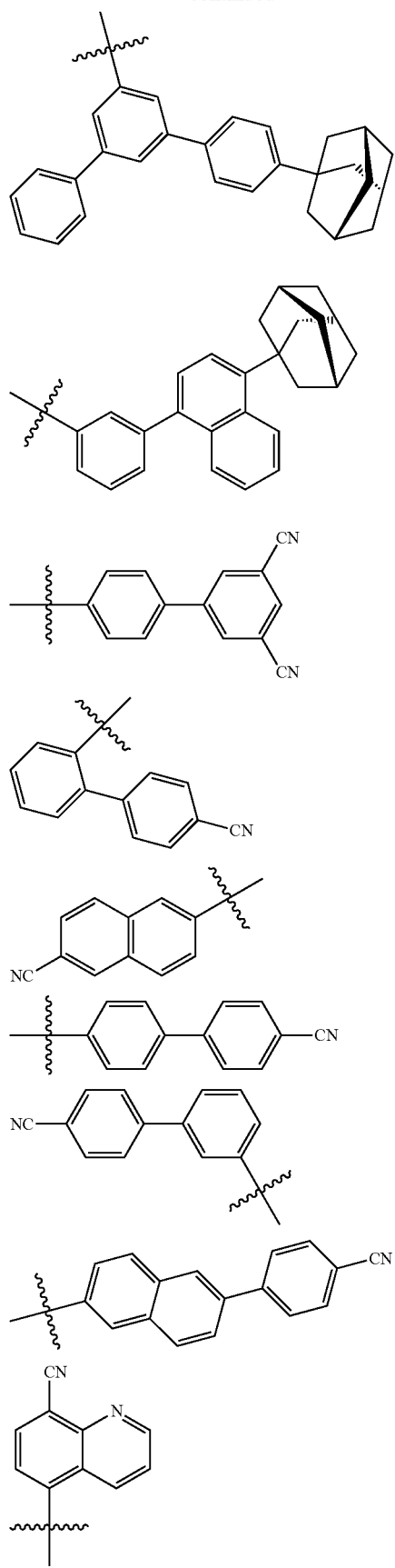
58
-continued
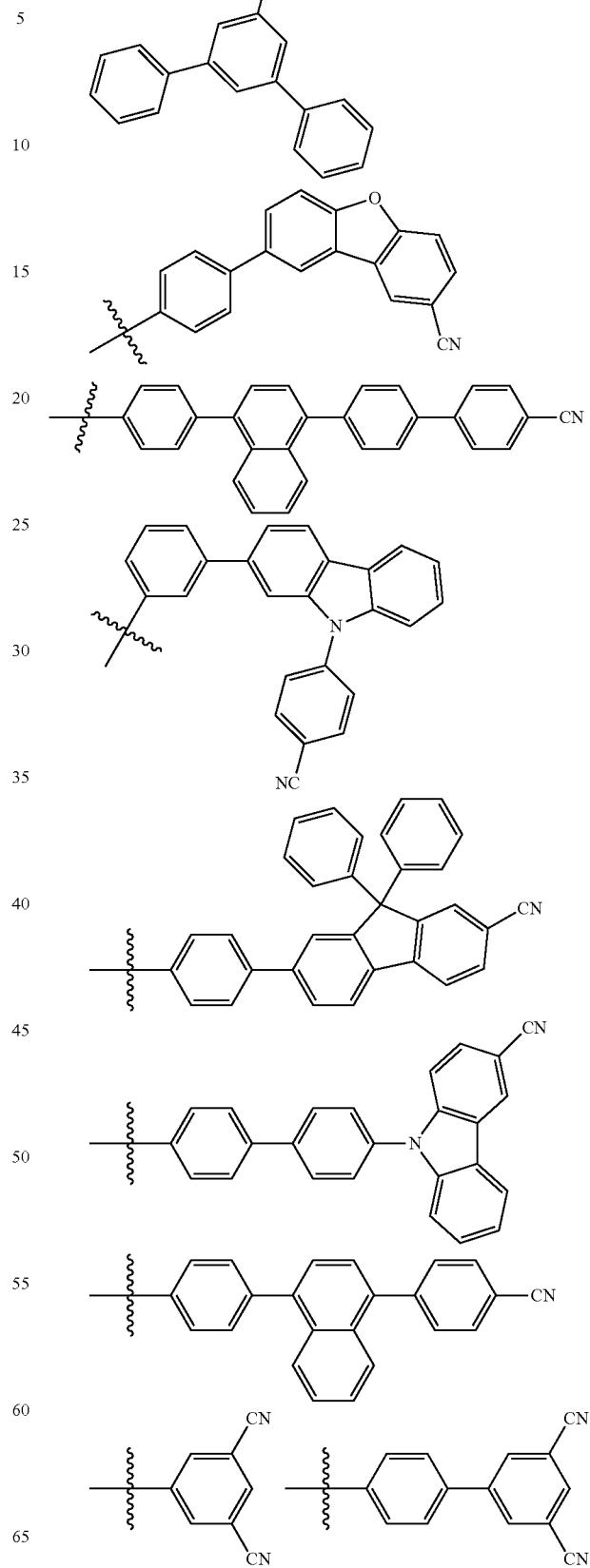

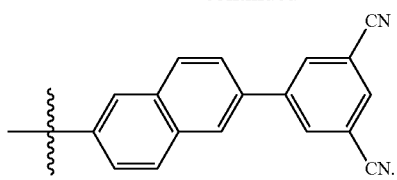
Optionally, in some embodiments, $Y_3$ is connected to at least one cyano, i.e., $m_3+q_3 \geq 1$, and/or $Y_3$ is connected to at least one adamantyl, i.e., $n_3+t_3 \geq 1$.
Optionally, in some embodiments, the nitrogen-containing compound is selected from the group consisting of the following compounds:
1
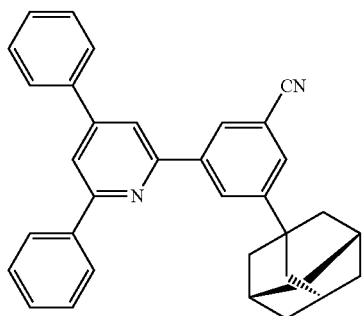
2
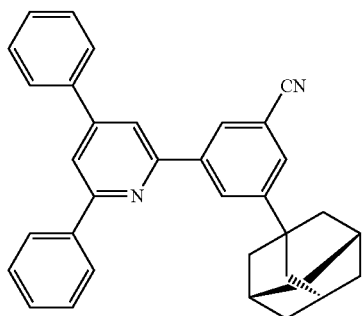
3
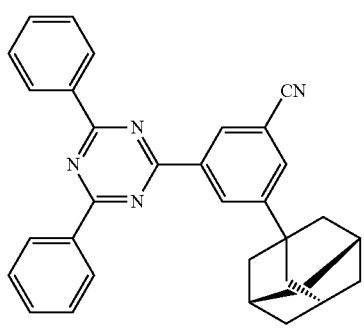
4
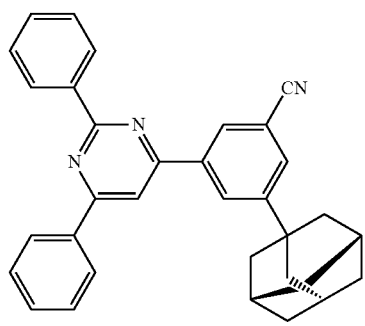
5
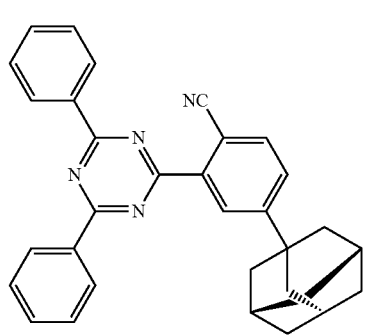
6
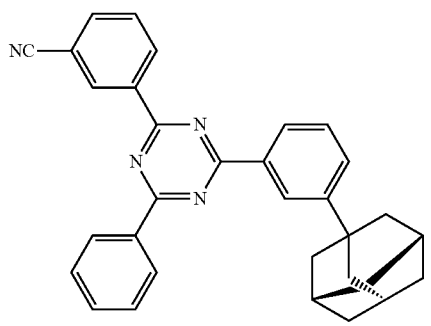
7
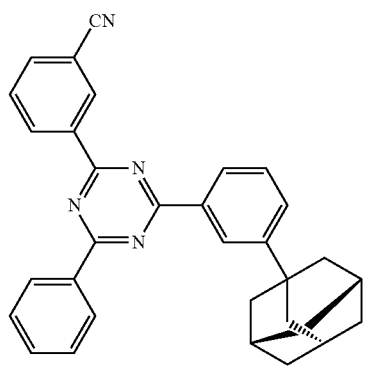

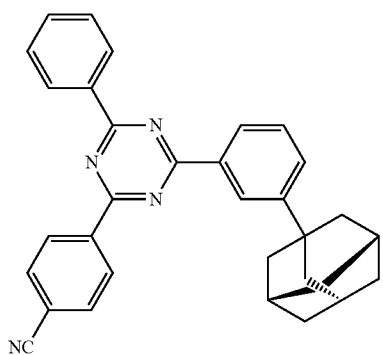
8
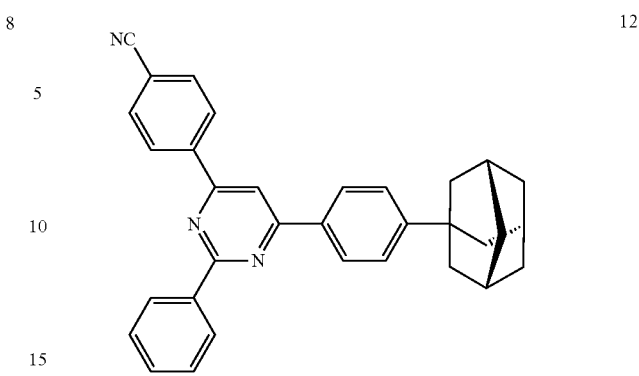
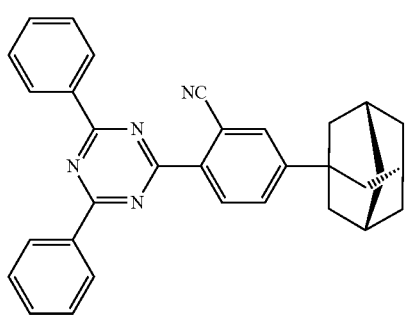
9
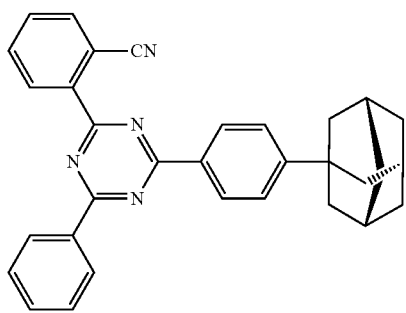
10
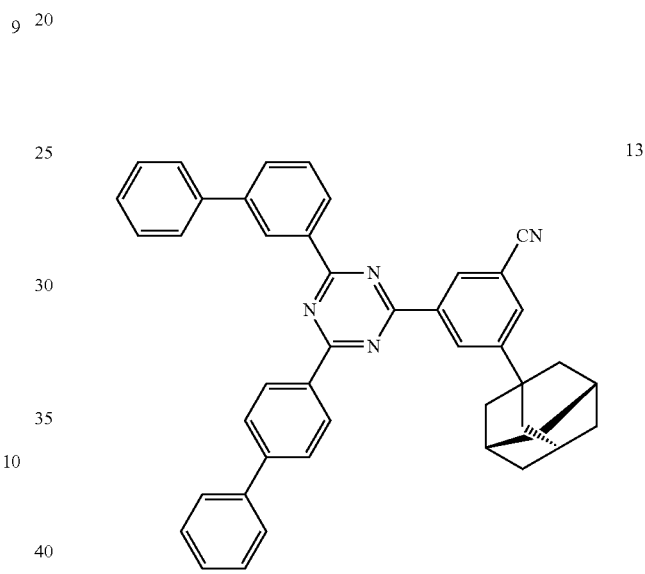
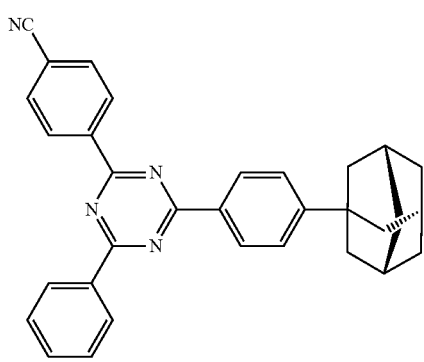
11
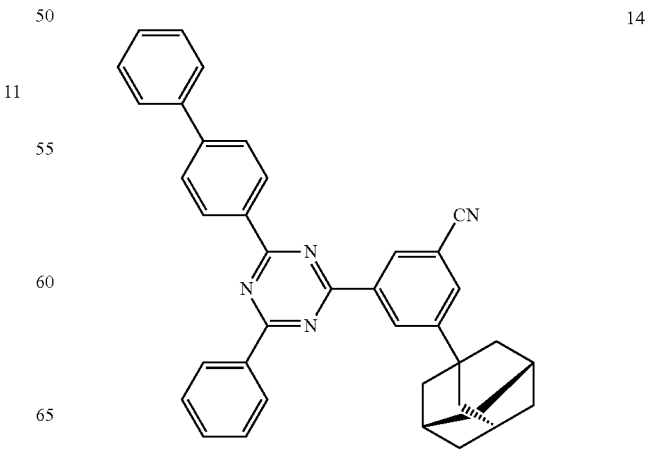

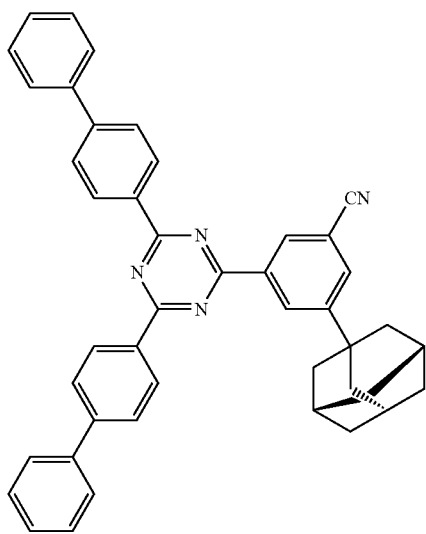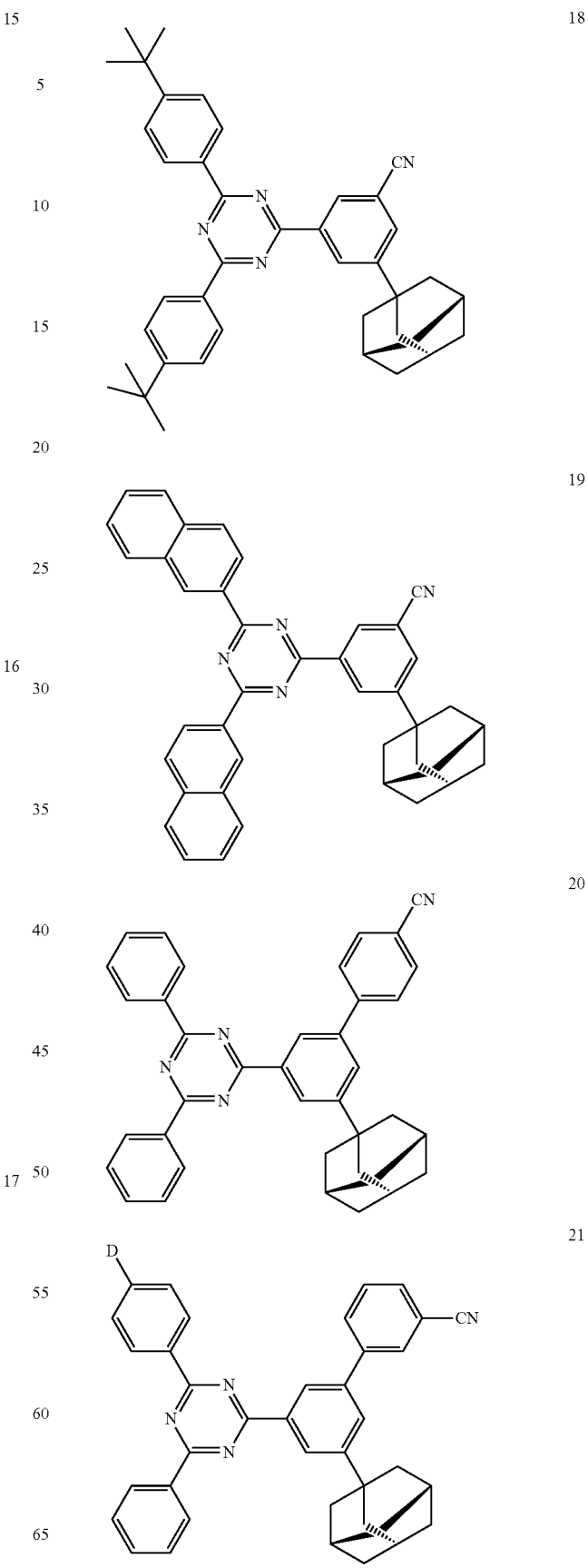

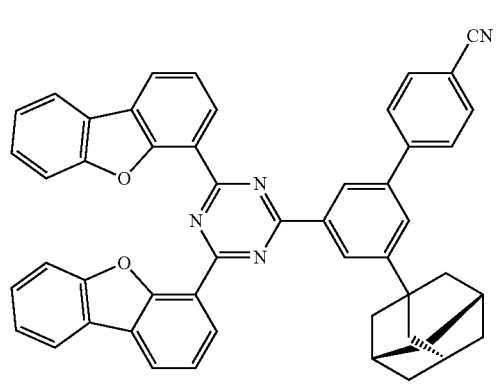
22
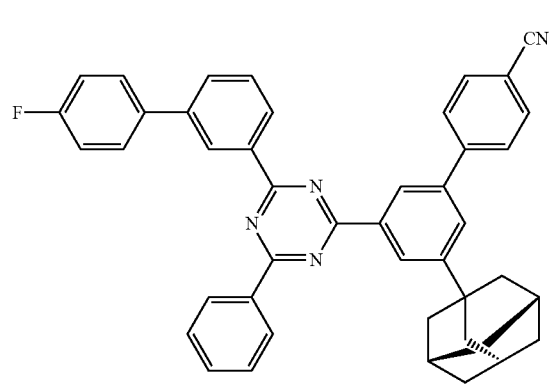
23
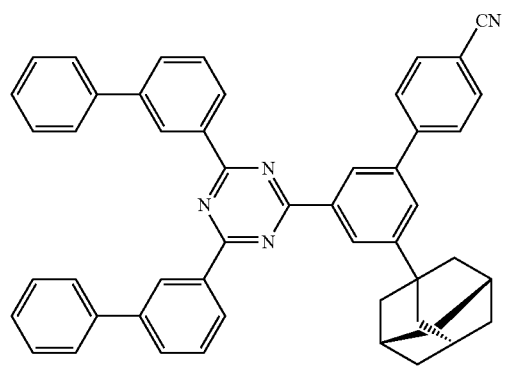
24
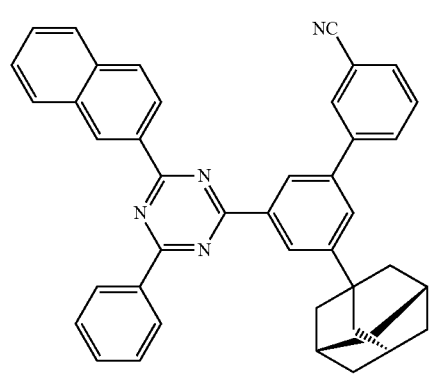
25
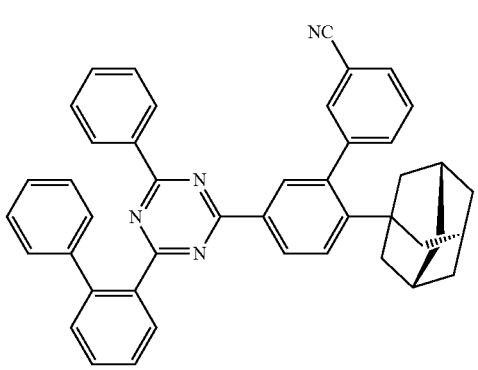
26
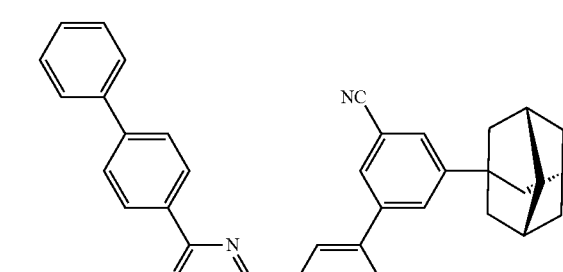
27
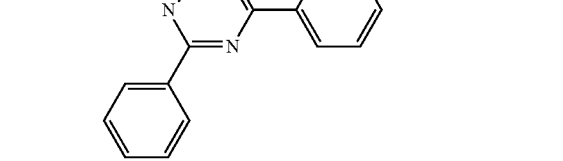
28
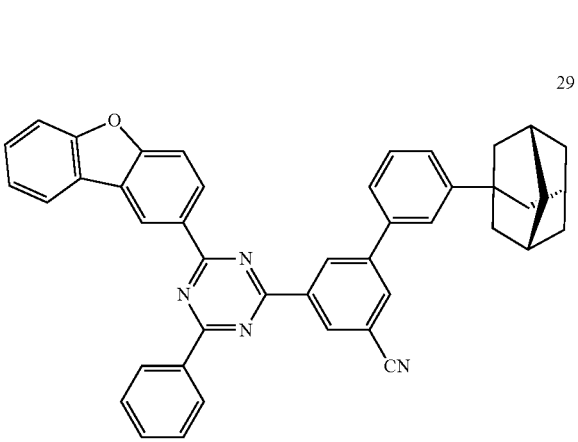
29

30
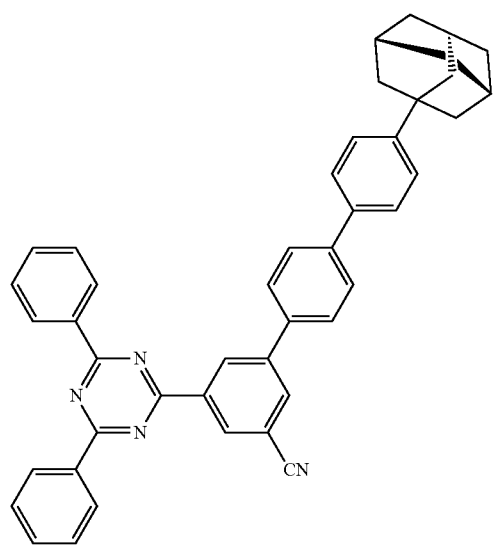
31
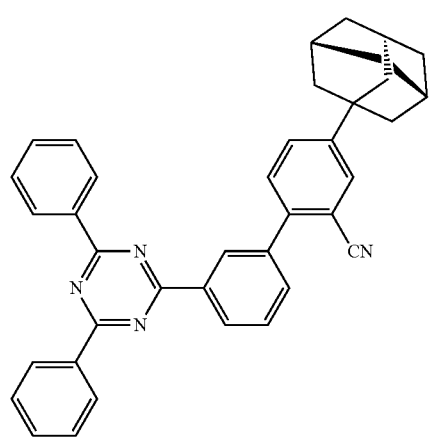
32
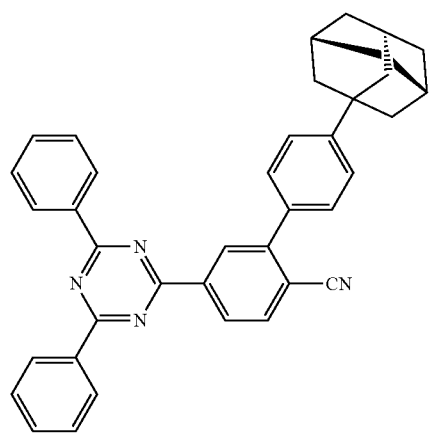
33
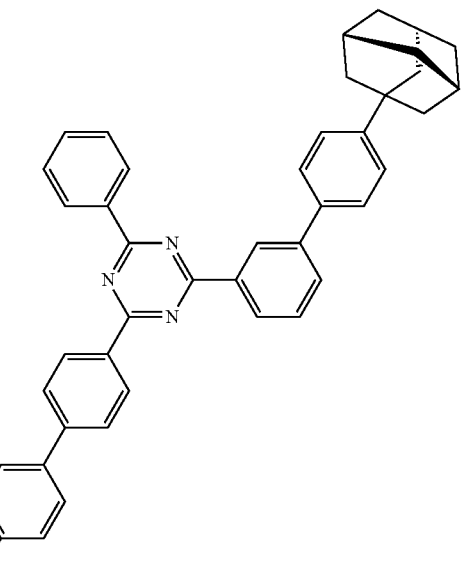
34
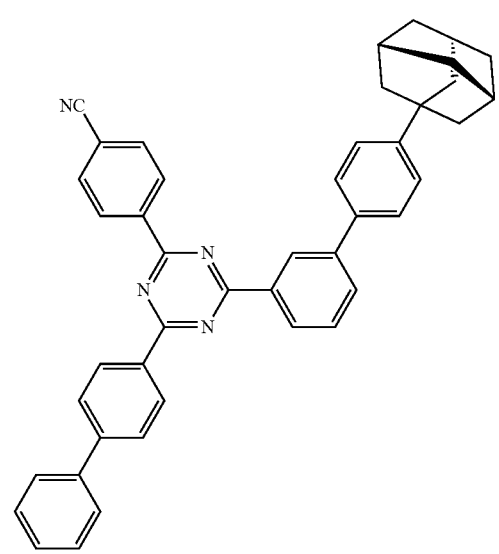

35
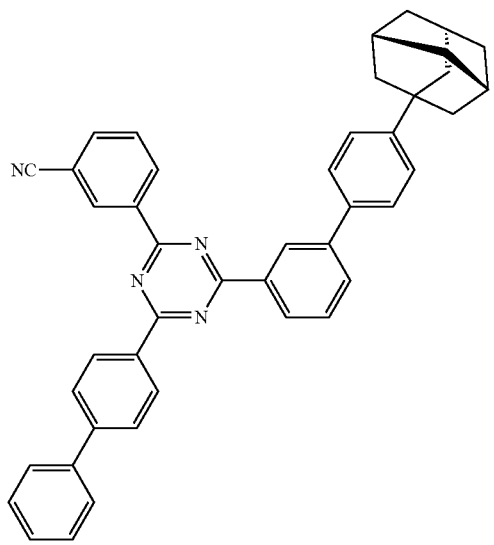
36
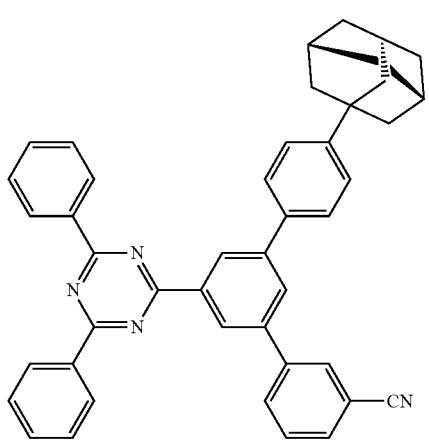
37
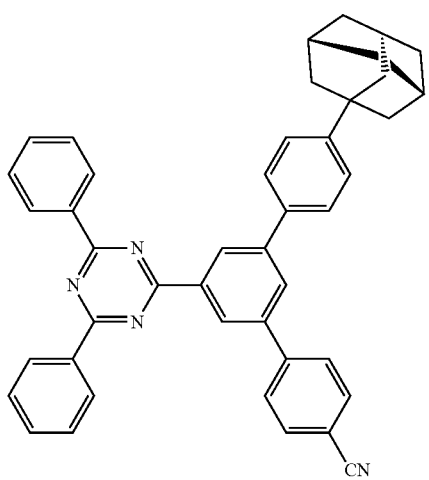
38
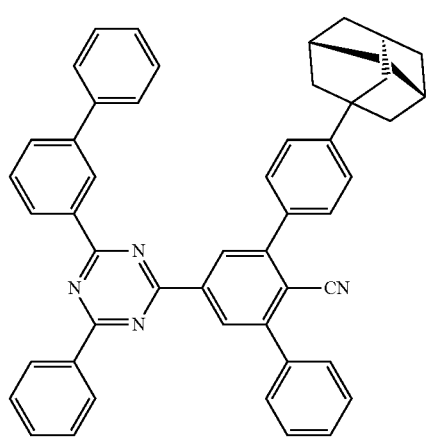
39
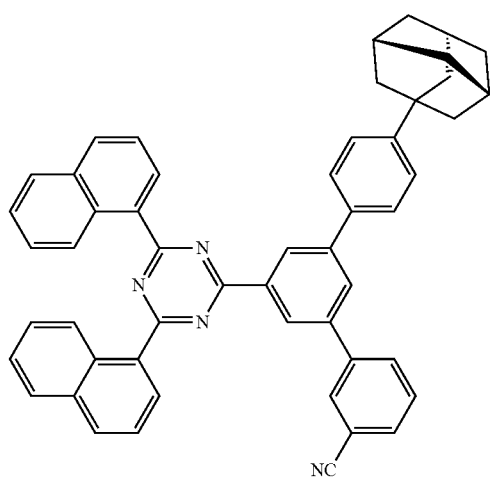
40
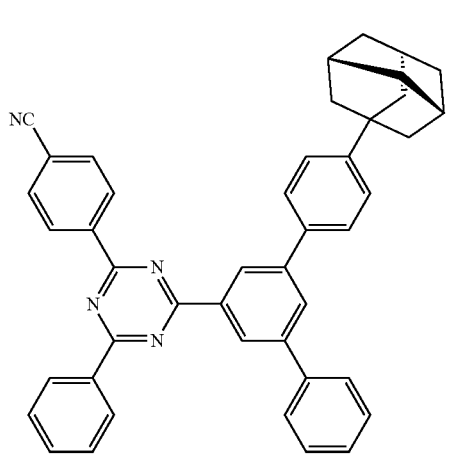

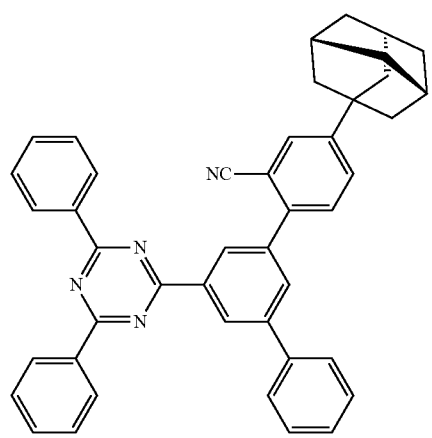
41
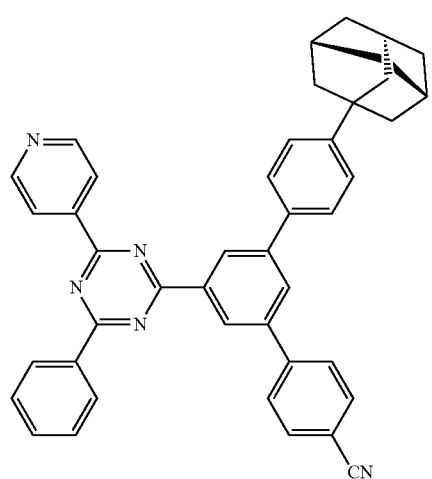
42
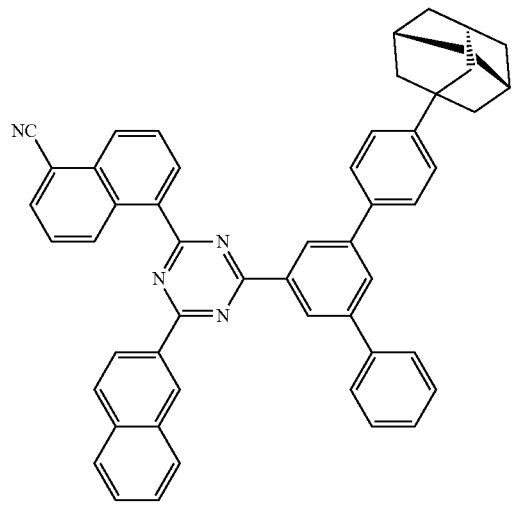
43
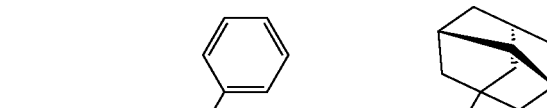
44
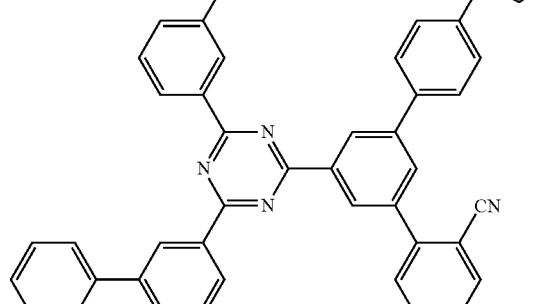
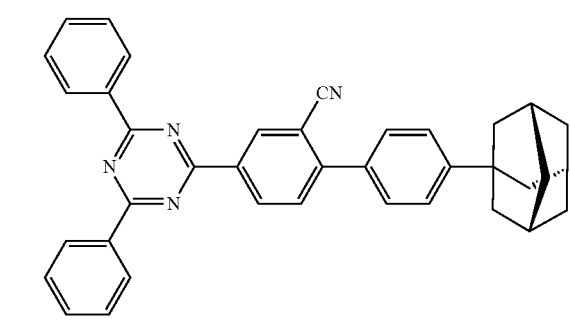
45
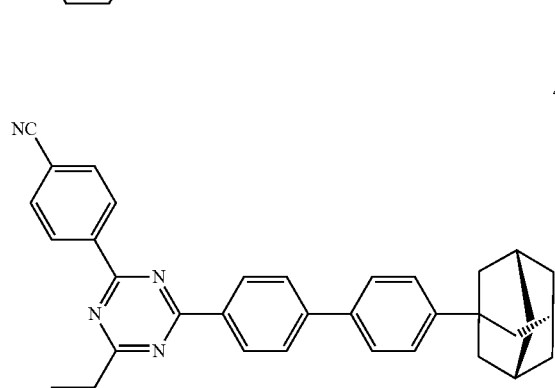
46
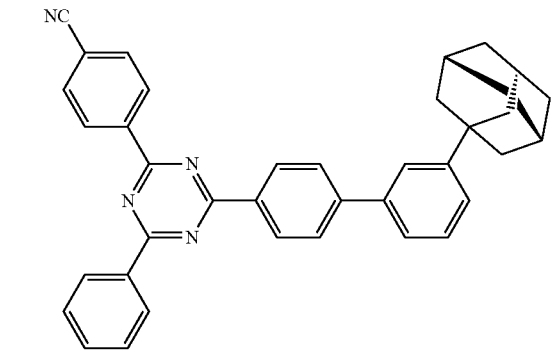
47

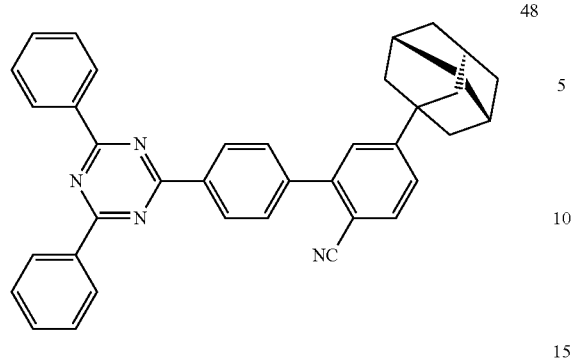
48
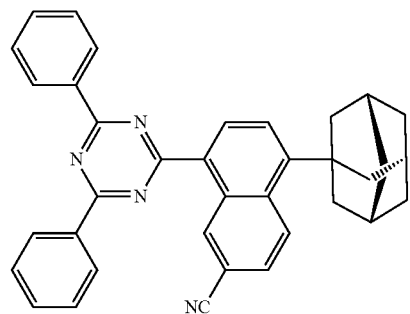
52
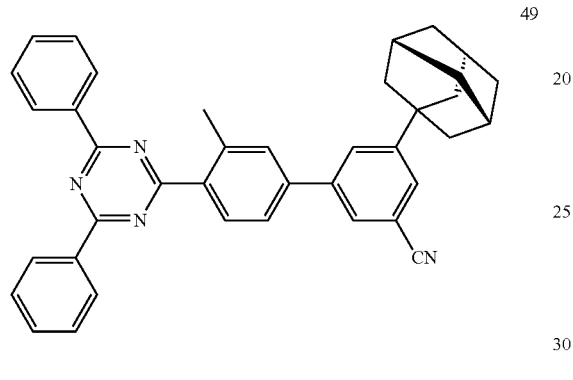
49
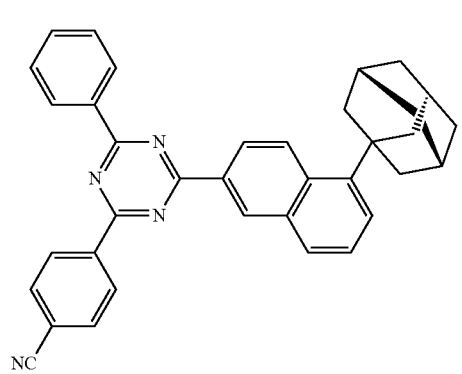
53
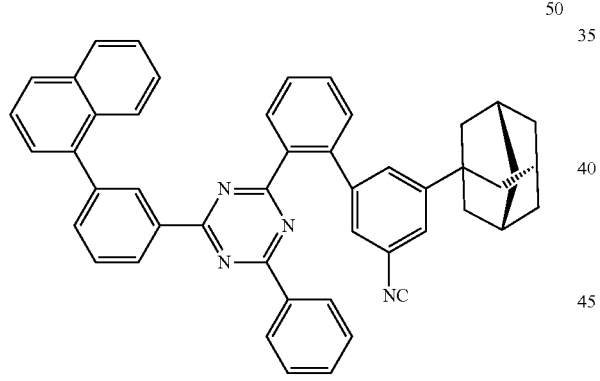
50
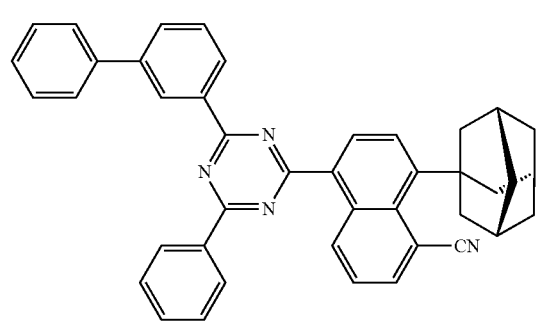
54
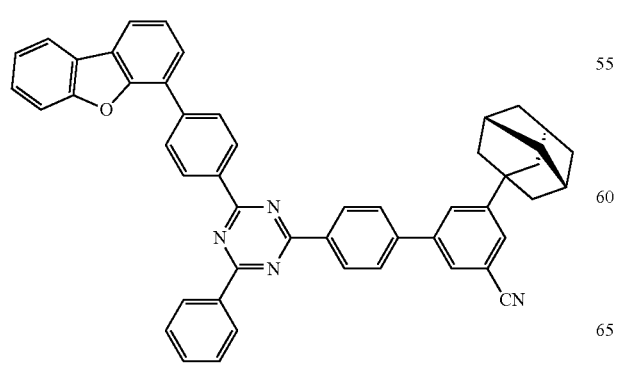
51
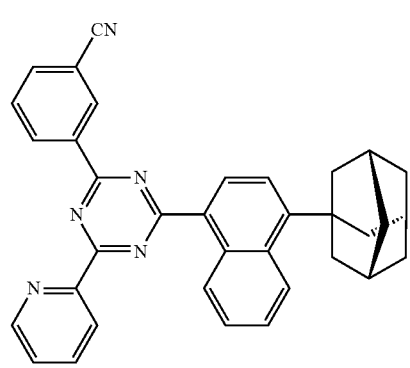
55

-continued
56
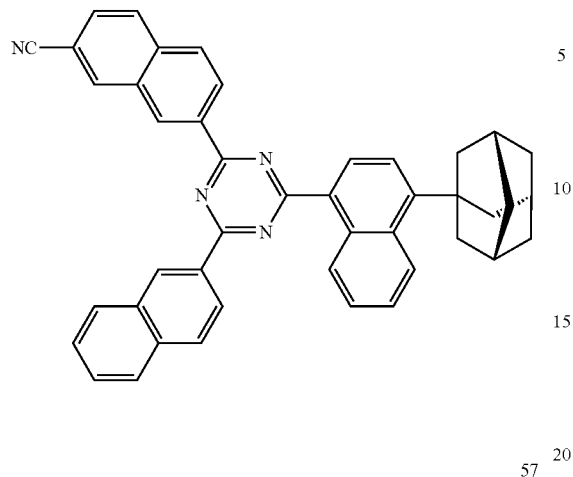
57
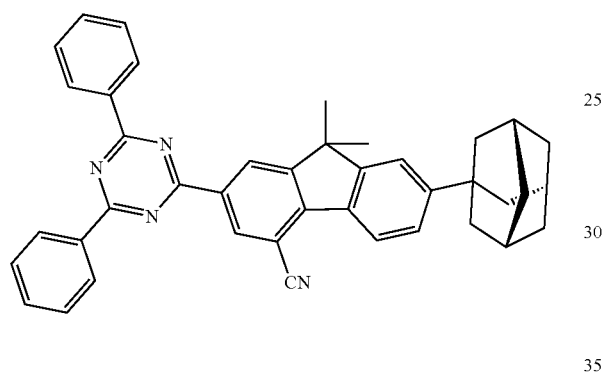
58
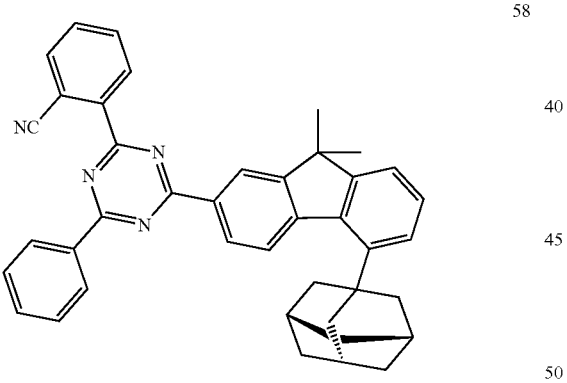
59
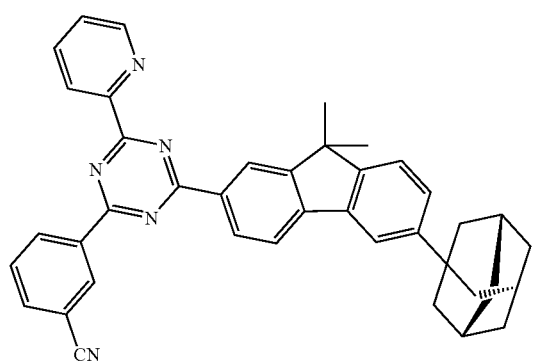
-continued
60
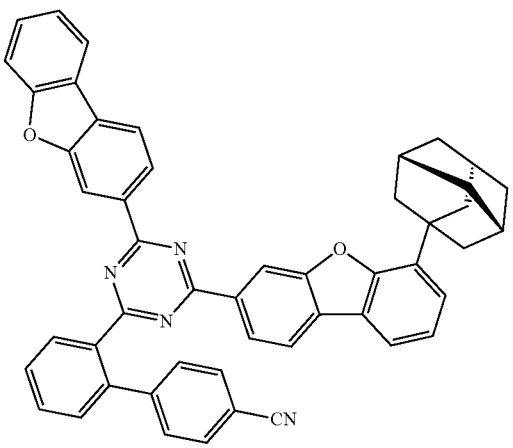
61
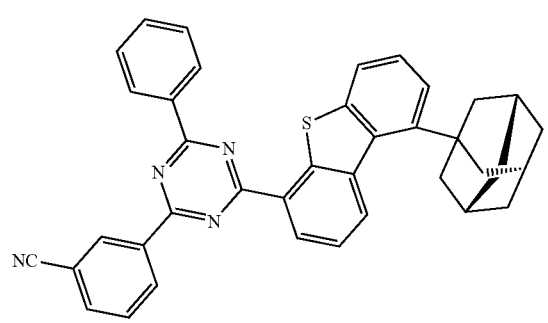
62
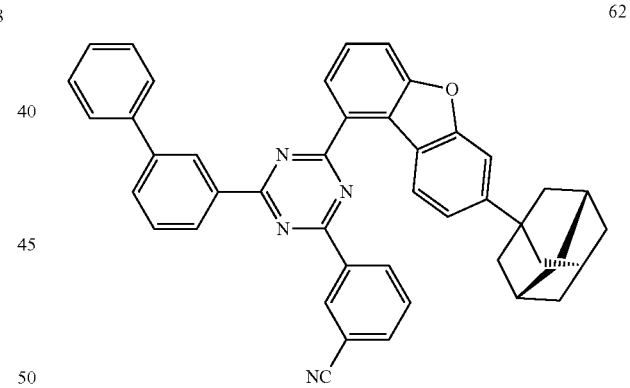
63
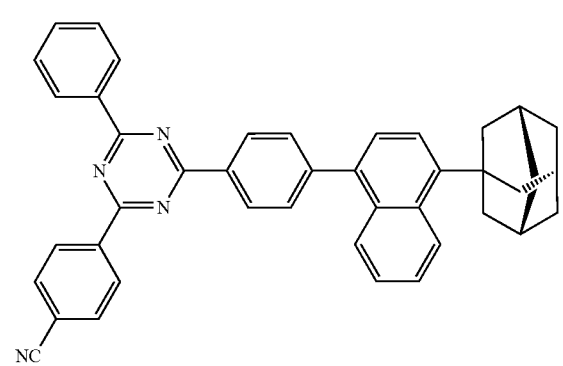

-continued
64
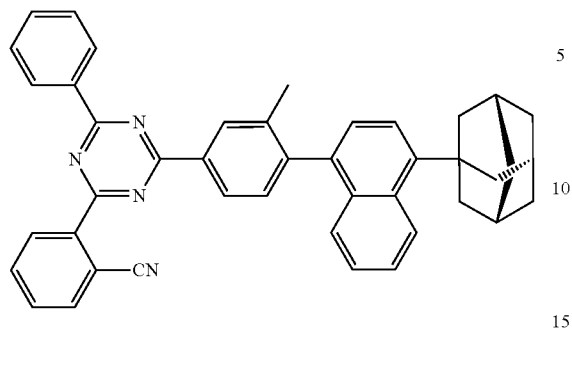
65
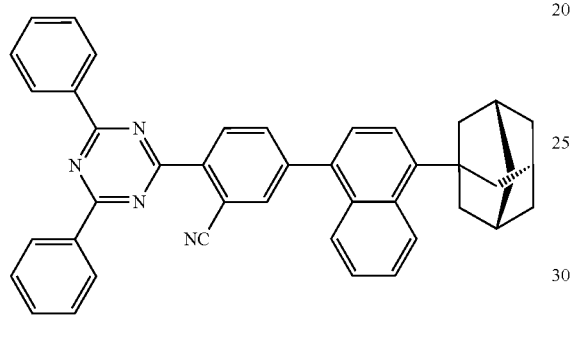
66
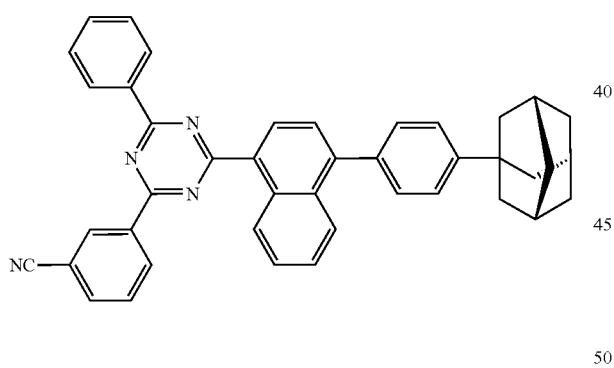
67
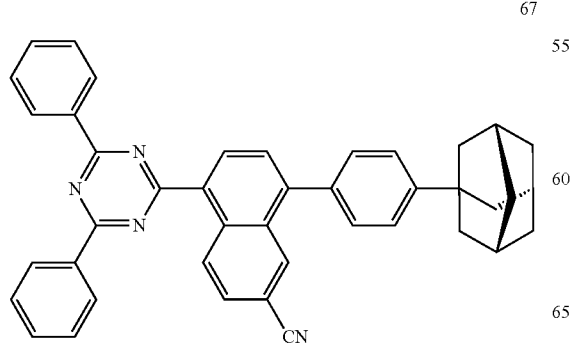
-continued
68
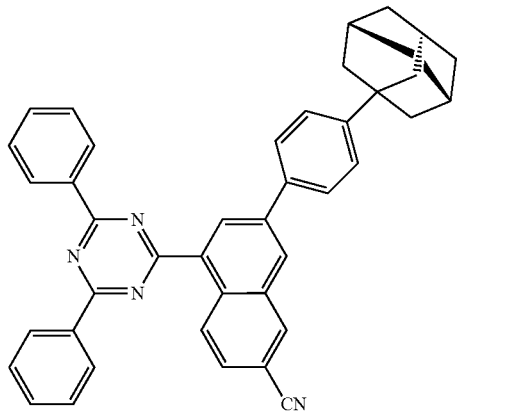
69
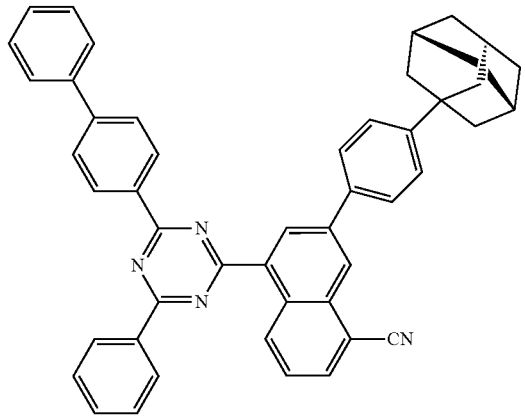
70
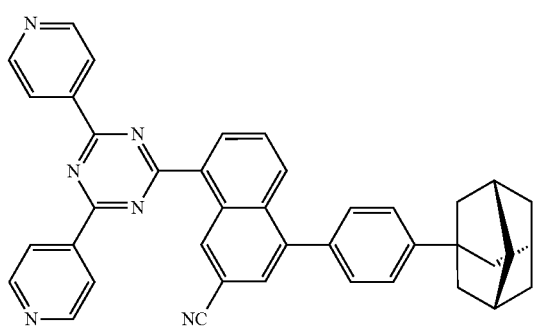
71
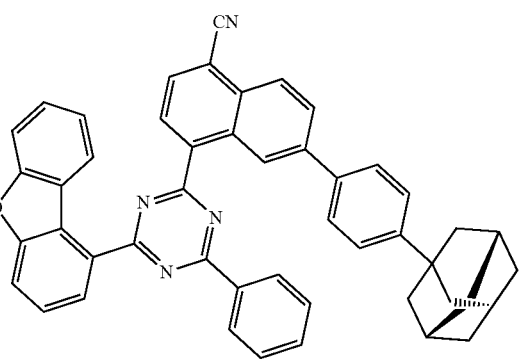

72
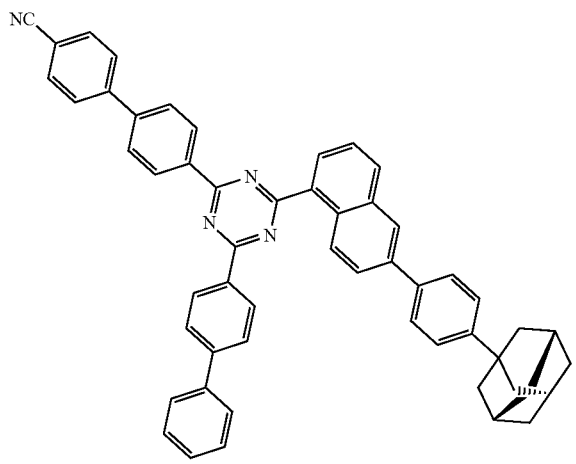
73
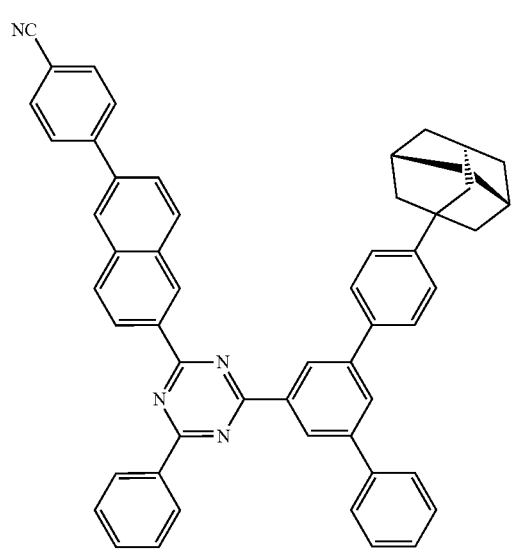
74
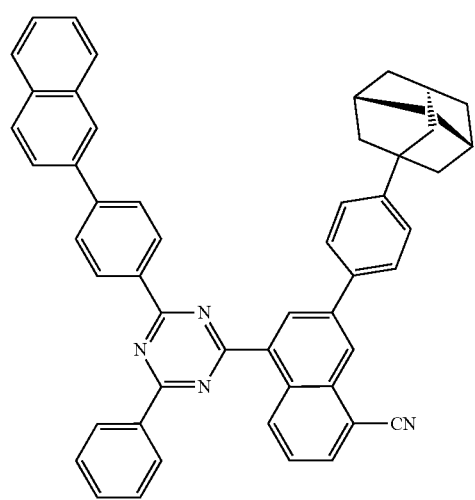
75
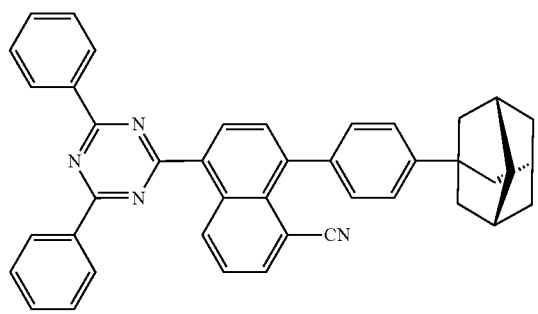
76
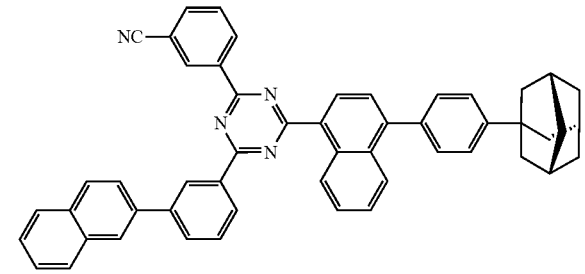
77
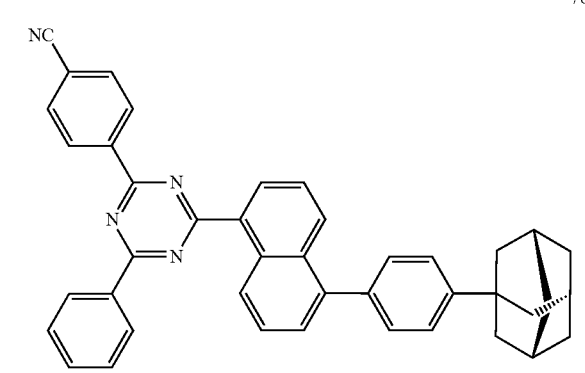
78
79
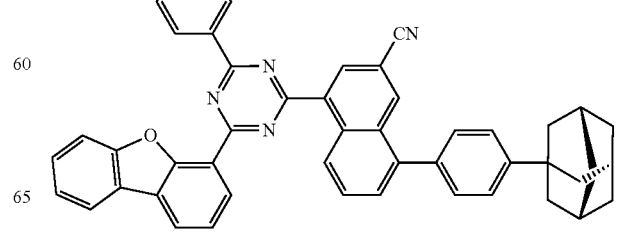

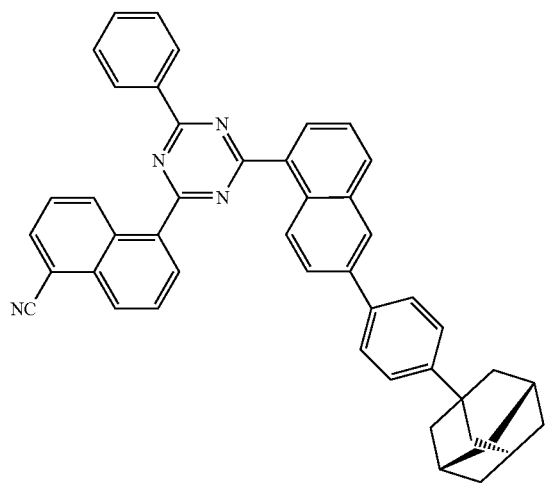
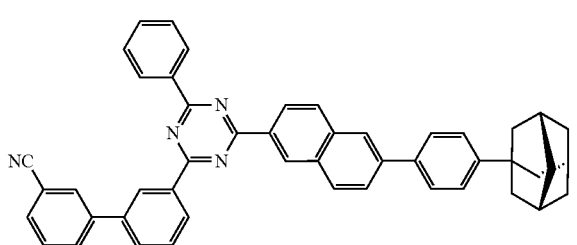
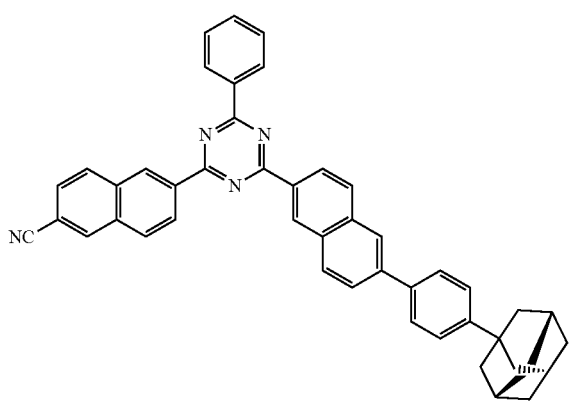
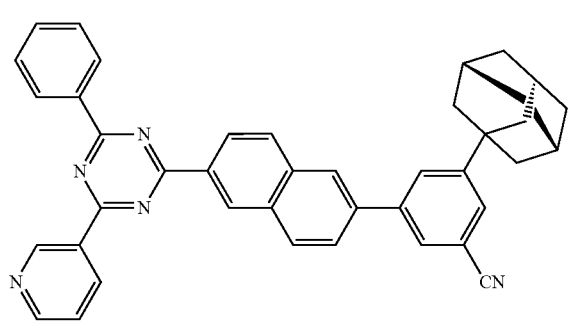
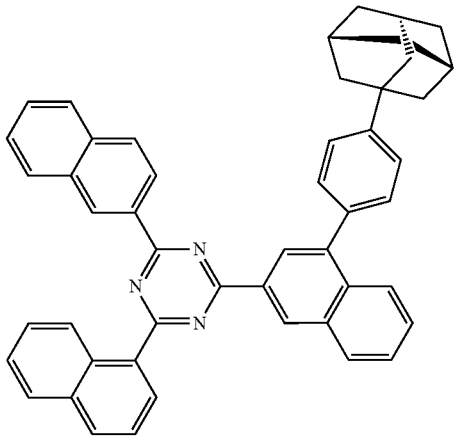
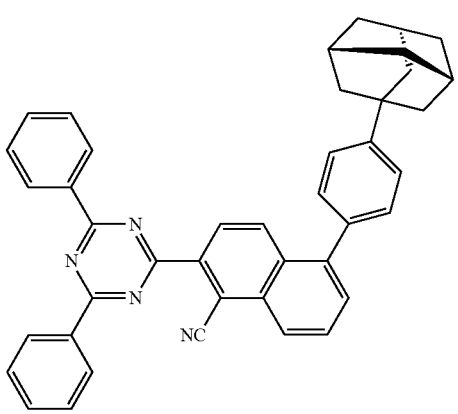
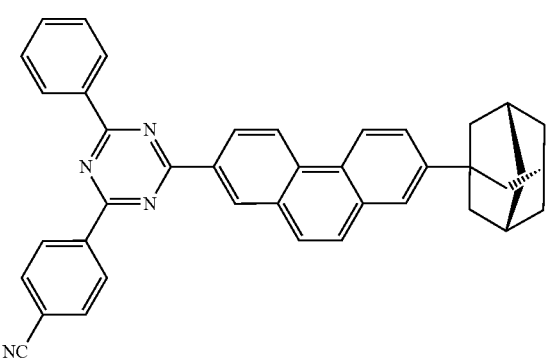
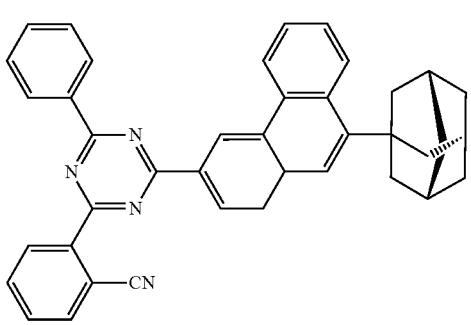

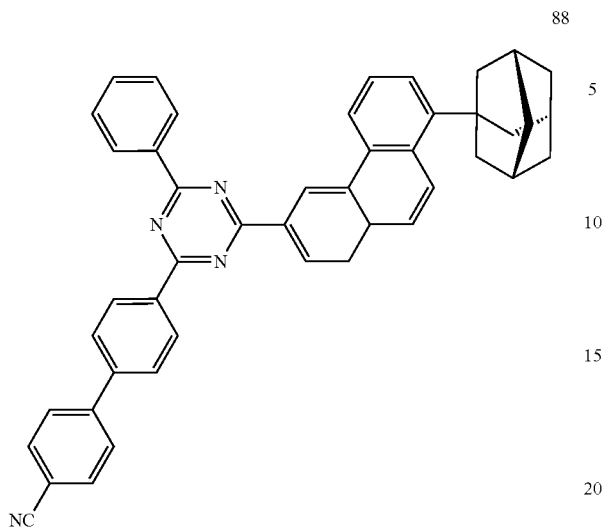
88
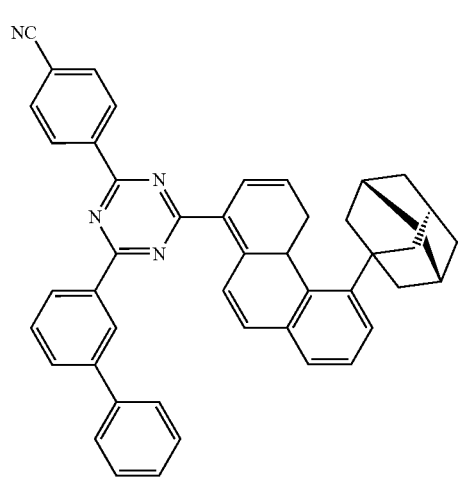
91
89
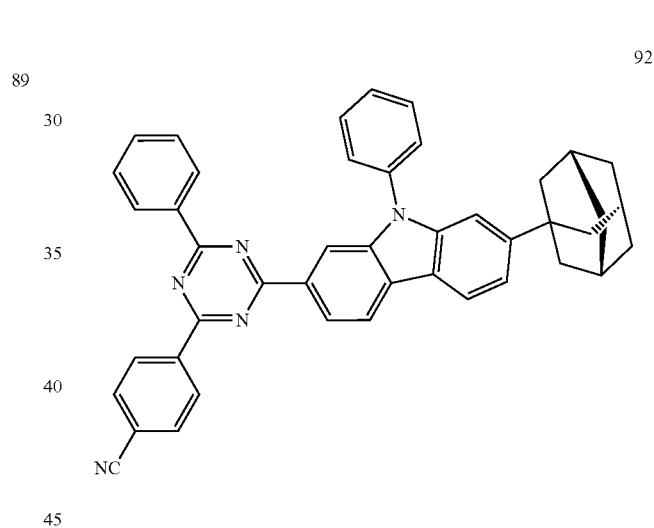
92
90
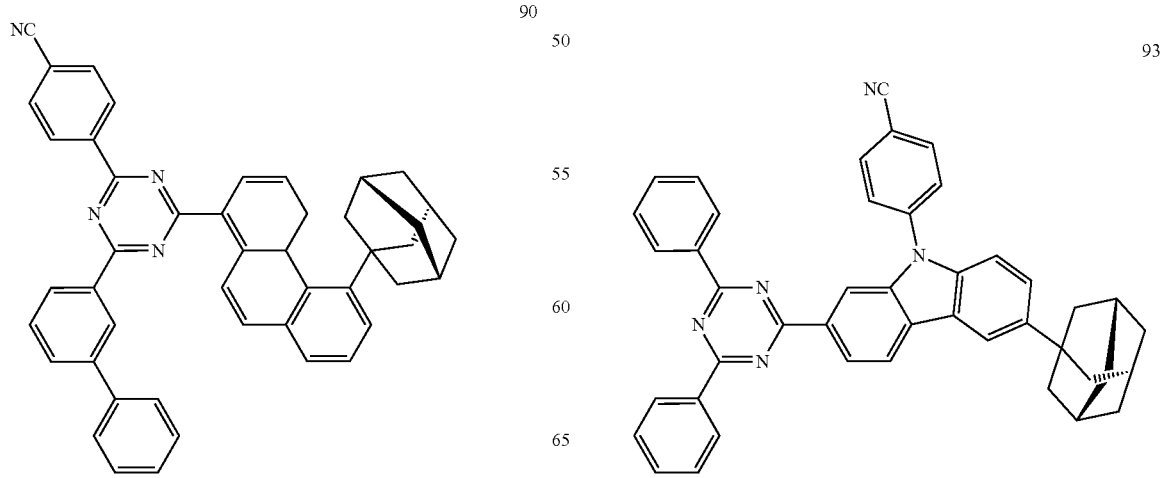
93

-continued
94
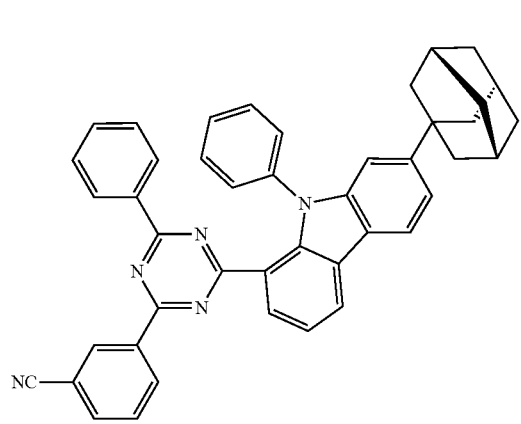
95
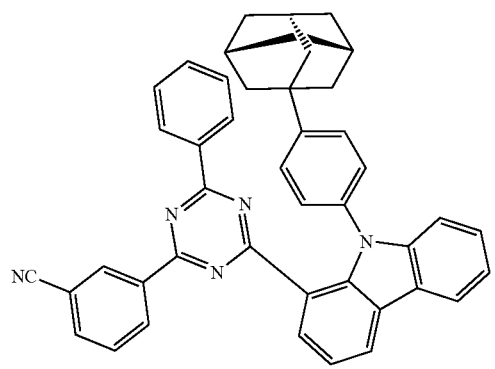
96
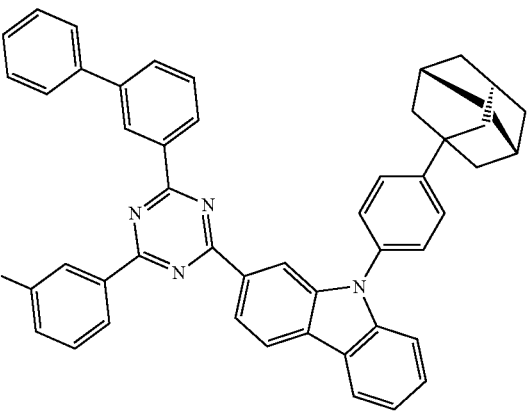
97
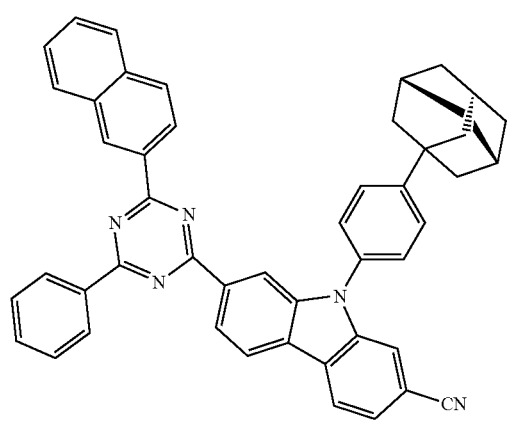
-continued
98
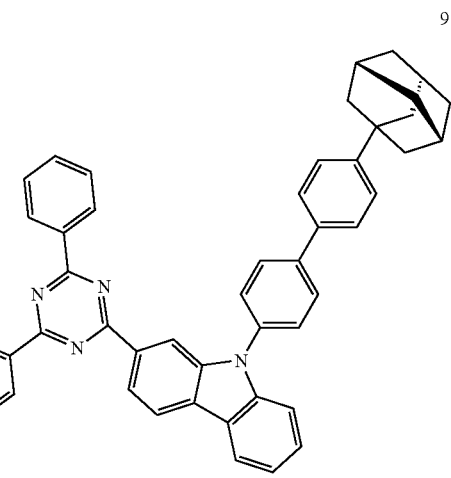
99
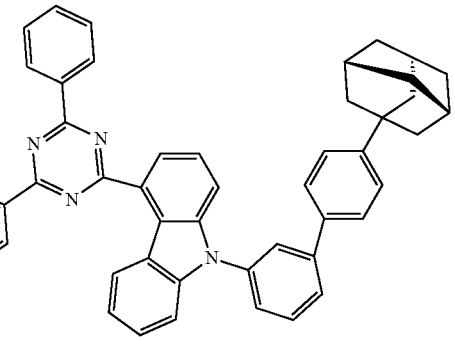
100

-continued
101
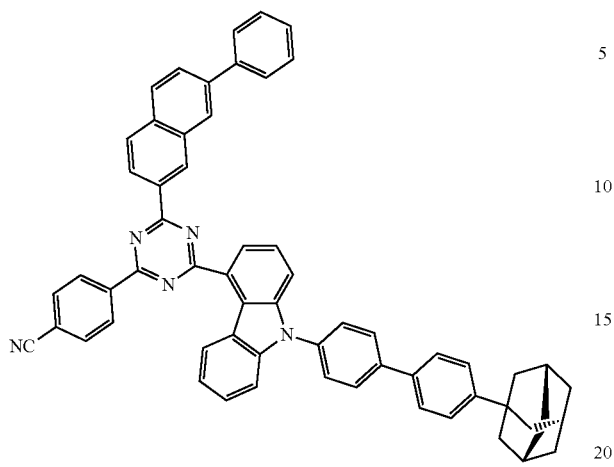
102
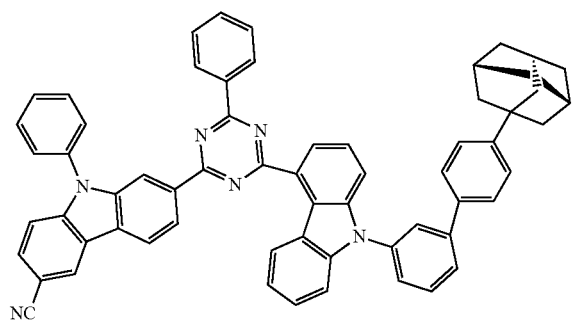
103
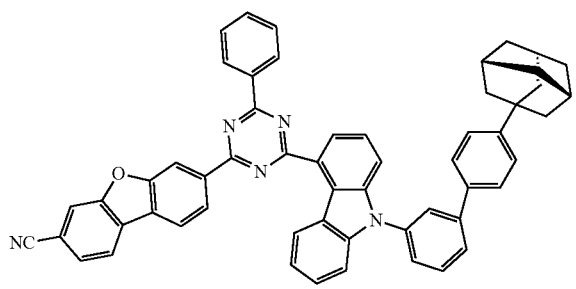
104
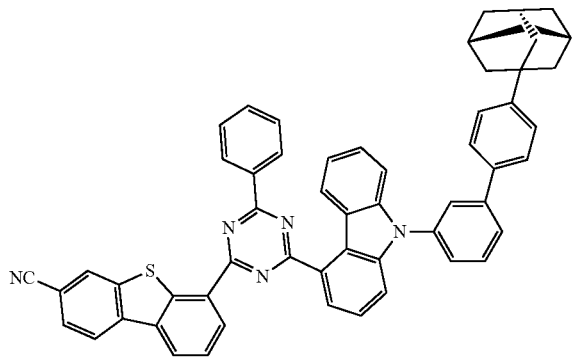
-continued
105
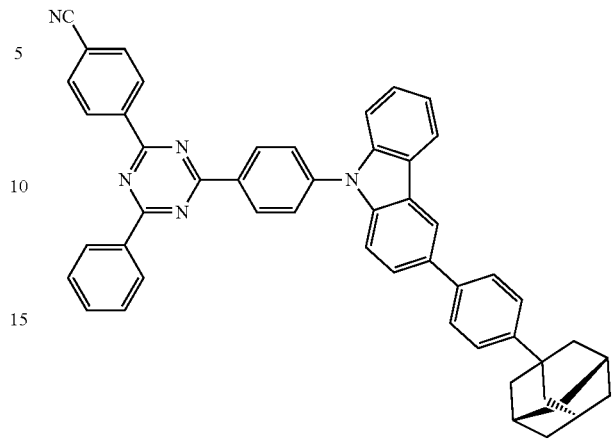
106
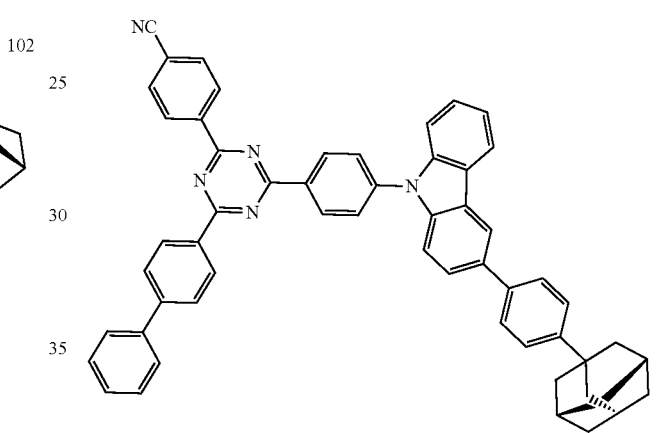
107
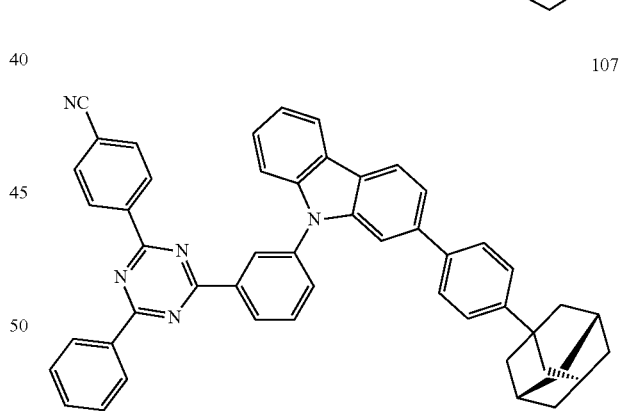
108
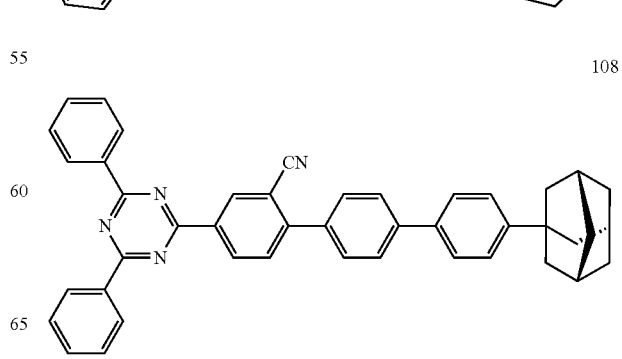

109 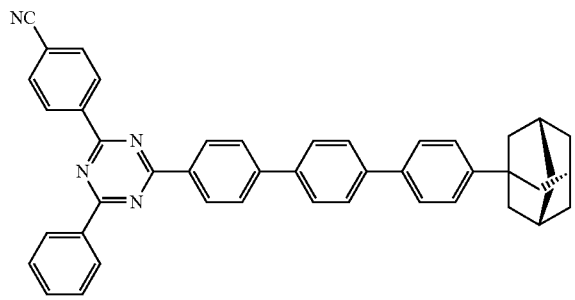
110 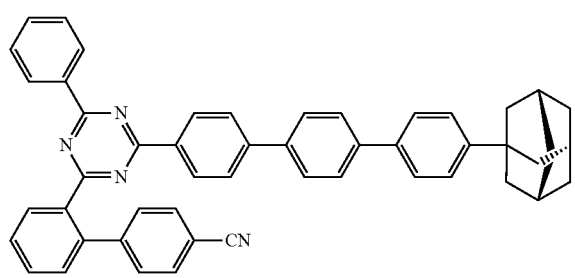
111 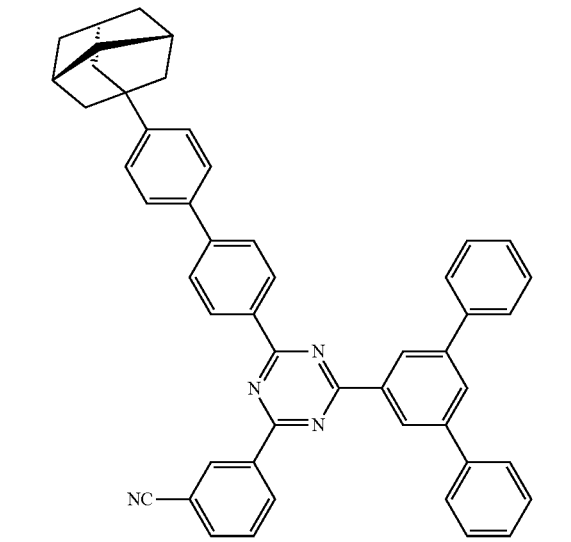
112 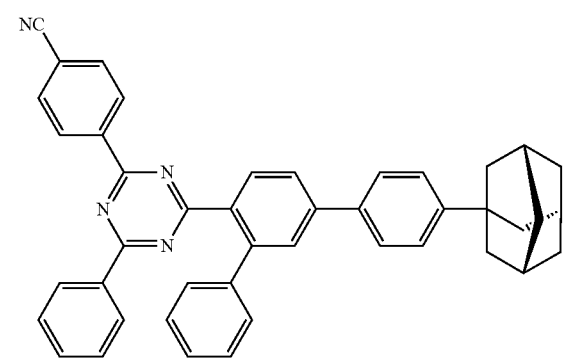
113 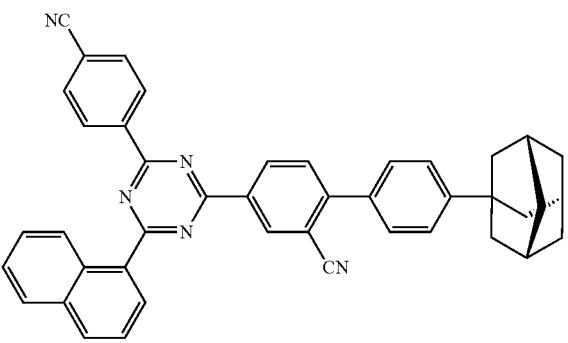
114 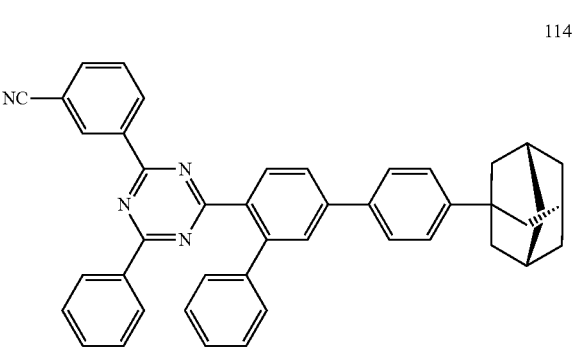
115 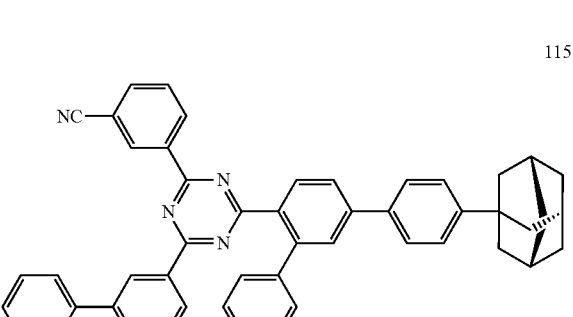
116 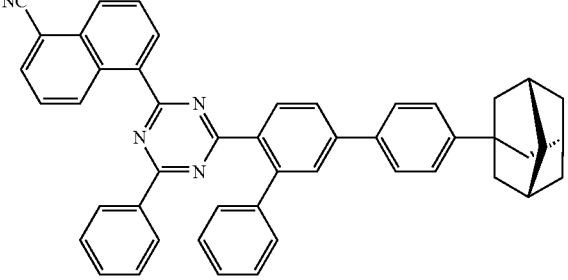
117 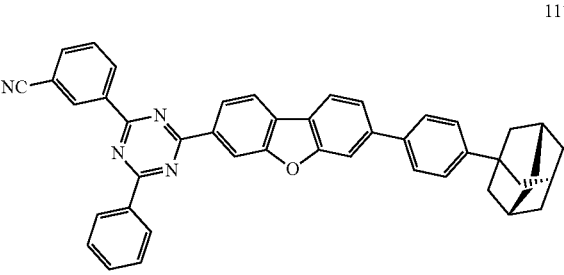

-continued
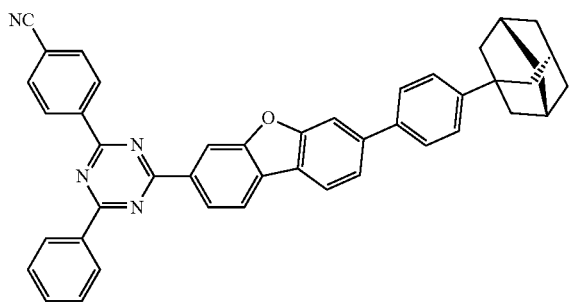
118
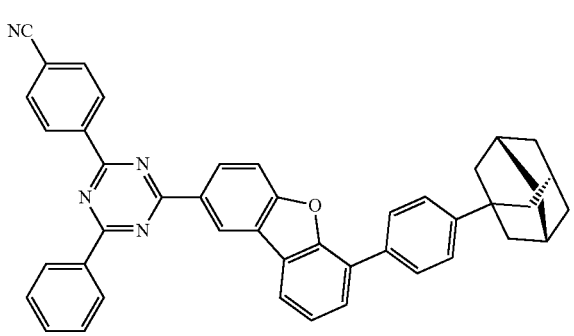
119
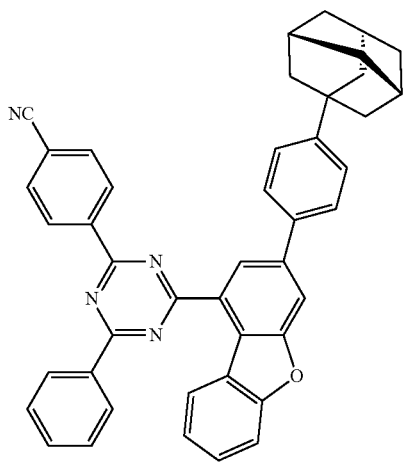
120
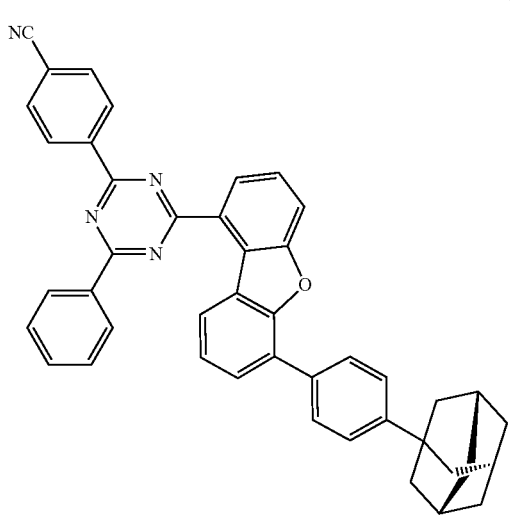
121
-continued
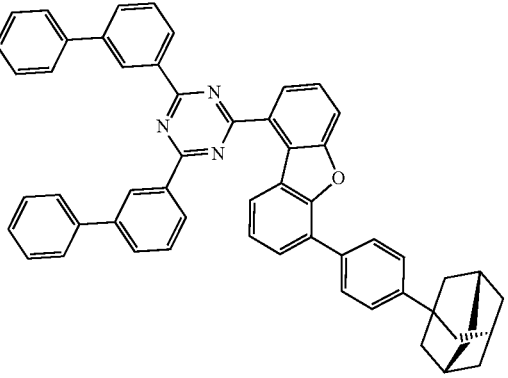
122
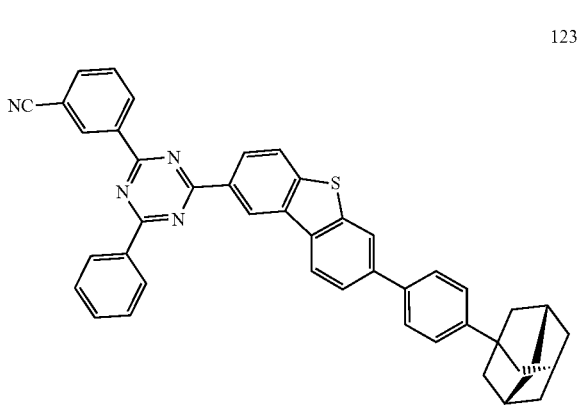
123
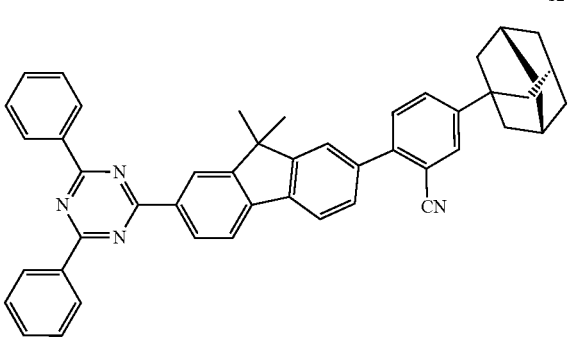
124
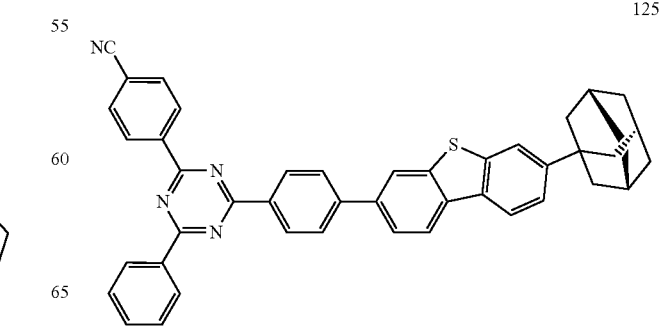
125

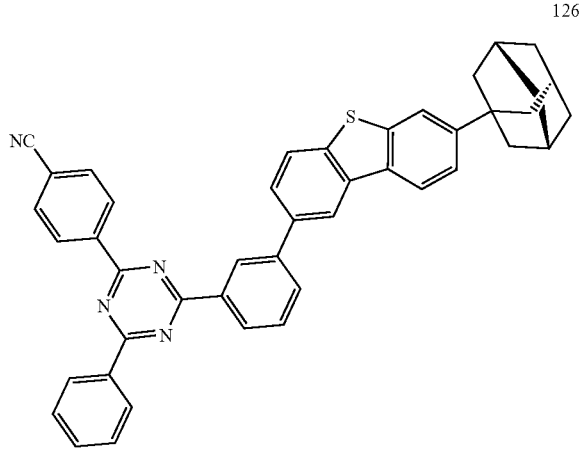
126
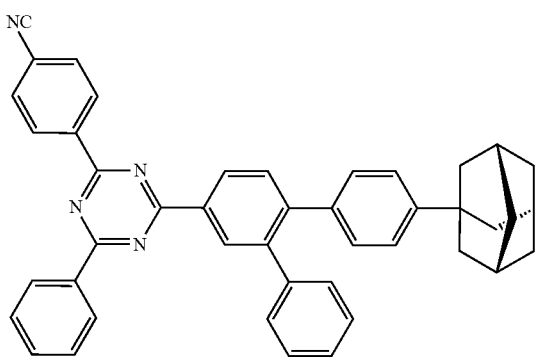
130
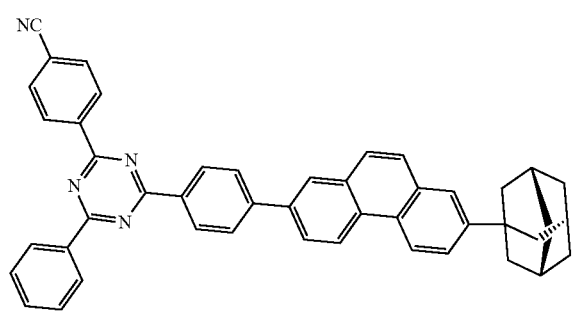
127
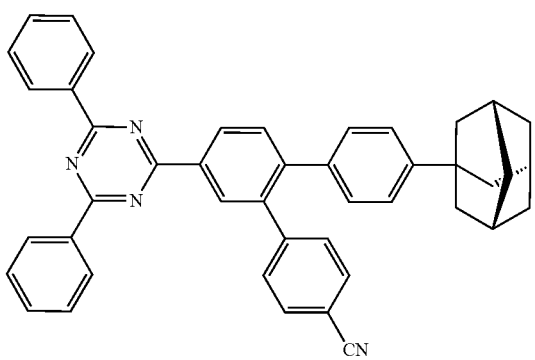
131
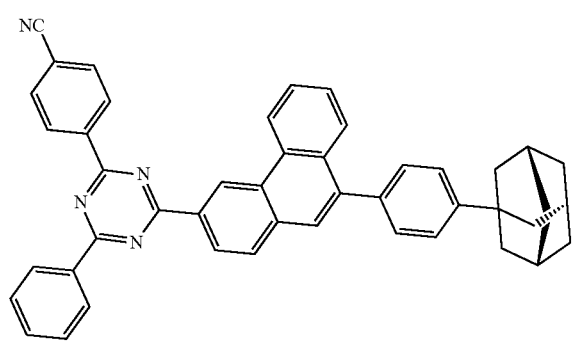
128
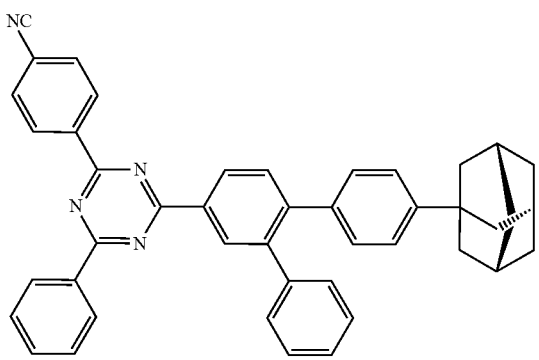
132
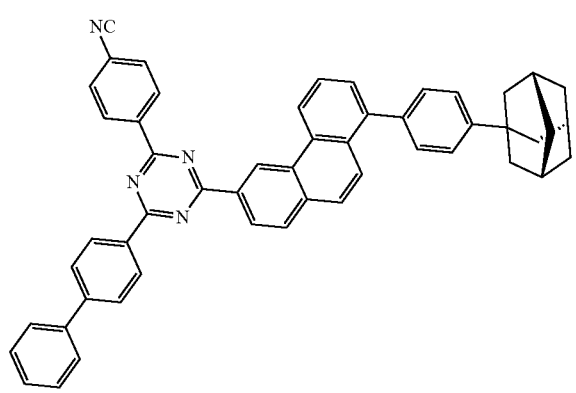
129
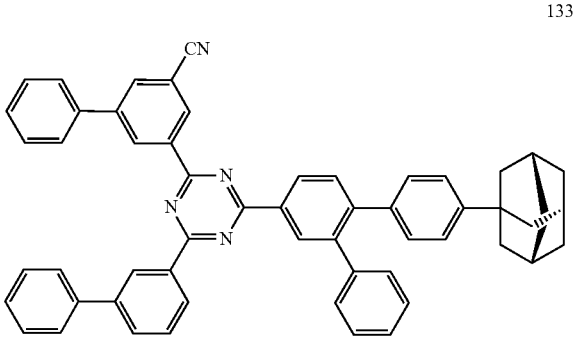
133

134
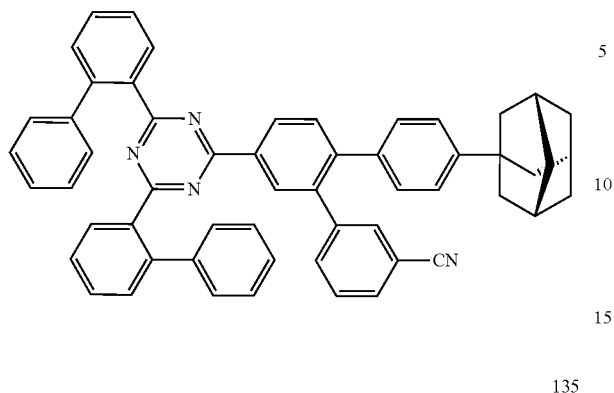
135
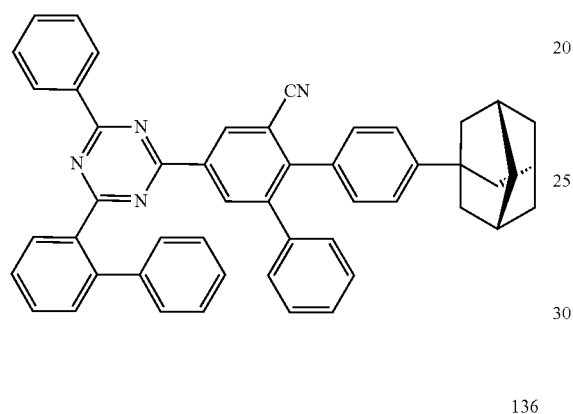
136
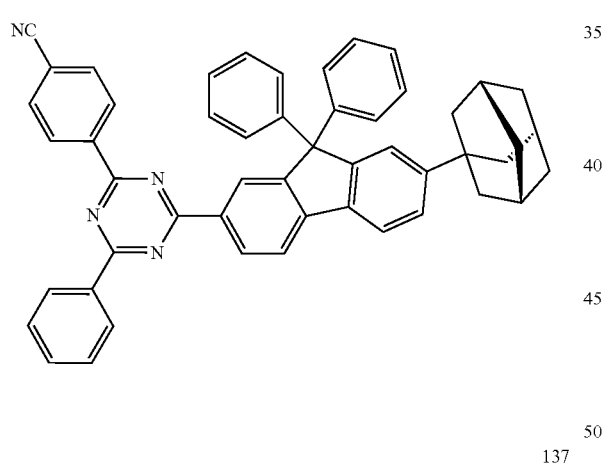
137
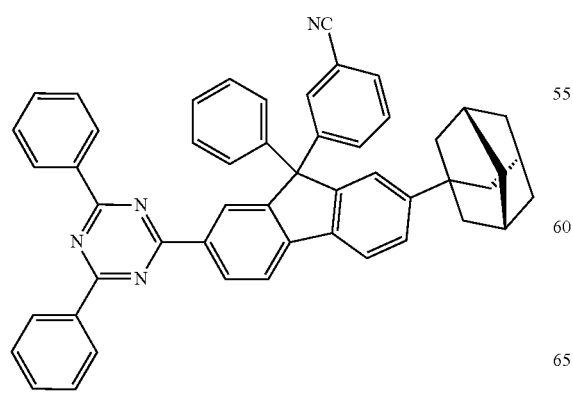
138
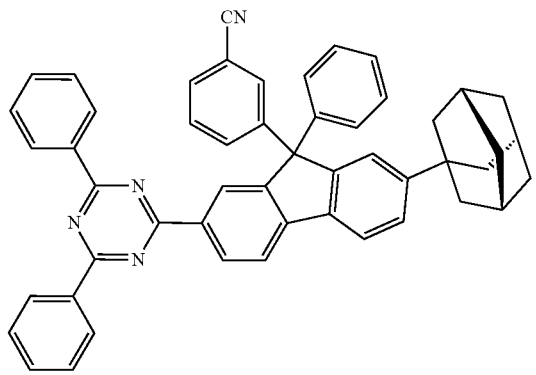
139
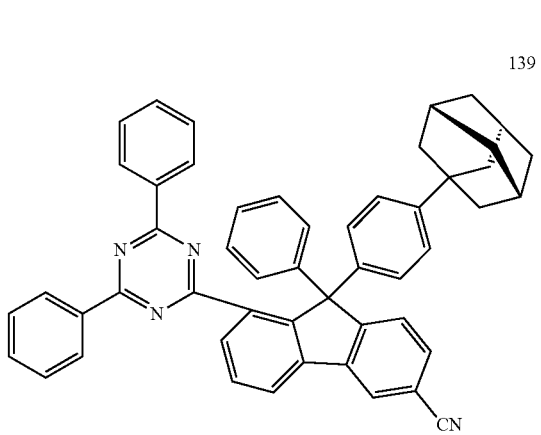
140
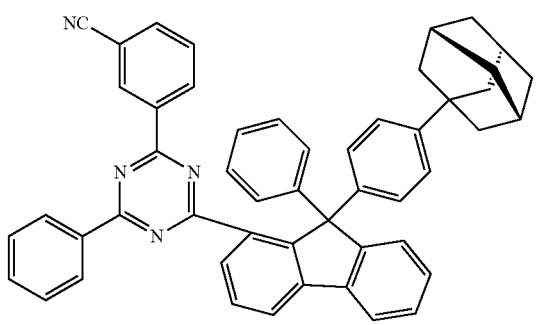
141
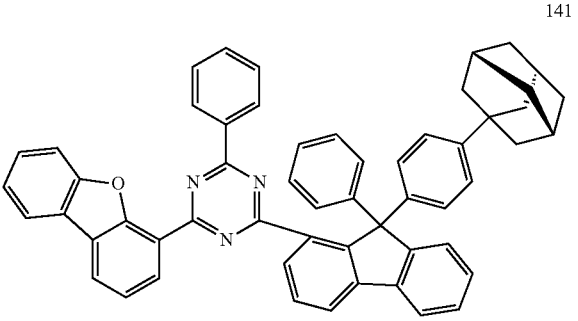

-continued
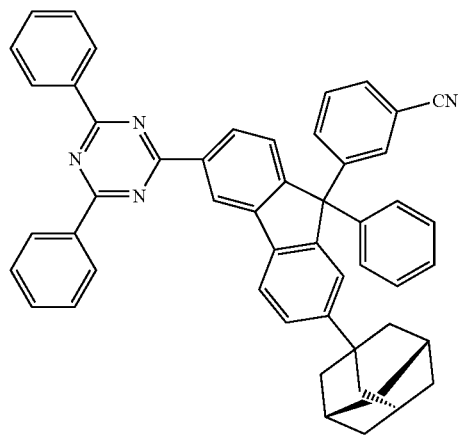
142
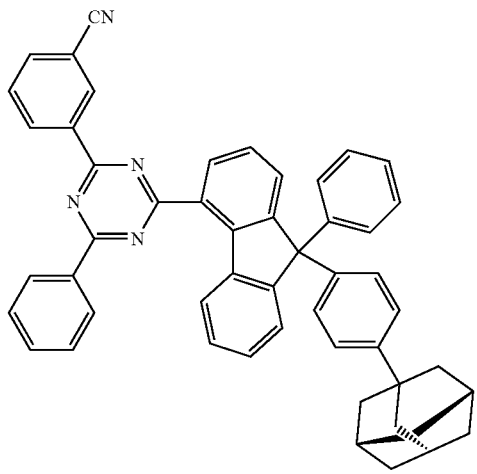
145
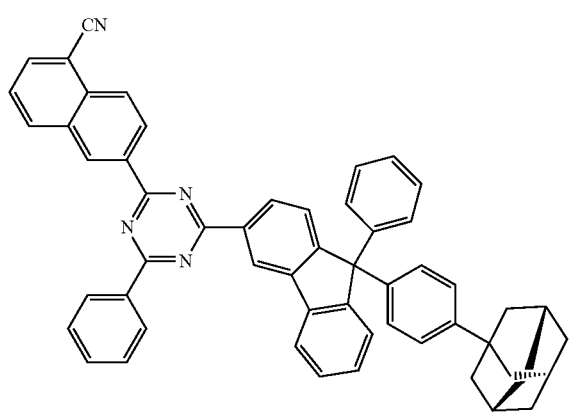
143
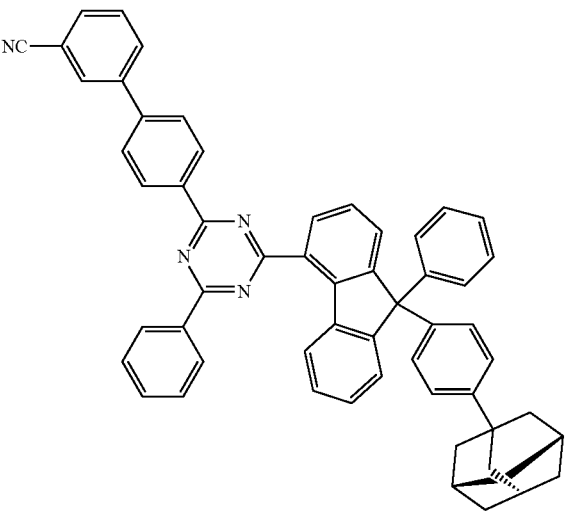
146
144
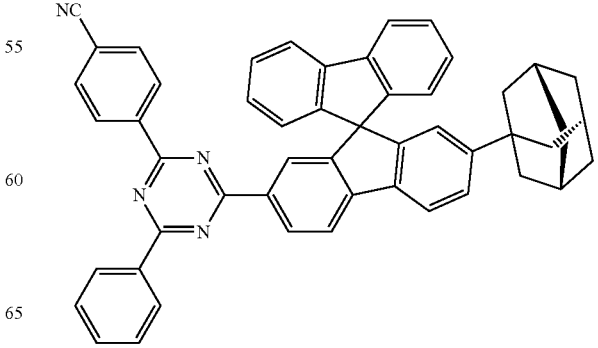
147

148
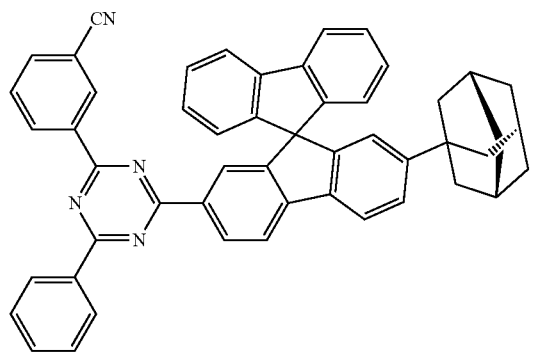
152
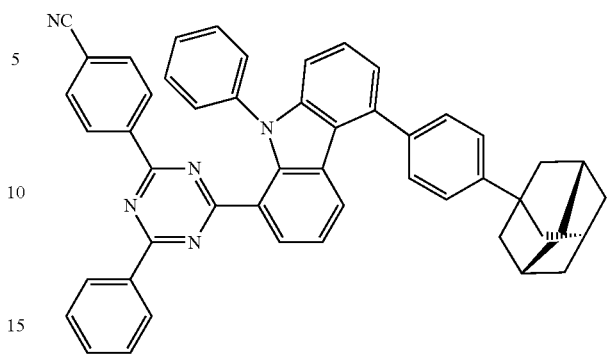
149
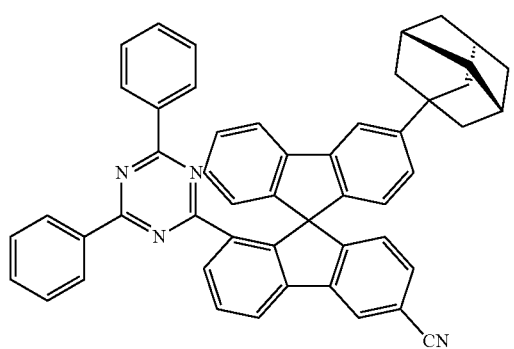
153
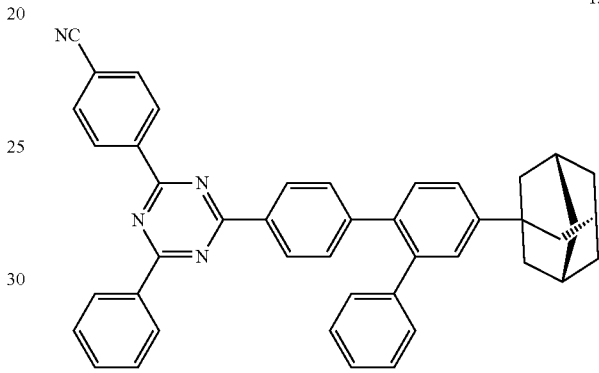
150
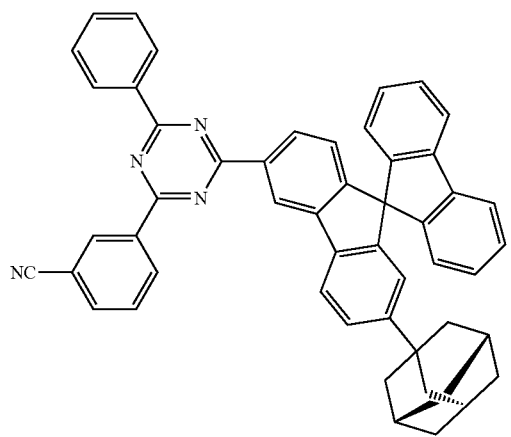
154
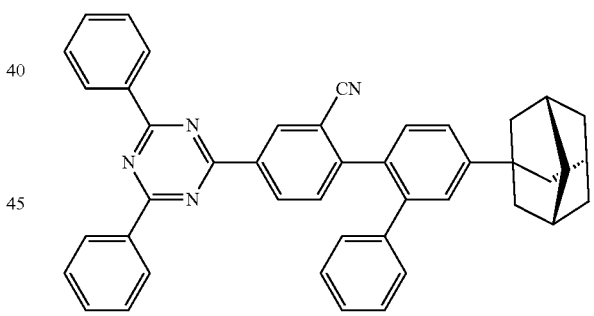
151
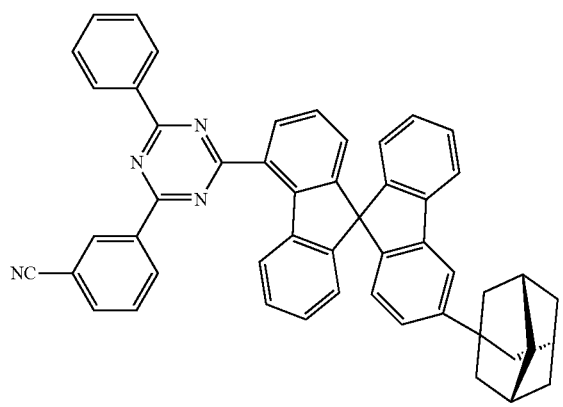
155
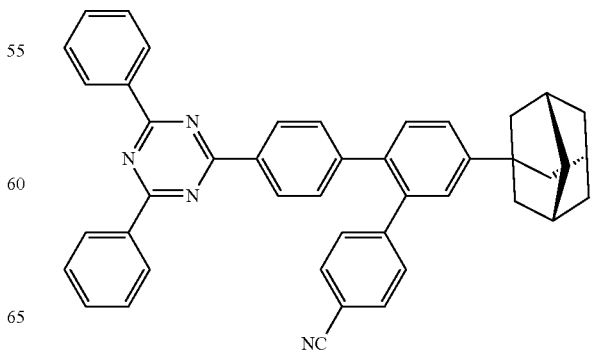

156
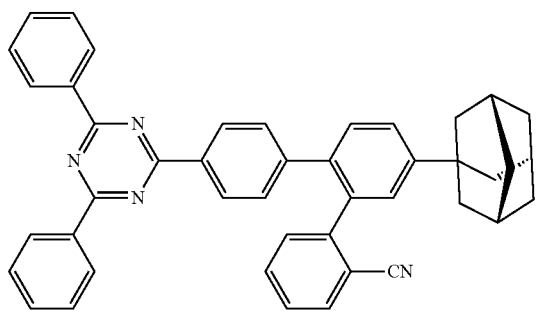
157
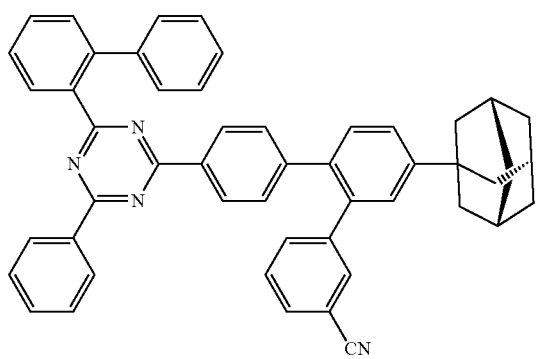
158
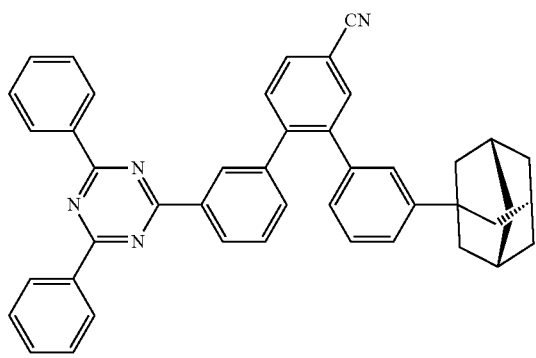
159
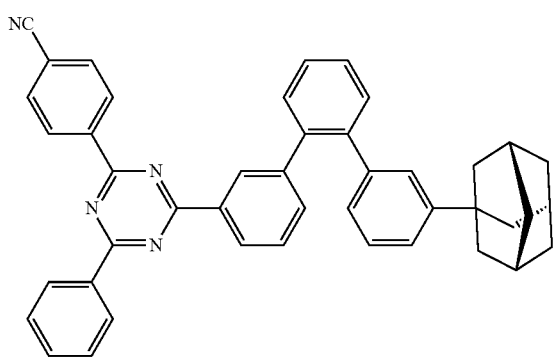
160
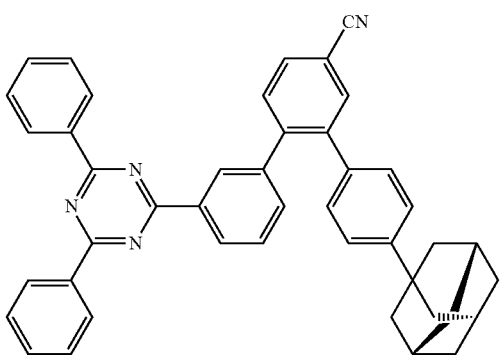
161
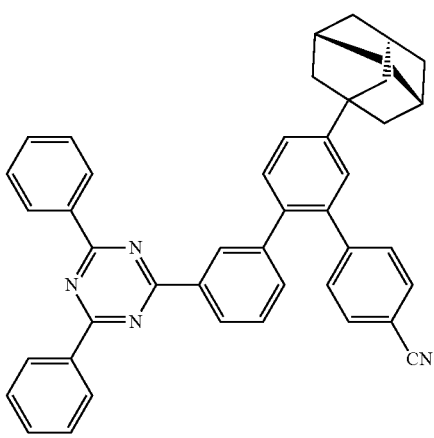
162
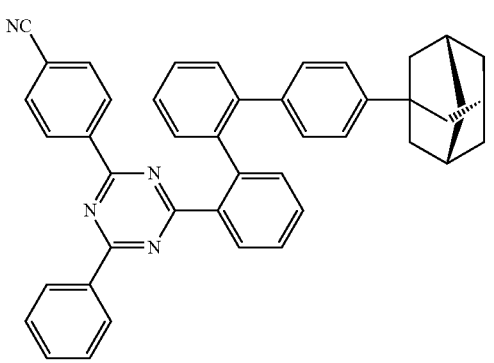
163
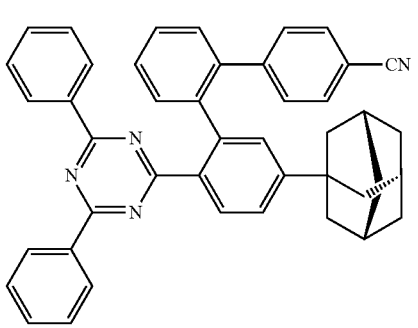

164
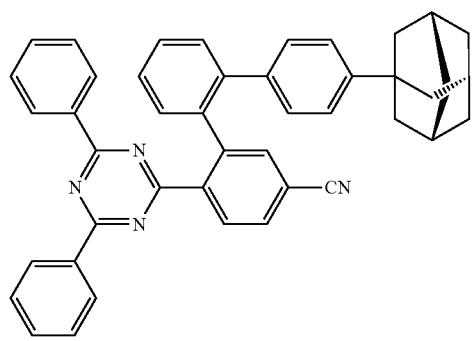
165
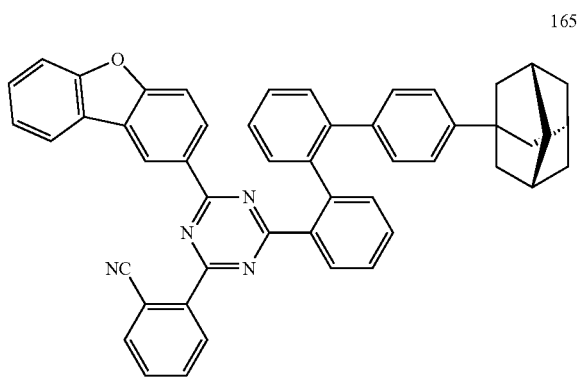
166
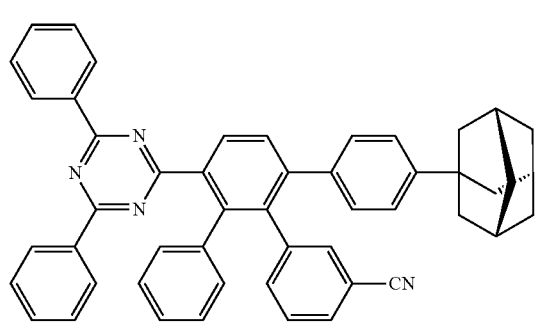
167
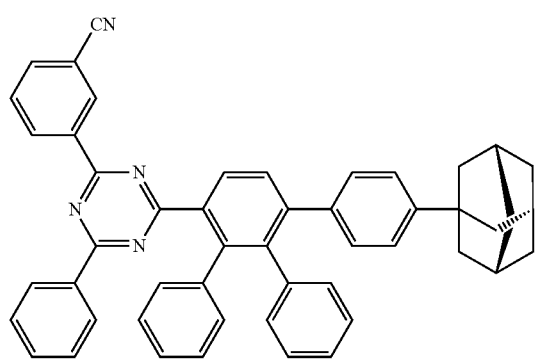
168
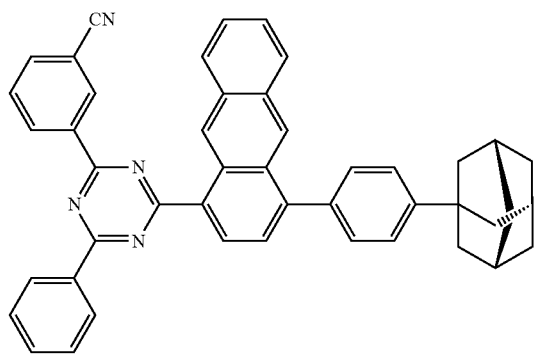
169
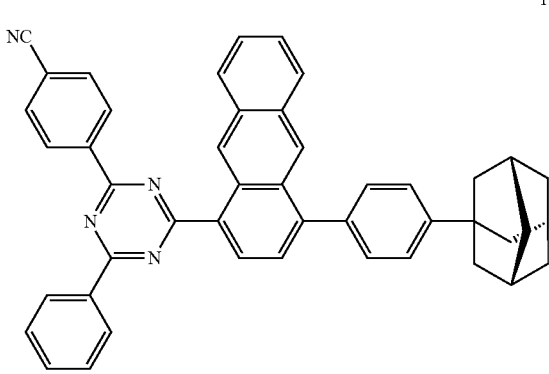
170
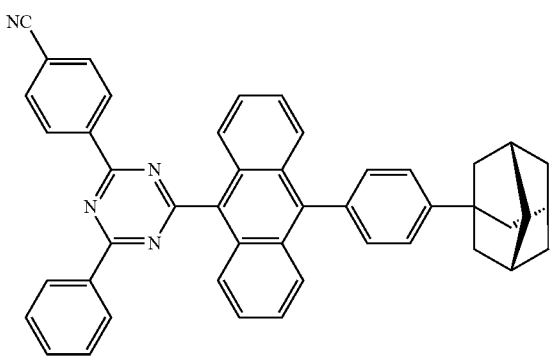
171
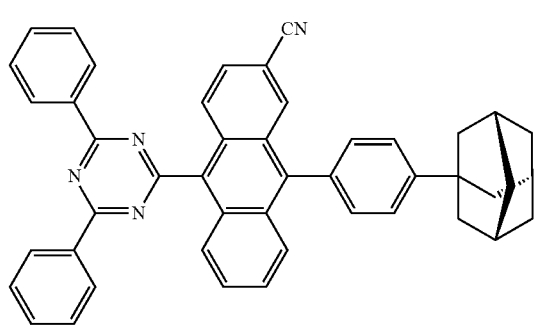

-continued
172
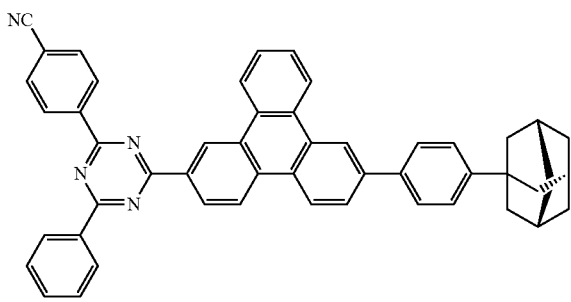
173
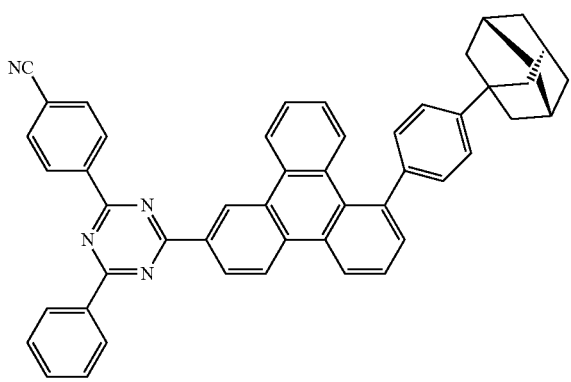
174
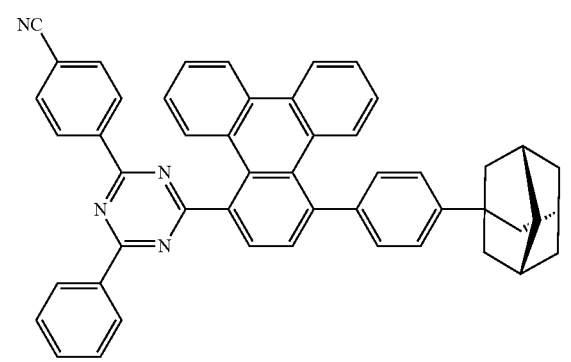
175
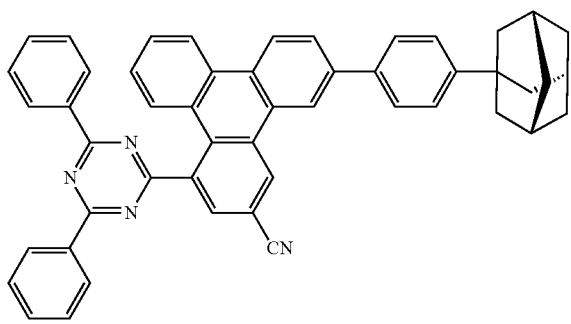
-continued
176
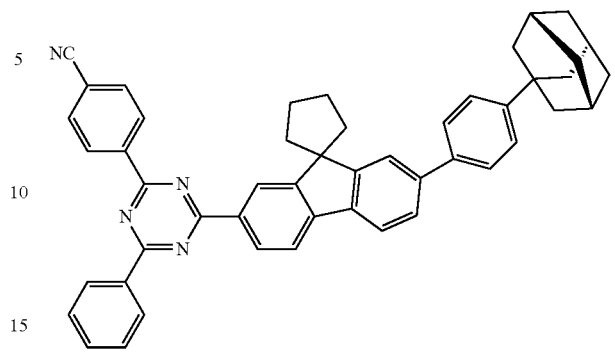
177
178
179
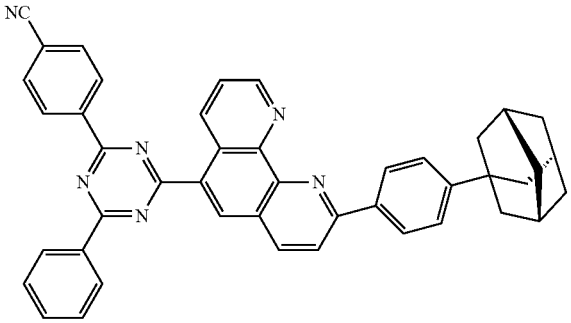

180
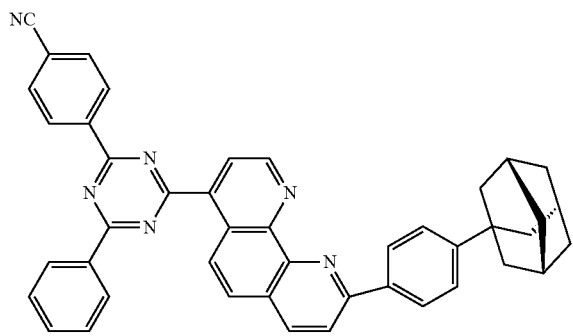
181
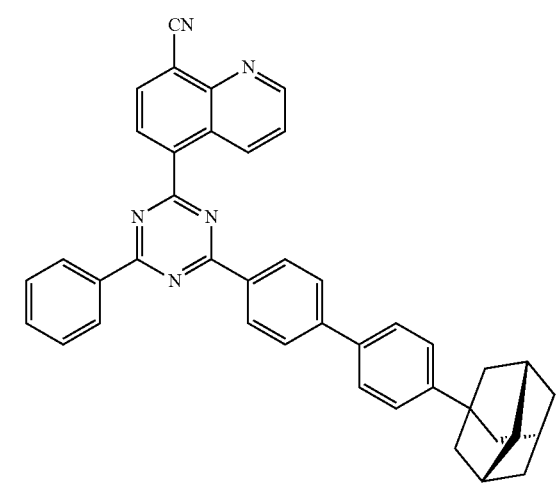
182
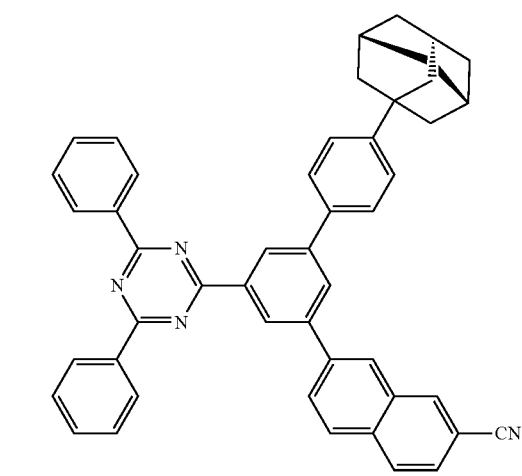
183
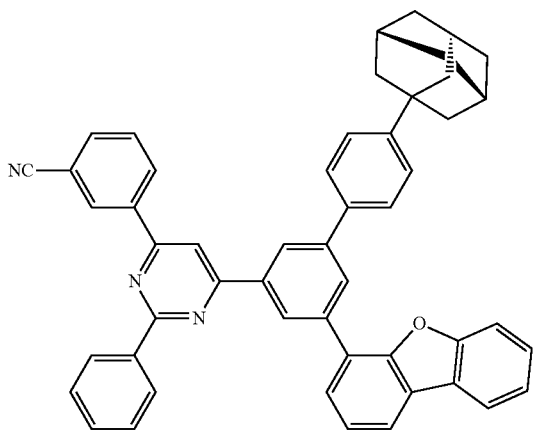
184
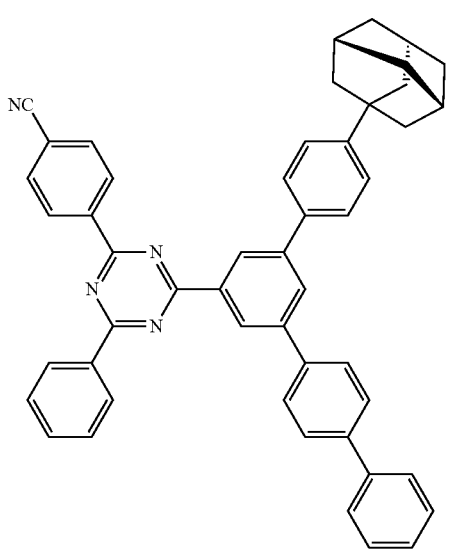
185
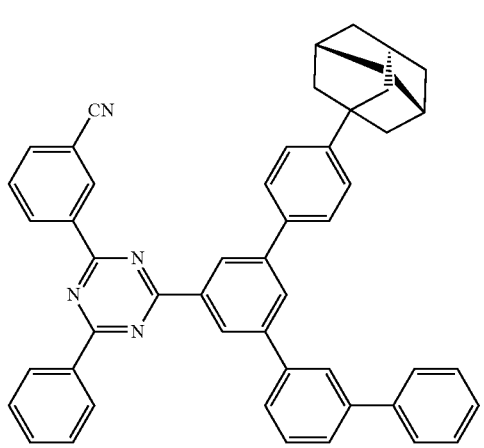

-continued

186

187

188

189

190

191

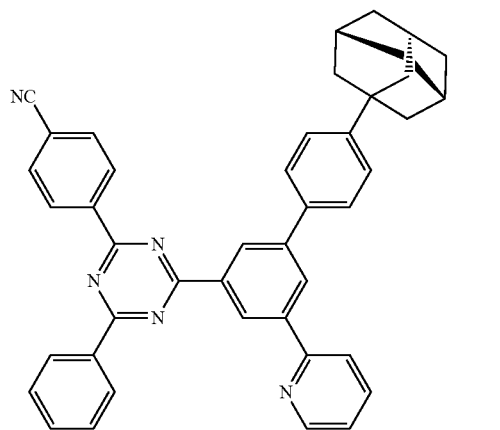
192
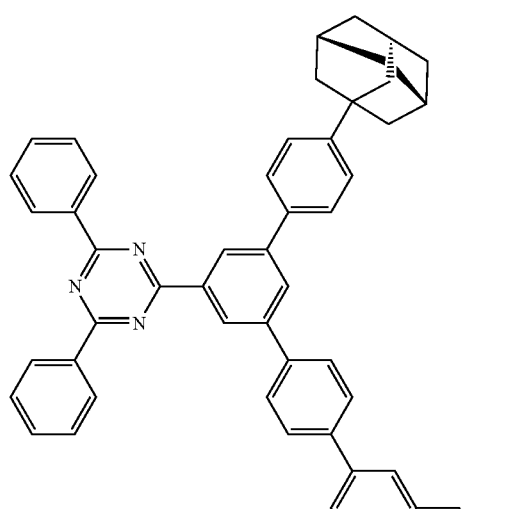
193
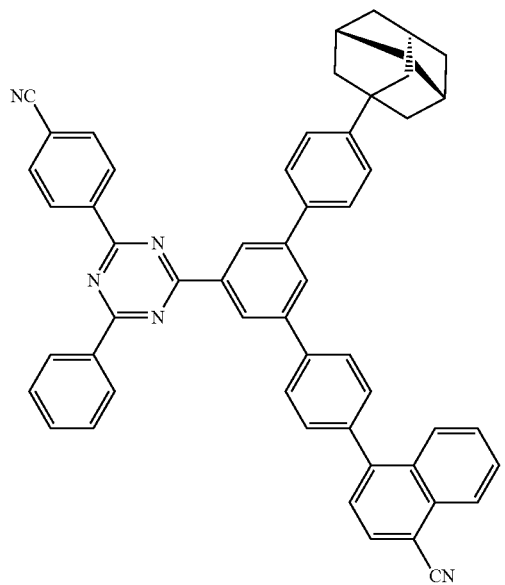
194
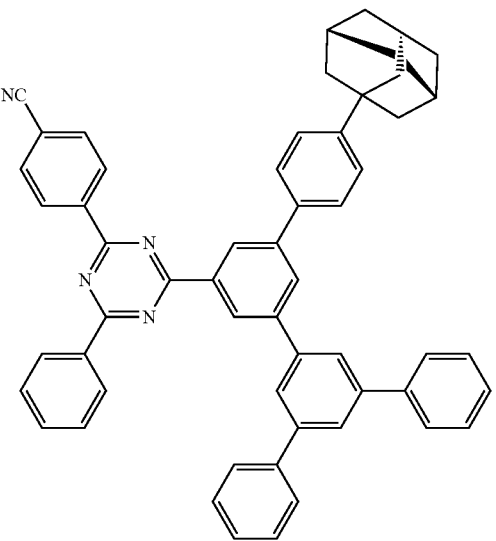
195
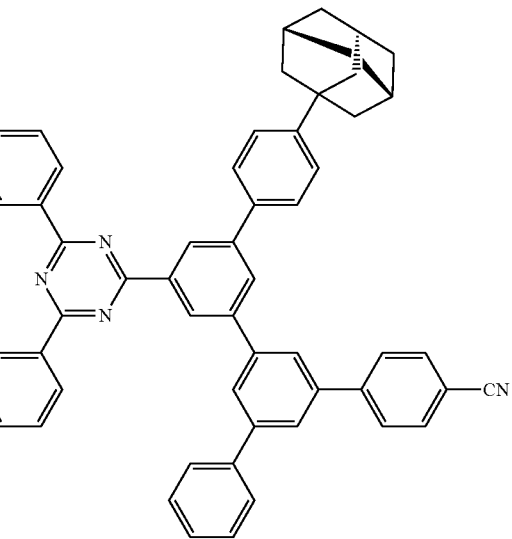
196
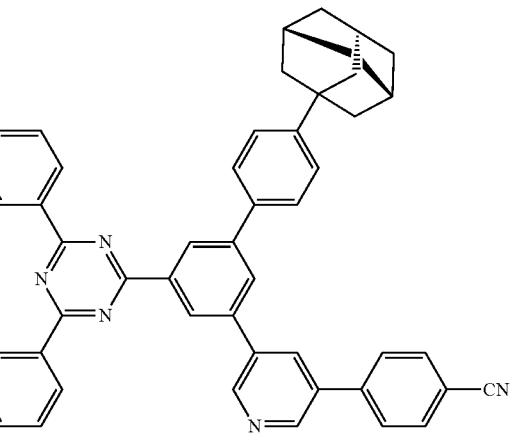
197

113
-continued
198
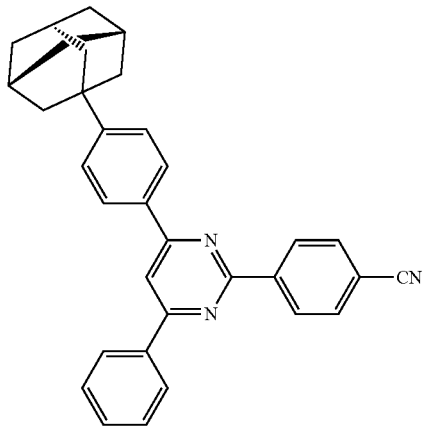
199
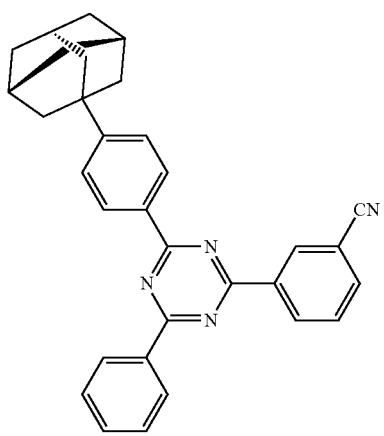
200
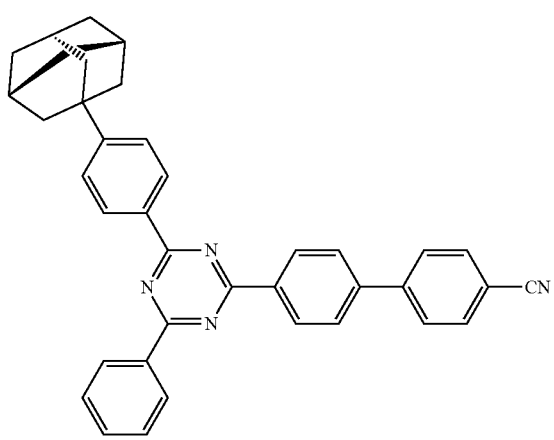
114
-continued
201
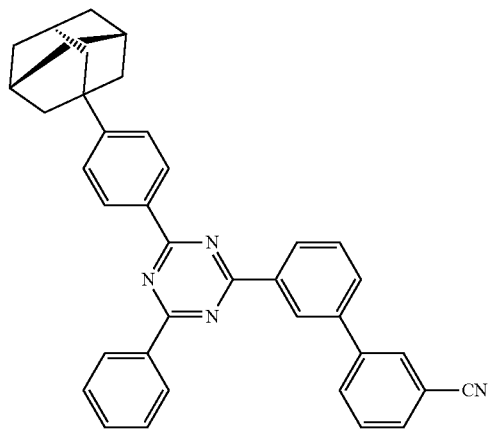
202
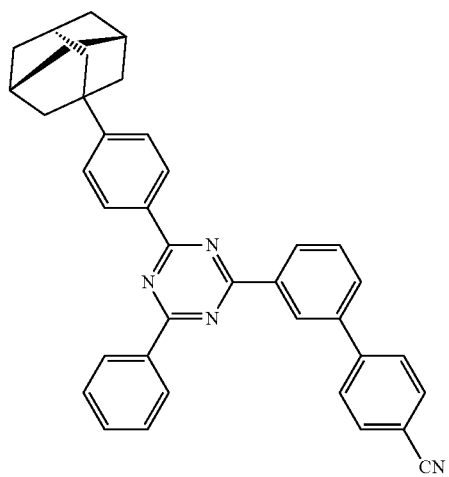
203
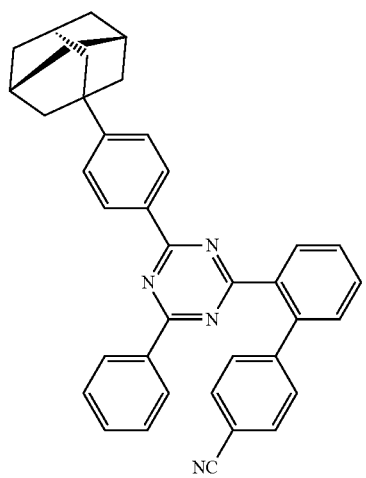

-continued
204
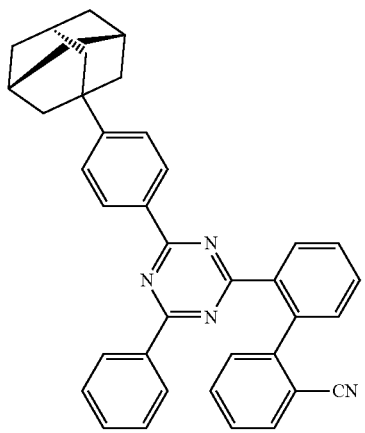
205
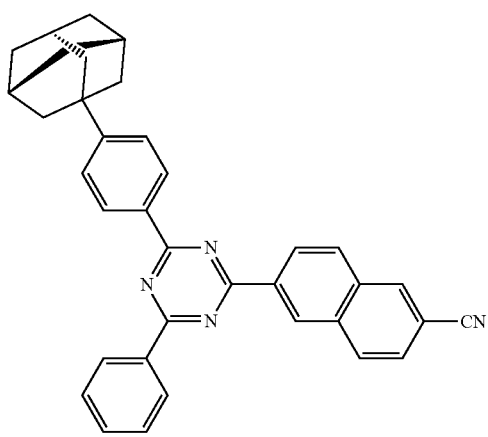
206
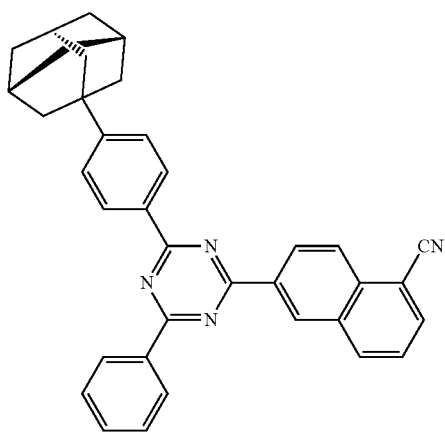
-continued
207
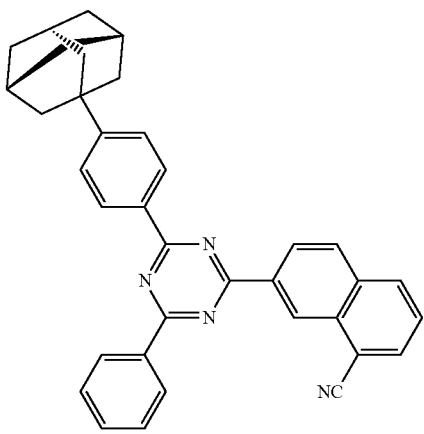
208
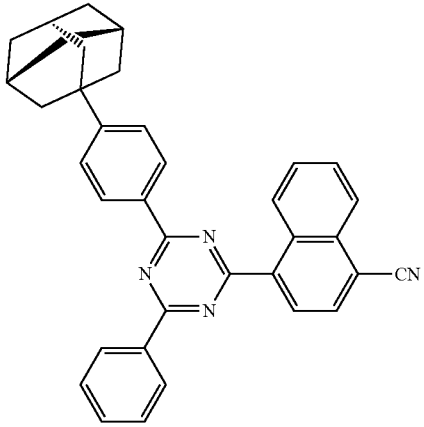
209
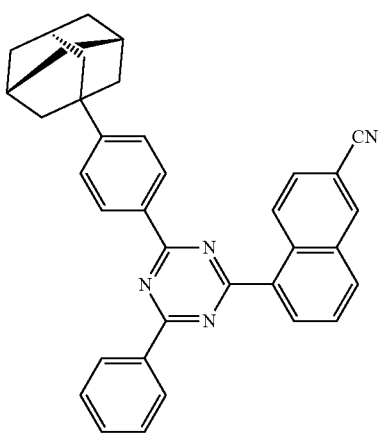

117
-continued
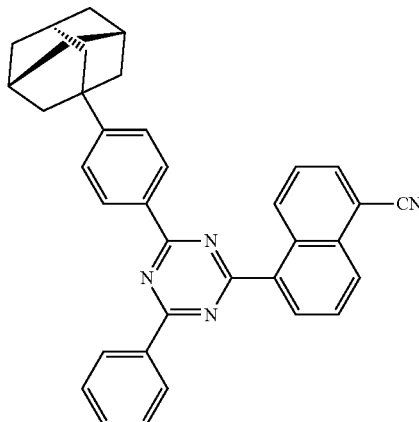
210
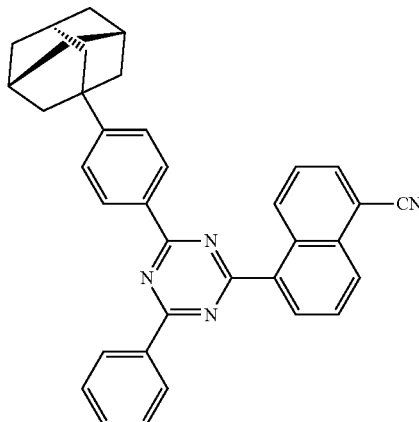
211
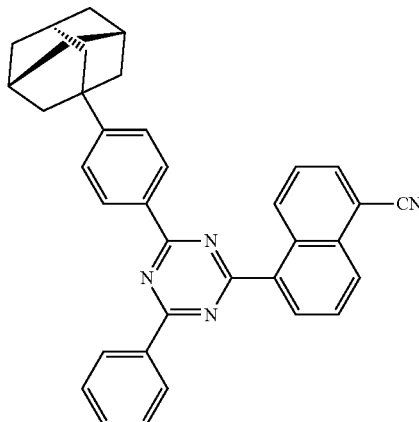
212
118
-continued
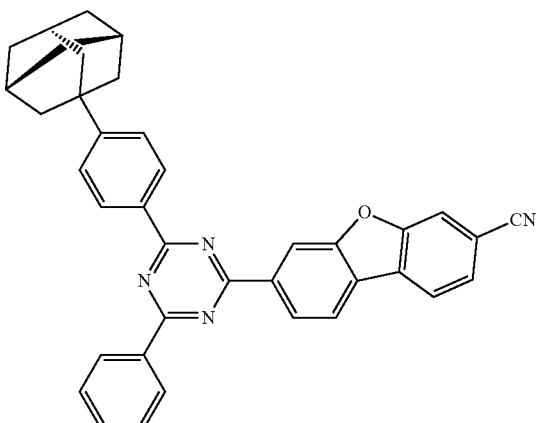
213
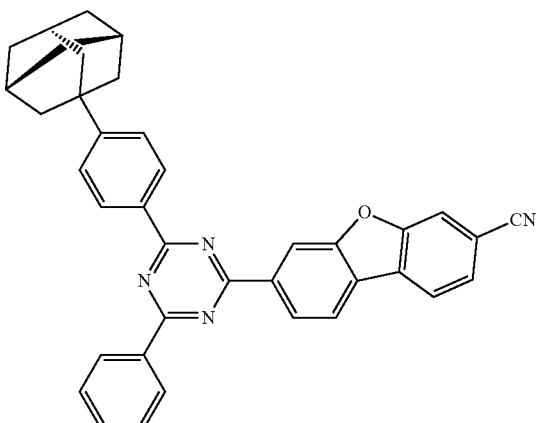
214
215

119
-continued
120
-continued
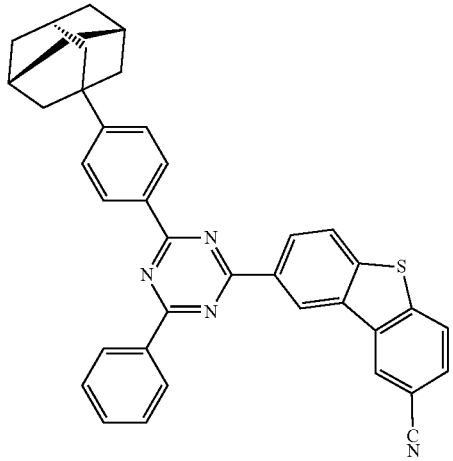
216
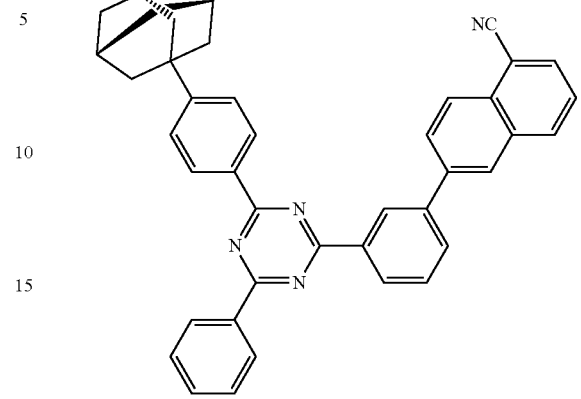
219
217
220
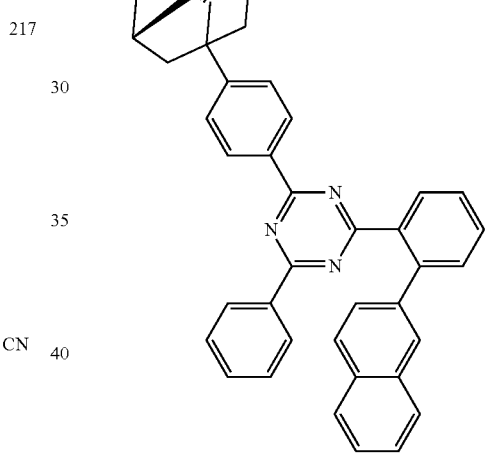
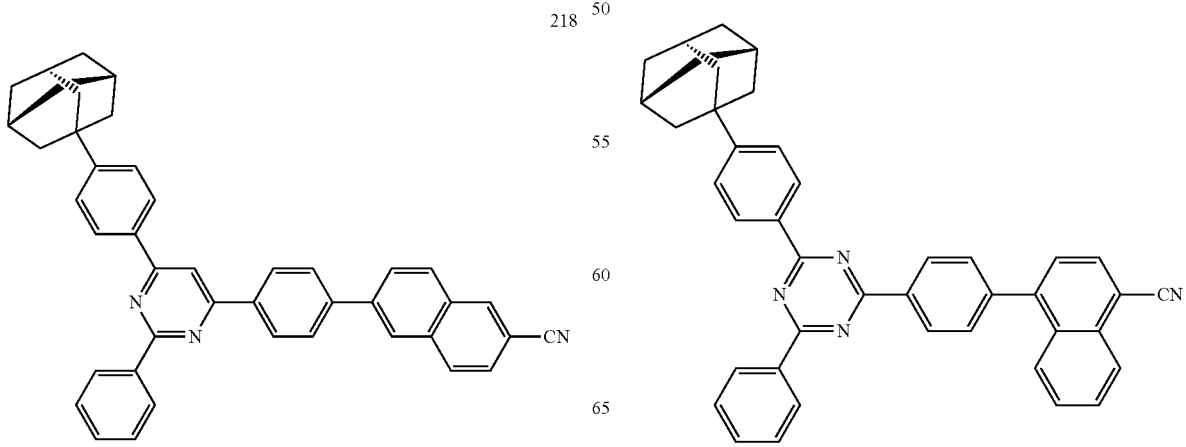
218
221

121
-continued
222
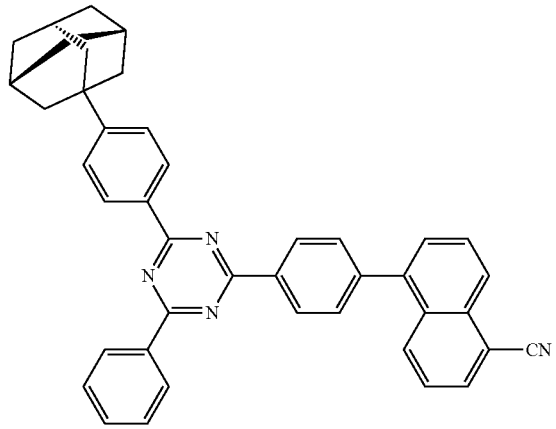
223
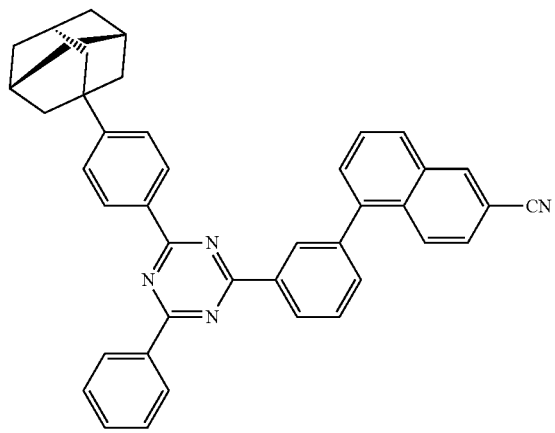
224
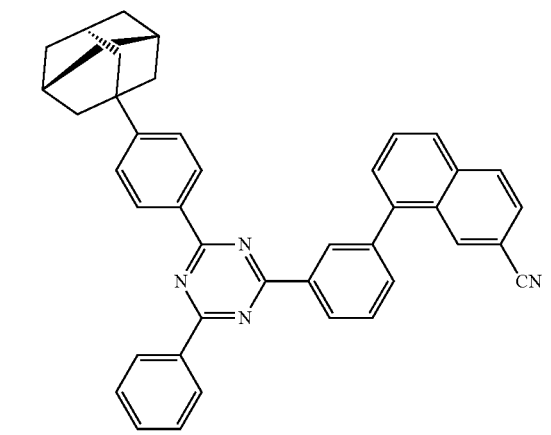
122
-continued
225
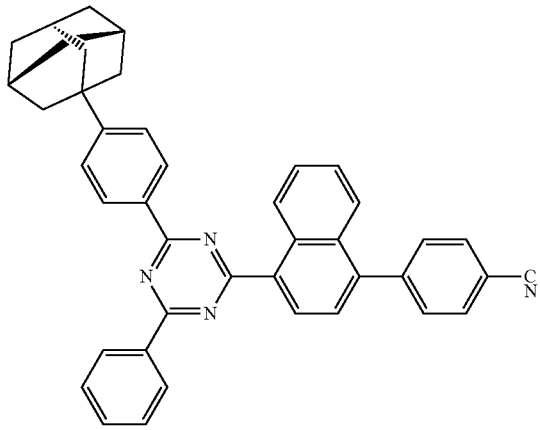
226
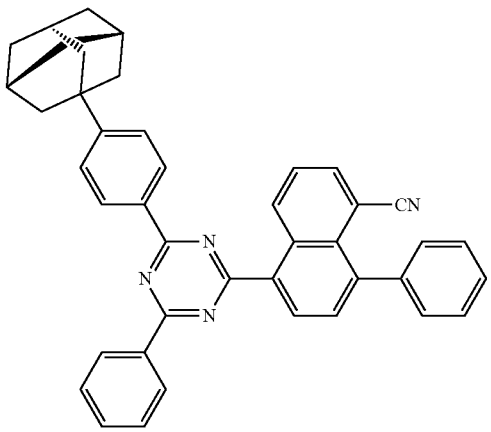
227
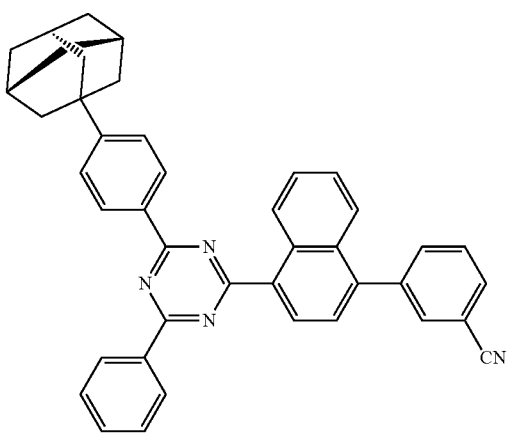

228
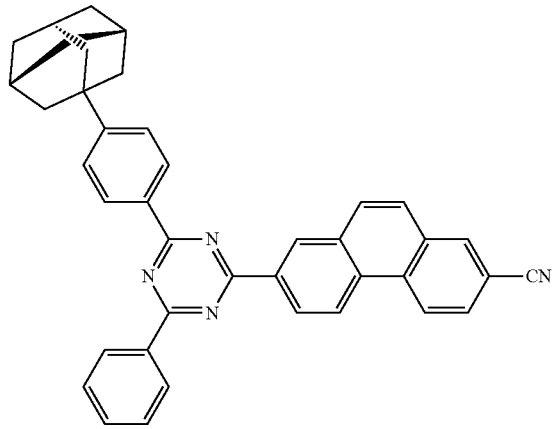
229
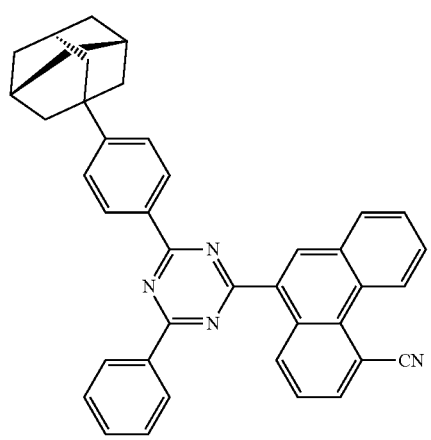
230
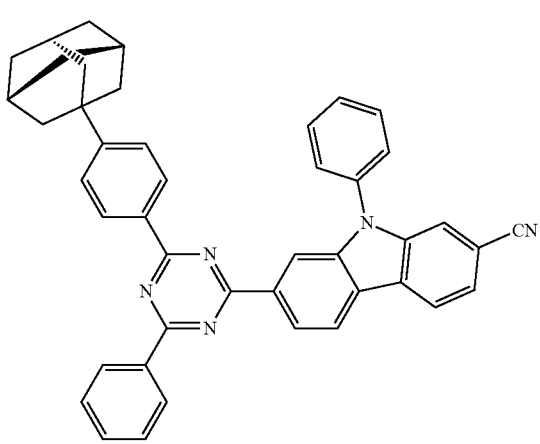
231
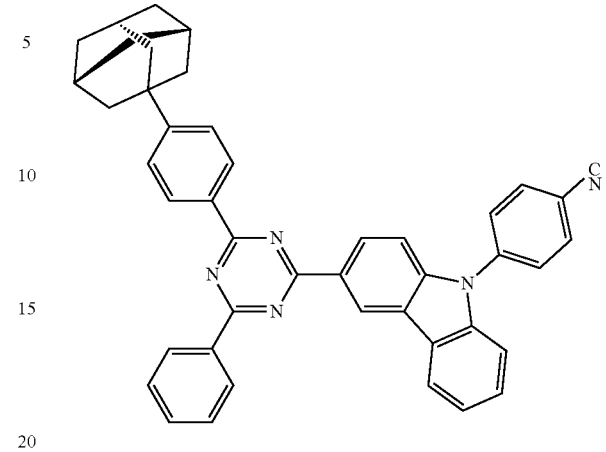
232
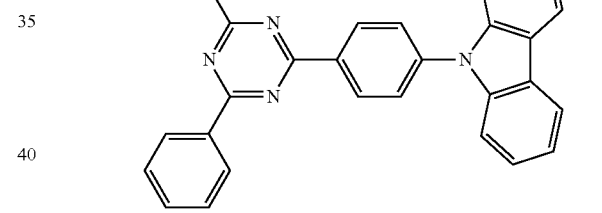
233
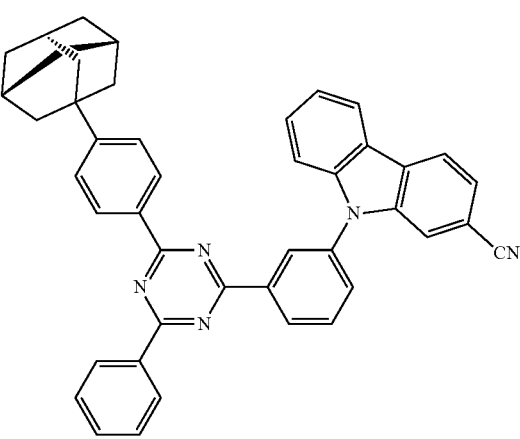

234
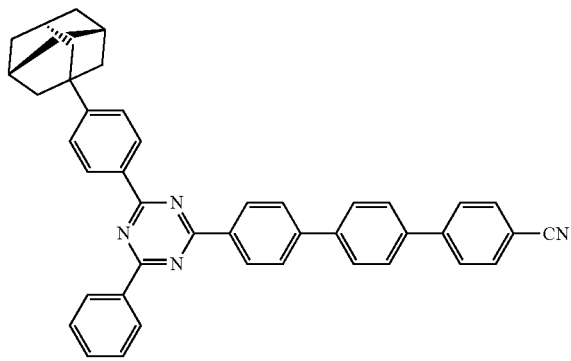
235
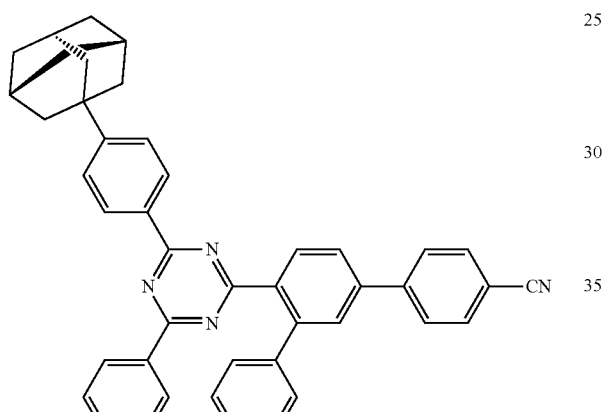
236
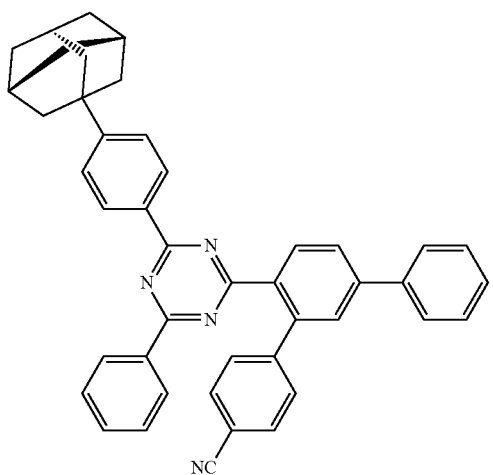
237
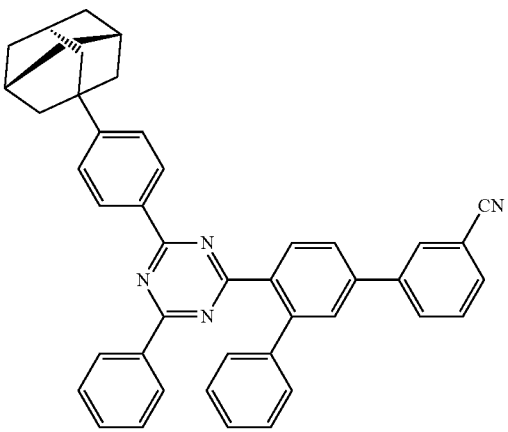
238
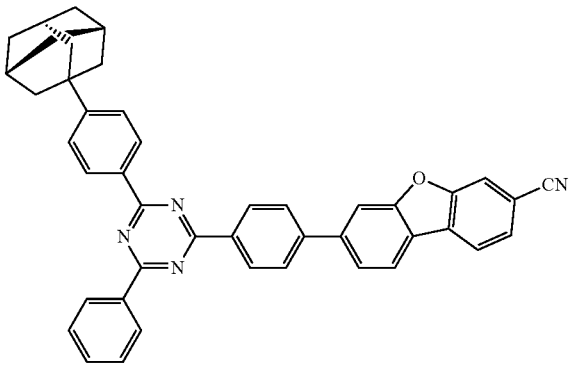
239
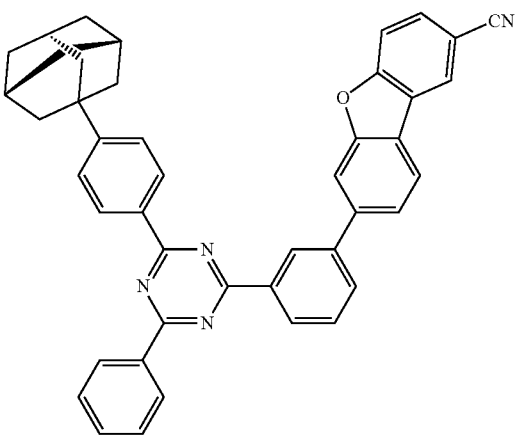

240
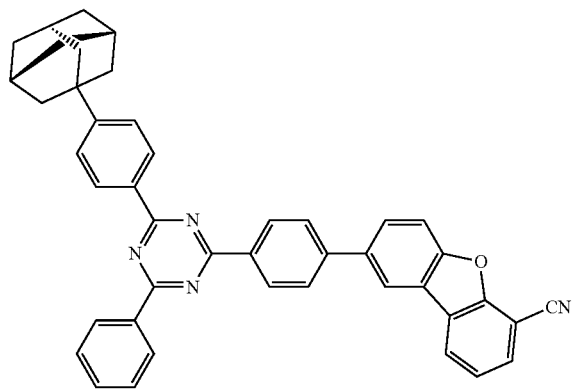
241
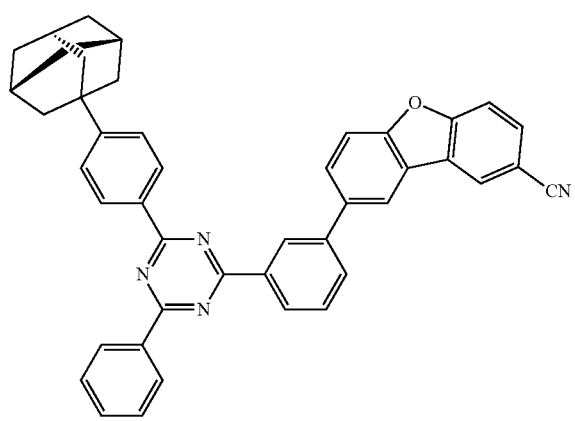
242
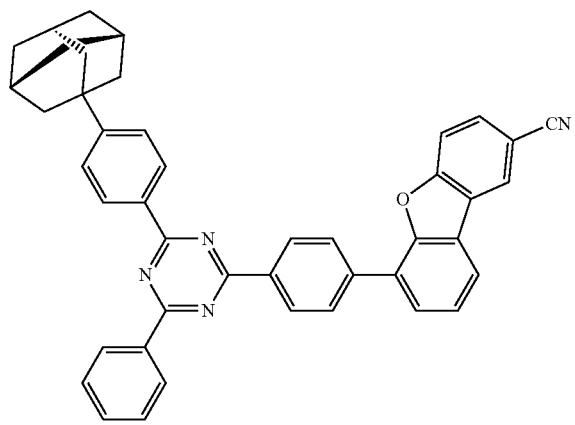
243
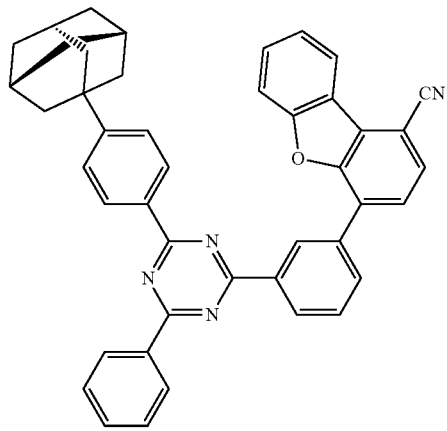
244
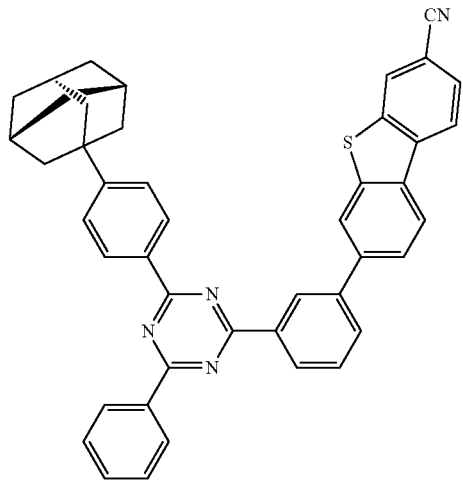
245
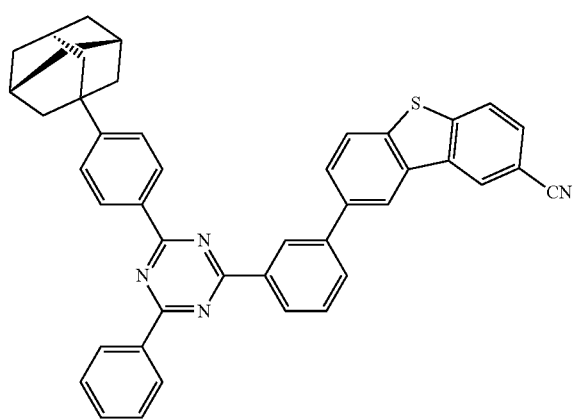

246
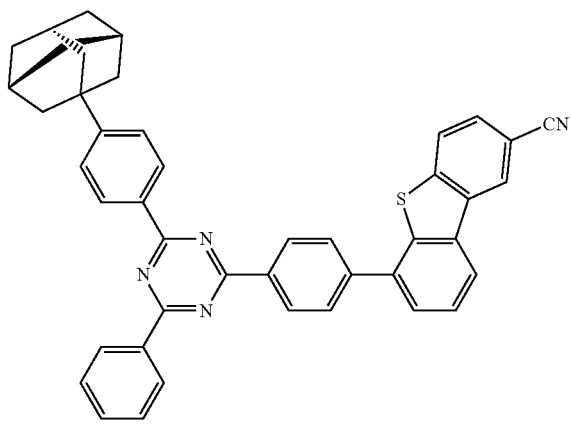
247
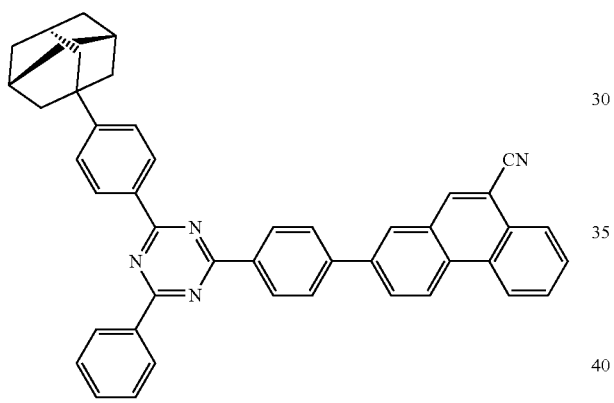
248
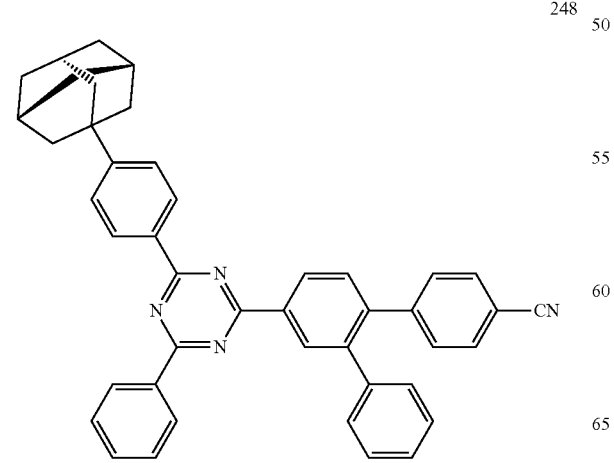
249
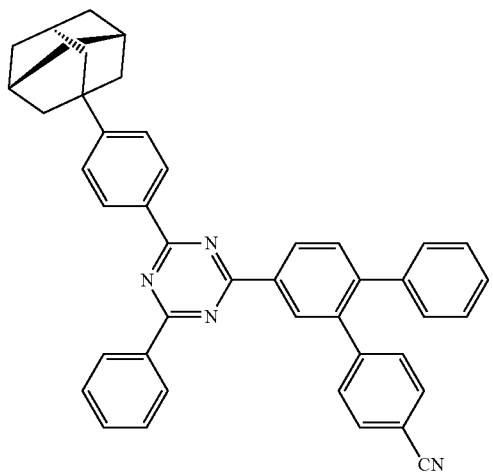
250
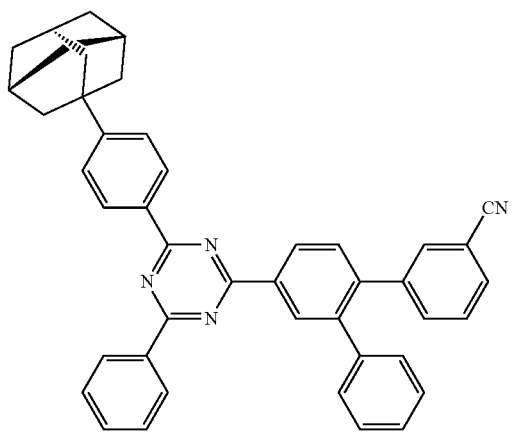
251
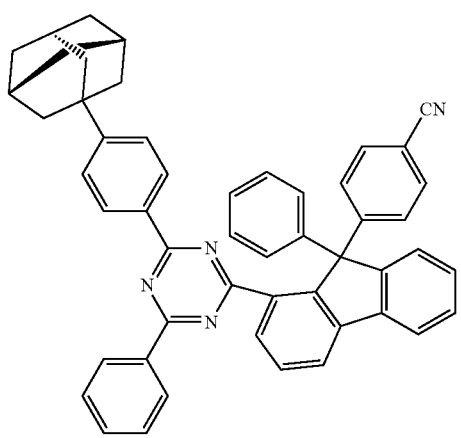

-continued
252
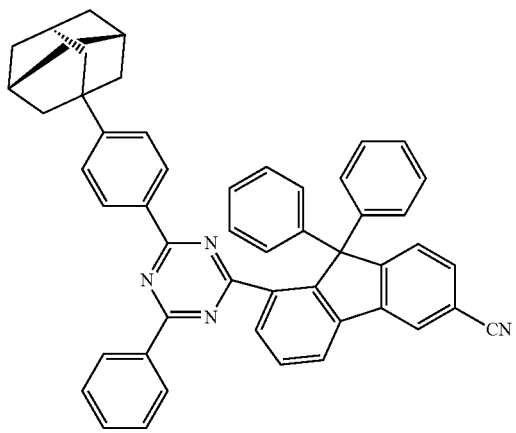
253
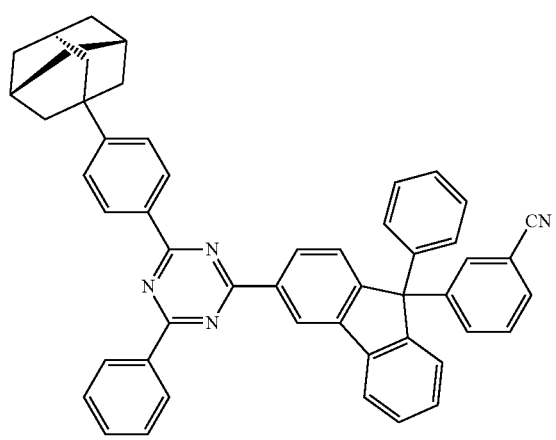
254
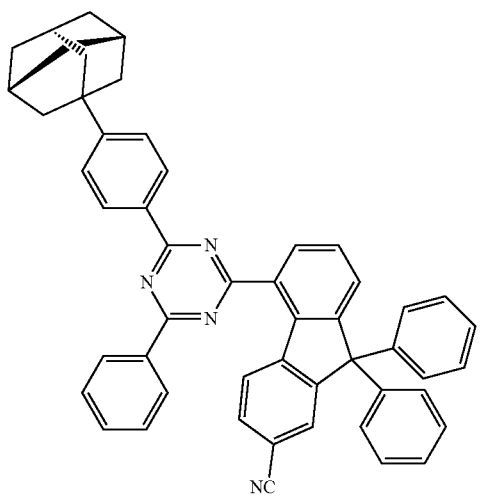
-continued
255
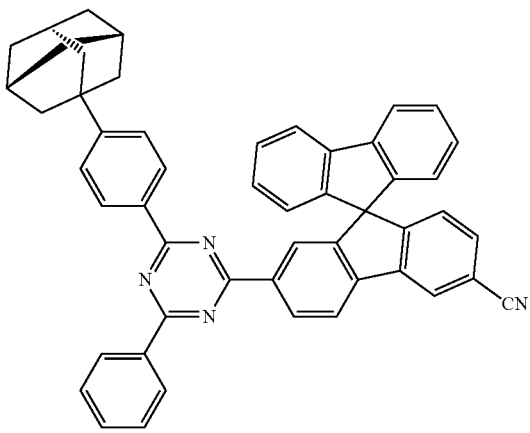
256
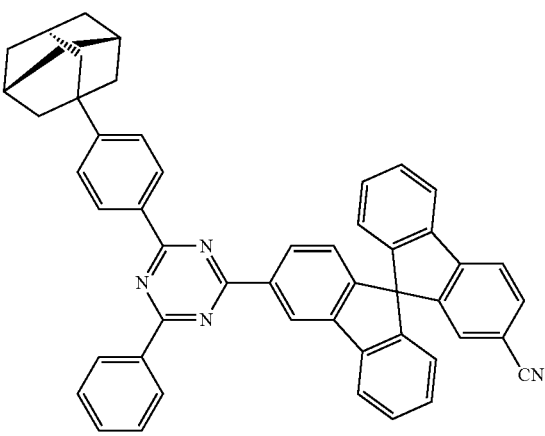
257
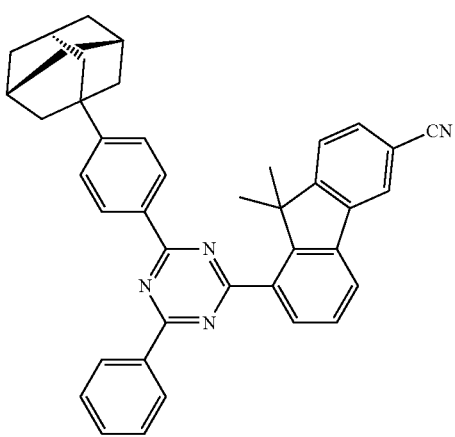

-continued
258
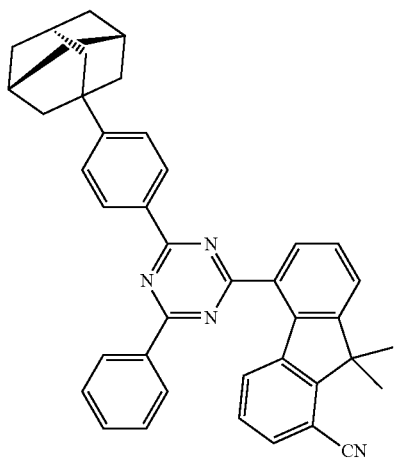
259
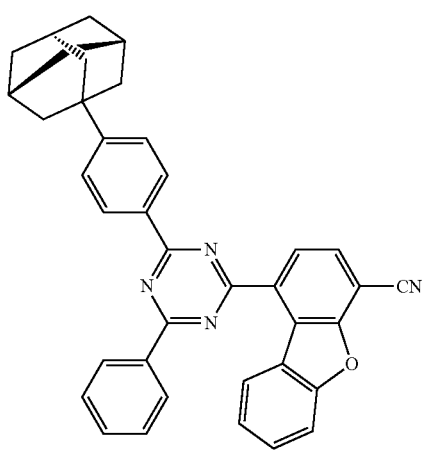
260
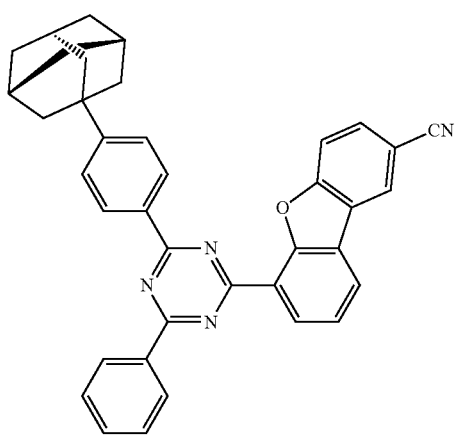
-continued
261
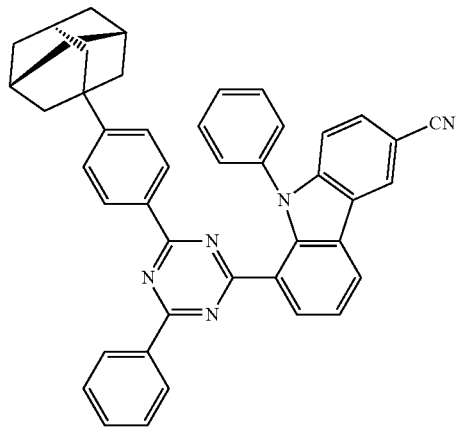
262
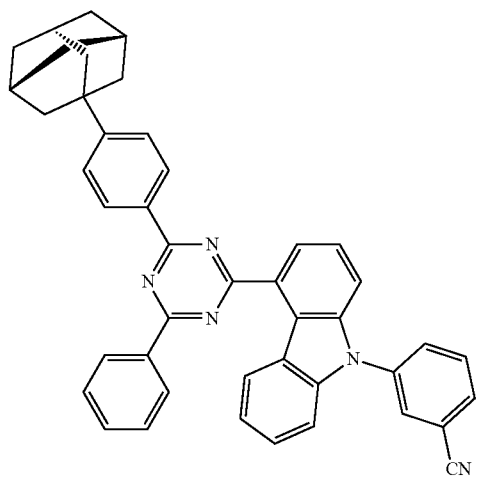
263
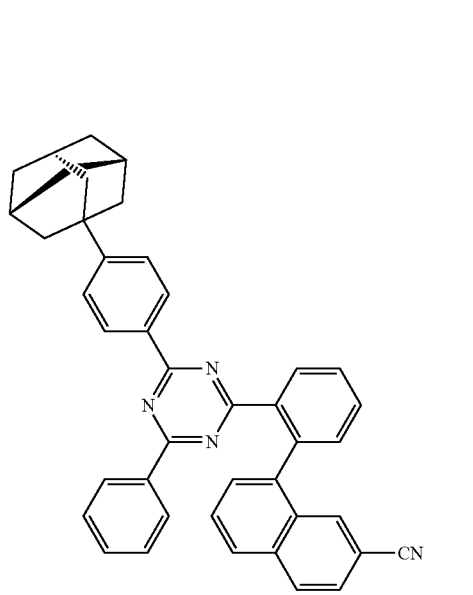

135
-continued
264
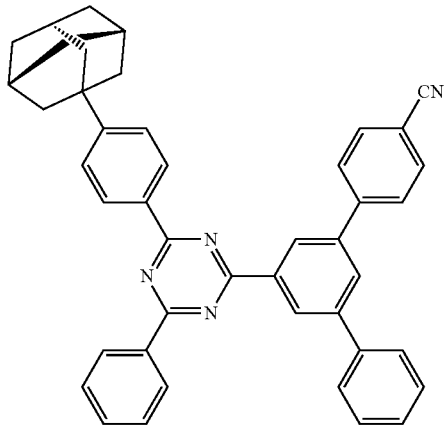
265
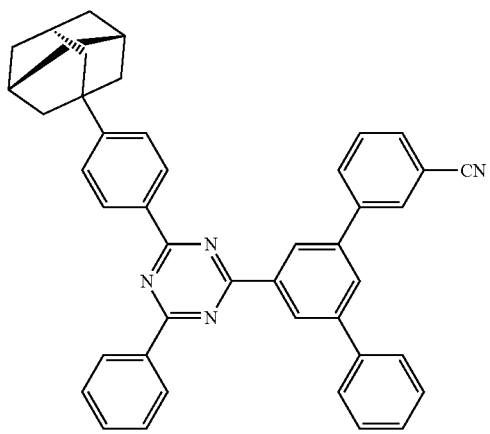
266
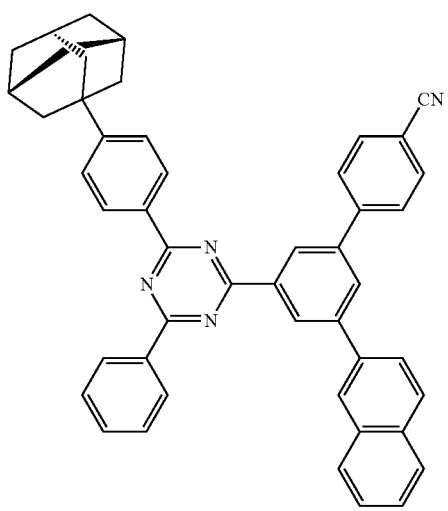
136
-continued
267
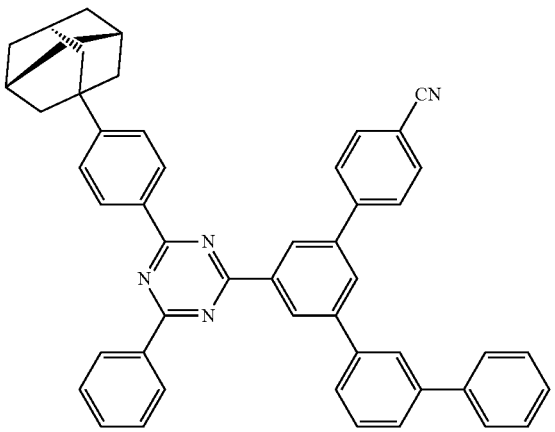
268
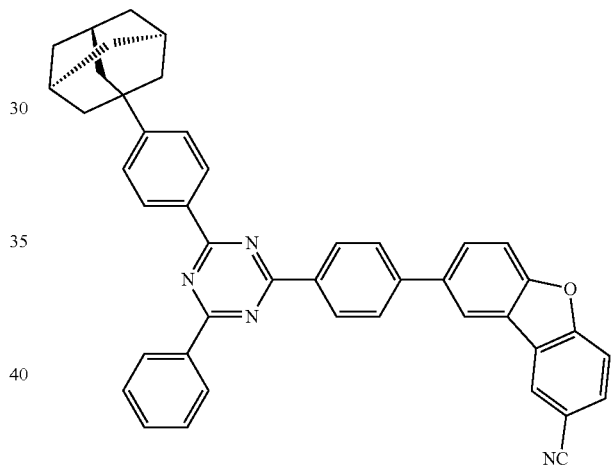
269
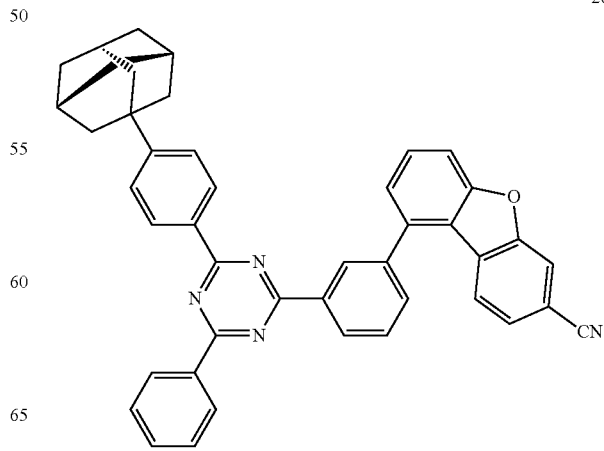

137
-continued
270
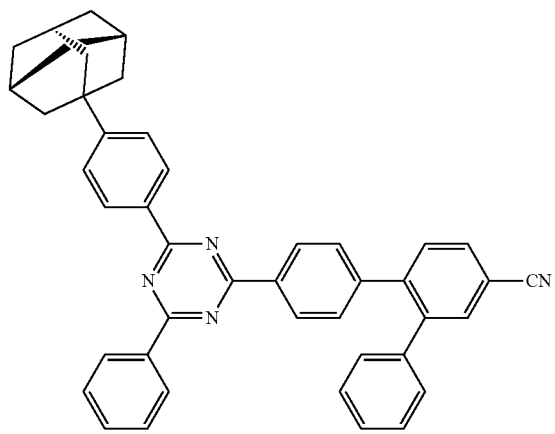
271
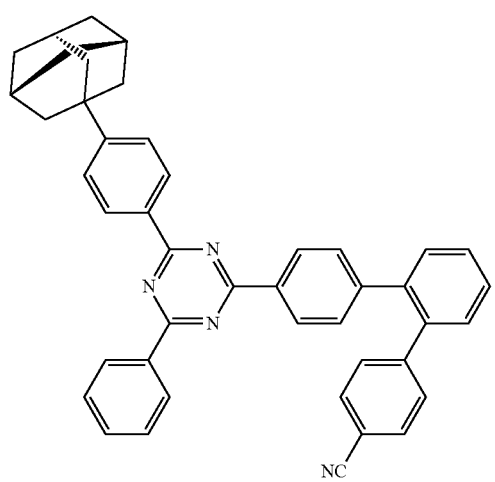
272
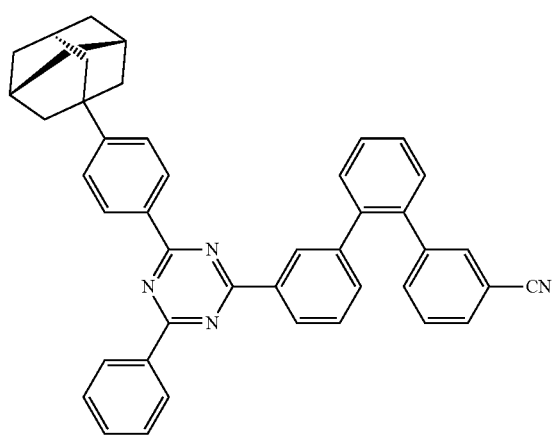
138
-continued
273
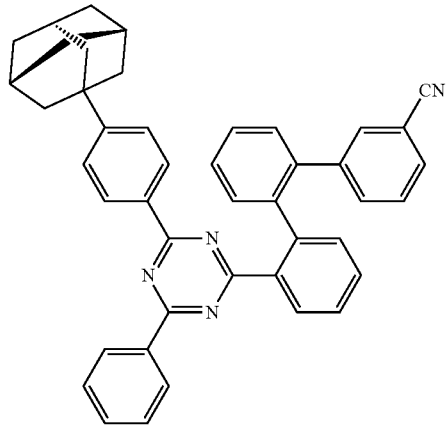
274
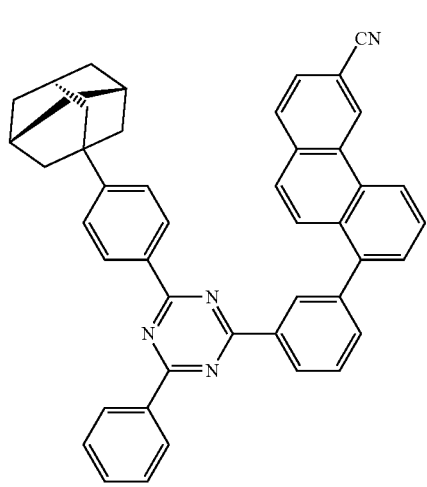
275
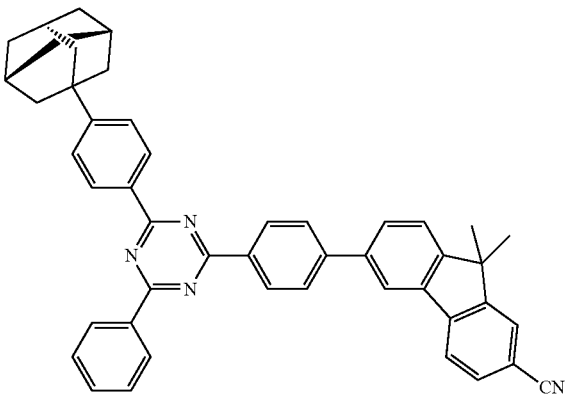

276
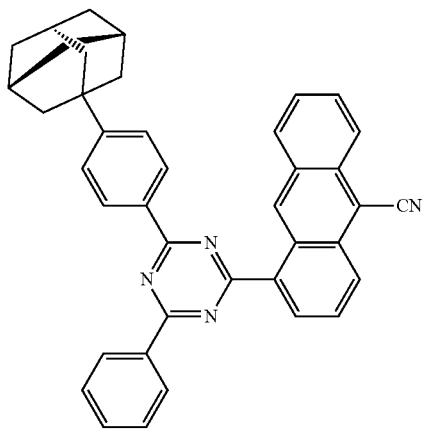
277
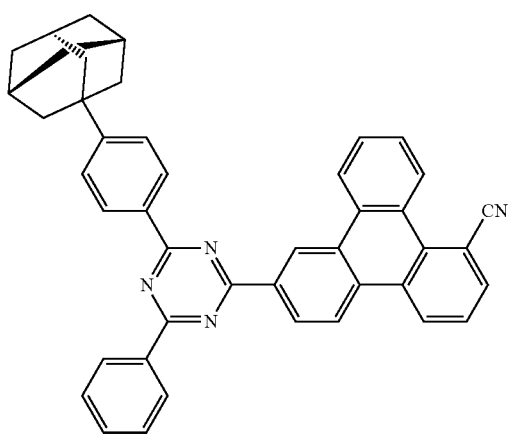
278
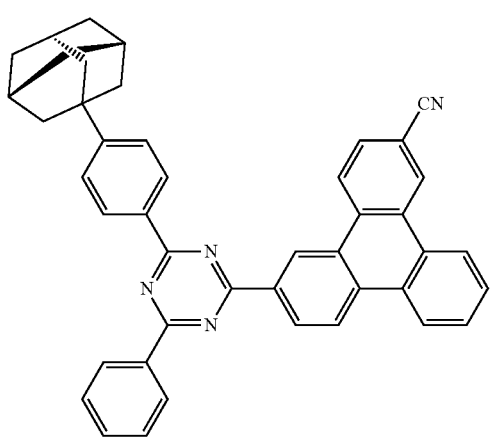
279
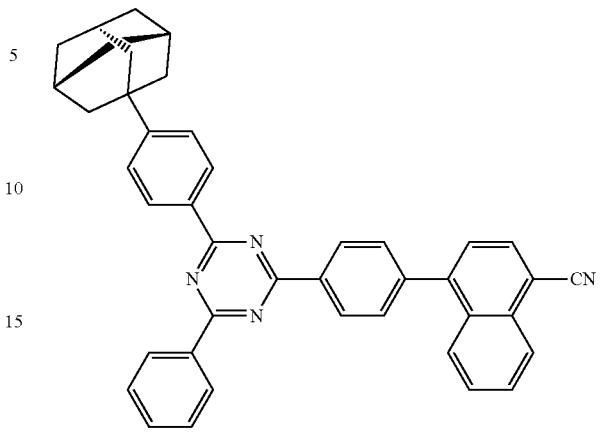
280
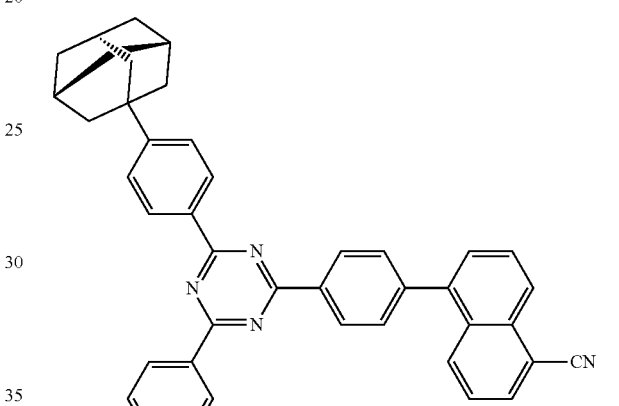
281
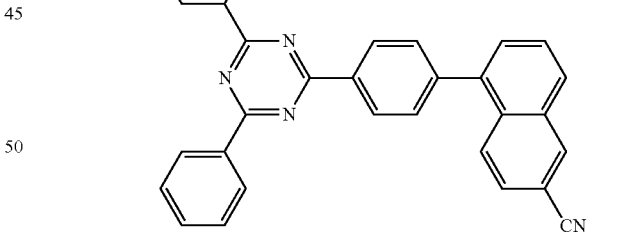
282
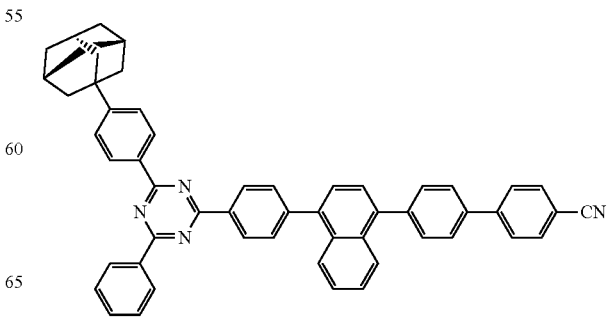

283
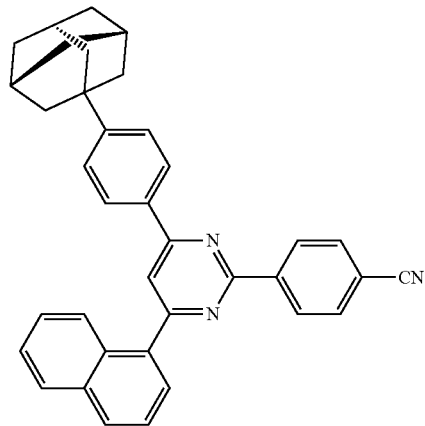
284
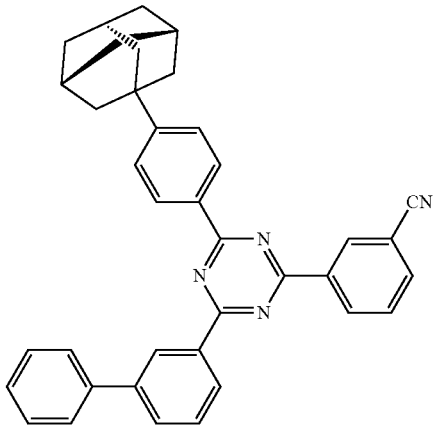
285
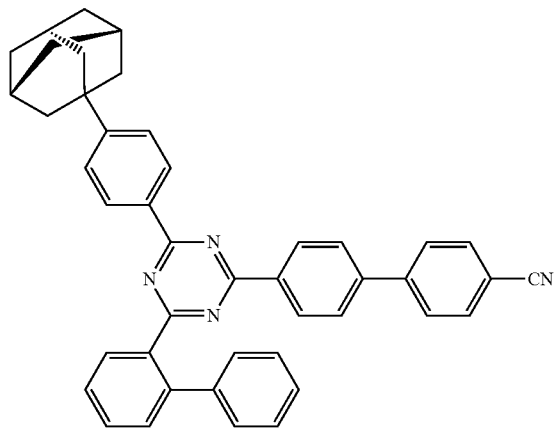
286
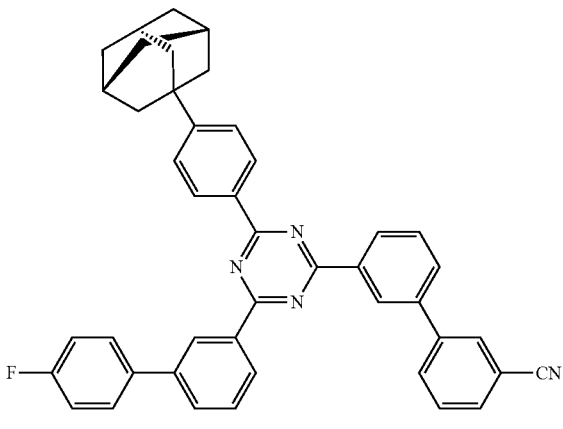
287
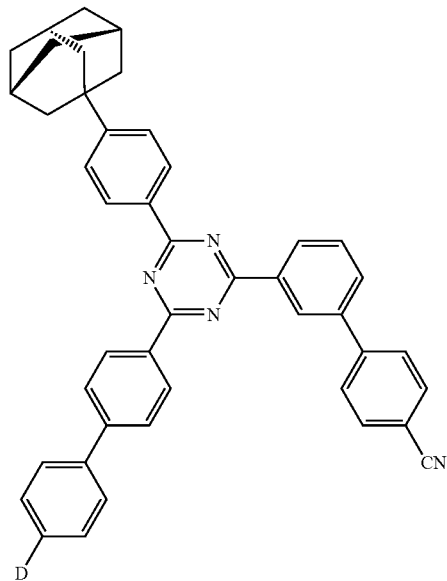
288
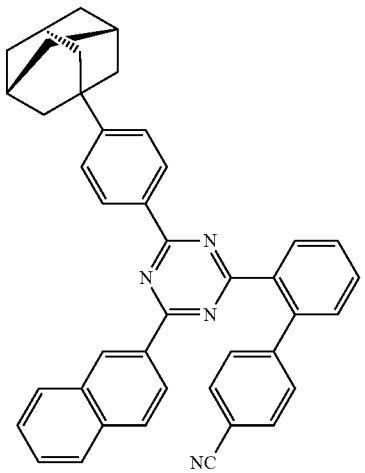

-continued
| 289 | 290 |
|---|---|
| 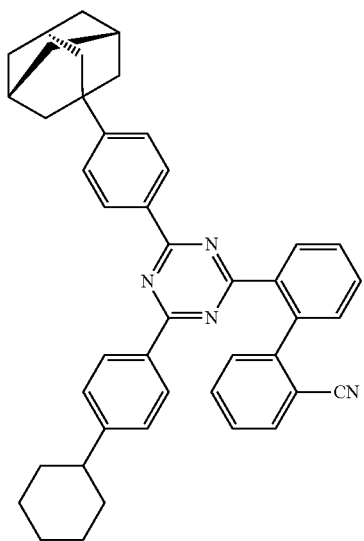 | 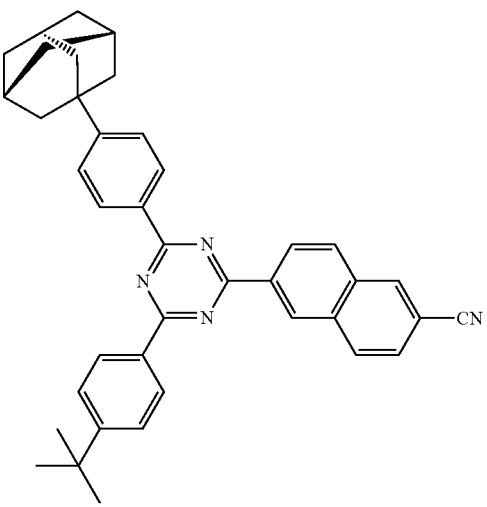 |
| 291 | 292 |
| 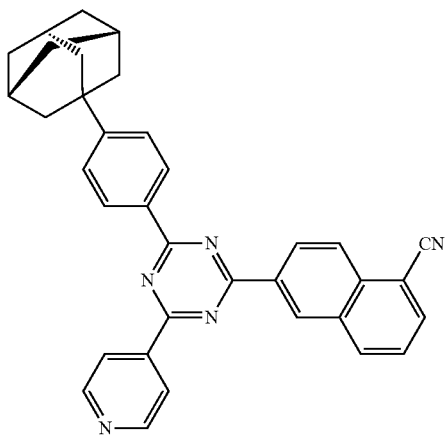 | 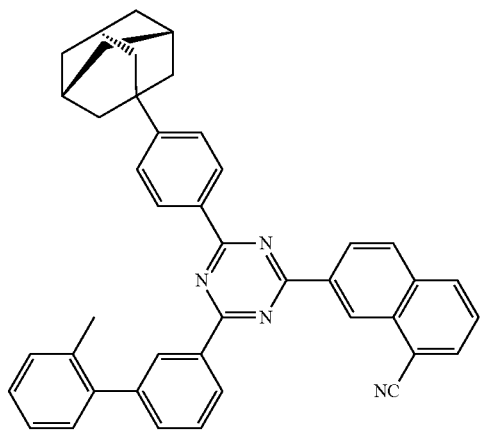 |
| 293 | 294 |
| 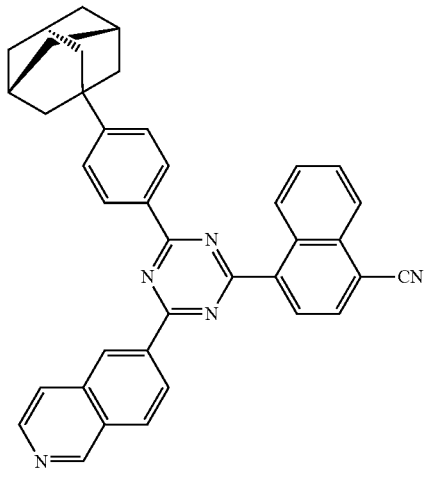 | 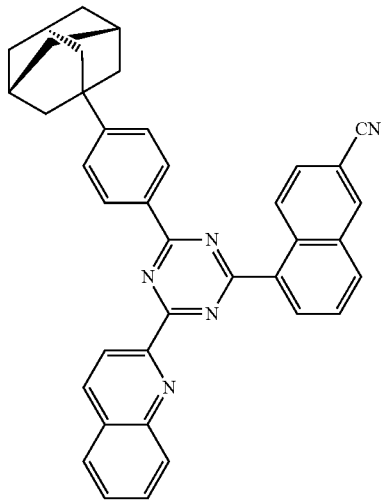 |

295
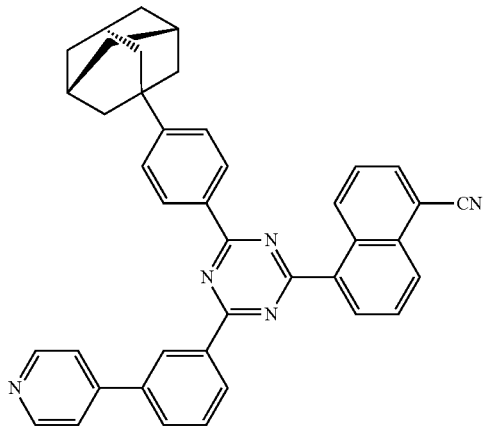
296
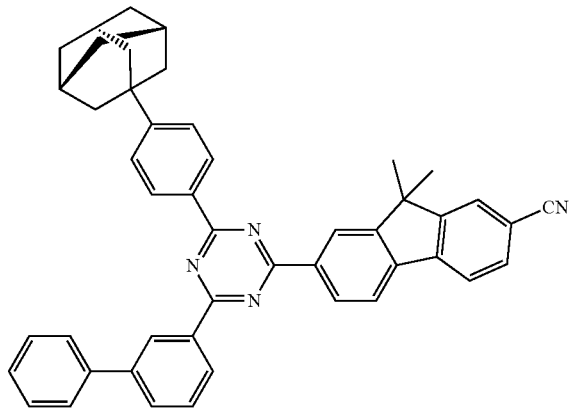
297
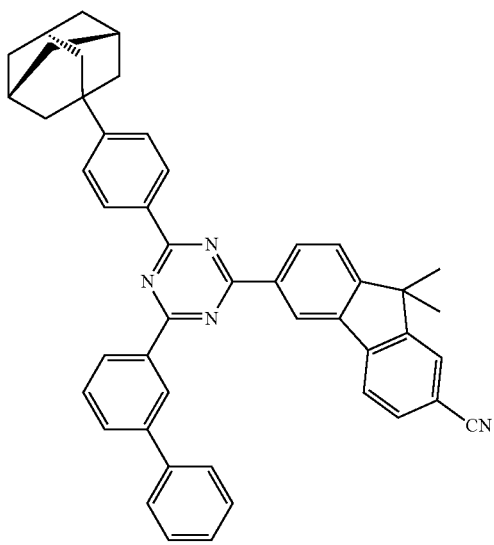
298
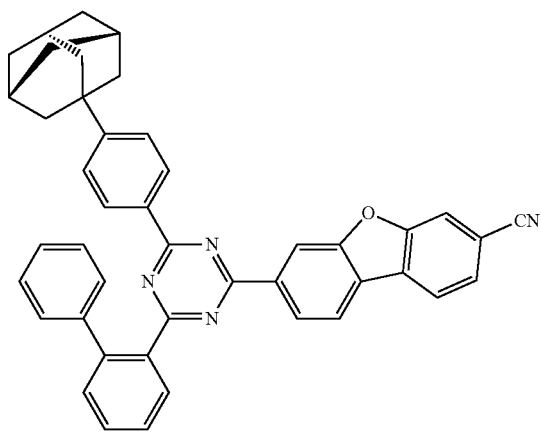
299
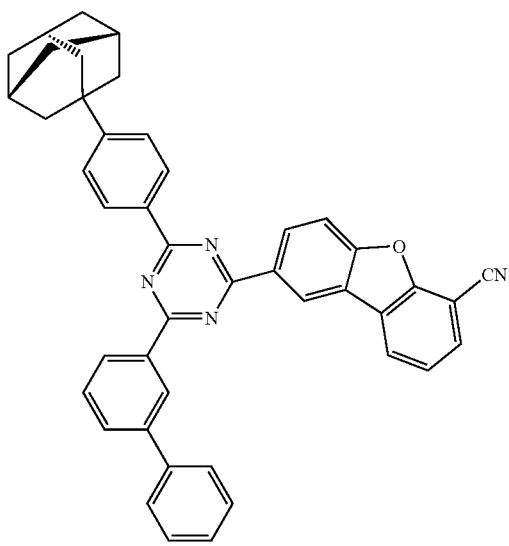
300
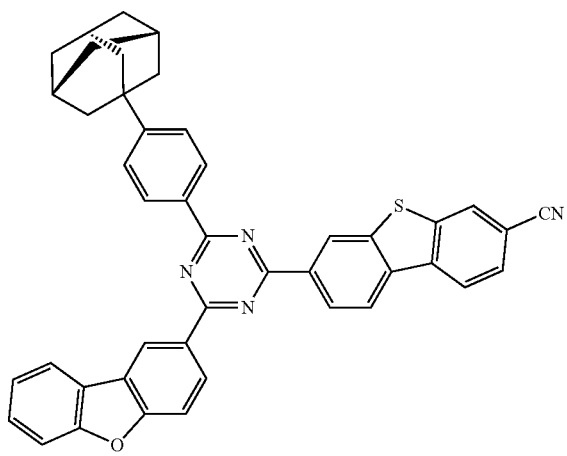

-continued
301
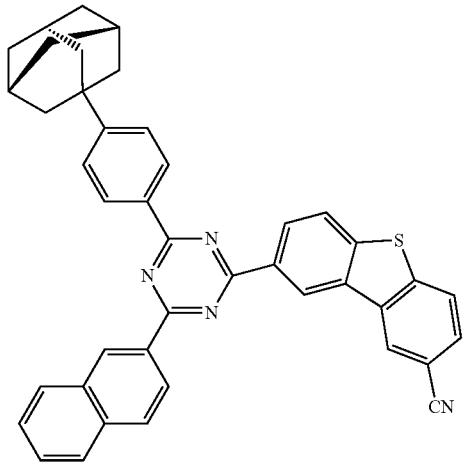
302
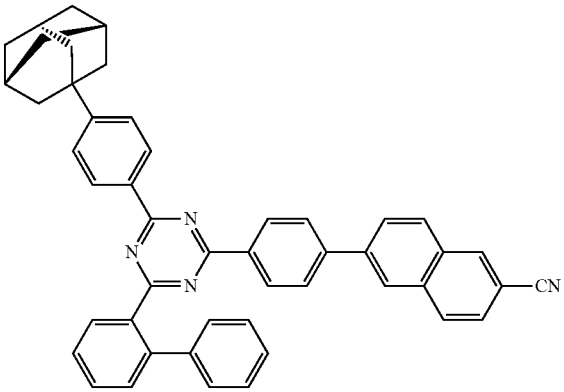
303
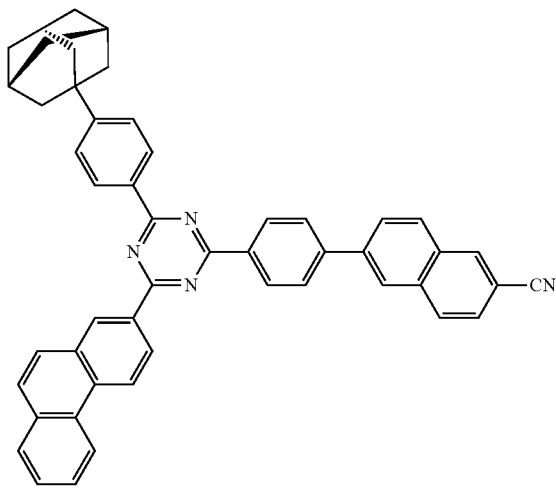
304
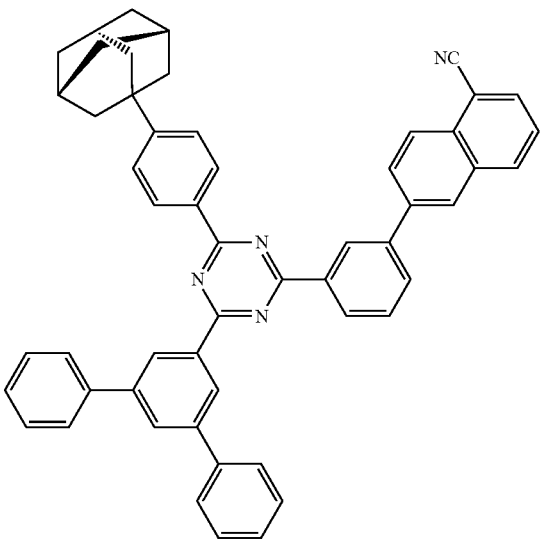
305
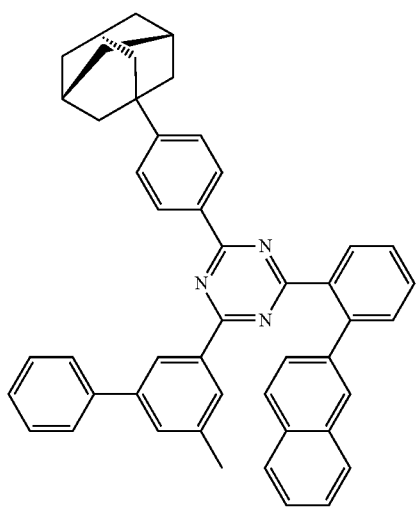
306
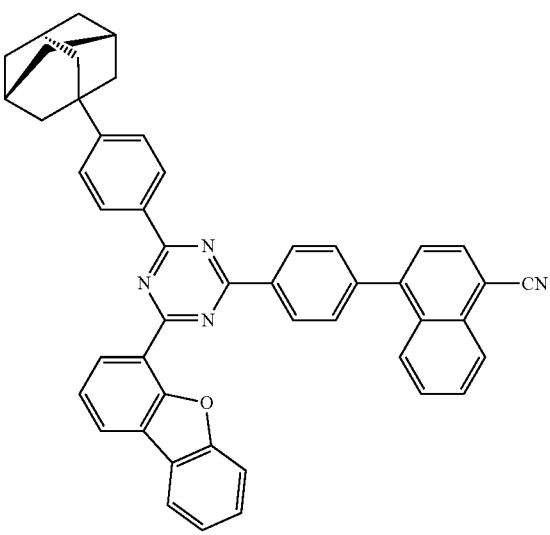

| 307 | 308 |
|---|---|
| 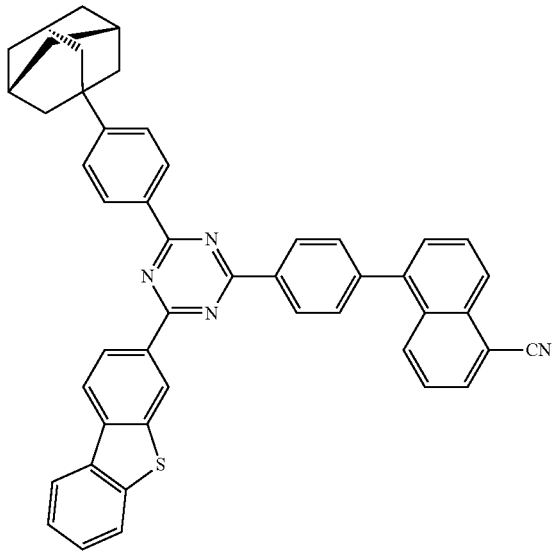 | 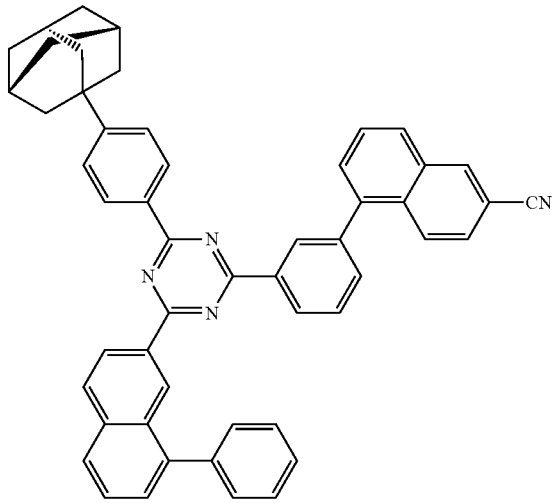 |
| 309 | 310 |
| 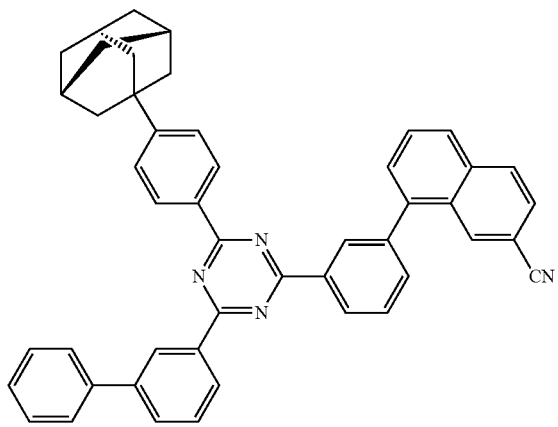 |  |
| 311 | 312 |
| 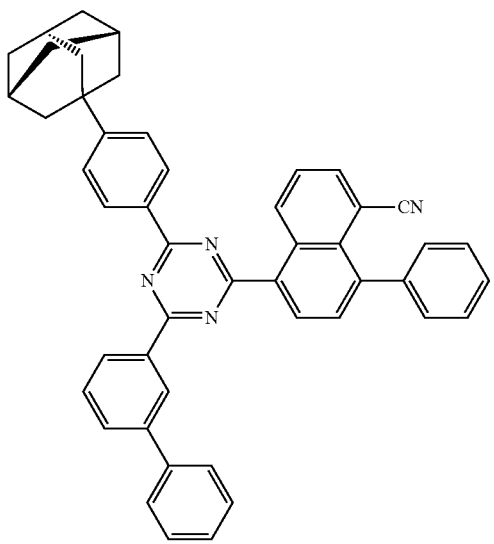 |  |

313
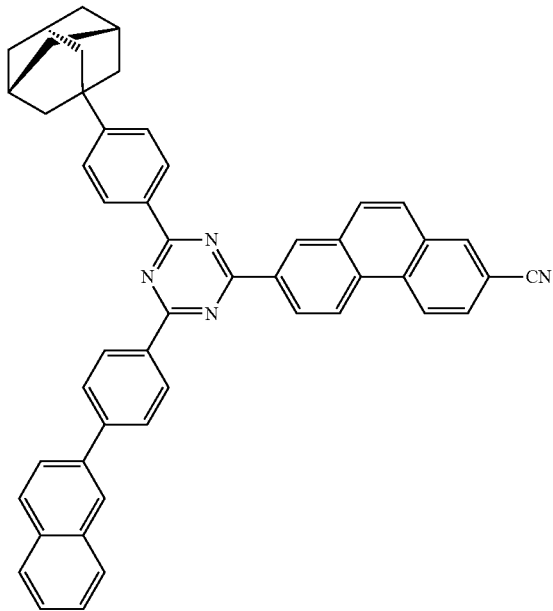
314
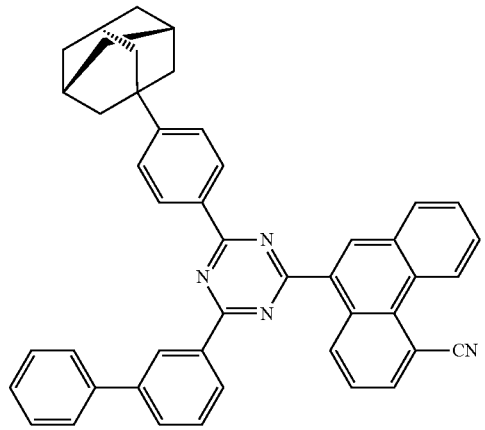
315
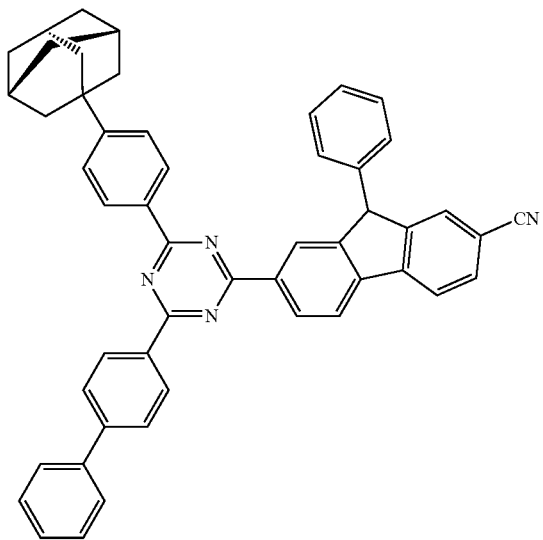
316
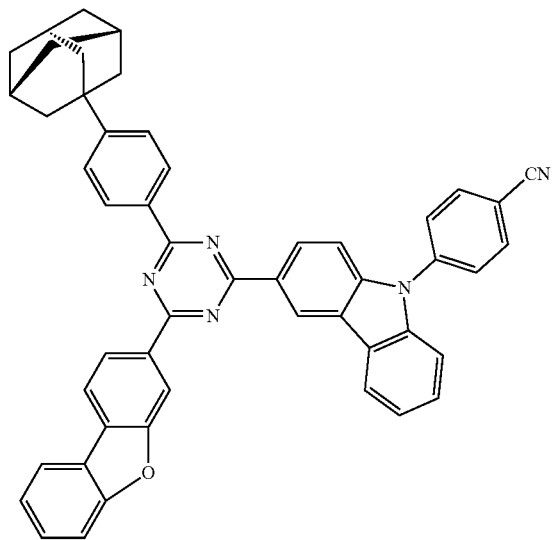

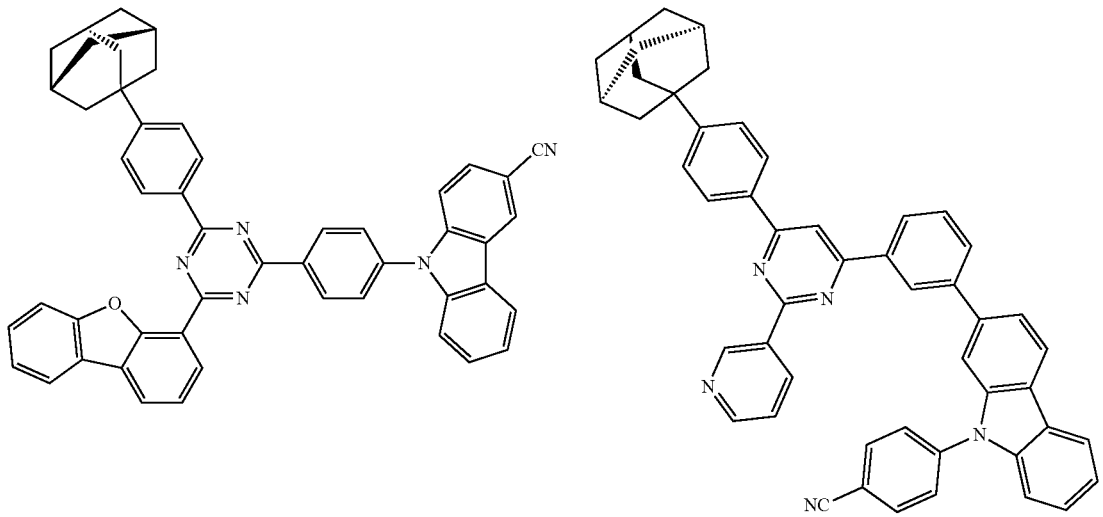
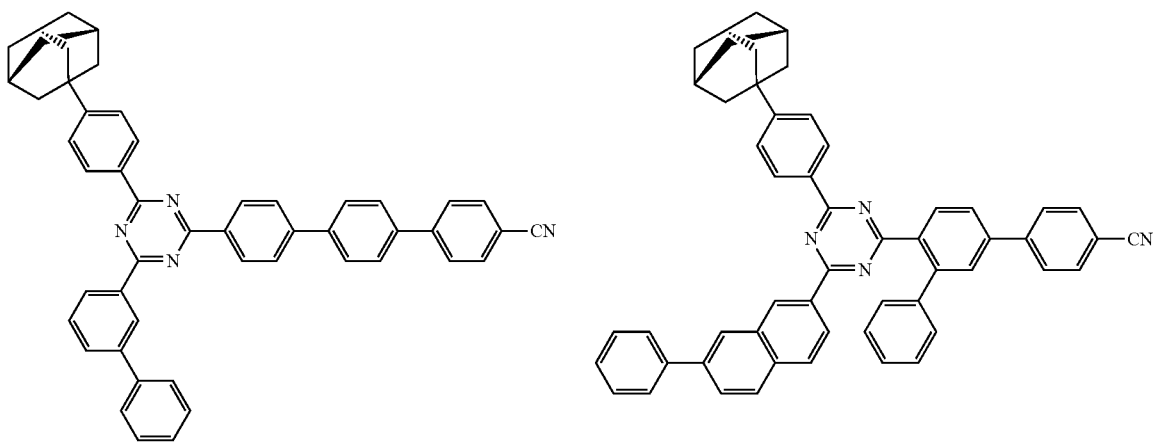
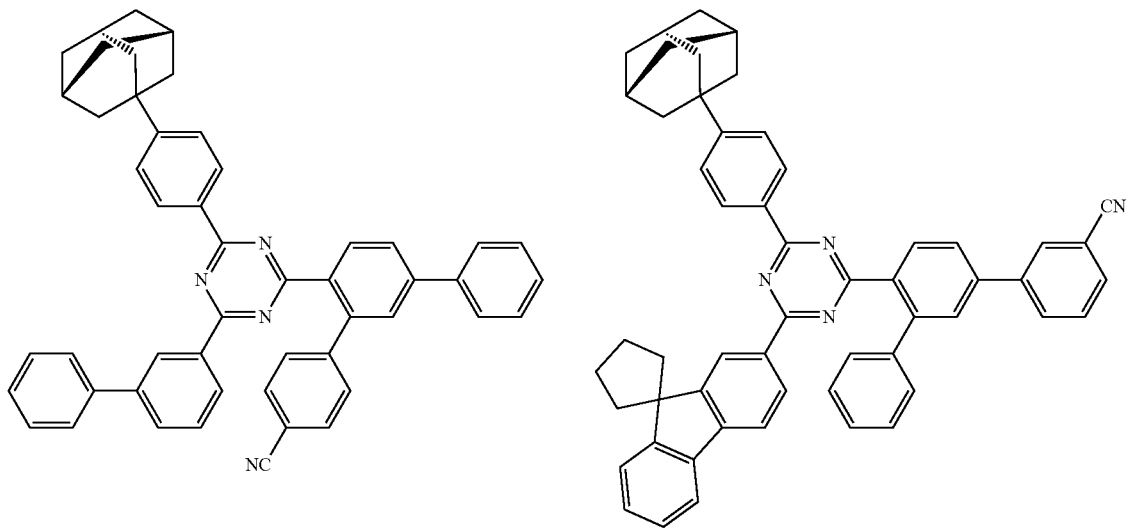

323
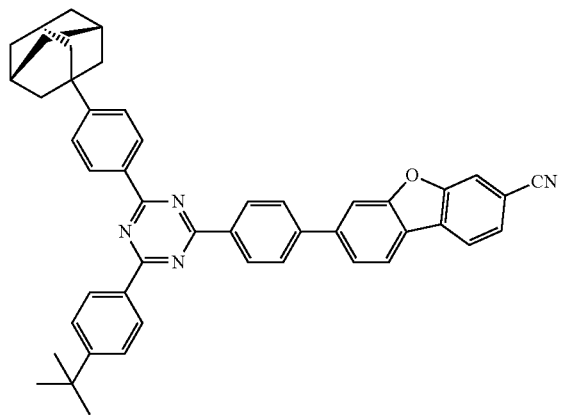
324
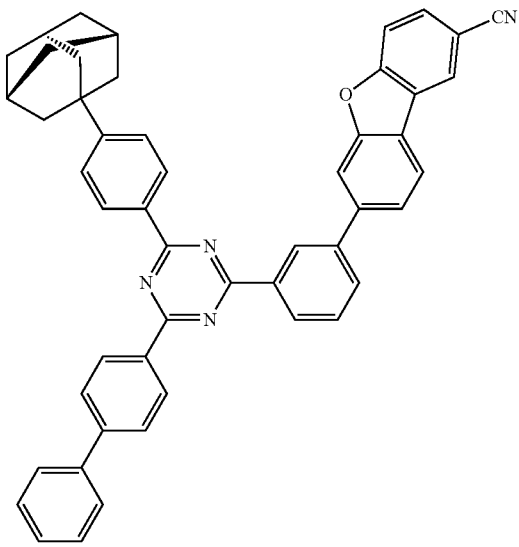
325
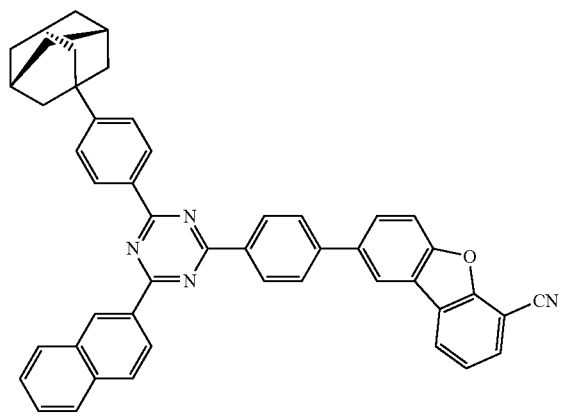
326
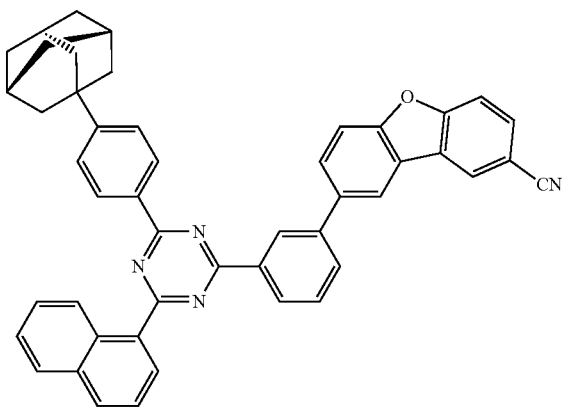
327
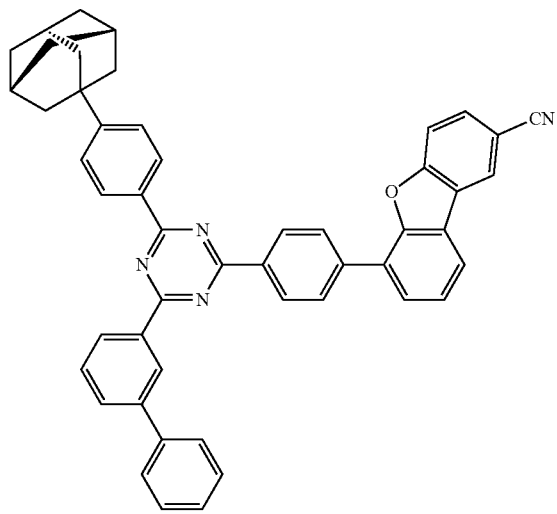
328
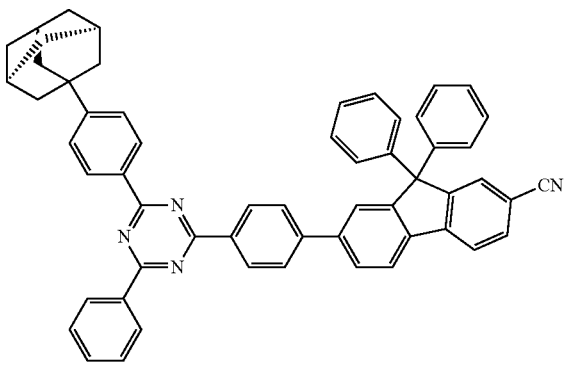

-continued
329
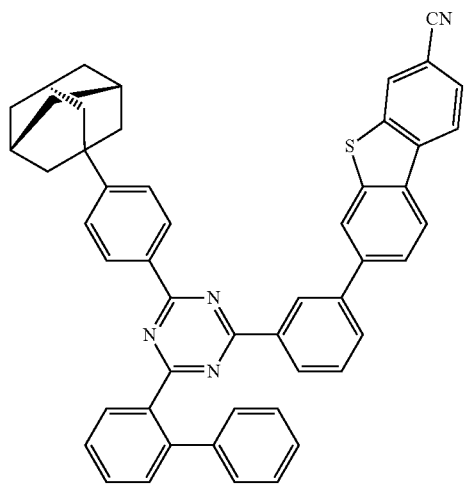
330
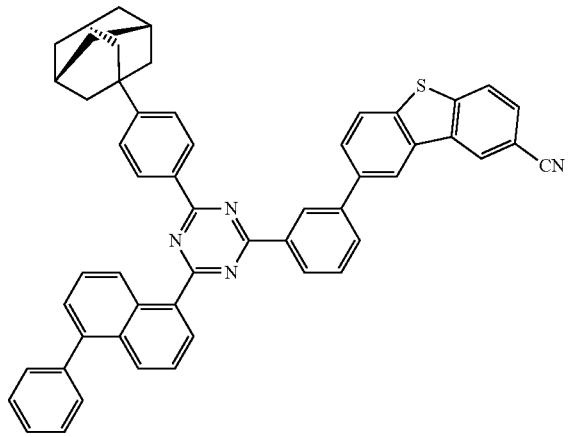
331
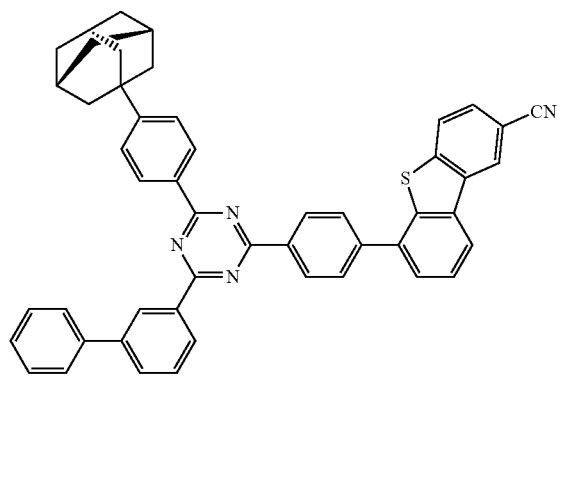
332
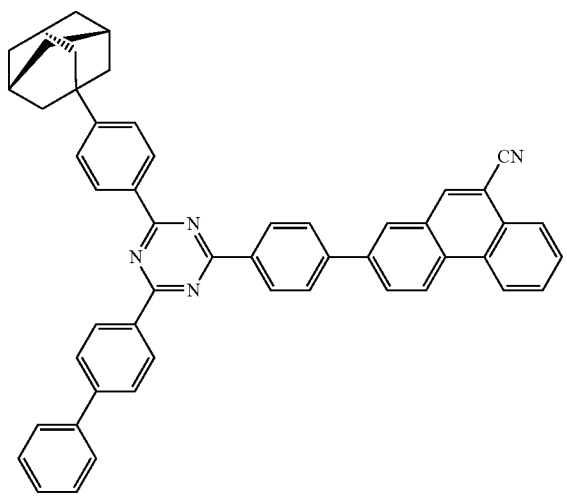
333
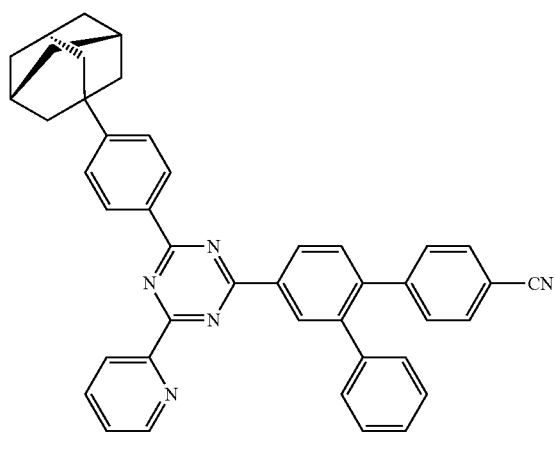
334
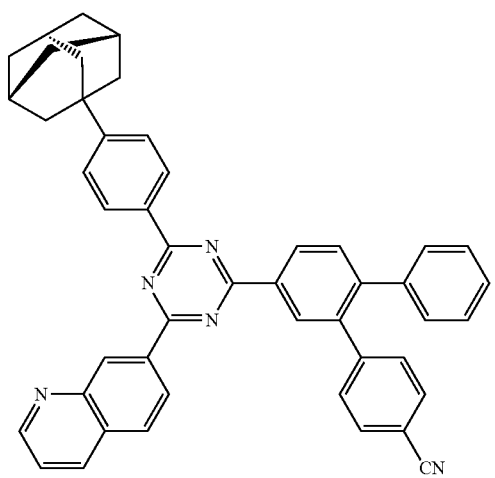

335
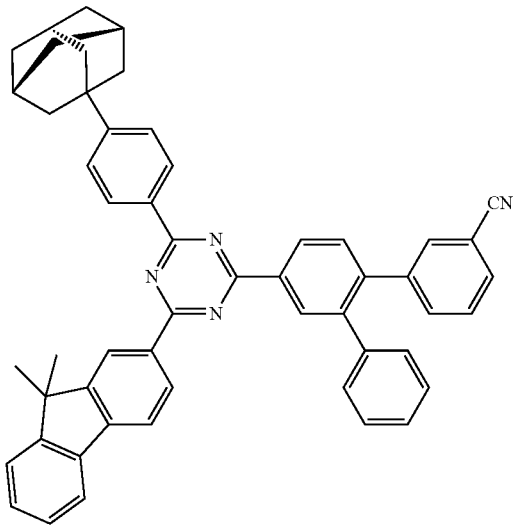
336
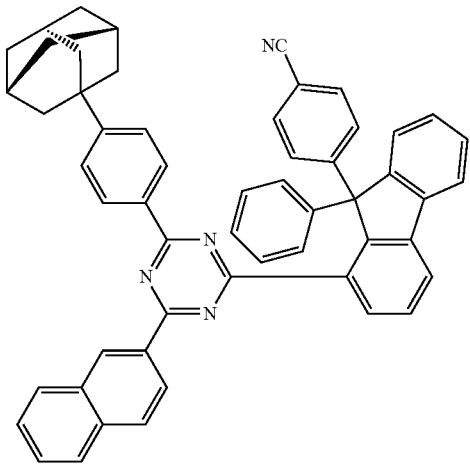
337
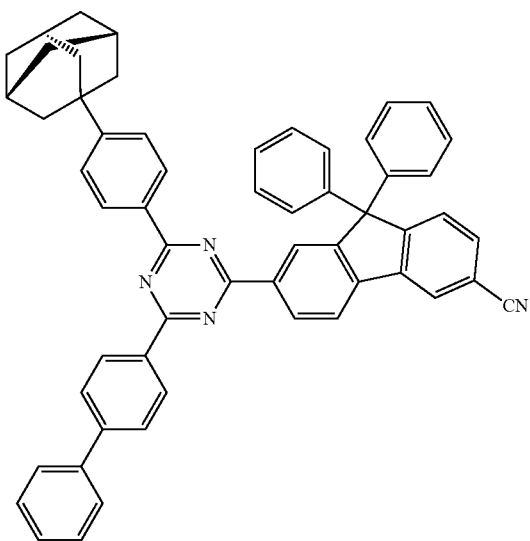
338
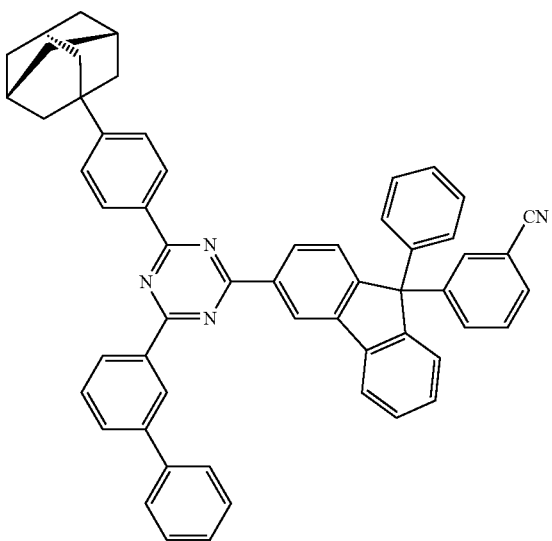
339
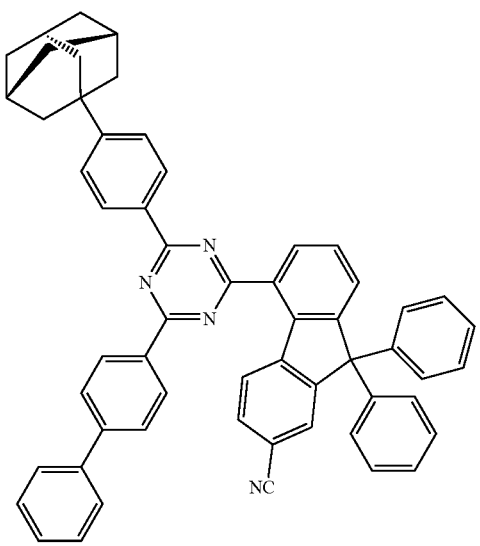
340
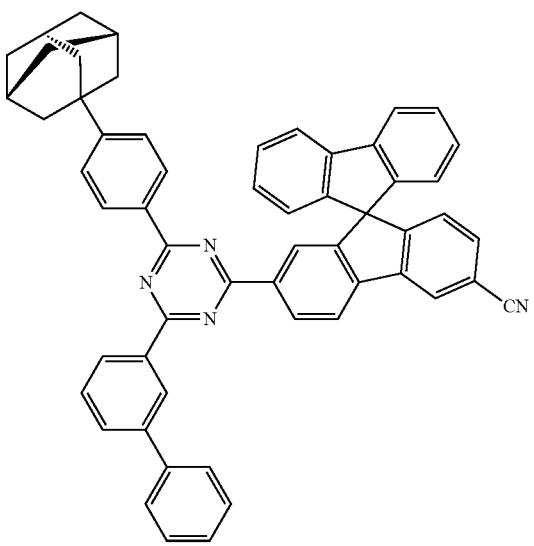

341
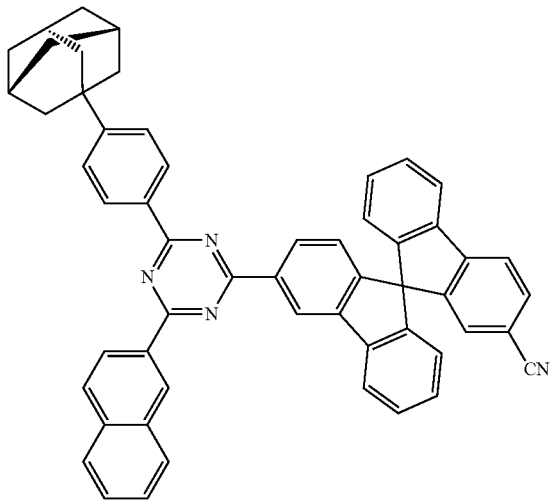
342
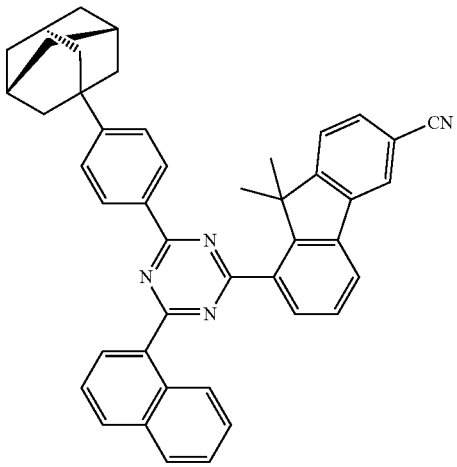
343
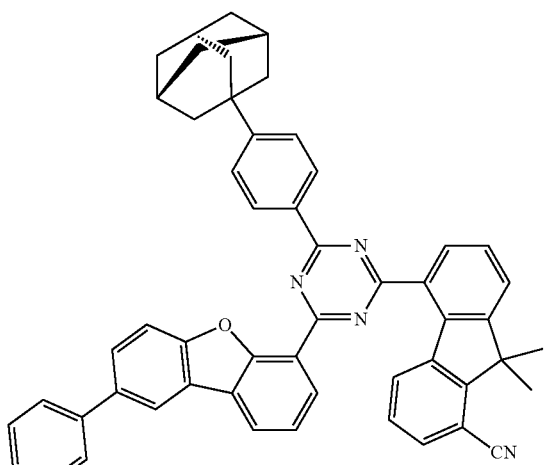
344
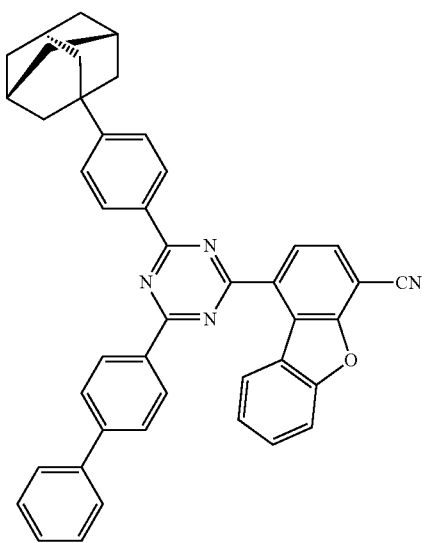
345
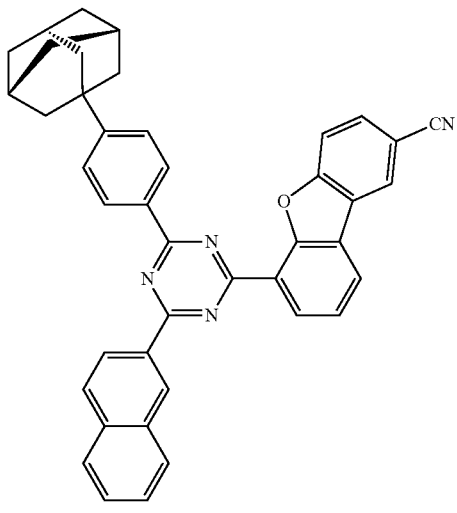
346
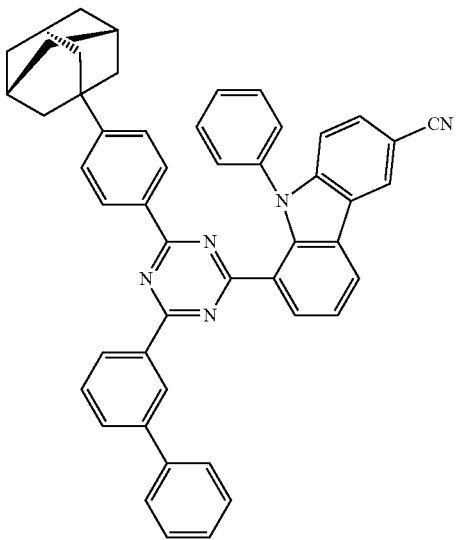

347
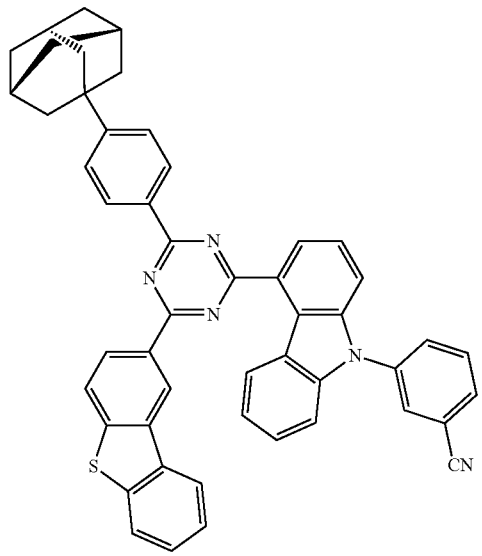
348
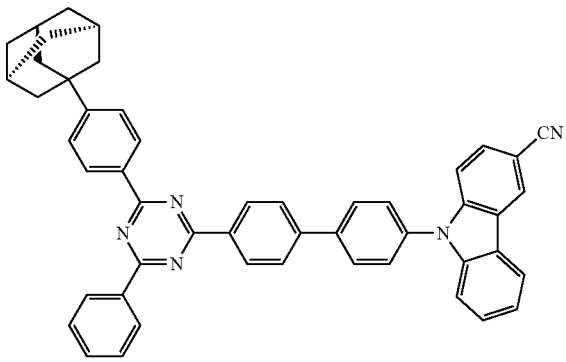
349
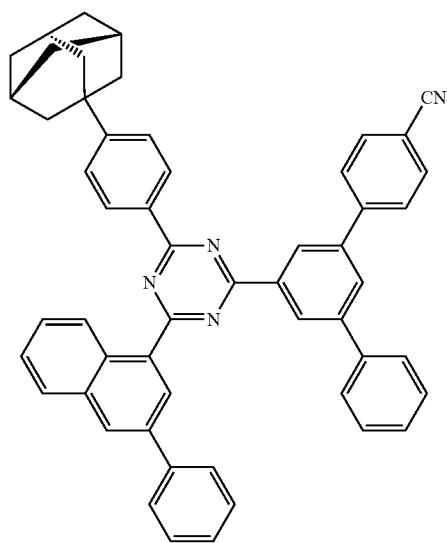
350
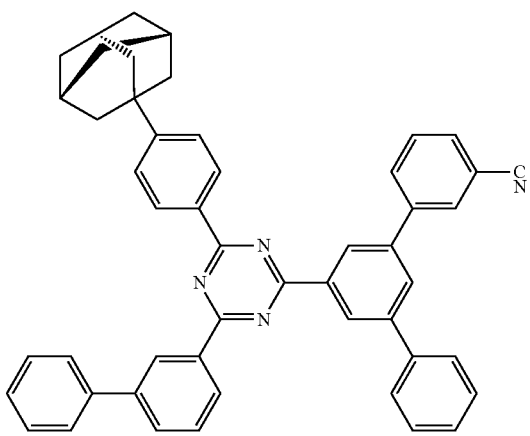

351
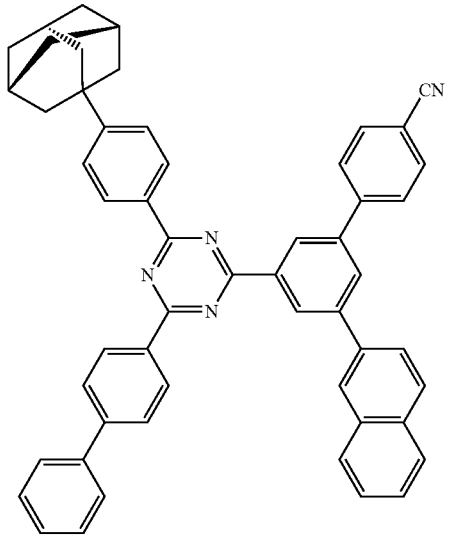
352
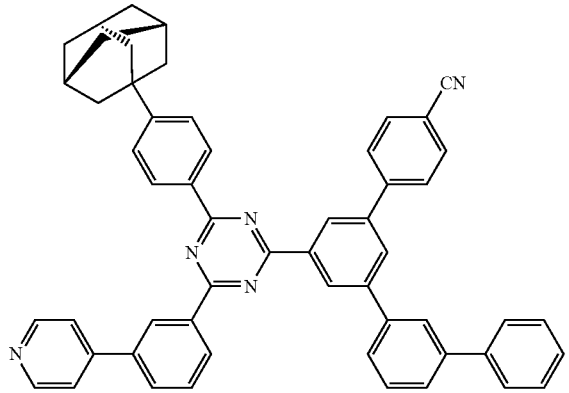
353
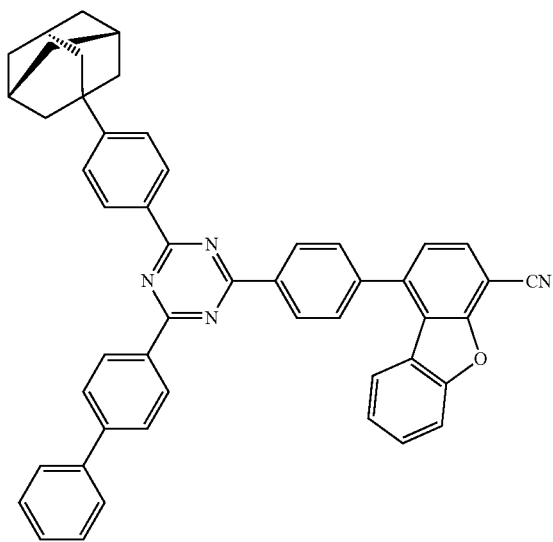
354
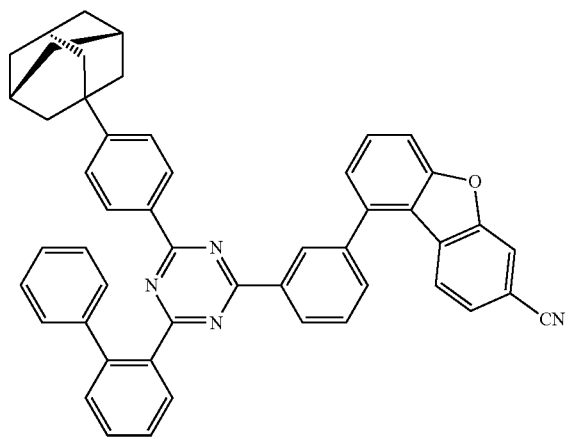

355
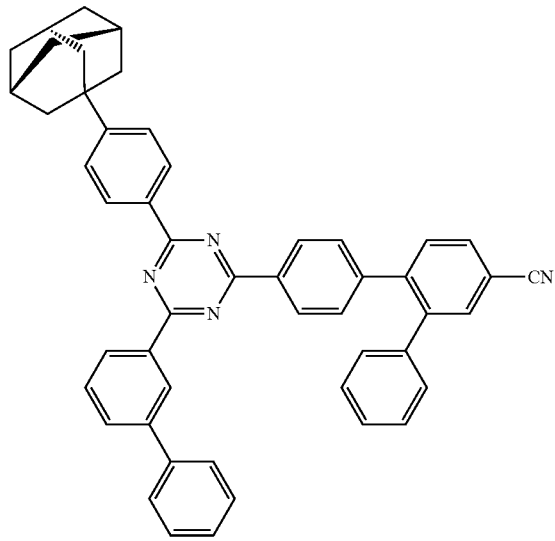
356
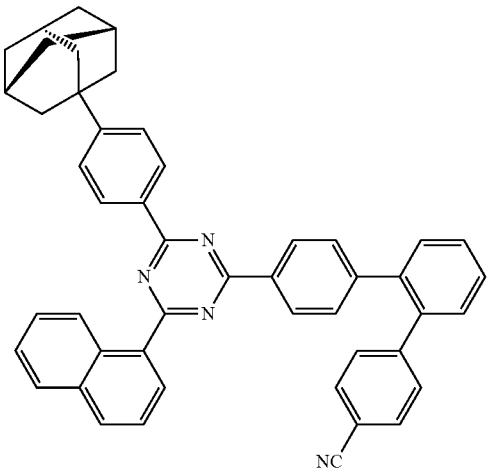
357
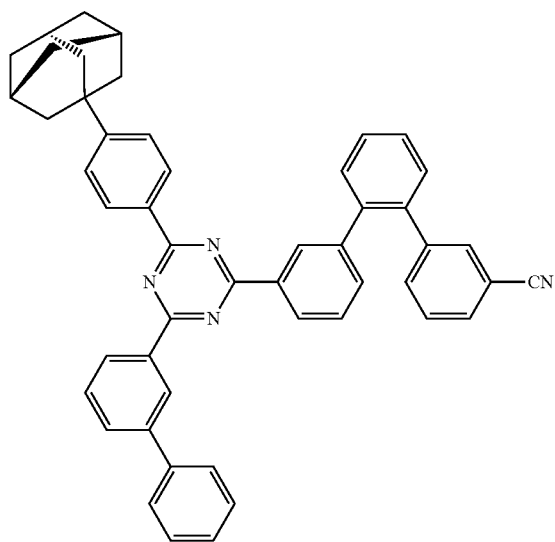
359
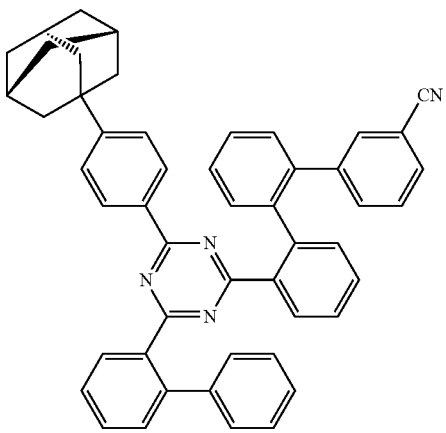

-continued
359
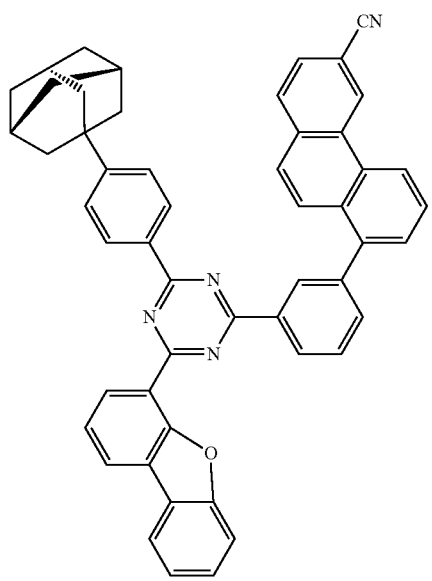
360
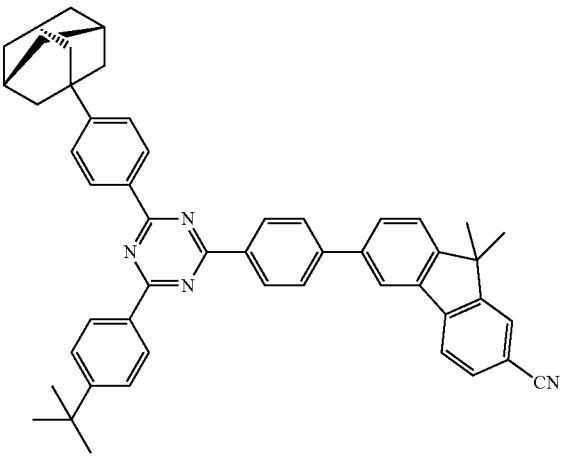
361
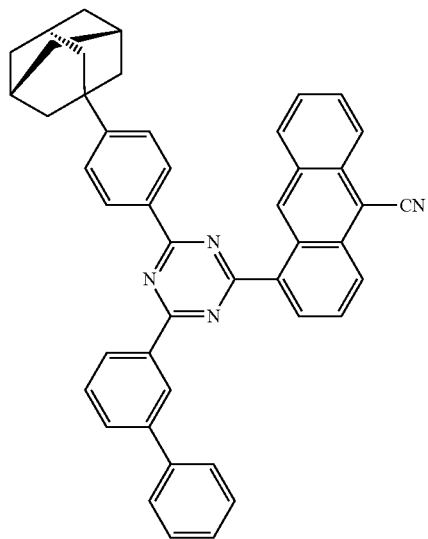
362
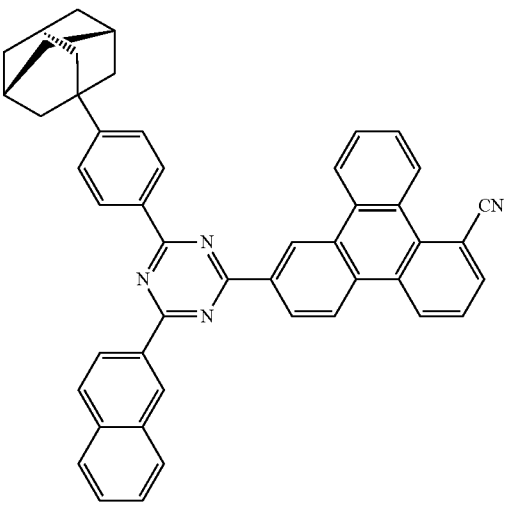
363
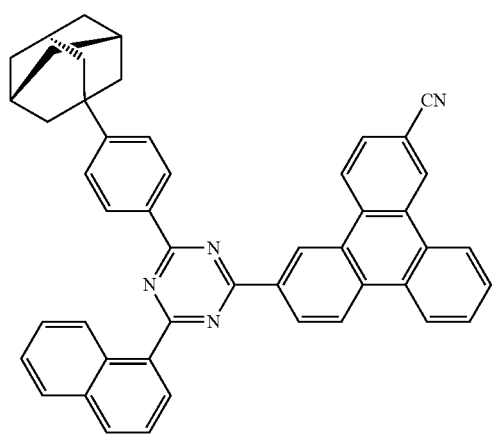
364
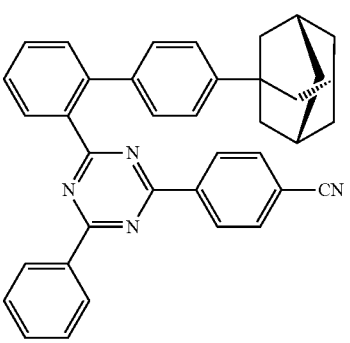

-continued
365
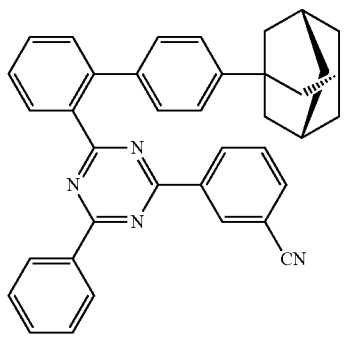
366
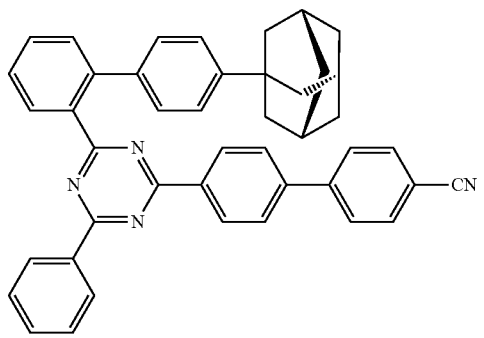
367
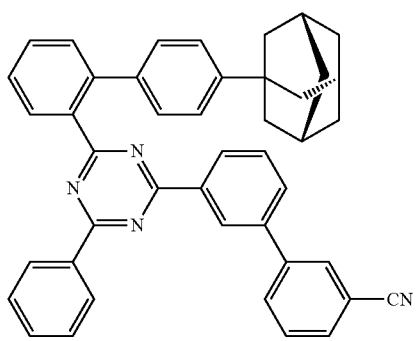
368
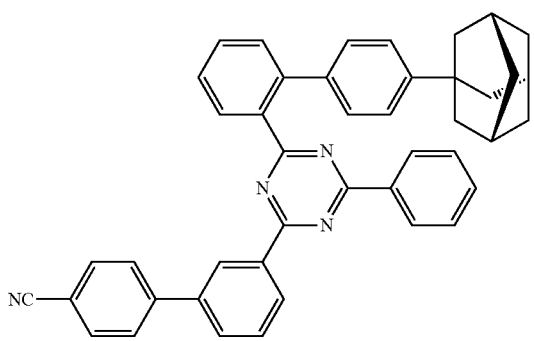
369
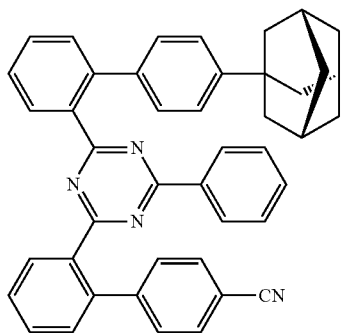
370
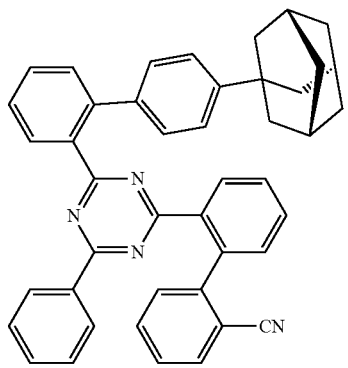
371
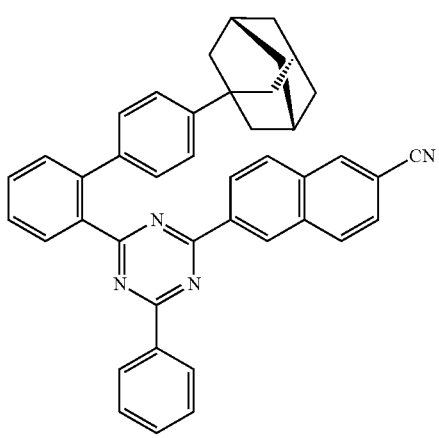
372
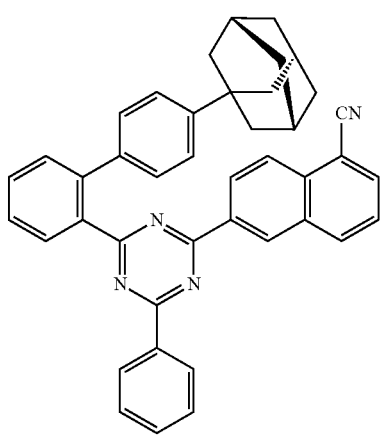

173 174
-continued
| 373 | 374 |
|---|---|
| 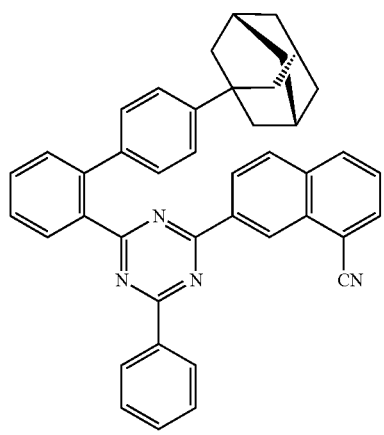 | 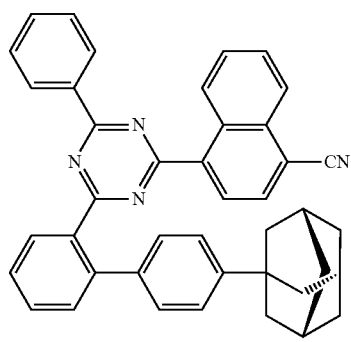 |
| 375 | 376 |
|---|---|
| 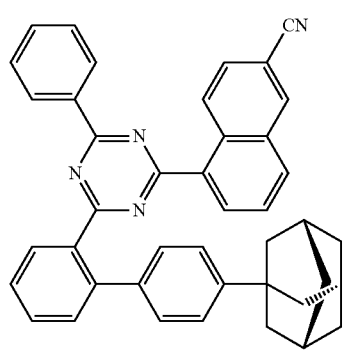 | 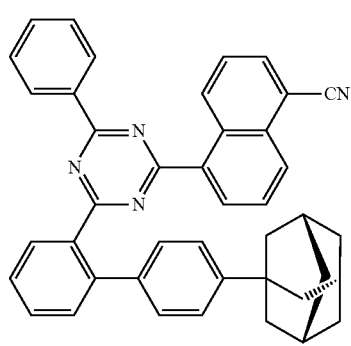 |
| 377 | 378 |
|---|---|
| 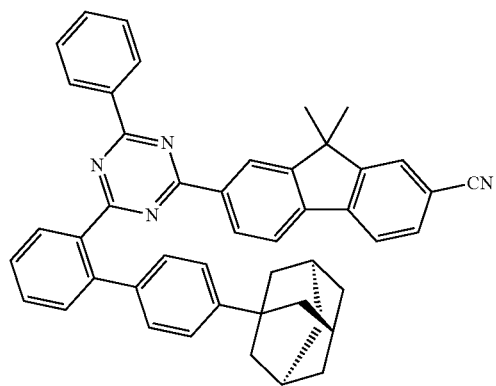 | 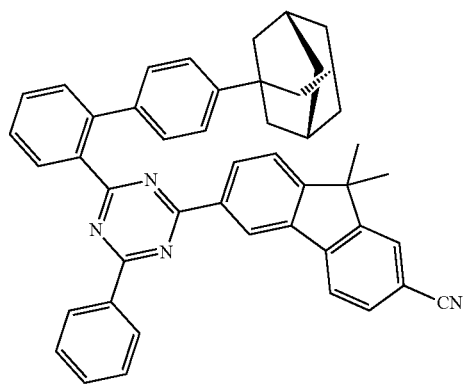 |
| 379 | 380 |
|---|---|
| 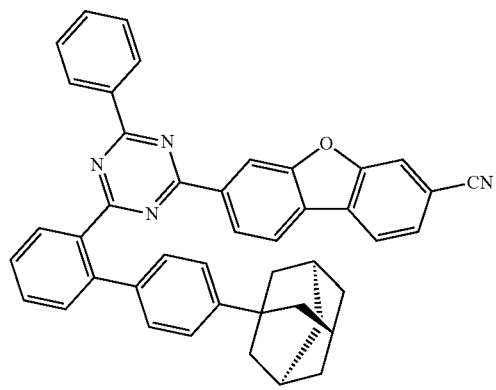 | 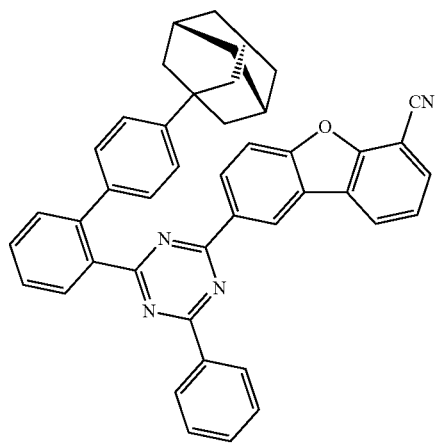 |

-continued
| 381 | 382 |
|---|---|
| 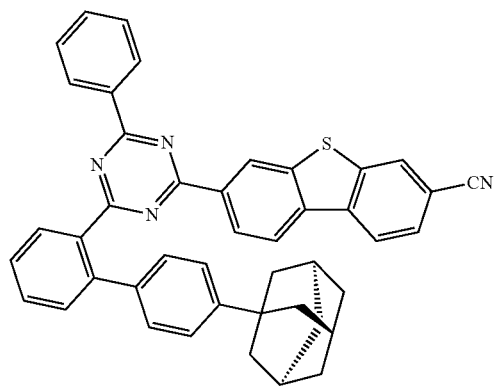 | 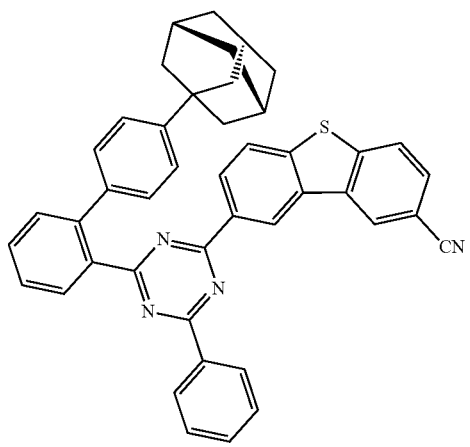 |
| 383 | 384 |
| 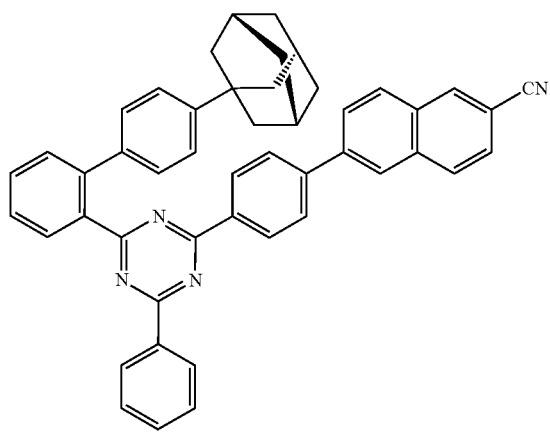 | 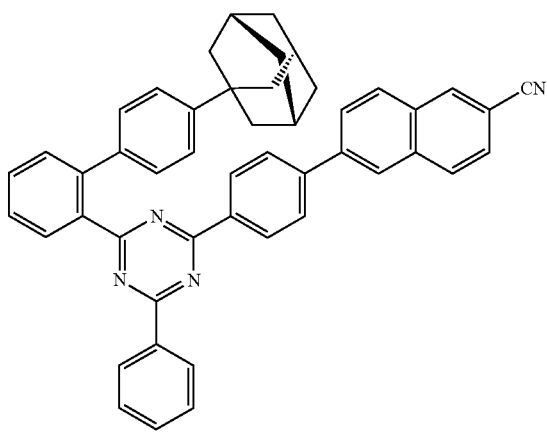 |
| 385 | 386 |
| 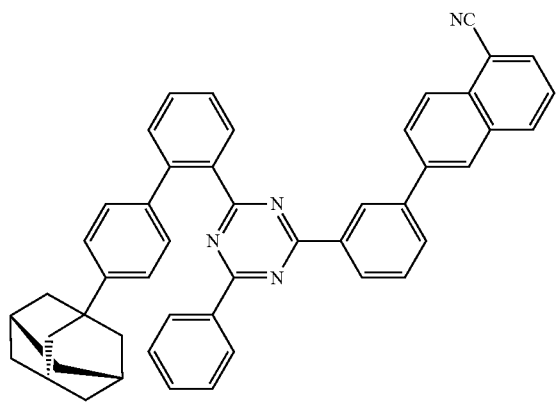 | 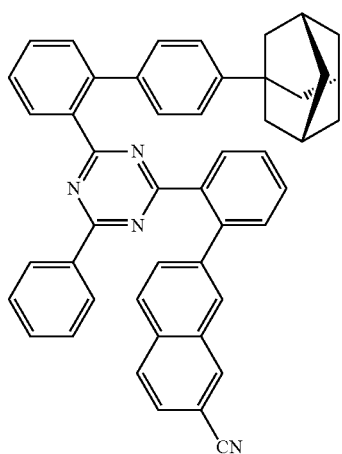 |

-continued
| 387 | 388 |
|---|---|
| 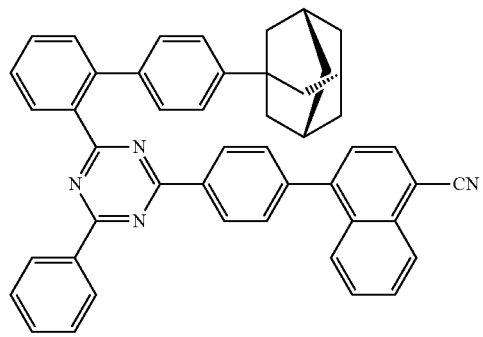 | 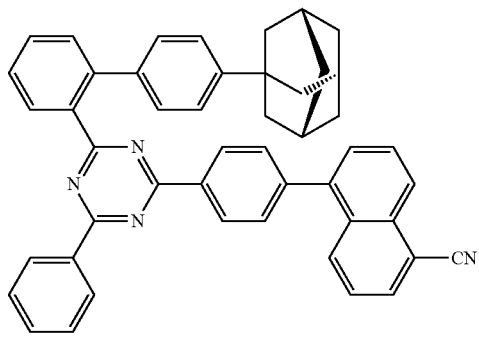 |
| 389 | 390 |
| 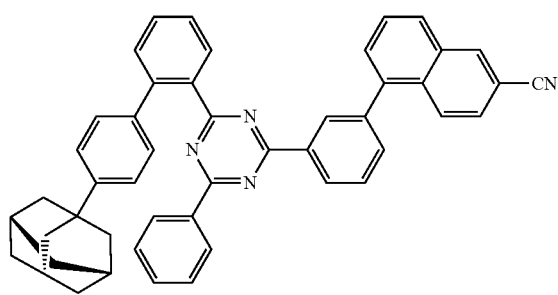 | 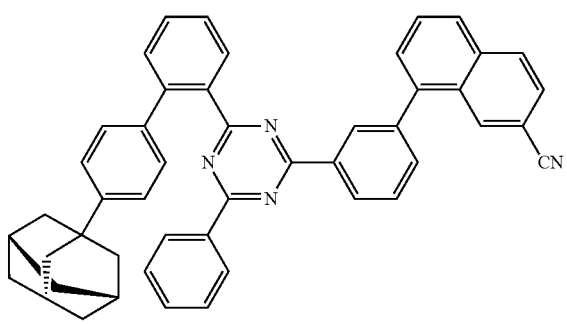 |
| 391 | 392 |
| 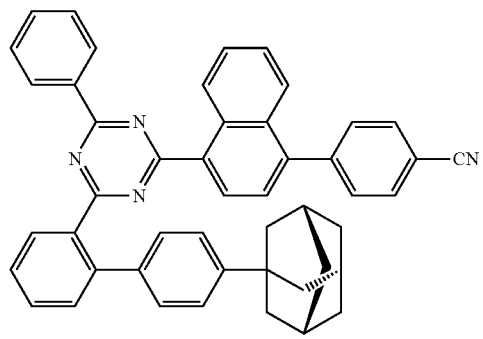 | 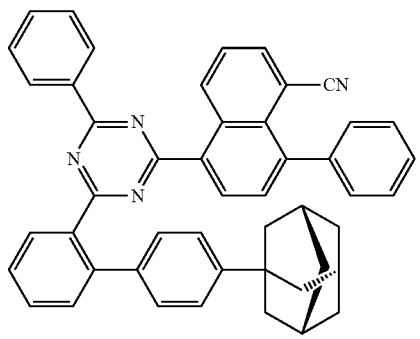 |
| 393 | 394 |
| 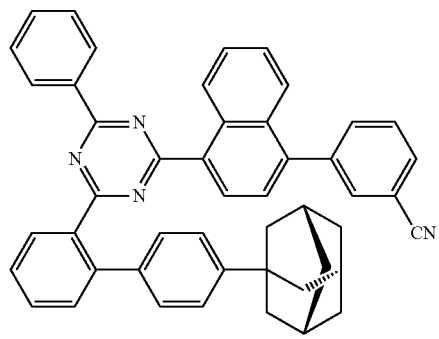 | 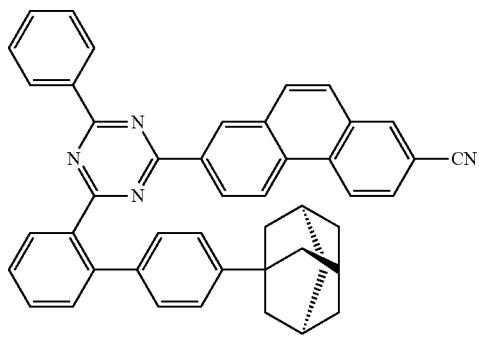 |

-continued
395
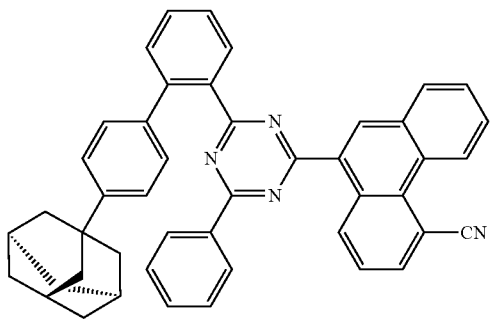
396
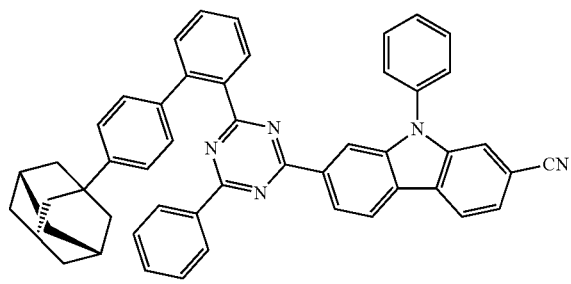
397
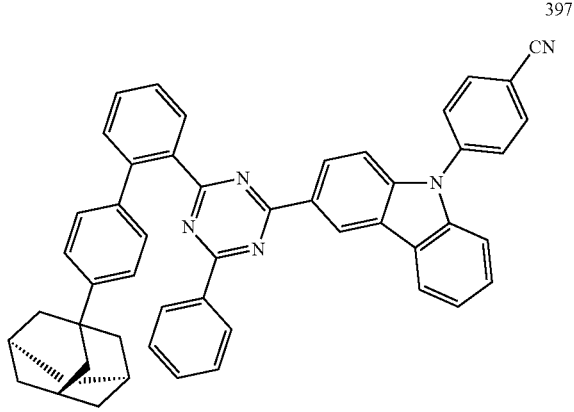
398
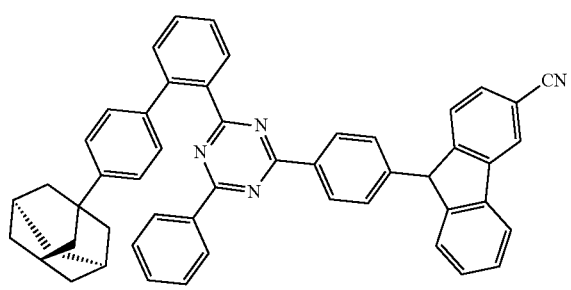
399
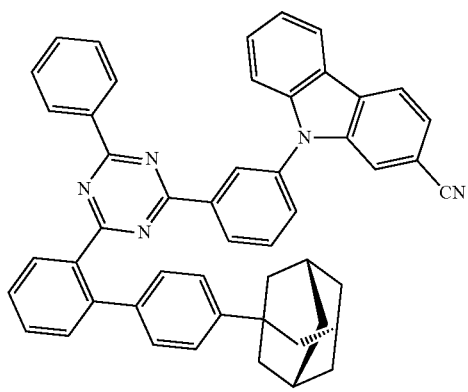
400
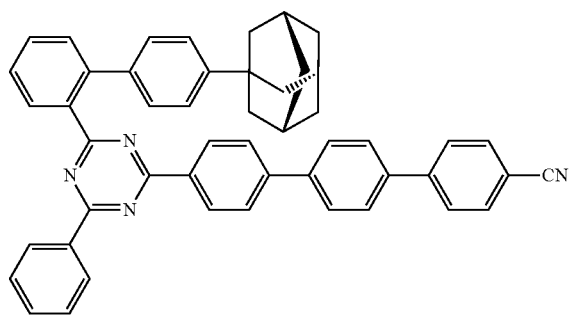
401
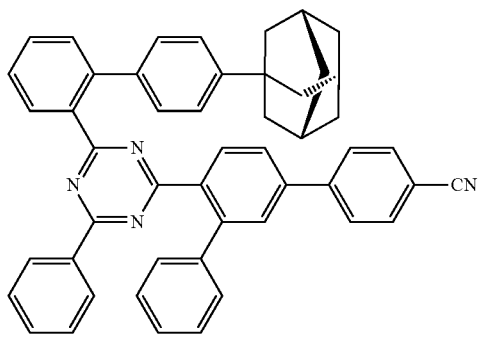
402
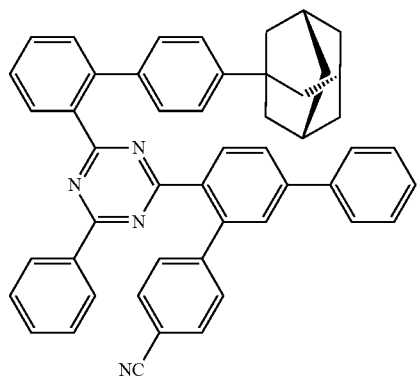

-continued
| 403 | 404 |
|---|---|
| 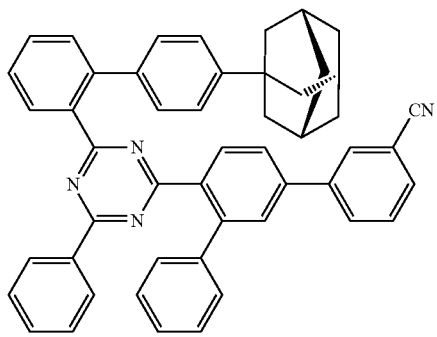 | 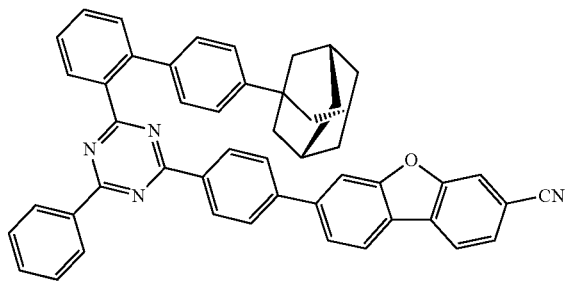 |
| 405 | 406 |
| 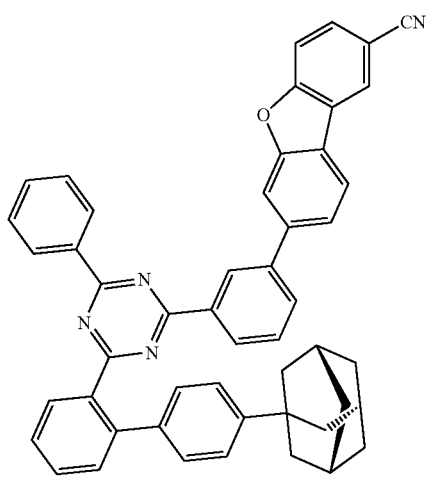 | 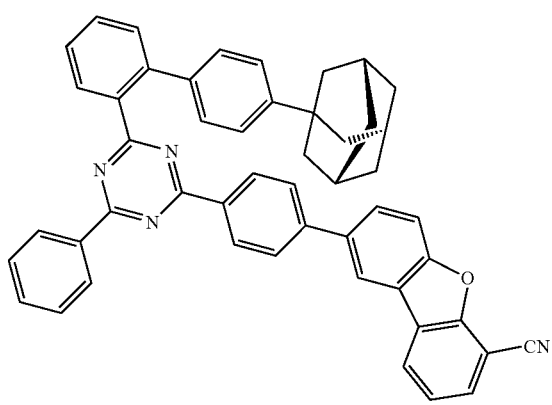 |
| 407 | 408 |
| 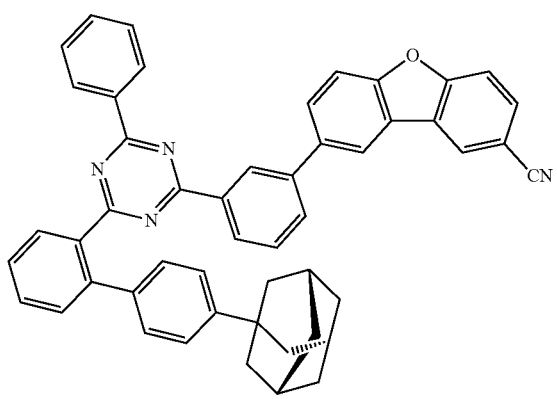 | 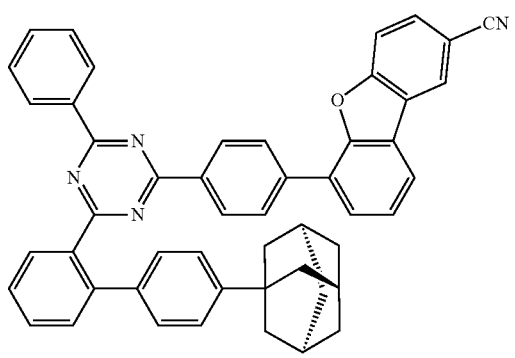 |

409
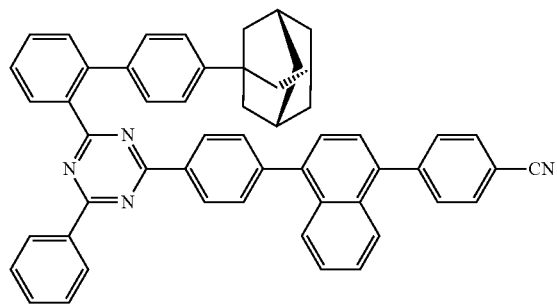
183
410
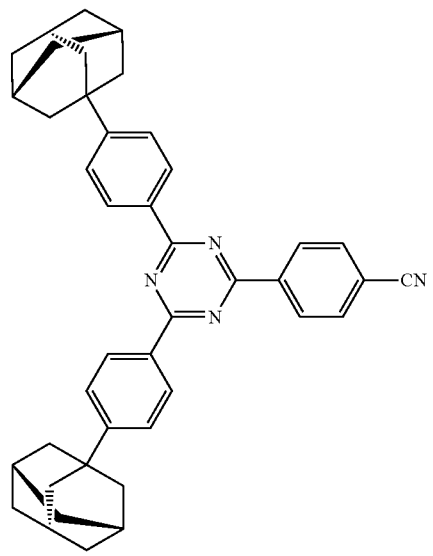
184
411
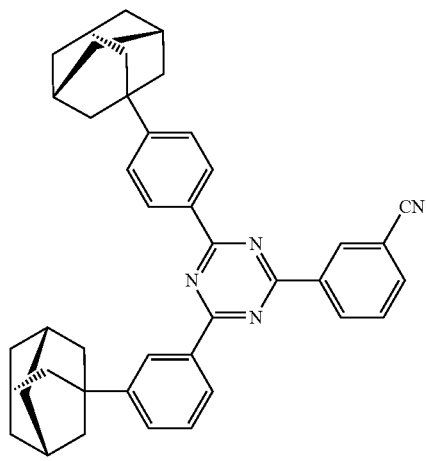
412
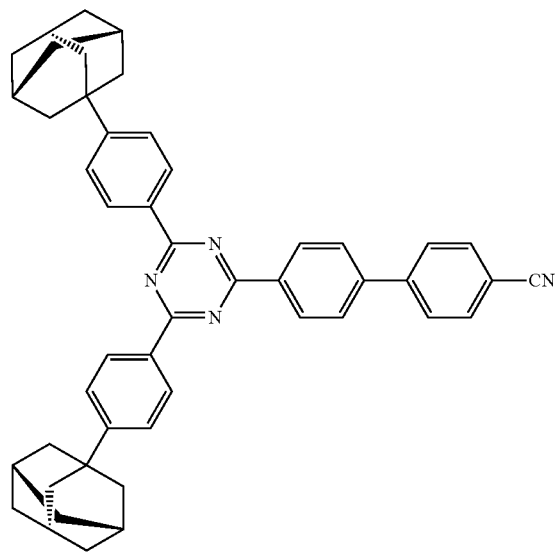

-continued
413
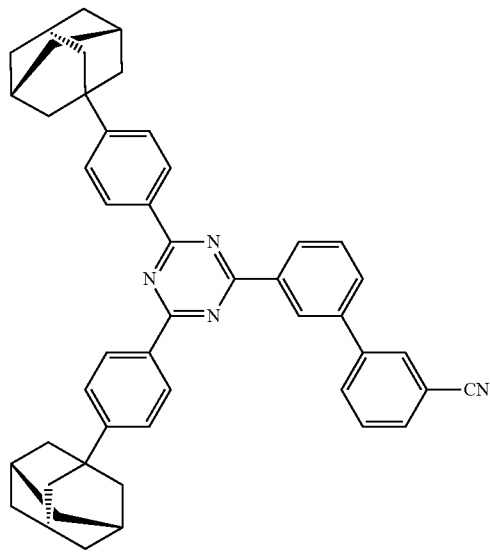
414
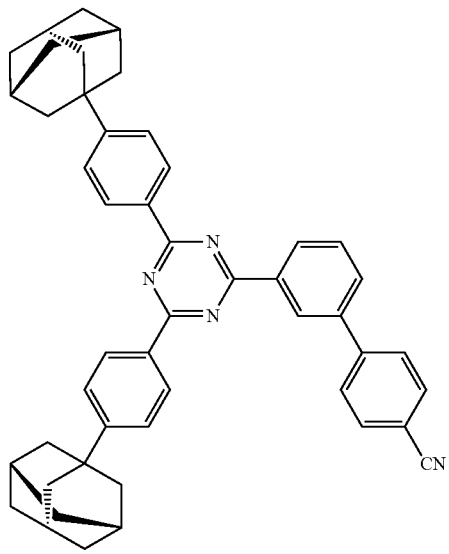
415
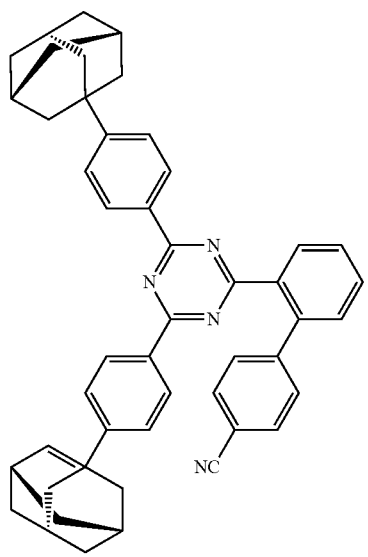
416
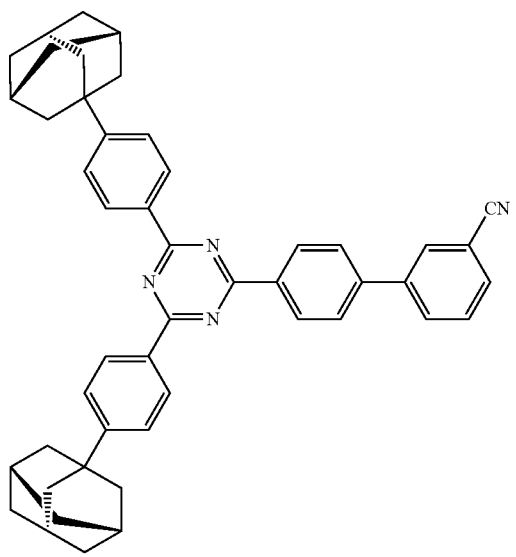
417
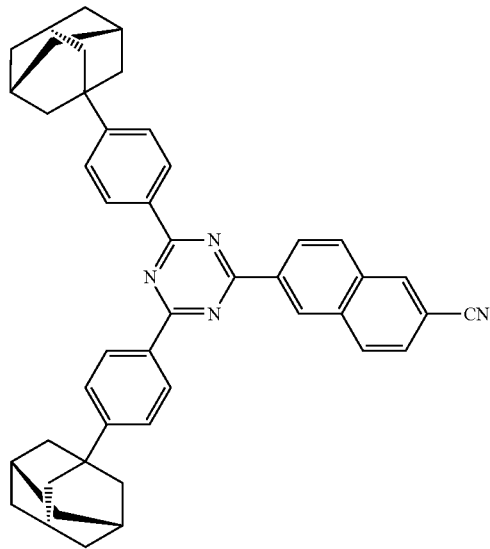
418
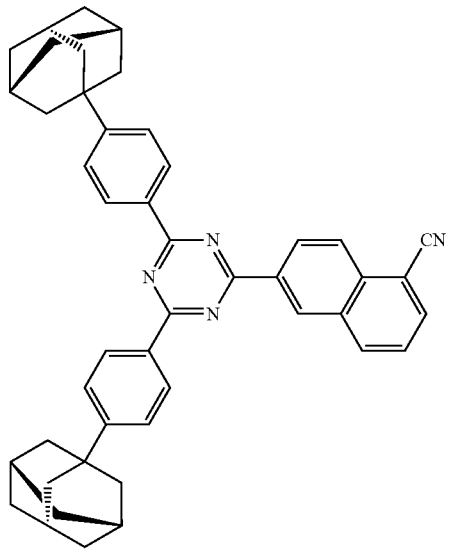

-continued
419
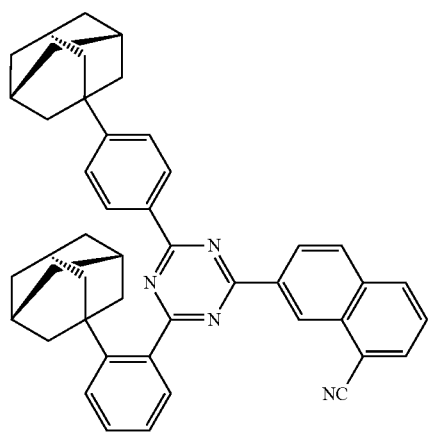
420
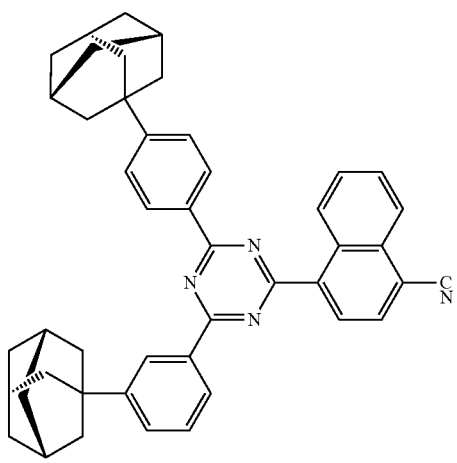
421
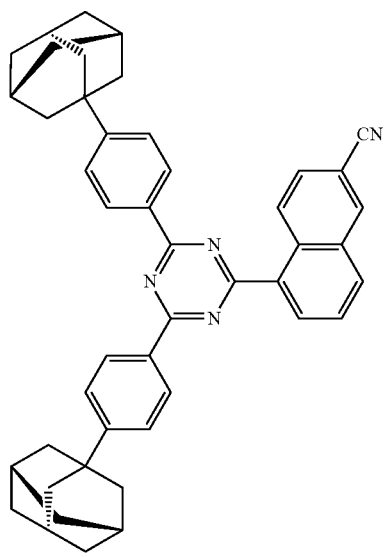
422
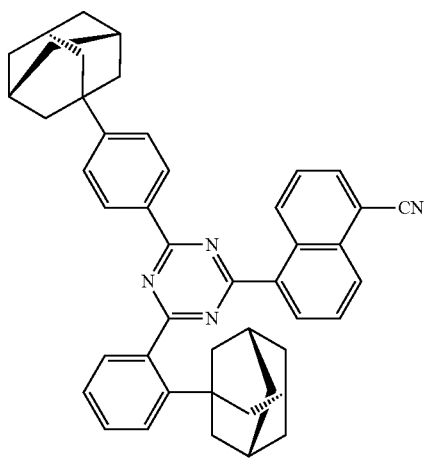
423
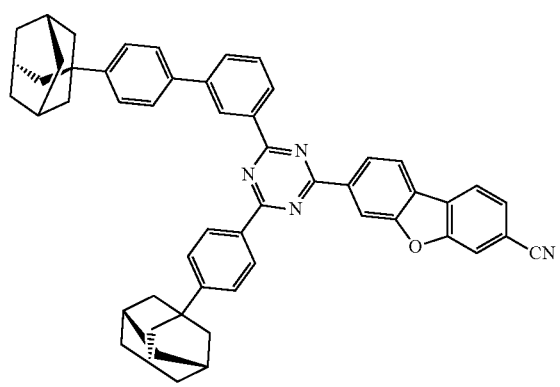
424
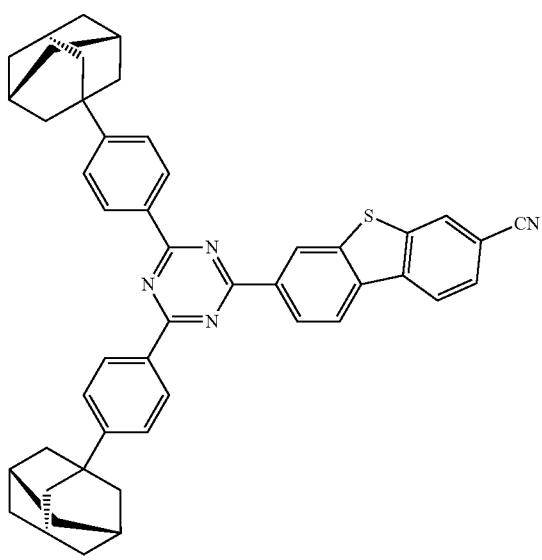

-continued
425
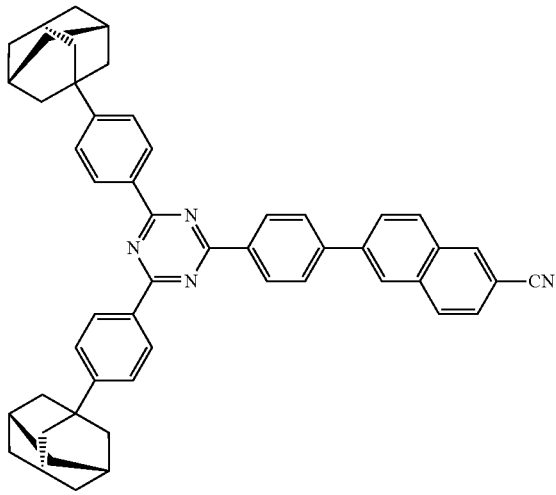
426
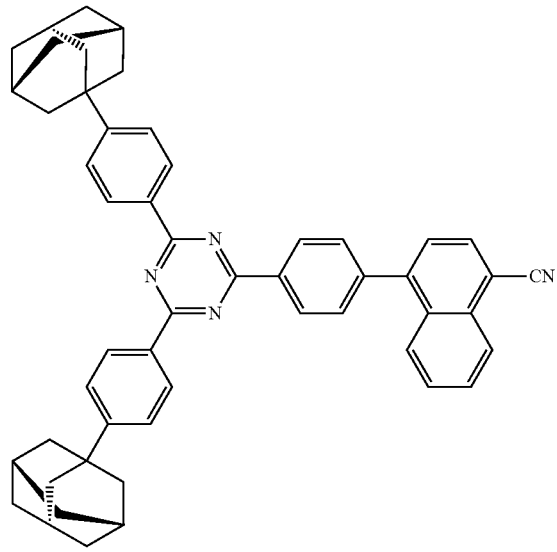
427
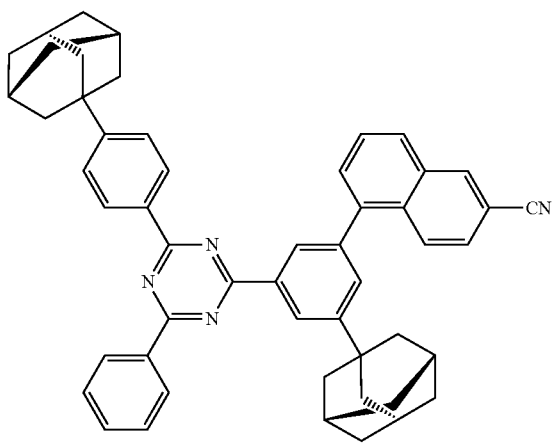
428
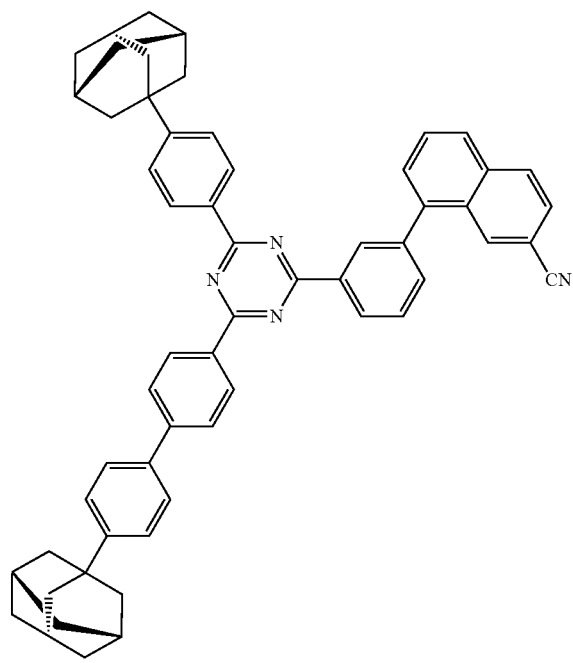
429
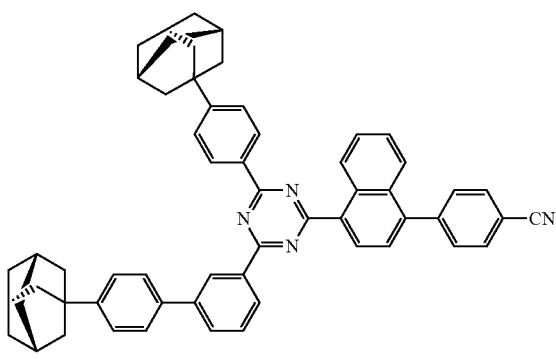
430
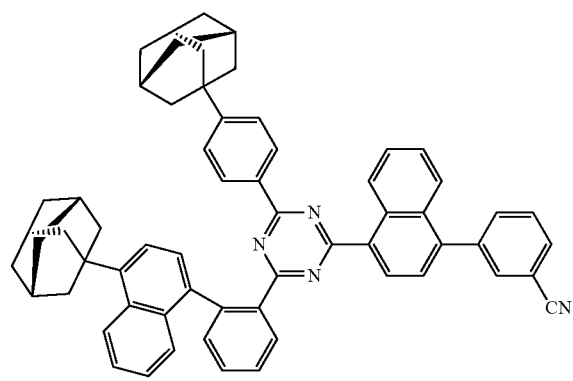

431
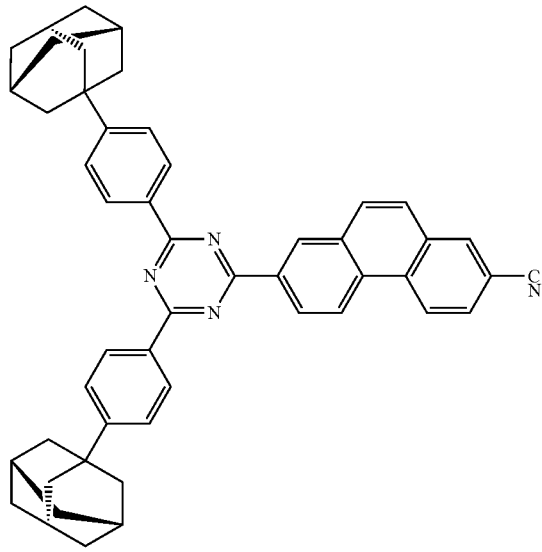
432
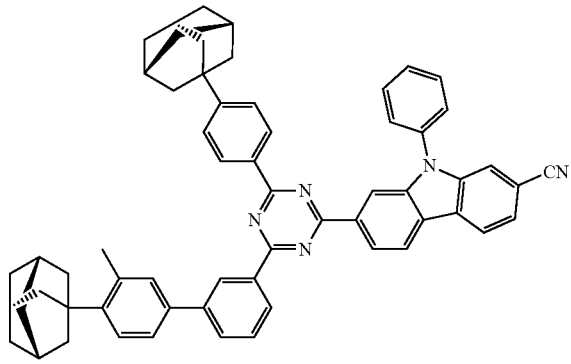
433
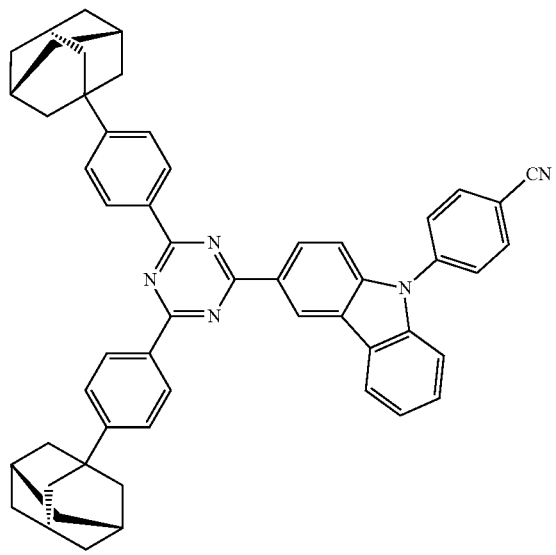
434
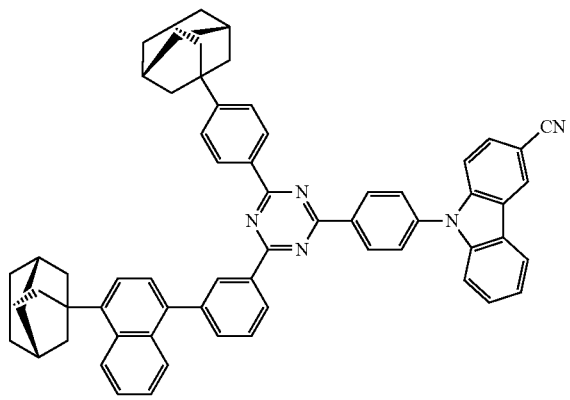

435
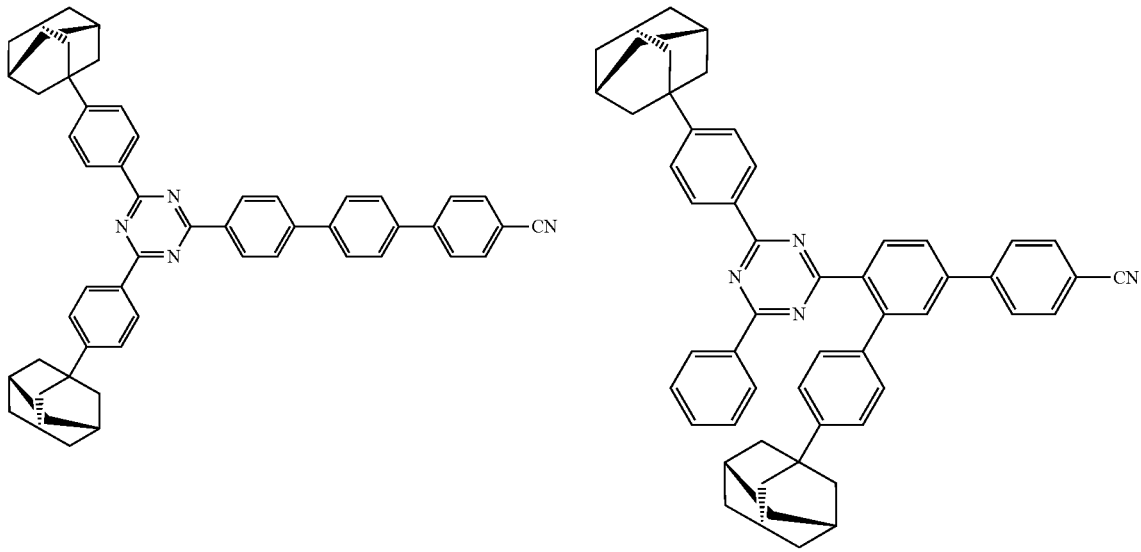
436
437
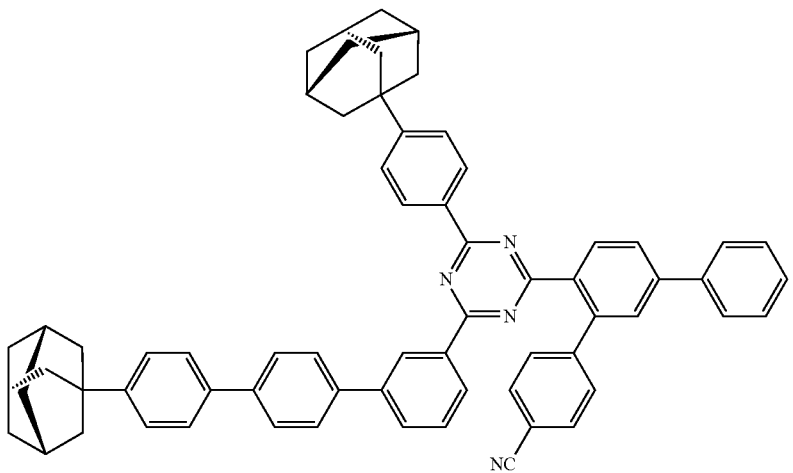
438
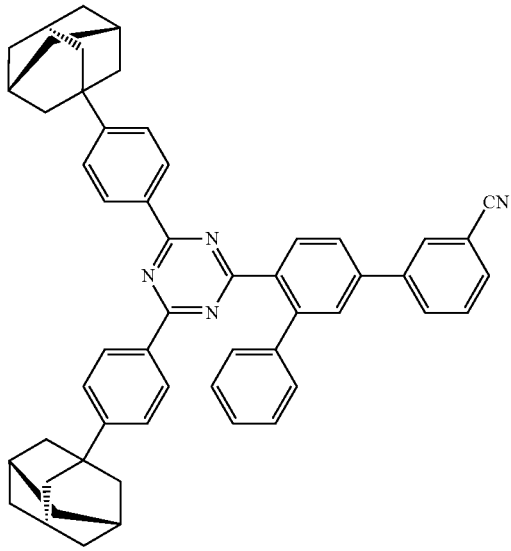

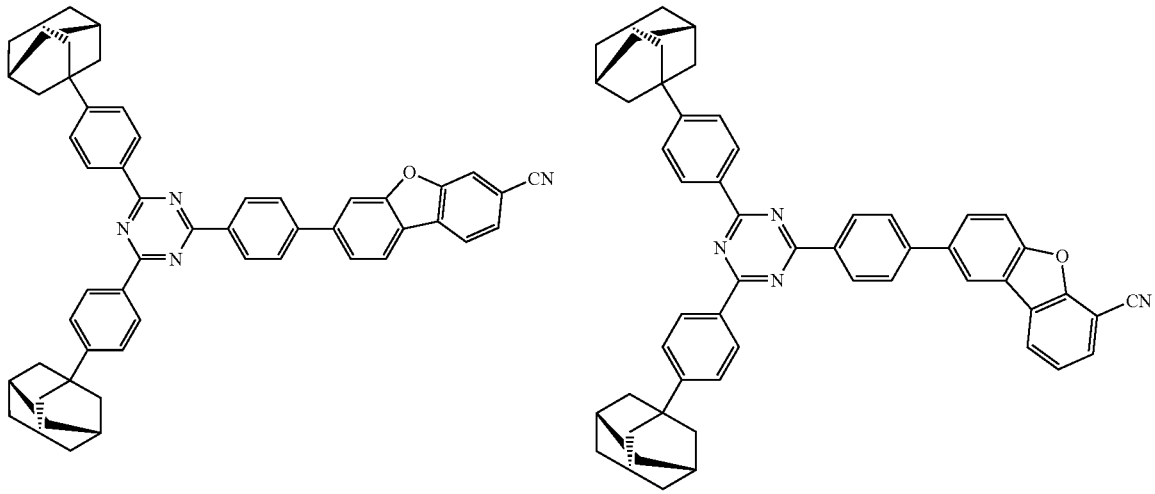
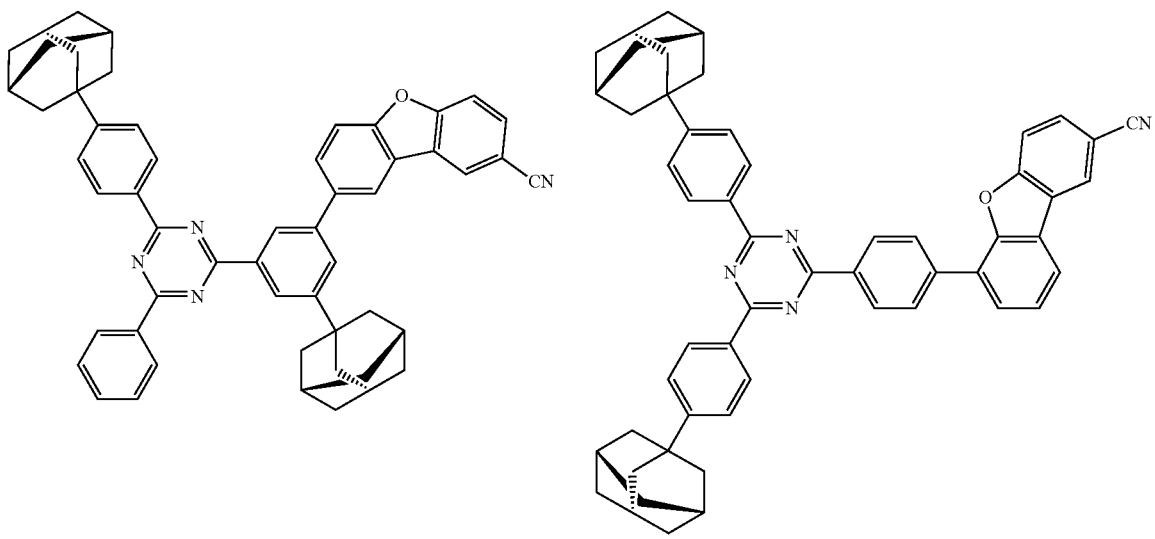

-continued
443
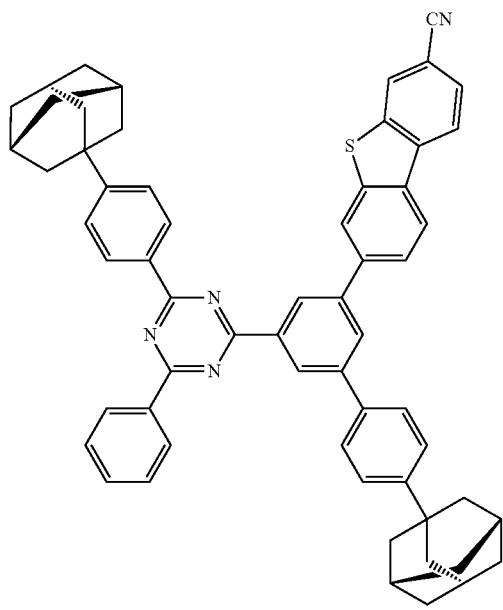
444
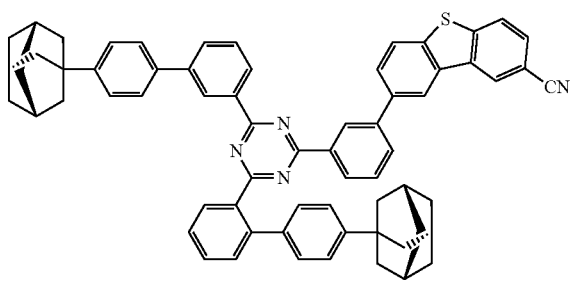
445
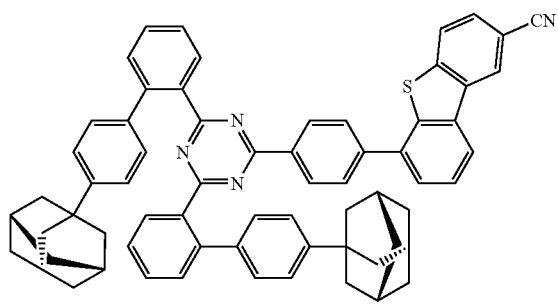
446
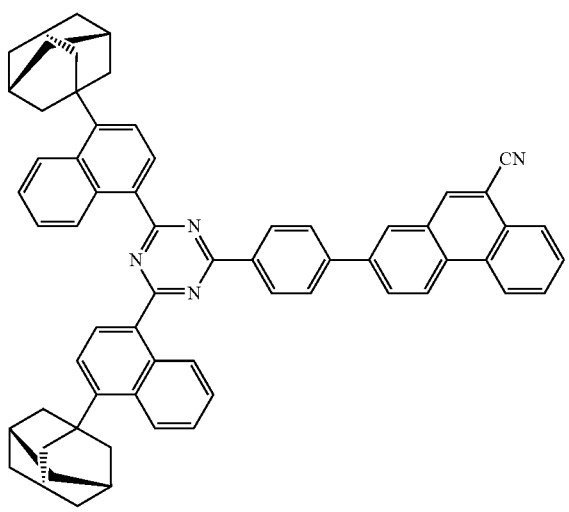

447
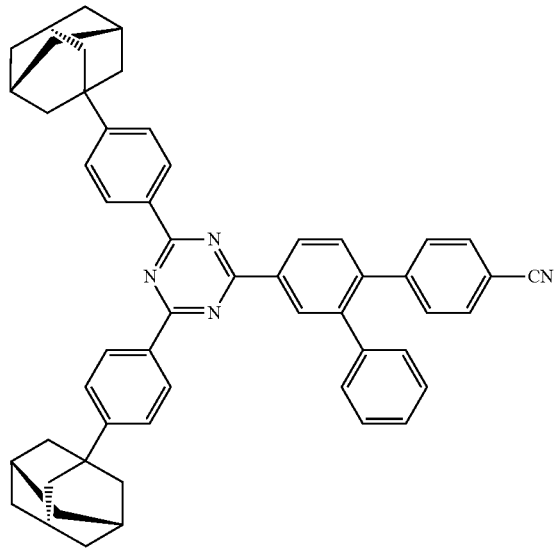
448
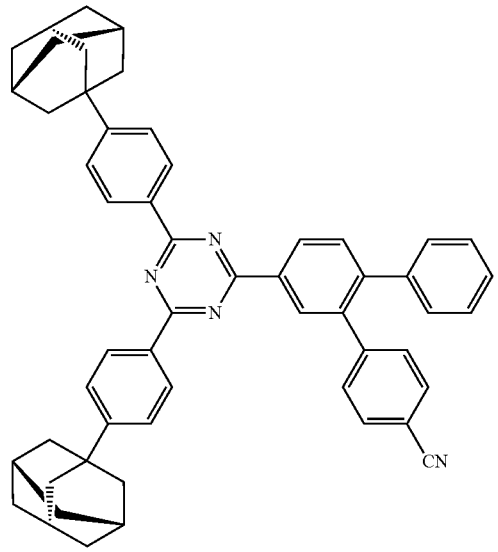
449
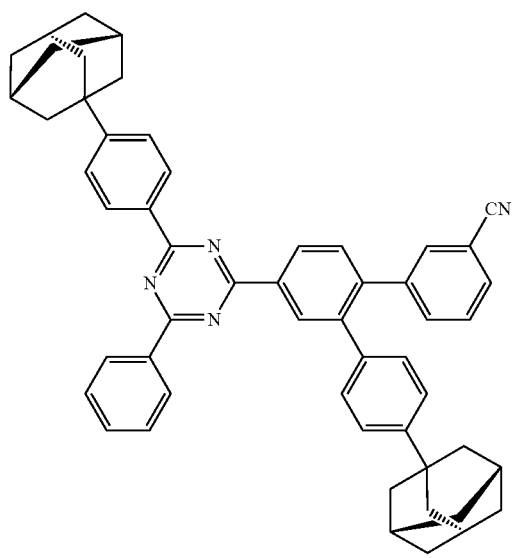
450
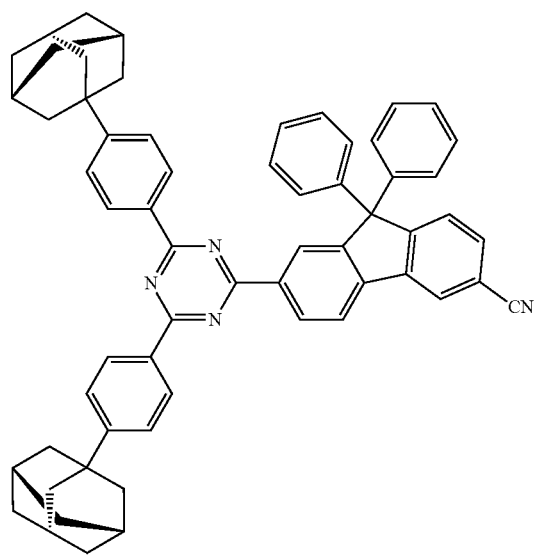

201 202
-continued
| 451 | 452 |
|---|---|
| 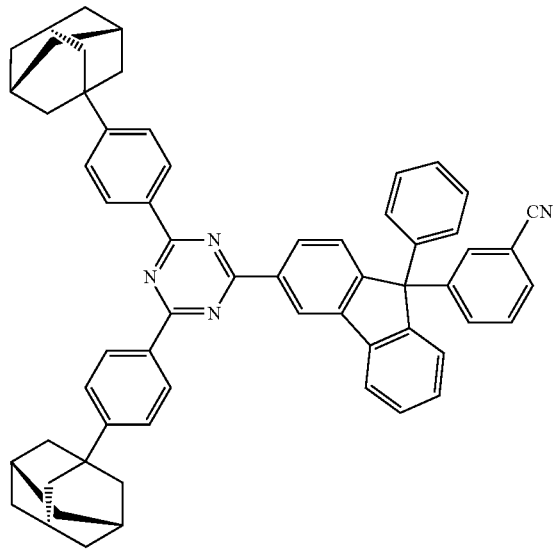 | 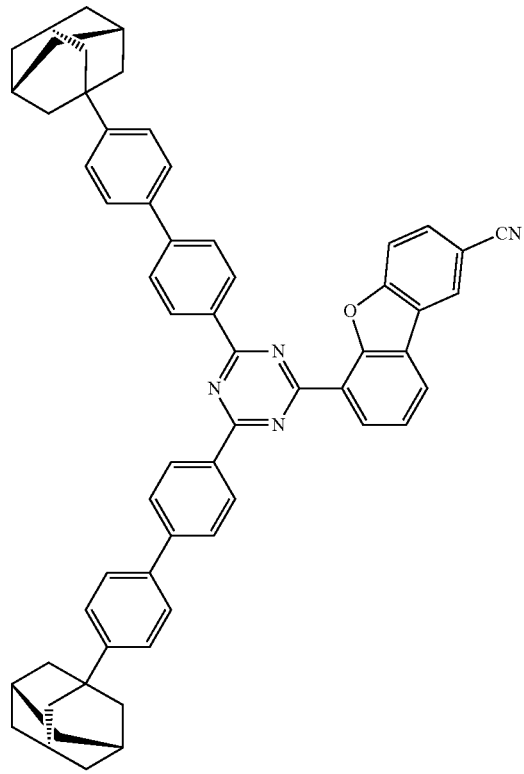 |
| 453 | 454 |
|---|---|
| 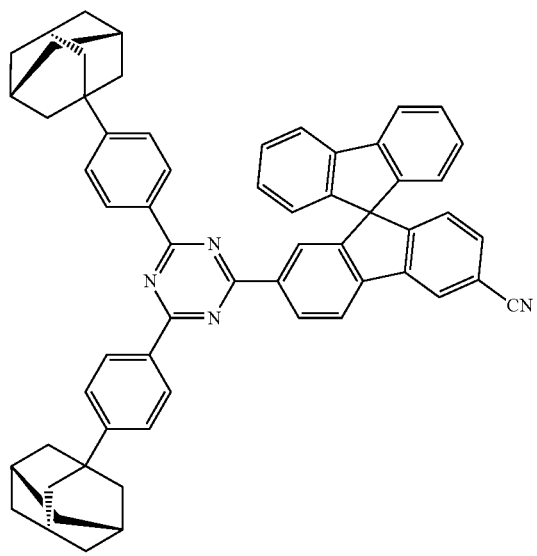 | 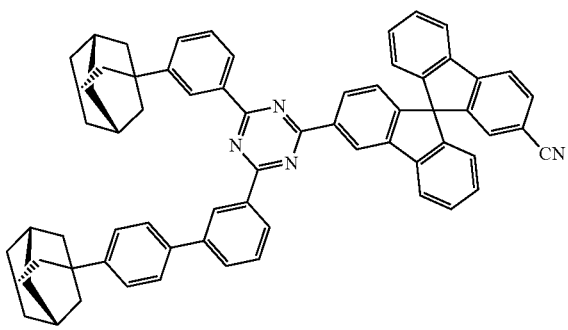 |

-continued
455
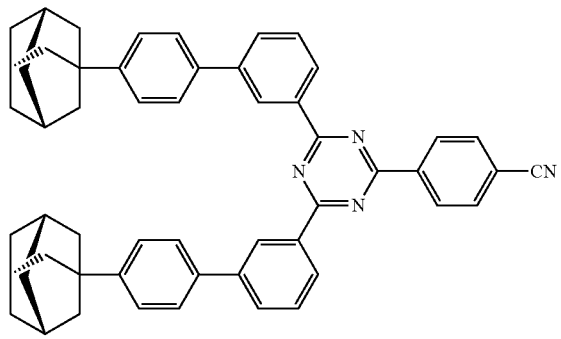
456
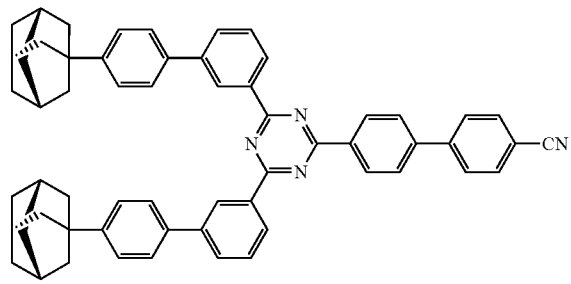
457
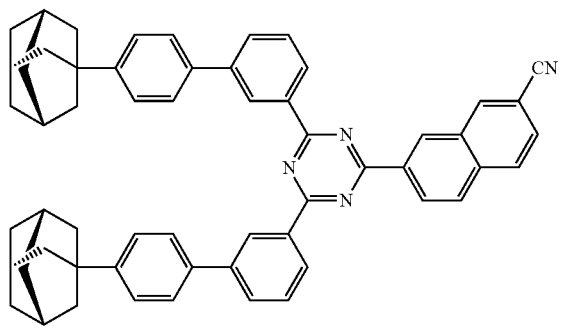
458
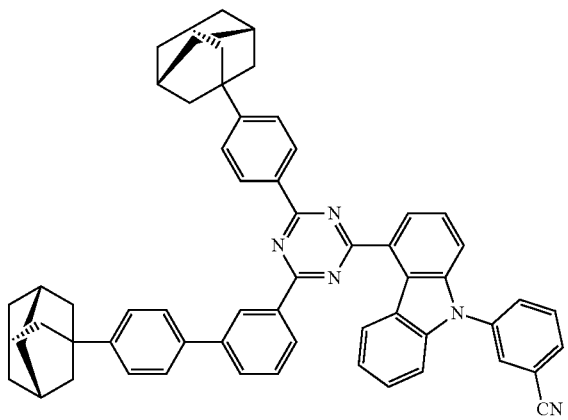
459
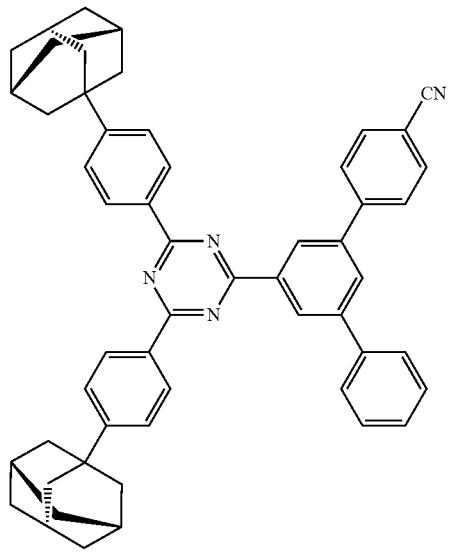
460
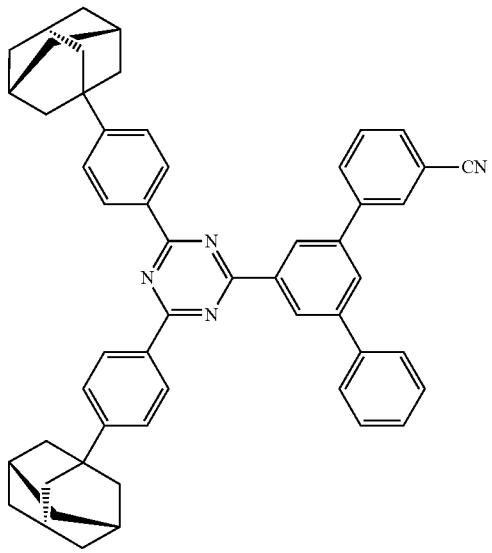

205 206
-continued
461
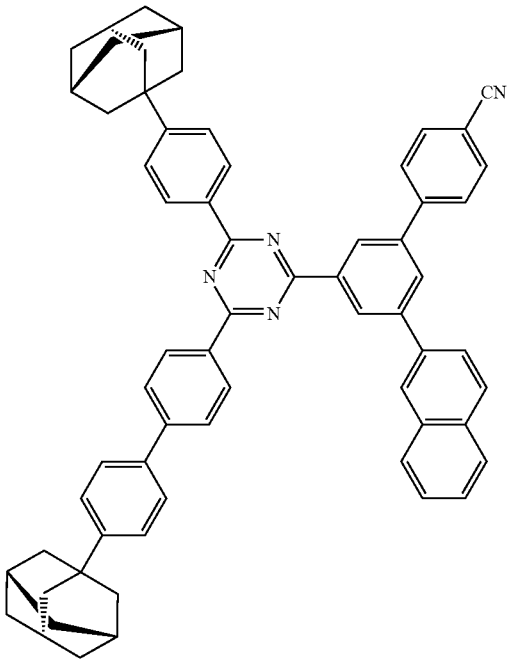
462
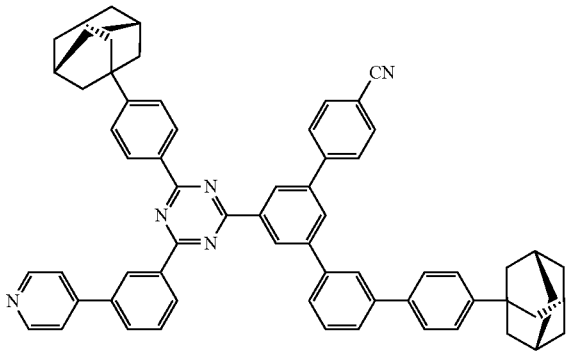
463
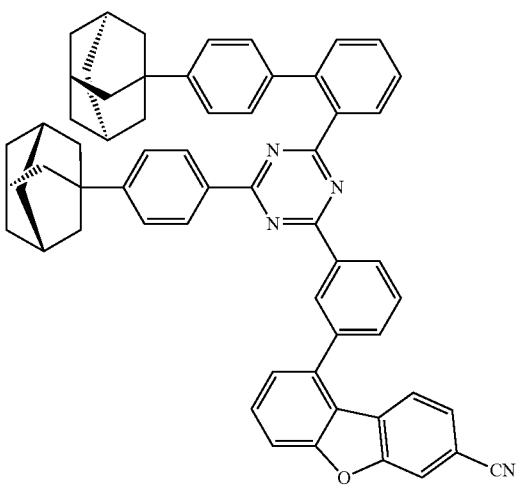
464
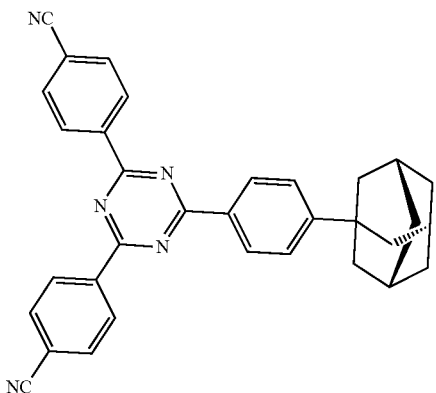
465
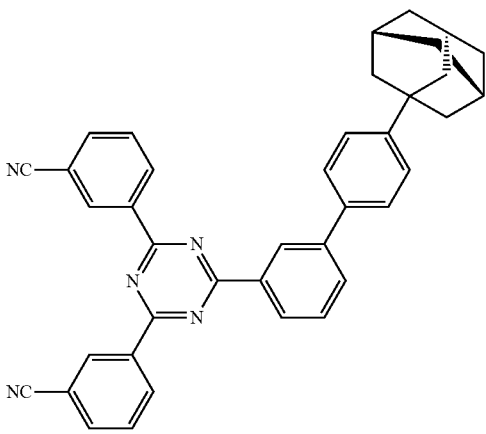
466
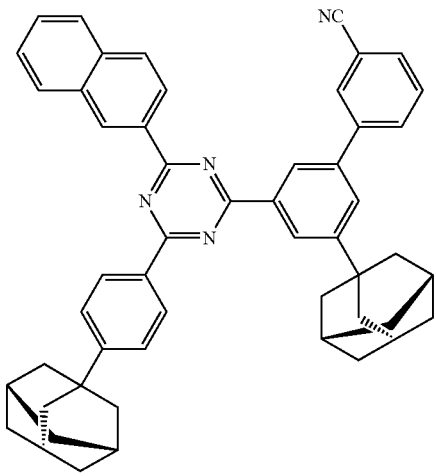

| 207 | 208 |
|---|---|
| 467 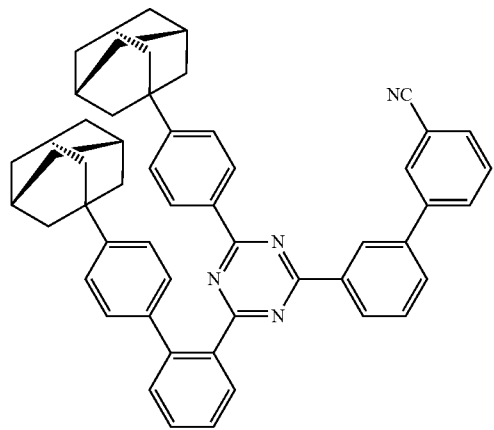 | 468 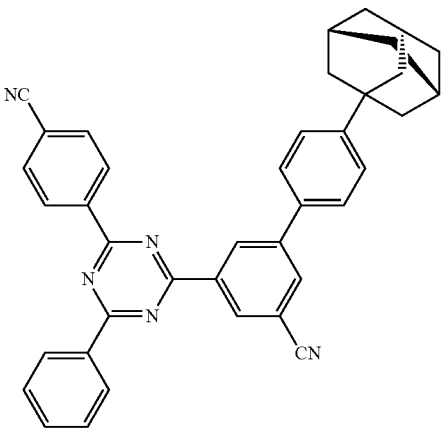 |
| 469 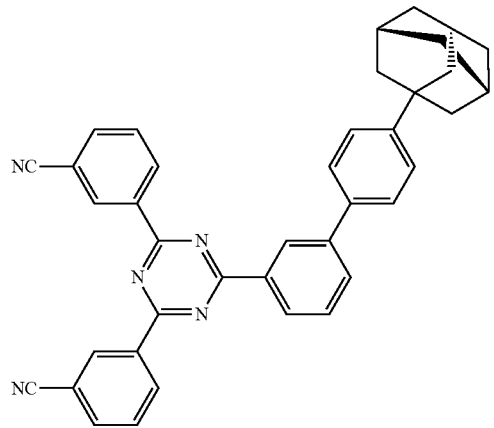 | 470 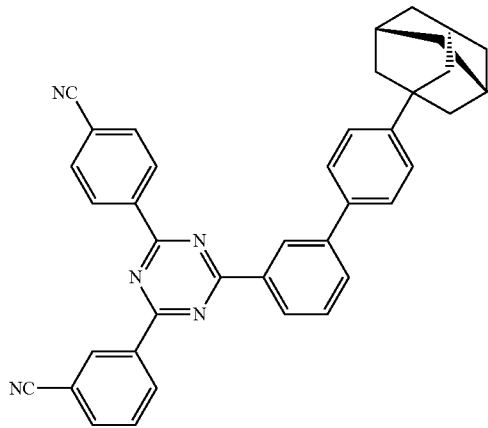 |
| 471 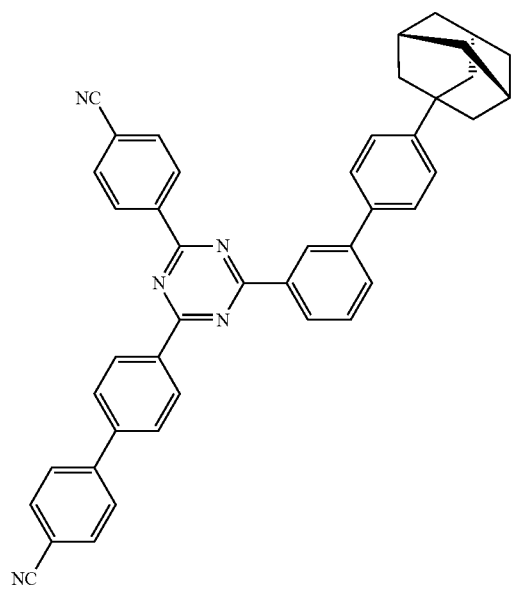 | 472 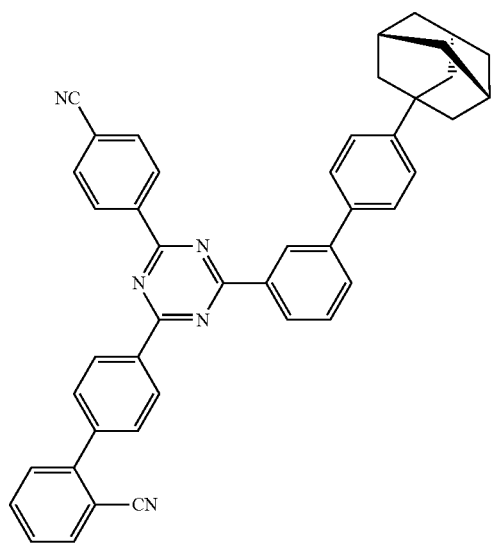 |

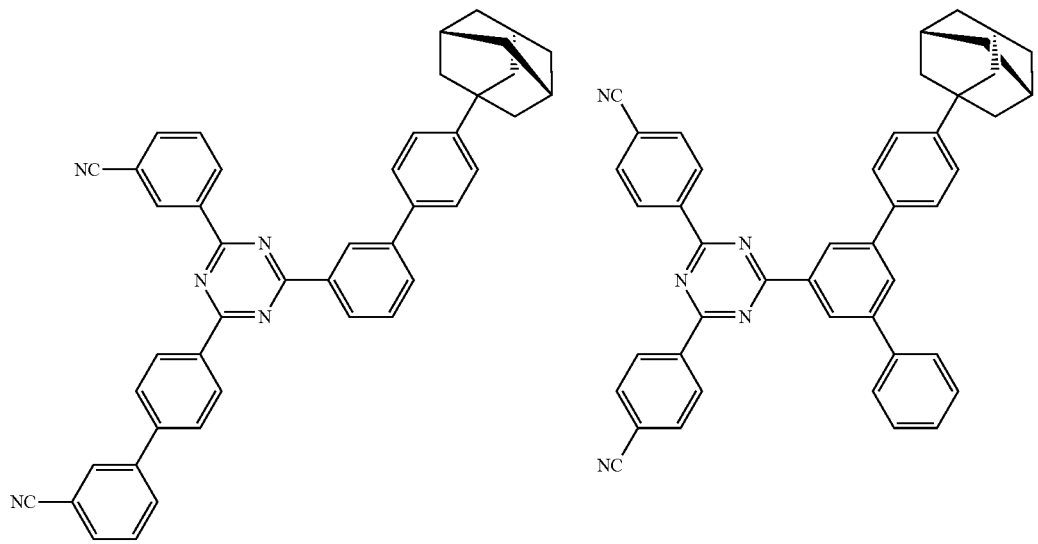
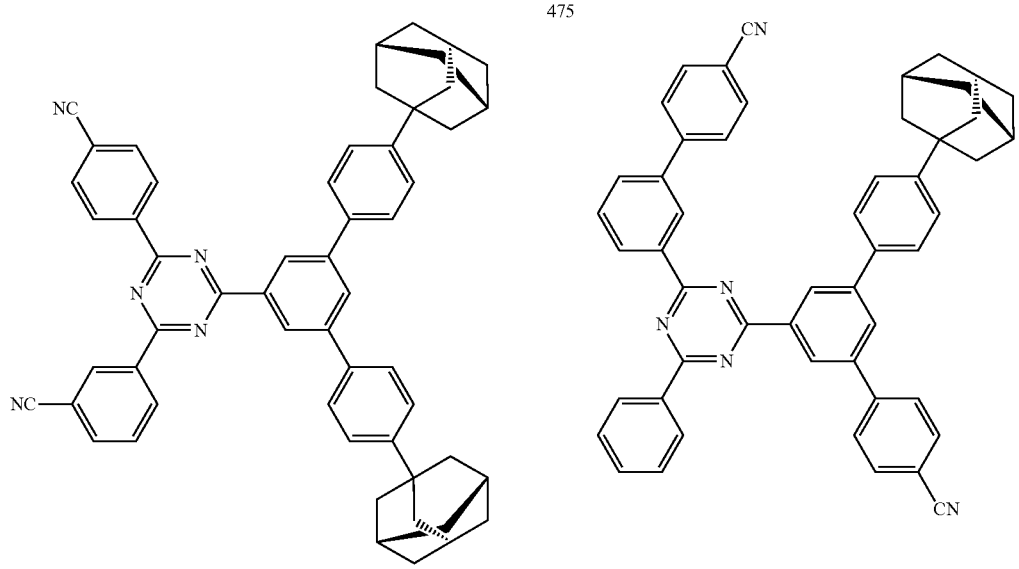
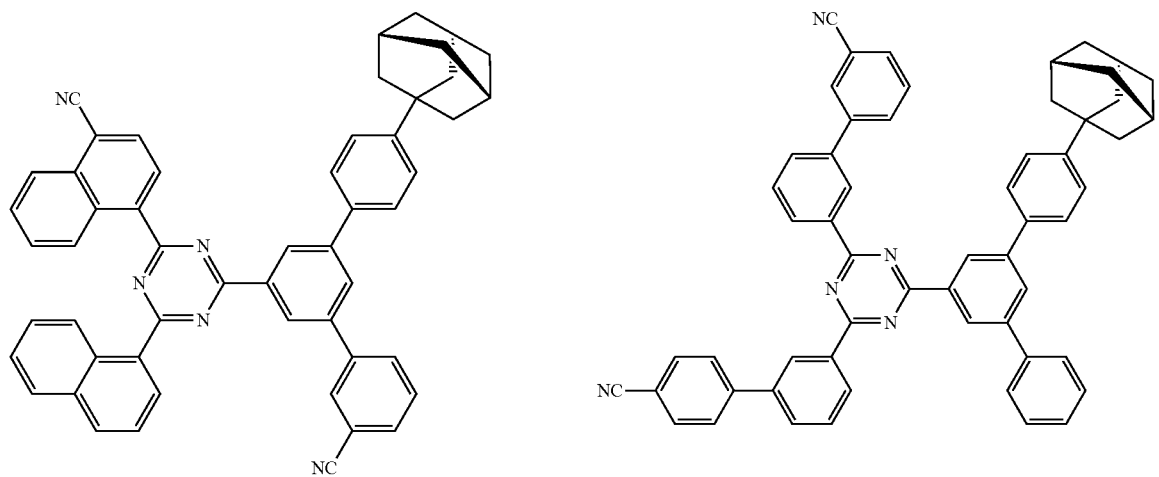

-continued
479
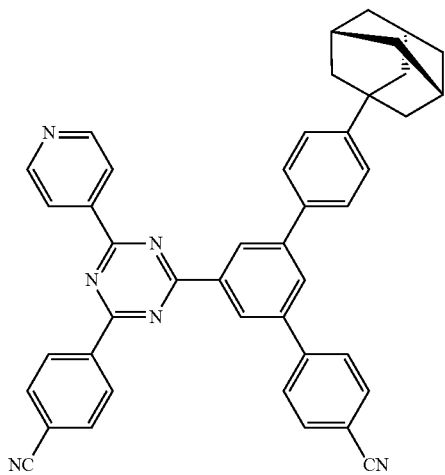
480
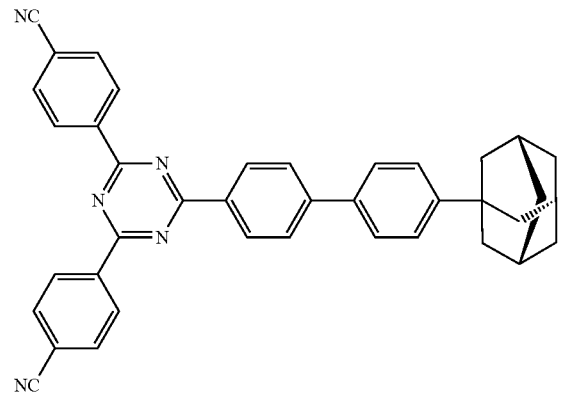
481
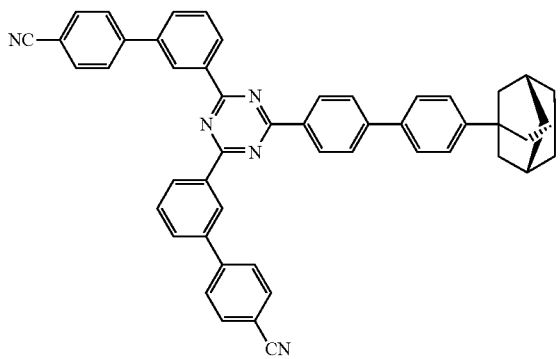
482
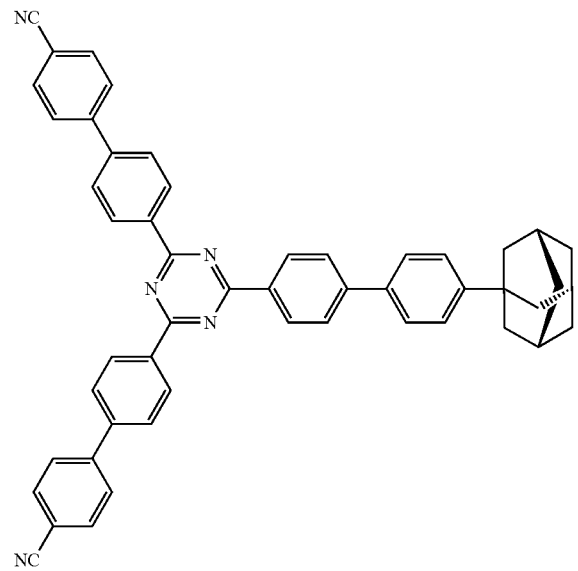
483
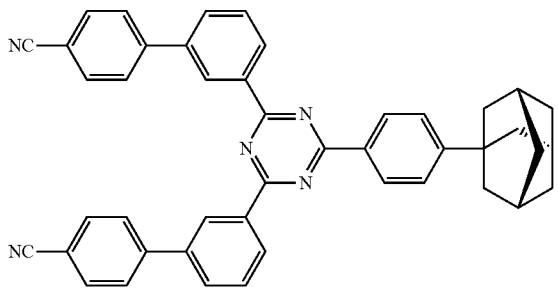
484
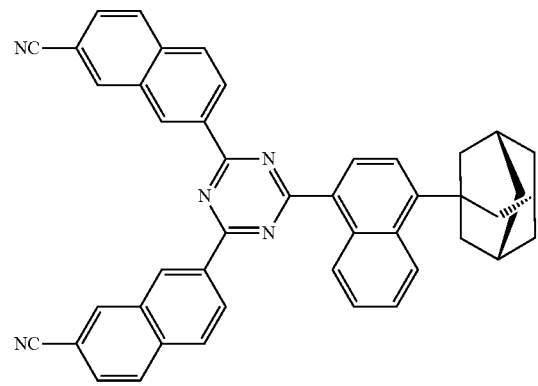

213 214
-continued
485
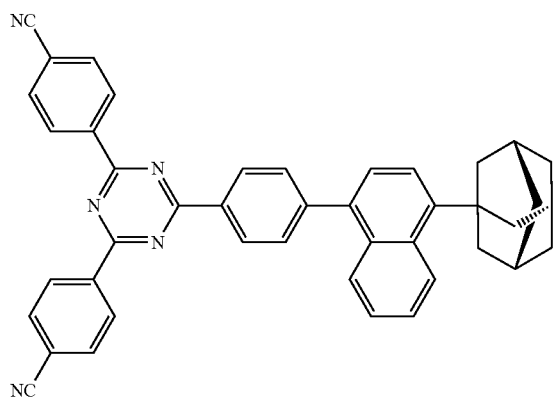
486
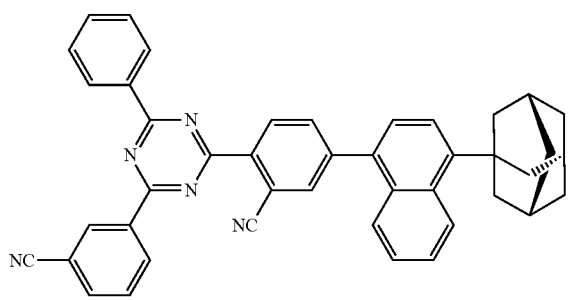
487
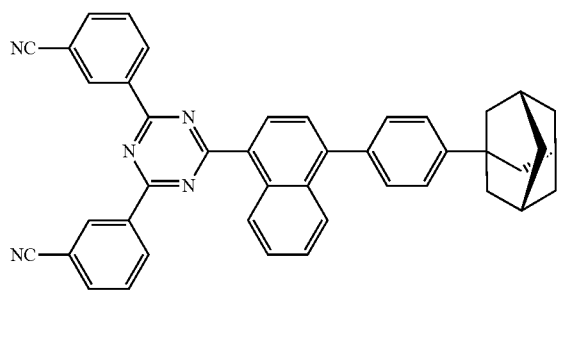
488
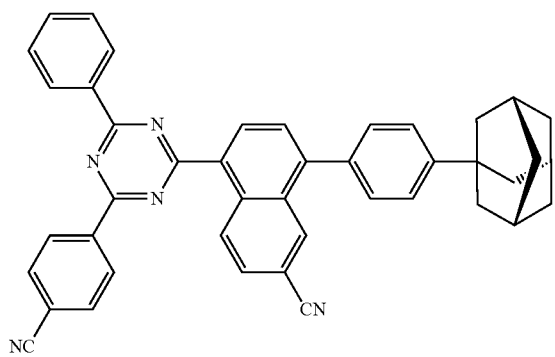
490
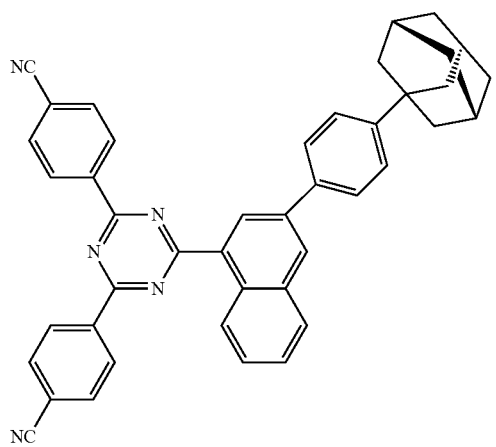
489
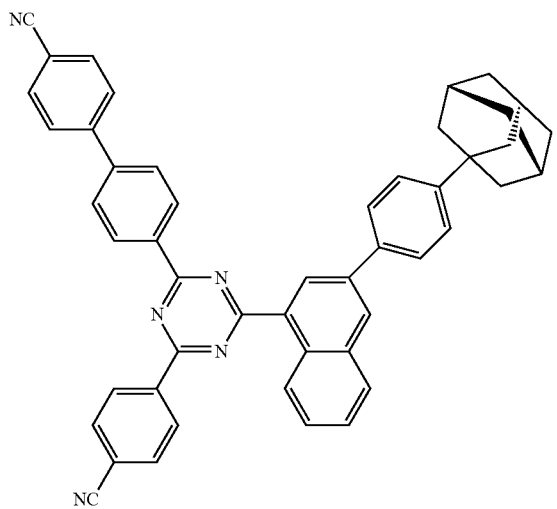

-continued
| 491 | 492 |
|---|---|
| 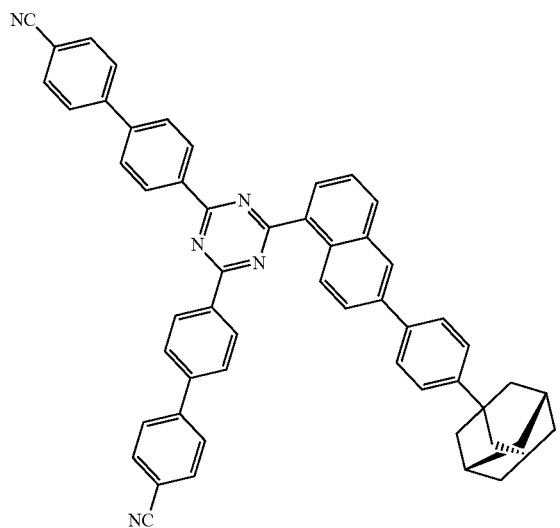 | 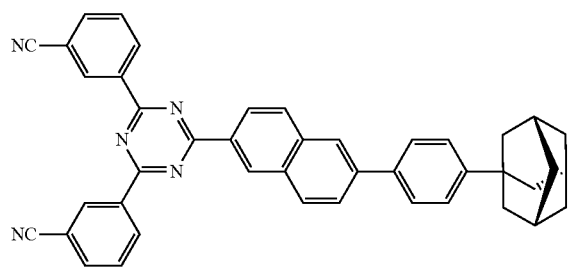 |
| 493 | 494 |
| 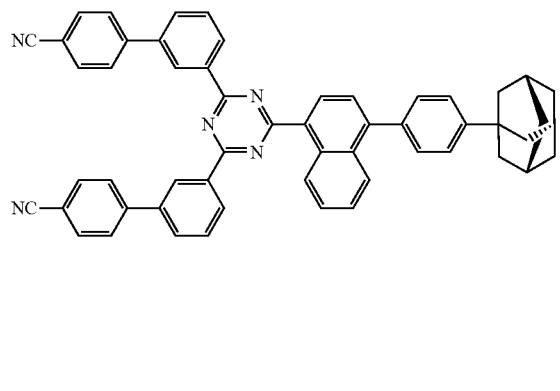 | 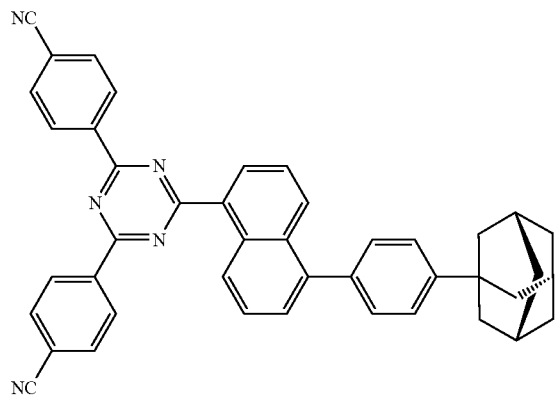 |
| 495 | 496 |
| 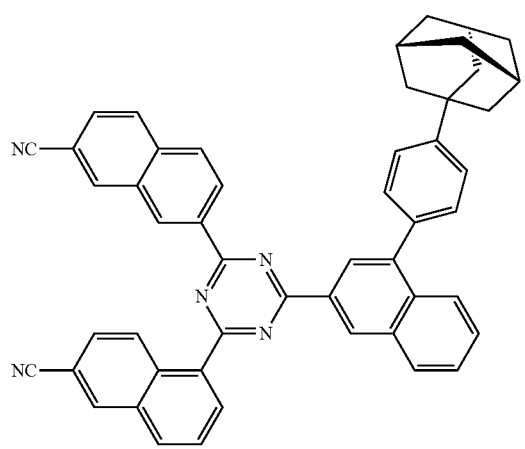 | 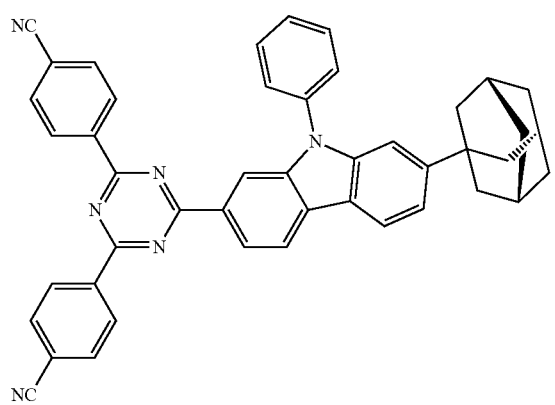 |

-continued
497
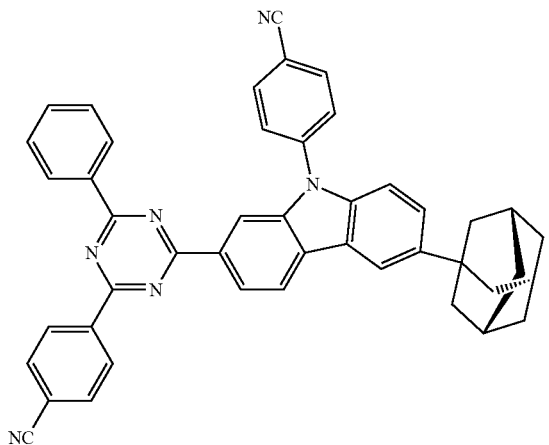
498
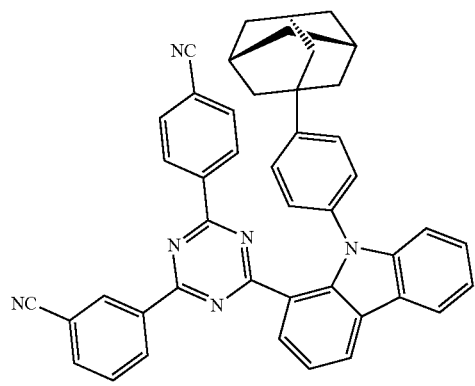
499
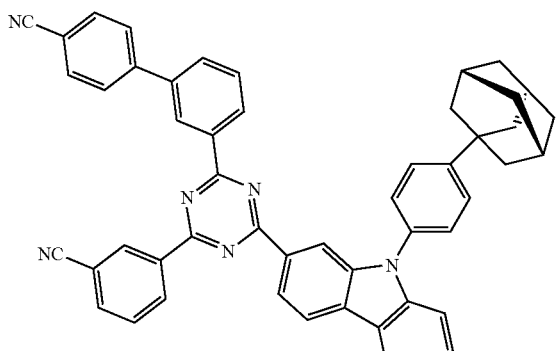
500
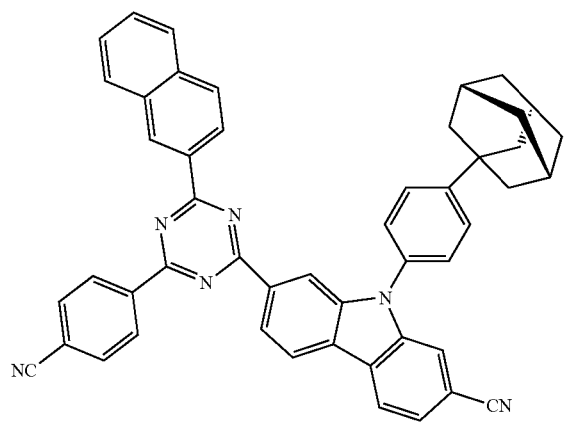
501
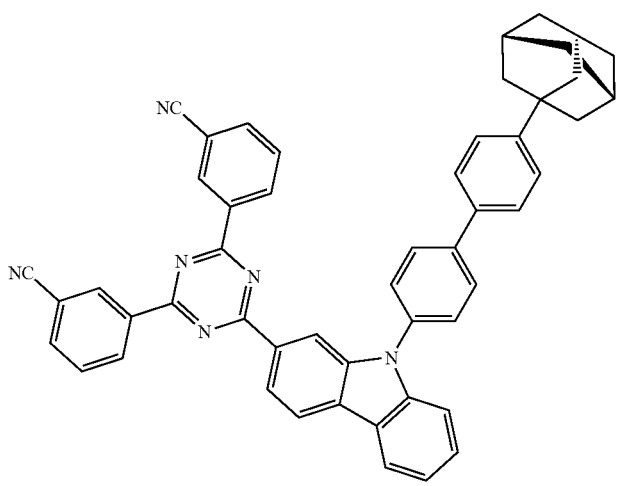

-continued
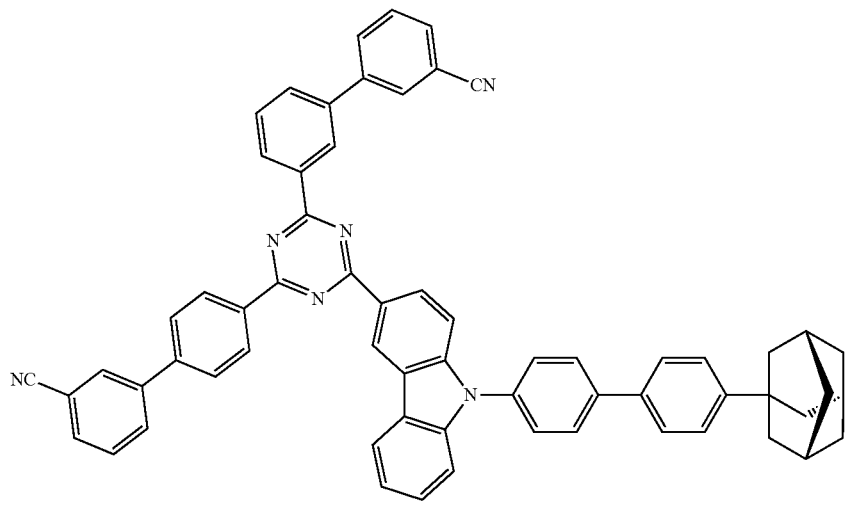
502
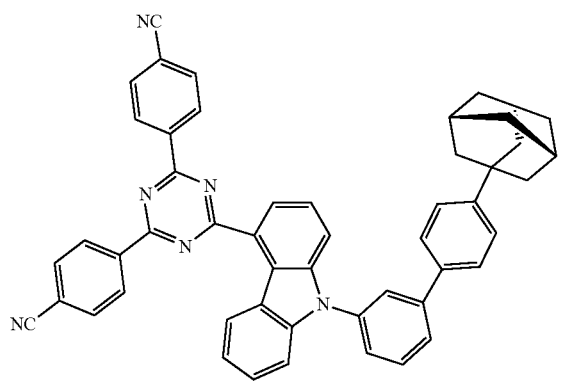
503
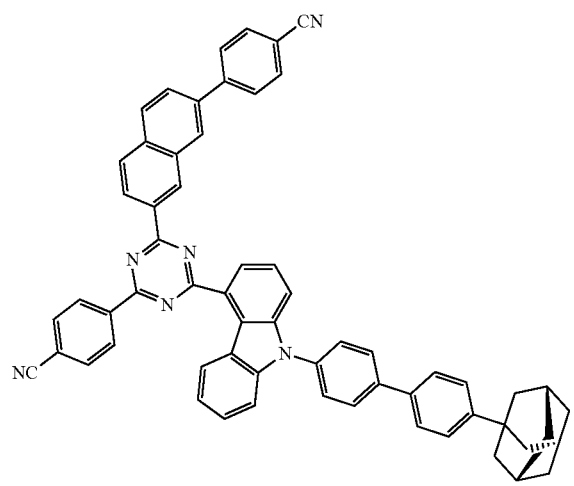
504
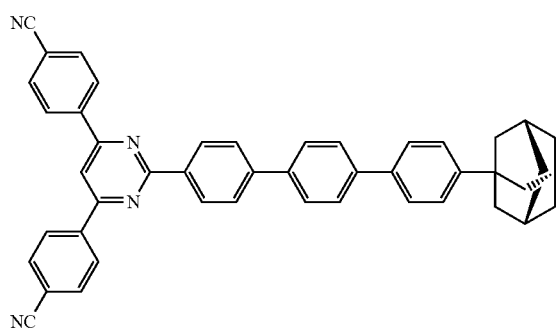
505
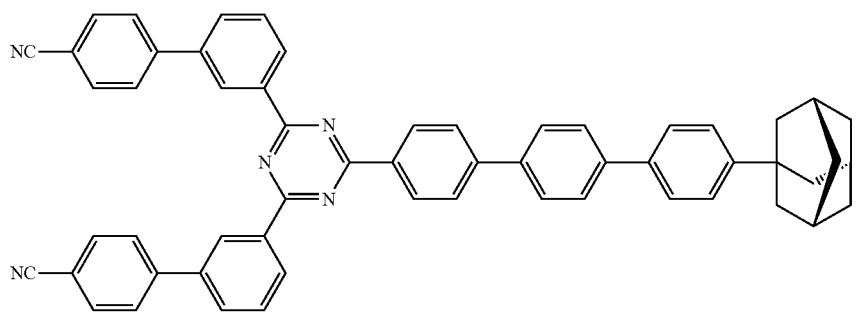
506
507

-continued
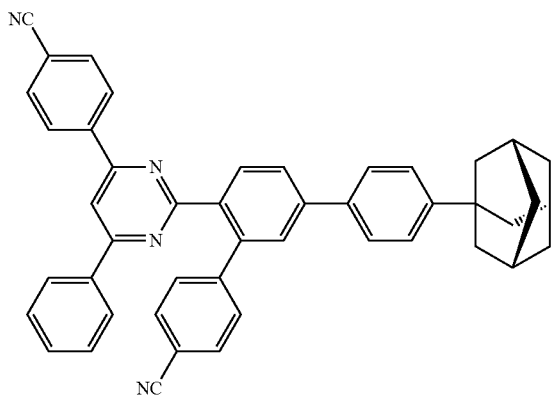
508
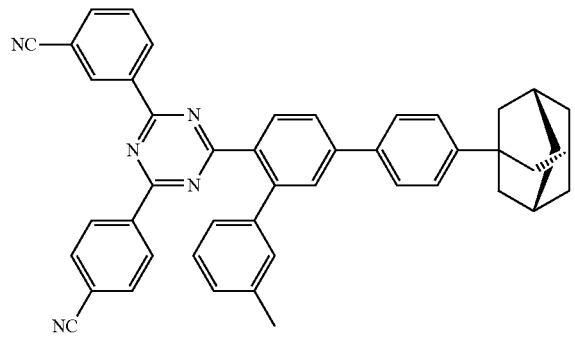
509
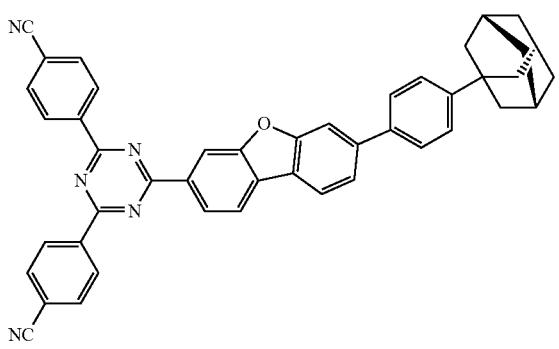
510
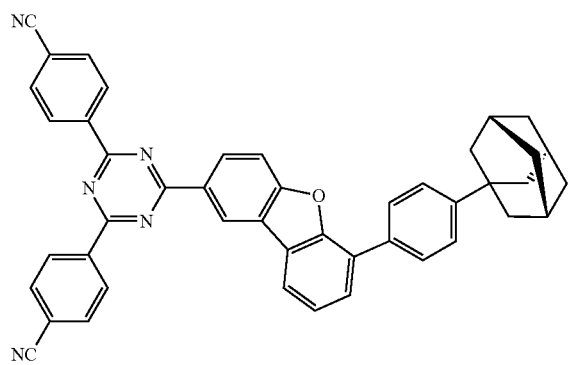
512
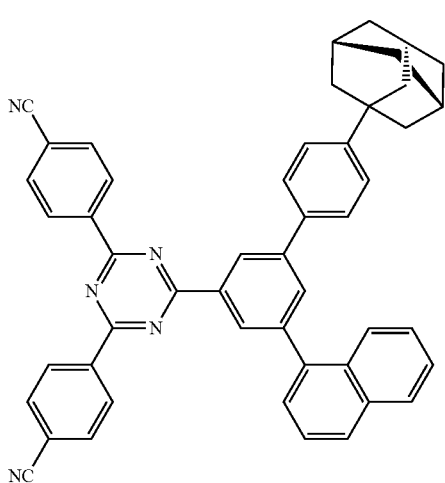
513
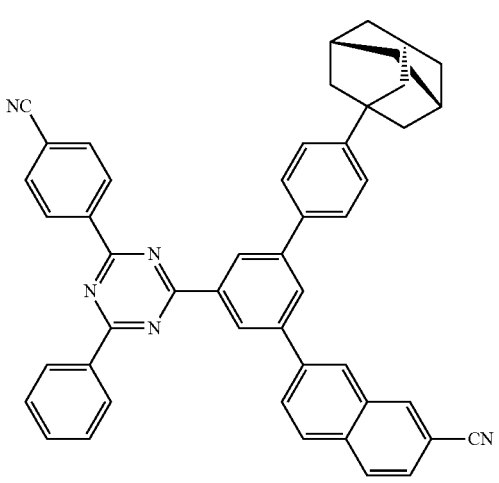
514

-continued
515
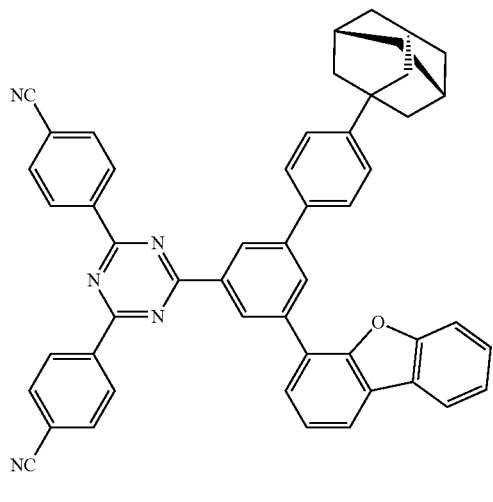
516
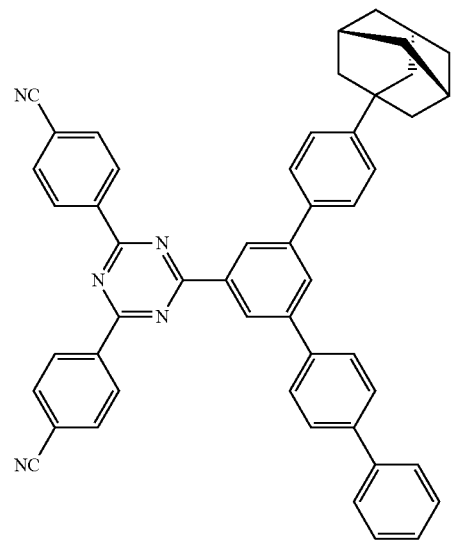
517
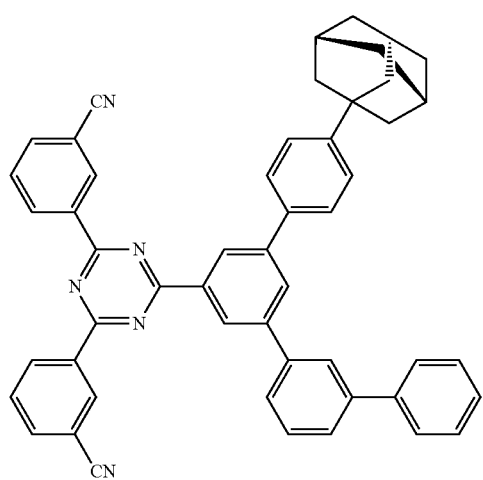
518
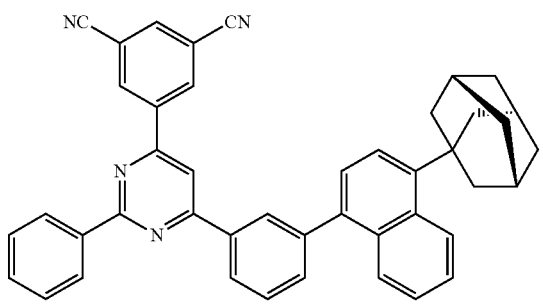
519
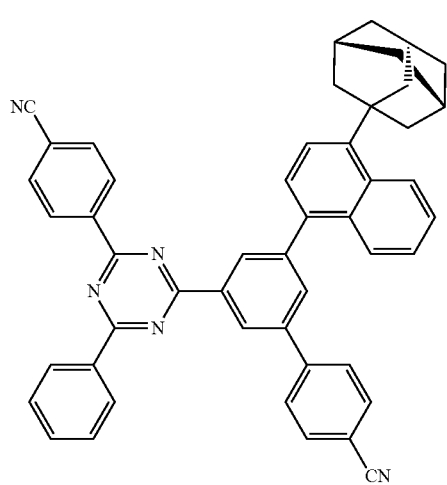
520
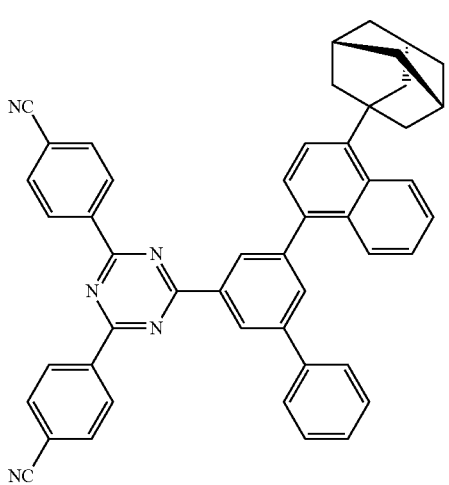

521 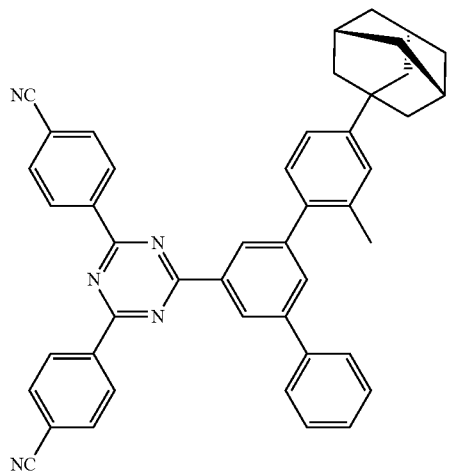
522 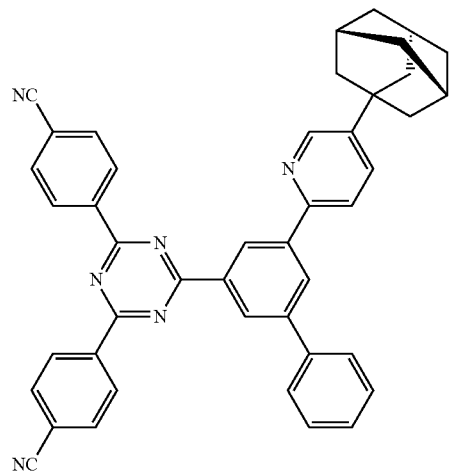
523 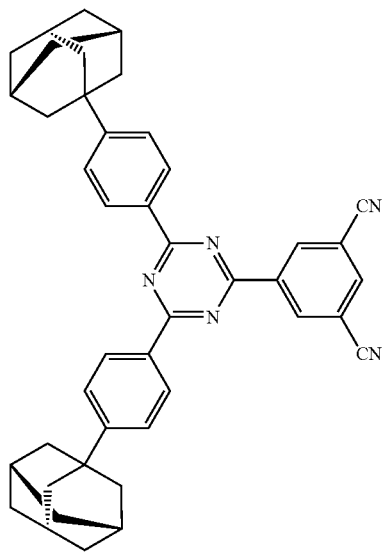
524 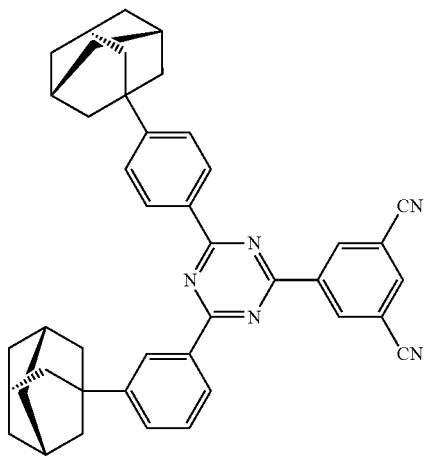
525 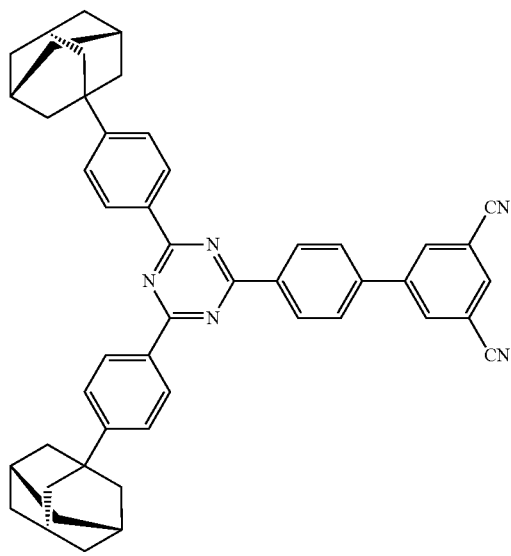

227             228
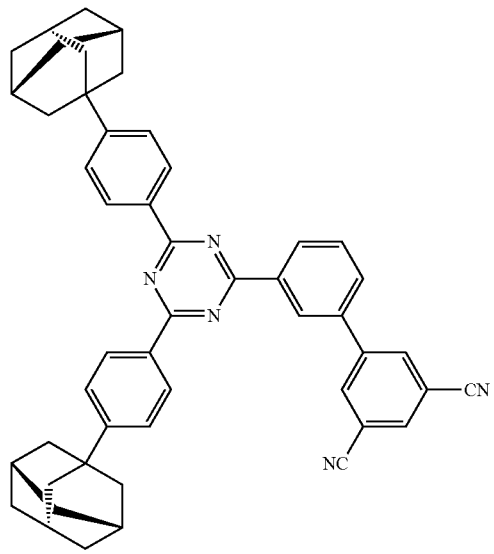 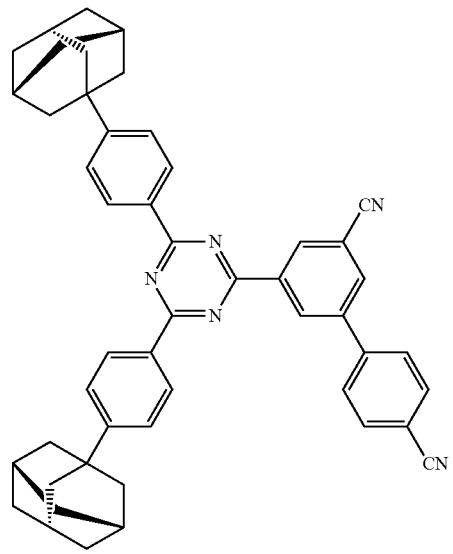
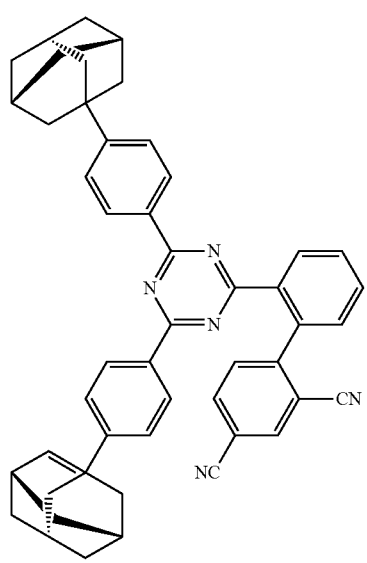 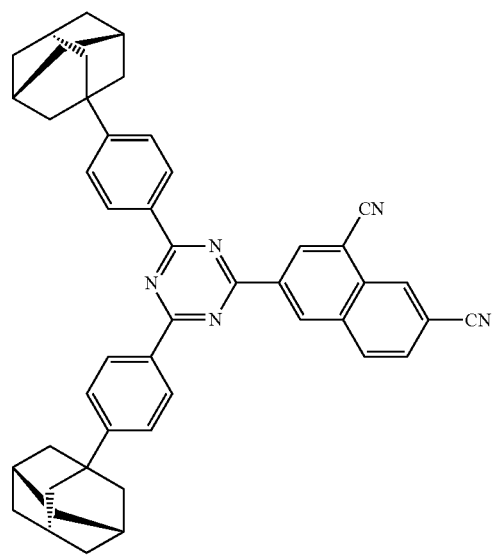

530 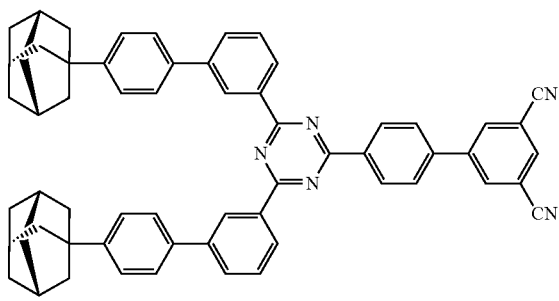
531
229
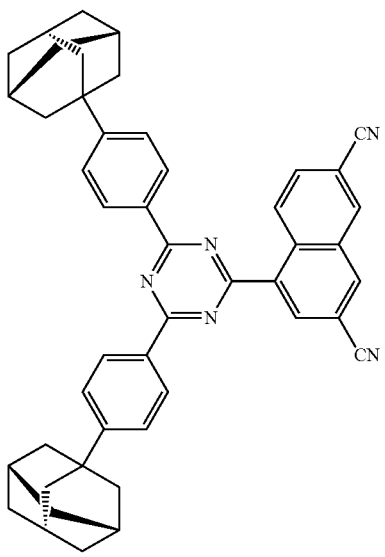
532 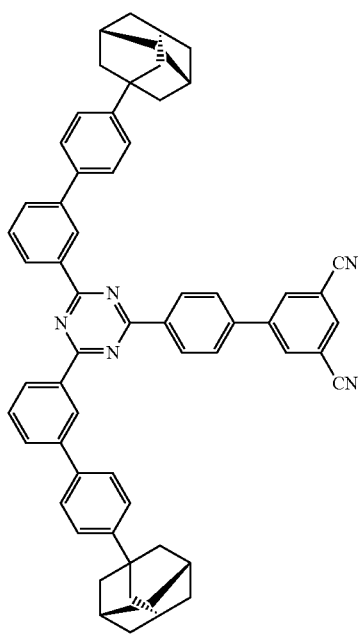
533 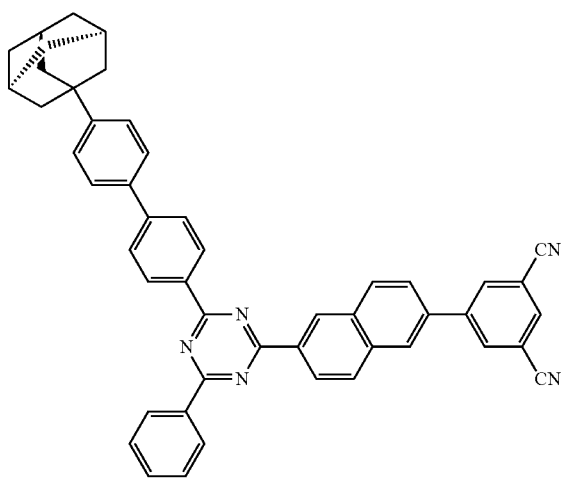

534
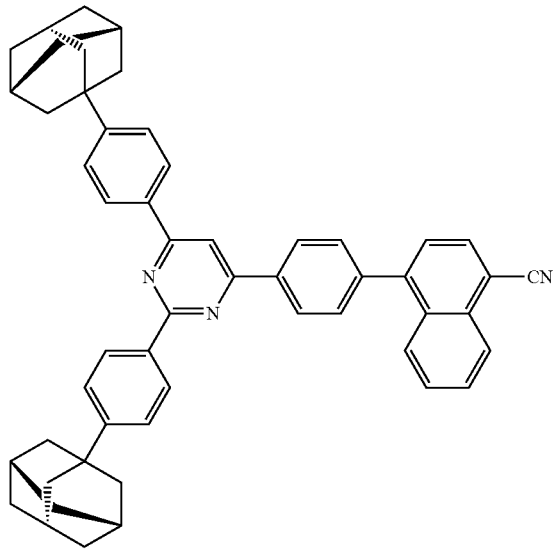
535
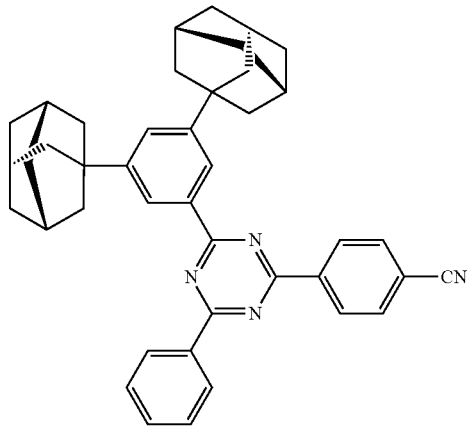
536
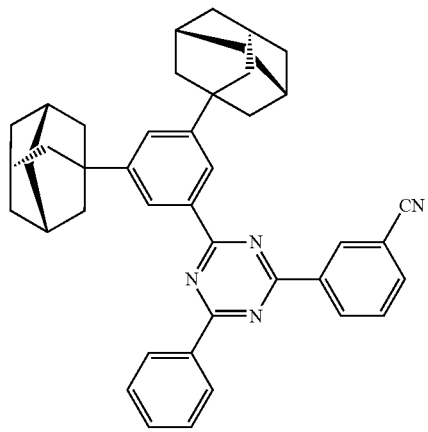
537
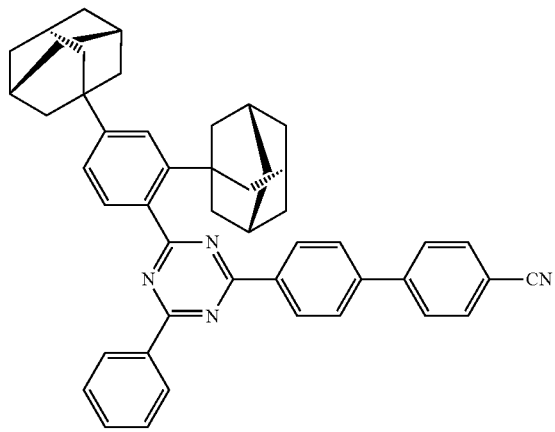
538
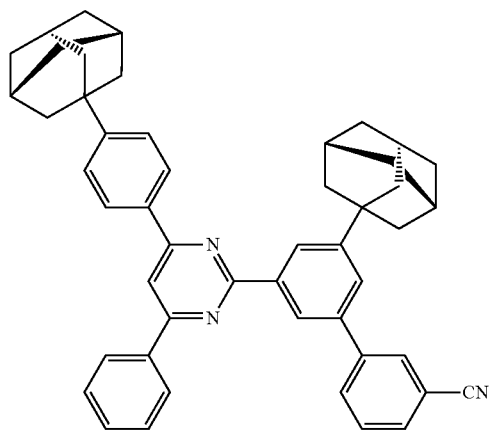
539
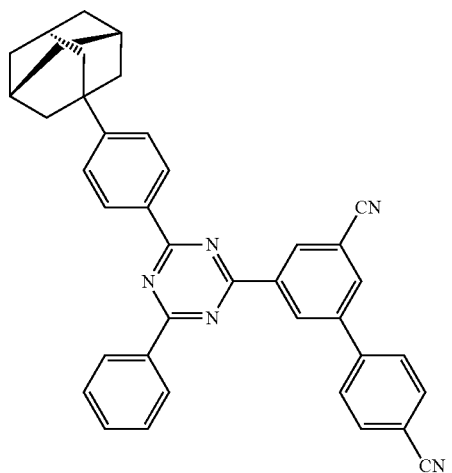

-continued
233
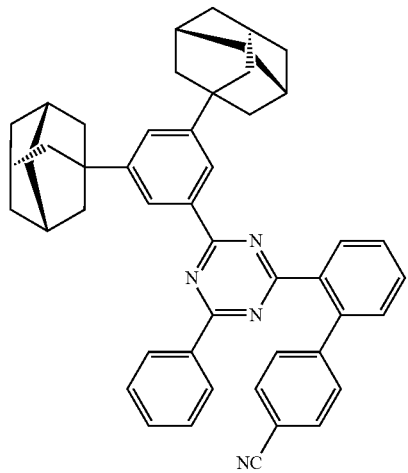
540
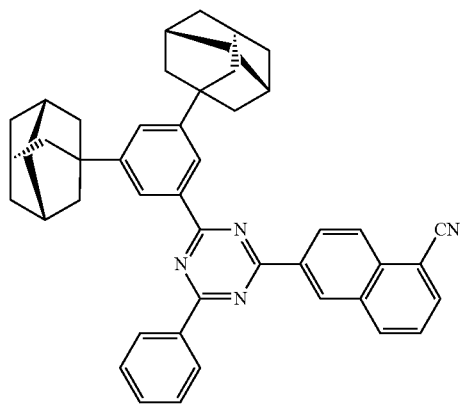
542
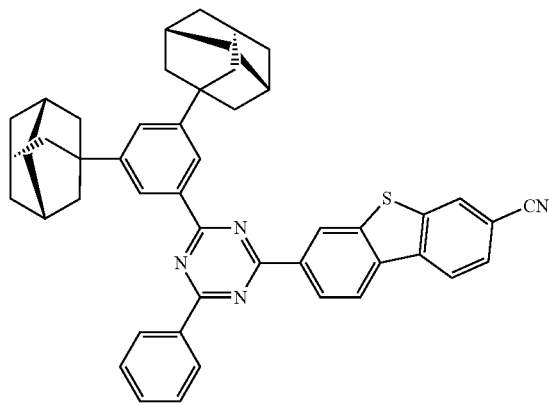
544
234
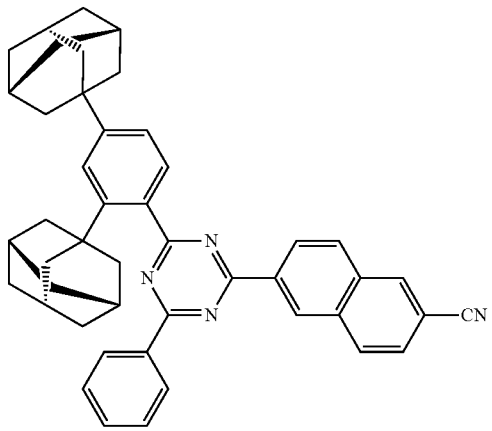
541
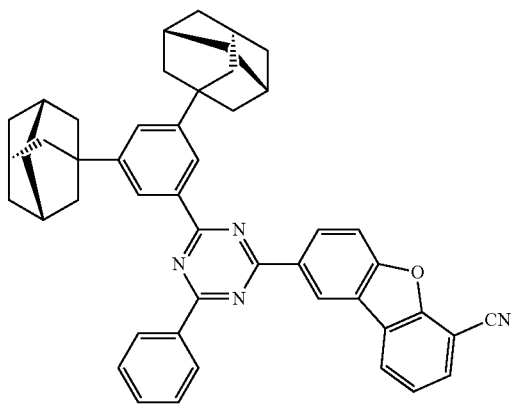
543
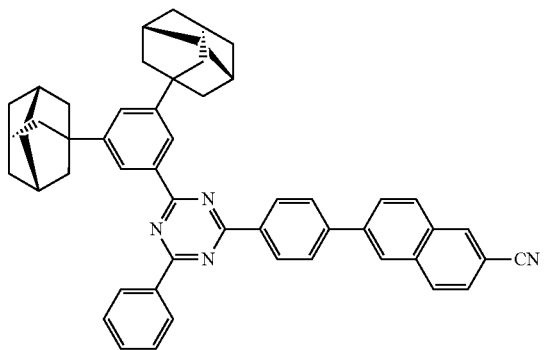
545

235 236
-continued
| 546 | 547 |
|---|---|
| 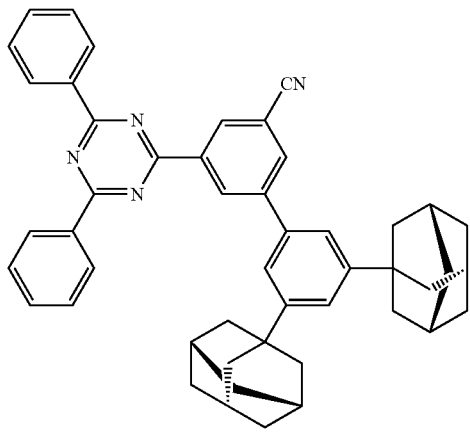 | 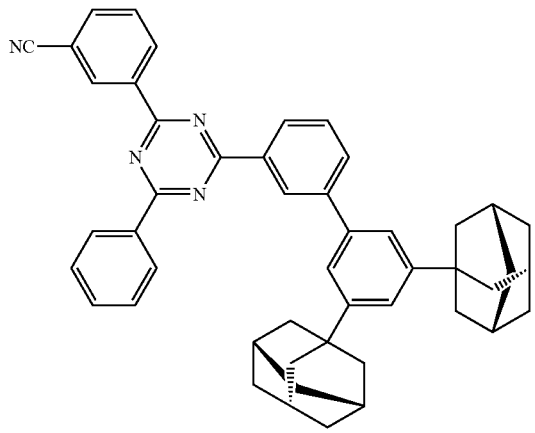 |
| 548 | 549 |
| 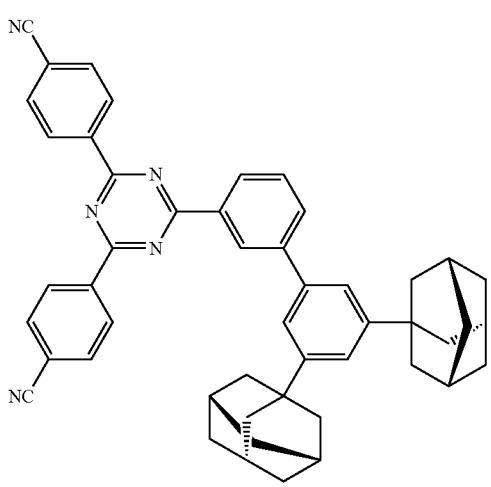 | 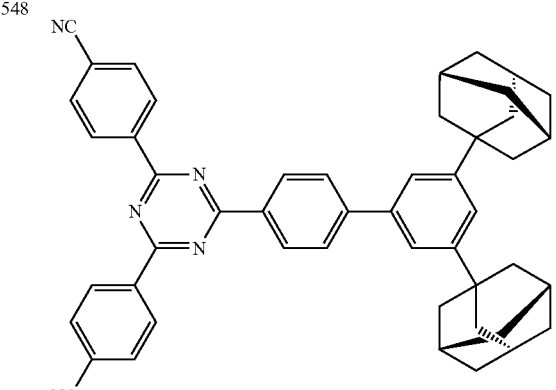 |
| 550 | 551 |
| 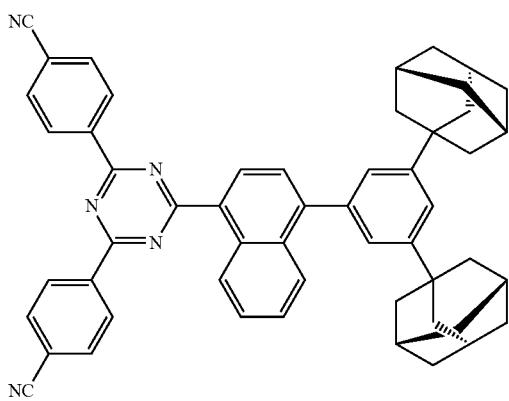 | 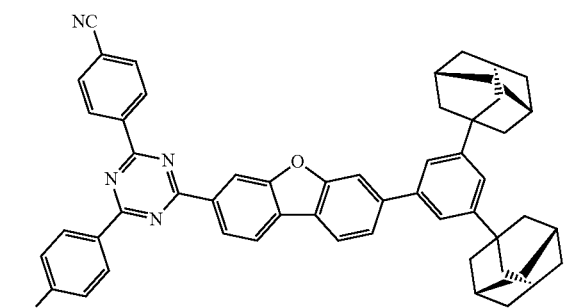 |

552
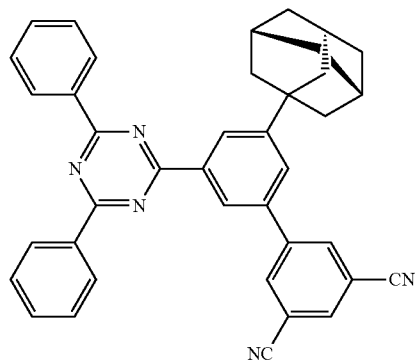
553
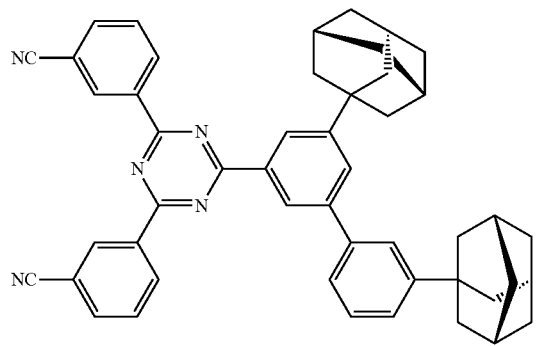
554
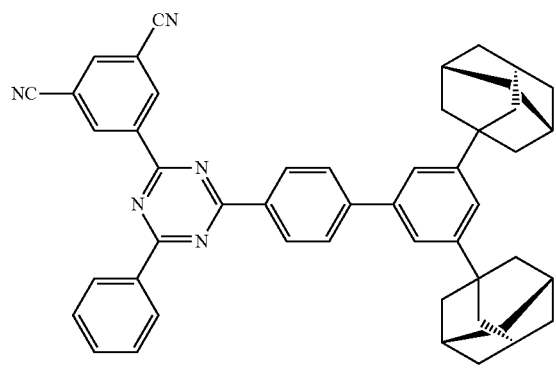
555
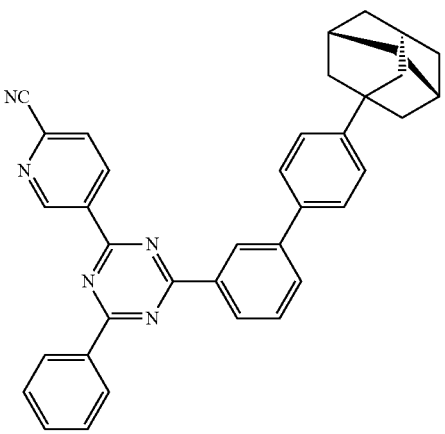
556
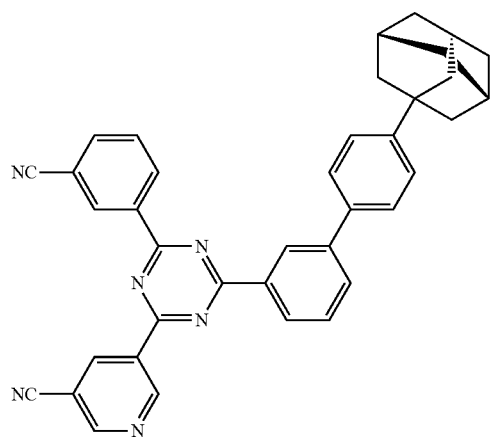
557
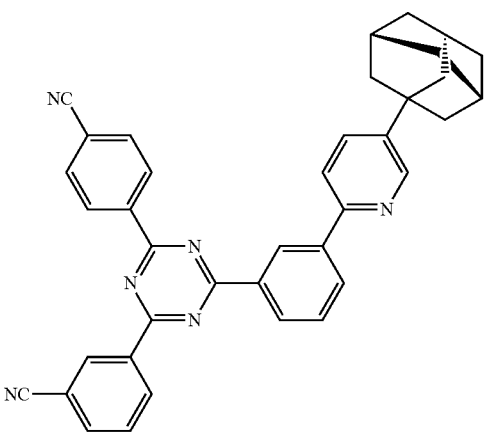

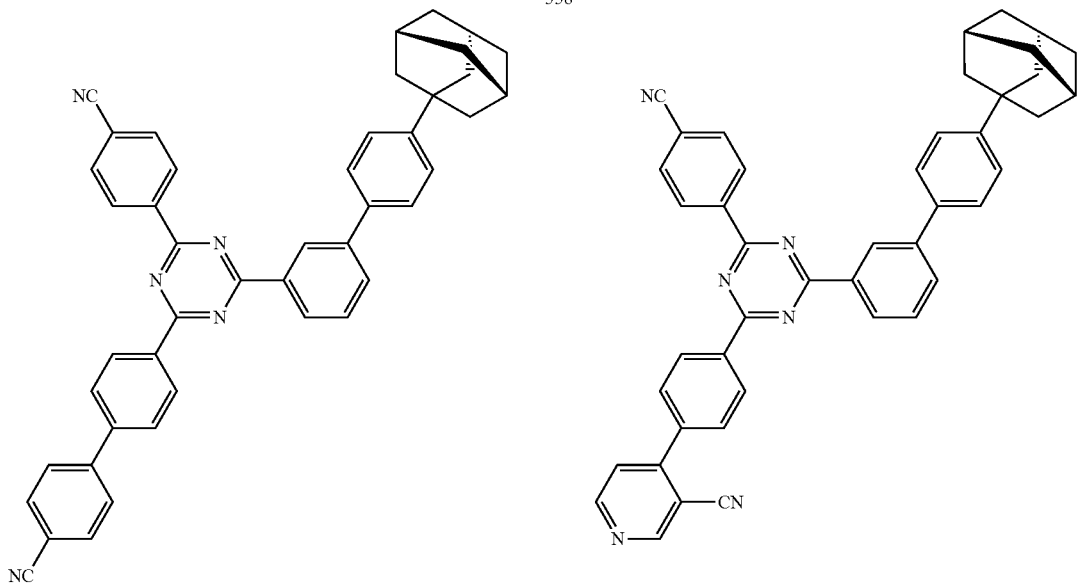
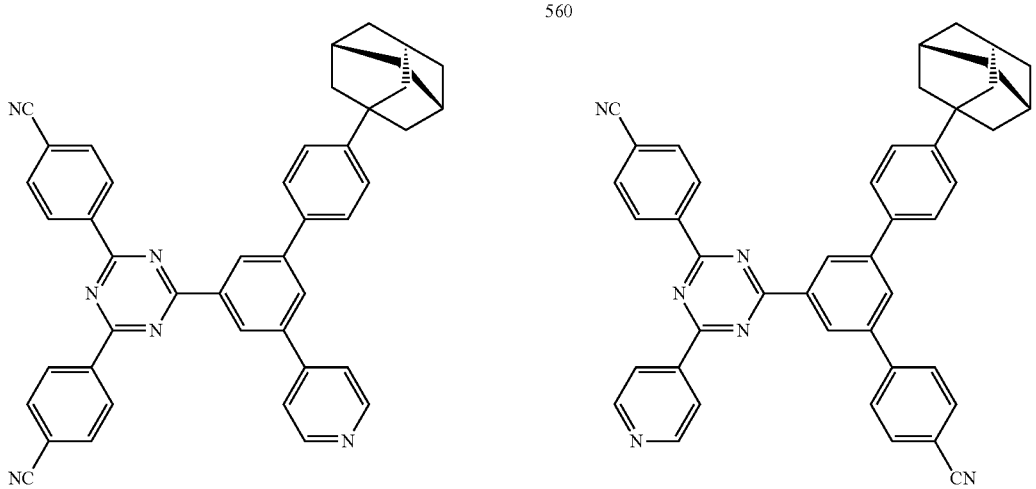
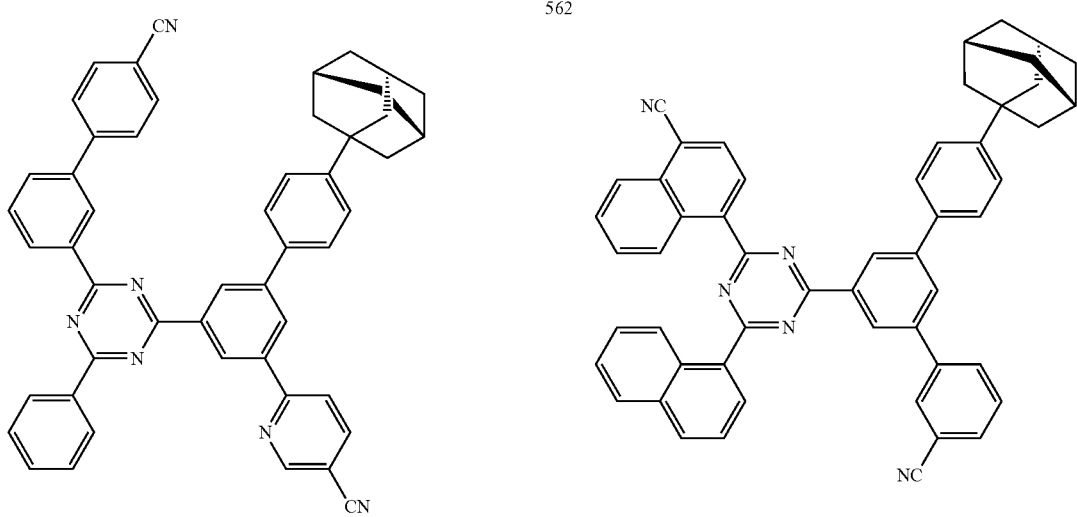

-continued
564
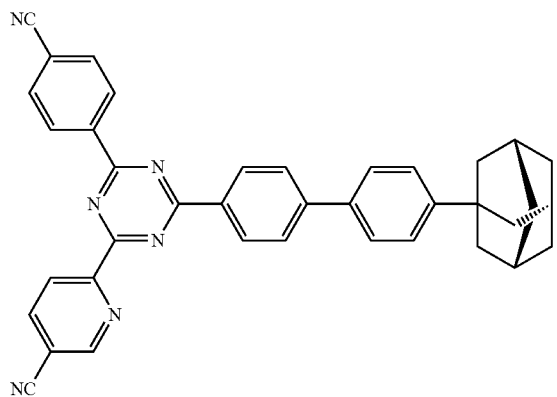
565
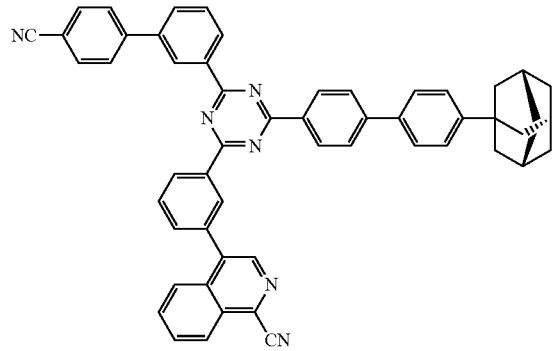
567
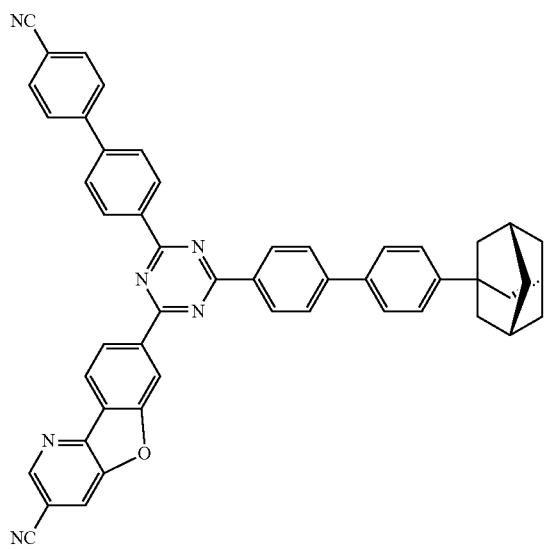
568
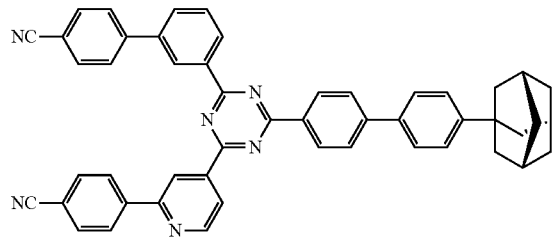
569
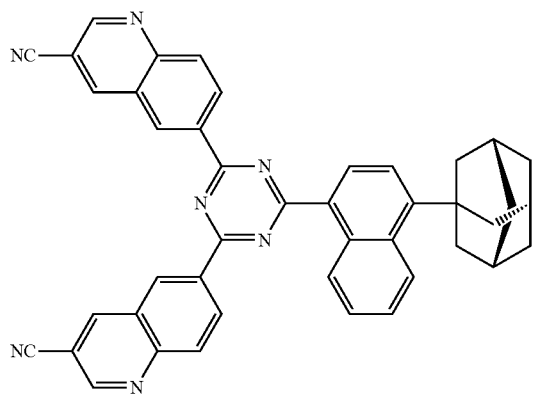
570
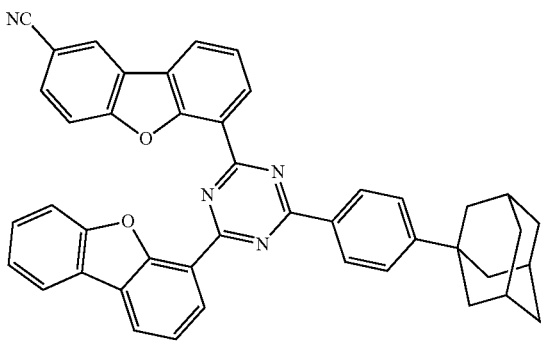

-continued
243
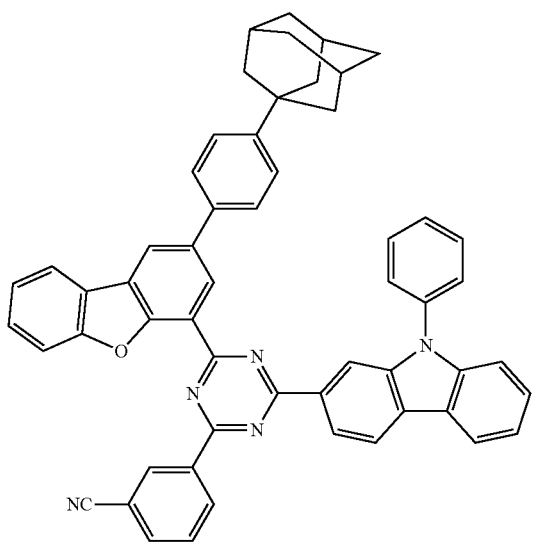
571
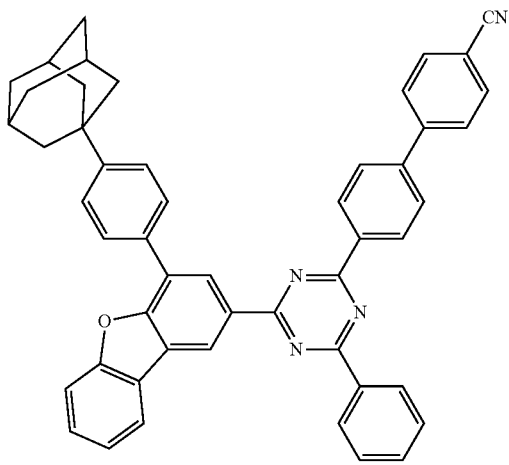
573
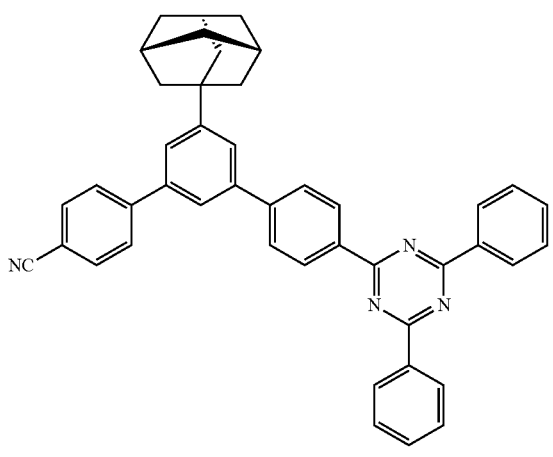
575
244
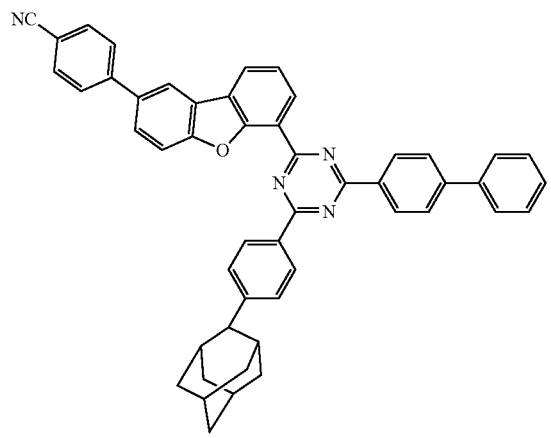
572
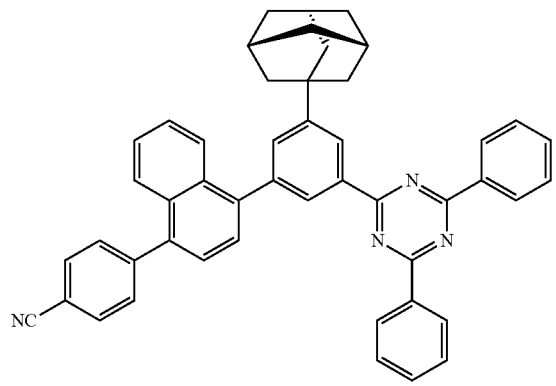
574
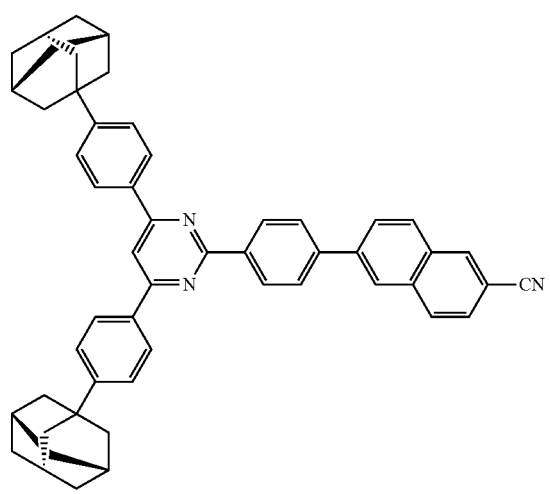
575

-continued
576
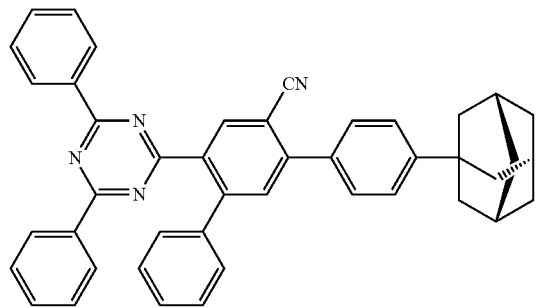
577
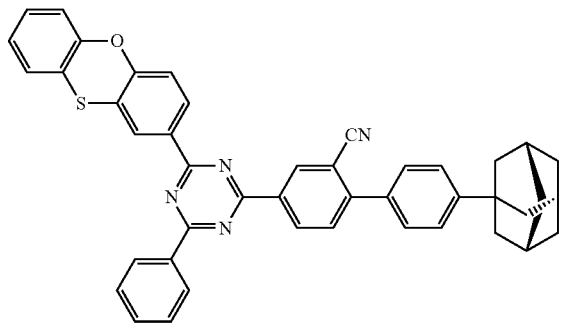
578
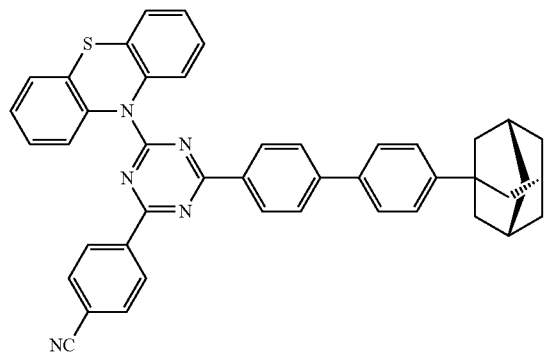
579
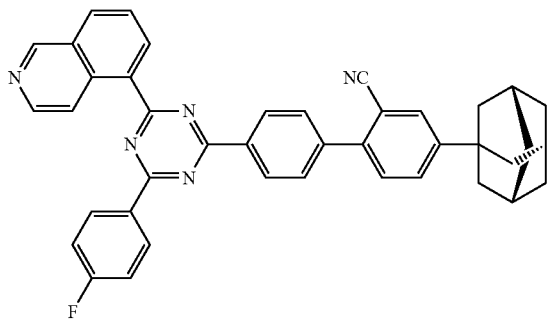
580
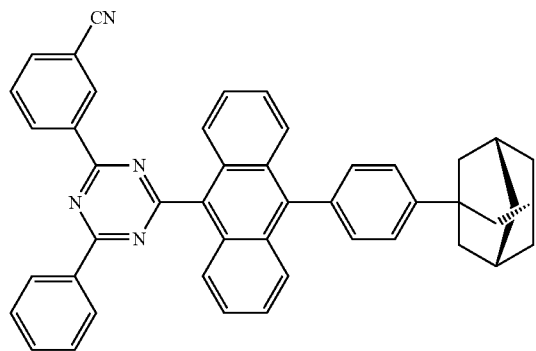
581
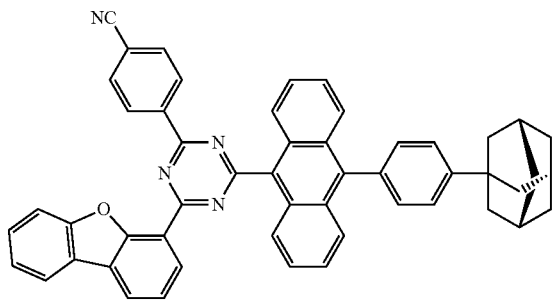
582
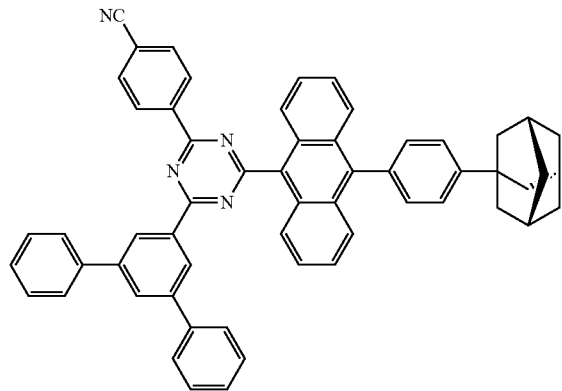
583
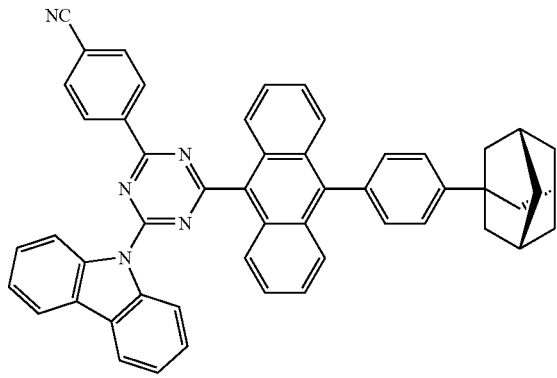

-continued
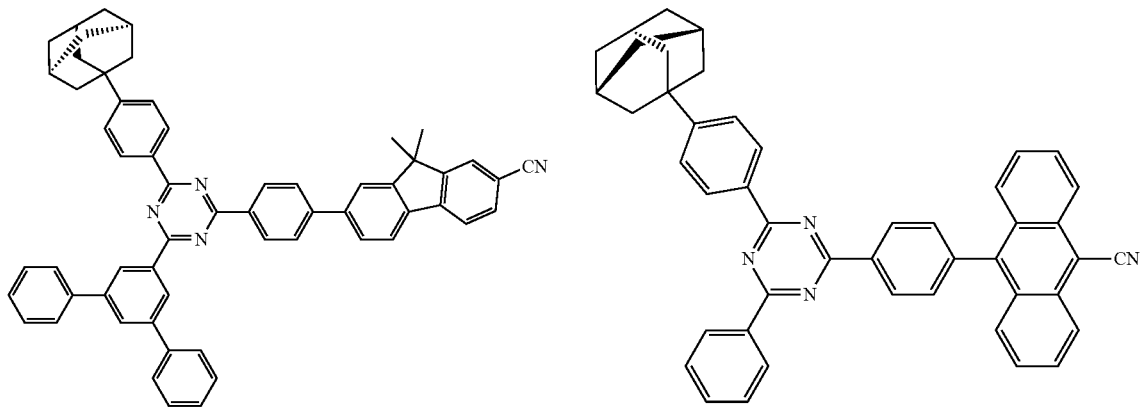
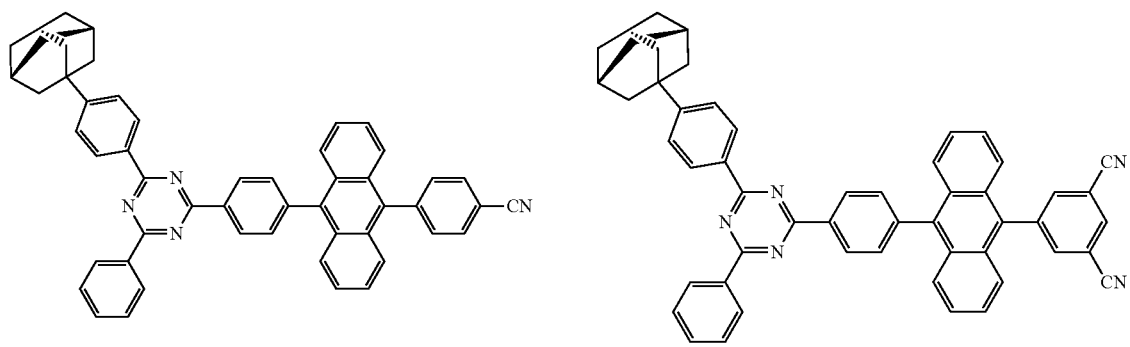
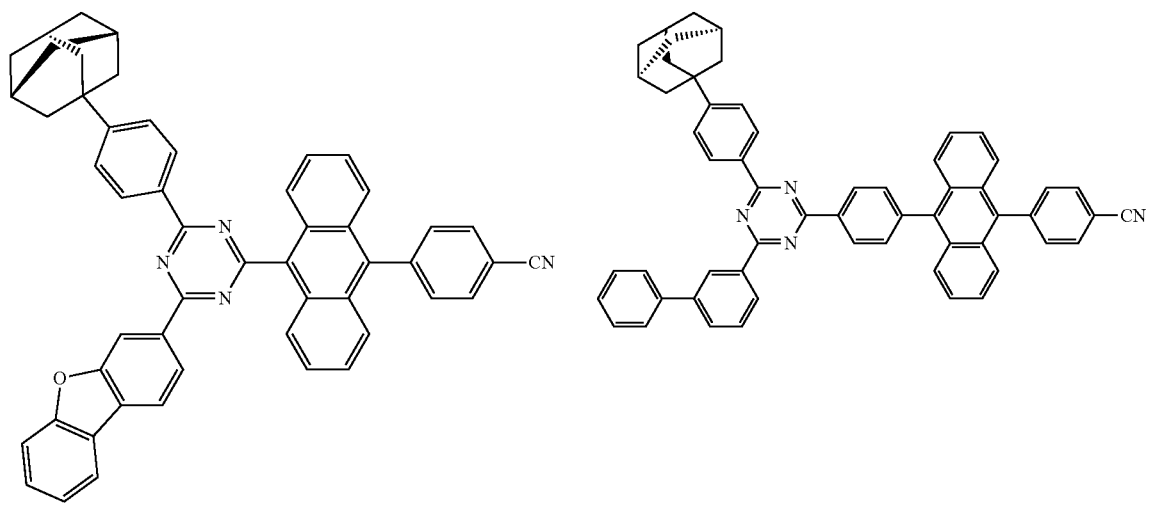

-continued
590
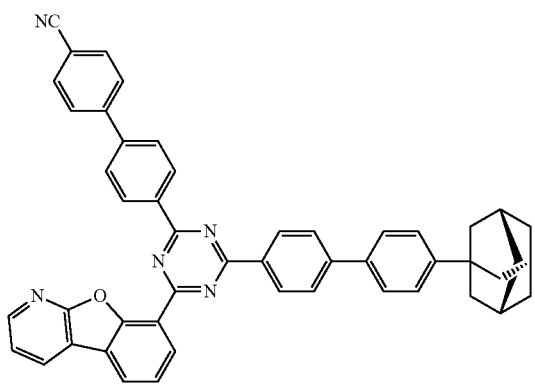
591
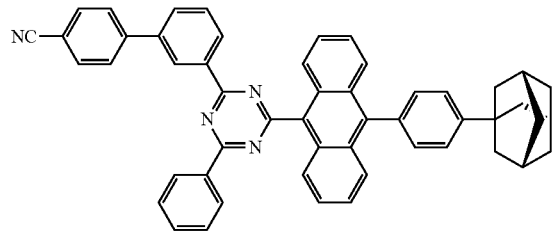
592
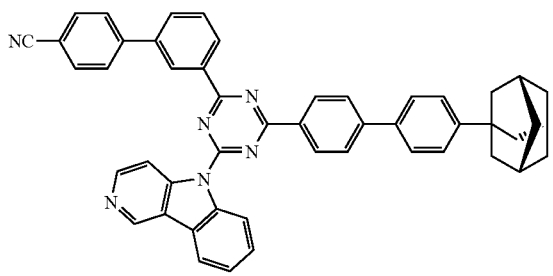
593
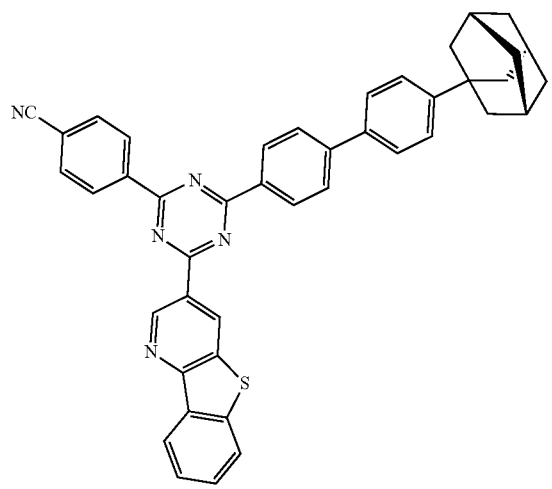
594
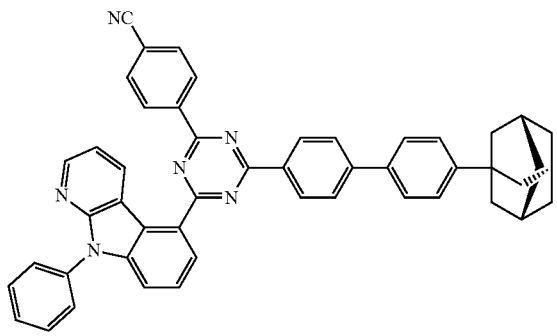
595
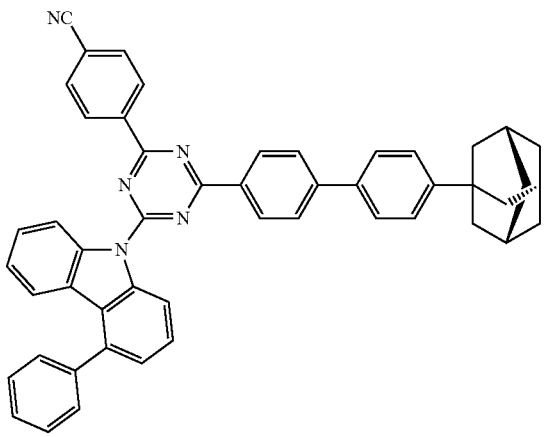

-continued
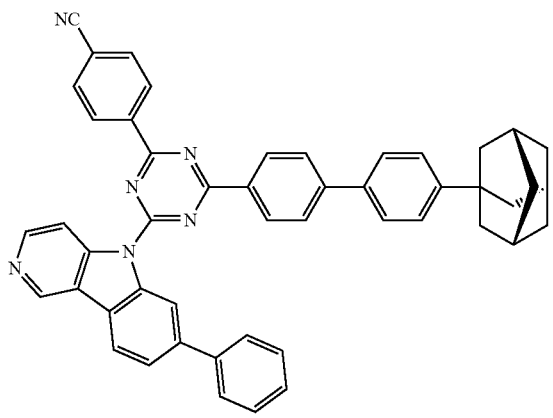
596
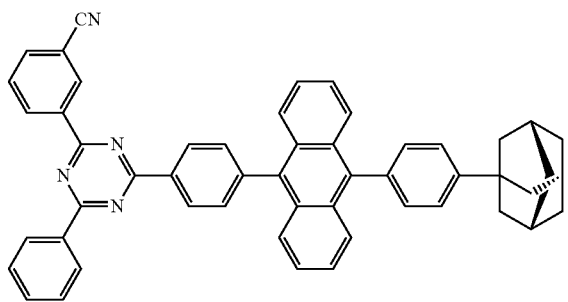
597
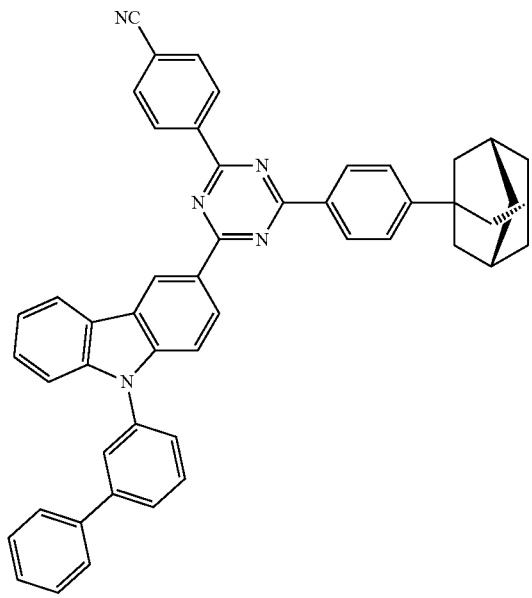
598
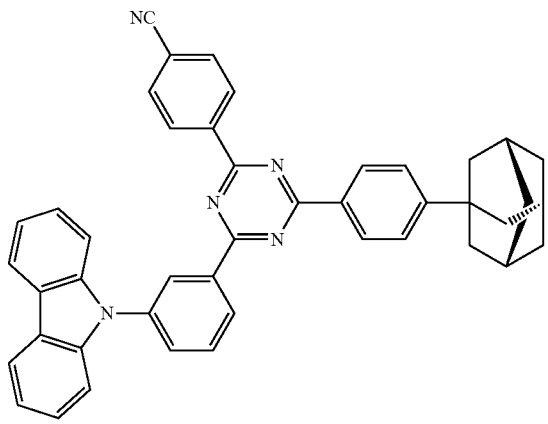
599
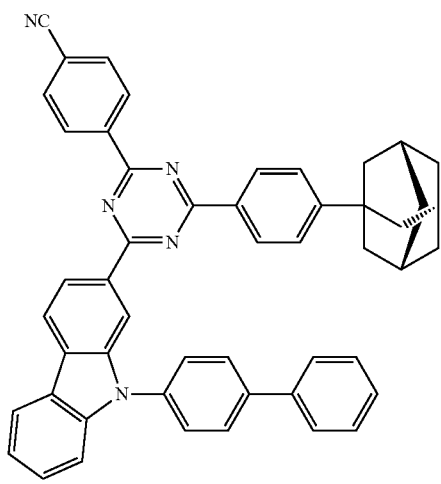
600
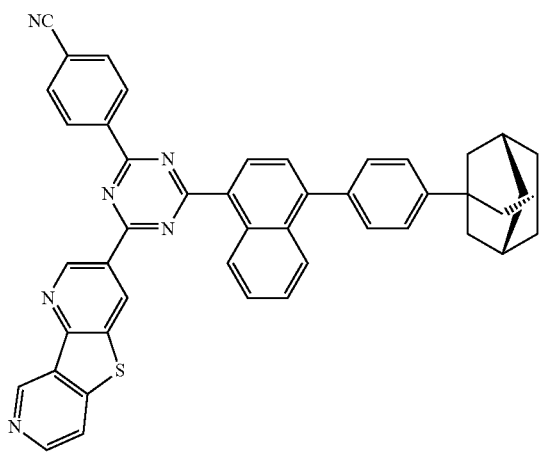
601

253 254
-continued
602 603
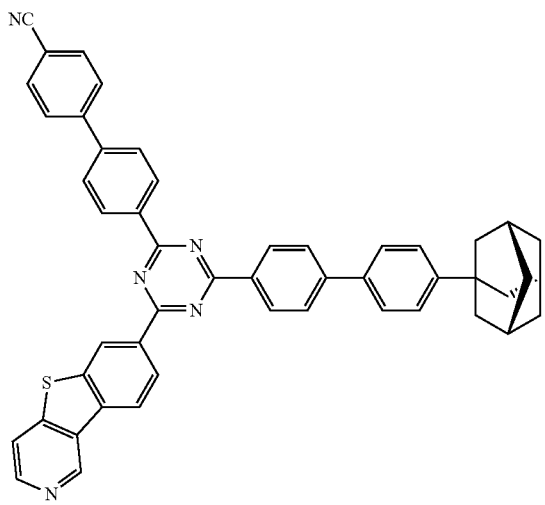 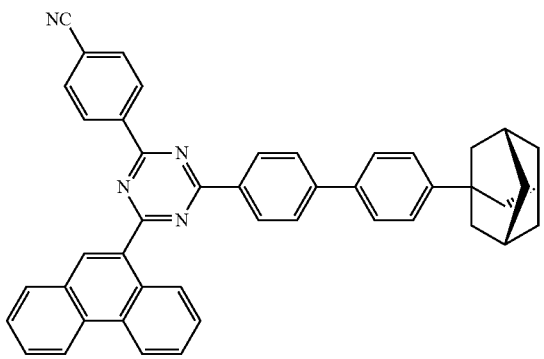
604 605
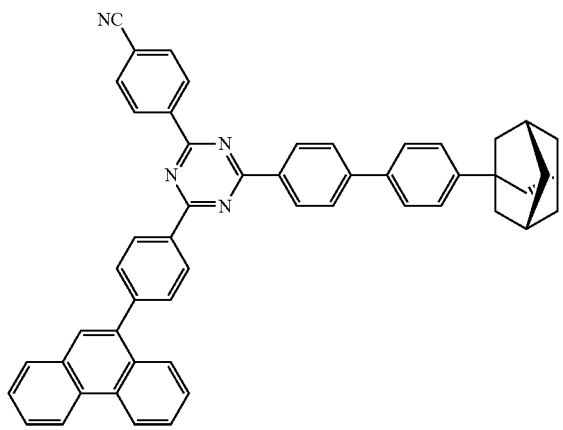 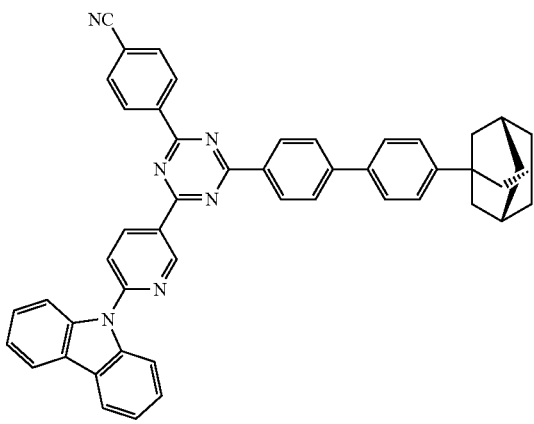
606 607
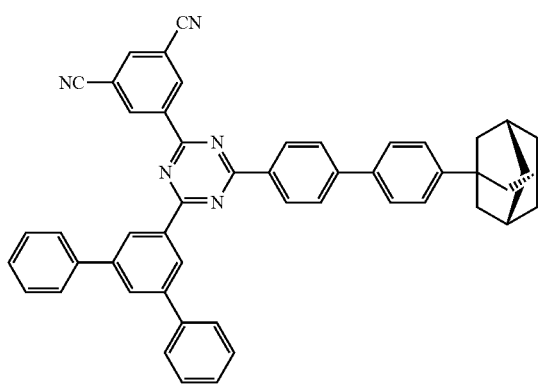 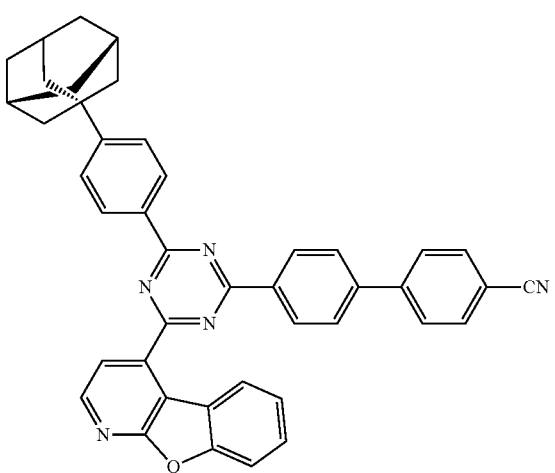

-continued
608
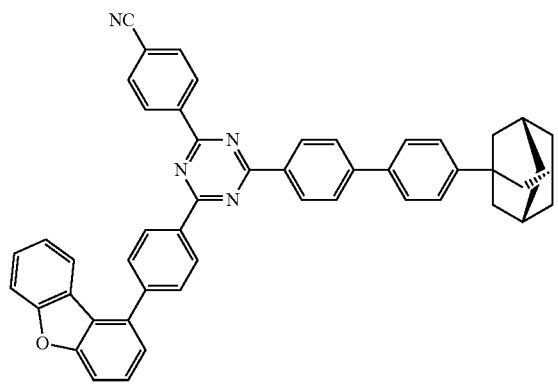
609
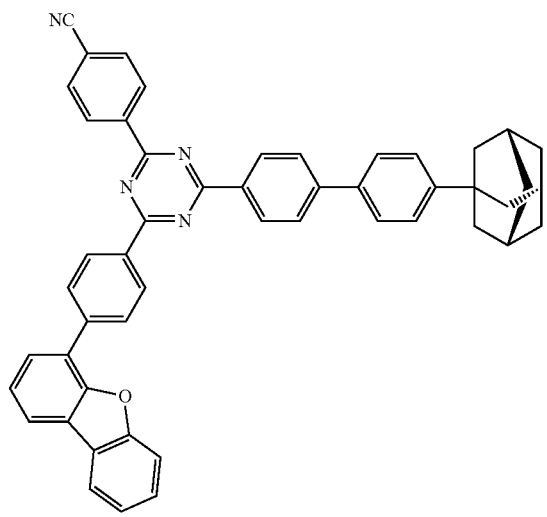
610
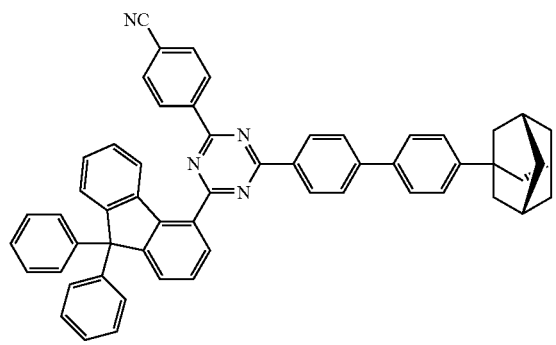
611
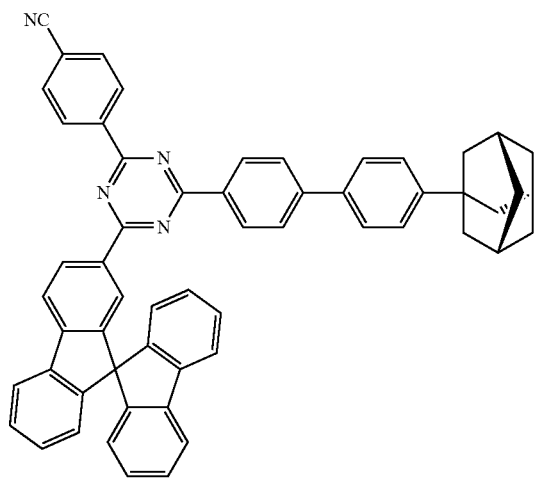
612
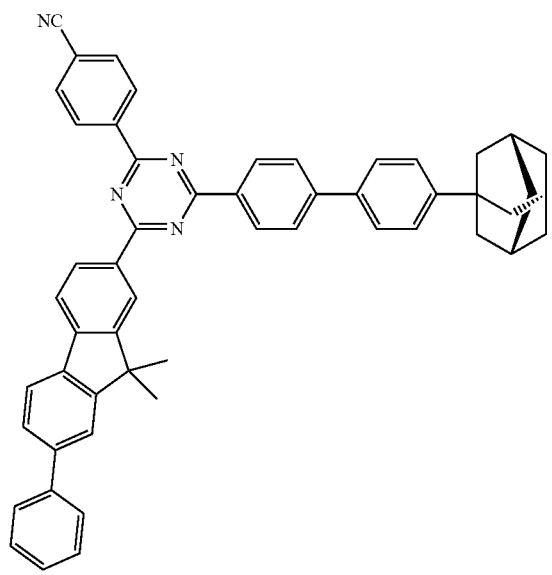
613
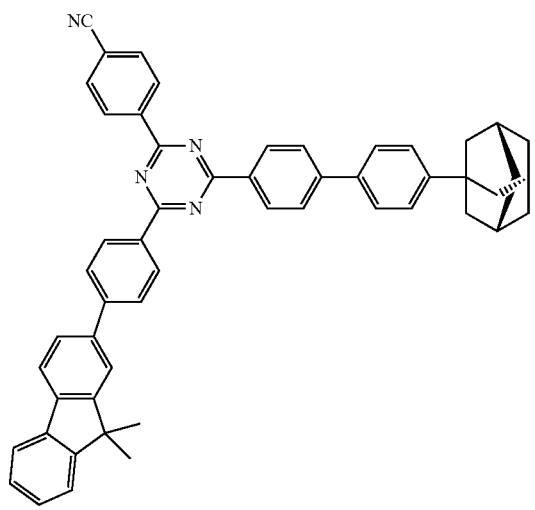

-continued
614
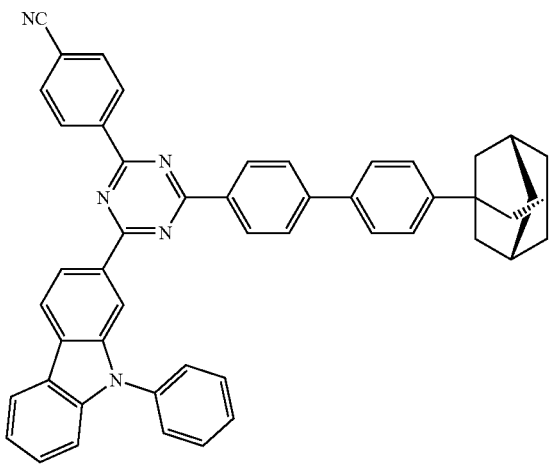
615
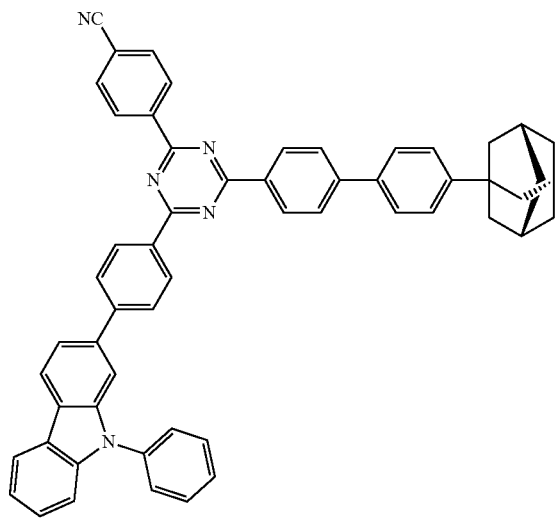
616
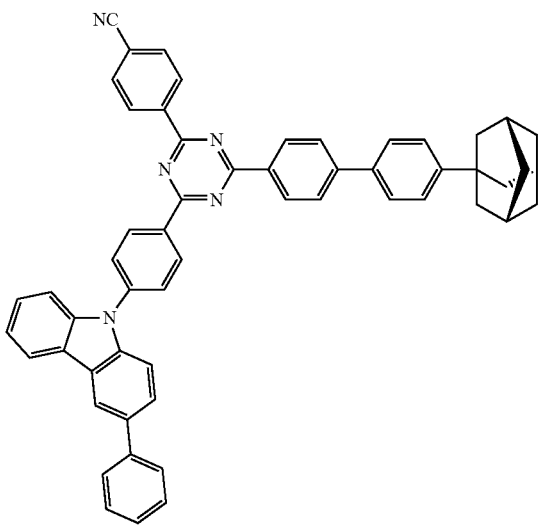
617
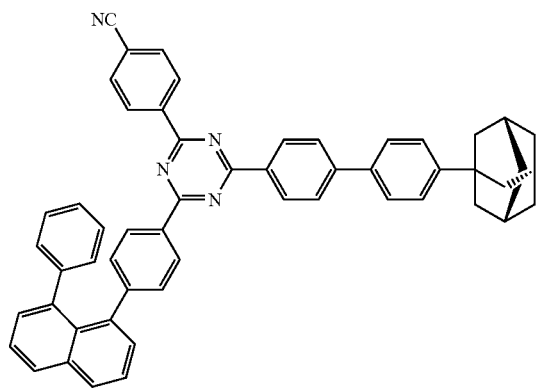
618
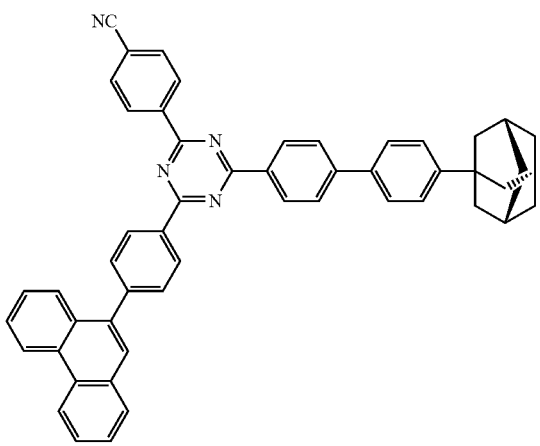
619
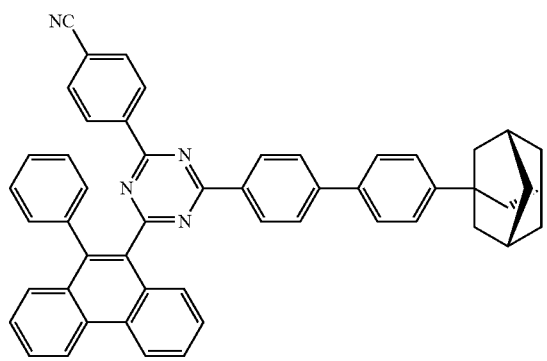

-continued
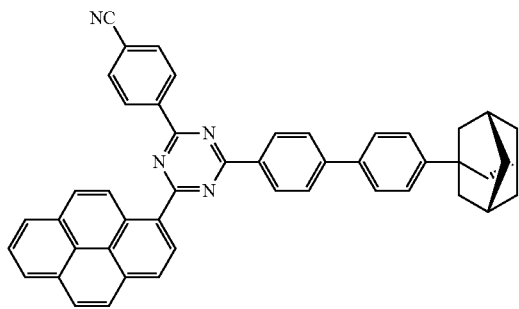
620
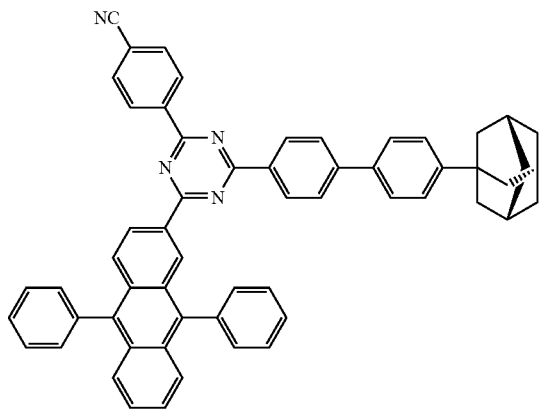
621
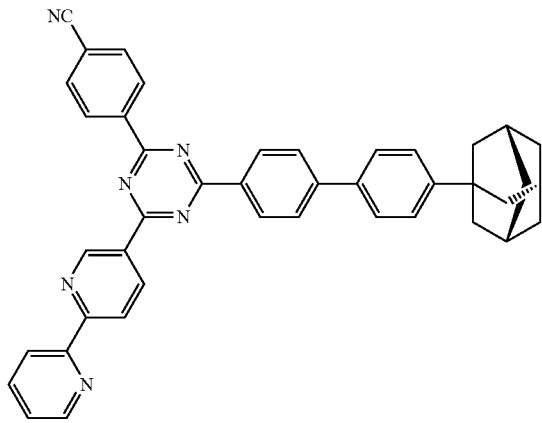
622
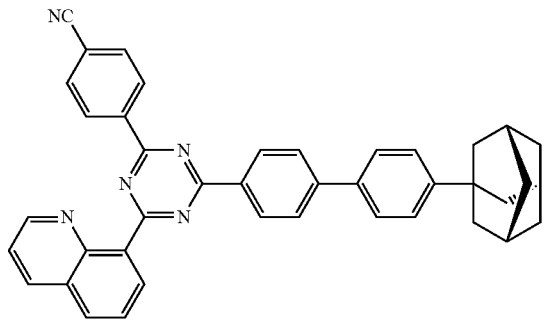
623
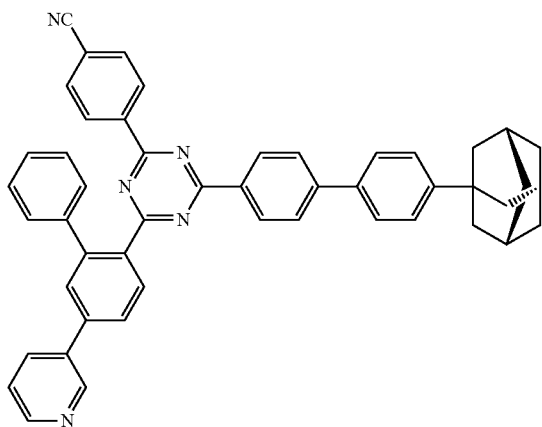
624
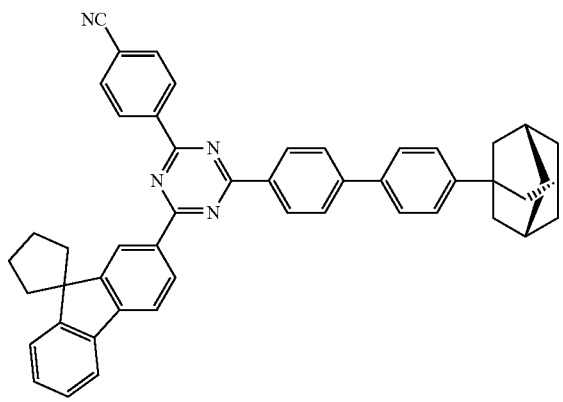
625

-continued
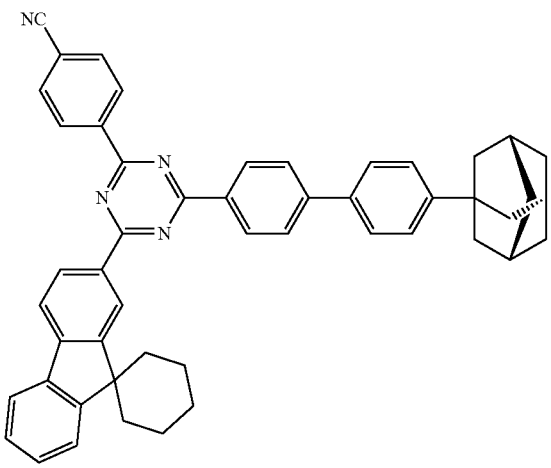
626
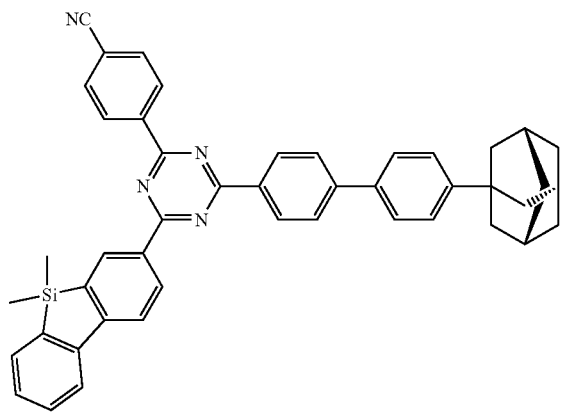
627
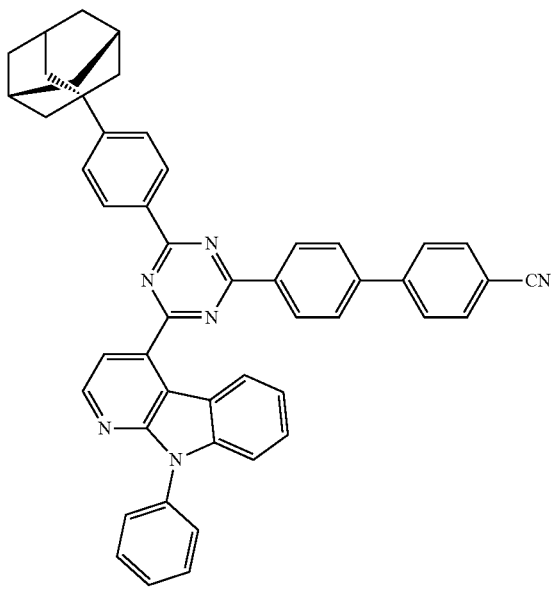
628
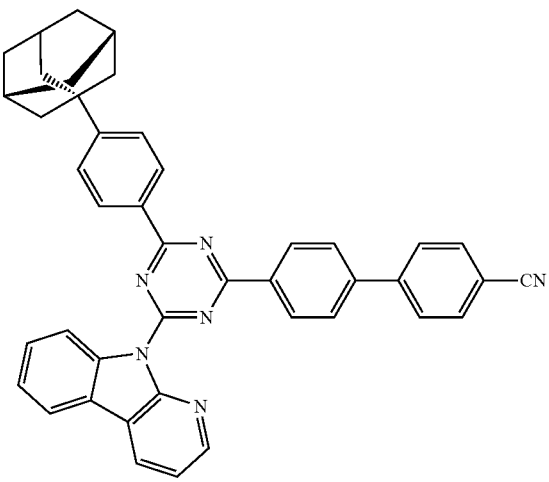
629
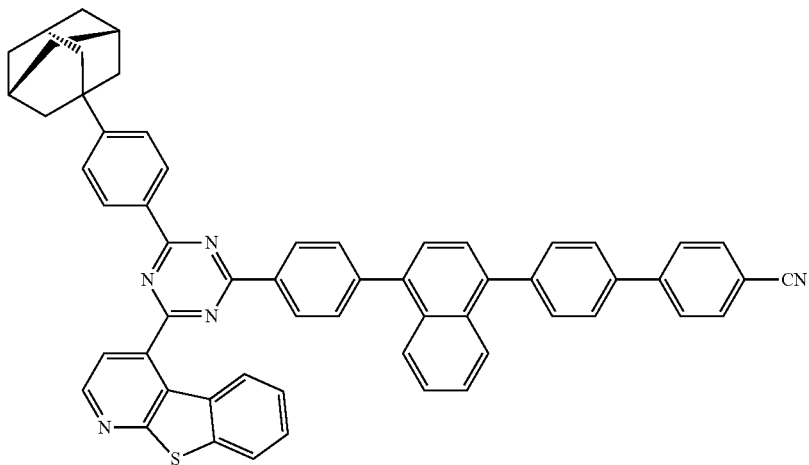
630

-continued

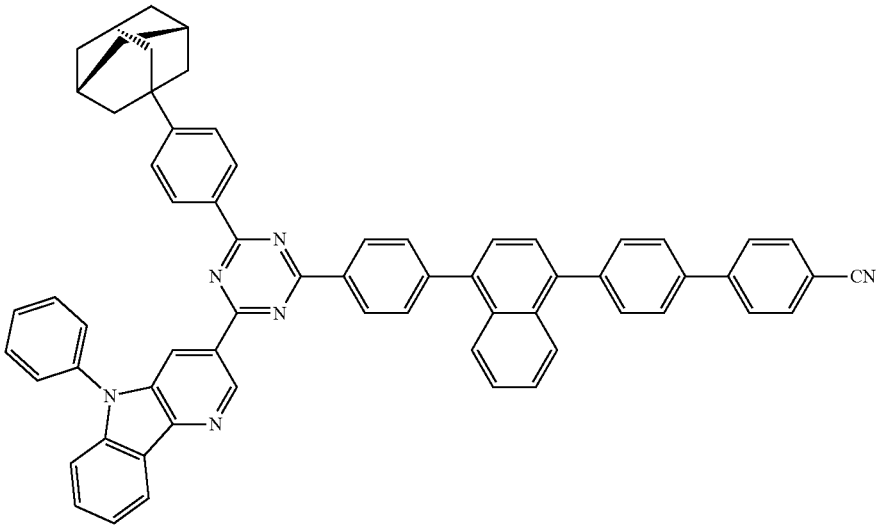

631

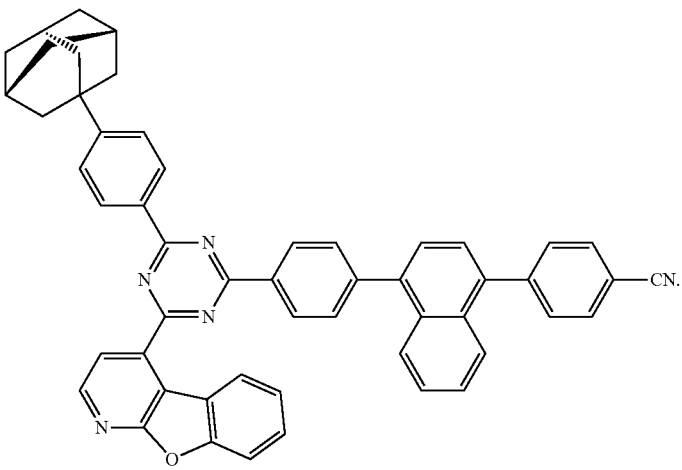

632

In the following, the present disclosure will be described in detail with reference to the examples. However, the examples according to this description may be modified to various other forms, and the scope of this description is not to be construed as limited to the examples described below. The examples of the description are provided in order to more fully describe the description to those skilled in the art.

EXAMPLES

In the synthesis examples described below, unless otherwise stated, all temperatures are in degrees Celsius. Some reagents were purchased from commercial suppliers such as Aldrich Chemical Company, Arco Chemical Company and Alfa Chemical Company and were used without further purification unless otherwise stated. Anhydrous tetrahydrofuran, dioxane, toluene, and diethyl ether were dried over metal sodium under reflux. Anhydrous dichloromethane and chloroform were dried over calcium hydride under reflux. Ethyl acetate, petroleum ether, n-hexane, N,N-dimethylacetamide and N,N-dimethylformamide were dried over anhydrous sodium sulfate in advance before use.

The following reactions were generally carried out under a positive pressure of nitrogen or argon or a drying tube sleeved anhydrous solvent (unless otherwise indicated), reaction flasks are plugged with suitable rubber stoppers, and a substrate was injected through a syringe. Glassware was dried.

During purification, a chromatographic column was a silica gel column and silica gel (100-200-mesh) was purchased from the Qingdao Ocean Chemical Factory.

In the synthesis examples, low resolution mass spectrum (MS) data were measured by using Agilent 6120 Quadrupole HPLC-M (column model: Zorbax SB-C18, 2.1×30 mm, 3.5 µm, 6 min at a flow rate of 0.6 mL/min. Mobile phase: 5% to 95% (a ratio of acetonitrile containing 0.1% formic acid in water containing 0.1% formic acid) using electrospray ionization (ESI) at 210 nm/254 nm with UV detection.

$^1$H NMR spectroscopy: Bruker 400 MHz Nuclear Magnetic Resonance Spectrometer, with $CDCl_3$ or $CD_2Cl_2$ as a solvent (in ppm) and TMS (0 ppm) as a reference standard at room temperature. When multiplets appear, the following abbreviations will be used: s (singlet), d (doublet), t (triplet), and m (multiplet).

Target compounds were detected by UV at 210 nm/254 nm by using Agilent 1260 pre-HPLC or Calesep pump 250 pre-HPLC (column model: NOVASEP 50/80 mm DAC).

Preparation Example 1

Preparation of Compound 3

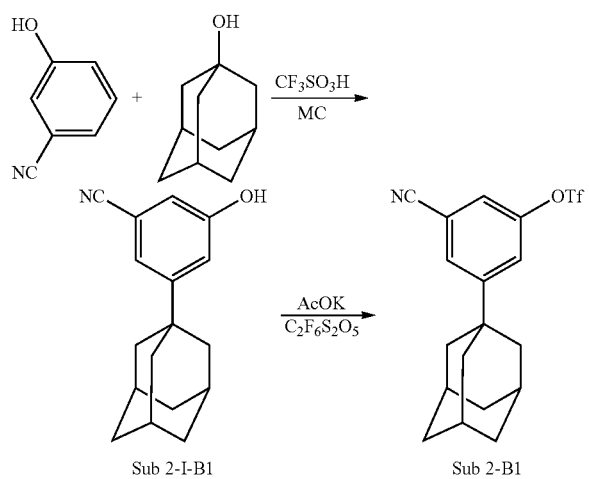

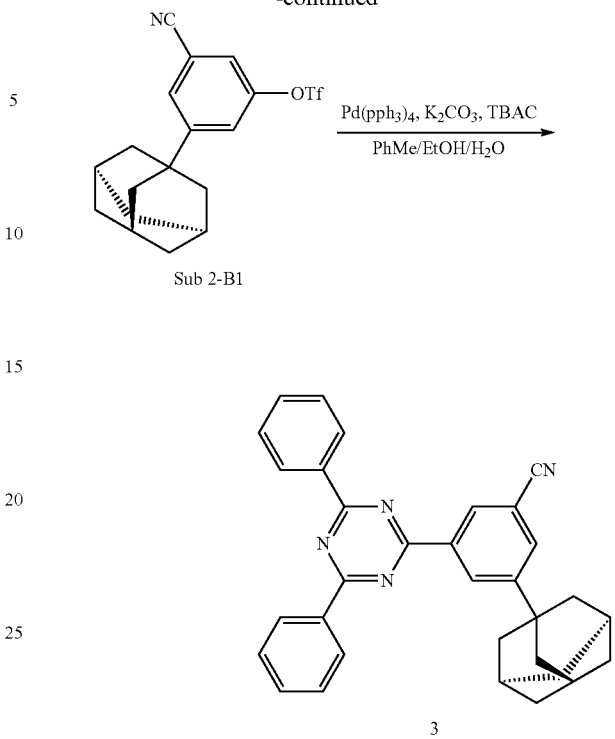

Synthesis of Sub 2-B1

1-Adamantanol (50.00 g, 328.45 mmol), 3-hydroxybenzonitrile (39.12 g, 328.45 mmol), and dichloromethane (500 mL) were added to a round bottom flask, and cooled to −5° C. under nitrogen atmosphere, trifluoromethanesulfonic acid (73.93 g, 492.67 mmol) was added dropwise at −5° C., and the reaction mixture was stirred for 3 h a the same temperature; the reaction solution was washed with deionized water (300 mL) to pH=7, and extracted with dichloromethane (100 mL), the organic phases were mixed, the combined organic phases were dried over anhydrous magnesium sulfate, and filtered, and then concentrated in a vacuum to obtain a crude product; and the obtained crude product was purified by silica gel column chromatography using n-heptane as a mobile phase to obtain an intermediate Sub 2-1-B1 (33.28 g, yield: 40.00%) as a white solid.

The white solid intermediate Sub 2-I-B1 (33.28 g) was added to a flask, potassium acetate was added, the mixture was dissolved with DCM, trifluoromethanesulfonic anhydride was added dropwise at room temperature, after the dropwise addition, pyridine was added; stirring was performed for 5 h, the reaction solution was washed with deionized water (300 mL) to pH=7, and extracted with dichloromethane (100 mL), the organic phases were mixed, and the combined organic phases were dried over anhydrous magnesium sulfate, and then filtered, and then concentrated in a vacuum to obtain a crude product; and the obtained crude product was purified by recrystallization using dichloromethane and n-heptane to obtain Sub 2-B1 (32.9 g, yield: 65%) as a white solid.

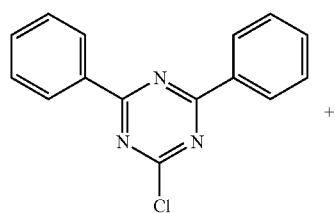

Synthesis of Compound 3

2-Chloro-4,6-diphenyl-1,3,5-triazine (5.36 g, 20.00 mmol), Sub 2-B1 (7.71 g, 20.00 mmol), tetrakis(triphenylphosphine)palladium (0.23 g, 0.20 mmol), potassium carbonate (5.57 g, 40.07 mmol), tetrabutylammonium chloride (0.64 g, 2.00 mmol), toluene (87 mL), ethanol (18 mL) and deionized water (18 mL) were added to a three-necked flask, the mixture was heated to 75° C. to 80° C. under nitrogen atmosphere, and stirred under heating and reflux for 8 h. After the reaction was completed, the reaction solution was cooled to room temperature, and extracted with toluene (100 mL), the organic phases were mixed, and the combined organic layers were dried over anhydrous magnesium sulfate, filtered and concentrated in a vacuum to obtain a crude product; and the crude product was purified by silica gel column chromatography to obtain a compound 3 (7.51 g, yield: 80%) as a solid. MS (ESI, pos.ion) m/z: 469.23 [M+H]$^+$.

Preparation Example 2

Preparation of Compound 14

A compound 14 was prepared in the same manner as that in Preparation example 1, except that 2-(4-biphenyl)-4-chloro-6-phenyl-1,3,5-triazine (6.50 g, 20.00 mmol) was used instead of 2-chloro-4,6-diphenyl-1,3,5-triazine in Preparation example 1 to obtain the compound 14 (7.72 g, yield: 75%). MS (ESI, pos.ion) m/z: 545.26 [M+H]$^+$.

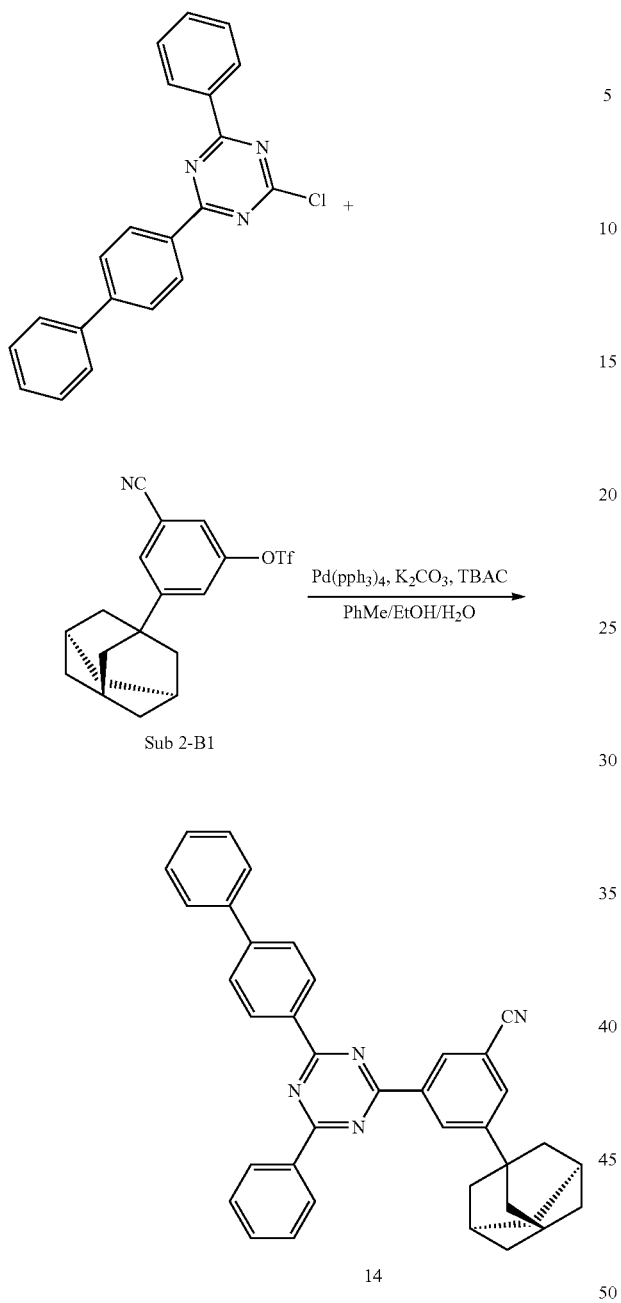
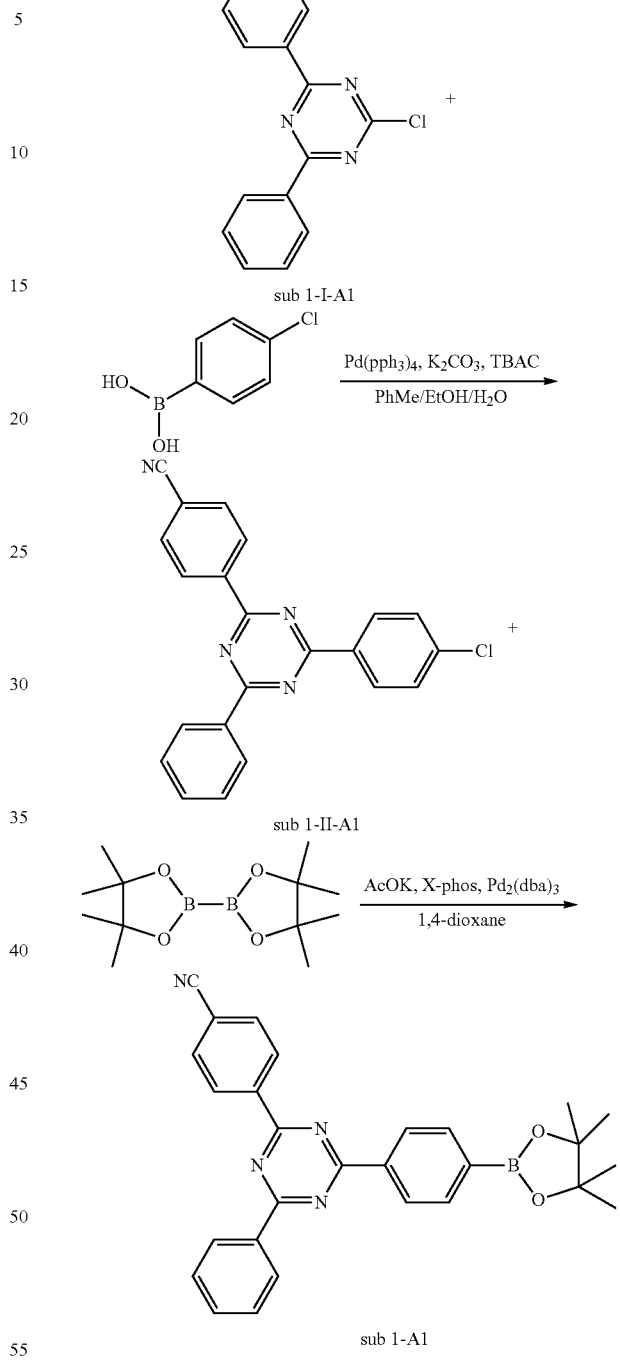

Preparation of Intermediates
<1. Synthesis of Sub 1-A1>
<Reaction Scheme 1>

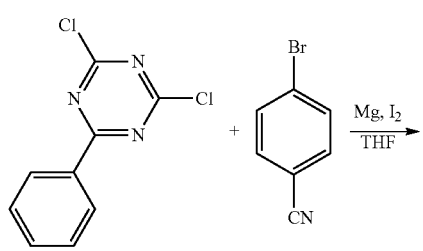

1> Synthesis of Sub 1-I-A1

Under nitrogen atmosphere, magnesium sheet (3.16 g, 131.85 mmol) and 30 ml of a solution of tetrahydrofuran were added into a three-necked flask, the system temperature was raised to 60° C., and iodine (0.55 g, 2.19 mmol) was added to the system. A compound 4-bromobenzonitrile (20.0 g, 109.87 mmol) was completely dissolved in 30 ml of a solution of THF, and slowly added dropwise to the system within 30 min while the temperature to be 60° C. After the dropwise addition, the reaction was stirred at 60° C. for 2 h. 2,4-Dichloro-6-phenyl-1,3,5-triazine (24.83 g, 109.87 mmol) dissolved in 80 ml of THF was added dropwise to the mixed solution after cooling at room temperature, and the reaction was completed after stirring for 3 h. After the reaction was completed, the reaction solution was extracted with toluene (200 mL), the organic phases were mixed, and the combined organic layer was dried over anhydrous magnesium sulfate, filtered and concentrated by distillation in a vacuum to obtain a crude product; and the crude product was purified by silica gel column chromatography, recrystallized, and filtered to obtain an intermediate sub 1-I-A1 (20.58 g, yield: 64%) as a solid.

2> Synthesis of Sub 1-II-A1

Sub 1-I-A1 (20.00 g, 68.32 mmol), p-chlorophenylboronic acid (10.89 g, 69.68 mmol), tetrakis(triphenylphosphine)palladium (1.57 g, 1.36 mmol), potassium carbonate (18.89 g, 136.64 mmol), tetrabutylammonium bromide (0.44 g, 1.36 mmol), toluene (160 mL), ethanol (80 mL) and deionized water (40 mL) were added to a three-necked flask, the mixture was heated to 78° C. under nitrogen protection, and stirred under heating and reflux for 8 h. After the reaction was completed, the reaction solution was cooled to room temperature, and extracted with toluene (200 mL), the organic phases were mixed, and the combined organic layer was dried over anhydrous magnesium sulfate, filtered and concentrated to obtain a crude product; and the crude product was purified by silica gel column chromatography to give an intermediate sub 1-II-A1 (16.87 g, yield: 67%) as a solid.

3> Synthesis of Sub 1-A1

Sub 1-II-A1 (15.00 g, 40.67 mmol), bis(pinacolato)diboron (15.49 g, 61.00 mmol), Pd$_2$(dba)$_3$ (0.37 g, 0.40 mmol), X-phos (0.38 g, 0.81 mmol), and KOAc (7.81 g, 81.34 mmol) were added to 1,4-dioxane (150 mL), and a reaction was carried out under reflux at 80° C. for 12 h. When the reaction was complete, extraction was performed with CH$_2$Cl$_2$ and water. An obtained organic layer was dried over MgSO$_4$ and concentrated, and the obtained compound was allowed to pass through a silica gel column, and recrystallized to obtain an intermediate sub 1-A1 (12.16 g, yield: 65%) as a solid.

Intermediates sub 1-A2 to sub 1-A17 were prepared in the same manner as that of sub 1-A1, except that a raw material 1 was used instead of 2-phenyl-4,6-dichloro-1,3,5-triazine in the synthesis of the intermediate sub 1-I-A1, a raw material 2 was used instead of 4-bromobenzonitrile in the synthesis of sub 1-I-A1 in Preparation example 1, and a raw material 3 was used instead of p-chlorophenylboronic acid in the synthesis of sub 1-II-A1 in Preparation example 1.

TABLE 1

| Intermediate | Raw material 1 | Raw material 2 | Raw material 3 | Sub 1-A | Yield/% |
|---|---|---|---|---|---|
| Sub 1-A2 | [structure] | [structure] | [structure] | [structure] | 54 |
| Sub 1-A3 | [structure] | [structure] | [structure] | [structure] | 61 |

TABLE 1-continued

| Intermediate | Raw material 1 | Raw material 2 | Raw material 3 | Sub 1-A | Yield/% |
|---|---|---|---|---|---|
| Sub 1-A4 | | | | | 62 |
| Sub 1-A5 | | | | | 54 |
| Sub 1-A6 | | | | | 56 |
| Sub 1-A7 | | | | | 66 |
| Sub 1-A9 | | | | | 52 |

TABLE 1-continued

| Intermediate | Raw material 1 | Raw material 2 | Raw material 3 | Sub 1-A | Yield/% |
|---|---|---|---|---|---|
| Sub 1-A10 | (structure) | (structure) | (structure) | (structure) | 64 |
| Sub 1-A11 | (structure) | (structure) | (structure) | (structure) | 55 |
| Sub 1-A12 | (structure) | (structure) a-1 | (structure) | (structure) | 63 |
| Sub 1-A13 | (structure) | (structure) b-1 | (structure) | (structure) | 57 |

TABLE 1-continued
| Intermediate | Raw material 1 | Raw material 2 | Raw material 3 | Sub 1-A | Yield/% |
|---|---|---|---|---|---|
| Sub 1-A14 | | | | | 61 |
| Sub 1-A15 | | | | | 59 |
| Sub 1-A16 | | | | | 54 |
| Sub 1-A17 | | | | | 50 |
Preparation method for some of raw materials in Table 1:
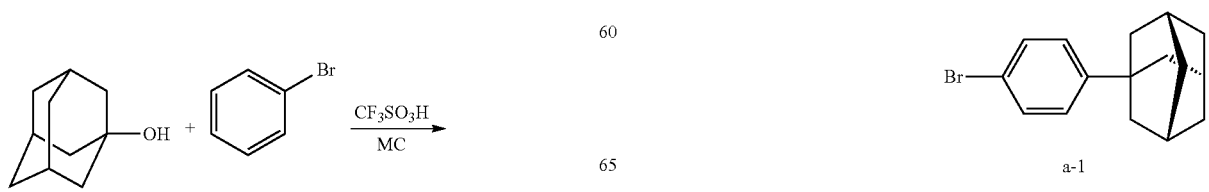

Bromobenzene (110 g, 0.72 mol) and 1-adamantanol (106 g, 0.72 mol) were added to a round bottom flask, and dissolved with 1.0 L of DCM to be clear, the obtained solution was cooled to 0° C. to 5° C., trifluoromethanesulfonic anhydride (162.65 g, 1.08 mol) was added dropwise, and the mixture was stirred for 3 h while heat preservation; after the reaction was completed, the reaction solution was washed with deionized water (1.0 L/time) to pH=7, liquid separation was performed, drying was performed by using anhydrous magnesium sulfate, filtering was performed, and the concentration was performed in a vacuum to obtain a crude product; and the obtained crude product was purified by silica gel column chromatography using n-heptane as a mobile phase to obtain 97 g of an intermediate a-1 as a white solid, with a purity of 99.8%, and a yield of 47.6%.

Intermediates b-1 to c-1 were prepared in the same manner as that of the intermediate a-1, except that a raw material 4 in Table 2 below was used instead of the preparation raw material bromobenzene.

TABLE 2

| Intermediate | Raw material 3 | Raw material 4 | Intermediate structure | Yield/% |
|---|---|---|---|---|
| b-1 | adamantan-1-ol | 4-bromobiphenyl | (structure) | 62 |
| c-1 | | 1-bromonaphthalene | (structure) | 54 |

Preparation Example 3
Preparation of Compound 46

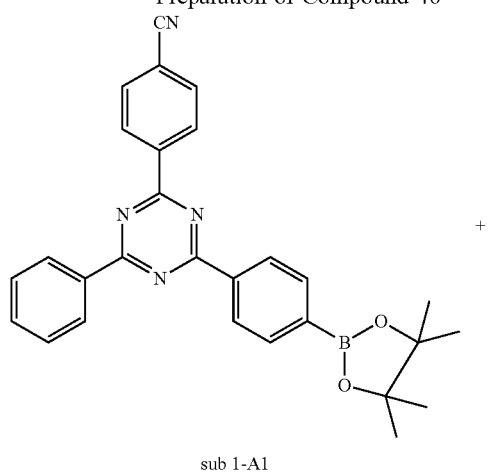

sub 1-A1

+

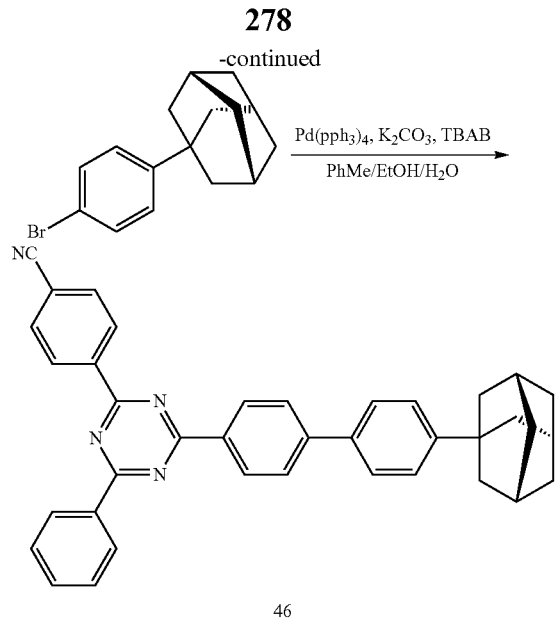

46

The intermediate sub 1-A1 (10.00 g, 21.72 mmol), a-1 (6.32 g, 21.72 mmol), tetrakis(triphenylphosphine)palladium (0.50 g, 0.43 mmol), potassium carbonate (6.00 g, 43.44 mmol), tetrabutylammonium bromide (0.07 g, 0.21 mmol), toluene (80 mL), ethanol (40 mL) and deionized water (20 mL) were added to a three-necked flask, heated to 78° C. under nitrogen atmosphere, and stirred under heating and reflux for 15 h. After the reaction was completed, the reaction solution was cooled to room temperature, and extracted with toluene (100 mL), the organic phases were mixed, and the combined organic layer was dried over anhydrous magnesium sulfate, filtered and concentrated; and a crude product was purified by silica gel column chromatography to obtain a compound 46 (6.70 g, yield: 57%) as a solid. MS (ESI, pos.ion) m/z: 545.26 [M+H]$^+$.

NMR data for the compound 46: ¹H NMR (400 MHZ, CD$_2$Cl$_2$) δ (ppm): 8.90 (d, 2H), 8.81 (d, 2H), 8.75 (d, 2H), 7.90 (d, 2H), 7.85 (d, 2H), 7.65-7.58 (m, 3H), 7.36-7.30 (m, 4H), 2.19 (s, 3H), 1.96 (s, 6H), 1.86-1.73 (m, 6H).

Compounds shown in Table 3 below were synthesized in a similar manner to that in preparation example 3 except that intermediates sub 1-A2 to sub 1-A17 were used instead of the intermediate sub 1-A1, and the intermediate a-1 was replaced by the following raw material 5:

TABLE 3

| Preparation example | Sub 1-A | Raw material 5 | Compound | Yield | Mass spectrum |
|---|---|---|---|---|---|
| 4 | 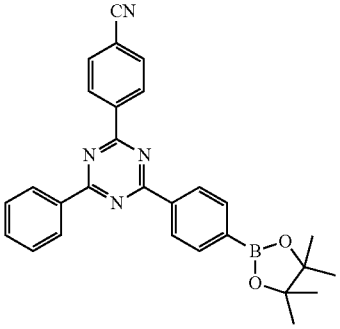 sub 1-A1 | 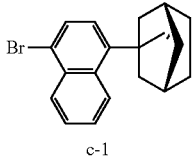 [SMILES: Brc1ccc(C23C[C@H]4C[C@@H](C2)C[C@@H](C3)C4)c2ccccc12] c-1 | 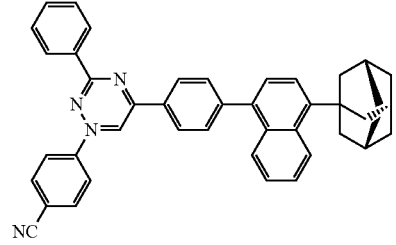 63 | 60 | 595.28 |
| 5 | 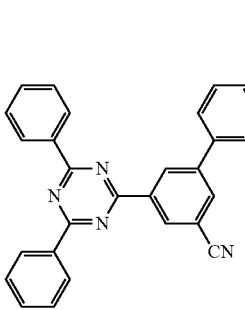 sub 1-A2 | 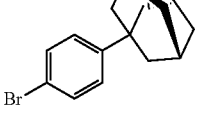 a-1 | 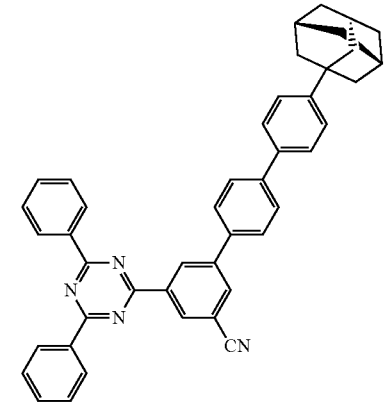 30 | 62 | 545.26 |
| 6 | 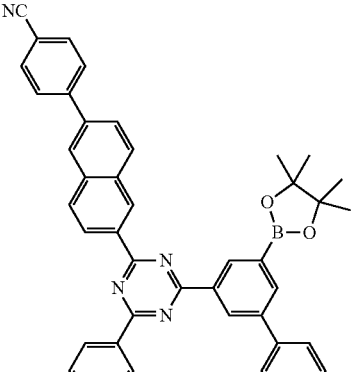 sub 1-A3 | 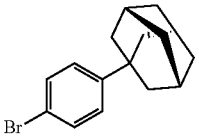 a-1 | 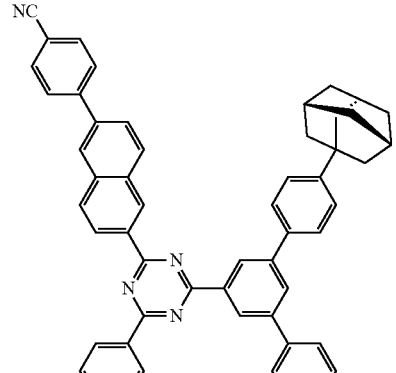 73 | 64 | 747.34 |

TABLE 3-continued

| Preparation example | Sub 1-A | Raw material 5 | Compound | Yield | Mass spectrum |
|---|---|---|---|---|---|
| 7 | sub 1-A4 | a-1 | 82 | 55 | 645.29 |
| 8 | sub 1-A5 | a-1 | 111 | 57 | 697.33 |
| 9 | sub 1-A6 | a-1 | 113 | 53 | 620.27 |
| 10 | sub 1-A7 | a-1 | 483 | 66 | 646.29 |

TABLE 3-continued

| Preparation example | Sub 1-A | Raw material 5 | Compound | Yield | Mass spectrum |
|---|---|---|---|---|---|
| 11 | sub 1-A9 | a-1 | 181 | 54 | 596.27 |
| 12 | sub 1-A10 | b-1 | 482 | 69 | 722.32 |
| 13 | sub 1-A11 | c-1 | 518 | 61 | 619.28 |
| 14 | sub 1-A12 | | 268 | 59 | 635.27 |

TABLE 3-continued

| Preparation example | Sub 1-A | Raw material 5 | Compound | Yield | Mass spectrum |
|---|---|---|---|---|---|
| 15 | sub 1-A12 | | 348 | 64 | 710.32 |
| 16 | sub 1-A12 | | 328 | 52 | 785.36 |
| 17 | sub 1-A14 | | 318 | 59 | 710.32 |
| 18 | sub 1-A13 | | 533 | 61 | 696.30 |

TABLE 3-continued

| Preparation example | Sub 1-A | Raw material 5 | Compound | Yield | Mass spectrum |
|---|---|---|---|---|---|
| 19 | sub 1-A15 | | 412 | 59 | 679.37 |
| 20 | sub 1-A15 | | 525 | 56 | 704.37 |
| 21 | sub 1-A16 | | 584 | 53 | 813.39 |
| 22 | sub 1-A17 | | 589 | 51 | 797.36 |

NMR data for some of the compounds in Table 3 above are shown in Table 4 below:
TABLE 4
| Compound No. | Compound structure | NMR data ¹H NMR (400 MHz, CD$_2$Cl$_2$) |
|---|---|---|
| 483 | 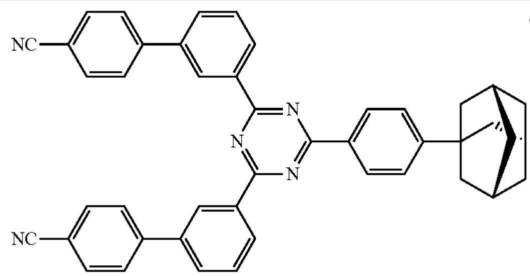 | δ (ppm): 8.99 (s, 2H), 8.84 (d, 2H), 8.75 (d, 2H), 7.92 (d, 4H), 7.75-7.62 (m, 8H), 7.47 (d, 2H), 2.18 (s, 3H), 1.95 (s, 6H), 1.81-1.75 (m, 6H) |
| 63 | 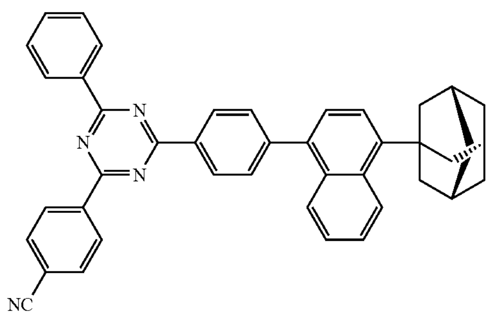 [SMILES: N#Cc1ccc(-c2nc(-c3ccccc3)nc(-c3ccc(-c4ccc(C56C[C@H]7C[C@@H](C5)C[C@@H](C6)C7)c5ccccc45)cc3)n2)cc1] | δ (ppm): 8.95 (d, 2H), 8.87 (d, 2H), 8.79 (d, 2H), 8.23 (d, 1H), 8.16 (d, 2H), 8.00 (d, 2H), 7.90 (d, 1H), 7.71 (d, 1H), 7.66-7.56 (m, 3H), 7.42 (t, 1H), 7.34 (t, 1H), 7.06 (d, 1H), 2.21 (s, 3H), 1.93 (s, 6H), 1.81-1.75 (m, 6H) |
Preparation Example 23
Preparation of Compound 591
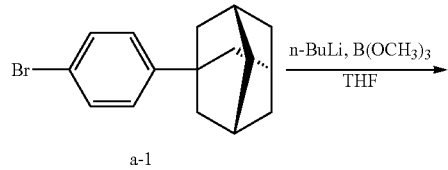
a-1
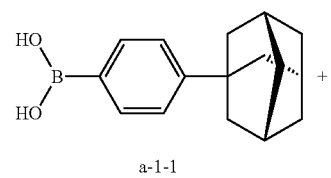
a-1-1
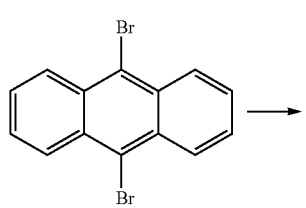
-continued
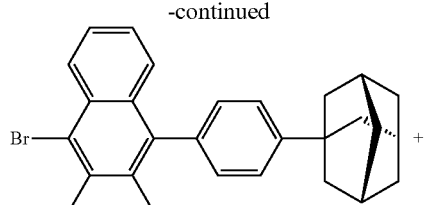
a-1-2
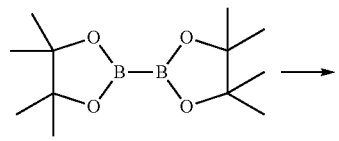
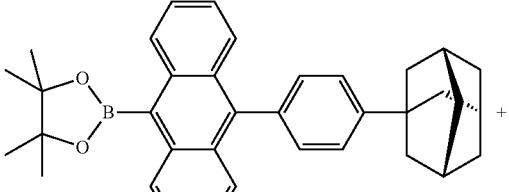
a-1-3
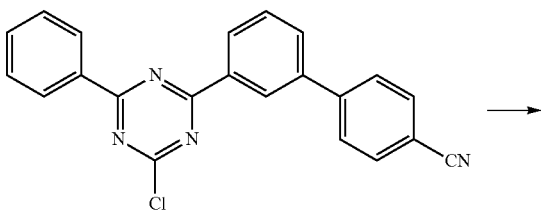

291

-continued

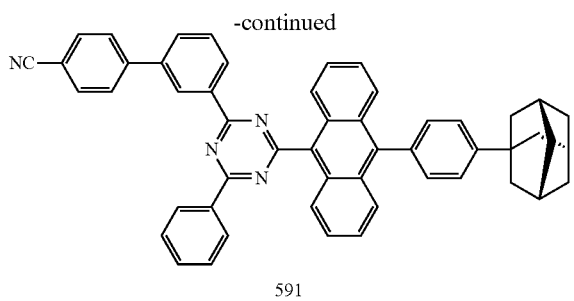

591

The intermediate a-1 (35.0 g, 120.1 mmol) was added to a round bottom flask, 630 mL of dry THF was added to the flask, and the system was cooled to −80° C. to −90° C. with liquid nitrogen, then n-butyllithium (8.46 g, 132.1 mmol) was added dropwise, and the reaction mixture was stirred for 1 h after dropwise addition. Trimethyl borate (13.7 g, 14.7 mL, 132.1 mmol) was added dropwise at the same temperature, after dropwise addition, the resulted mixture was stirred at −80° C. to −90° C. for 1 h, then naturally heated to room temperature, the reaction was completed. 100 mL of an aqueous solution of HCl (a concentration of 2 mol/L) was added, and stirring was performed for 0.5 h. Dichloromethane and water were added for extraction, an organic phase was washed to be neutral pH=7, the obtained organic phases were mixed, the combined organic phases was dried over anhydrous $MgSO_4$ for 10 min, and filtered, and the filtrate was concentrated in a vacuum, and stirred with n-heptane twice to obtain an intermediate a-1-1 (20.9 g, yield: 68%) as a white solid.

The intermediate a-1-1 (19.5 g, 76.1 mmol), 9,10-dibromoanthracene (32.0 g, 95.2 mmol), tetrakis(triphenylphosphine)palladium (2.2 g, 1.9 mmol), potassium carbonate (26.3 g, 190.4 mmol), tetrabutylammonium bromide (0.3 g, 0.9 mmol), toluene (250 mL), ethanol (60 mL), and deionized water (60 mL) were added to a three-necked flask, heated to 76° C. under nitrogen atmosphere, and stirred under heating and reflux for 15 h. After the reaction was completed, the solution was cooled to room temperature, the reaction solution was extracted with toluene and water, the organic phases were mixed, and the combined organic layer was dried over anhydrous magnesium sulfate, filtered, and concentrated to obtain a crude product; and the crude product was purified by silica gel column chromatography to obtain an intermediate a-1-2 (19.5 g, yield: 55%) as a solid.

The intermediate a-1-2 (24.0 g, 51.3 mmol), bis(pinacolato)diboron (19.5 g, 77.0 mmol), Pd(dppf)Cl$_2$ (0.7 g, 1.0 mmol), and KOAc (10.0 g, 102.6 mmol) were added into 1,4-dioxane (200 mL), and a reaction was carried out under reflux at 80° C. for 12 h. When the reaction was completed, the reaction solution was cooled to room temperature, and extracted with $CH_2Cl_2$ and water. The separated organic phase was dried over $MgSO_4$, the obtained organic layer was concentrated to obtained a residue, and the residue was subjected to silica gel column chromatography to obtain an intermediate a-1-3 (16.1 g, yield: 61%).

The intermediate a-1-3 (14.6 g, 28.4 mmol), 3'-(4-chloro-6-phenyl-1,3,5-triazin-2-yl)-[1,1'-biphenyl]-4-carbonitrile (10.0 g, 27.1 mmol), tetrakis(triphenylphosphine)palladium (0.6 g, 0.5 mmol), potassium carbonate (7.5 g, 54.2 mmol), tetrabutylammonium bromide (0.2 g, 0.6 mmol), toluene (120 mL), ethanol (30 mL) and deionized water (30 mL) were added to a three-necked flask, heated to 76° C. under nitrogen atmosphere, and stirred under heating and reflux for 15 h. After the reaction was completed, the solution was cooled to room temperature, the reaction solution was extracted with toluene and water, the organic phases were mixed, and the combined organic layer was dried over anhydrous magnesium sulfate, filtered, and concentrated to obtain a crude product; and crude product was purified by silica gel column chromatography to obtain a compound 591 (13.1 g, yield: 67%) as a solid.

MS (ESI, pos.ion) m/z: 721.33 [M+H]$^+$.

Preparation Example 24

Preparation of Compound 590

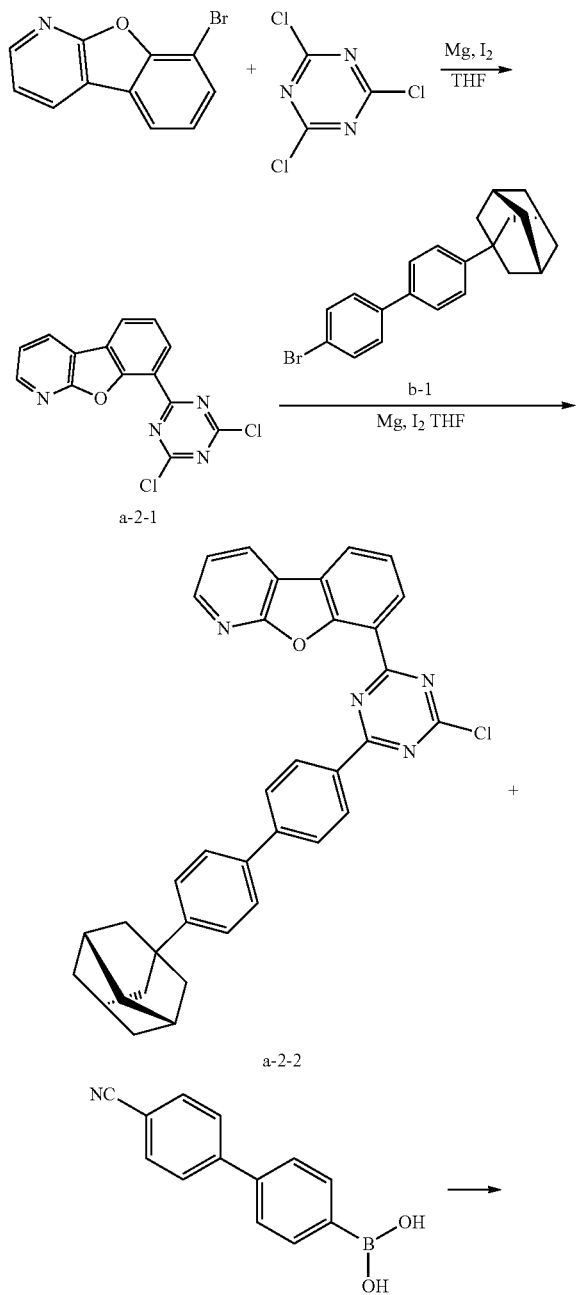

-continued

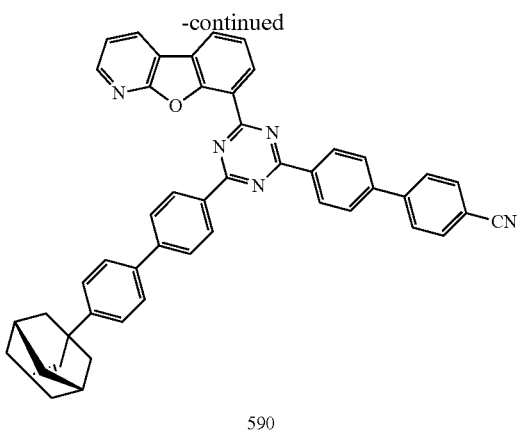

590

Under nitrogen atmosphere, magnesium sheet (2.9 g, 120.9 mmol) and 30 mL of tetrahydrofuran (THF) were added into a three-necked flask, the system temperature was raised to 80° C., iodine (0.6 g, 2.4 mmol) was added to the solution, 8-bromobenzofuro[2,3-B]pyridine (30.0 g, 120.9 mmol) was dissolved completely in 30 mL of THF solvent, and slowly added dropwise to the solution within 30 min while the temperature was kept at 80° C. After the dropwise addition was complete, a reaction was carried out under stirring at 80° C. for 2 h to obtain a mixed solution. After cooling at room temperature, 2,4,6-trichloro-1,3,5-triazine (22.3 g, 120 mmol) dissolved in 80 mL of THF was added dropwise to the mixed solution, and after stirring for 3 h, the reaction was completed After the reaction was completed, the reaction solution was extracted with toluene (200 mL), the organic phases were mixed, and the combined organic layer was dried over anhydrous magnesium sulfate, filtered and concentrated in a vacuum to obtain a crude product; and the crude product was purified by silica gel column chromatography, recrystallized with methanol, and filtered to obtain an intermediate a-2-1 (22.6 g, yield:59%) as a solid.

Under nitrogen atmosphere, magnesium sheet (1.6 g, 69.3 mmol) and 10 mL of tetrahydrofuran (THF) were added into a three-necked flask, the mixture was heated to 80° C., iodine (0.3 g, 1.4 mmol) was added to the mixture, b-1 (30.0 g, 120.9 mmol) was dissolved completely in 15 mL of THF solvent, and slowly added dropwise to the mixture within 30 min while the temperature was kept at 80° C. After the dropwise addition was complete, a reaction was carried out under stirring at 80° C. for 2 h to obtain a mixed solution. After cooling at room temperature, a-I-1 (22.0 g, 69.3 mmol) dissolved in 50 mL of THF was added dropwise to the mixed solution, and after stirring for 3 h, the reaction was completed. After the reaction was completed, the reaction solution was extracted with toluene (200 mL), the organic phases were mixed, and the combined organic layer was dried over anhydrous magnesium sulfate, filtered and concentrated in a vacuum to obtain a crude product; and the crude product was purified by silica gel column chromatography, recrystallized with methanol, and filtered to obtain an intermediate a-2-2 (21.3 g, yield:54%) as a solid.

The intermediate a-2-2 (21.0 g, 6.8 mmol), 4-cyano-4-biphenylboronic acid (8.4 g, 37.6 mmol), tetrakis(triphenylphosphine)palladium (0.8 g, 0.7 mmol), potassium carbonate (10.1 g, 73.7 mmol), tetrabutylammonium bromide (0.12 g, 0.37 mmol), toluene (160 mL), ethanol (80 mL) and deionized water (40 mL) were added to a three-necked flask, the mixture was heated to reflux at 76° C. under nitrogen atmosphere, and stirred for 15 h. After the reaction was completed, the solution was cooled to room temperature, the reaction solution was extracted with toluene and water, the organic phases were mixed, and the combined organic layer was dried over anhydrous magnesium sulfate, filtered, and concentrated; and a crude product was purified by silica gel column chromatography to obtain a compound 590 (17.0 g, yield:65%) as a solid. MS (ESI, pos.ion) m/z: 712.30 [M+H]⁺.

Preparation Examples 25 to 31 a compound 55, a compound 81, a compound 216, a compound 570, a compound 577, a compound 598 and a compound 619 were also prepared by using purchased intermediates as raw materials by reference to the preparation methods and operation processes of the above compounds.

Preparation Example 25 the compound 55 was synthesized by reference to the process for the preparation of the compound 63 to obtain the compound 55 (5.70 g) as a solid. MS (ESI, pos.ion) m/z: 520.18 [M+H]⁺.

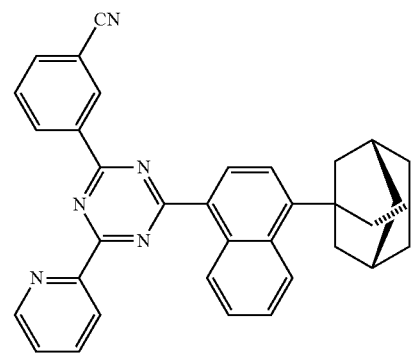

55

Preparation Example 26 the compound 81 was synthesized by reference to the process for the preparation of the compound 63 to obtain the compound 81 (5.50 g) as a solid. MS (ESI, pos.ion) m/z: 695.28 [M+H]⁺.

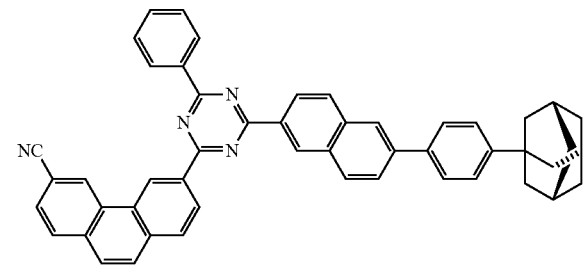

81

Preparation Example 27 the compound 216 was synthesized by referring to the process for the preparation of the compound 483 to obtain the compound 216 (3.70 g) as a solid. MS (ESI, pos.ion) m/z: 575.13 [M+H]⁺.

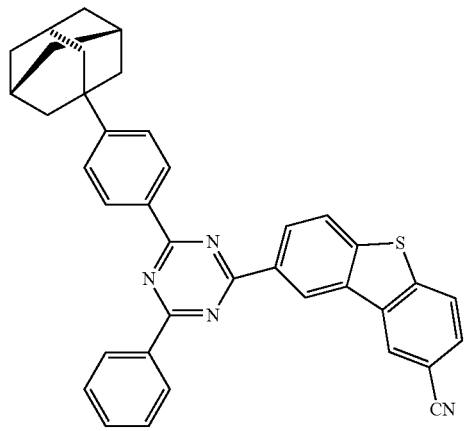

216

Preparation Example 28 the compound 570 was synthesized by reference to the process for the preparation of compound 482 to obtain the compound 570 (5.35 g) as a solid. MS (ESI, pos.ion) m/z: 549.25 [M+H]⁺.

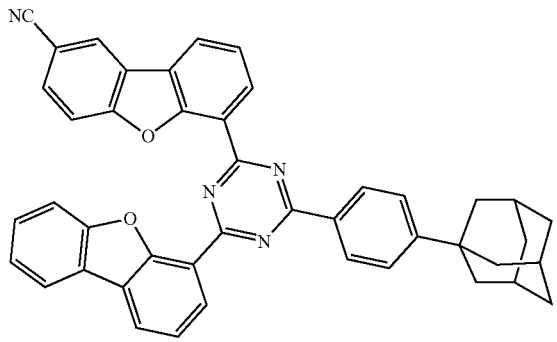

570

Preparation Example 29 the compound 577 was synthesized by reference to the process for the preparation of the compound 30 to obtain the compound 577 (8.45 g) as a solid. MS (ESI, pos.ion) m/z: 667.25 [M+H]⁺.

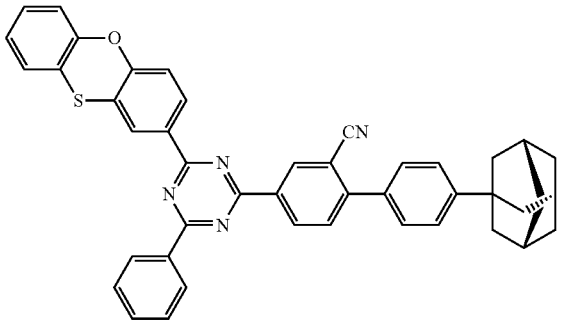

577

Preparation Example 30 the compound 598 was synthesized by reference to the process for the preparation of the compound 483 to obtain the compound 598 (5.80 g) as a solid. MS (ESI, pos.ion) m/z: 710.32 [M+H]⁺.

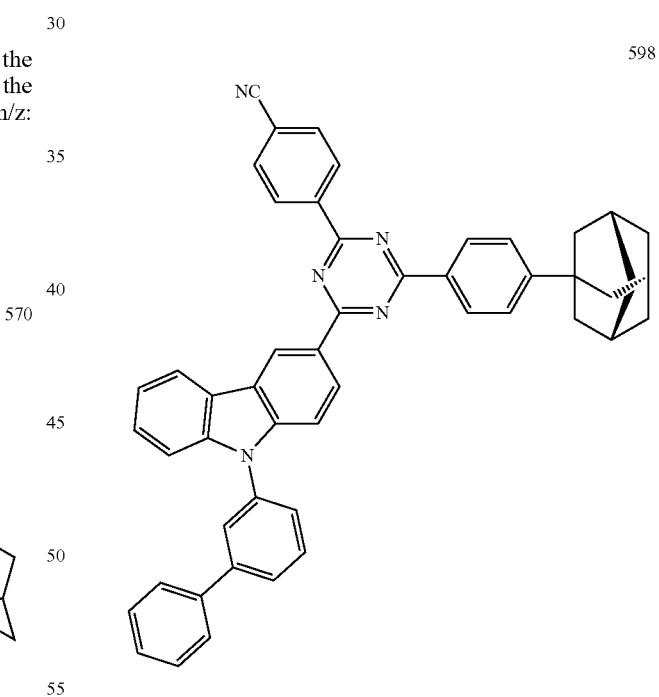

598

Preparation Example 31 the compound 619 was synthesized by reference to the process for the preparation of the compound 483 to obtain the compound 619 (8.27 g) as a solid. MS (ESI, pos.ion) m/z: 721.33 [M+H]⁺.

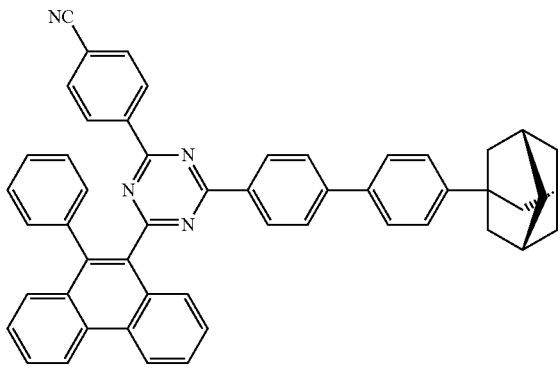

619

Embodiments of the present disclosure also provide an organic electroluminescent device, including an anode, a cathode and a functional layer between the anode and the cathode, and the functional layer includes the above nitrogen-containing compound of the present disclosure.

In one specific embodiment, the functional layer includes an electron transport layer including the nitrogen-containing compound of the present disclosure. When the nitrogen-containing compound of the present disclosure is used as an electron transport layer material of an electronic element, the efficiency, and service life of the device can be improved, and the operating voltage can be reduced.

In one specific embodiment, the electronic element may be an organic electroluminescent device. As shown in FIG. 1, the organic electroluminescent device may include an anode 100, a hole transport layer 320, an electron blocking layer 322, an organic luminescence layer 330 as an energy conversion layer, a hole blocking layer 341, an electron transport layer 340, and a cathode 200 which are sequentially stacked. The hole transport layer 320, the electron blocking layer 322, the organic luminescence layer 330 as the energy conversion layer, the hole blocking layer 341, and the electron transport layer 340 together constitute the functional layer 300.

Optionally, the anode 100 includes an anode material, which is preferably a material with a large work function that facilitates hole injection into the functional layer. Specific examples of the anode material include metals such as nickel, platinum, vanadium, chromium, copper, zinc, and gold, or their alloys; metal oxides such as zinc oxide, indium oxide, indium tin oxide (ITO) and indium zinc oxide (IZO); combined metals and oxides, such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, but are not limited to these. A transparent electrode containing indium tin oxide (ITO) as the anode is preferably included.

Optionally, the hole transport layer 320 and the electron blocking layer 322 each include one or more hole transport materials, and the hole transport materials may be selected from a carbazole polymer, carbazole-linked triarylamine compounds, or other types of compounds, which are not particularly limited in the present disclosure. For example, the hole transport layer 320 may be composed of a compound NPB or a compound HT-01, and the electron blocking layer 322 may include a compound EB-01 or TCTA.

Optionally, the organic luminescence layer 330 may be composed of a single luminescence material, and may also include a host material and a doping material. Optionally, the organic luminescence layer 330 is composed of the host material and the doping material, and holes injected into the organic luminescence layer 330 and electrons injected into the organic luminescence layer 330 can be recombined in the organic luminescence layer 330 to form excitons, the excitons transfer energy to the host material, and the host material transfers energy to the doping material, thus enabling the doping material to emit light.

The host material of the organic luminescence layer 330 can be a metal chelate compound, a bis-styryl derivative, an aromatic amine derivative, a dibenzofuran derivative or other types of materials, which is not specially limited in the present disclosure. In one embodiment of the present disclosure, the host material of the organic luminescence layer 330 is BH-01 or α,β-AND.

The doping material of the organic luminescence layer 330 may be a compound having a condensed aryl ring or its derivative, a compound having a heteroaryl ring or its derivative, an aromatic amine derivative, or other materials, which is not particularly limited in the present disclosure. In one embodiment of the present disclosure, the doping material of the organic luminescence layer 330 is BD-01.

The electron transport layer 340 may be of a single-layer structure or a multi-layer structure, and may include one or more electron transport materials, and the electron transport materials may be selected from, but are not limited to, a benzimidazole derivative, an oxadiazole derivative, a quinoxaline derivative, or other electron transport materials. In one embodiment of the present disclosure, the electron transport layer material contains the organic compound of the present disclosure.

In the present disclosure, the cathode 200 may include a cathode material, which is a material having a small work function that facilitates electron injection into the functional layer. Specific examples of the cathode material include, but are not limited to, metals such as magnesium, calcium, sodium, potassium, titanium, indium, yttrium, lithium, gadolinium, aluminum, silver, tin, and lead or their alloys; or multilayer materials such as LiF/Al, Liq/Al, $LiO_2$/Al, LiF/Ca, LiF/Al, and $BaF_2$/Ca. A metal electrode containing magnesium and silver as the cathode is preferably included.

Optionally, as shown in FIG. 1, a hole injection layer 310 may also be arranged between the anode 100 and the hole transport layer 320 to enhance the ability to inject holes into the hole transport layer 320. The hole injection layer 310 can be made of a benzidine derivative, a starburst arylamine compound, a phthalocyanine derivative or other materials, which is not specially limited in the present disclosure. For example, the hole injection layer 310 is composed of F4-TCNQ or m-MTDATA.

Optionally, as shown in FIG. 1, an electron injection layer 350 can also be arranged between the cathode 200 and the electron transport layer 340 so as to enhance the ability to inject electrons into the electron transport layer 340. The electron injection layer 350 may include an inorganic material such as an alkali metal sulfide, and an alkali metal halide, or may include a complex of an alkali metal and an organic substance. For example, the electron injection layer 350 may include Yb.

According to another embodiment, the electronic element may be a photoelectric conversion device. The photoelectric conversion device may include an anode and a cathode which are disposed oppositely, and a functional layer disposed between the anode and the cathode; and the functional layer includes the nitrogen-containing compound provided by the present disclosure.

Figure 2:
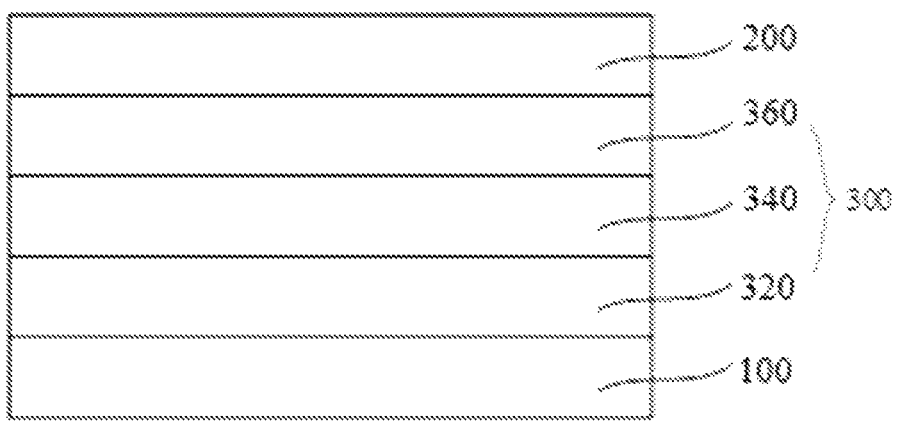
FIG. 2 is a structural schematic diagram of a photoelectric conversion device according to a embodiment of the present disclosure.

According to one specific embodiment, as shown in FIG. 2, a photoelectric conversion device may include an anode 100, a hole transport layer 320, a photoelectric conversion layer 360, an electron transport layer 340, and a cathode 200 which are sequentially stacked. The hole transport layer 320, the photoelectric conversion layer 360, and the electron transport layer 340 constitute the functional layer 300.

Optionally, the photoelectric conversion device can be a solar cell, in particular an organic thin-film solar cell. For example, in one embodiment of the present disclosure, the solar cell may include an anode, a hole transport layer, an organic luminescence layer, an electron transport layer and a cathode which are sequentially stacked, and the electron transport layer includes the organic compound of the present disclosure.

In a third aspect, the present disclosure provides an electronic device, including the electronic element according to the second aspect of the present disclosure.

Figure 3:
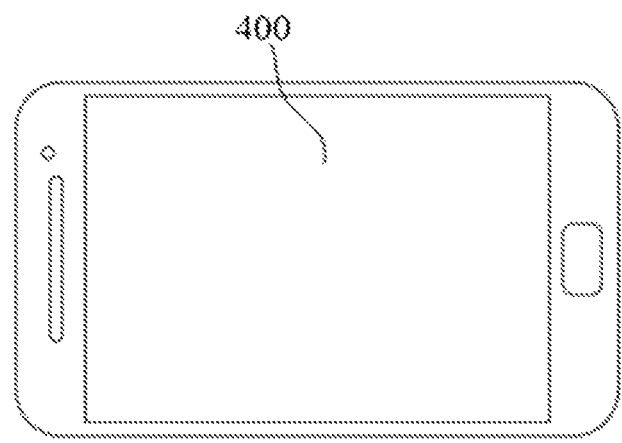
FIG. 3 is a structural schematic diagram of an electronic device according to one embodiment of the present disclosure.

According to one embodiment, as shown in FIG. 3, the electronic device is a first electronic device 400 including the organic electroluminescent device described above. The first electronic device 400 may, for example, be a display device, a lighting device, an optical communication device, or other types of electronic devices, and may include, for example, but is not limited to, a computer screen, a mobile phone screen, a television, electronic paper, an emergency lighting lamp, an optical module, and the like.

Figure 4:
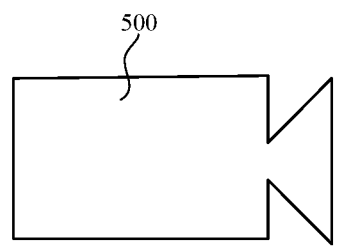
FIG. 4 is a structural schematic diagram of an electronic device according to another embodiment of the present disclosure.

According to another embodiment, as shown in FIG. 4, the electronic device is a second electronic device 500 including the photoelectric conversion device described above. The second electronic device 500 may, for example, be a solar power plant, a light detector, a fingerprint recognition device, an optical module, a CCD camera, or other types of electronic devices.

The synthesis methods of the nitrogen-containing compounds of the present disclosure are specifically illustrated below in conjunction with synthesis examples, but the present disclosure is not limited in any way.

Specific organic electroluminescent device preparation examples are given below.

Example 1

Manufacture of Blue Organic Electroluminescent Device

An anode was prepared by the following process: an ITO substrate having a thickness of 1500 Å was cut into a dimension of 40 mm×40 mm×0.7 mm to be prepared into a top-emitting experimental substrate with a cathode overlap region, an anode and an insulating layer pattern by adopting a photoetching process, and surface treatment was performed by utilizing ultraviolet ozone and $O_2:N_2$ plasma so as to increase the work function of the anode (the experimental substrate) and clean the experimental substrate.

m-MTDATA (4,4',4''-tris(N-3-methylphenyl-N-phenylamino)triphenylamine) was vacuum-evaporated on the experimental substrate (the anode) to form a hole injection layer (HIL) having a thickness of 120 Å, and NPB was vacuum-evaporated on the hole injection layer to form a hole transport layer (HTL) having a thickness of 1030 Å.

TCTA was evaporated on the hole transport layer to form an electron blocking layer (EBL) having a thickness of 100 Å.

α,β-ADN was used as a host while BD-1 was doped, and the host and the dopant form an organic luminescence layer (EML) having a thickness of 220 Å at a film thickness ratio of 30:3.

A compound 1 of the present disclosure was evaporated on the luminescence layer to form an electron transport layer (ETL) having a thickness of 300 Å, Yb was evaporated on the electron transport layer to form an electron injection layer (EIL) having a thickness of 10 Å, and then magnesium (Mg) and silver (Ag) were mixed and vacuum-evaporated on the electron injection layer at an evaporation rate of 1:10 to form a cathode having a thickness of 120 Å.

In addition, CP-1 having a thickness of 700 Å was evaporated on the cathode to form a capping layer (CPL), thus completing the manufacture of an organic luminescence device.

The structural formulas of m-MTDATA, NPB, TCTA, α,β-ADN, BD-1 and CP-1 are as follows:

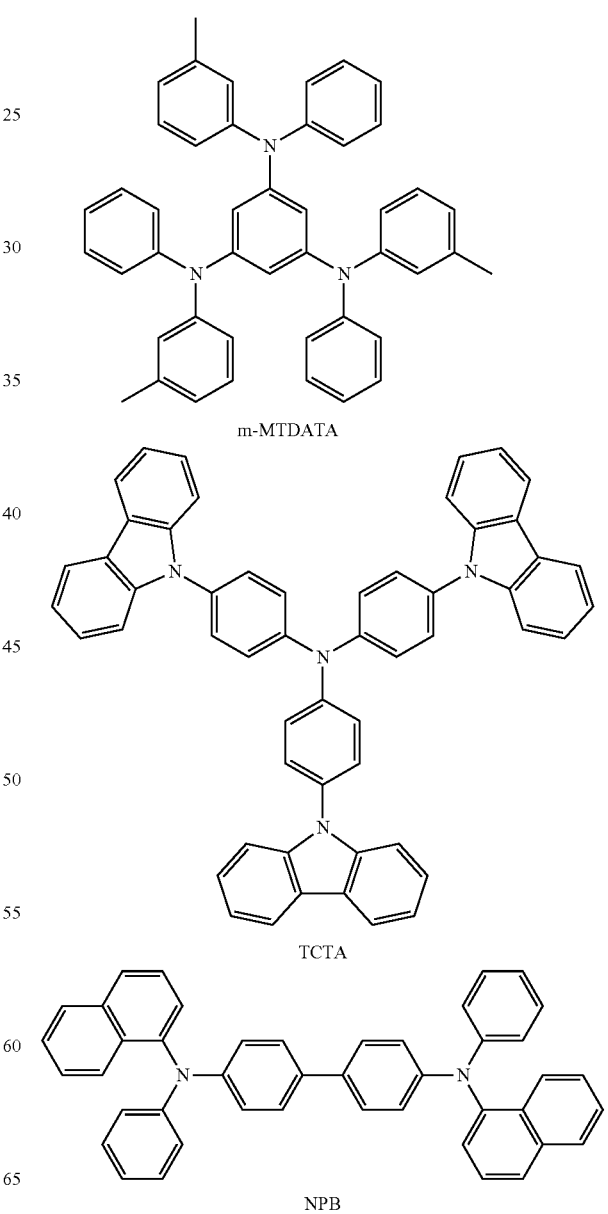

m-MTDATA

TCTA

NPB

-continued

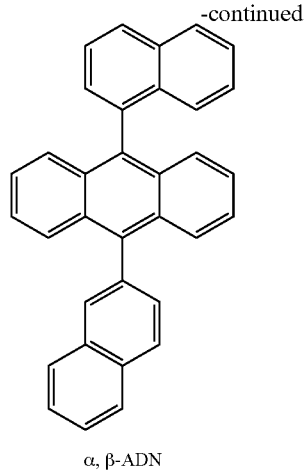

α, β-ADN

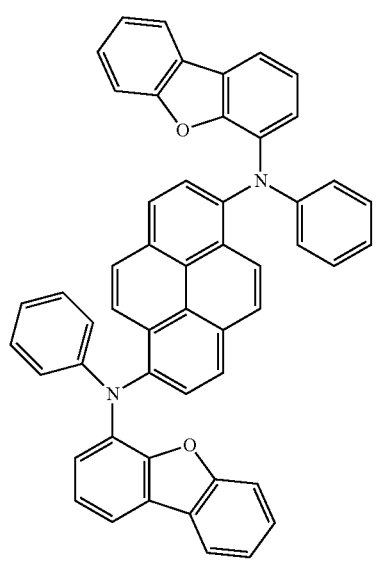

BD-1

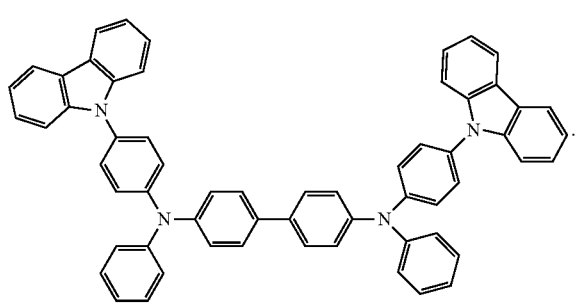

CP-1

Examples 2 to 31

An organic electroluminescent device was manufactured by the same method as that in Example 1 except that compounds shown in Table 5 were respectively used when the electron transport layer (ETL) was formed.

Comparative Examples 1 to 6

In Comparative examples 1 to 6, an organic electroluminescent device was manufactured by the same method as that in Example 1, except that compounds A, B, C, E, F and G were used as the electron transport layer instead of the compound 1.

Compound A

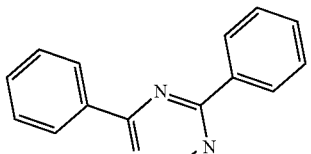

Compound B

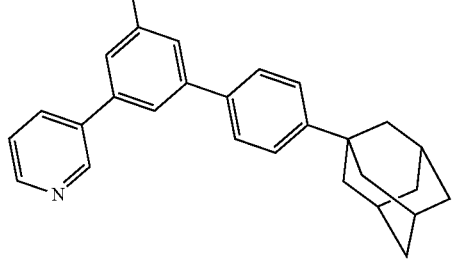

Compound C

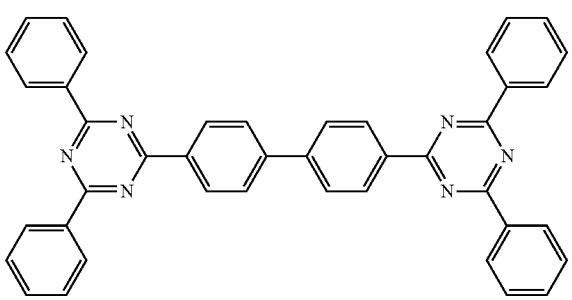

Compound E

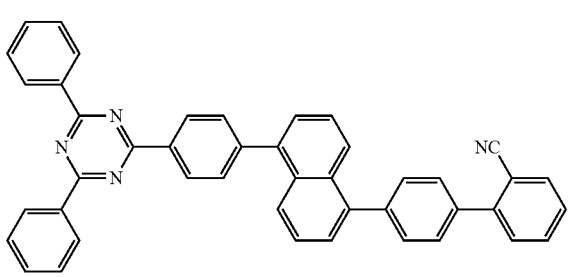

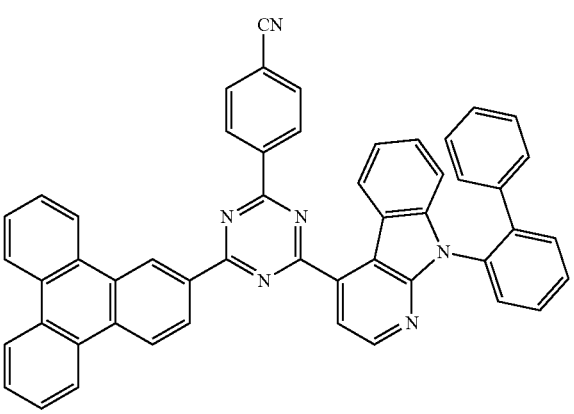

-continued

Compound F

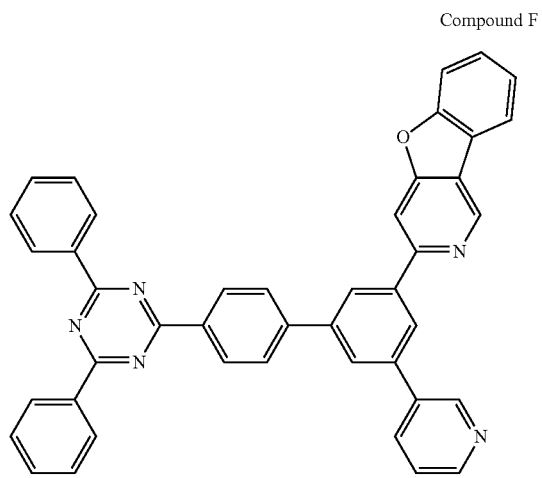

Compound G

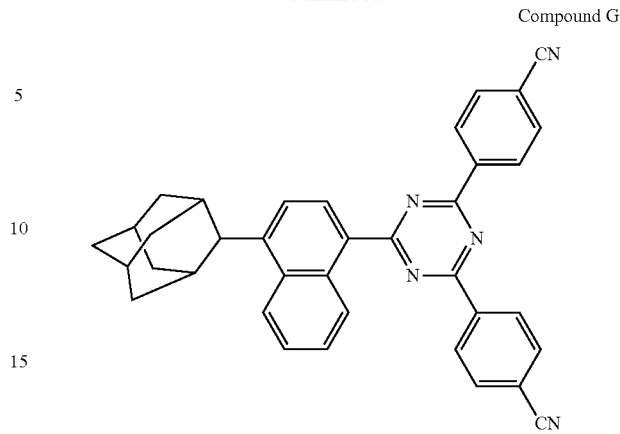

The IVL data compares the test results at 10 mA/cm², and the service life is a test result at a current density of 20 mA/cm².

TABLE 5

Performance of devices in Examples 1 to 31 and Comparative examples 1 to 6

| Example | Compound | Operating voltage volt (V) | Luminous efficiency (Cd/A) | External quantum efficiency EQE (%) | T95 device service life (h) | Chromaticity coordinate CIEy |
|---|---|---|---|---|---|---|
| Example 1 | Compound 3 | 3.86 | 6.4 | 13.5 | 161 | 0.049 |
| Example 2 | Compound 14 | 3.80 | 6.4 | 13.6 | 168 | 0.048 |
| Example 3 | Compound 46 | 3.85 | 6.7 | 14.5 | 172 | 0.049 |
| Example 4 | Compound 63 | 3.84 | 6.9 | 14.9 | 183 | 0.049 |
| Example 5 | Compound 30 | 3.89 | 6.7 | 14.5 | 177 | 0.048 |
| Example 6 | Compound 73 | 3.78 | 6.7 | 14.5 | 175 | 0.048 |
| Example 7 | Compound 81 | 3.87 | 6.3 | 12.9 | 150 | 0.050 |
| Example 8 | Compound 82 | 3.86 | 6.9 | 14.9 | 173 | 0.049 |
| Example 9 | Compound 111 | 3.82 | 6.6 | 14.2 | 169 | 0.049 |
| Example 10 | Compound 113 | 3.86 | 7.0 | 15.4 | 175 | 0.048 |
| Example 11 | Compound 216 | 3.86 | 6.3 | 12.9 | 149 | 0.049 |
| Example 12 | Compound 483 | 3.87 | 7.1 | 15.5 | 184 | 0.049 |
| Example 13 | Compound 181 | 3.90 | 6.3 | 12.9 | 169 | 0.048 |
| Example 14 | Compound 482 | 3.86 | 6.9 | 14.9 | 174 | 0.049 |
| Example 15 | Compound 518 | 3.89 | 6.8 | 14.7 | 148 | 0.049 |
| Example 16 | Compound 268 | 3.81 | 6.6 | 14.2 | 173 | 0.048 |
| Example 17 | Compound 348 | 3.83 | 6.5 | 14.0 | 169 | 0.048 |
| Example 18 | Compound 328 | 3.84 | 6.6 | 12.9 | 161 | 0.049 |
| Example 19 | Compound 318 | 3.81 | 6.3 | 12.9 | 169 | 0.049 |
| Example 20 | Compound 412 | 3.86 | 6.5 | 14.0 | 182 | 0.049 |
| Example 21 | Compound 533 | 3.89 | 7.1 | 15.5 | 171 | 0.048 |
| Example 22 | Compound 555 | 3.83 | 6.3 | 12.9 | 151 | 0.048 |

TABLE 5-continued

Performance of devices in Examples 1 to 31 and Comparative examples 1 to 6

| Example | Compound | Operating voltage volt (V) | Luminous efficiency (Cd/A) | External quantum efficiency EQE (%) | T95 device service life (h) | Chromaticity coordinate CIEy |
|---|---|---|---|---|---|---|
| Example 23 | Compound 525 | 3.87 | 6.9 | 14.9 | 176 | 0.049 |
| Example 24 | Compound 570 | 3.78 | 6.3 | 12.9 | 153 | 0.049 |
| Example 25 | Compound 577 | 3.84 | 6.4 | 12.9 | 149 | 0.050 |
| Example 26 | Compound 584 | 3.86 | 6.8 | 14.7 | 175 | 0.048 |
| Example 27 | Compound 589 | 3.82 | 6.5 | 14.0 | 174 | 0.049 |
| Example 28 | Compound 591 | 3.87 | 6.7 | 14.5 | 169 | 0.049 |
| Example 29 | Compound 590 | 3.86 | 6.9 | 14.9 | 170 | 0.049 |
| Example 30 | Compound 598 | 3.87 | 6.3 | 12.9 | 155 | 0.048 |
| Example 31 | Compound 619 | 3.84 | 6.2 | 12.8 | 145 | 0.049 |
| Comparative example 1 | Compound A | 4.19 | 5.0 | 10.8 | 125 | 0.048 |
| Comparative example 2 | Compound B | 4.14 | 4.0 | 8.9 | 97 | 0.049 |
| Comparative example 3 | Compound C | 4.09 | 5.5 | 10.8 | 109 | 0.048 |
| Comparative example 4 | Compound E | 4.11 | 5.3 | 10.5 | 109 | 0.048 |
| Comparative example 5 | Compound F | 4.13 | 5.0 | 9.2 | 100 | 0.049 |
| Comparative example 6 | Compound G | 4.14 | 5.4 | 10.9 | 107 | 0.049 |

From the results of Table 5 above, it can be seen that by comparing Examples 1 to 31 using the compounds of the present disclosure with Comparative examples 1 to 6 using the well-known compounds A, B, C, E, F and G, for the organic electroluminescent devices in Examples 1 to 31, the driving voltage is reduced by about 0.2 V, the luminous efficiency (Cd/A) is improved by at least 12.7%, and the service life of the device is improved by at least about 16%.

In summary, the organic electroluminescent device prepared by using the compound of the present disclosure in the electron transport layer (ETL) can achieve higher luminous efficiency, and the service life of the device can be significantly improved. The adamantyl and the cyano group are connected to the nitrogen-containing heteroaryl core structure via the linking group in the nitrogen-containing compound structure of the present disclosure, highly polar cyano makes this part of the structure have a large dipole moment, thus the polarity of the compound is increased, and the organic materials with a high electron mobility are obtained, and when the compound is used as the electron transport layer of the electronic element, the efficiency, and service life of the device can be improved, and the operating voltage can be reduced. As a rigid and bulky polycyclic alkane structure, 1-adamantyl itself can avoid the stacking of conjugated planes to form π aggregation, so that the film-forming properties of the material can be improved, the molecular weight and asymmetry are simultaneously enhanced at the same time, the thermal stability of the molecule is improved, the crystallinity of the material is also improved to a certain extent. Therefore, the stability of the compound can be improved when applied to the organic electroluminescent device, resulting in increased the service life of the device, and easier to be mass-production. From the test data of Examples 1 to 31 and Comparative example 4, it can be seen that 1-adamantyl connected at the end of the compound is superior to 2-adamantyl in increasing the polarity and thermal stability of the compound.

Thermal Stability Test of Compounds

When the compounds were used in mass production of devices, the compounds needed to be heated under evaporation conditions for a long period of time. If the thermal stability of the molecular structures of the compounds was poor under heated conditions, the purity of the compounds decreased under heated conditions over a long period of time, resulting in large differences in the performance of devices prepared early, middle and late stages of mass production.

In the present disclosure, the stability of the molecular structures of the compounds of the present disclosure under heated conditions over a long period of time during evaporation in mass production was evaluated by the following method:

Heat resistance tests (heat preservation treatments) were carried out on the compounds of the present disclosure and comparative compounds D, E, A and G, respectively, in a high vacuum environment ($<10^{-6}$ Pa) at a temperature corresponding to an evaporation rate of 5 Å/s for 200 h. The stability of the compounds of the present disclosure under the mass production condition was determined by a purity drop value before and after the heat resistance test, purity drop value (%)=purity before heat treatment (%)−purity after heat treatment (%).

Comparative Compounds D and G:

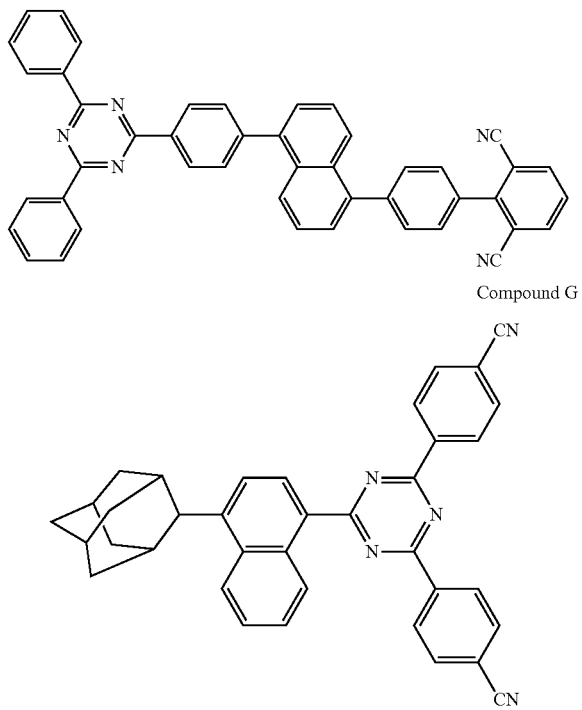

TABLE 6

Test temperature and purity drop values for nitrogen-containing compounds

| Test example No. | Compound | Evaporation temperature at 5 Å/s (° C.) | Purity drop value (HPLC, %) |
|---|---|---|---|
| Test example 1 | Compound 3 | 205 | 0.06 |
| Test example 2 | Compound 14 | 208 | 0.13 |
| Test example 3 | Compound 46 | 210 | 0.13 |
| Test example 4 | Compound 63 | 212 | 0.14 |
| Test example 5 | Compound 30 | 205 | 0.17 |
| Test Example 6 | Compound 73 | 219 | 0.23 |
| Test example 7 | Compound 81 | 217 | 0.15 |
| Test example 8 | Compound 82 | 213 | 0.27 |
| Test example 9 | Compound 111 | 221 | 0.25 |
| Test example 10 | Compound 113 | 219 | 0.37 |
| Test example 11 | Compound 216 | 230 | 0.19 |
| Test example 12 | Compound 483 | 212 | 0.26 |
| Test example 13 | Compound 181 | 216 | 0.13 |
| Test example 14 | Compound 482 | 208 | 0.27 |
| Test example 15 | Compound 518 | 208 | 0.25 |
| Test example 16 | Compound 268 | 229 | 0.17 |
| Test example 17 | Compound 348 | 223 | 0.14 |
| Test example 18 | Compound 328 | 235 | 0.37 |
| Test example 19 | Compound 318 | 236 | 0.35 |
| Test example 20 | Compound 412 | 209 | 0.03 |
| Test example 21 | Compound 533 | 218 | 0.11 |
| Test example 22 | Compound 55 | 206 | 0.11 |
| Test example 23 | Compound 525 | 219 | 0.25 |
| Test example 24 | Compound 570 | 234 | 0.36 |
| Test example 25 | Compound 577 | 232 | 0.28 |
| Test example 26 | Compound 584 | 222 | 0.38 |
| Test example 27 | Compound 589 | 221 | 0.23 |
| Test example 28 | Compound 591 | 225 | 0.25 |
| Test example 29 | Compound 590 | 227 | 0.28 |
| Test example 30 | Compound 598 | 223 | 0.21 |
| Test example 31 | Compound 619 | 230 | 0.32 |
| Test example 32 | Compound D | 268 | 2.4 |
| Test example 33 | Compound E | 262 | 2.7 |
| Test example 34 | Compound A | 258 | 2.1 |
| Test example 35 | Compound G | 228 | 2.1 |

It can be seen from Table 6 that the purity drop values of the nitrogen-containing compounds of the present disclosure after heating are all less than 0.4%, with most of them being less than 0.3%. When the purity drop value of the compound is more than 1%, the efficiency and service life of the device will be significantly reduced; and thermally unstable compounds can lead to large differences in the performance of devices prepared early, middle and late stages of mass production in actual production. The heat resistance tests of the compounds in the present disclosure demonstrated that purity drop values of the compounds are all less than 0.4%, and the purity drop values of the comparative compounds D, E, A, and G are all more than 2% at the evaporation temperature, exceeding the limit of 1%, and thus the nitrogen-containing compounds of the present disclosure also have excellent mass production thermal stability compared with the comparative compounds.

Those skilled in the art will easily think of other embodiments of the present disclosure after considering the description and practicing the present disclosure disclosed here. The present disclosure is intended to cover any variations, uses or adaptations of the present disclosure, and these variations, uses or adaptations follow the general principles of the present disclosure and include common general knowledge or conventional technical means in the art not disclosed by the present disclosure. The description and the embodiments are only considered as exemplary, and the true scope and spirit of the present disclosure are indicated by the appended claims.

What is claimed is:

1. A nitrogen-containing compound, having a structure as shown in a formula 1:

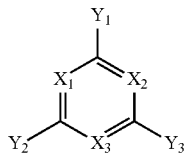

formula 1 wherein $X_1$, $X_2$, and $X_3$ are the same or different, and are each independently selected from $C(R_0)$ or N, and at least two of $X_1$, $X_2$, and $X_3$ are N;

$Y_1$ is

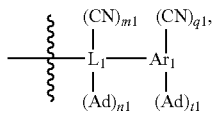

$Y_2$ is

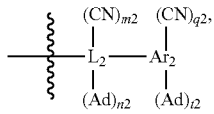

and $Y_3$ is

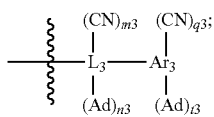

$L_1$, $L_2$, and $L_3$ are the same as or different from each other, and are each independently selected from a single bond, substituted or unsubstituted phenylene, substituted or unsubstituted biphenylene, substituted or unsubstituted naphthylene, substituted or unsubstituted carbazolylene, substituted or unsubstituted anthrylene, or is a group formed by connecting two or three of the above subunit groups by a single bond;

and substituents in the $L_1$, the $L_2$, and the $L_3$ are the same as or different from each other, and are each independently selected from the group consisting of deuterium, fluorine, chlorine, cyano, methyl, ethyl, isopropyl, n-propyl, tert-butyl and phenyl;

$Ar_1$, $Ar_2$, and $Ar_3$ are the same as or different from each other, and are each independently selected from a substituted or unsubstituted group V, and the unsubstituted group V is selected from the group consisting of:

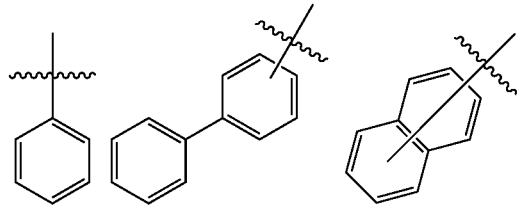

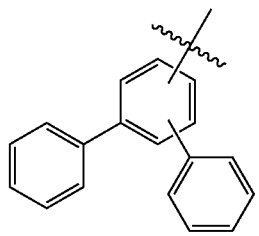

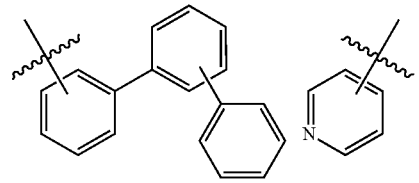

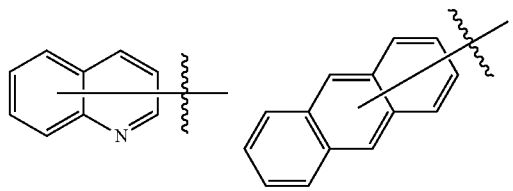

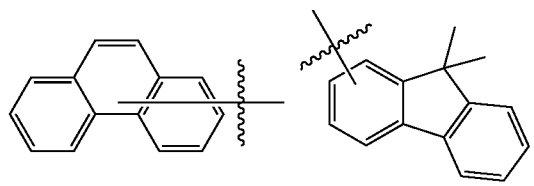

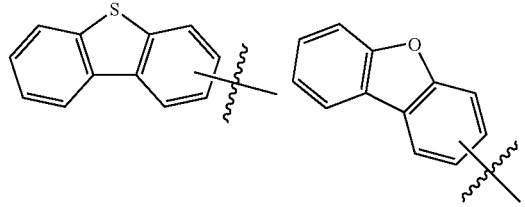

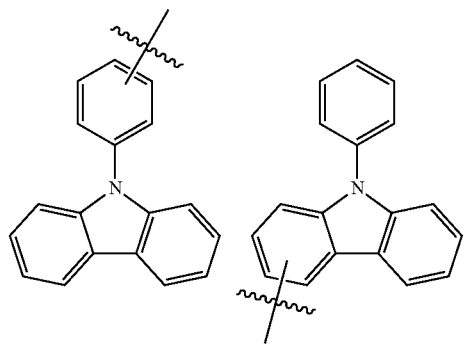

311
-continued

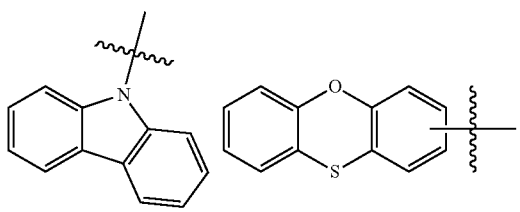

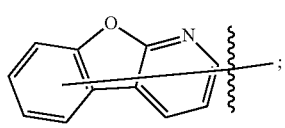

the substituted group V has one or two or more substituents, and the substituents are each independently selected from deuterium, fluorine, cyano, methyl, ethyl, isopropyl, n-propyl, tert-butyl, phenyl, or naphthyl;

Ad is

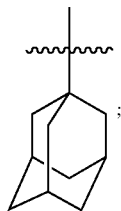 [SMILES: *C12CC3CC(CC(C3)C1)C2]

$m_1$ to $m_3$ is represented by $m_i$, $n_1$ to $n_3$ is represented by $n_i$, $q_1$ to $q_3$ is represented by $q_i$, and $t_1$ to $t_3$ is represented by $t_i$; and i is a variable, and is selected from 1, 2 or 3;

$m_i$ represents the number of cyano on $L_i$, $n_i$ represents the number of Ad on $L_i$, $q_i$ represents the number of cyano on $Ar_i$, and $t_i$ represents the number of Ad on $Ar_i$;

$m_i$ is independently selected from 0, 1, or 2, and when $m_i$ is greater than 1, any two $m_i$ are the same or different;

$n_i$ is independently selected from 0 or 1, and when $n_i$ is greater than 1, any two $n_i$ are the same or different;

$q_i$ is independently selected from 0, 1, or 2, and when $q_i$ is greater than 1, any two $q_i$ are the same or different;

$t_i$ is independently selected from 0 or 1, and when $t_i$ is greater than 1, any two $t_i$ are the same or different;

$m_1+m_2+m_3+q_1+q_2+q_3 \geq 1$, and $n_1+n_2+n_3+t_1+t_2+t_3 \geq 1$;

each $R_0$ is the same as or different from each other, and is independently selected from hydrogen, and the nitrogen-containing compound does not comprise the following compounds:

312

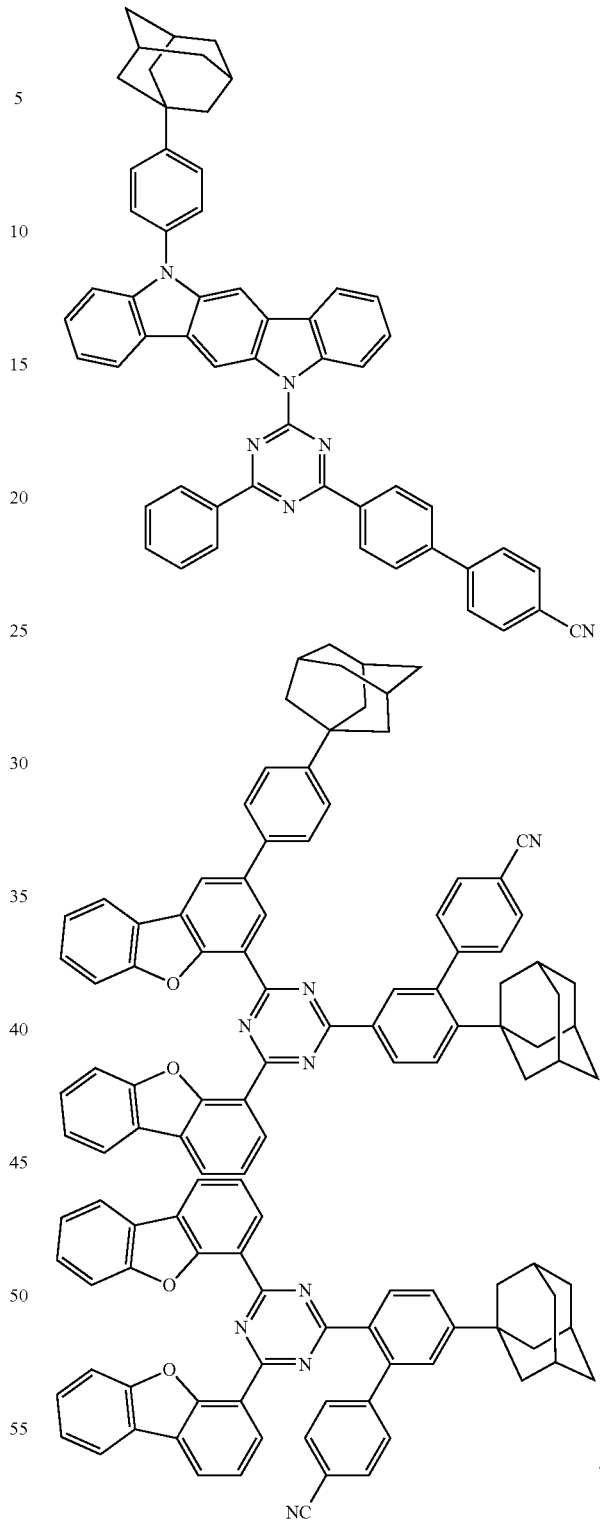

2. The nitrogen-containing compound according to claim 1, wherein $m_1+m_2+m_3+q_1+q_2+q_3$ is 1 or 2, and $n_1+n_2+n_3+t_1+t_2+t_3$ is 1 or 2.

3. The nitrogen-containing compound according to claim 1, wherein the $Ar_1$, the $Ar_2$, and the $Ar_3$ are the same or different, and are each independently selected from the group consisting of:

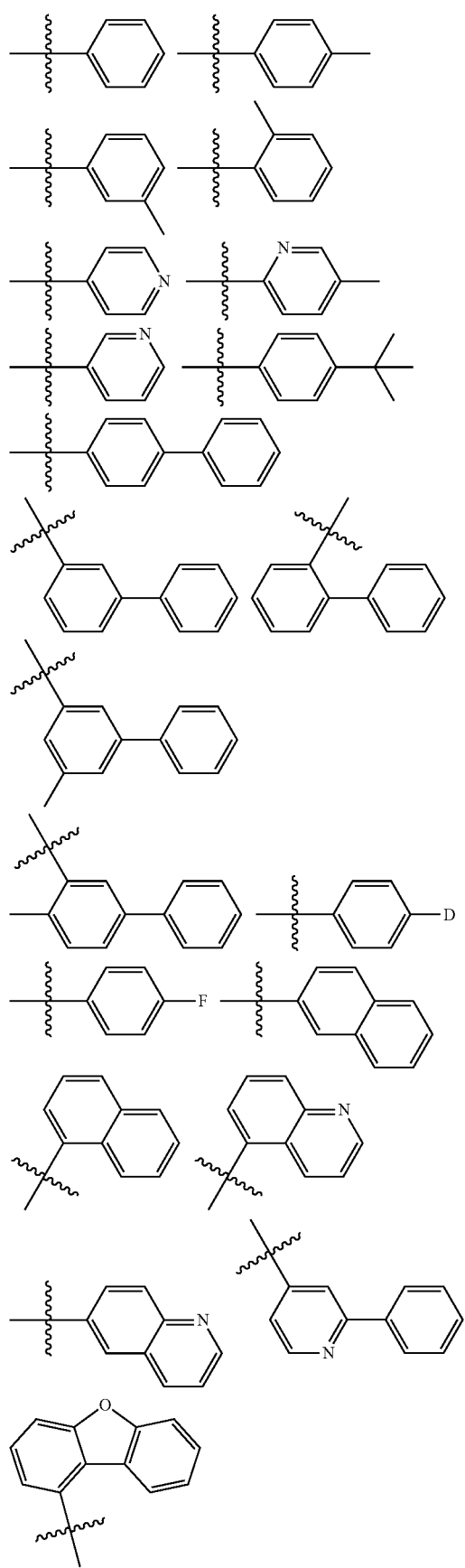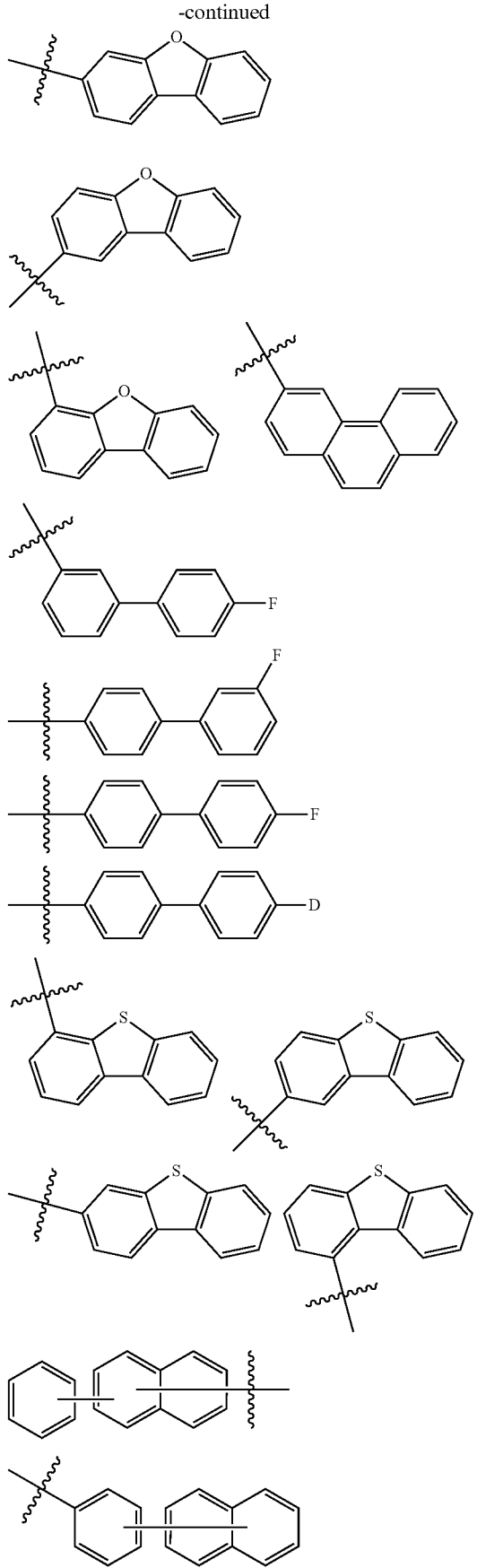

315
-continued
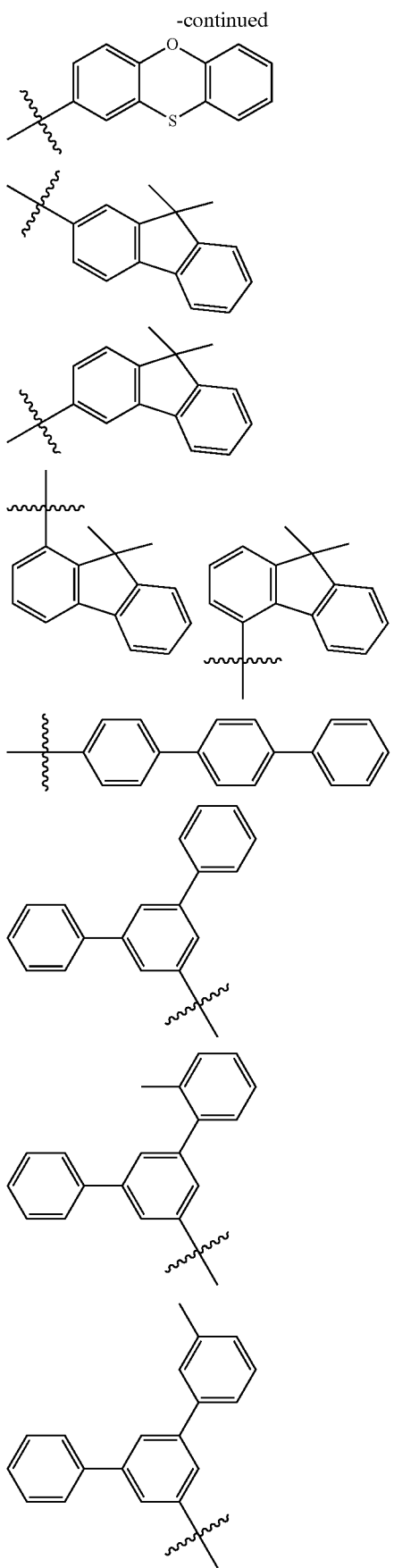
316
-continued
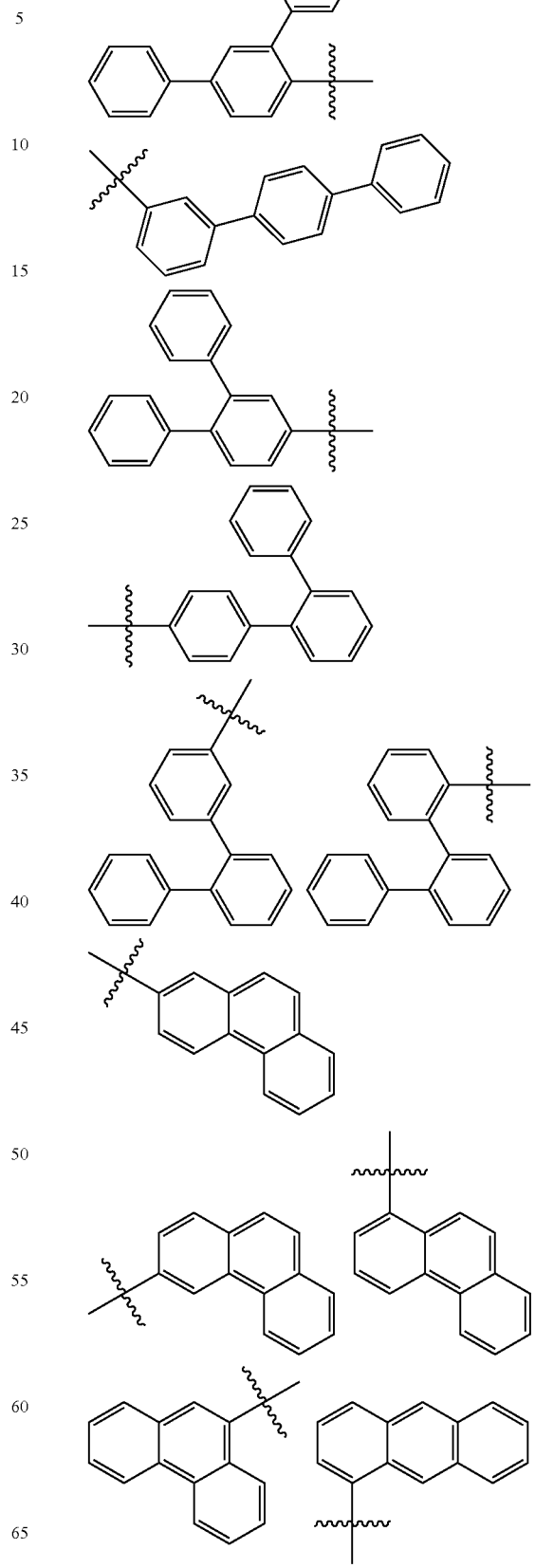

317
-continued
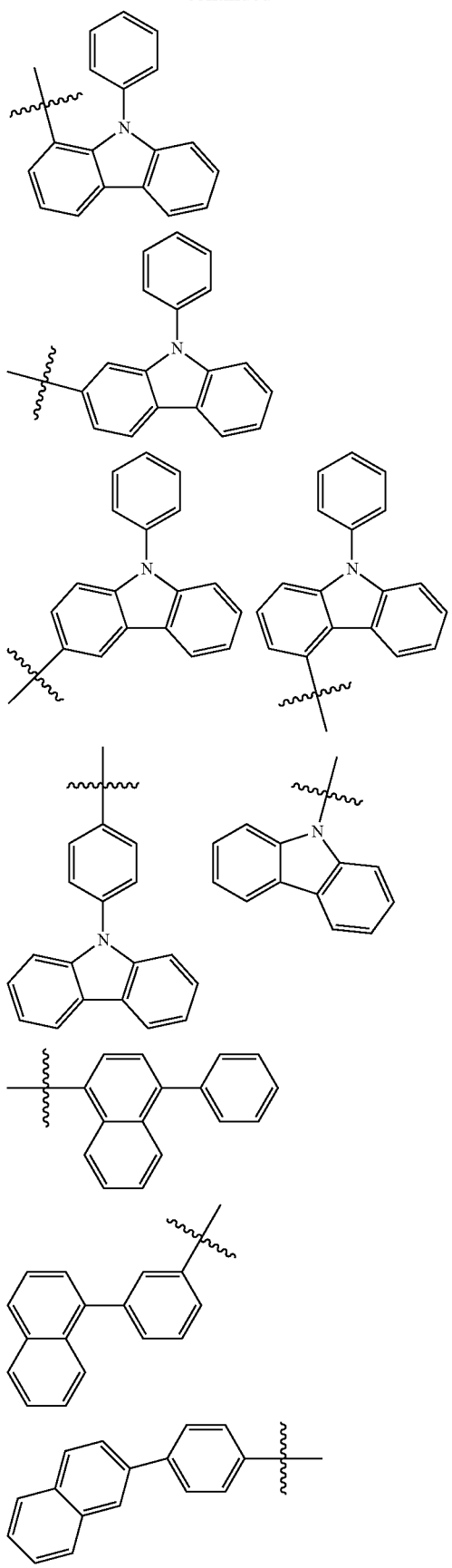
318
-continued
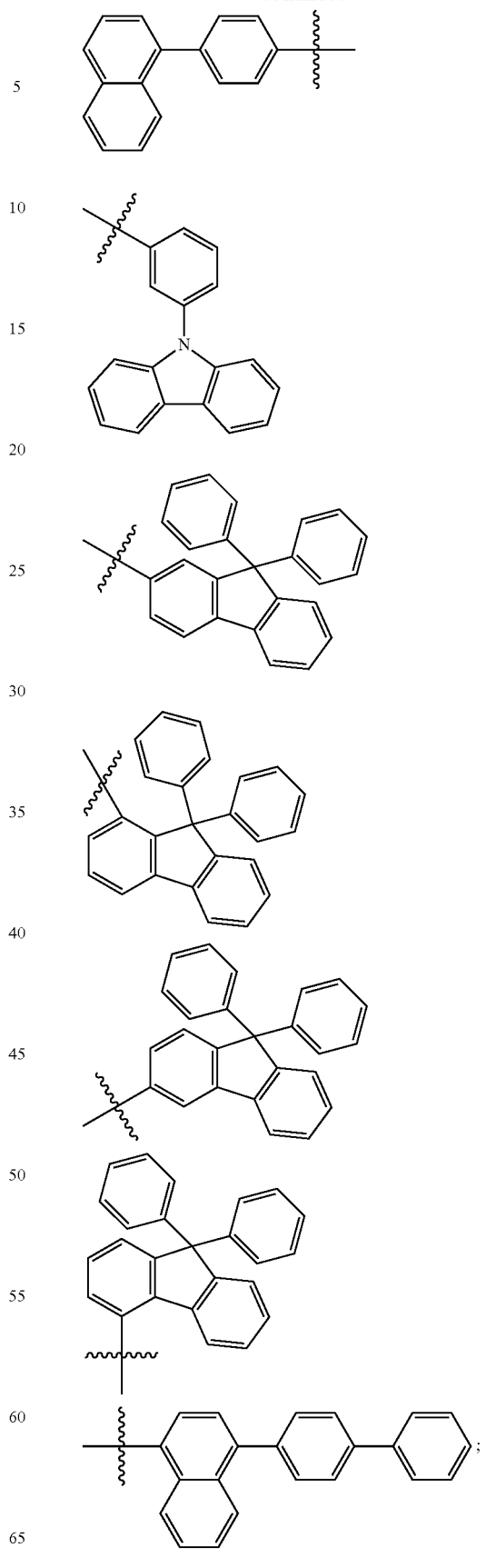

or are selected from the group consisting of:

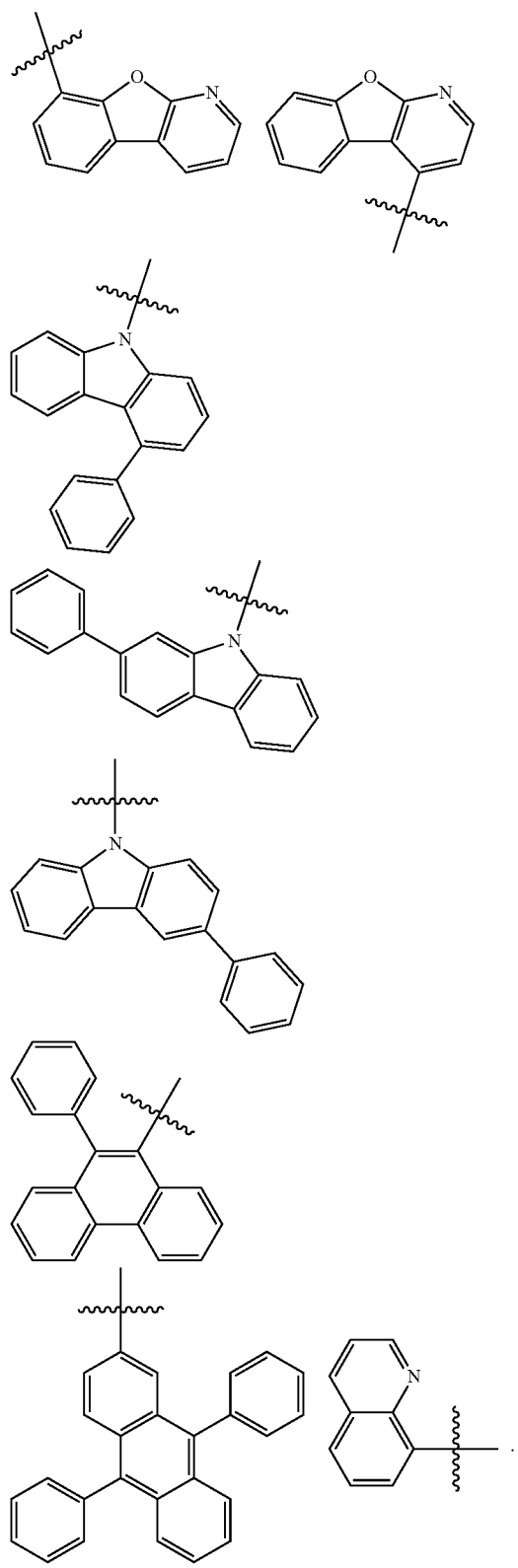

the unsubstituted group W is selected from the group consisting of:

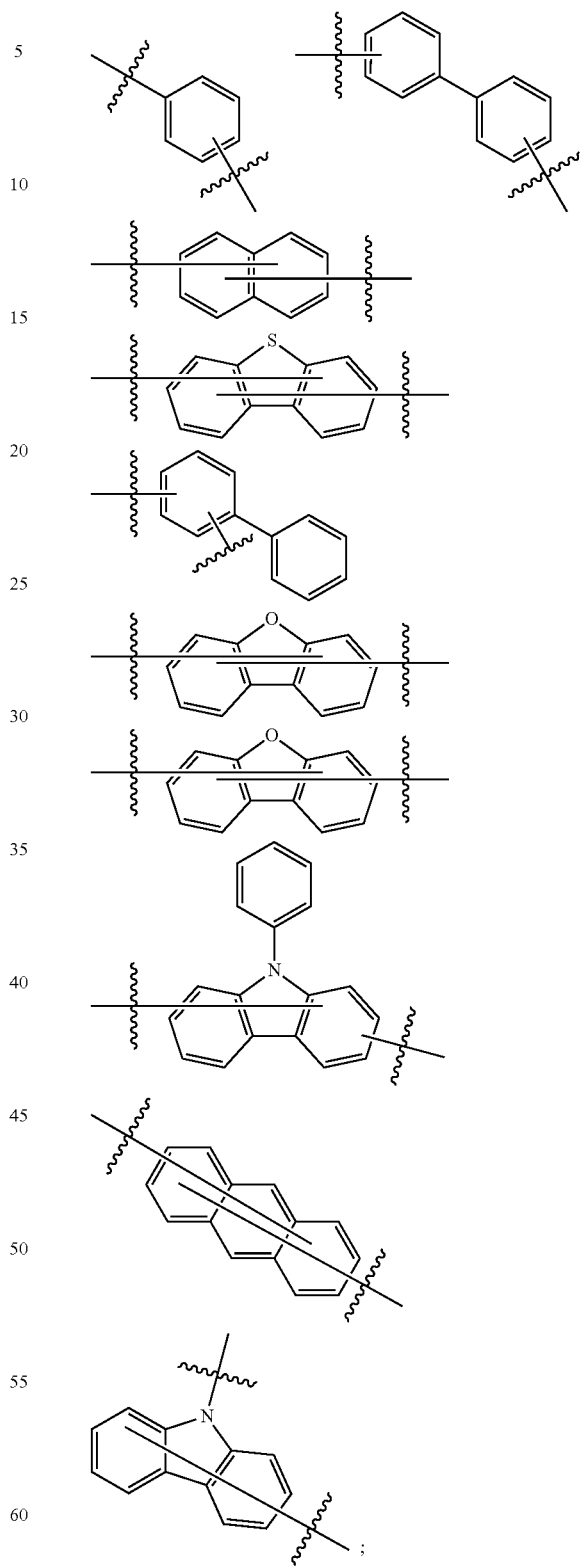

and

4. The nitrogen-containing compound according to claim 1, wherein the $L_1$, the $L_2$, and the $L_3$ are the same or different, and are each independently selected from a single bond, and a substituted or unsubstituted group W, wherein when the group W is substituted with one or more substituents, the substituents in the group W are each independently selected from the group consisting of deuterium, fluorine, chlorine, cyano, methyl, ethyl, isopropyl, n-propyl, tert-butyl and phenyl; and when the number of the substituents in the group W is more than 1, the substituents are the same or different.

5. The nitrogen-containing compound according to claim 1, wherein the $L_1$ and the $L_2$ are the same or different, and are each independently selected from a single bond or the group consisting of:

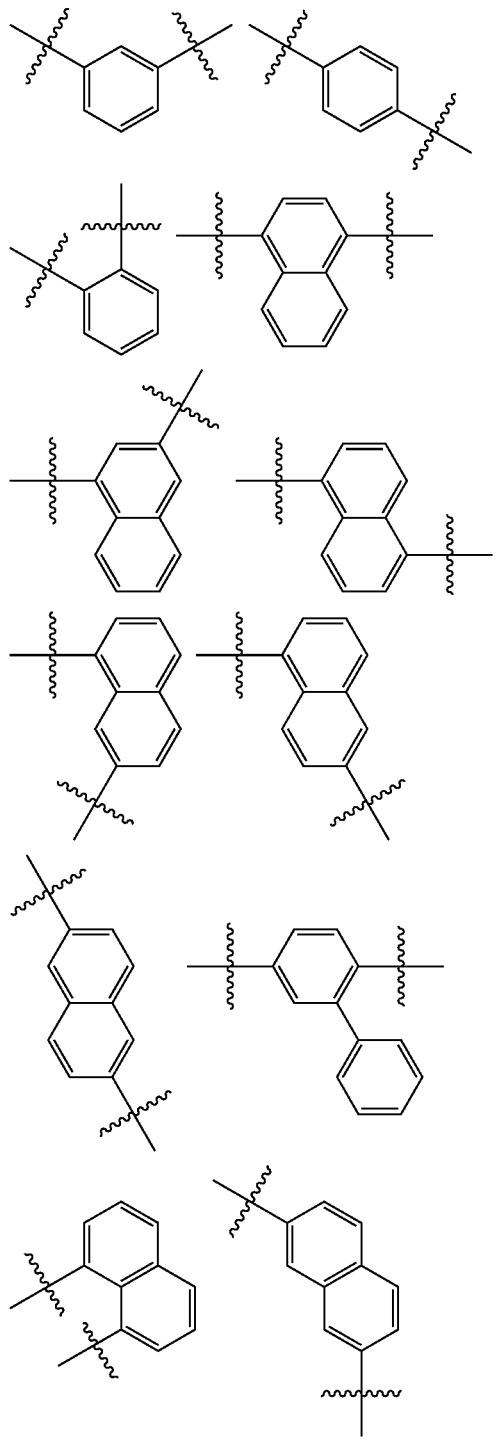

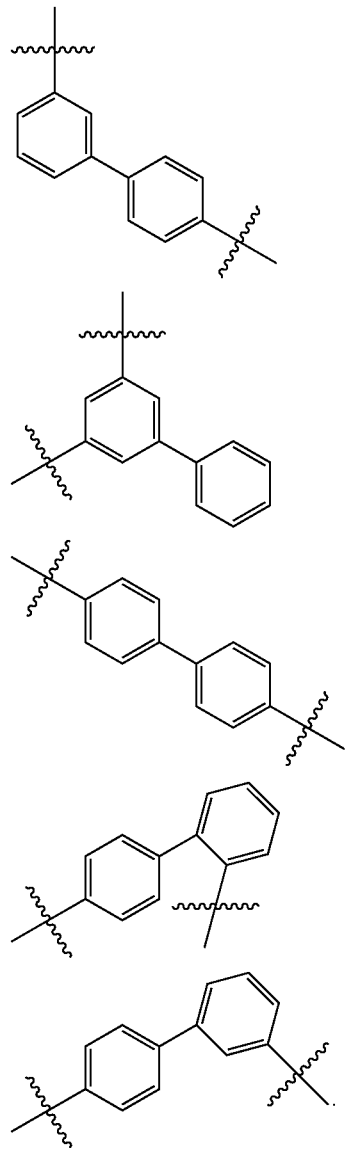

6. The nitrogen-containing compound according to claim 1, wherein the $L_3$ is selected from a single bond or the group consisting of:

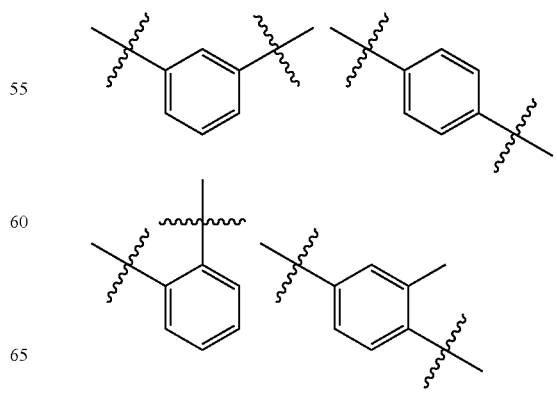

323
-continued
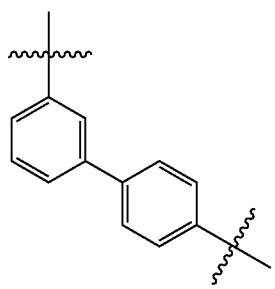
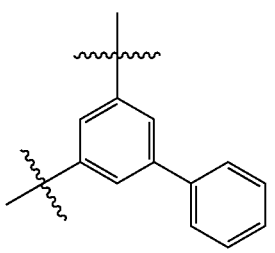
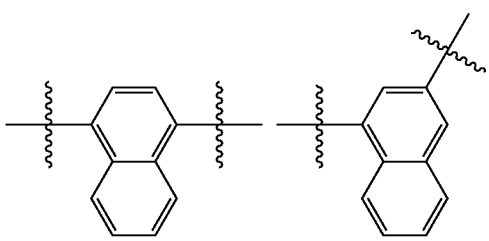
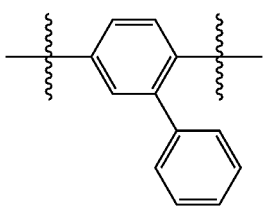
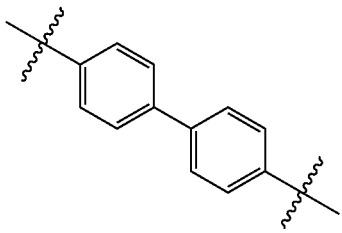
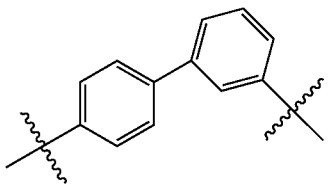
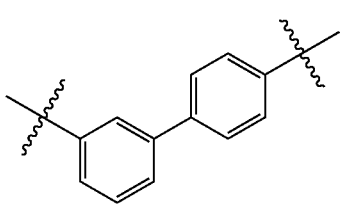
324
-continued
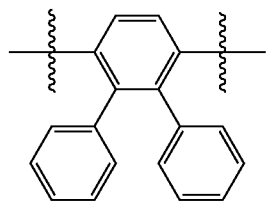
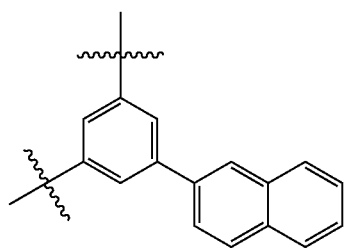
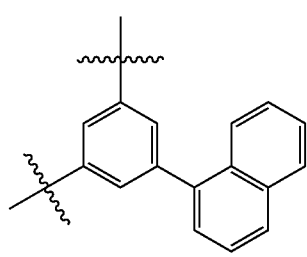
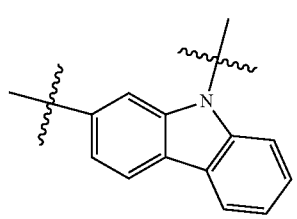
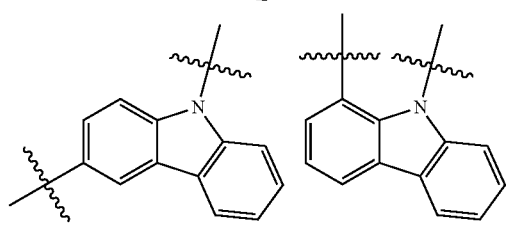
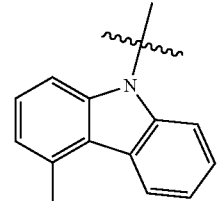
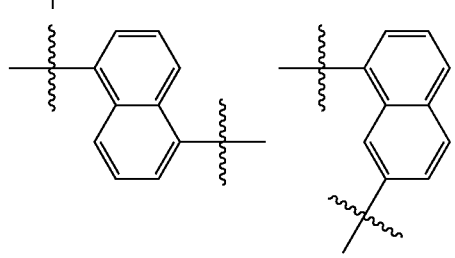

325
-continued
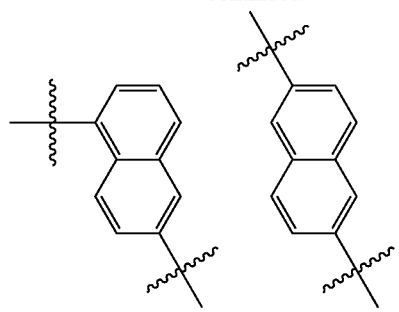
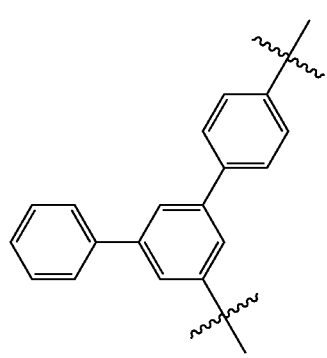
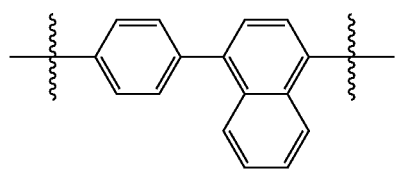
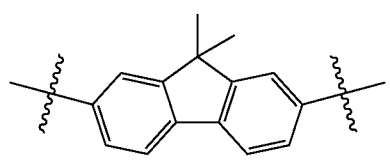
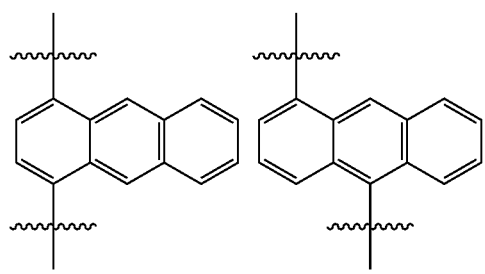
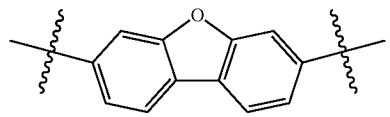
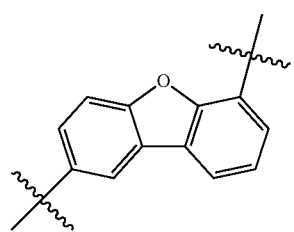
326
-continued
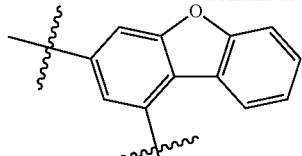
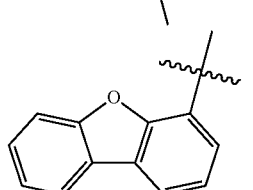
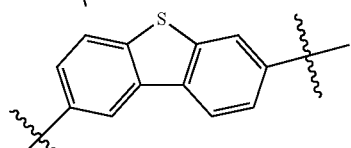
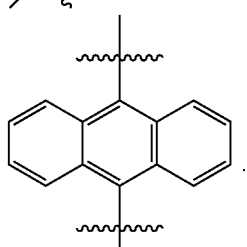
7. The nitrogen-containing compound according to claim 1, wherein the nitrogen-containing compound is selected from the group consisting of the following compounds:
2
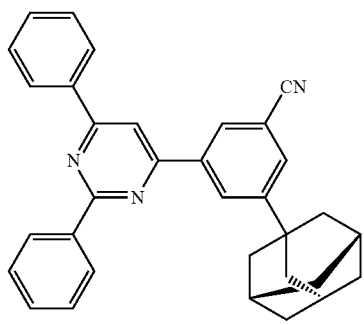
3
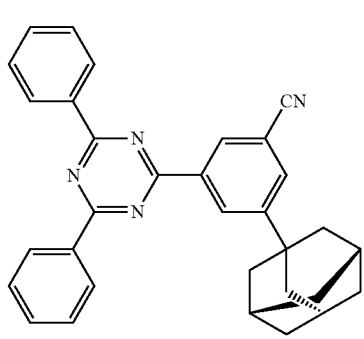

327
-continued
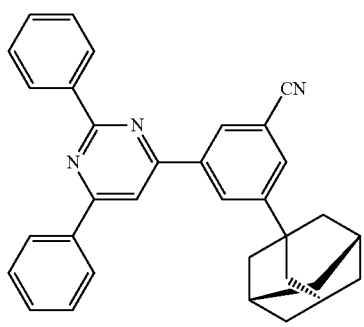
4
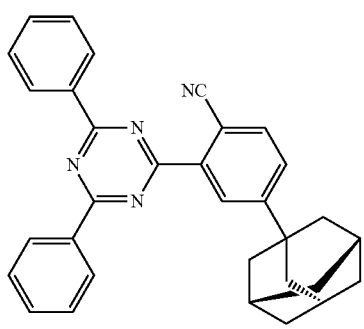
5
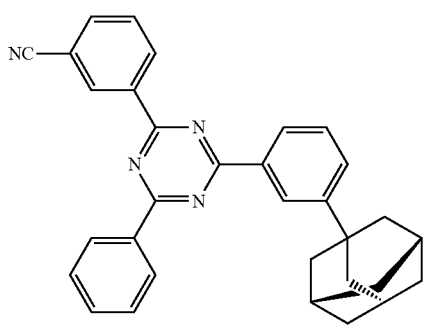
6
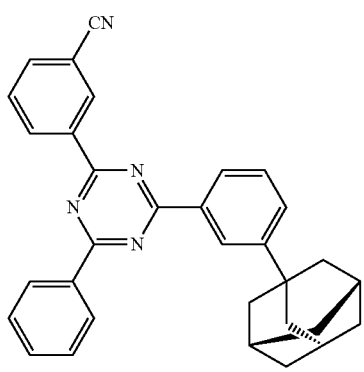
7
328
-continued
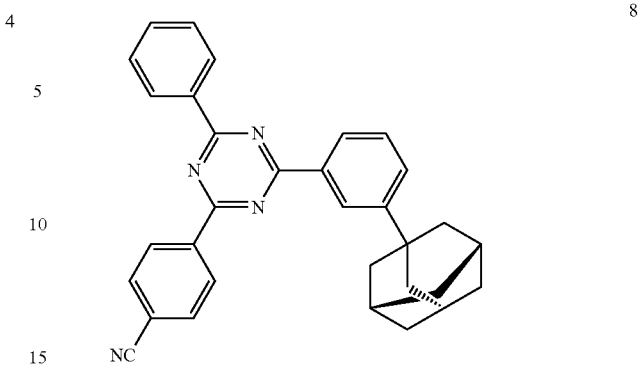
8
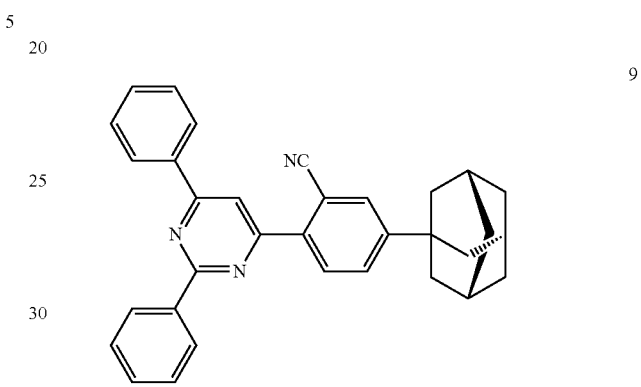
9
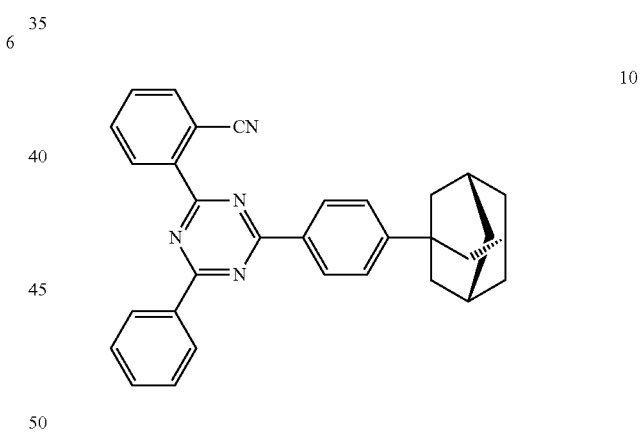
10
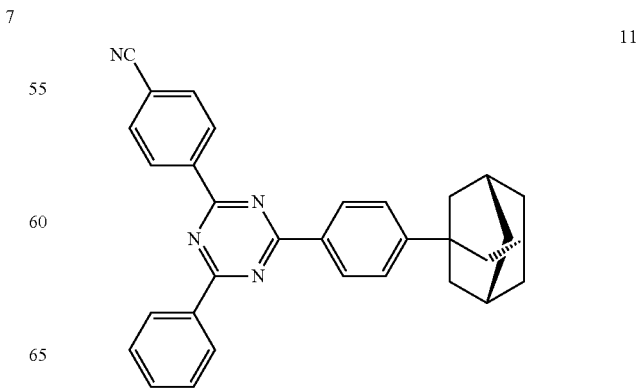
11

329
-continued
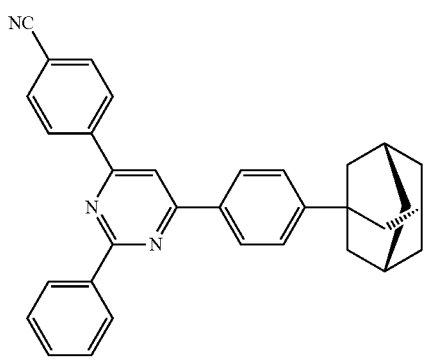
12
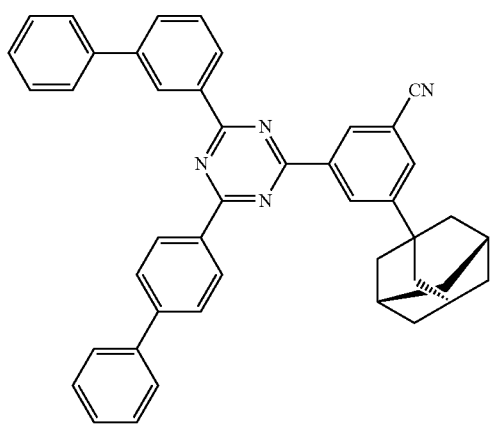
13
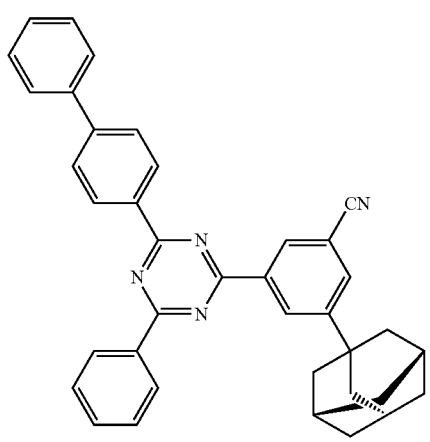
14
330
-continued
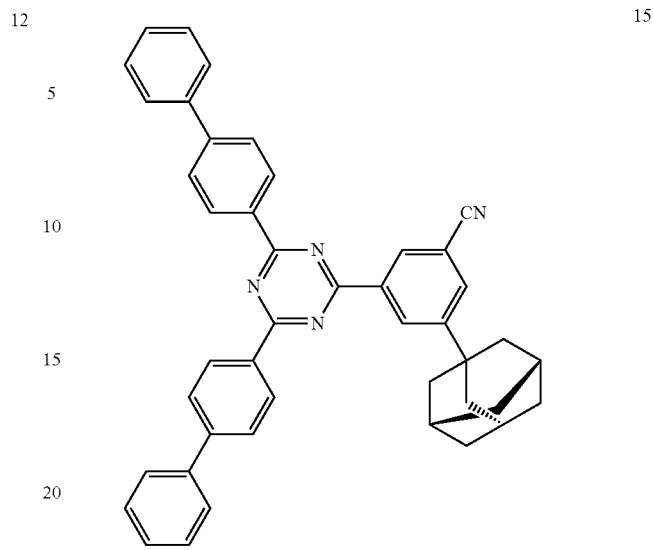
15
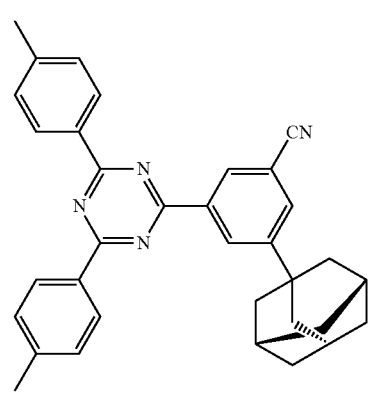
16
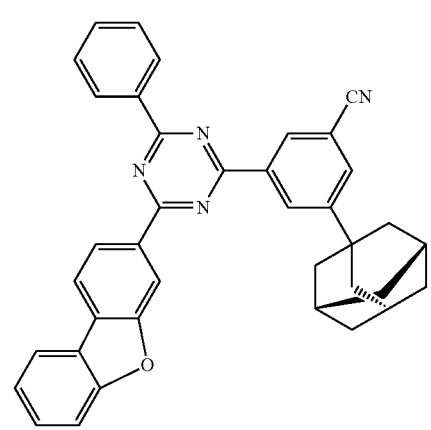
17

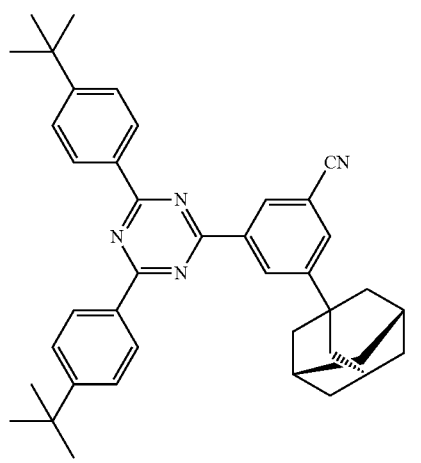
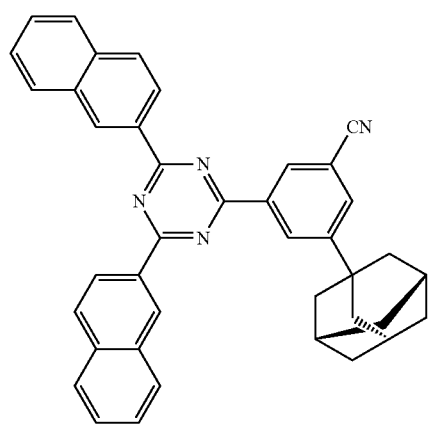
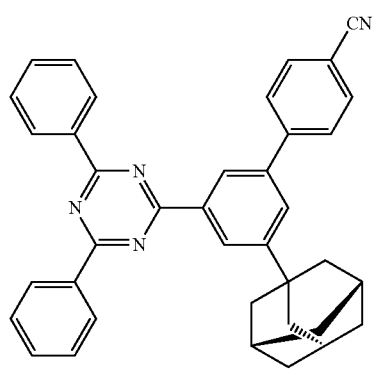
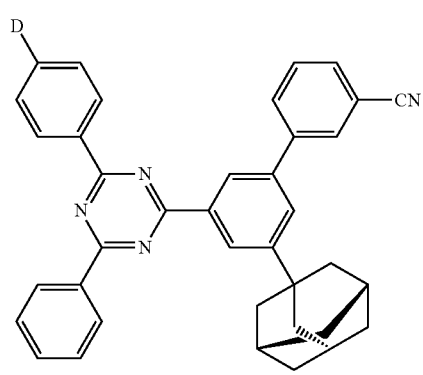
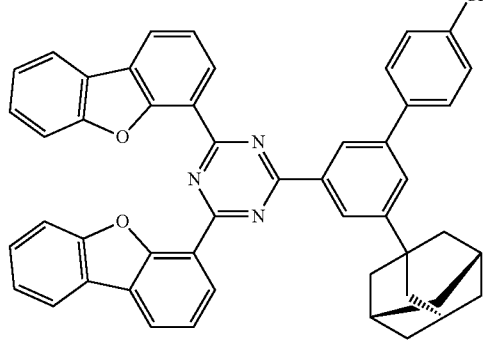
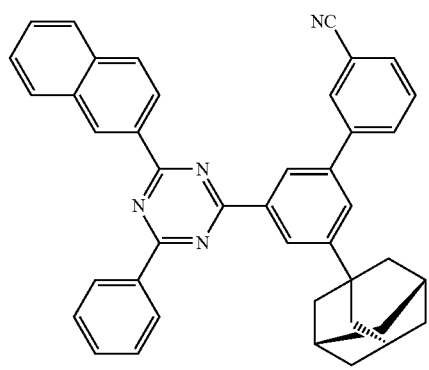

-continued
26
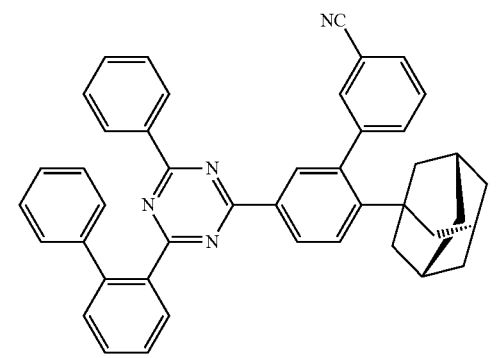
27
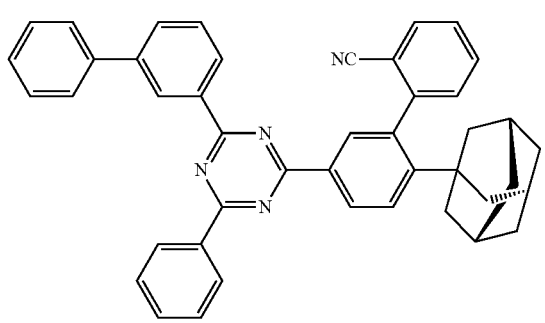
28
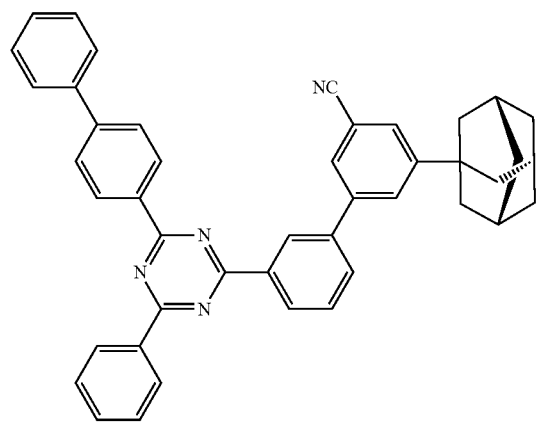
29
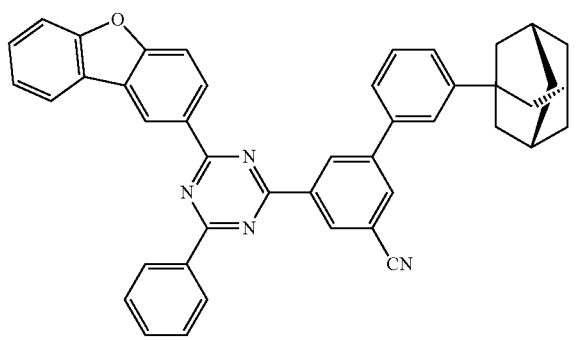
-continued
30
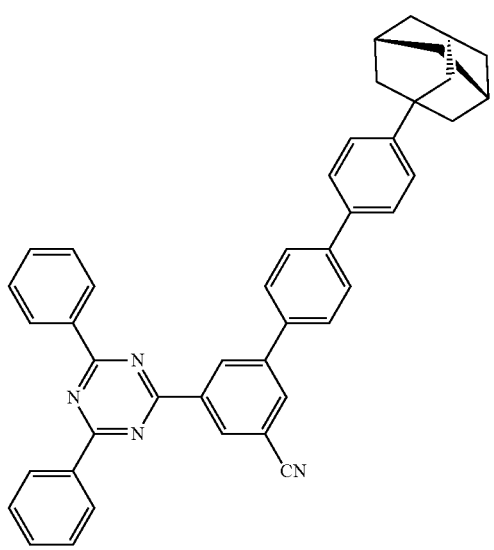
31
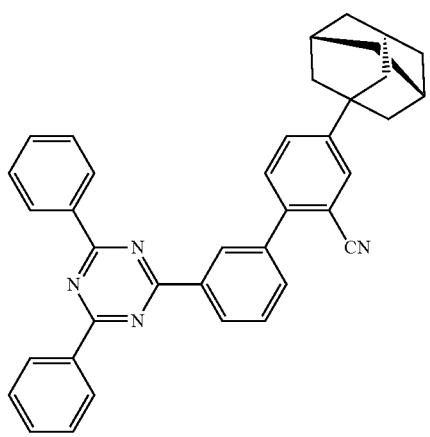
32
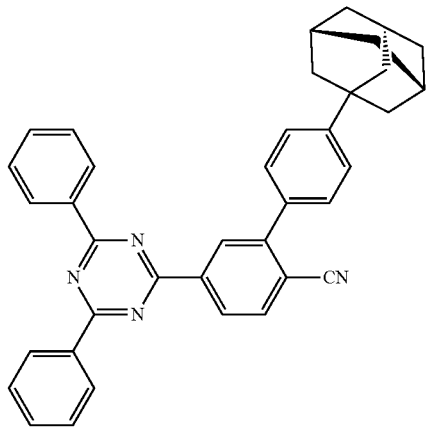

-continued
33
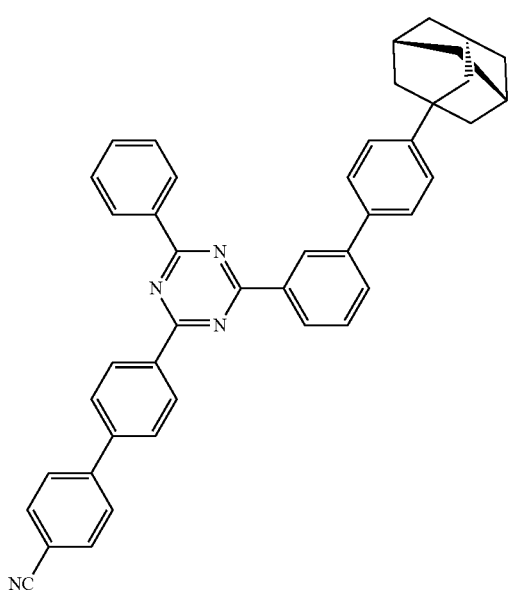
34
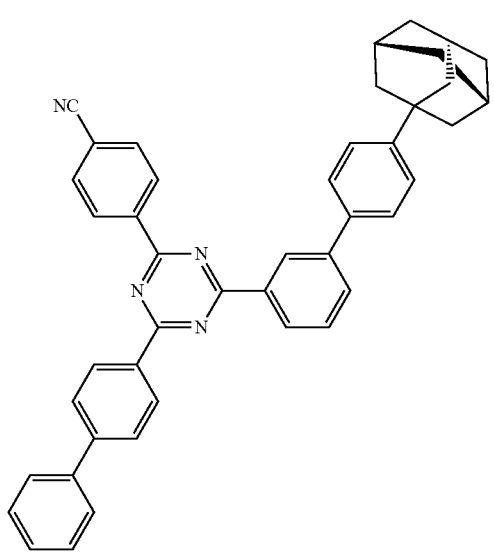
35
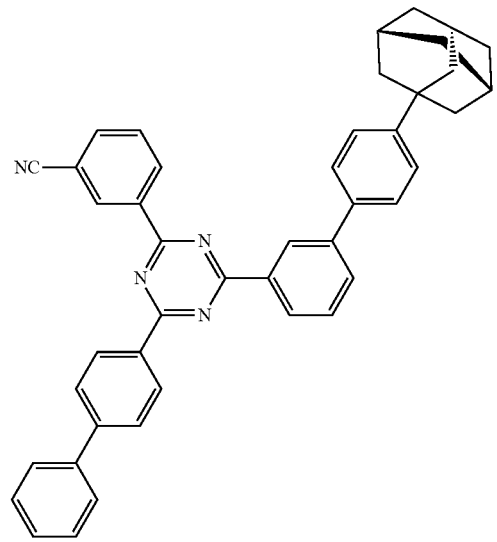
36
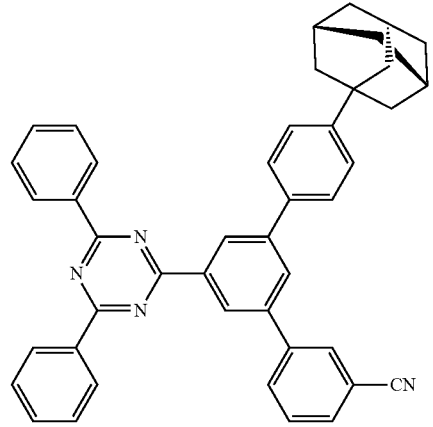
37
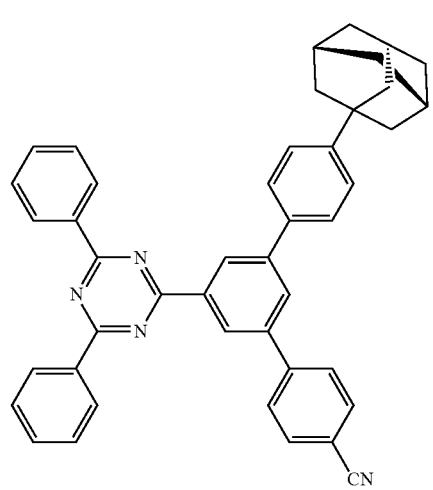

337
-continued
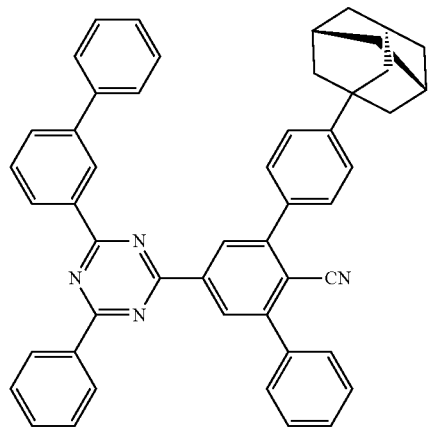
38
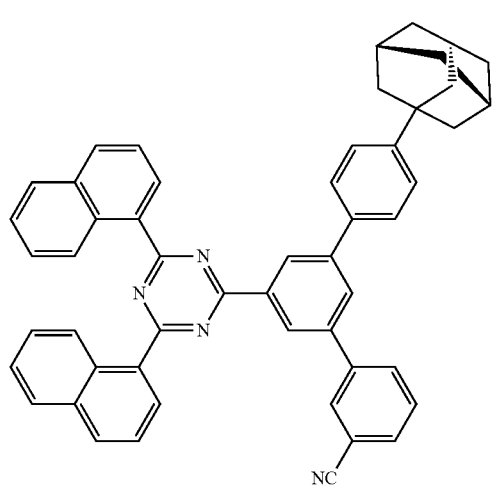
39
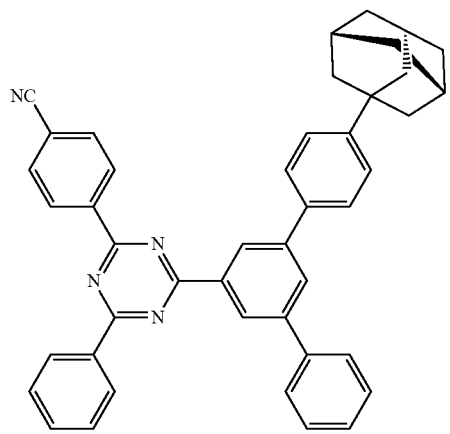
40
338
-continued
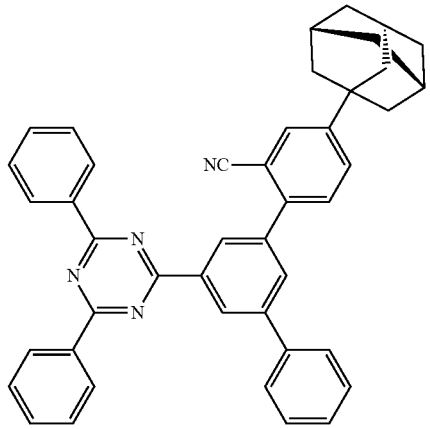
41
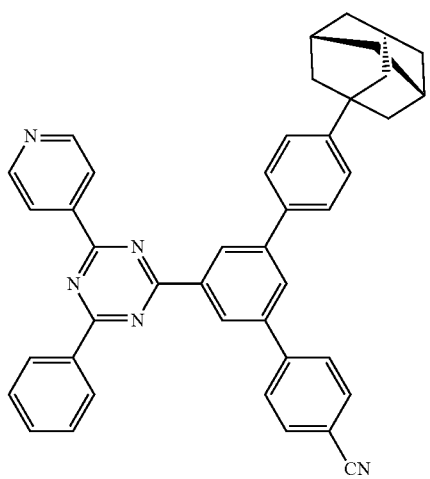
42
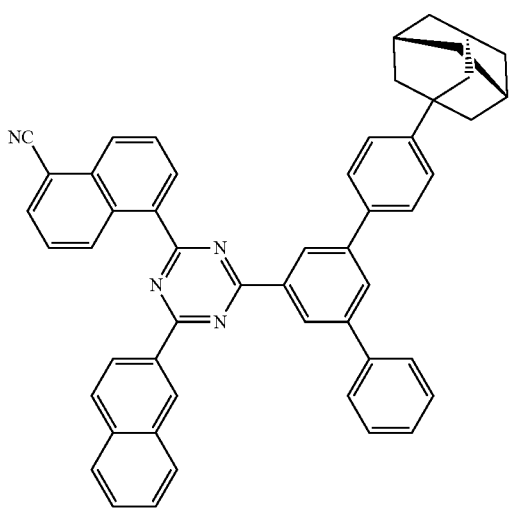
43

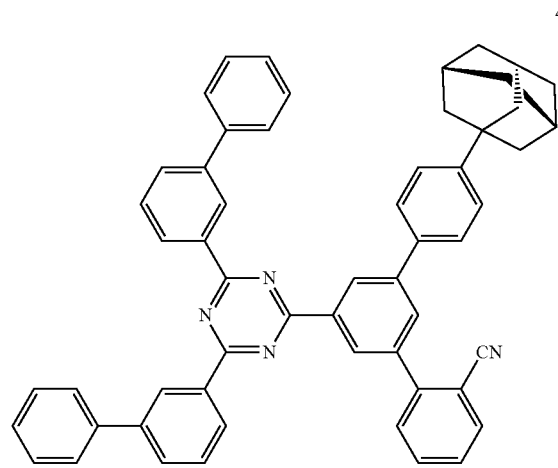
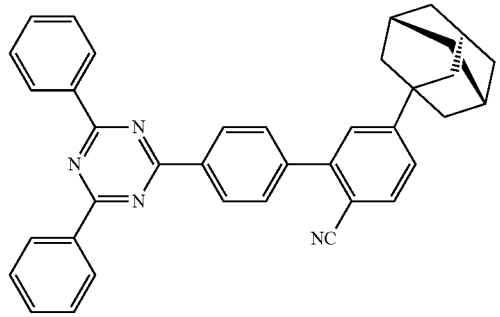
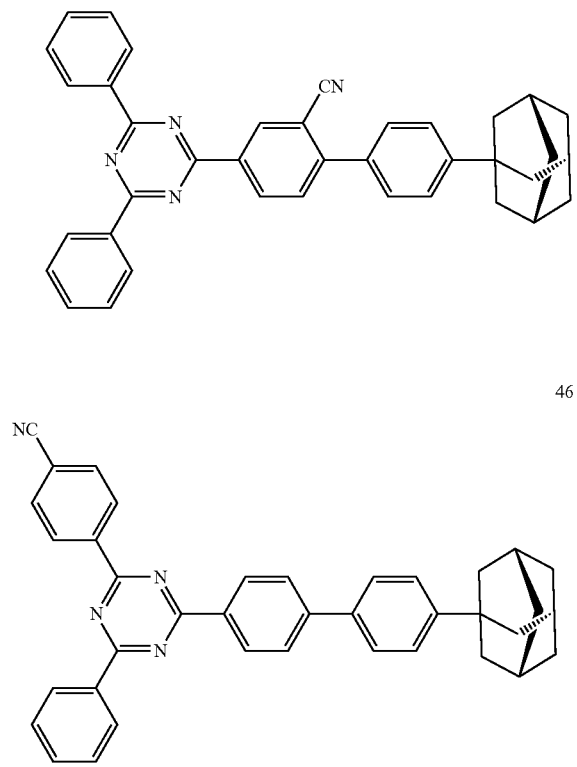
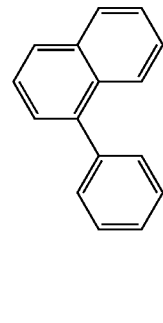
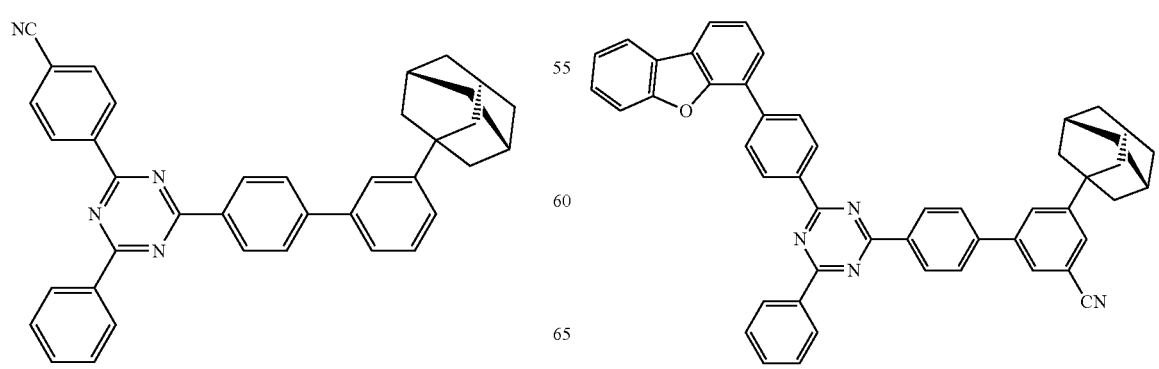

341
-continued
52
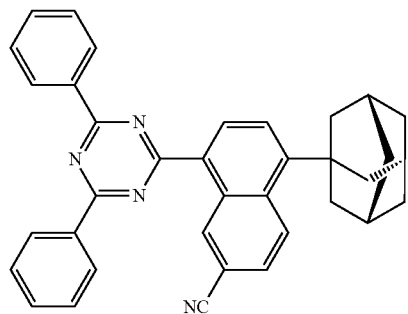
53
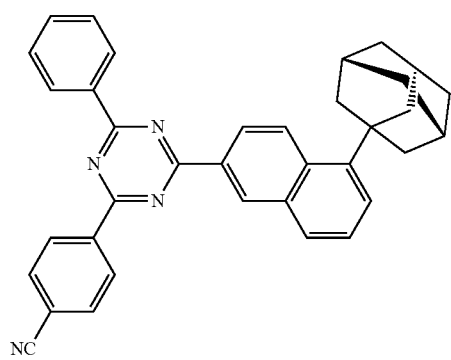
54
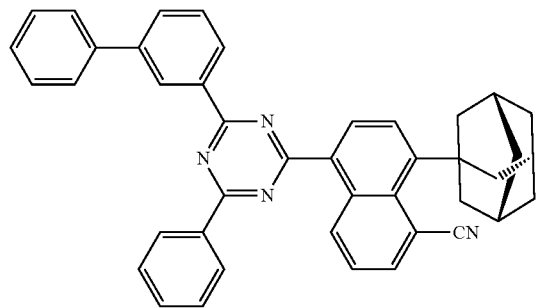
55
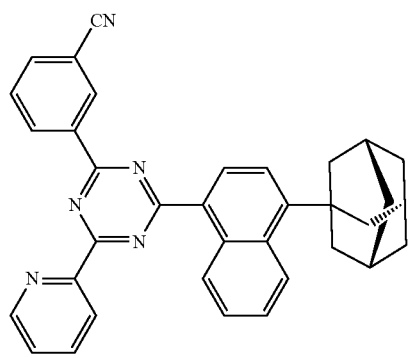
342
-continued
56
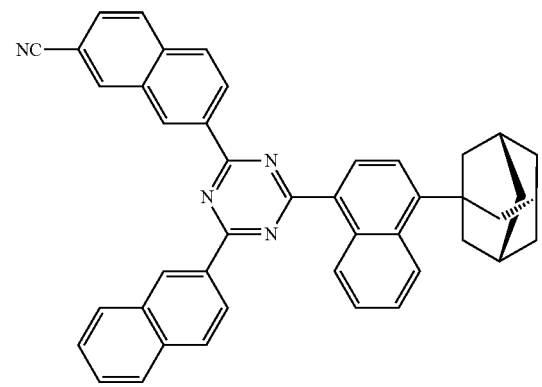
57
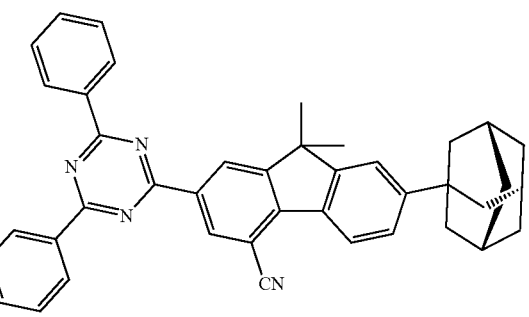
58
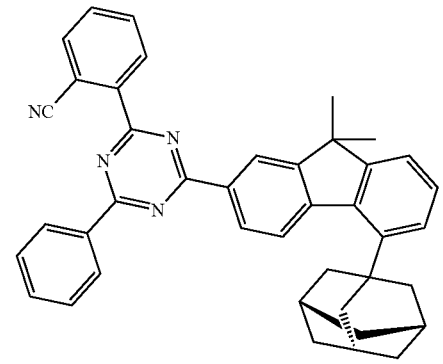
59
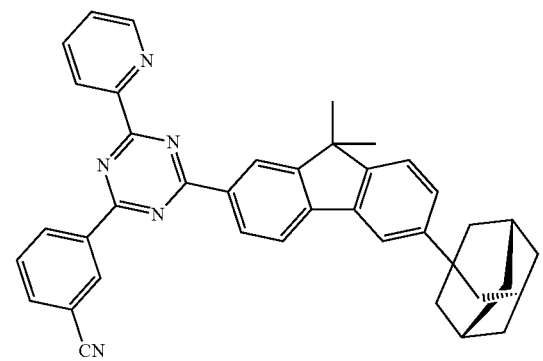

343
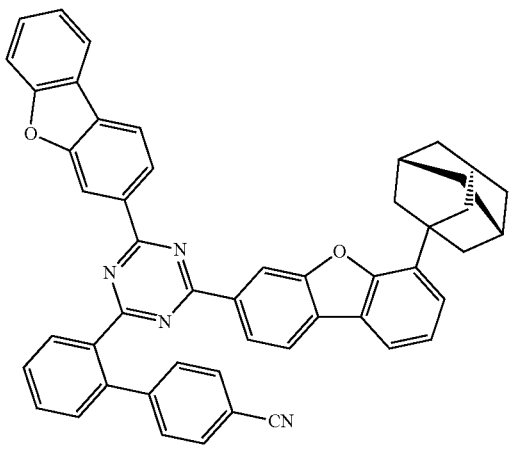
60
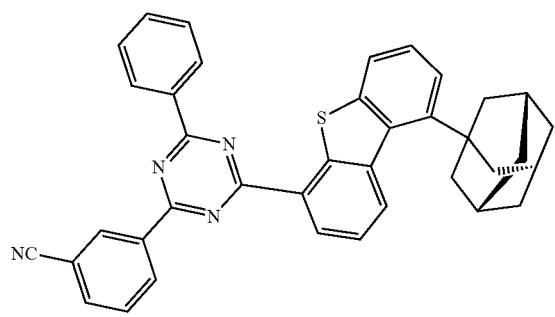
61
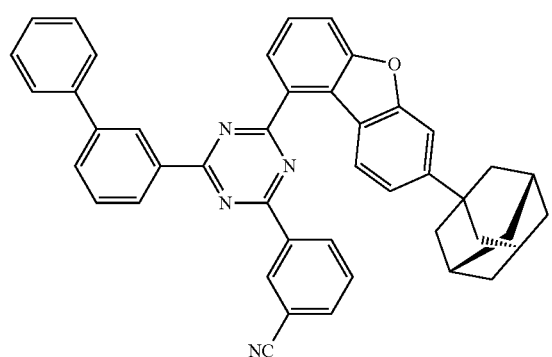
62
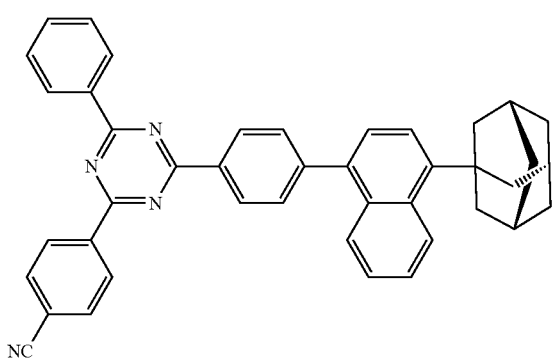
63
344
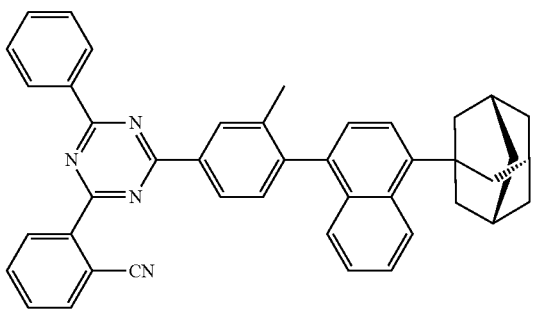
64
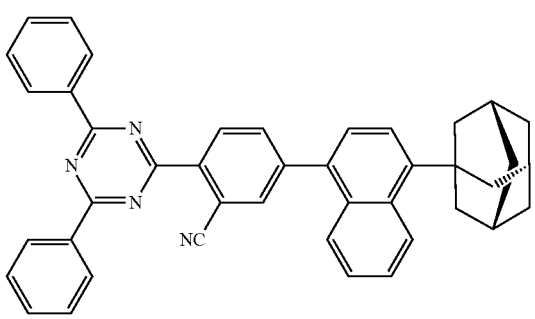
65
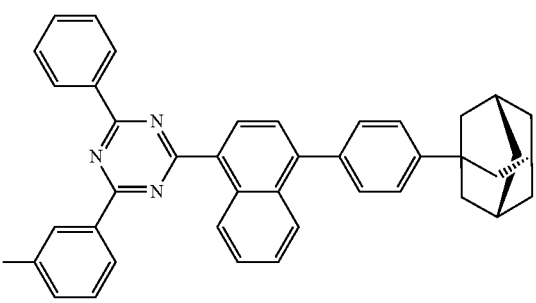
66
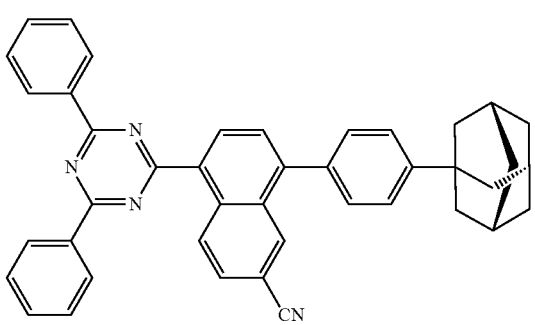
67

-continued
68
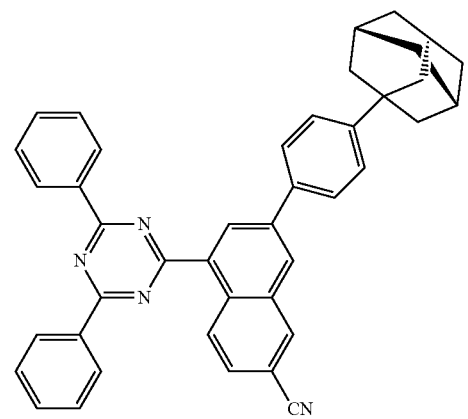
69
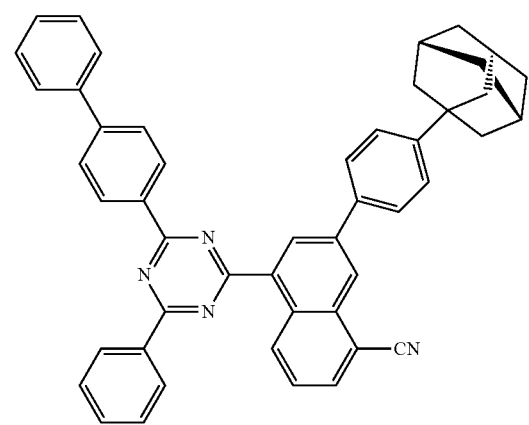
70
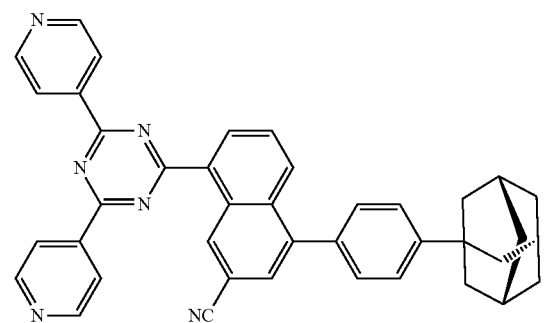
71
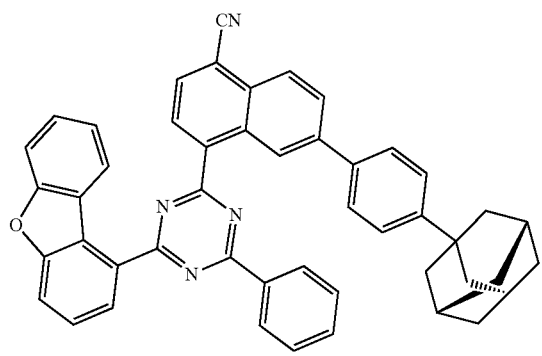
-continued
72
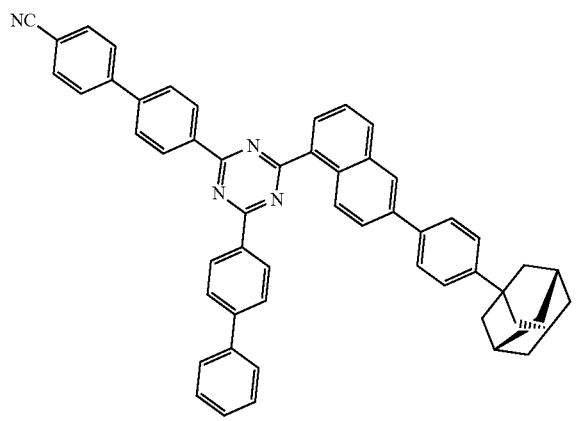
73
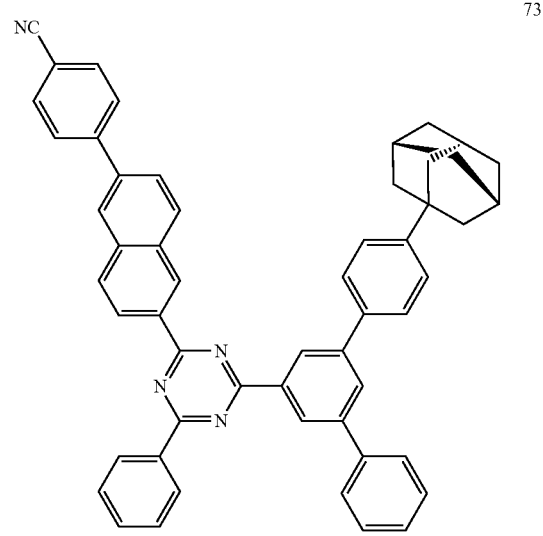
74
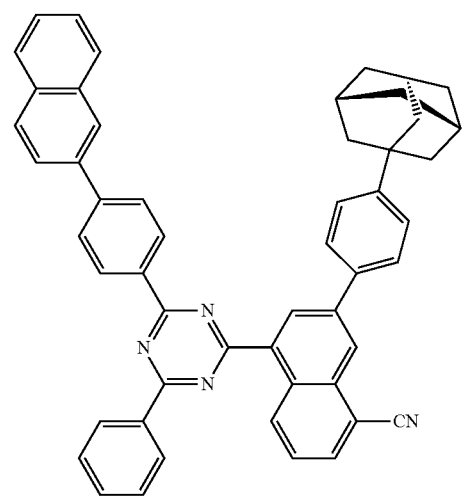

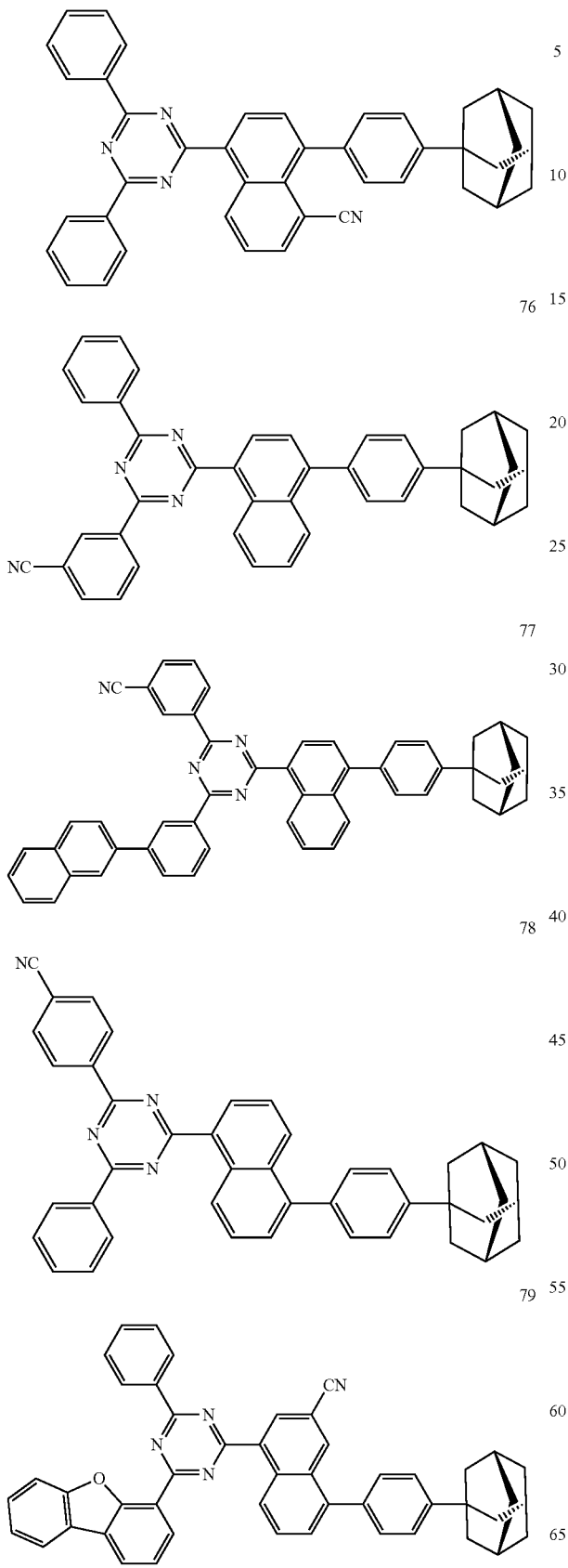
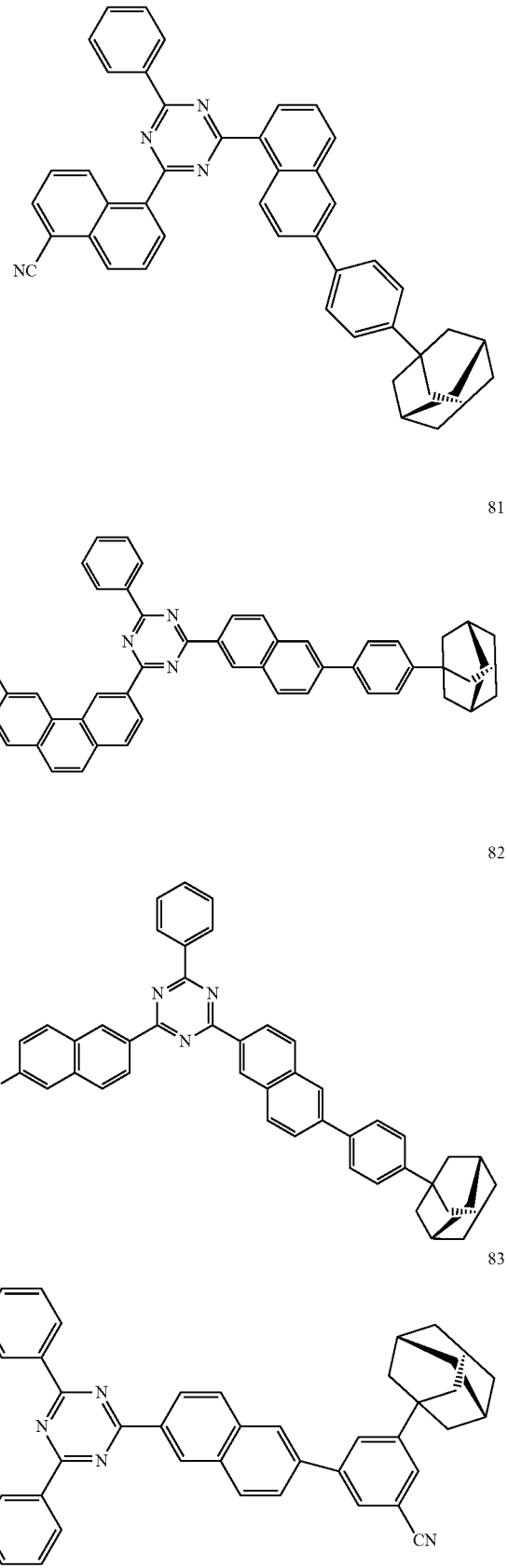

349
-continued
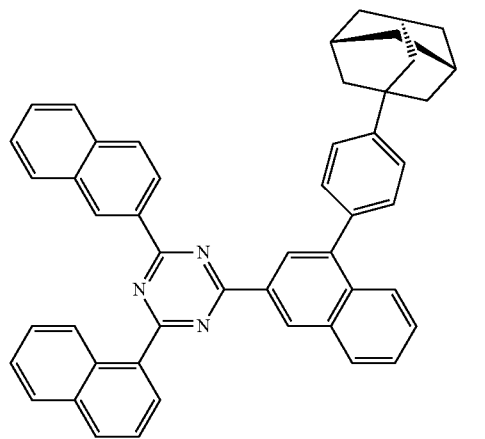
84
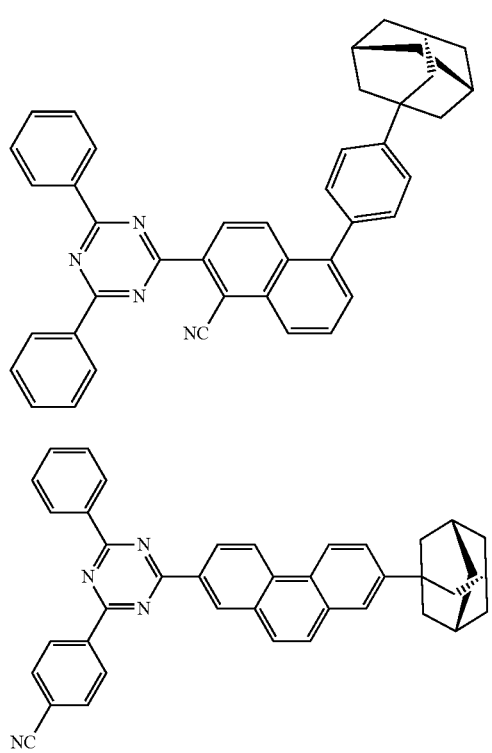
85
86
90
350
-continued
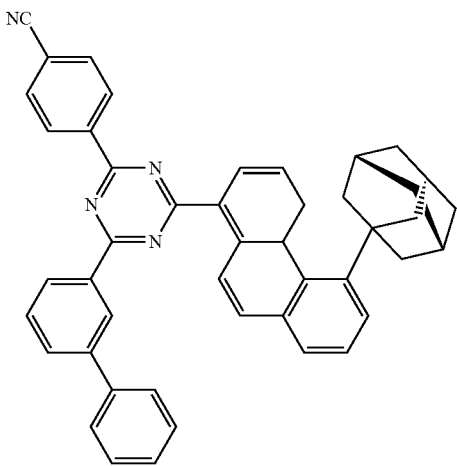
91
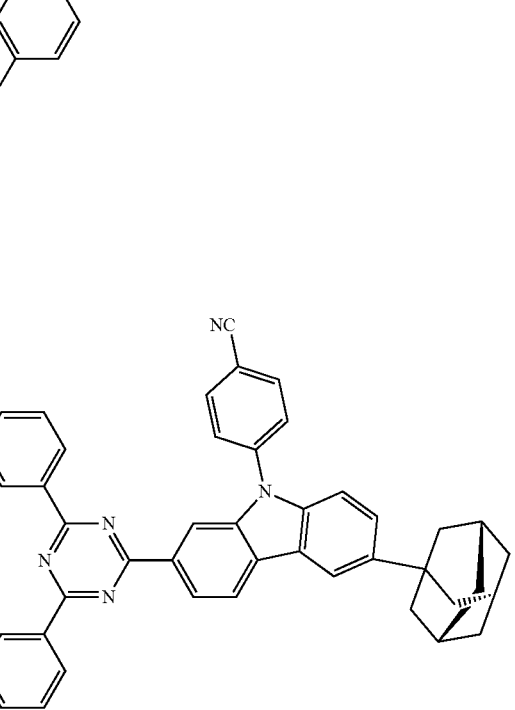
92
93

-continued

101
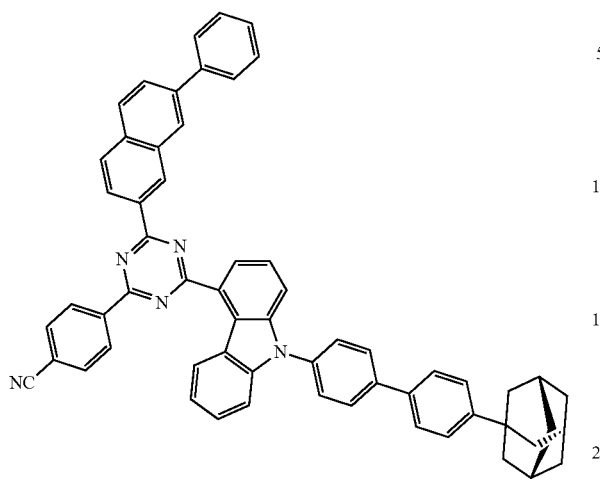
102
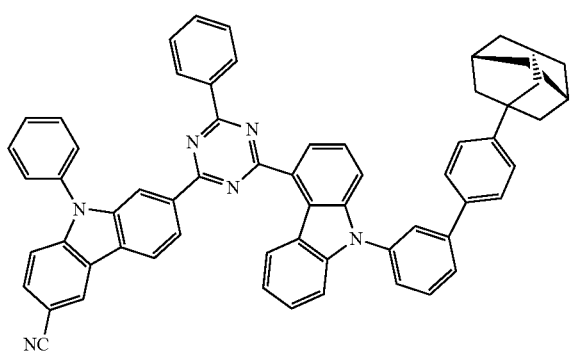
103
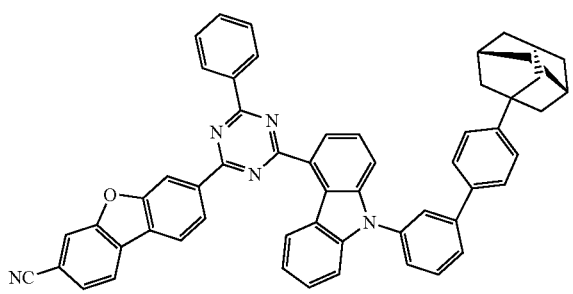
104
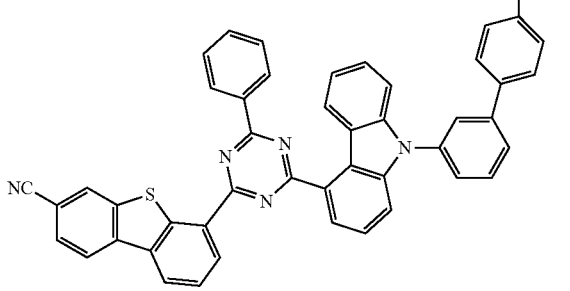
105
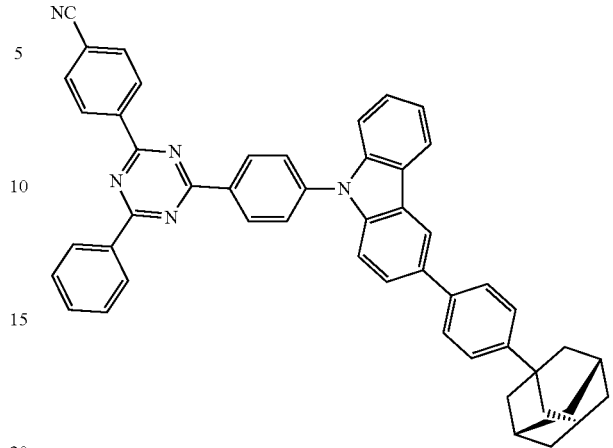
106
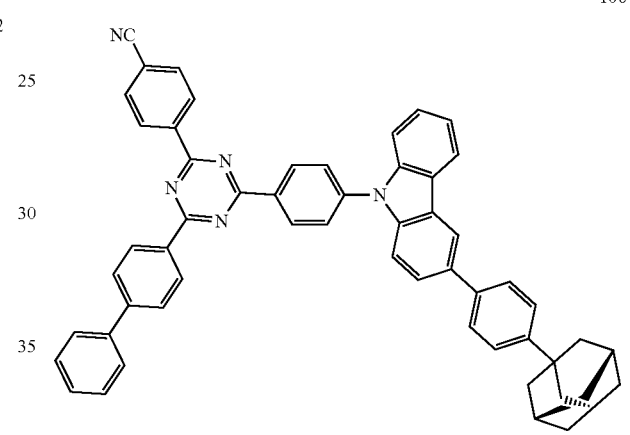
107
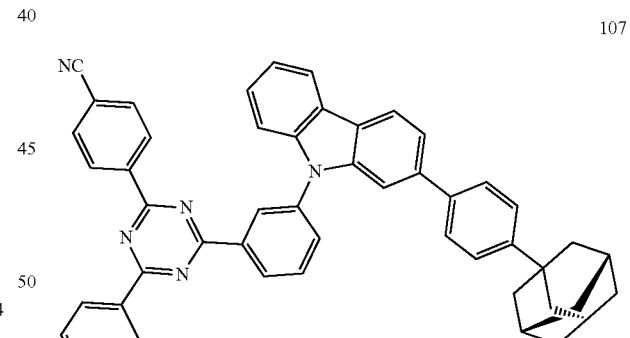
108
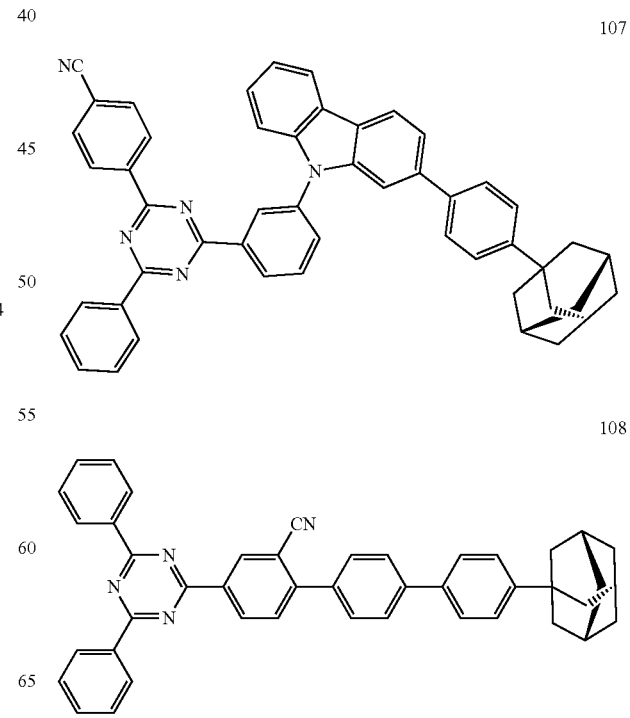

355
-continued
109
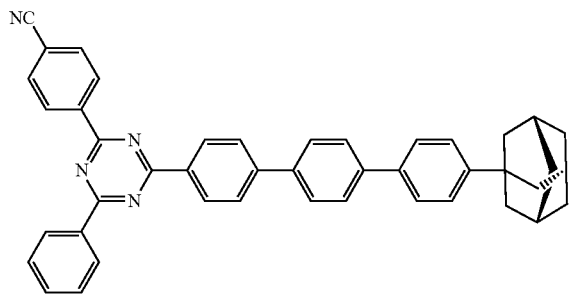
110
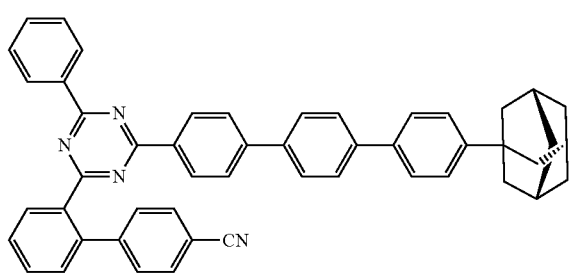
111
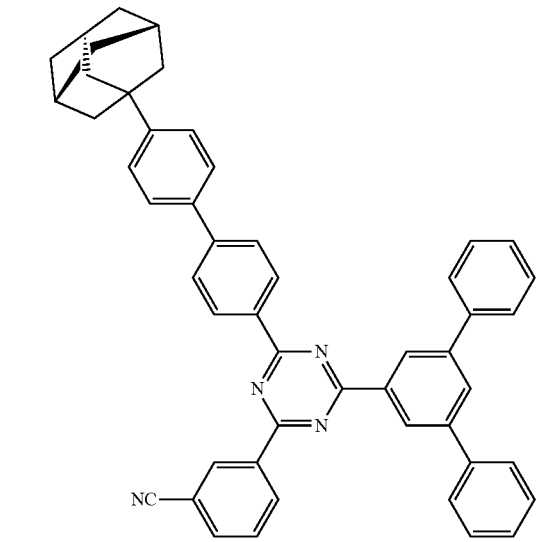
112
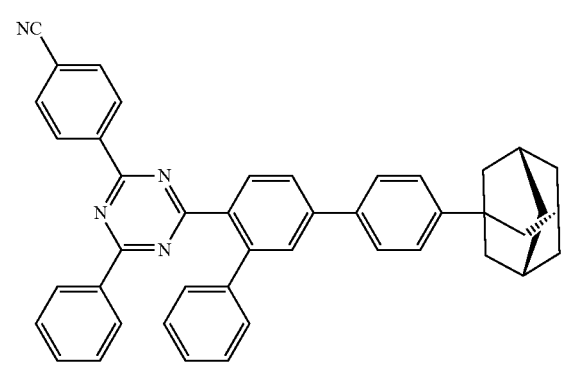
356
-continued
113
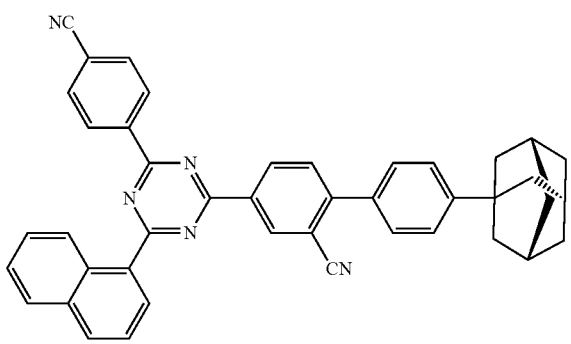
114
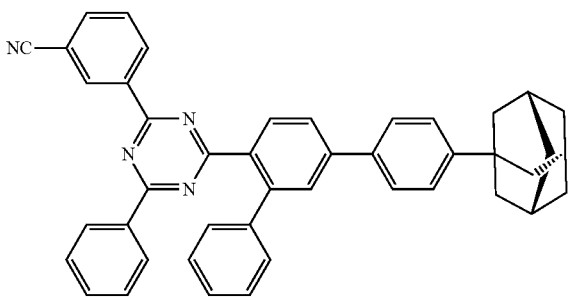
115
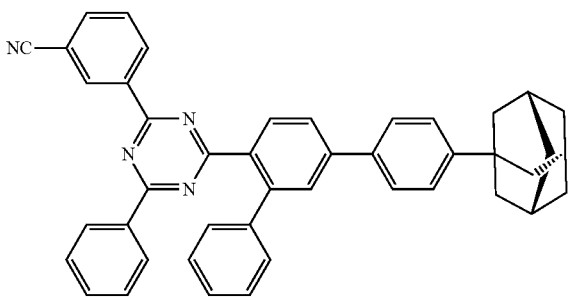
116
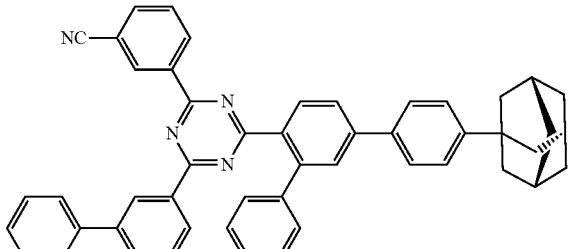
117
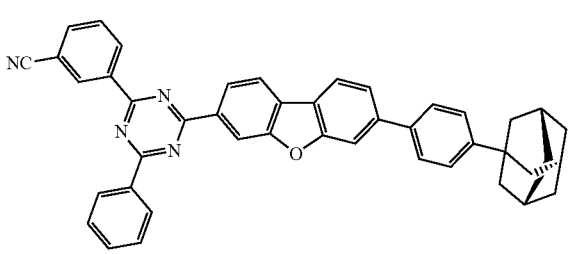

-continued
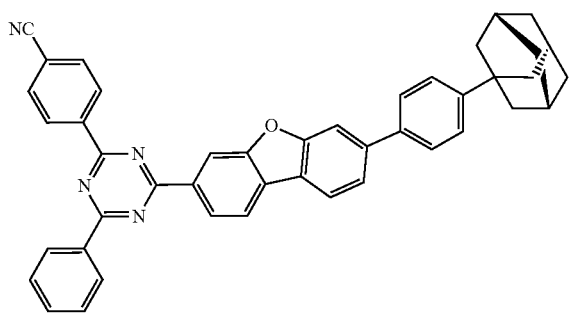
118
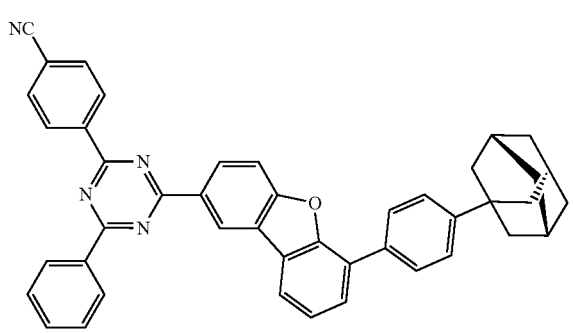
119
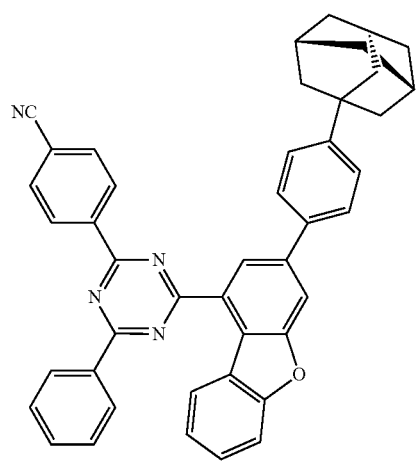
120
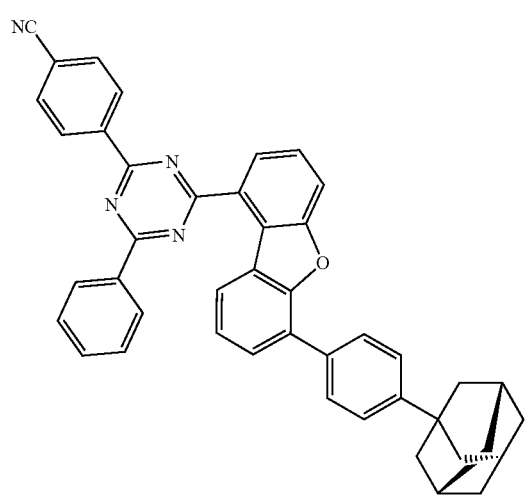
121
-continued
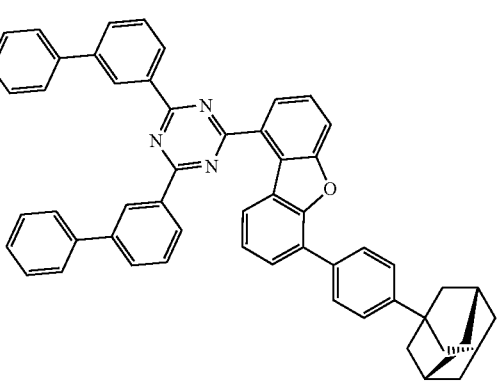
122
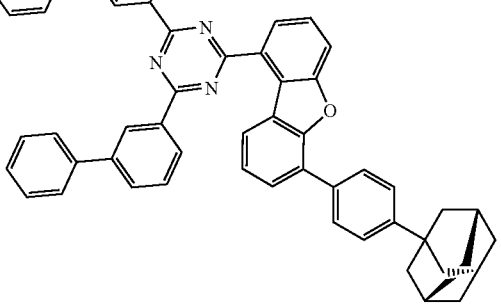
123
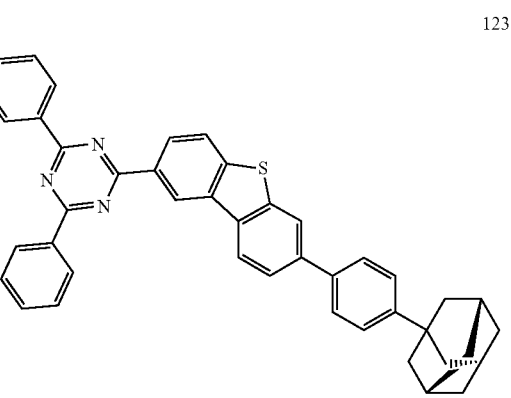
124
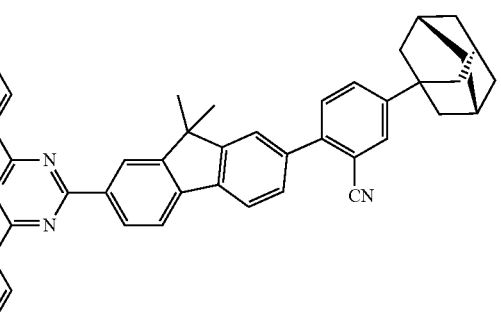
125

126
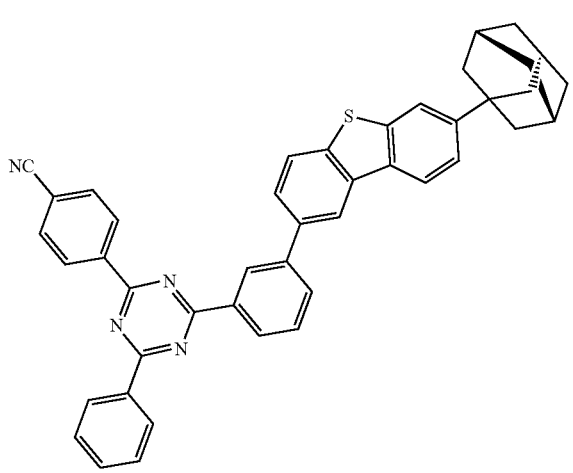
130
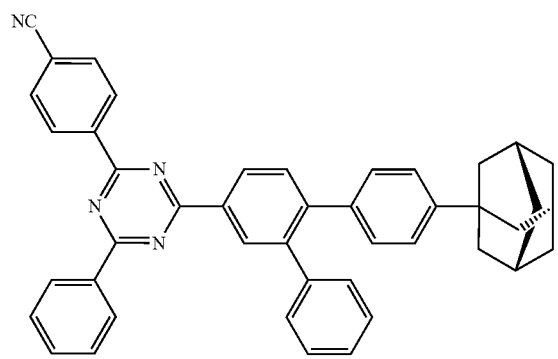
127
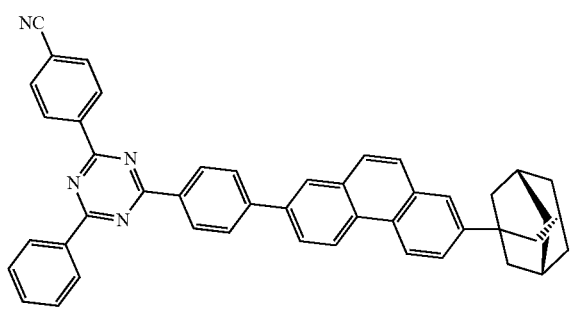
131
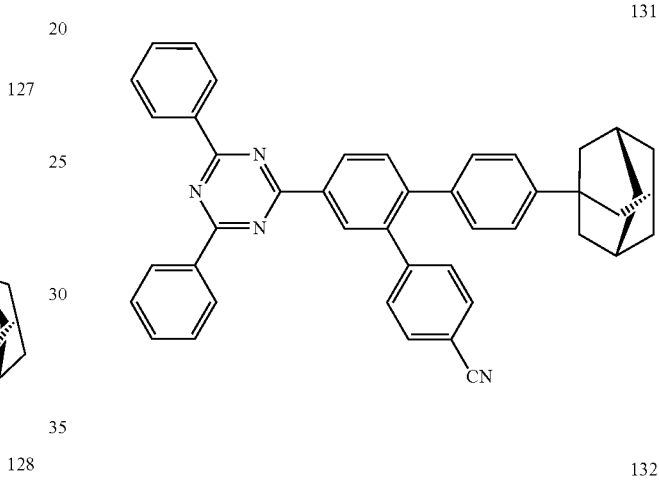
128
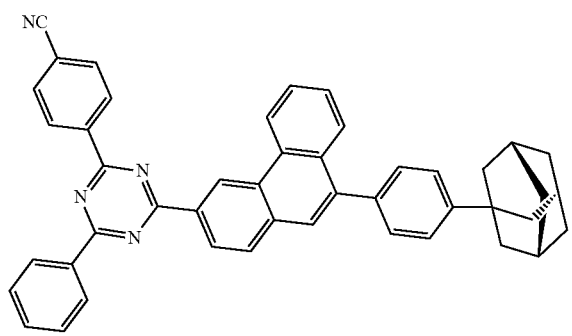
132
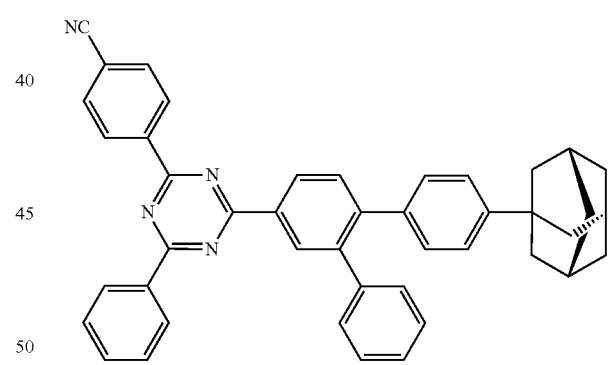
129
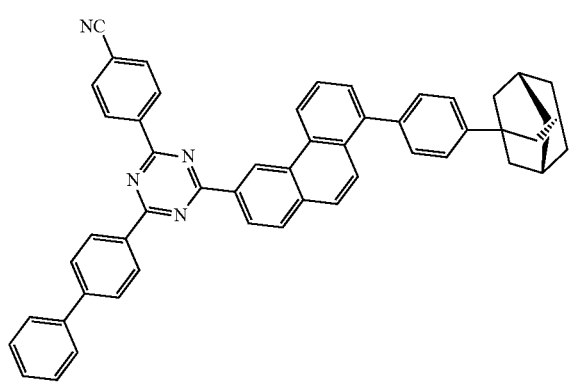
133
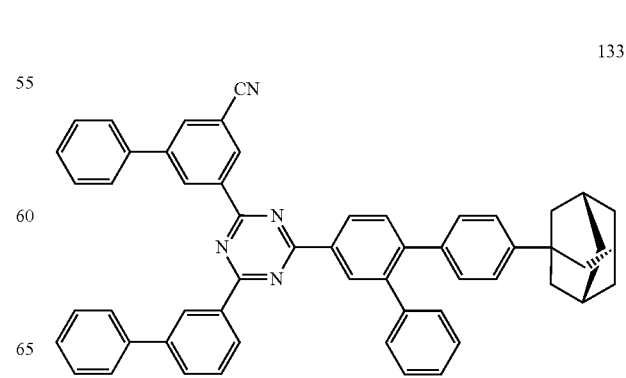

134
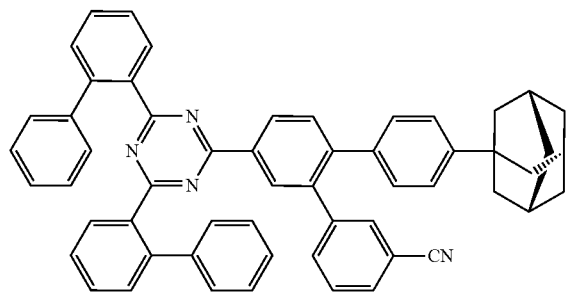
135
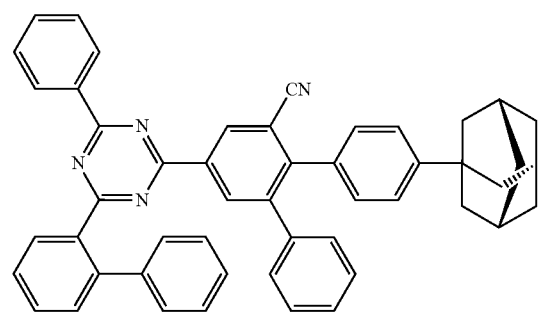
136
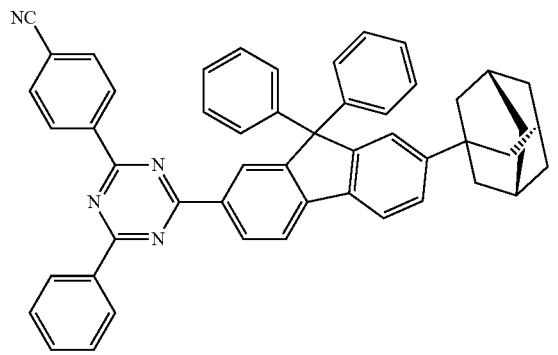
137
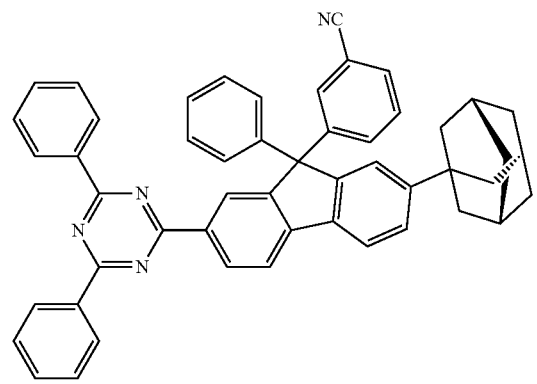
138
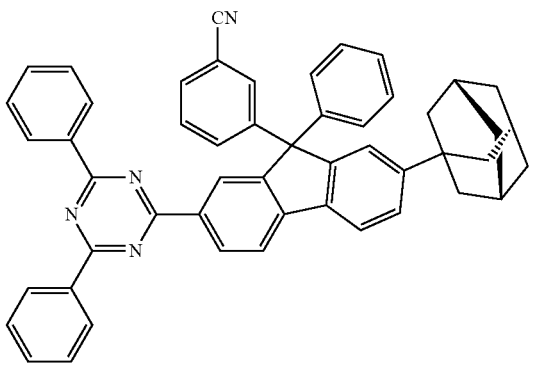
139
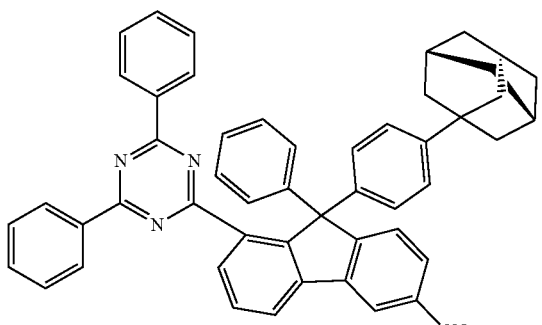
140
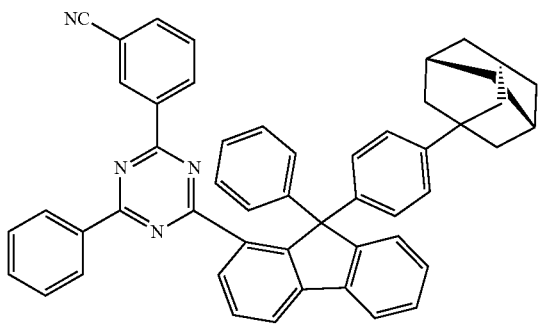
141
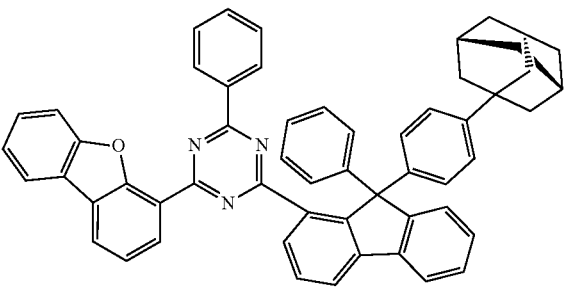

363
-continued
142
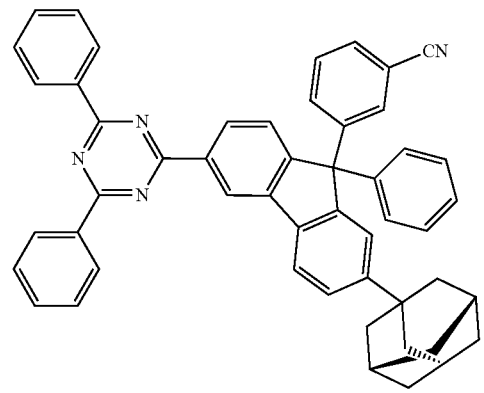
143
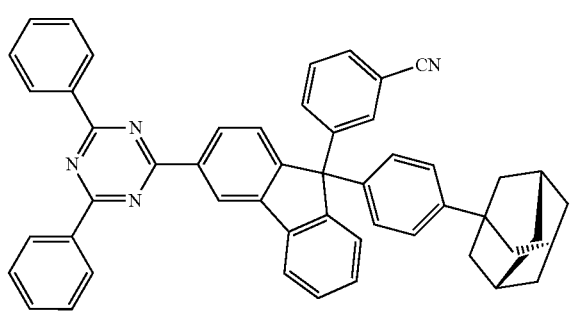
144
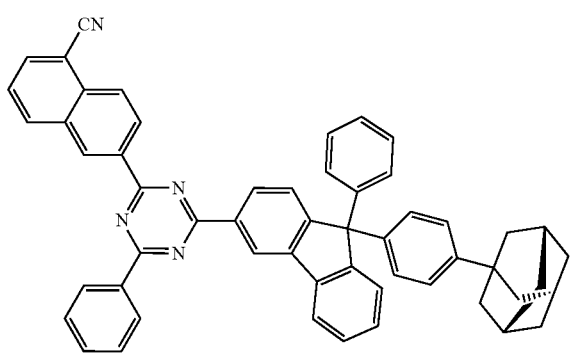
145
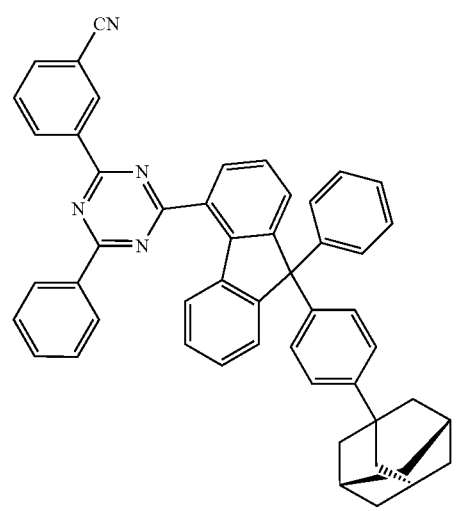
364
-continued
146
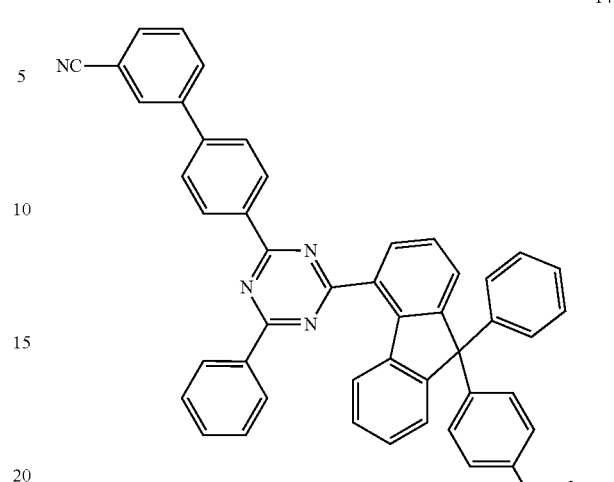
147
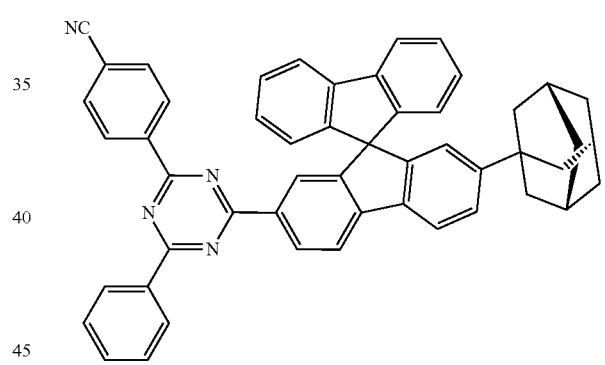
148
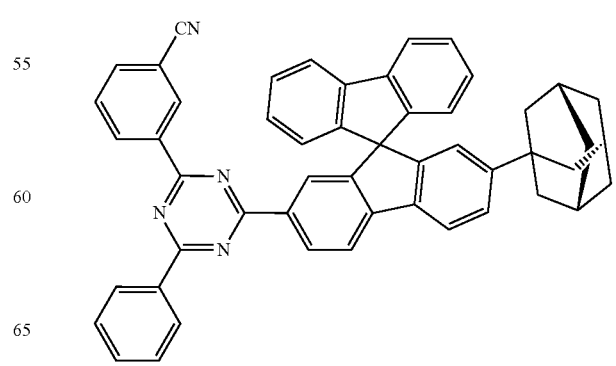

365
-continued
152
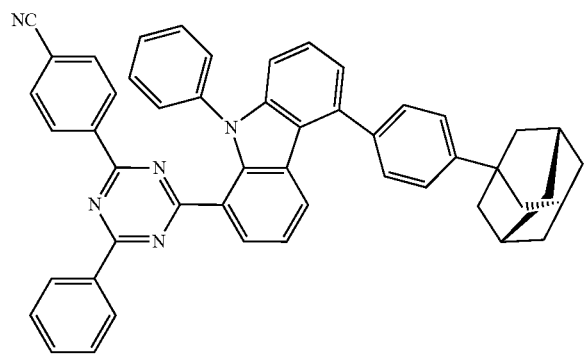
153
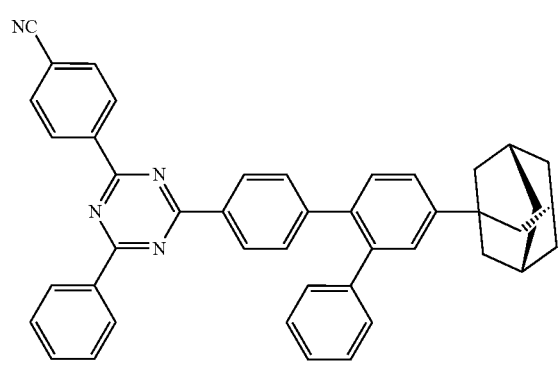
154
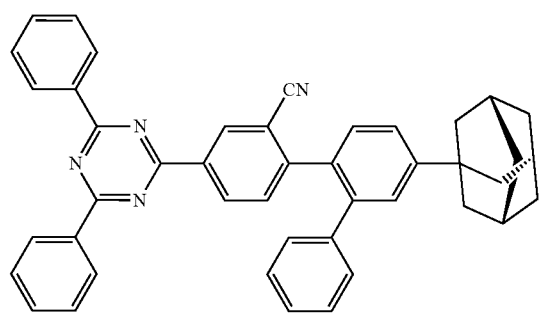
155
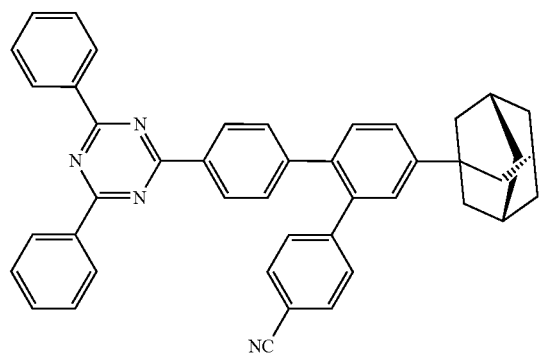
366
-continued
156
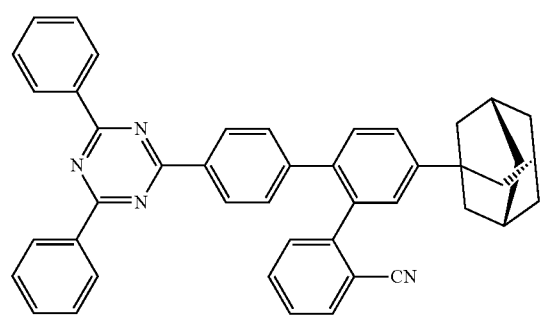
157
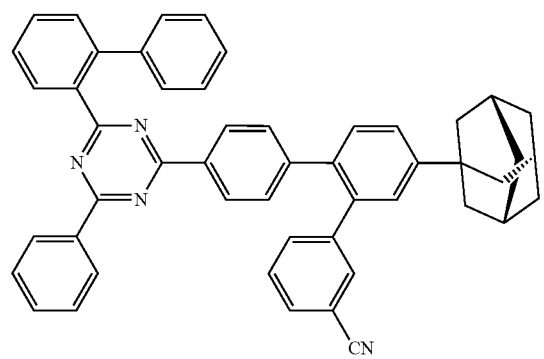
158
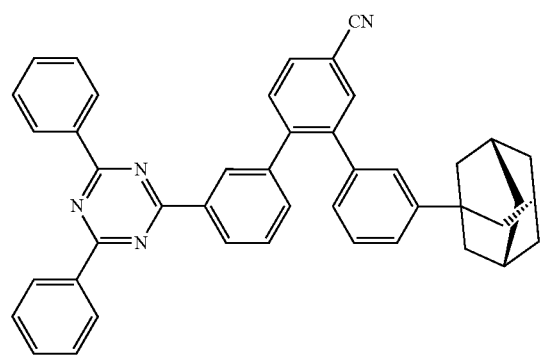
159
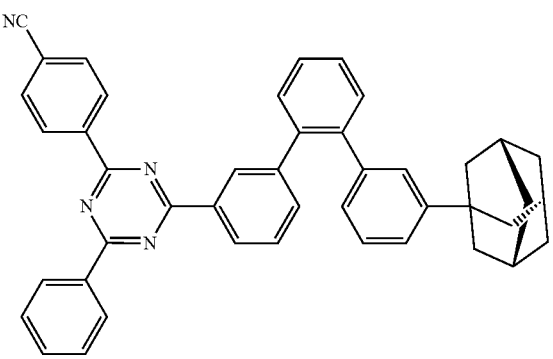

160
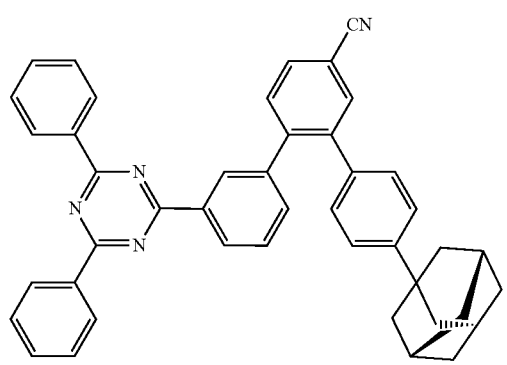
161
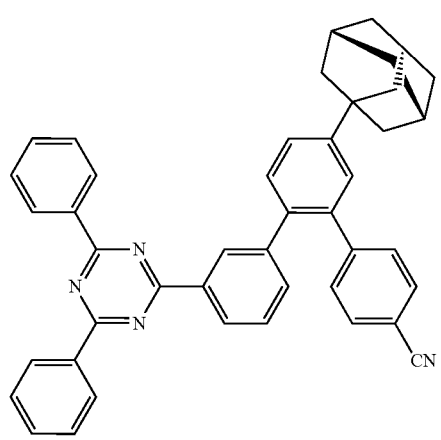
162
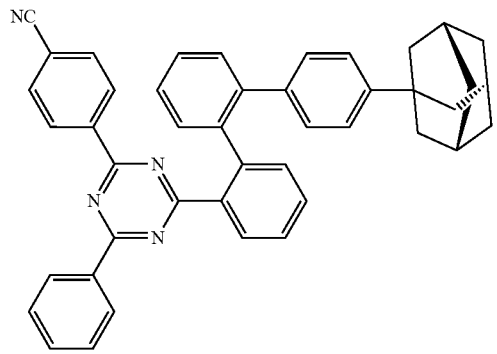
163
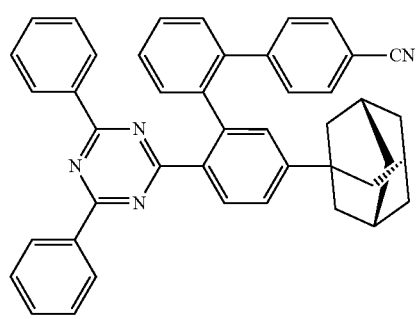
164
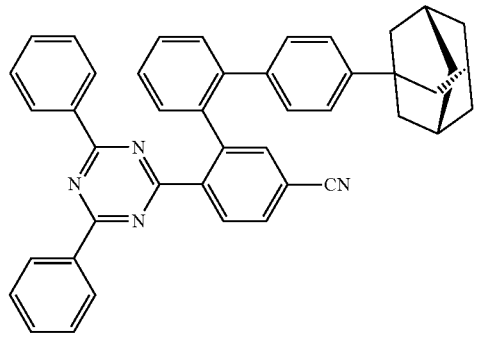
165
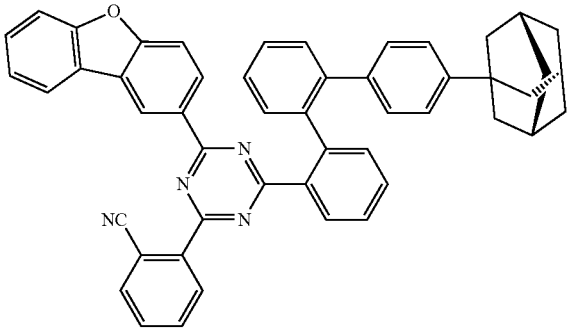
166
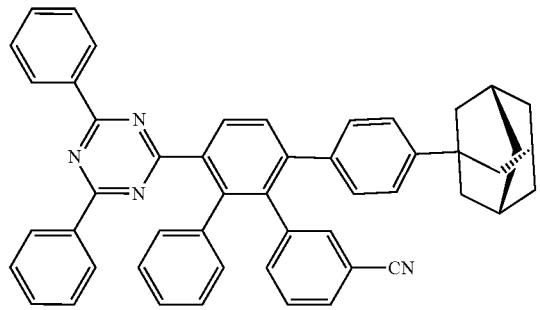
167
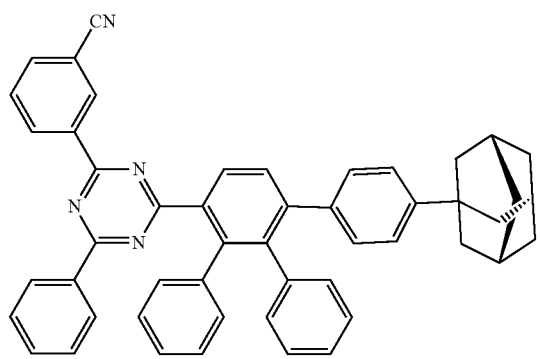

-continued
168
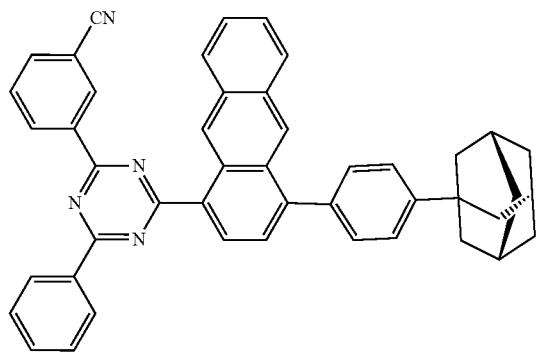
169
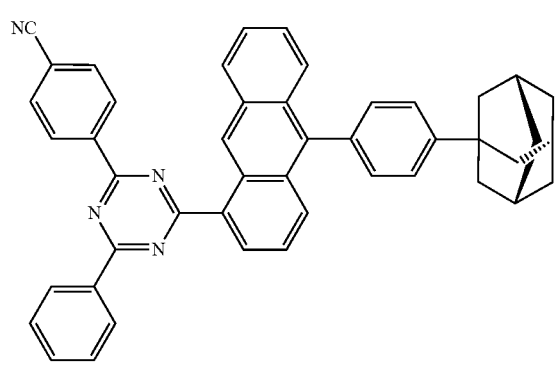
170
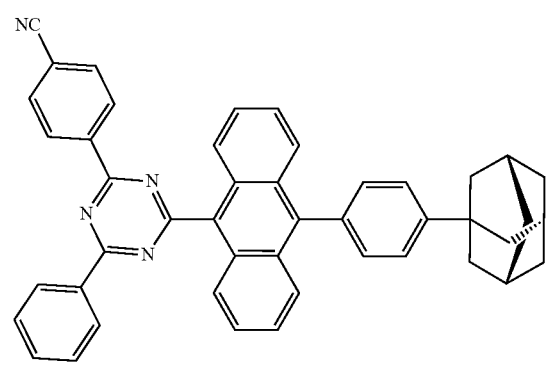
171
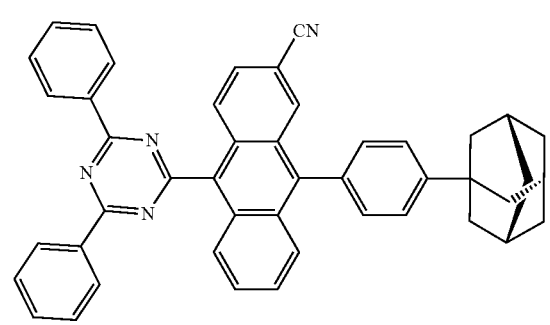
-continued
181
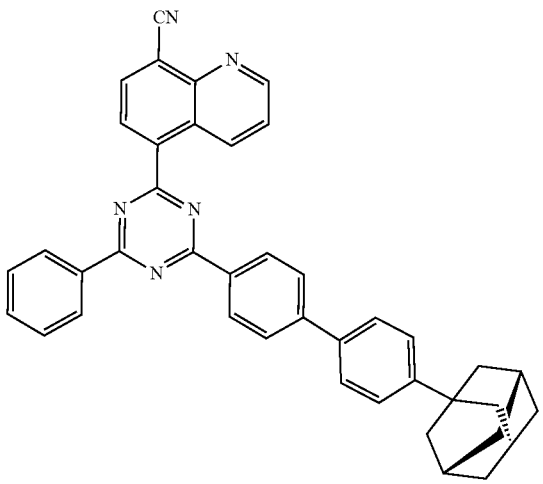
182
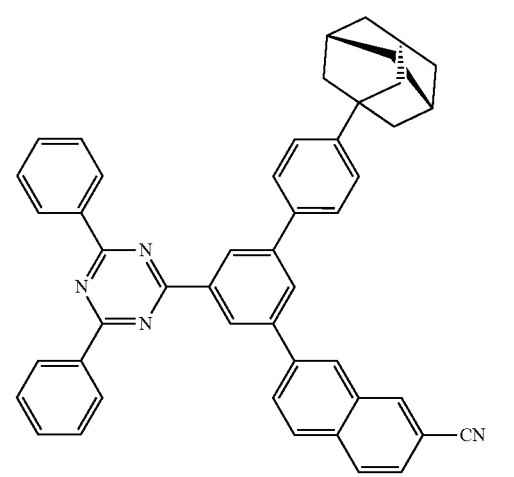
183
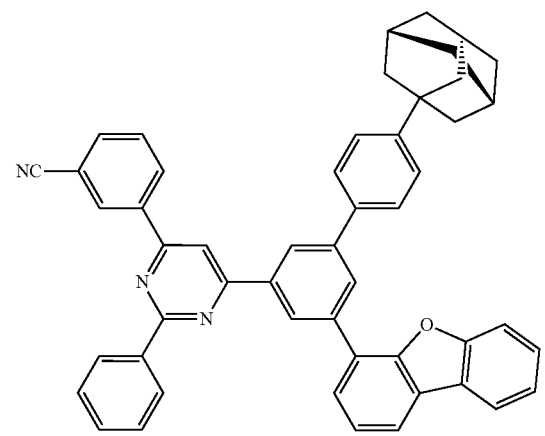

371
-continued
184
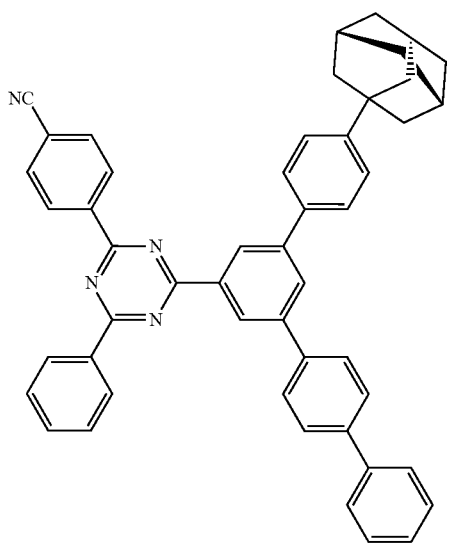
185
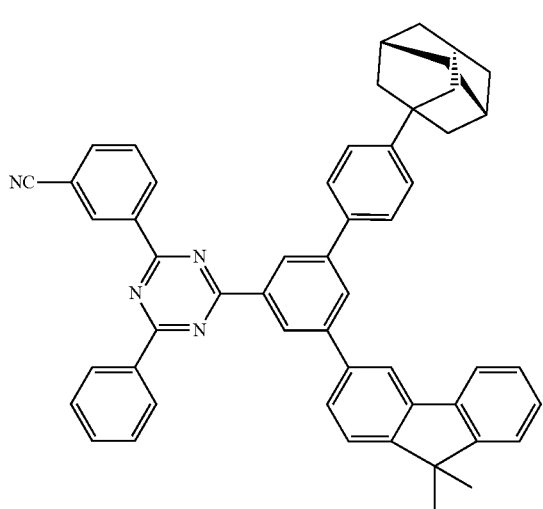
186
372
-continued
187
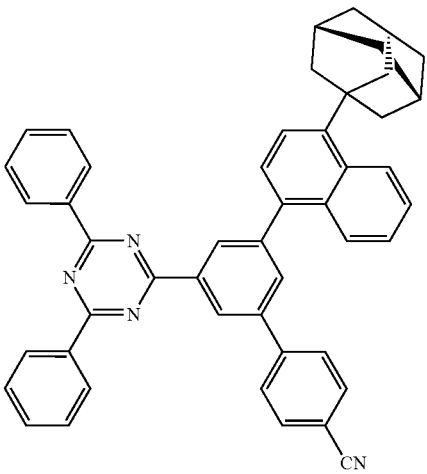
188
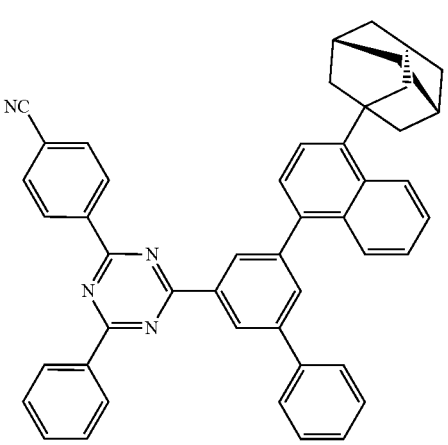
189
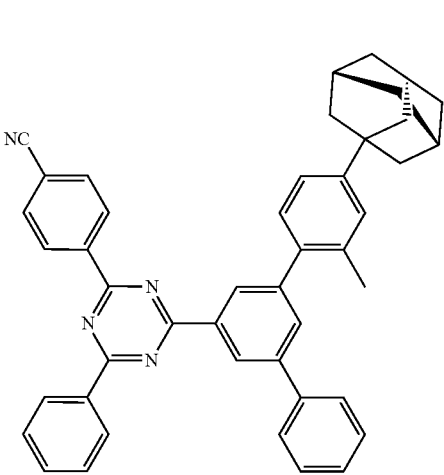

373
-continued
374
-continued
190
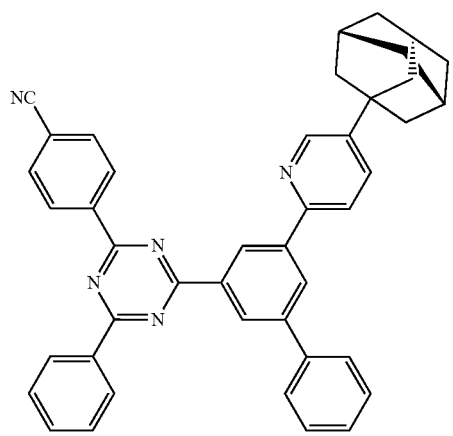
193
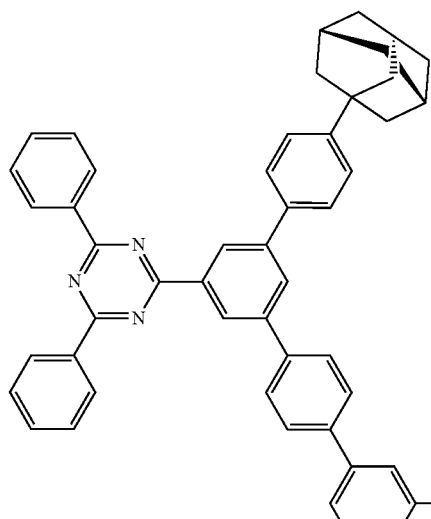
191
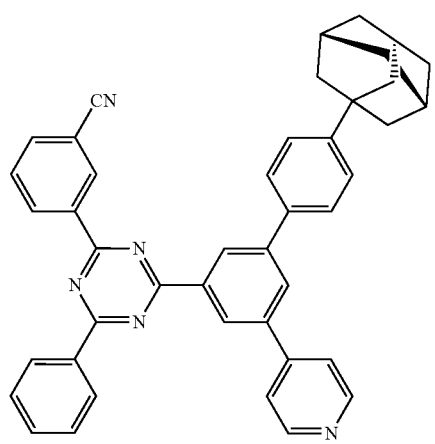
192
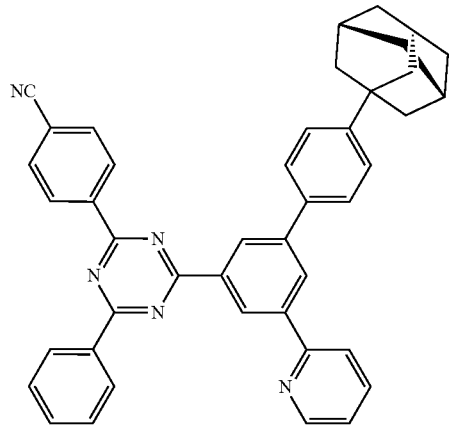
194
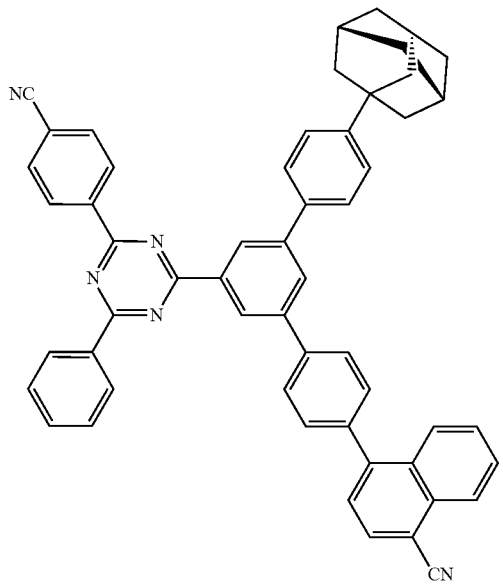

-continued
195
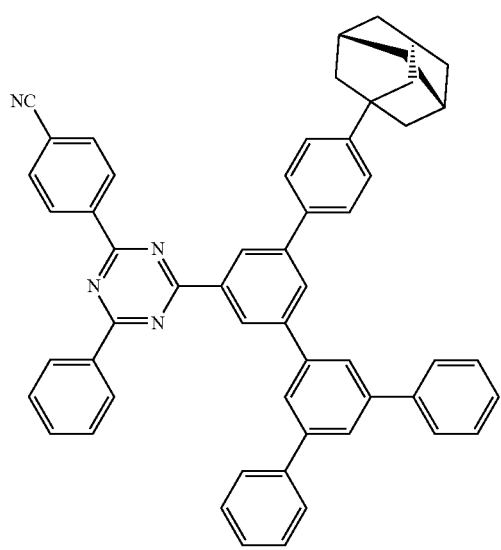
196
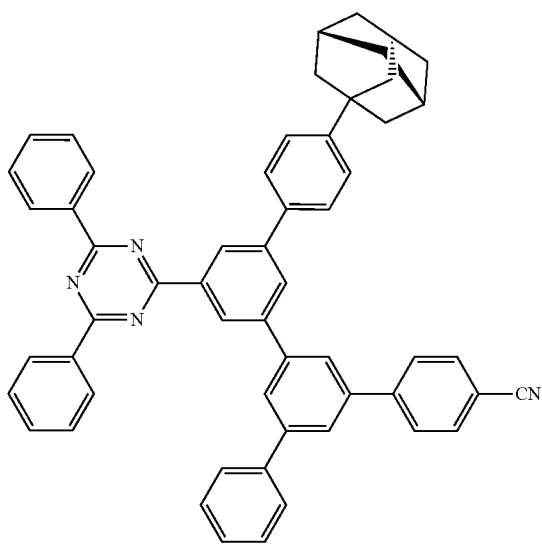
197
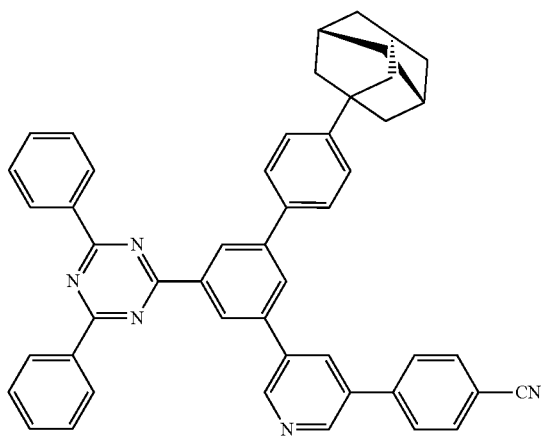
-continued
198
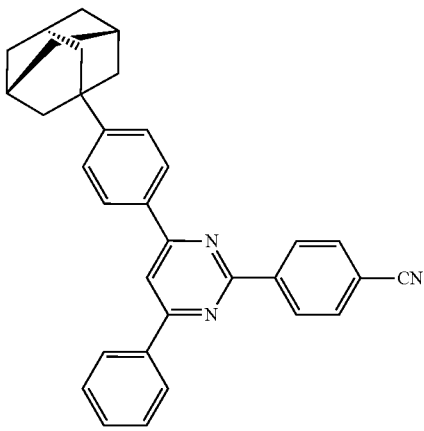
199
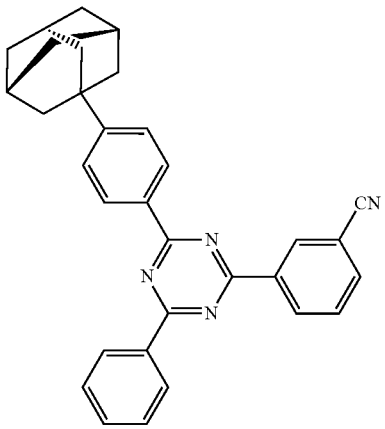
200
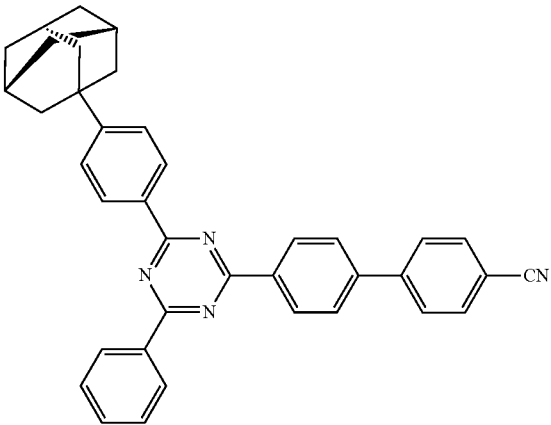

| 201 | 204 |
|---|---|
| 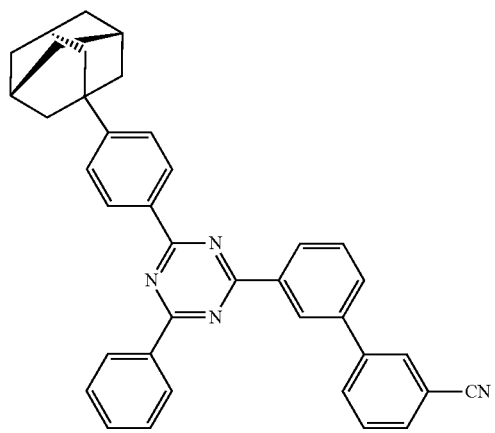 | 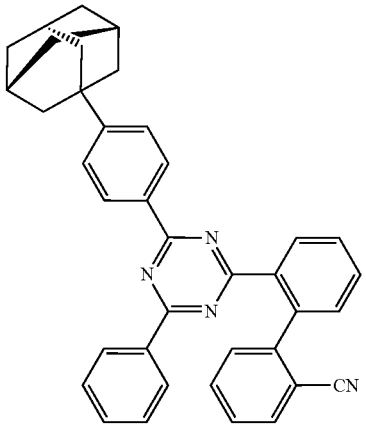 |
| 202 | 205 |
|---|---|
| | 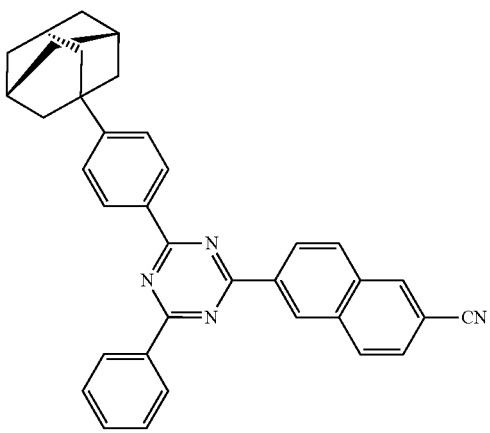 |
| 203 | 206 |
|---|---|
| 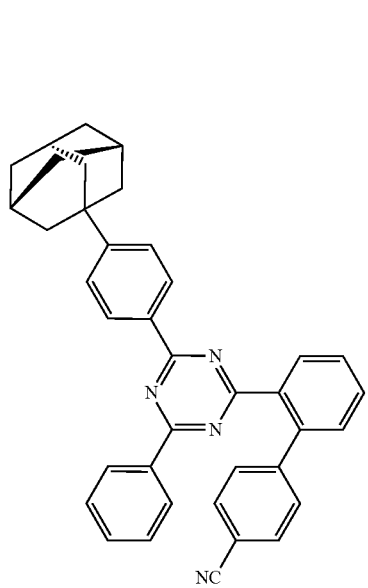 | 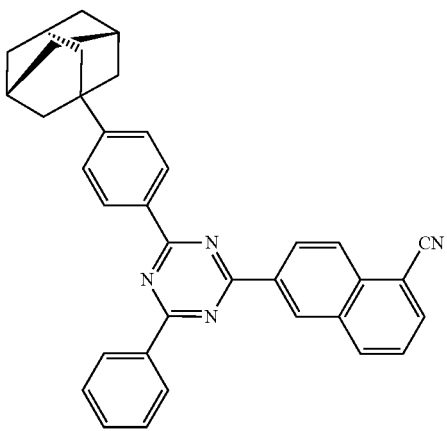 |

379
-continued
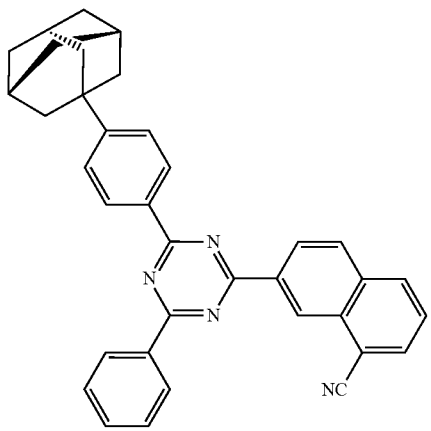
207
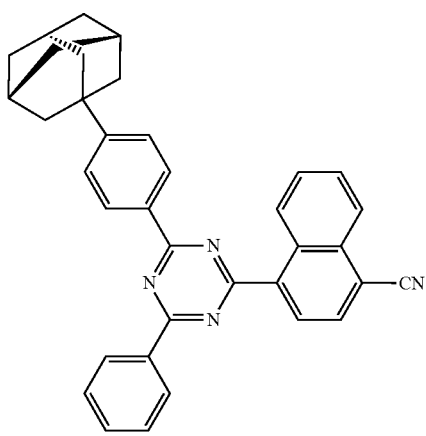
208
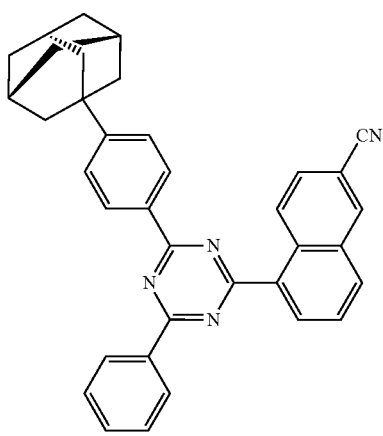
209
380
-continued
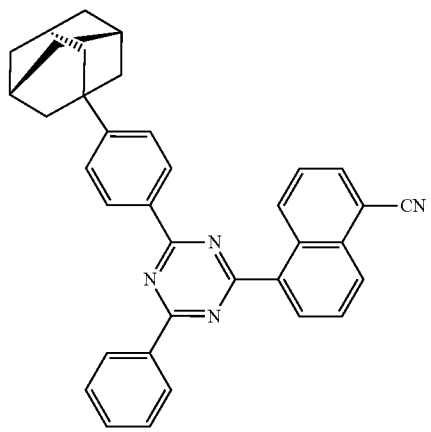
210
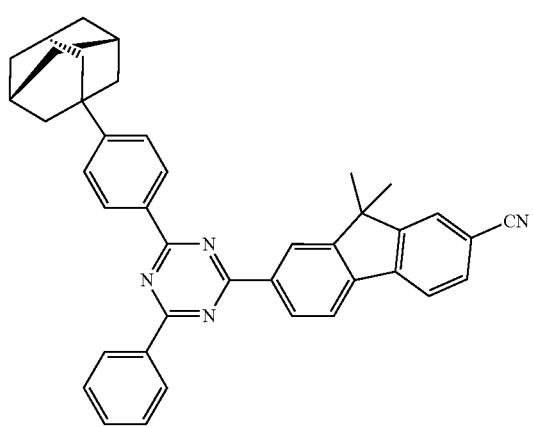
211
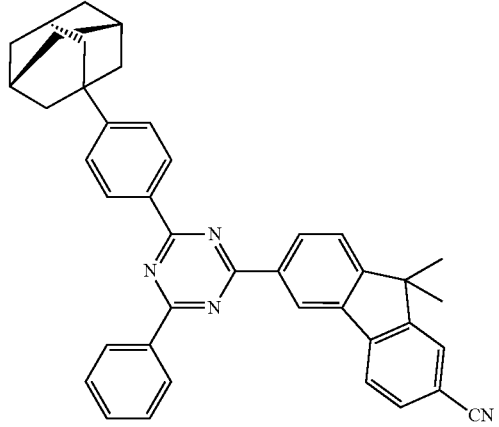
212

381
-continued
213
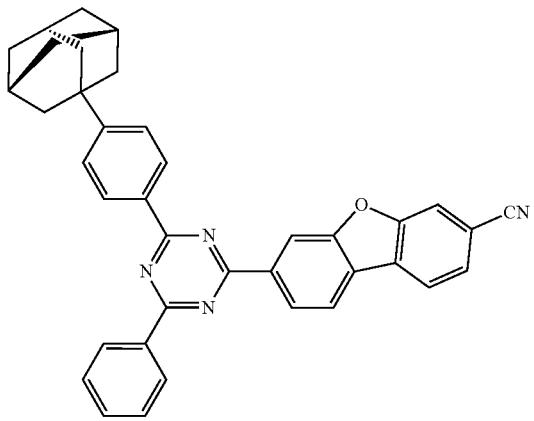
214
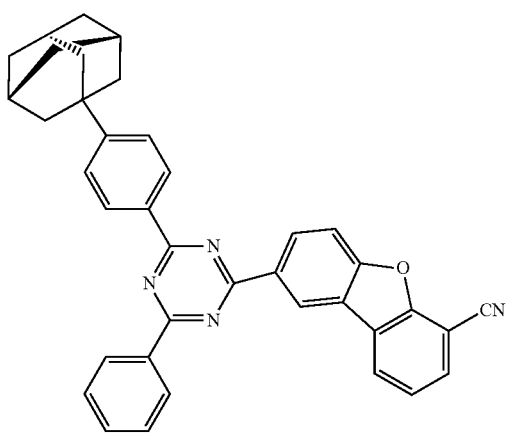
215
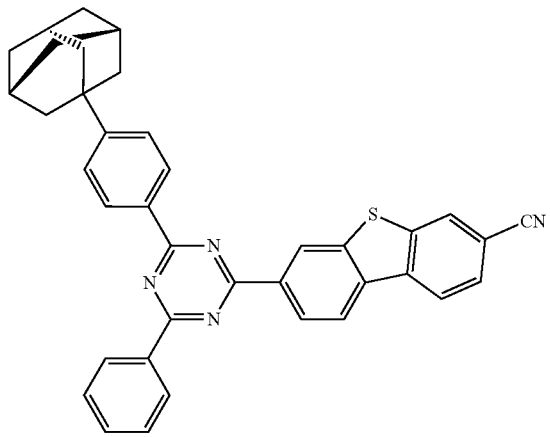
382
-continued
216
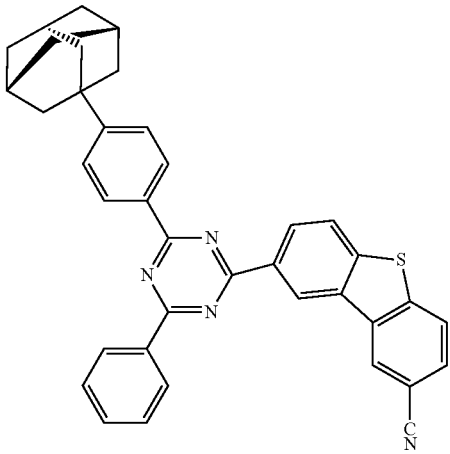
217
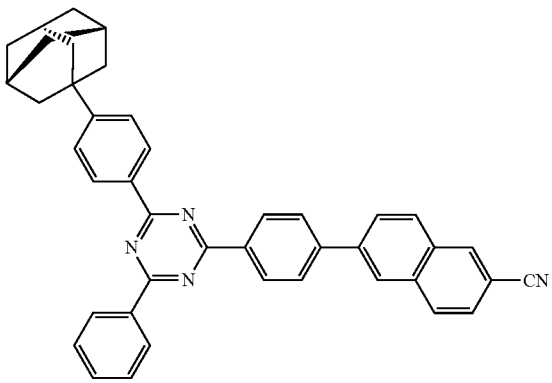
218
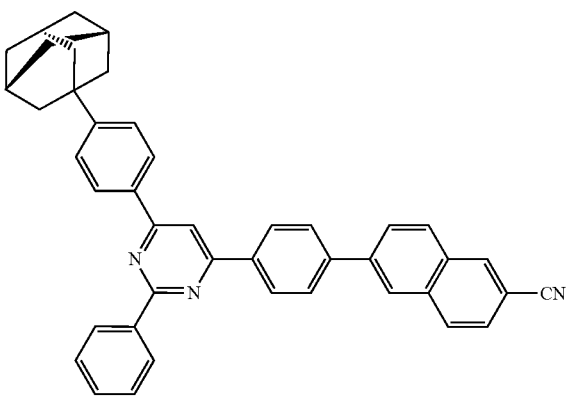

383
-continued
219
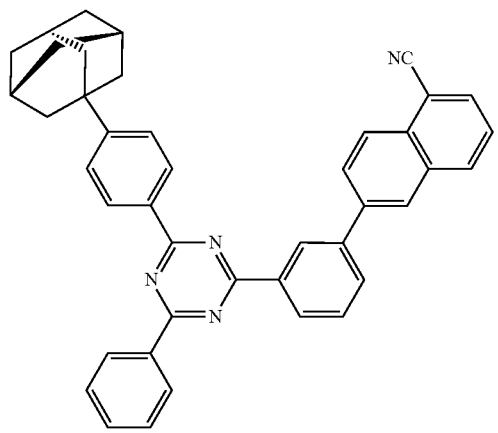
220
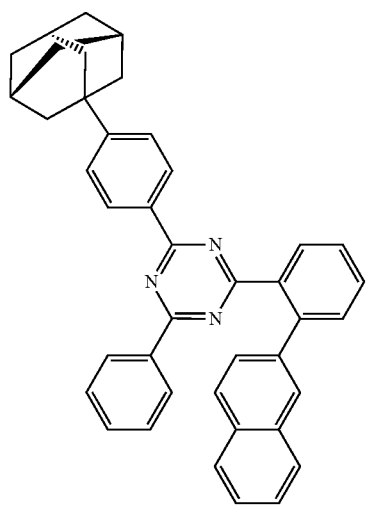
221
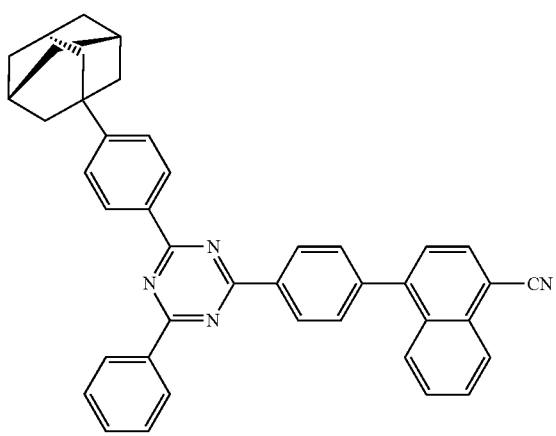
384
-continued
222
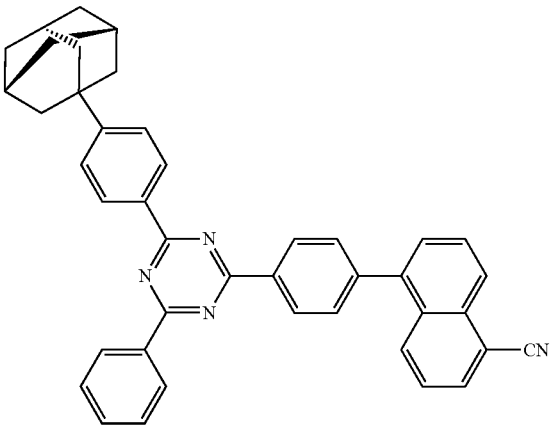
223
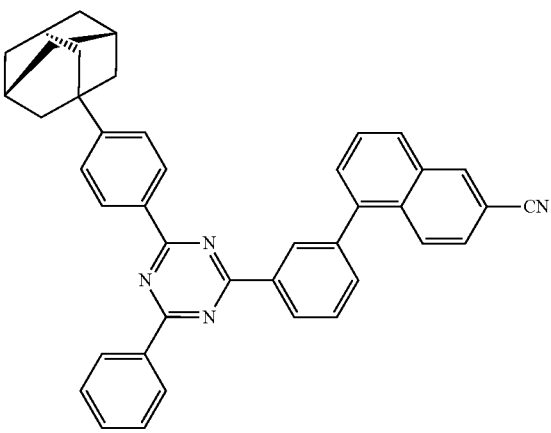
224
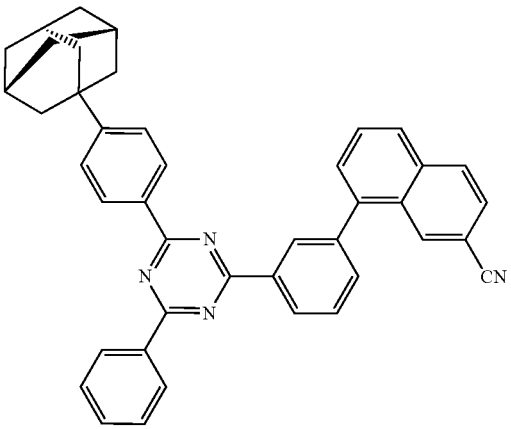

225
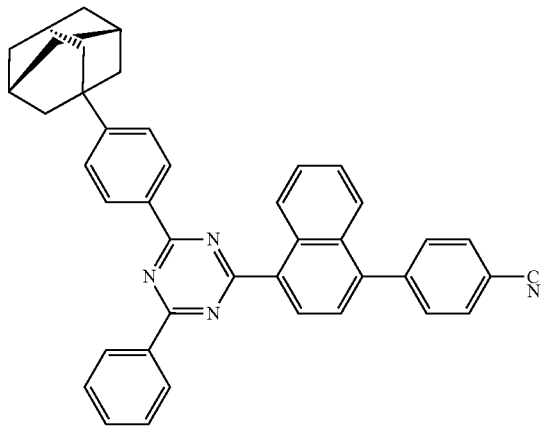
228
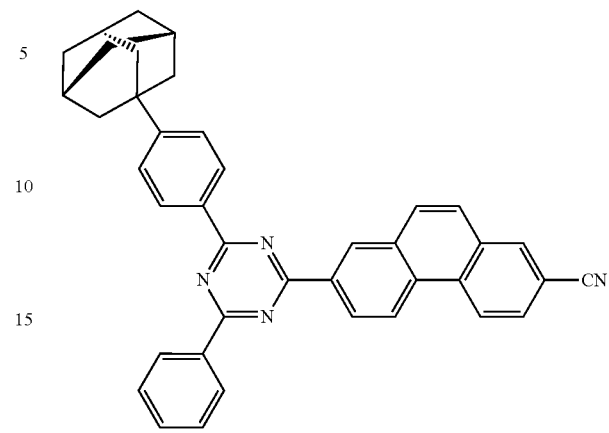
226
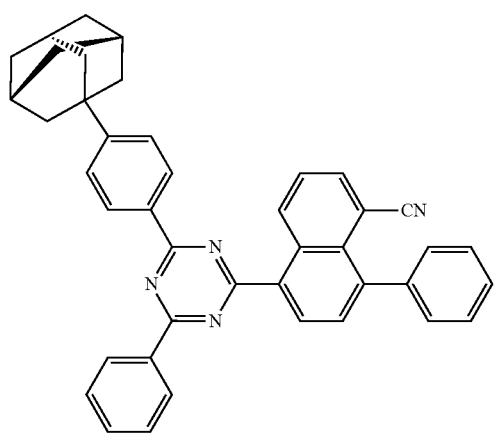
229
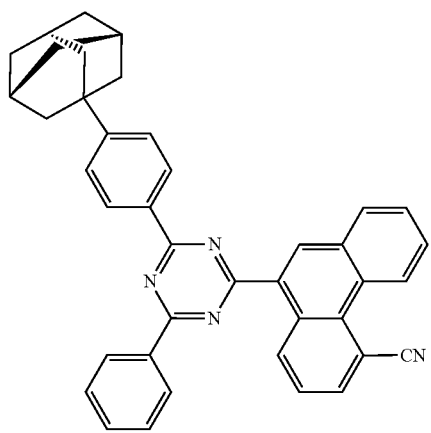
227
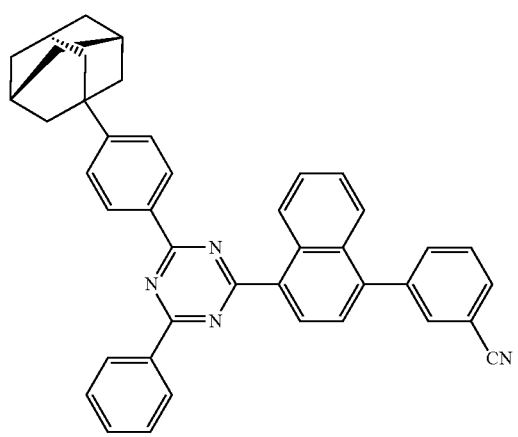
230
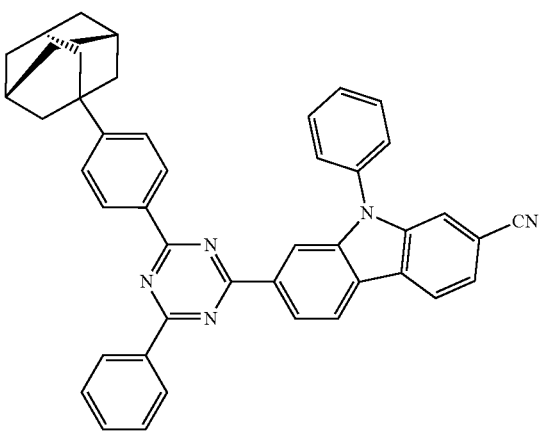

387
-continued
231
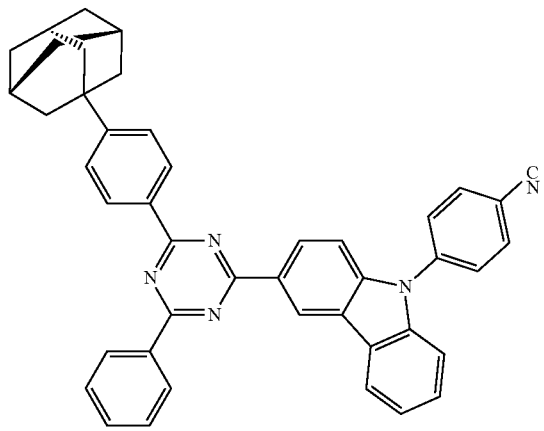
232
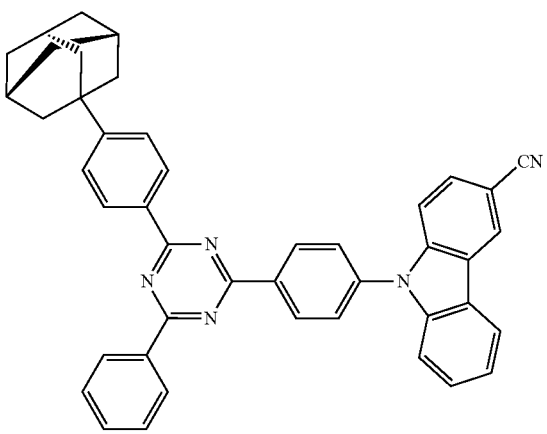
233
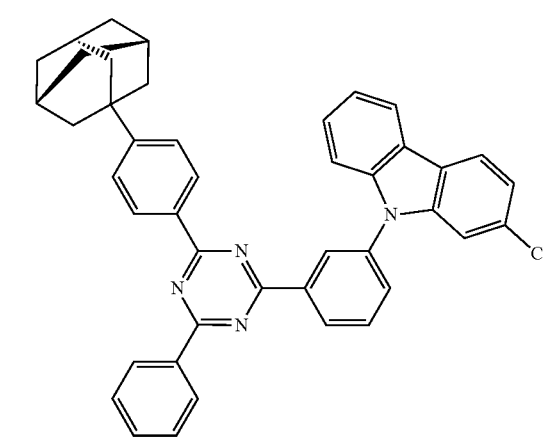
388
-continued
234
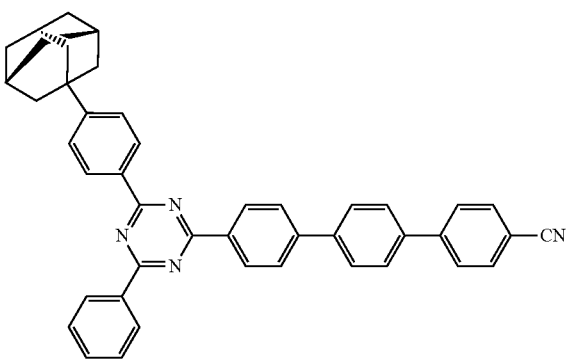
235
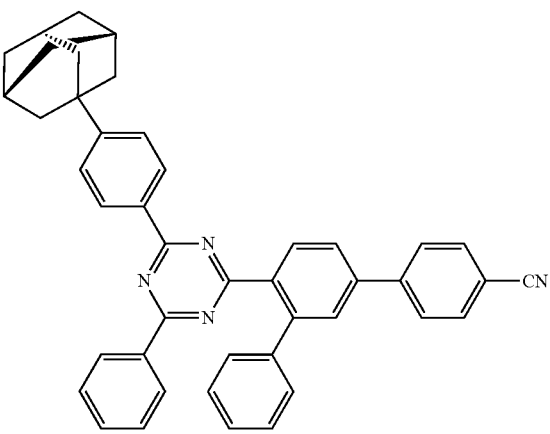
236
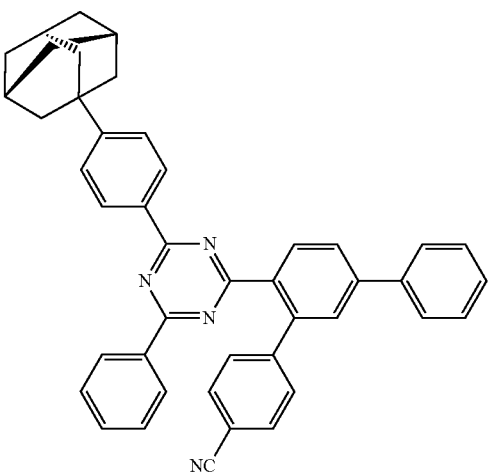

389
-continued
390
-continued
237
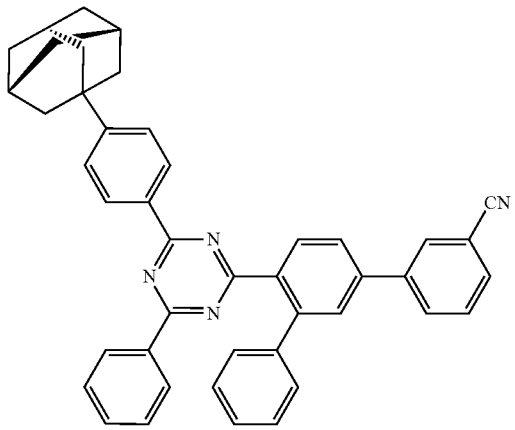
240
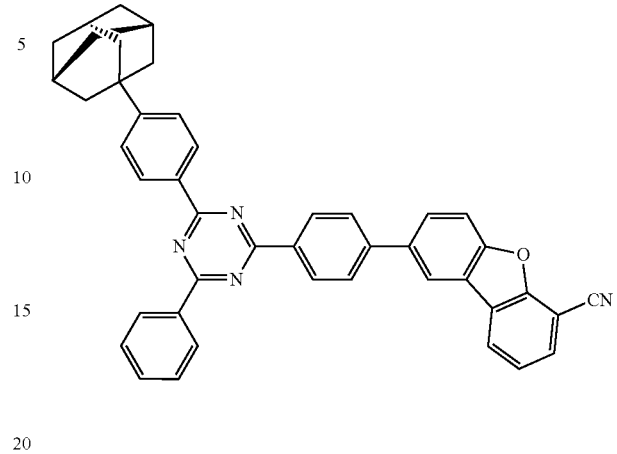
238
241
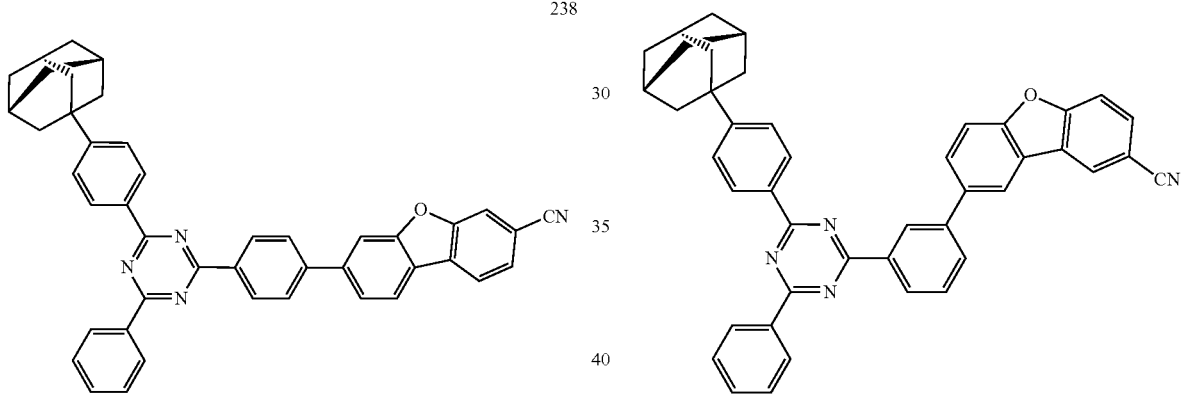
239
242
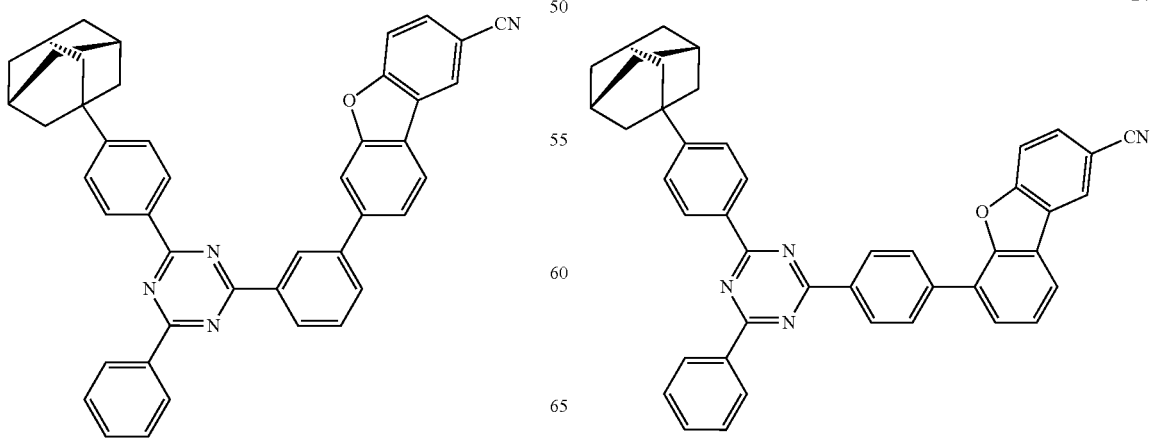

391
-continued
392
-continued
243
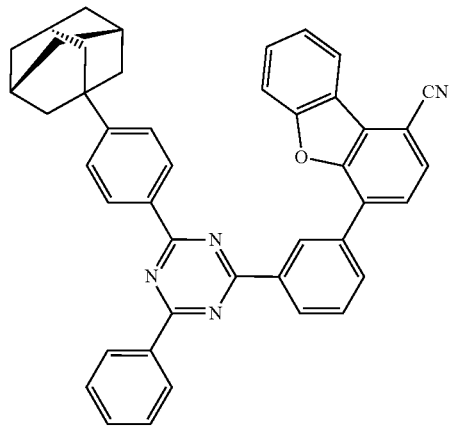
246
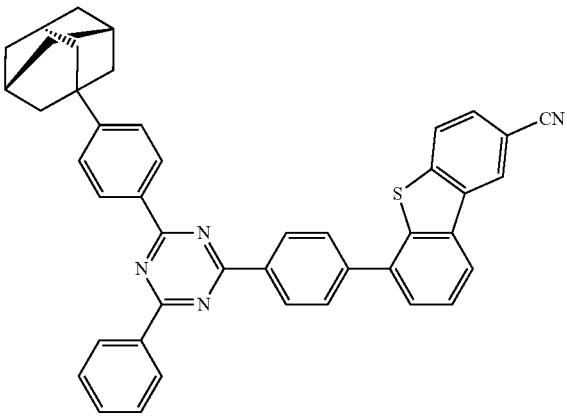
244
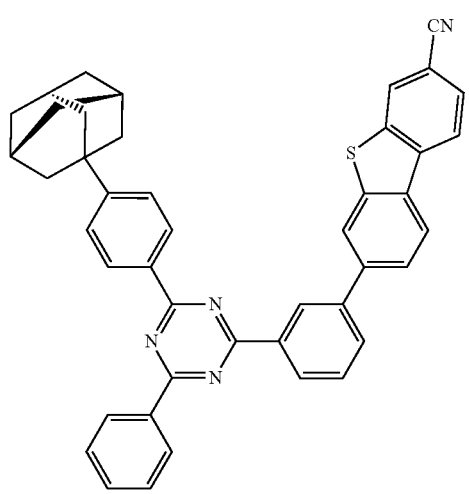
247
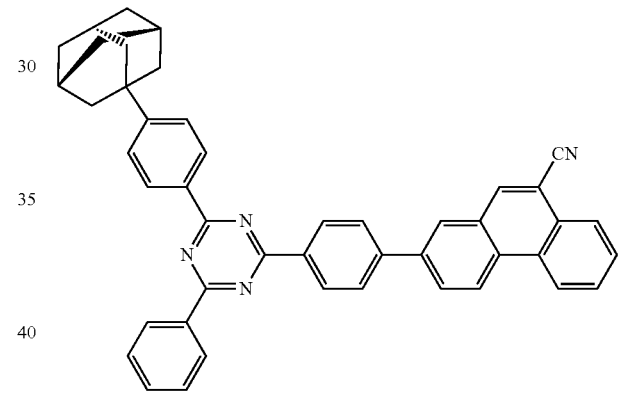
245
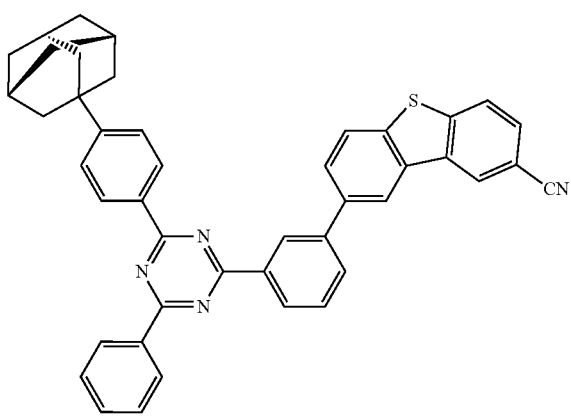
248
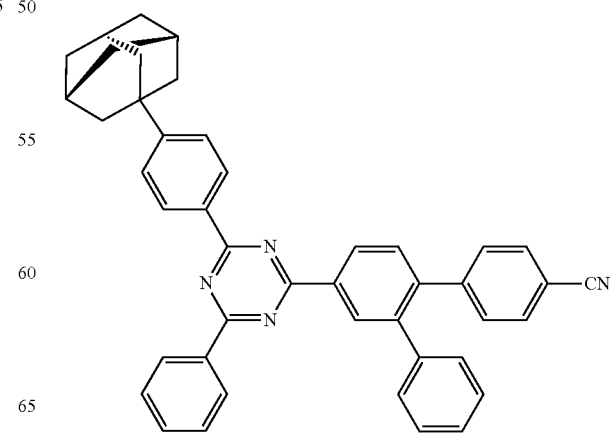

393
-continued
249
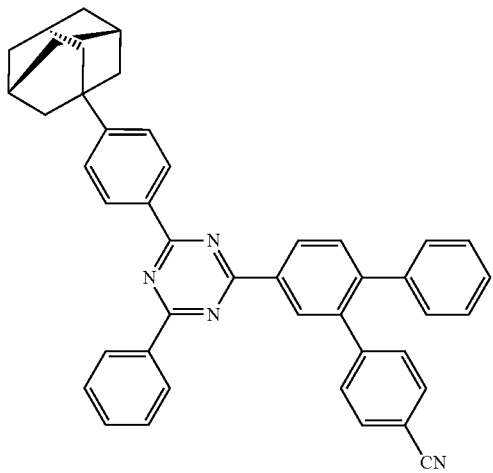
250
251
394
-continued
252
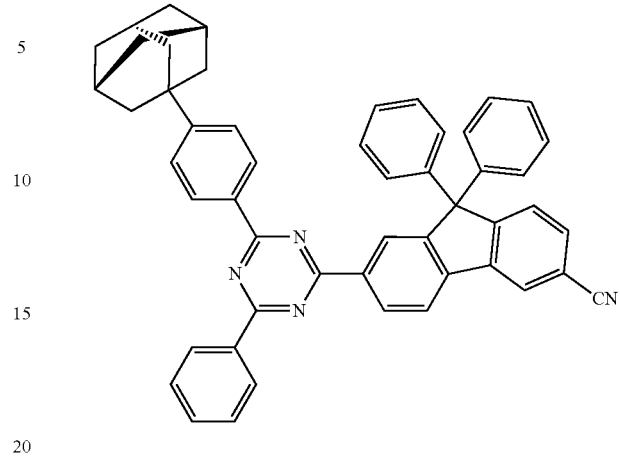
253
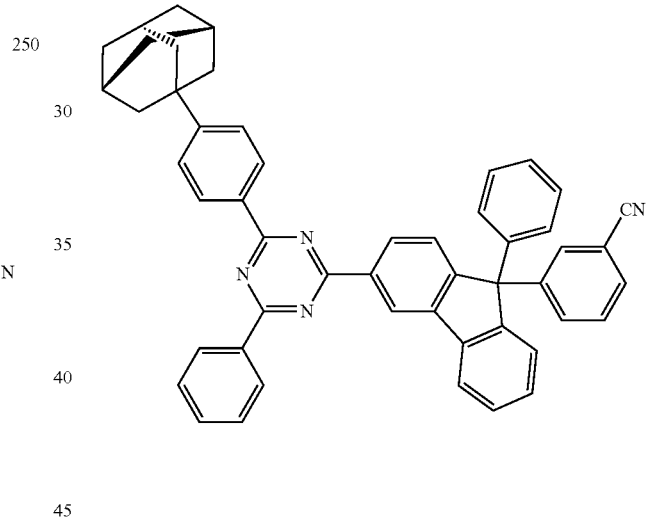
254
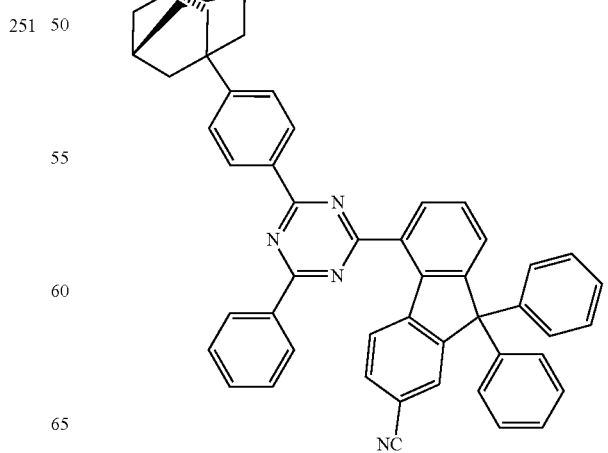

-continued

257

258

259

-continued

260

261

262

397
-continued
263
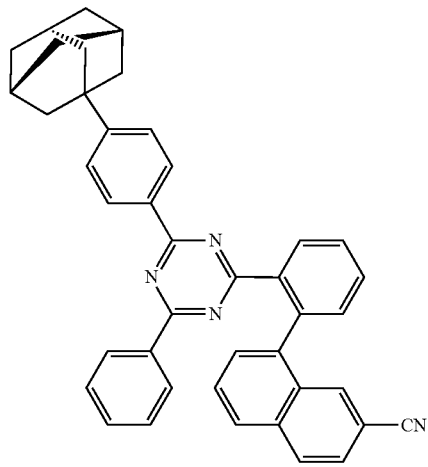
264
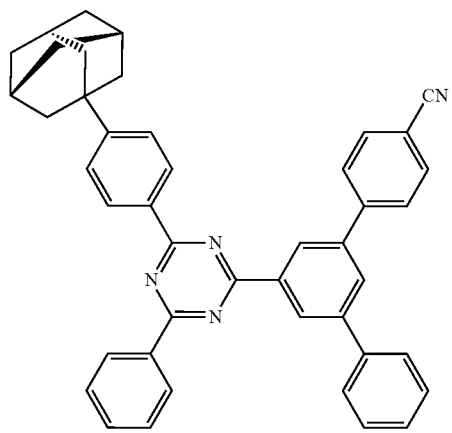
265
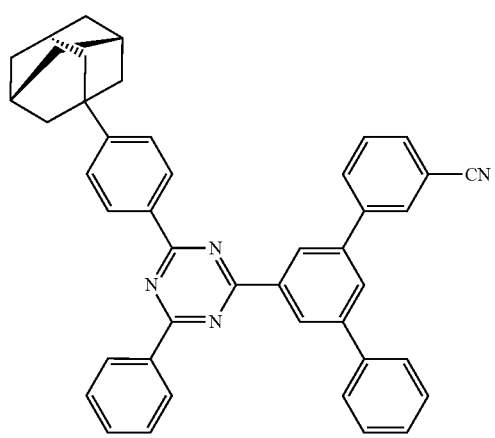
398
-continued
266
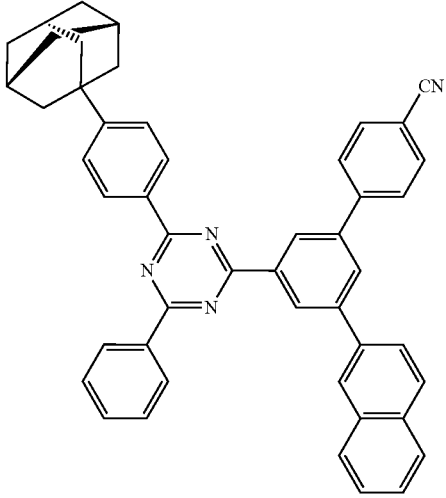
267
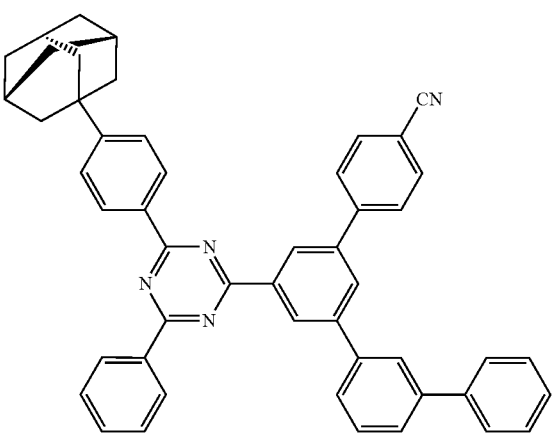
268
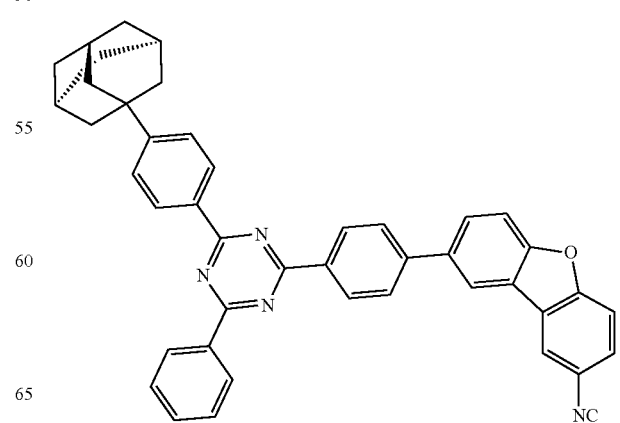

| 399 -continued | 400 -continued |
|---|---|
| 269 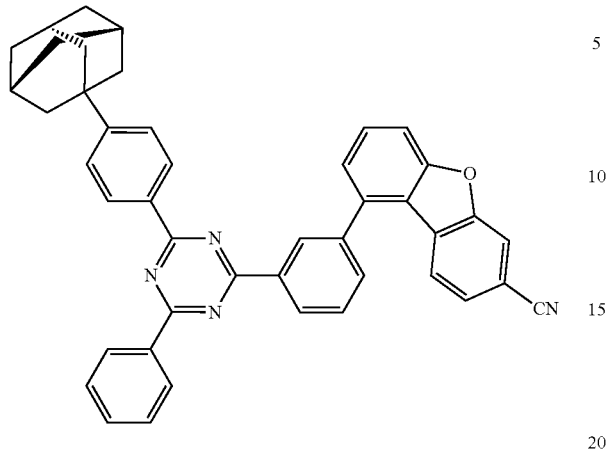 | 272 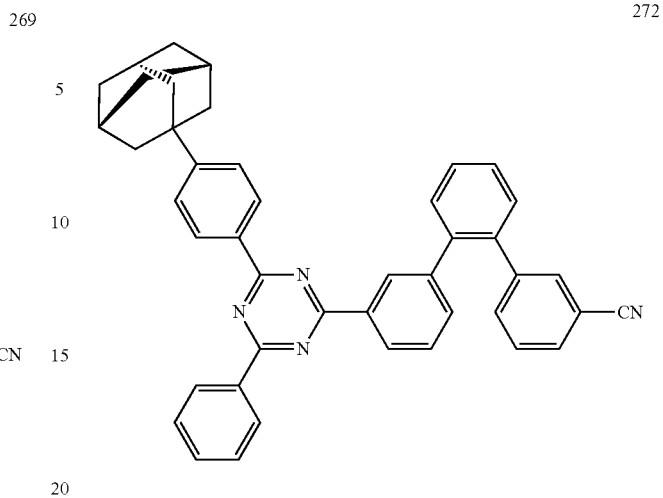 |
| 270 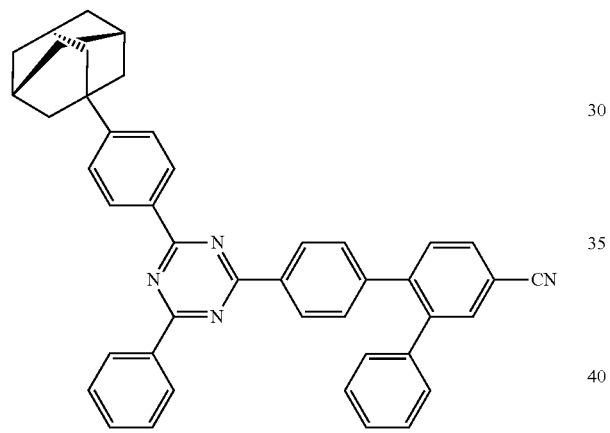 | 273 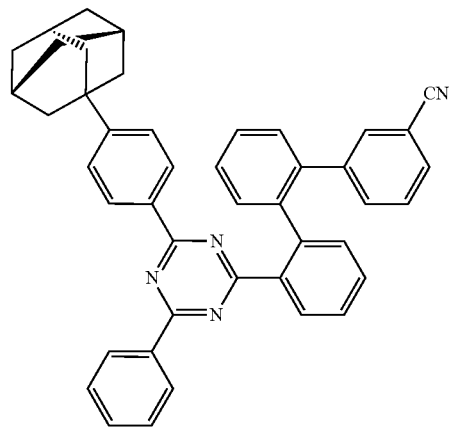 |
| 271 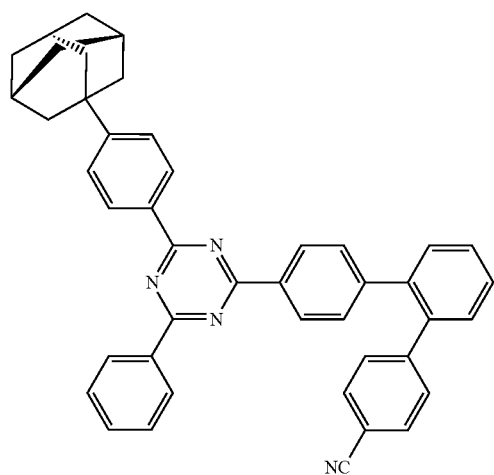 | 274 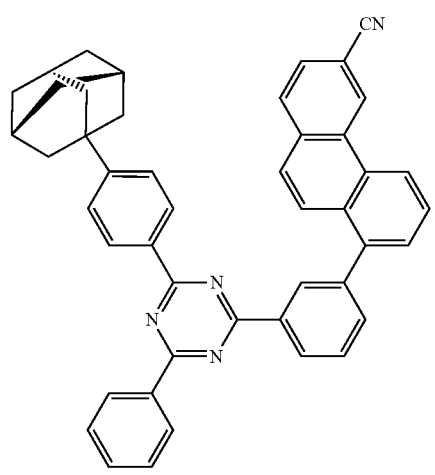 |

401
-continued
275
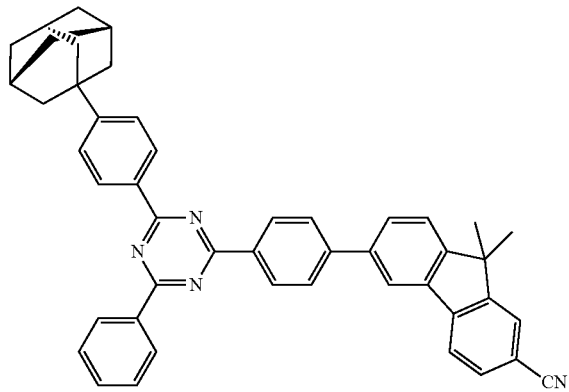
276
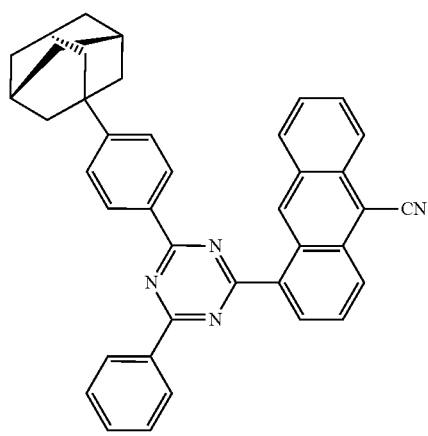
279
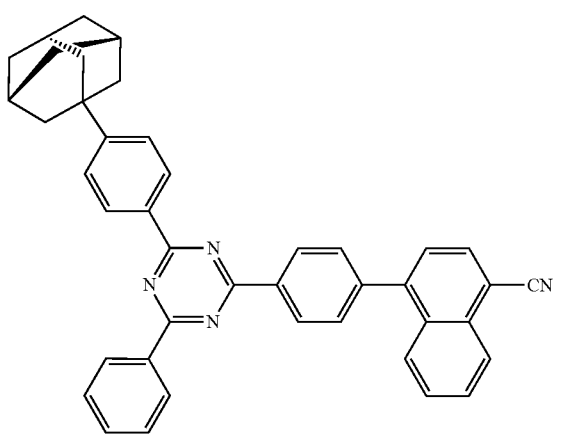
402
-continued
280
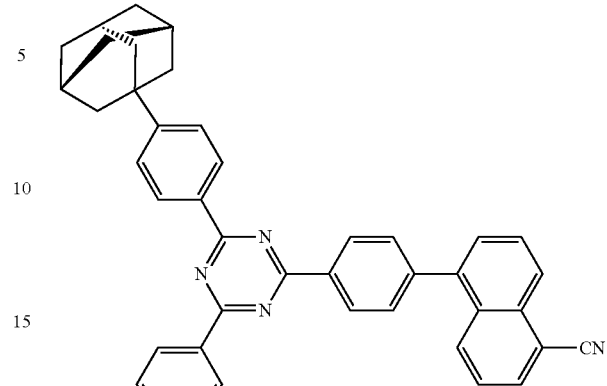
281
282
283
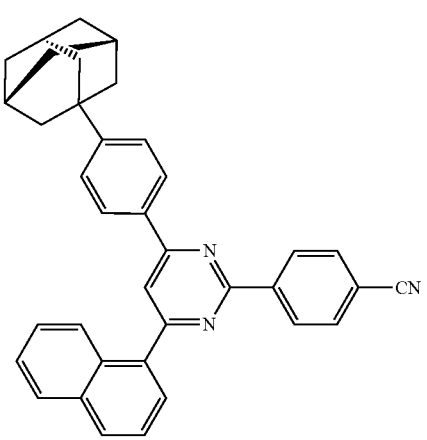

403
-continued
284
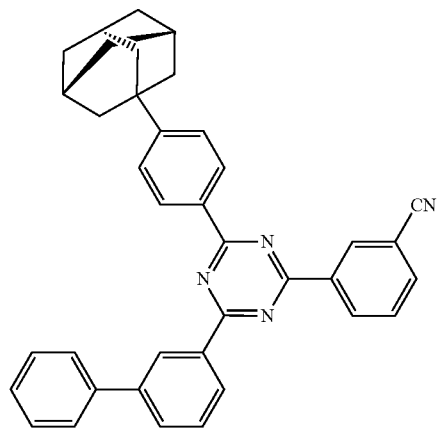
285
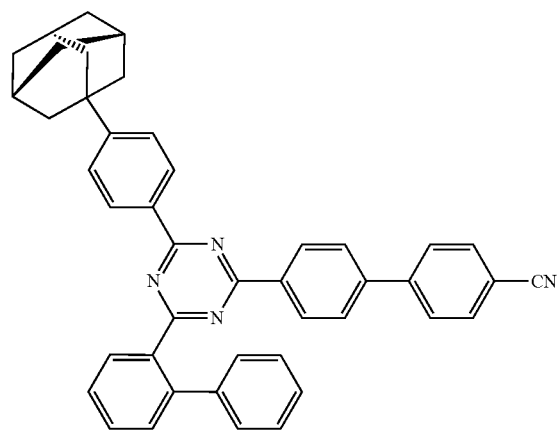
286
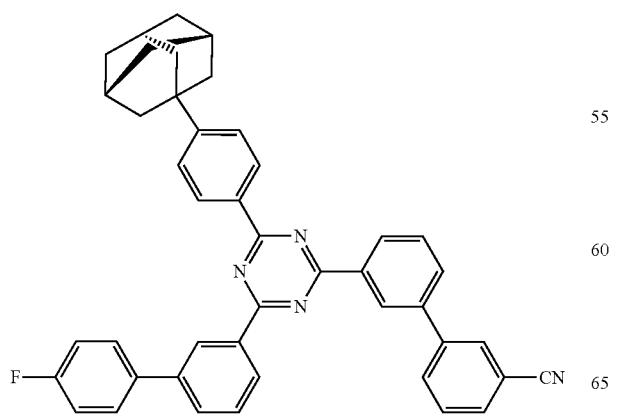
404
-continued
287
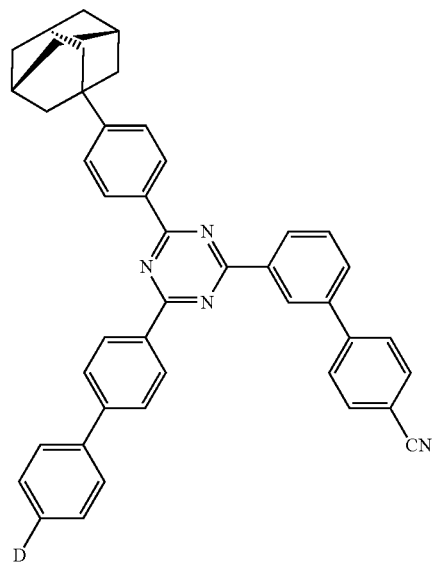
288
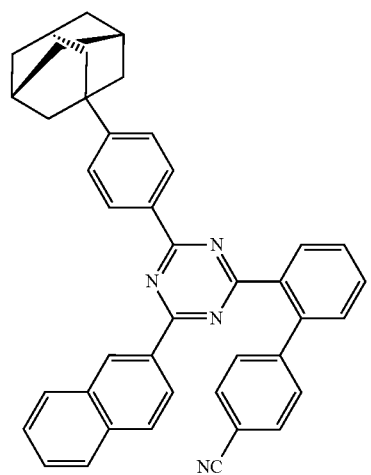

405 406
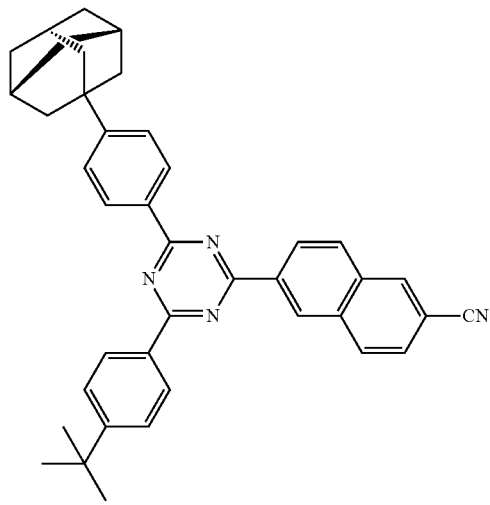
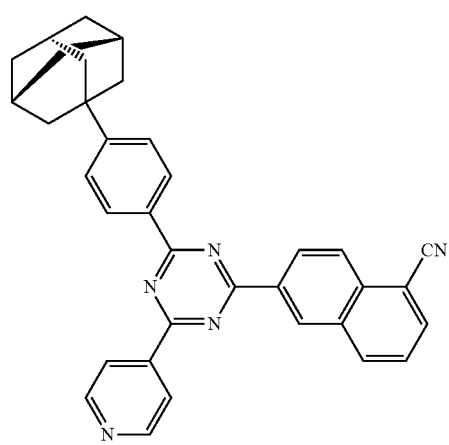
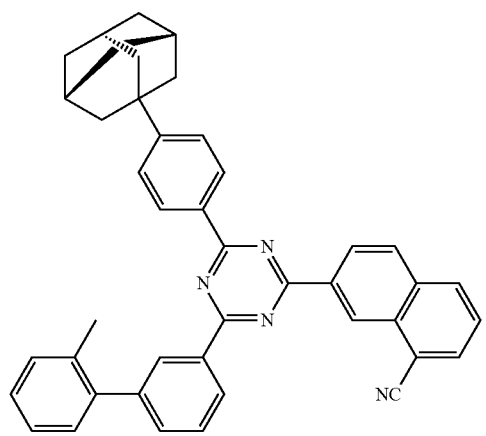
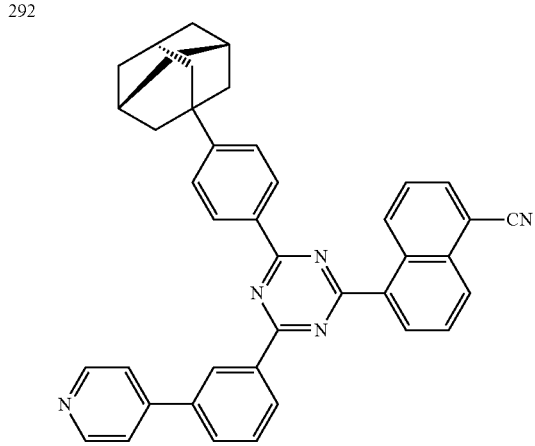
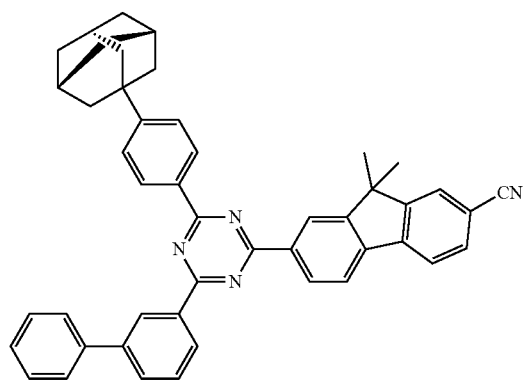
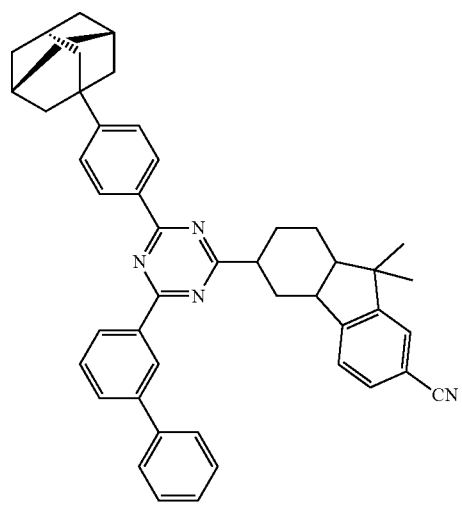

-continued
298
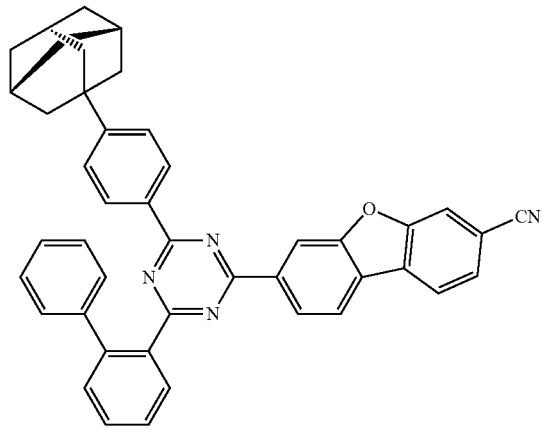
299
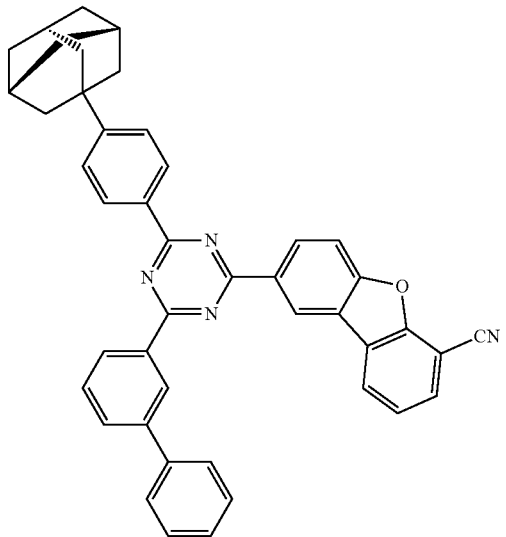
300
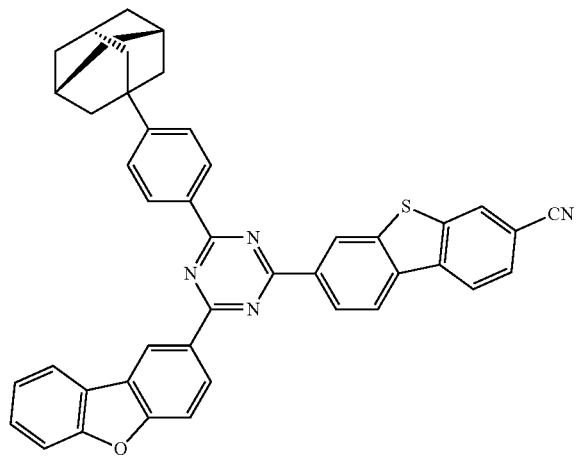
301
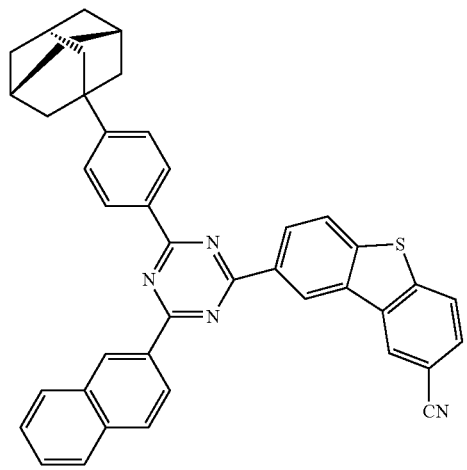
302
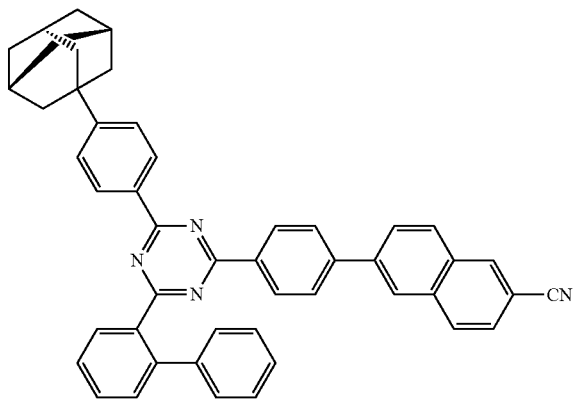

-continued
409
303
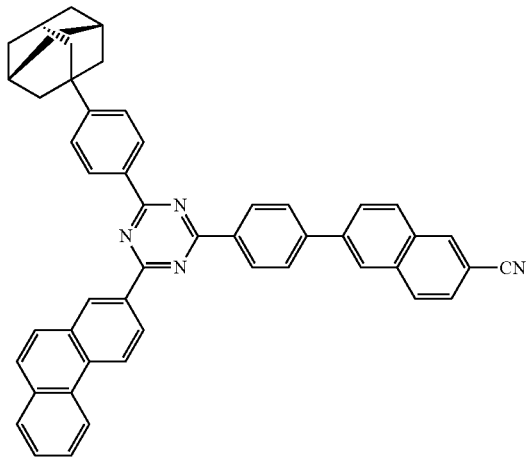
410
304
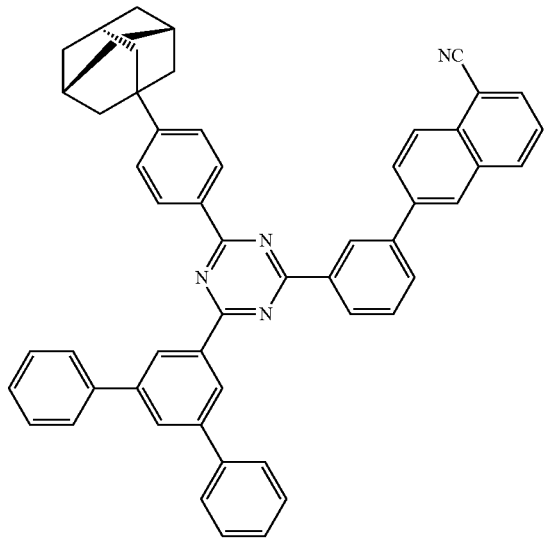
305
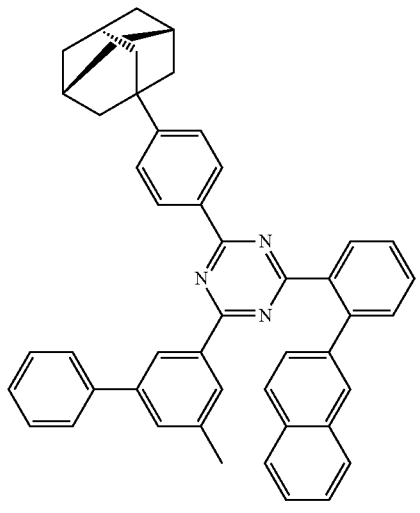
306
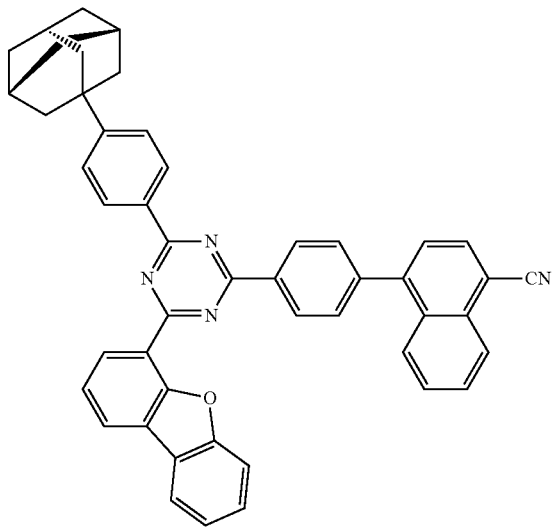

411 412
-continued
307 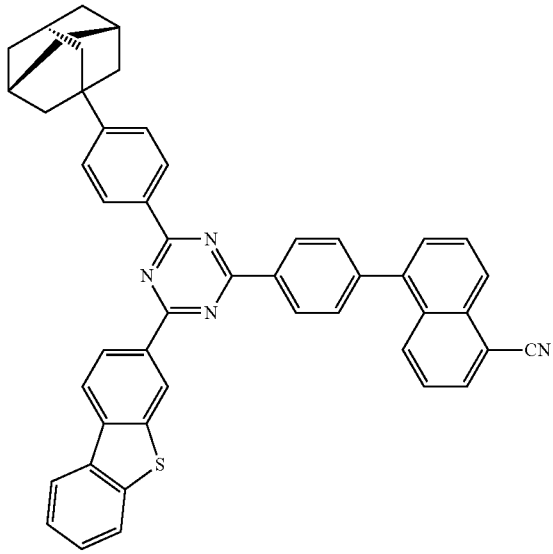 308 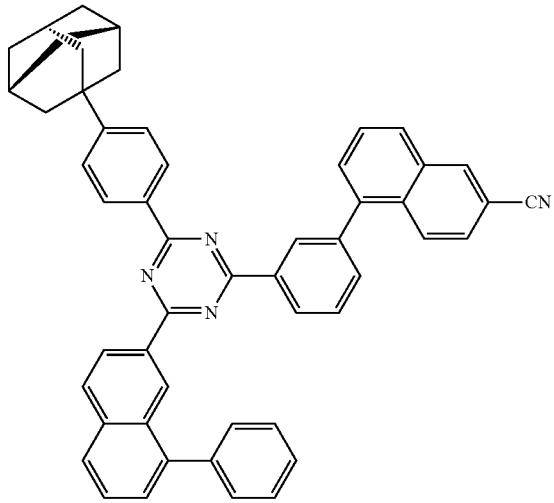
309 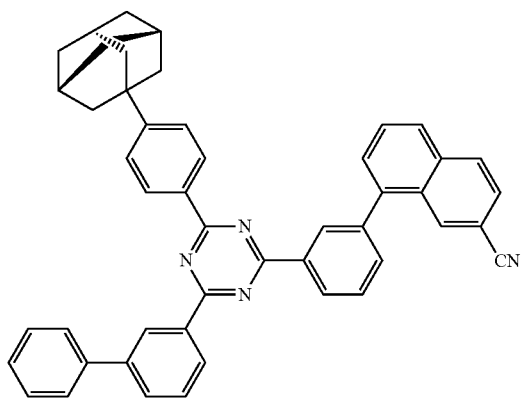 310 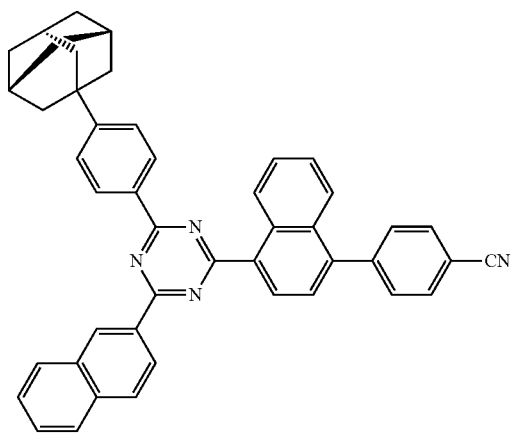
311 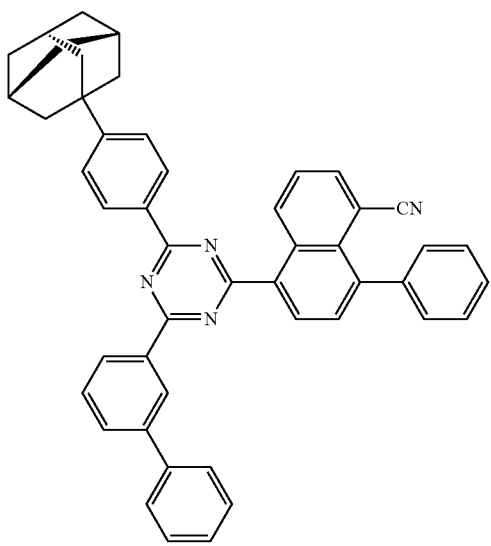 312 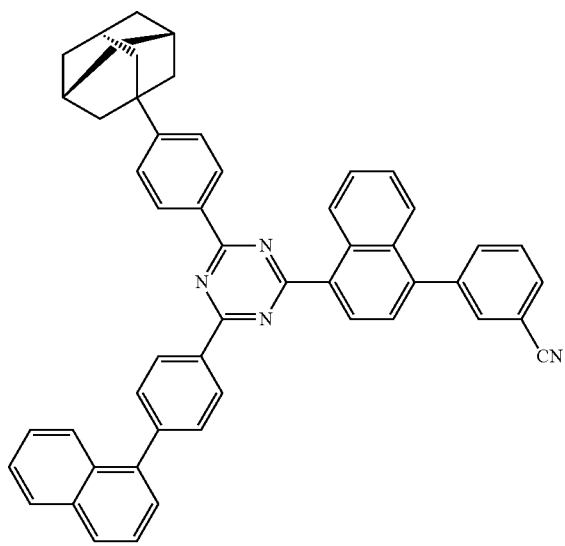

413
414
-continued
313
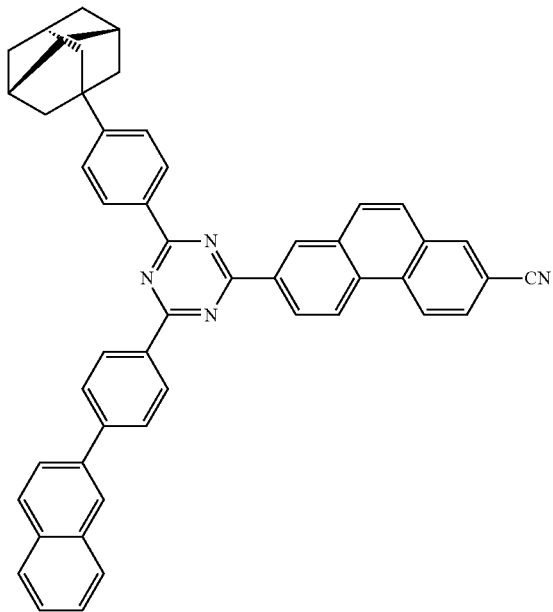
314
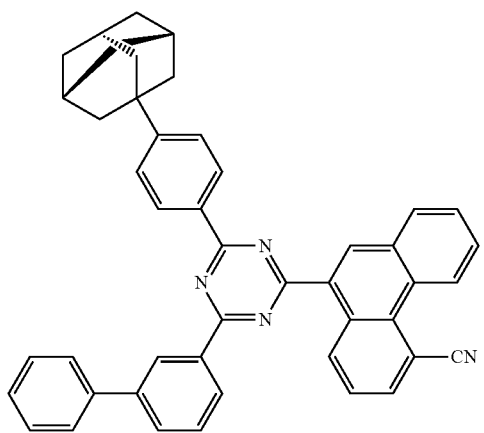
315
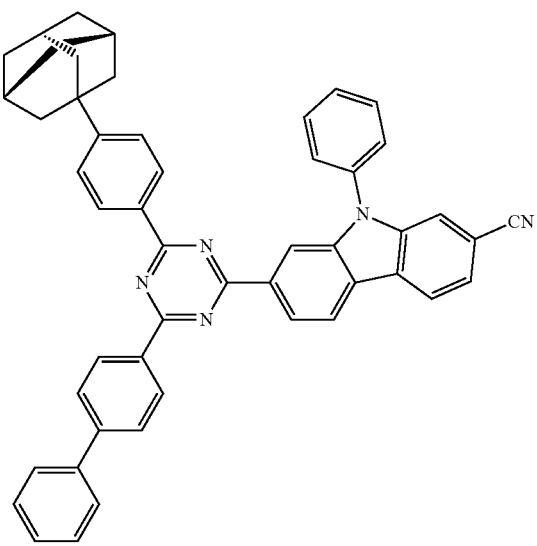

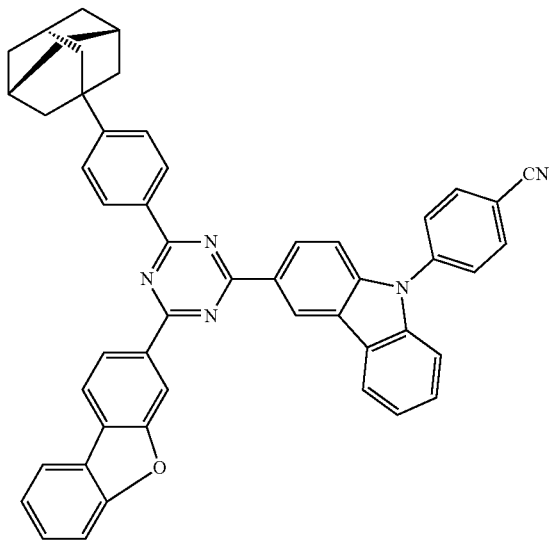
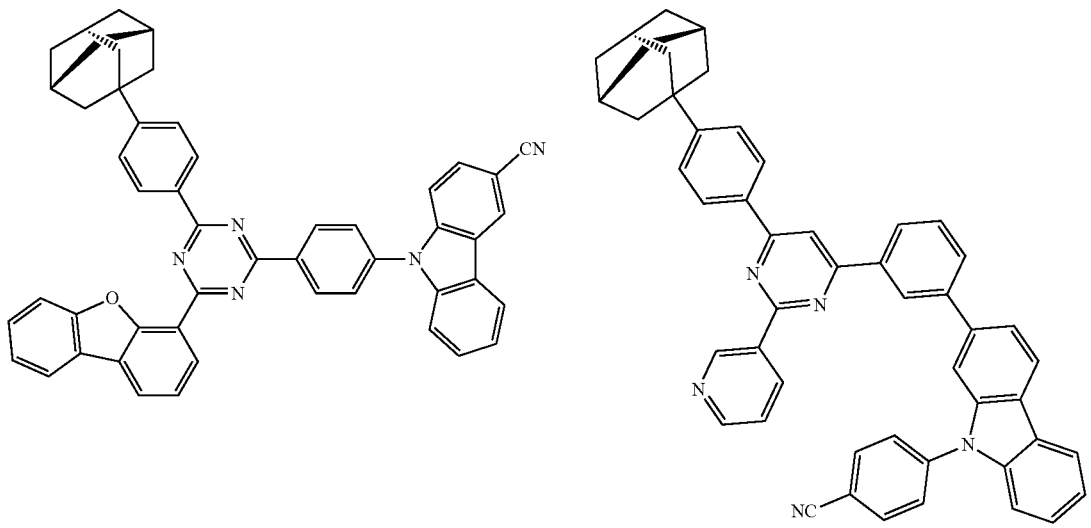
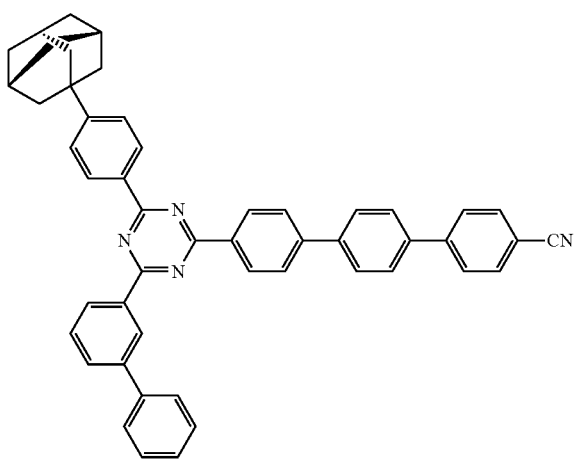

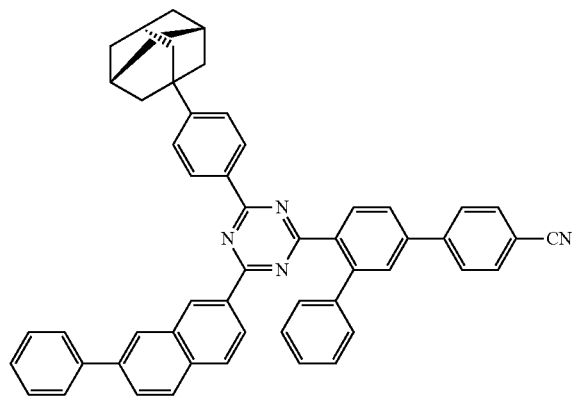
320
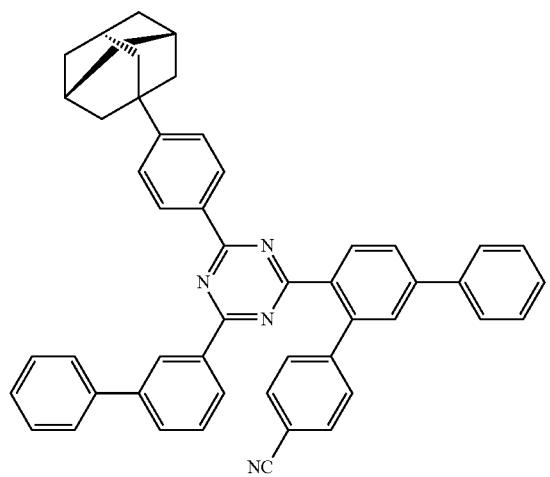
321
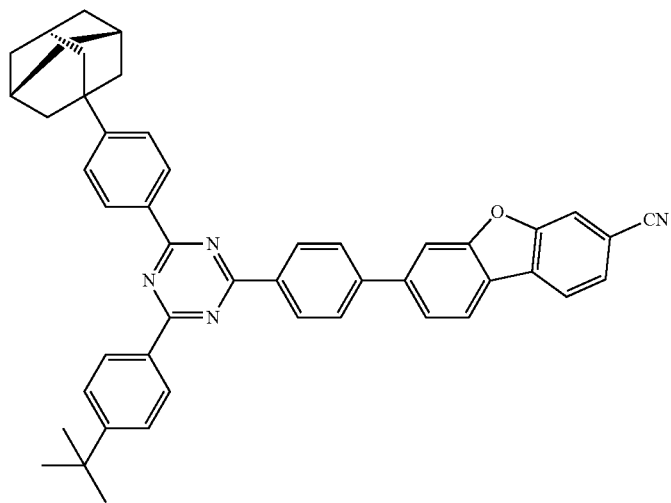
323

324
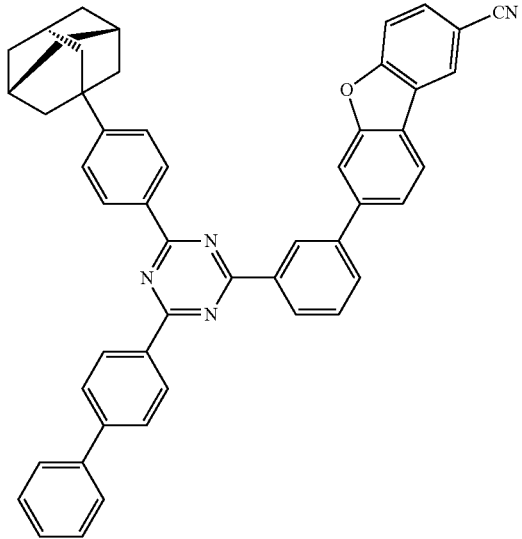
325
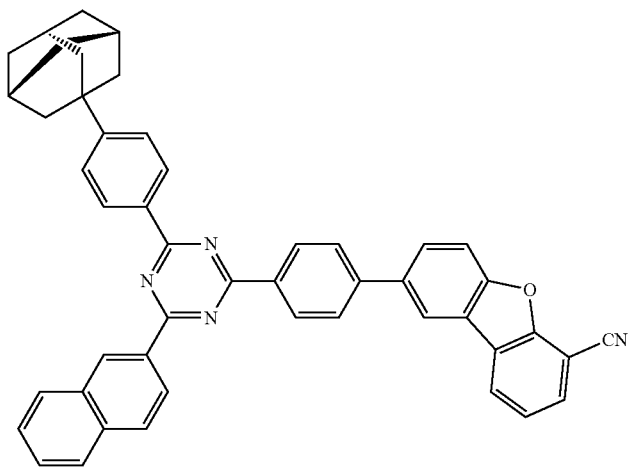
326
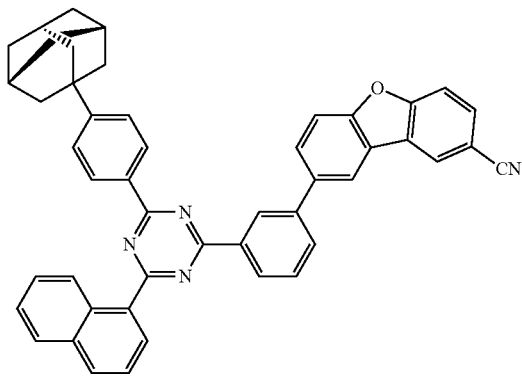
327
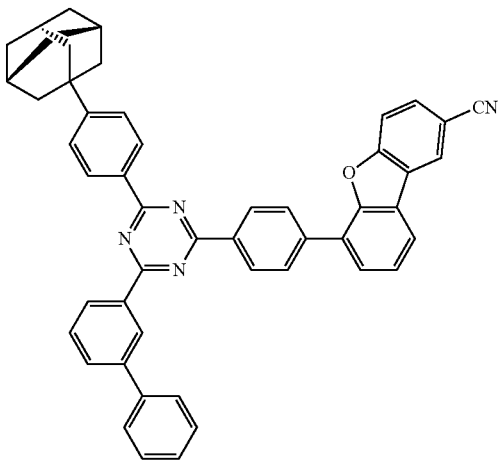

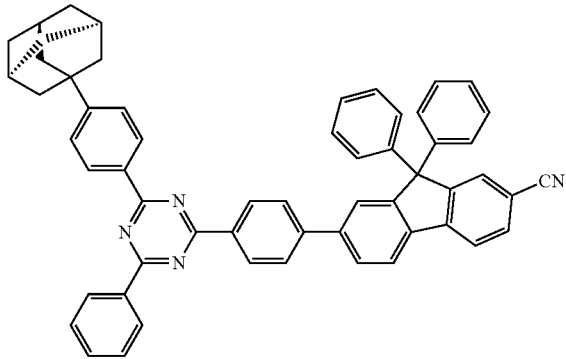
328
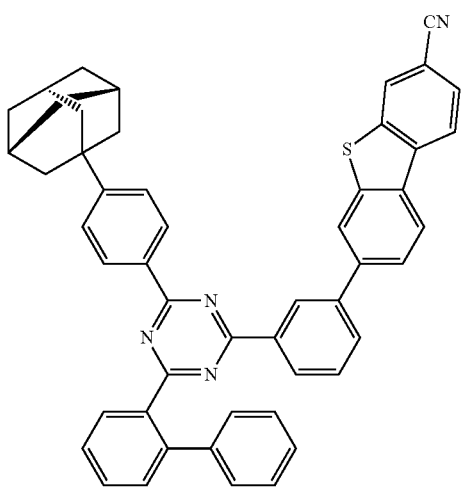
329
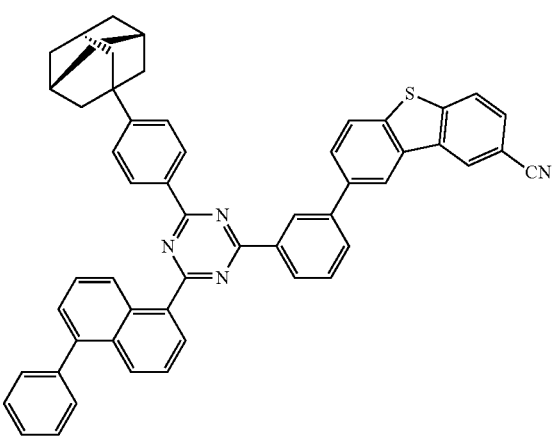
330
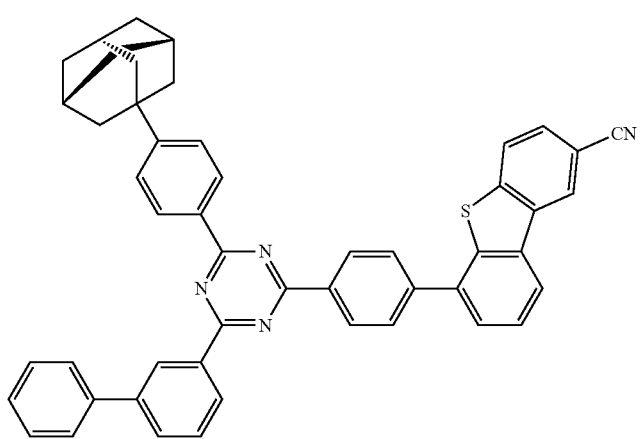
331

332
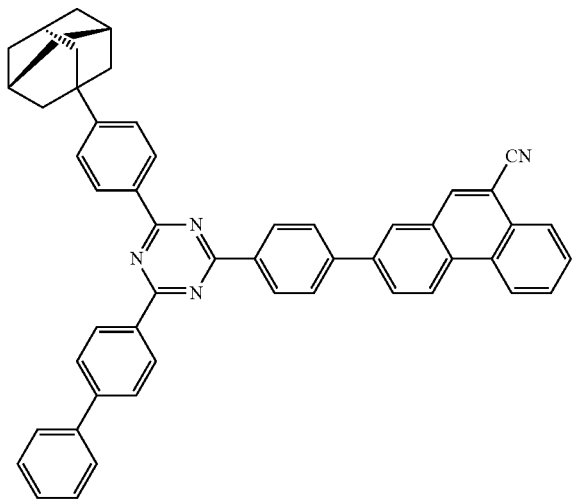
333
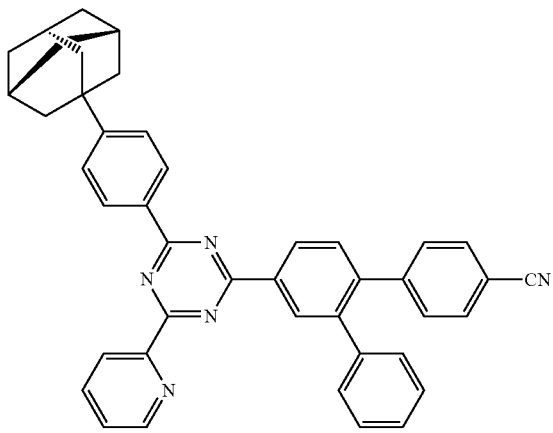
335
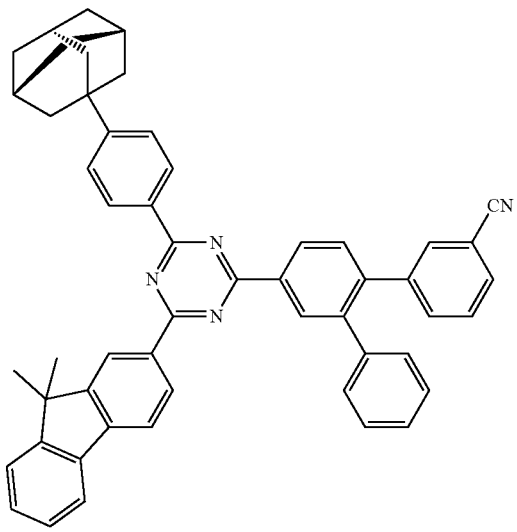
336
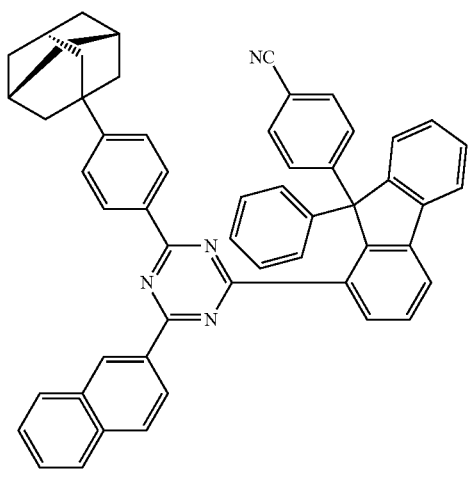
337
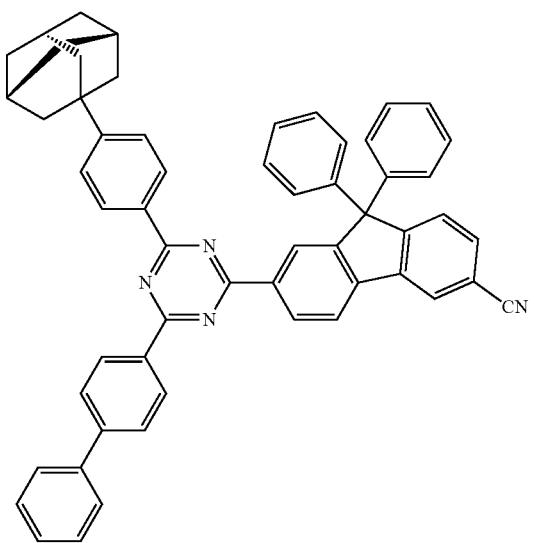

338
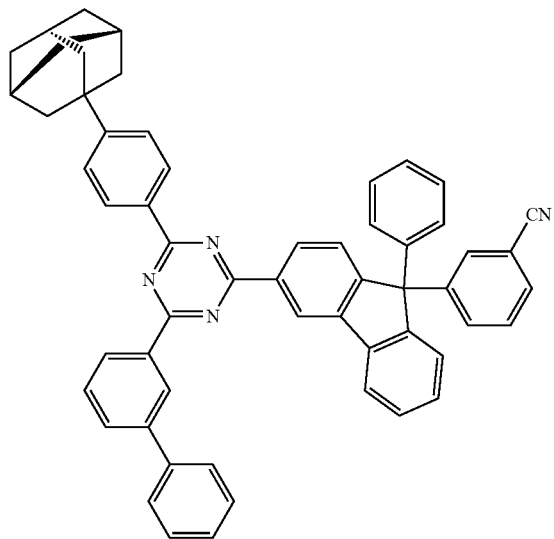
339
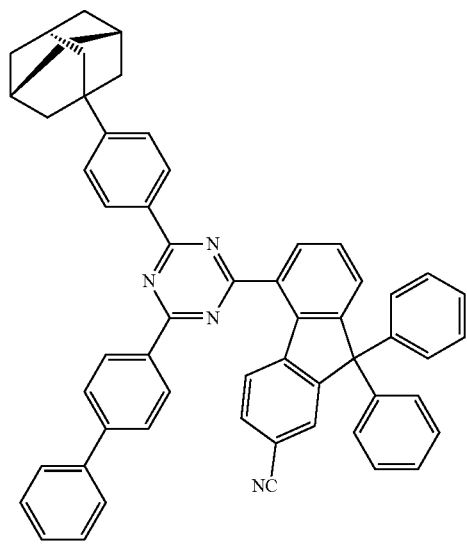
342
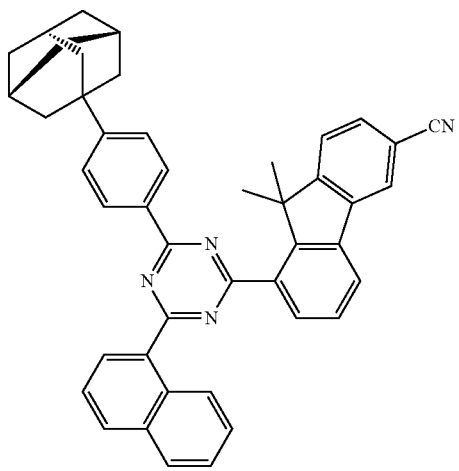
343
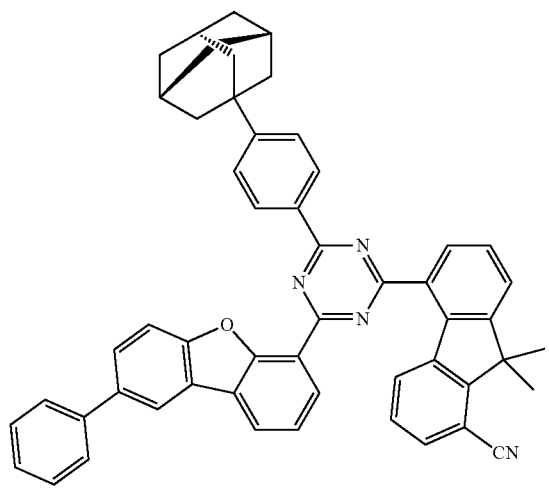
344
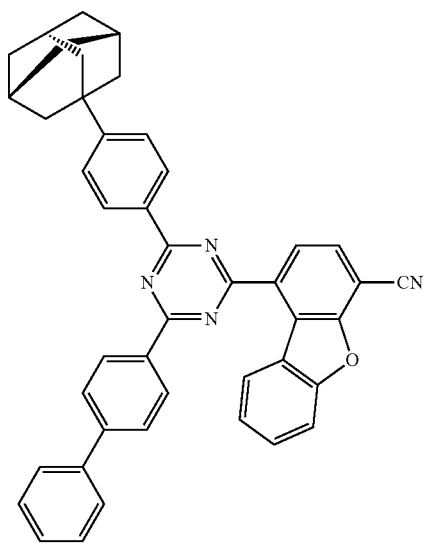

-continued
345
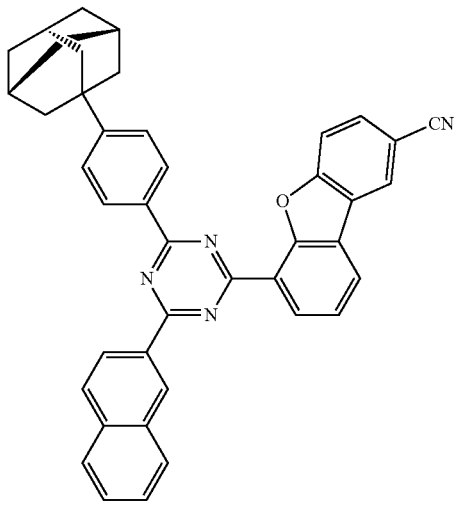
346
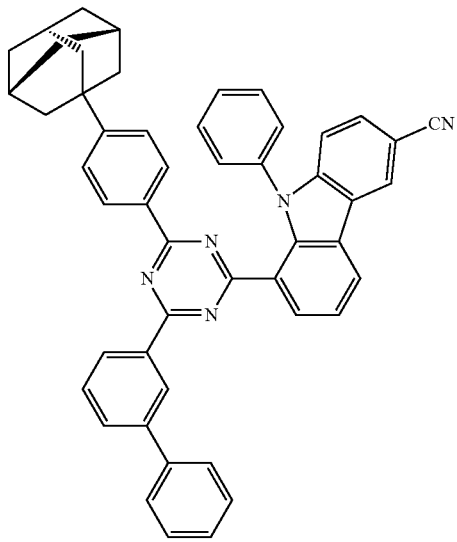
347
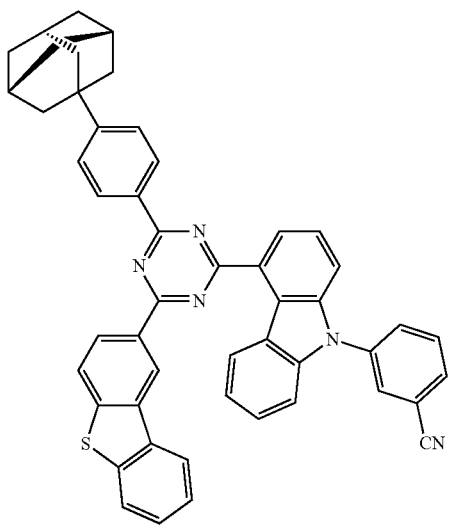
348
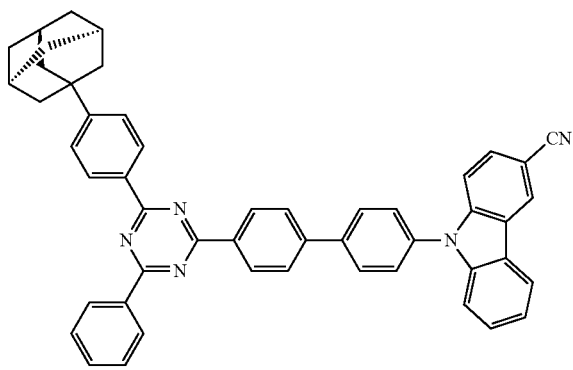
349
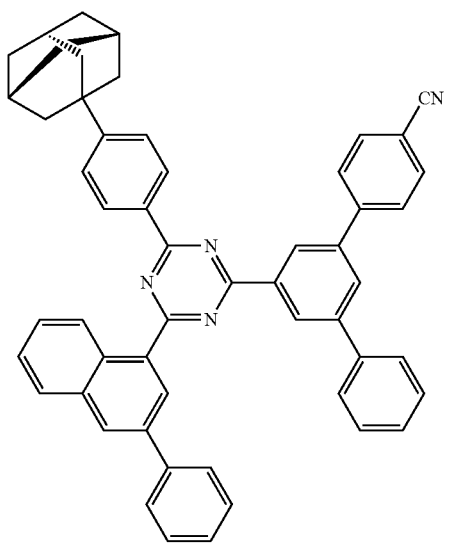
350
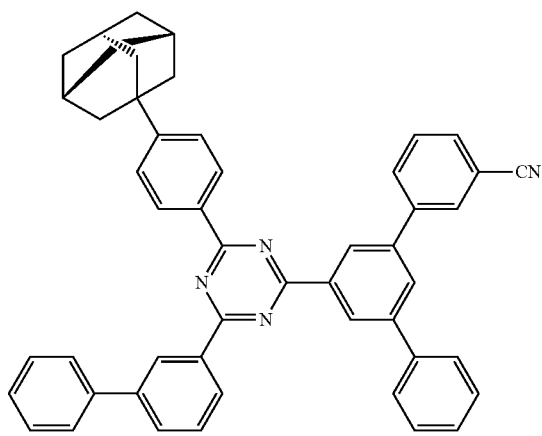

-continued
351
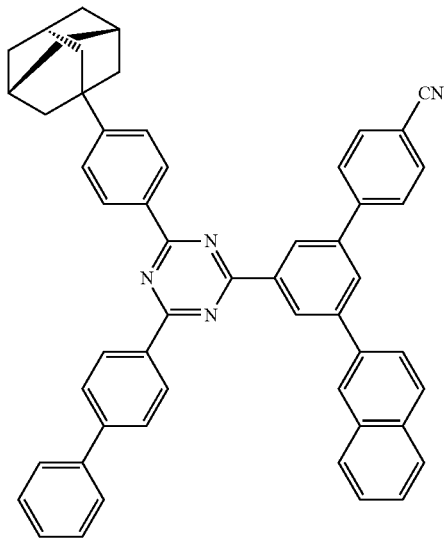
352
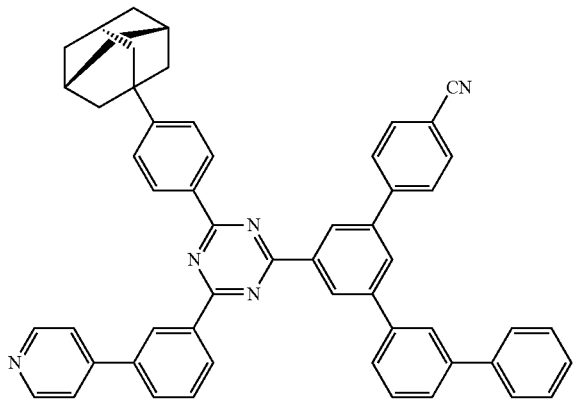
353
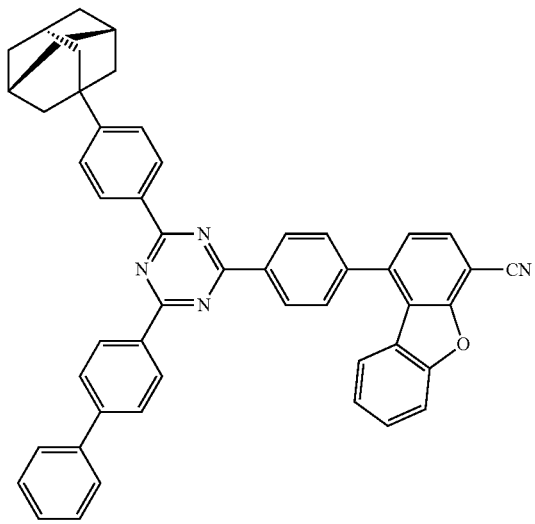
354
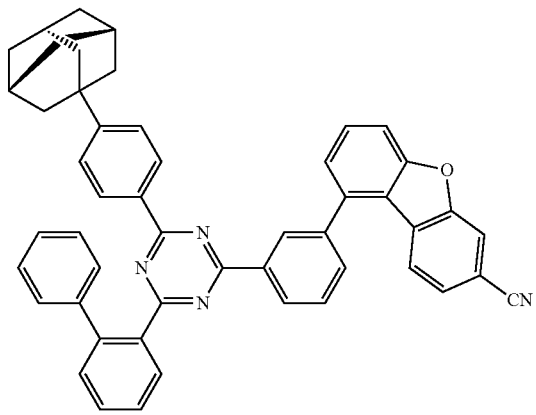
355
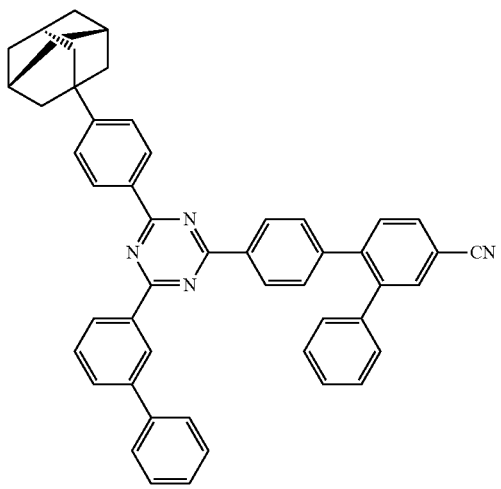
356
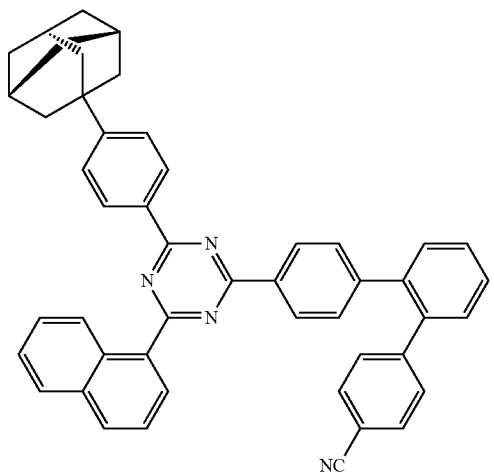

431
432
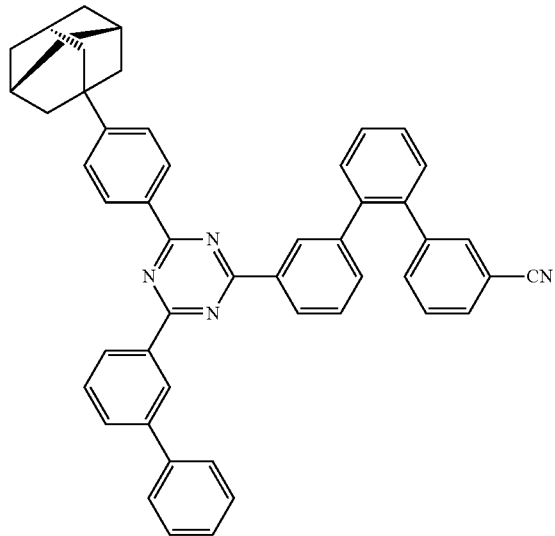
357
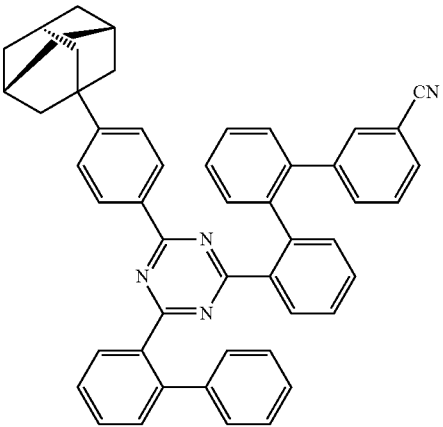
358
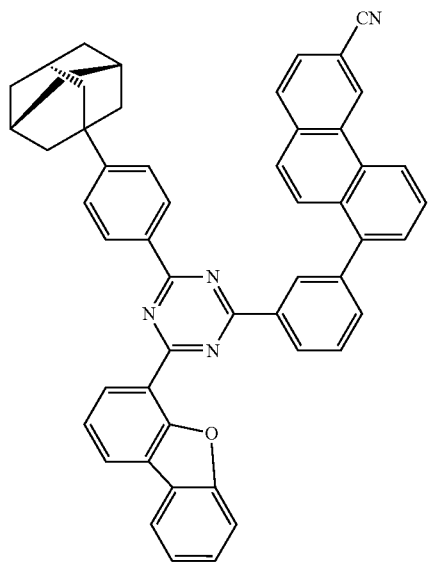
359
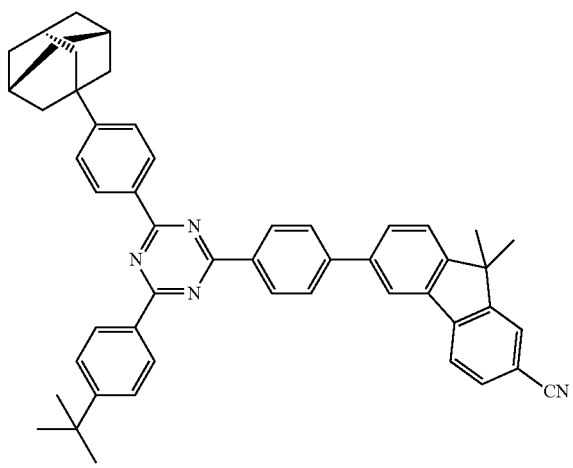
360

361
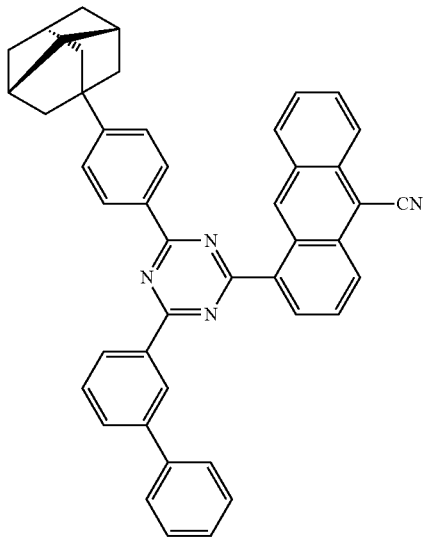
364
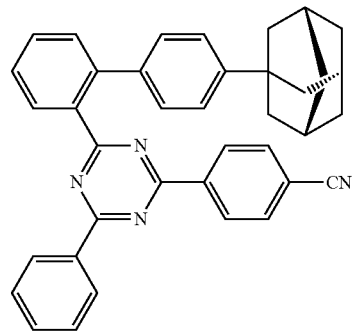
365
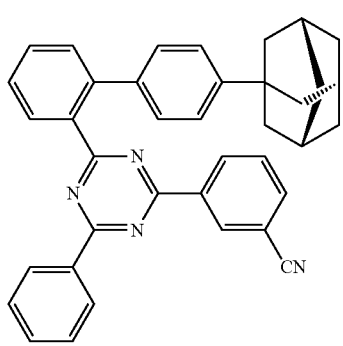
366
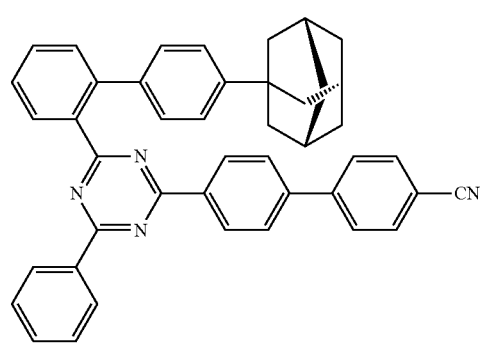
367
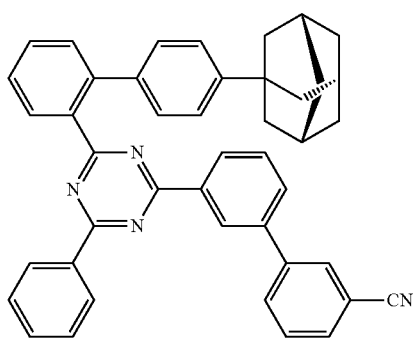
368
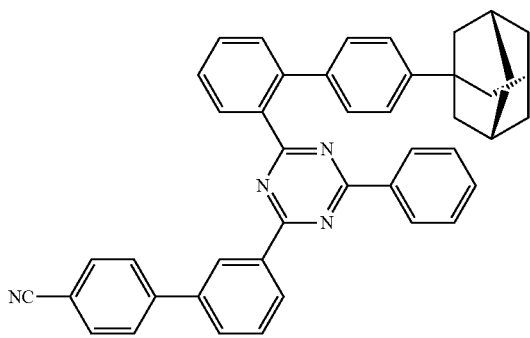
369
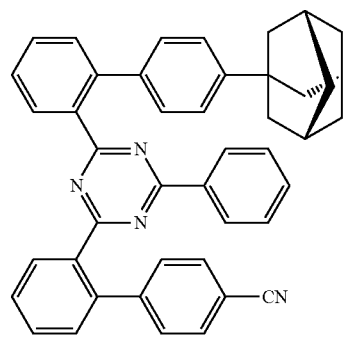

-continued
370
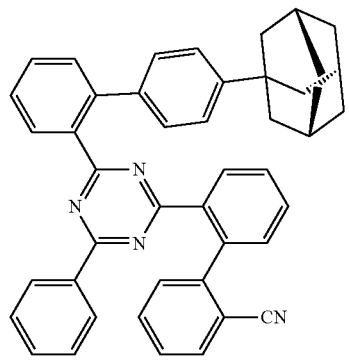
371
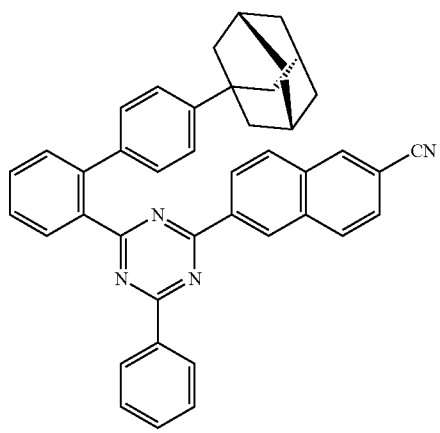
372
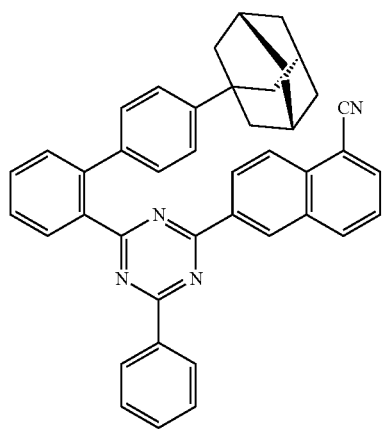
373
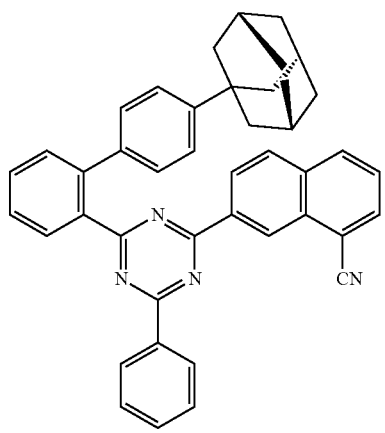
374
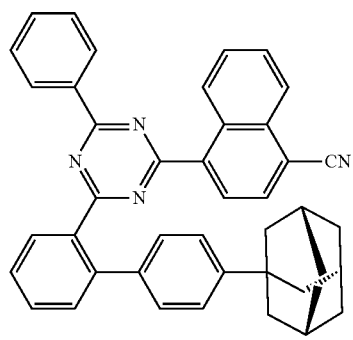
375
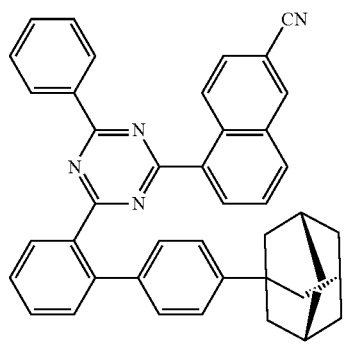
376
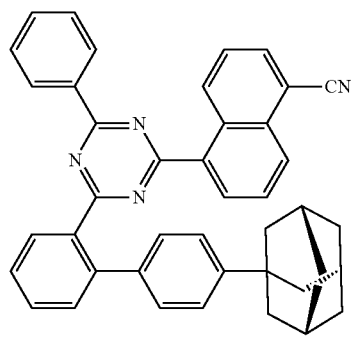
377
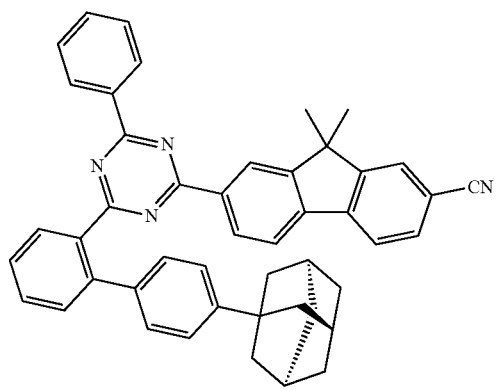

-continued
378
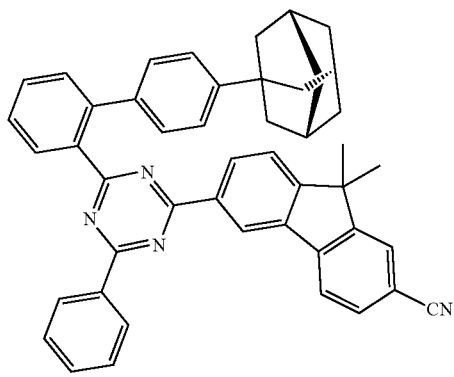
379
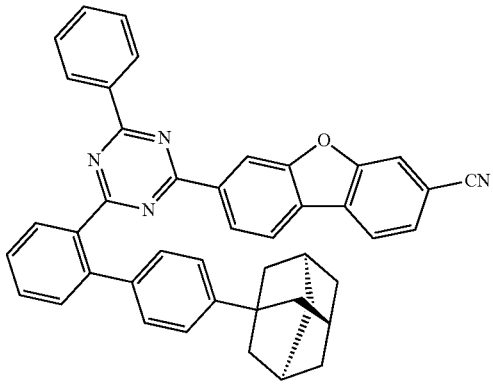
380
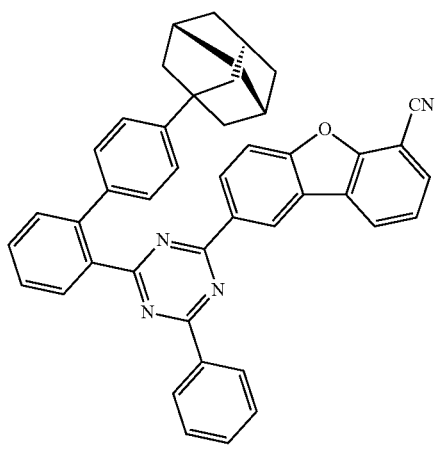
381
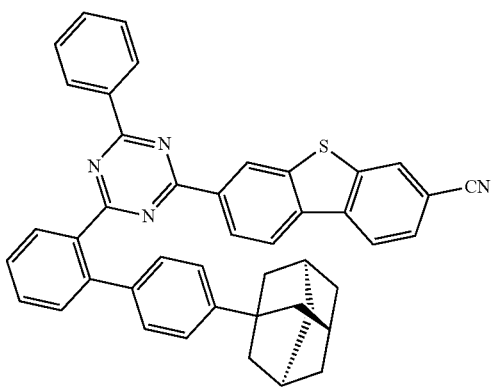
382
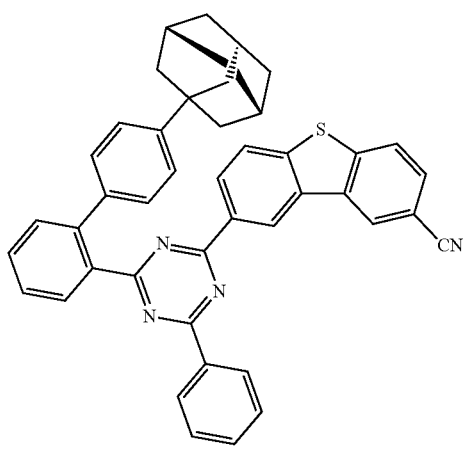
383
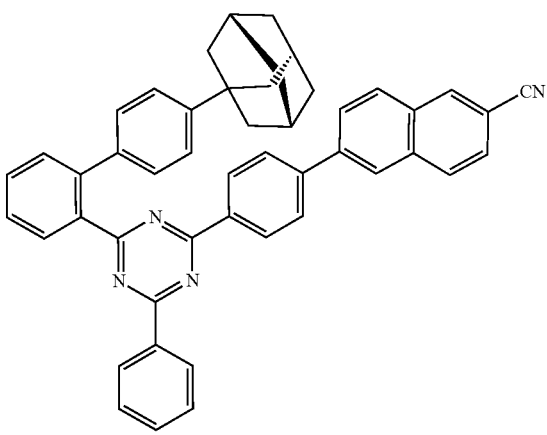

-continued
| 439 | 440 |
|---|---|
| 384 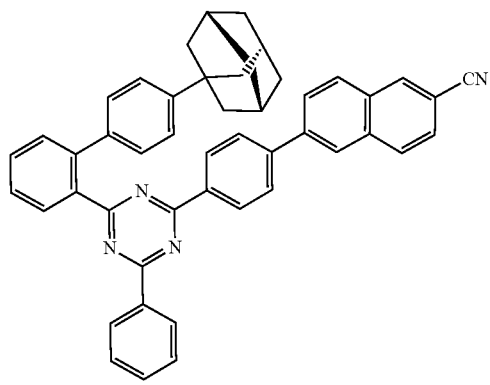 | 385 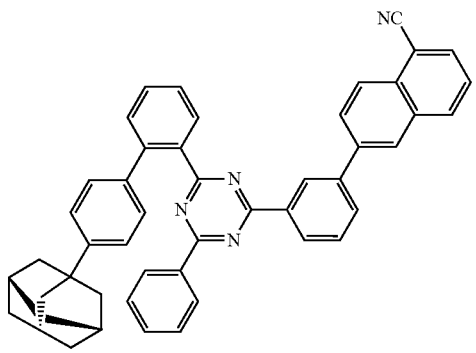 |
| 386 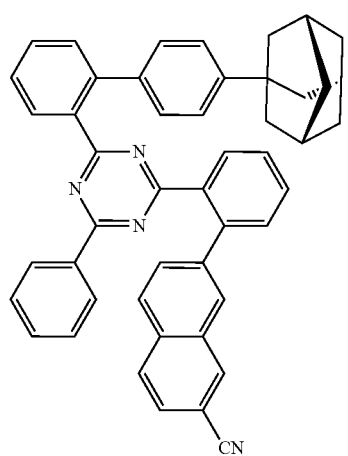 | 387 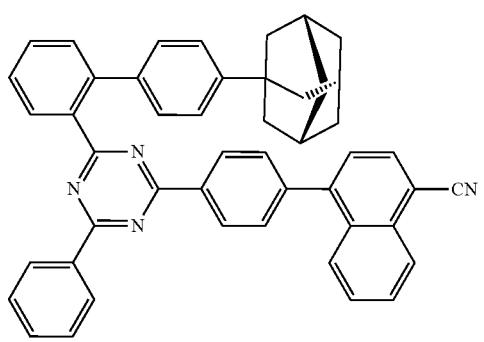 |
| 388 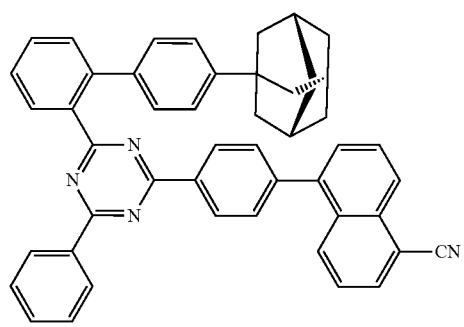 | 389 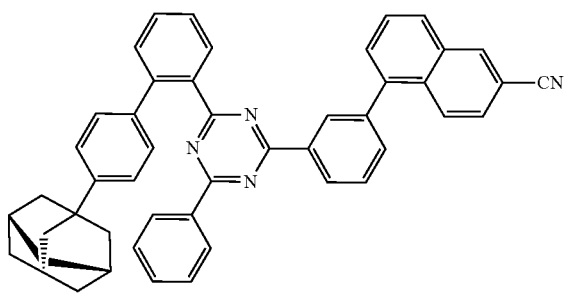 |
| 390 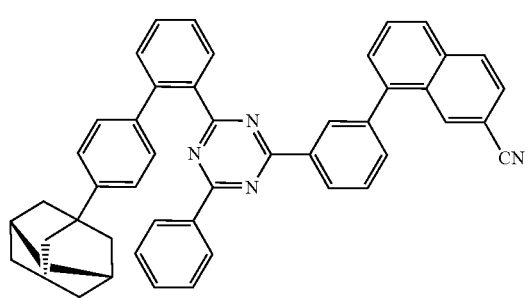 | 391 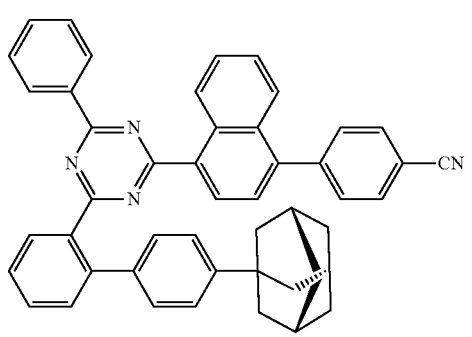 |

-continued
392
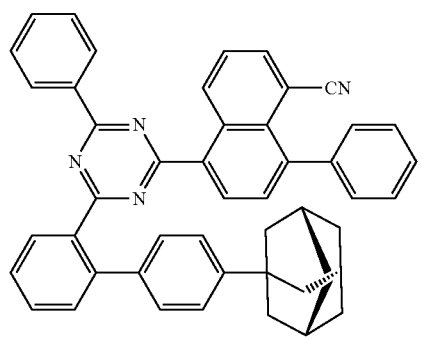
393
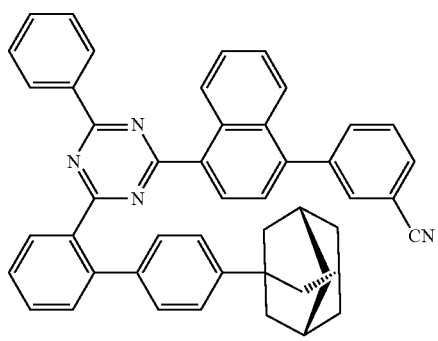
394
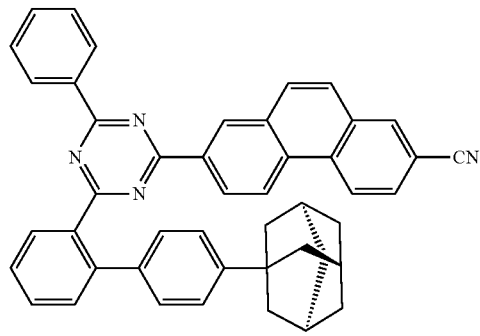
395
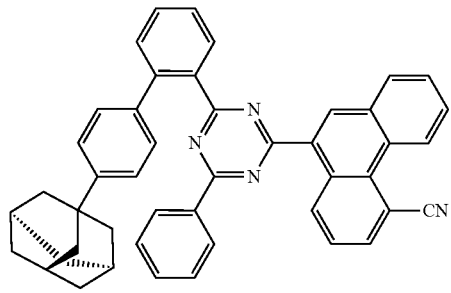
396
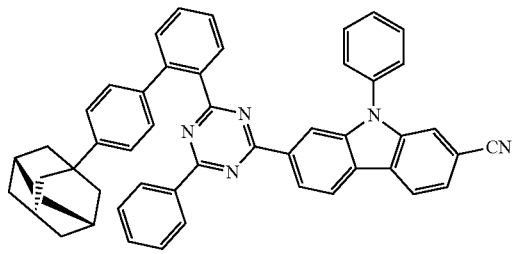
397
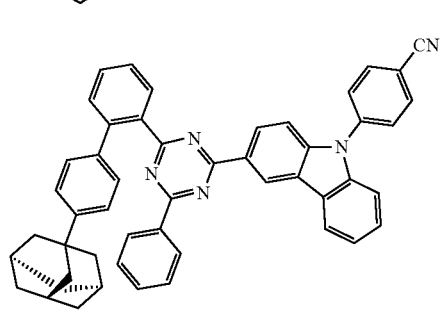
398
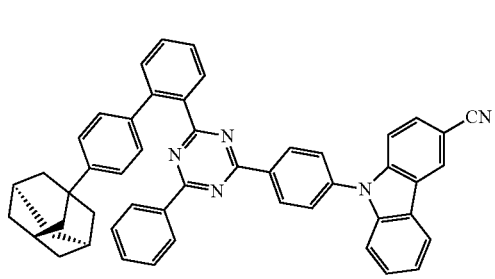
399
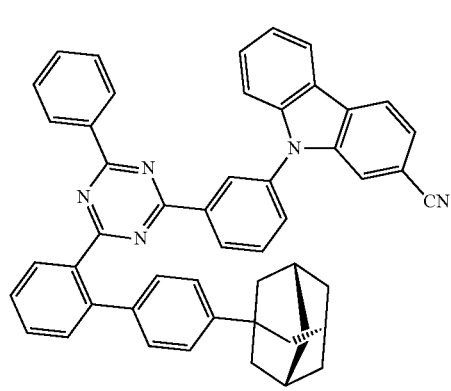
400
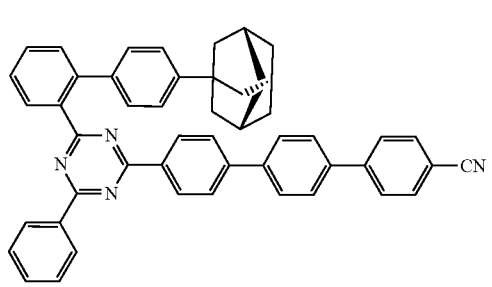

-continued
401 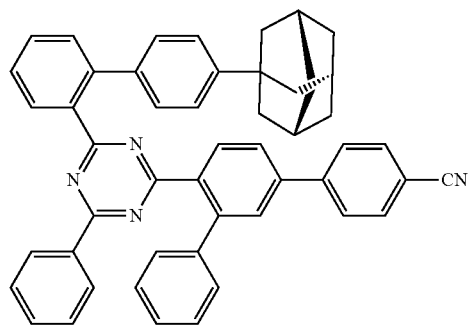
402 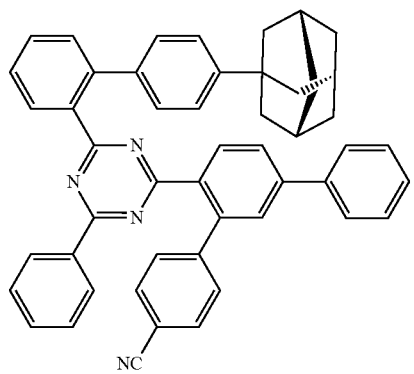
403 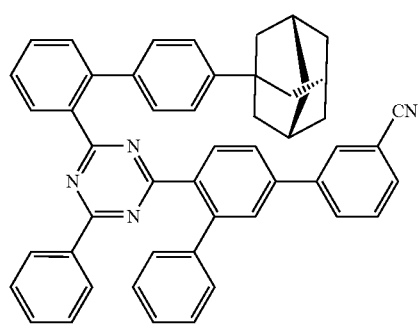
404 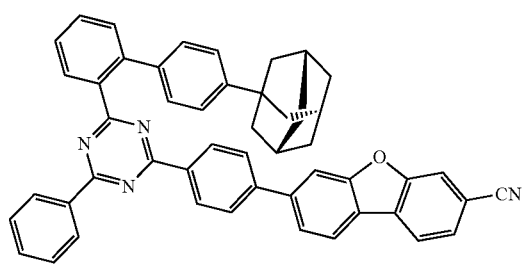
405 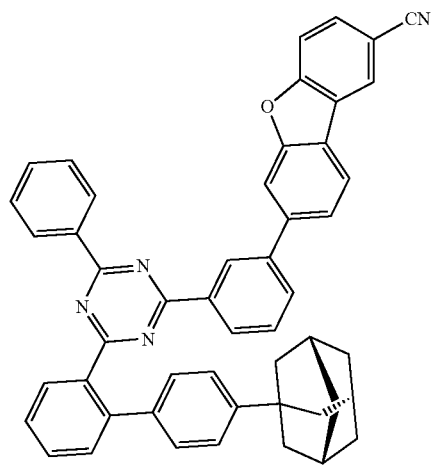
406 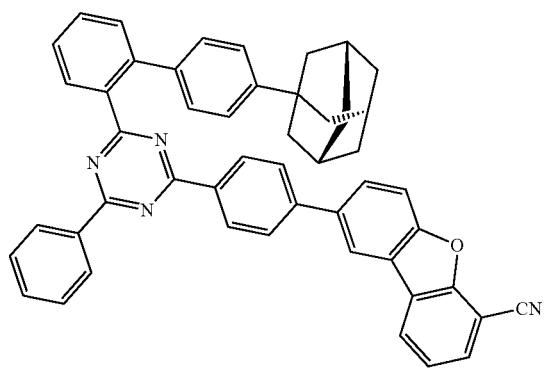
407 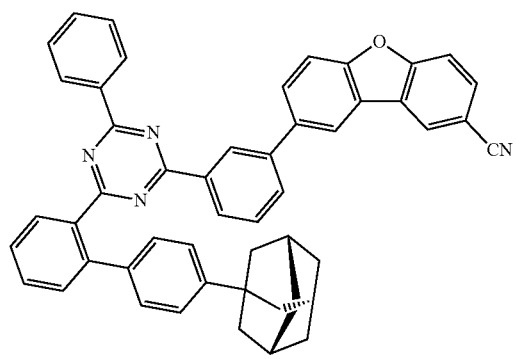
408 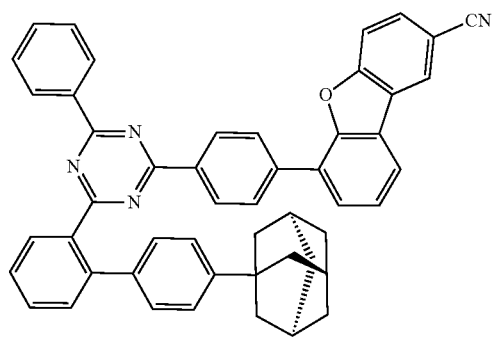

409
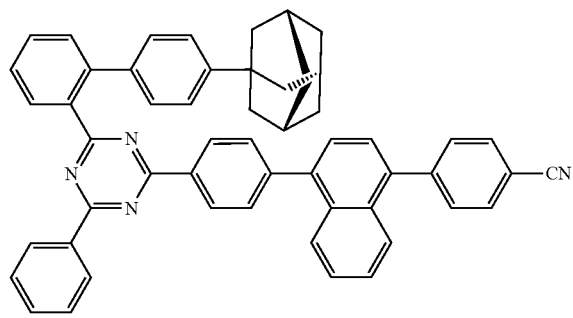
410
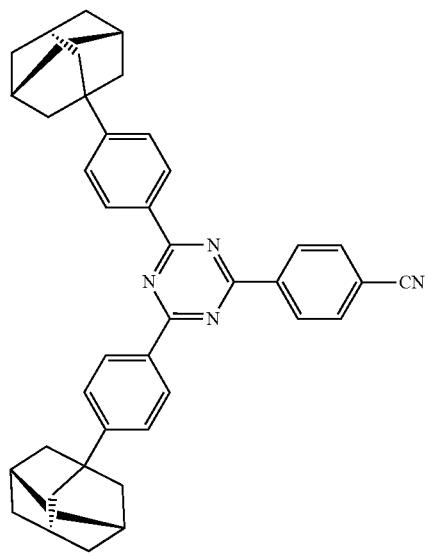
411
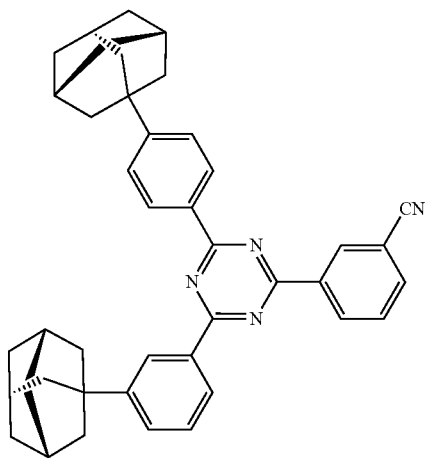
412
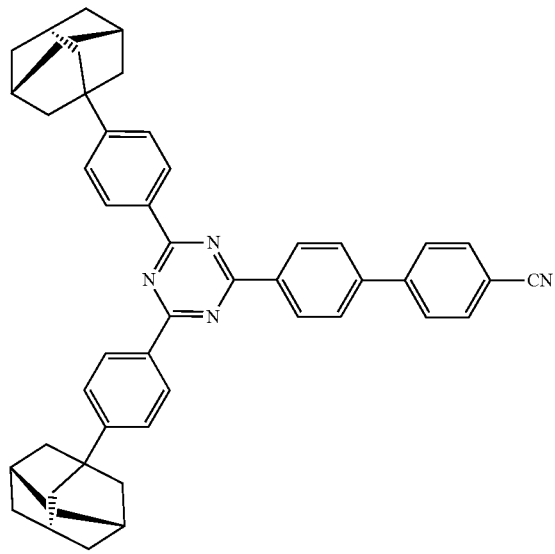

-continued
413
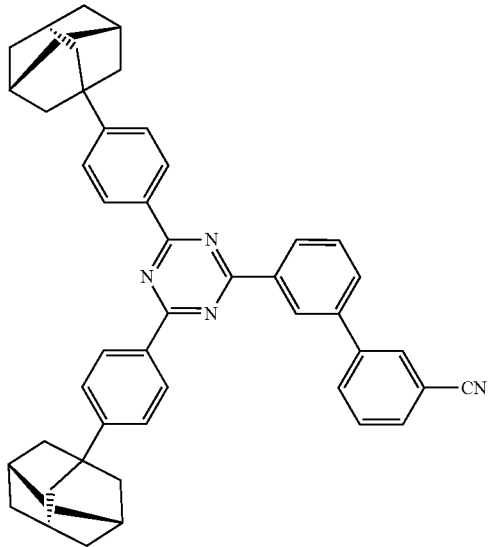
414
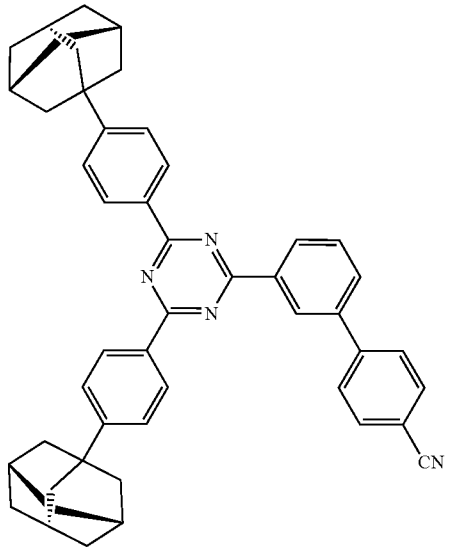
415
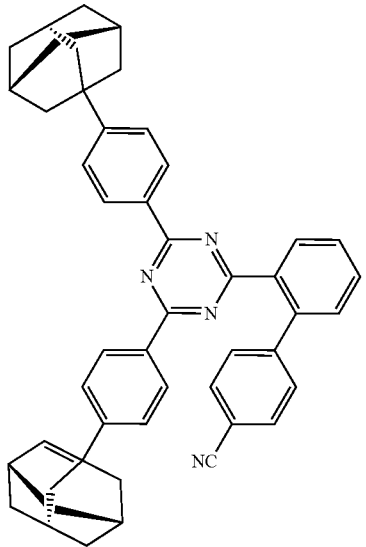
416
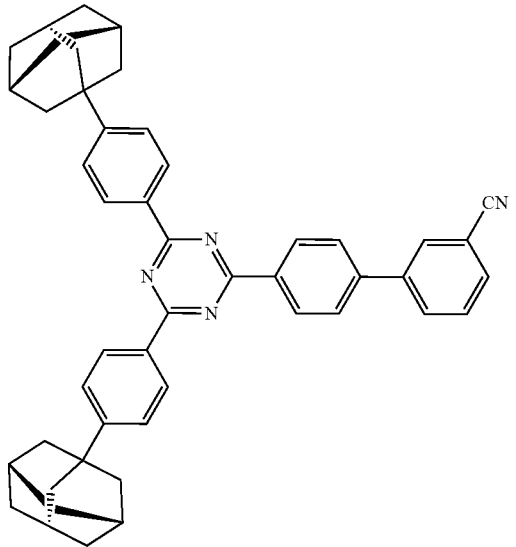
417
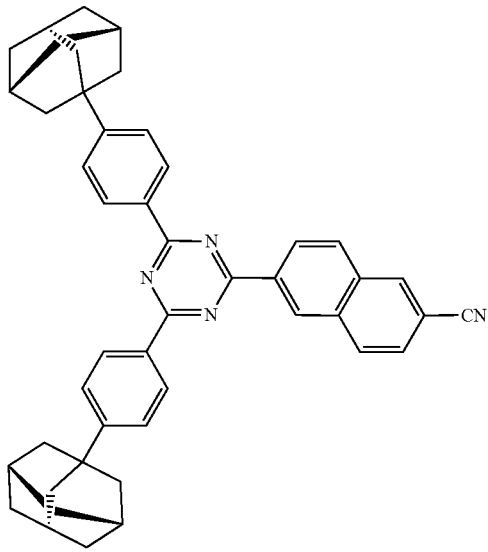

-continued
418
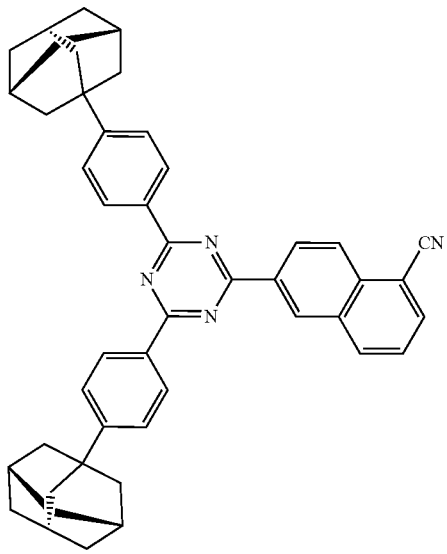
419
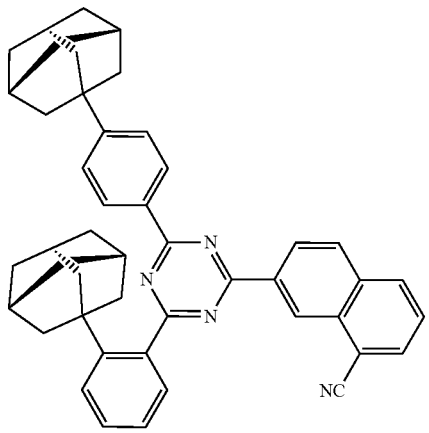
420
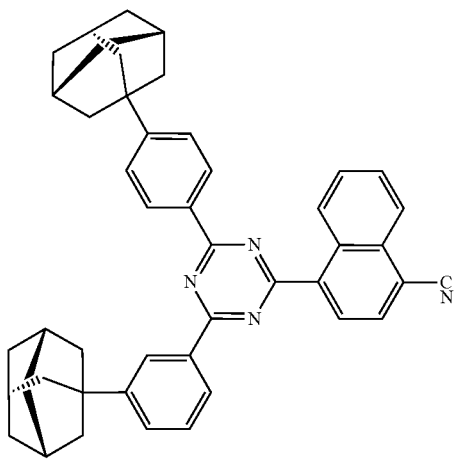
421
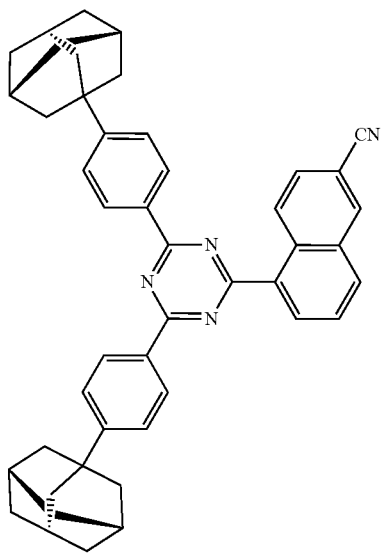
422
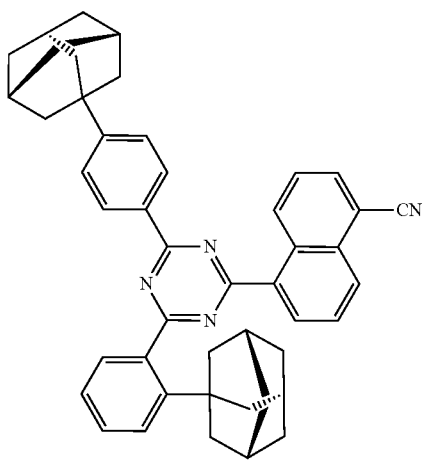

423
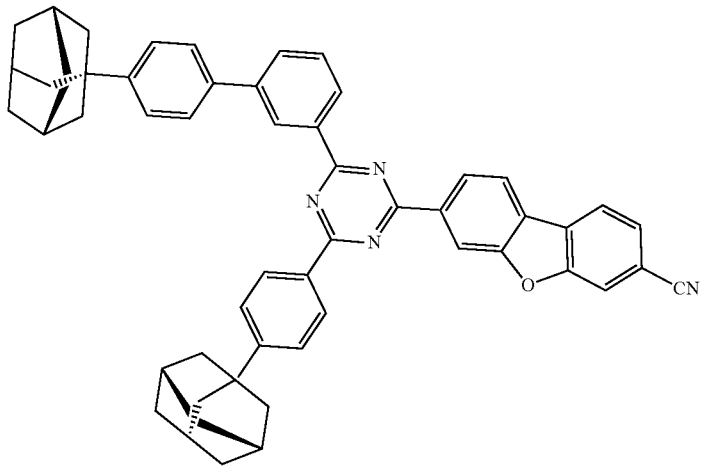
424
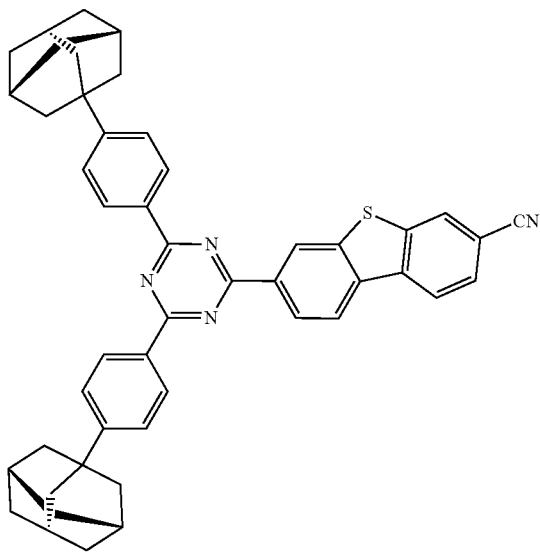
425
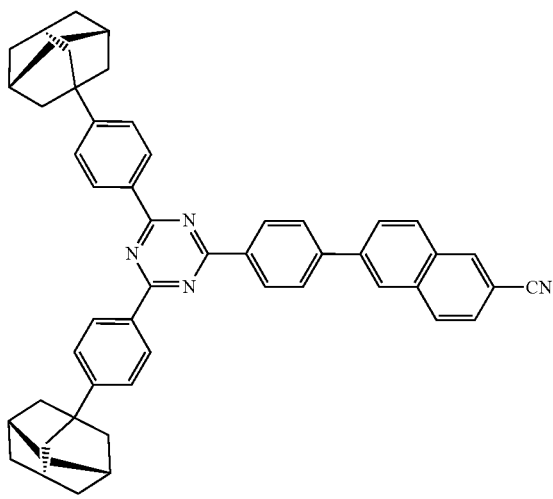
426
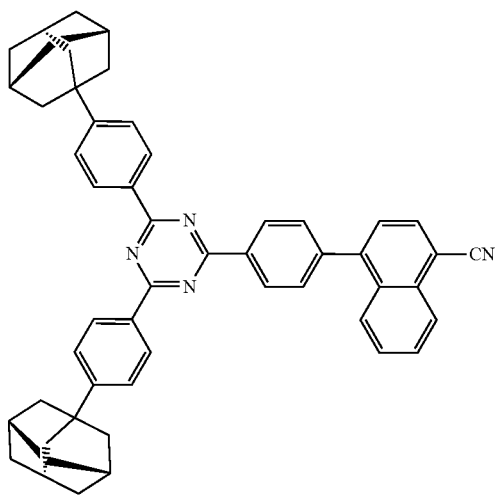

-continued
427
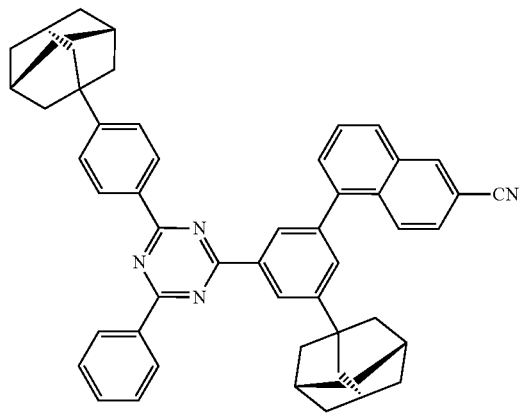
453
428
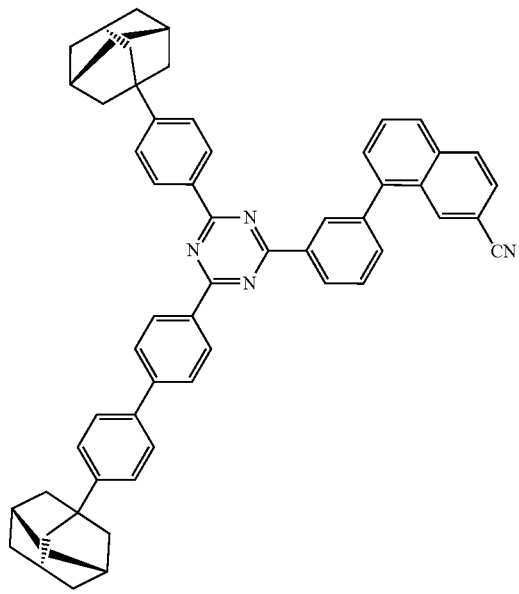
454
429
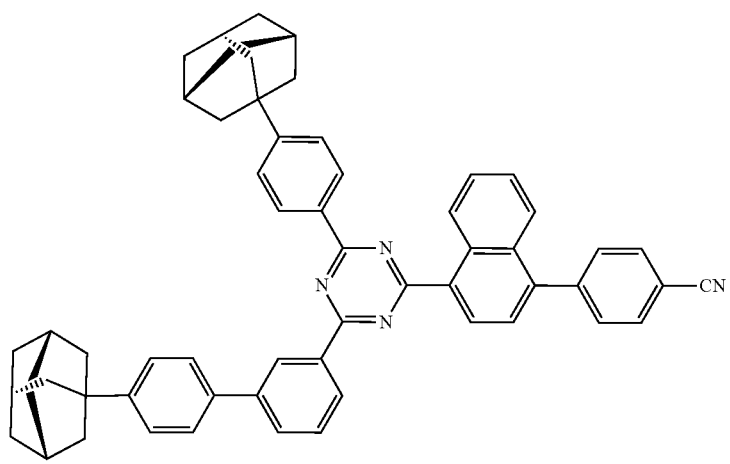
430
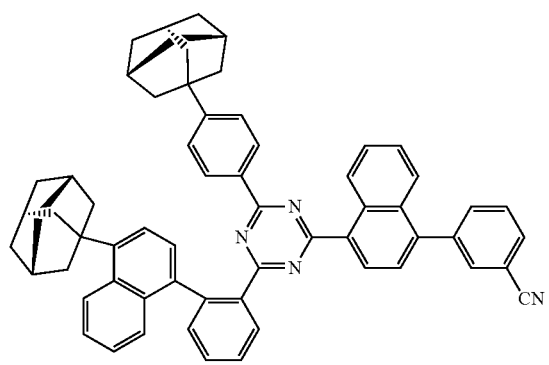
431
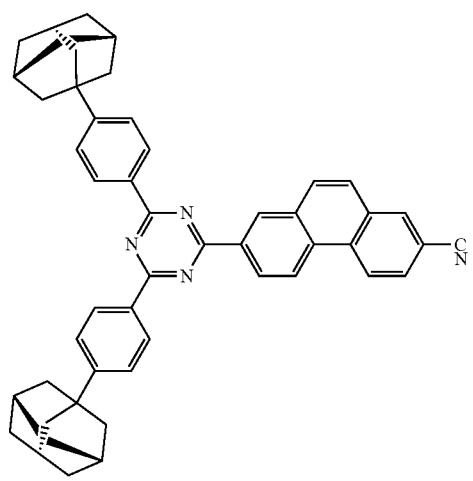

432
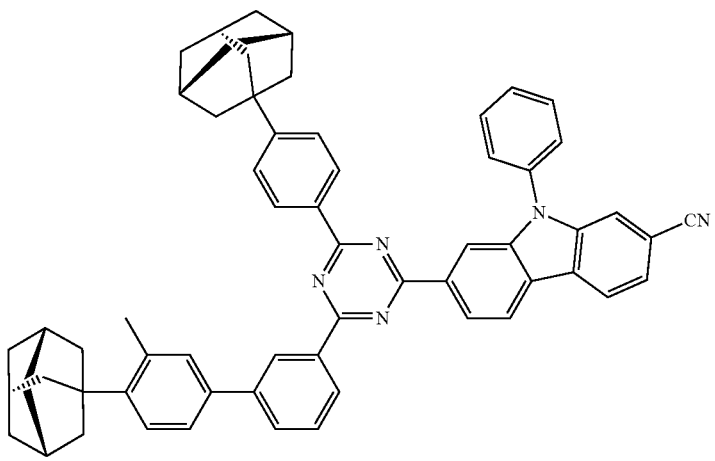
433
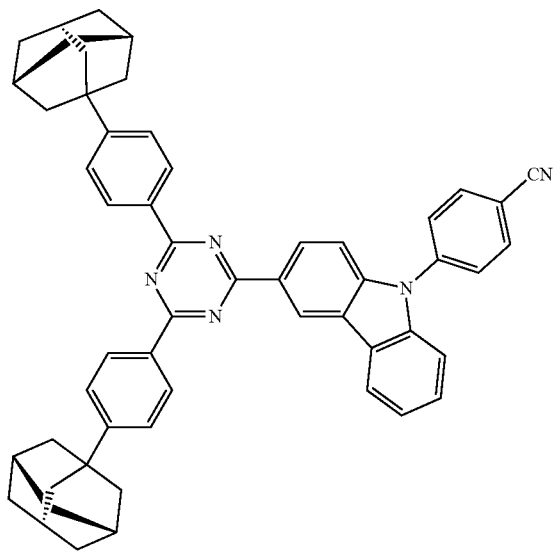
434
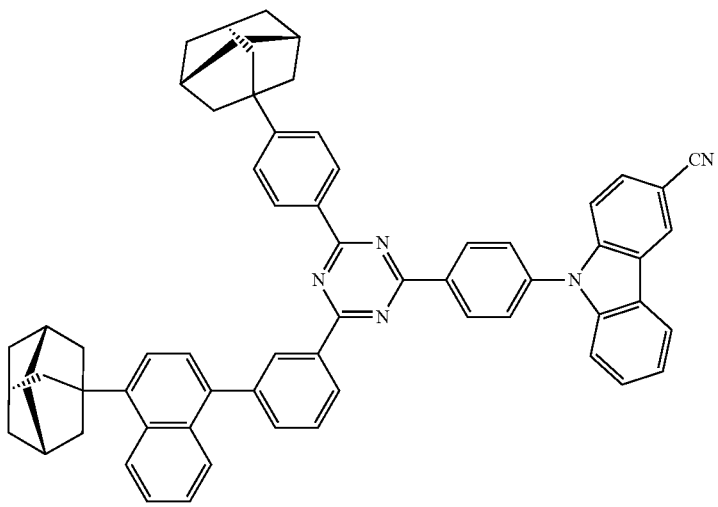

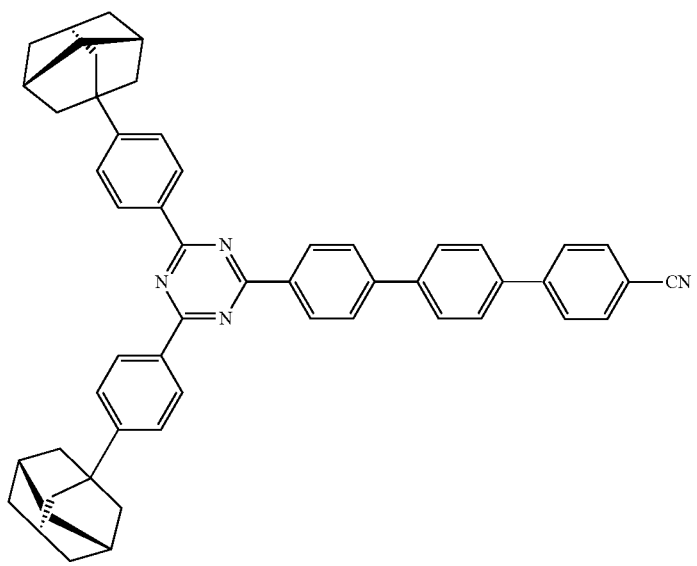
435
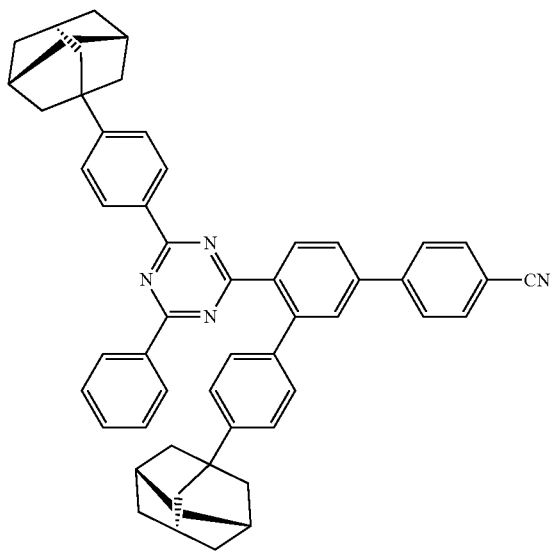
436
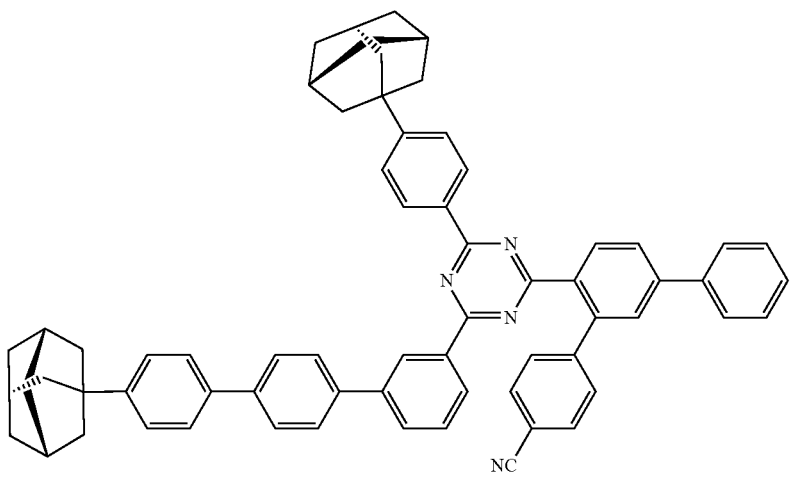
437

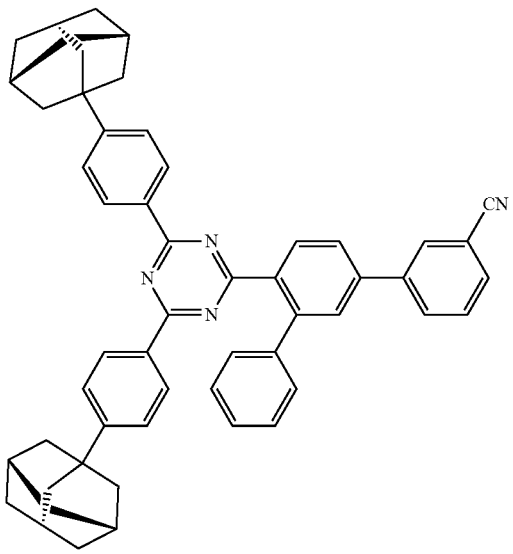
438
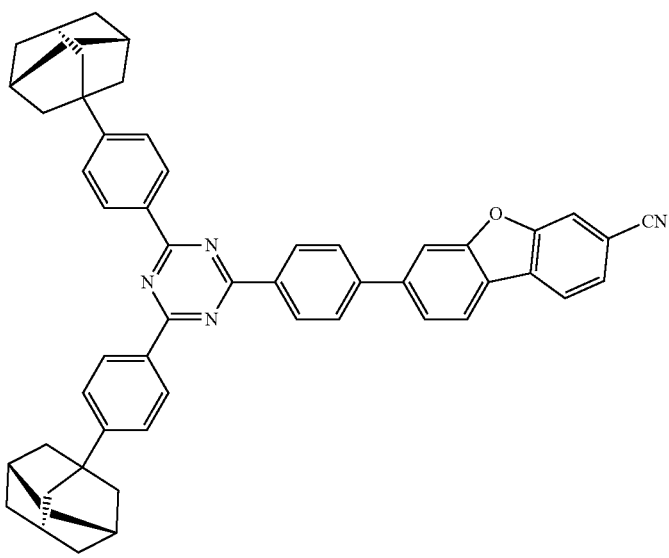
439
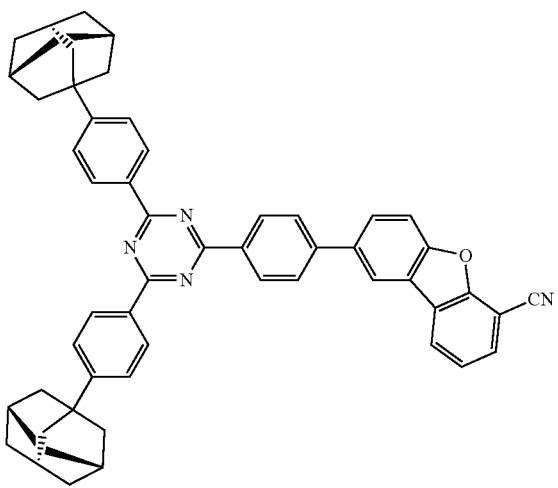
440
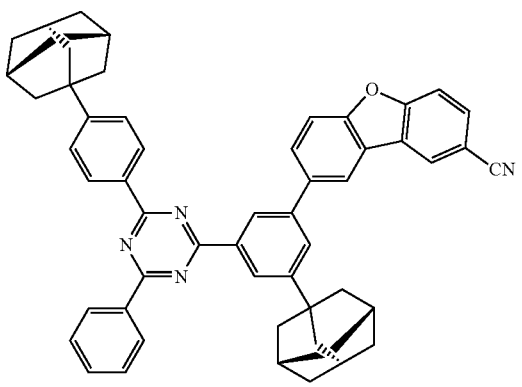
441

-continued
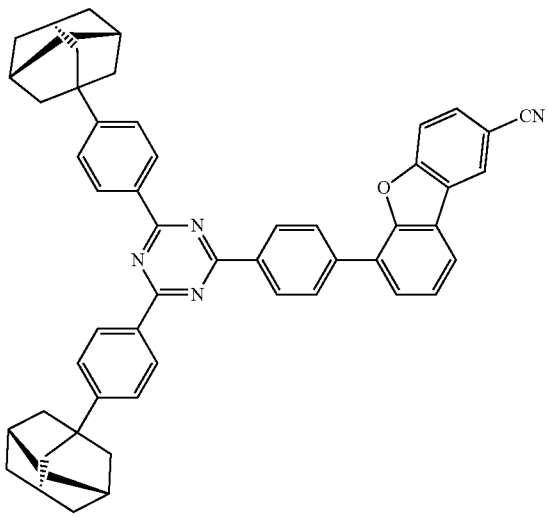
442
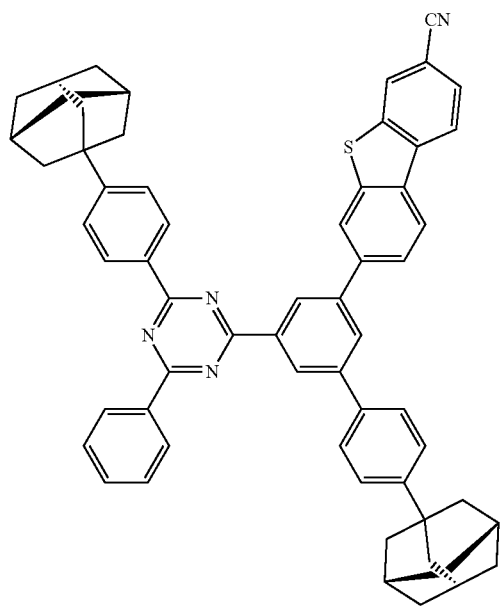
443
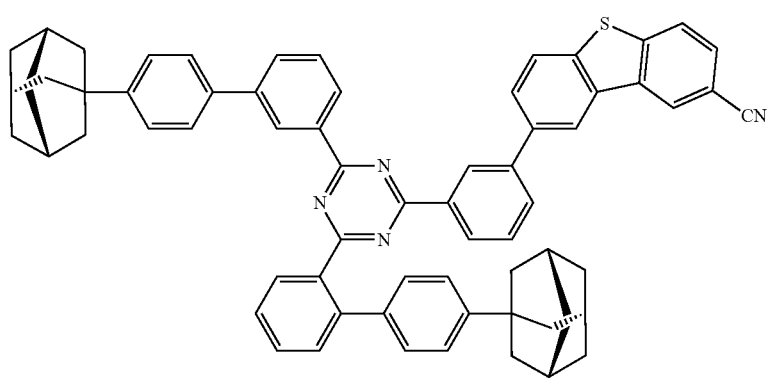
444

445
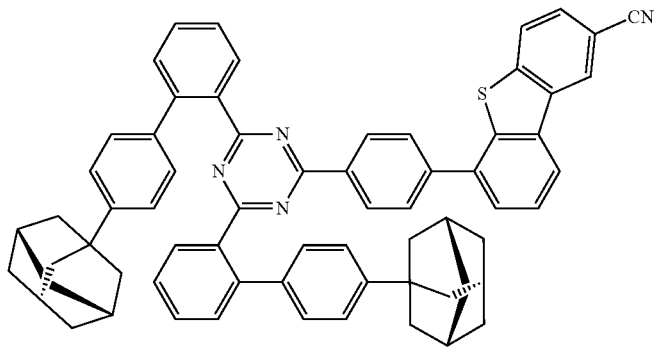
446
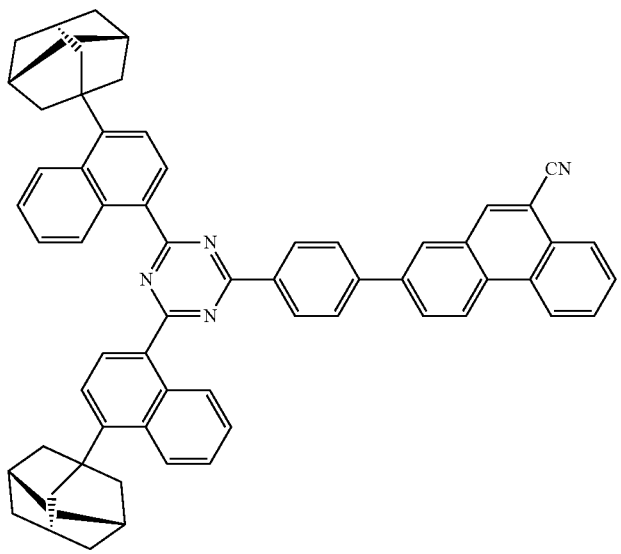
447
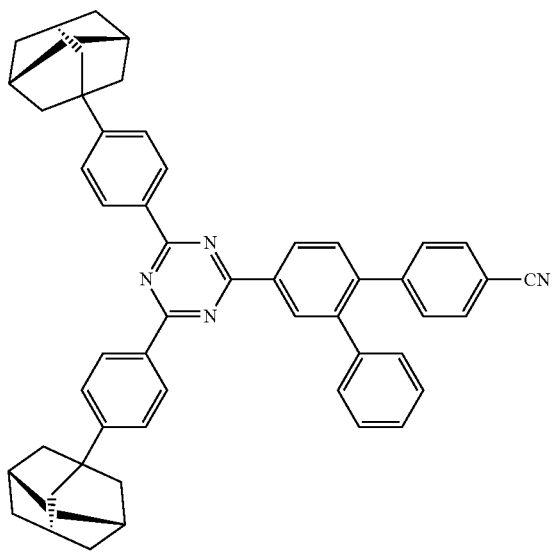
448
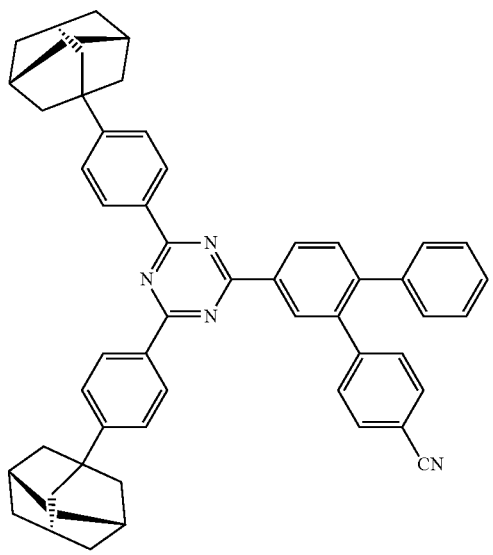

449
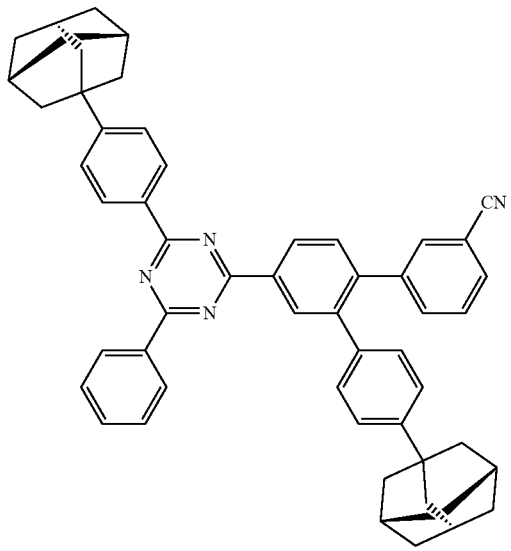
450
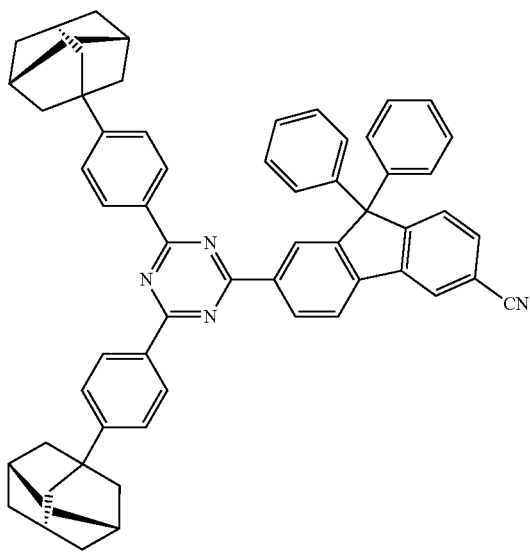
451
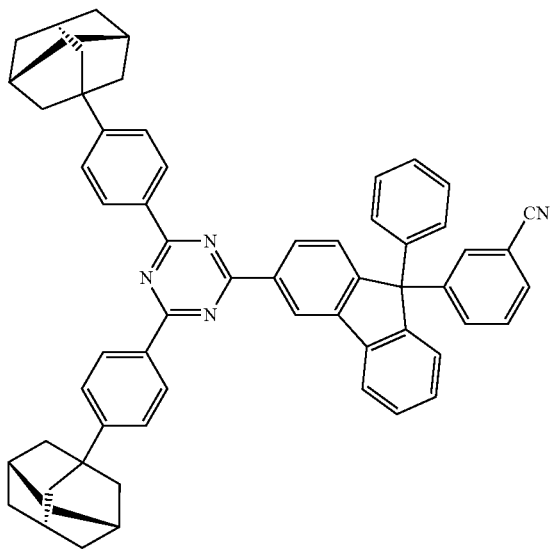

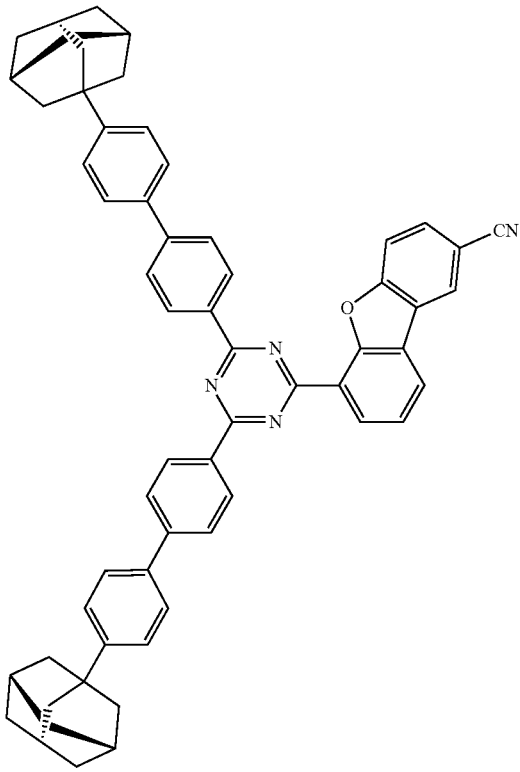
452
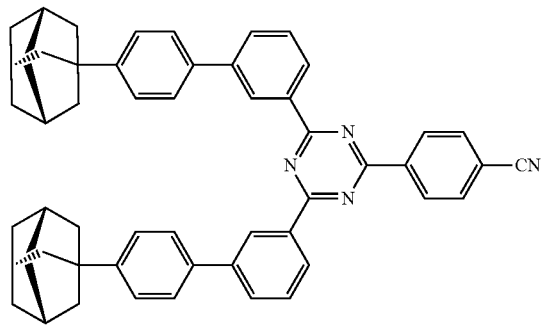
455
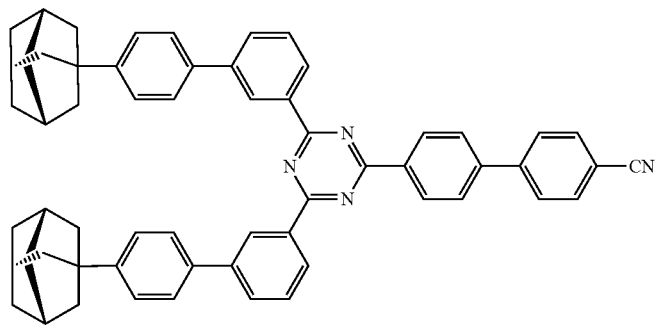
456

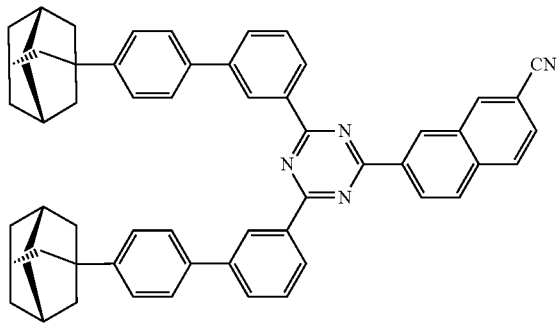
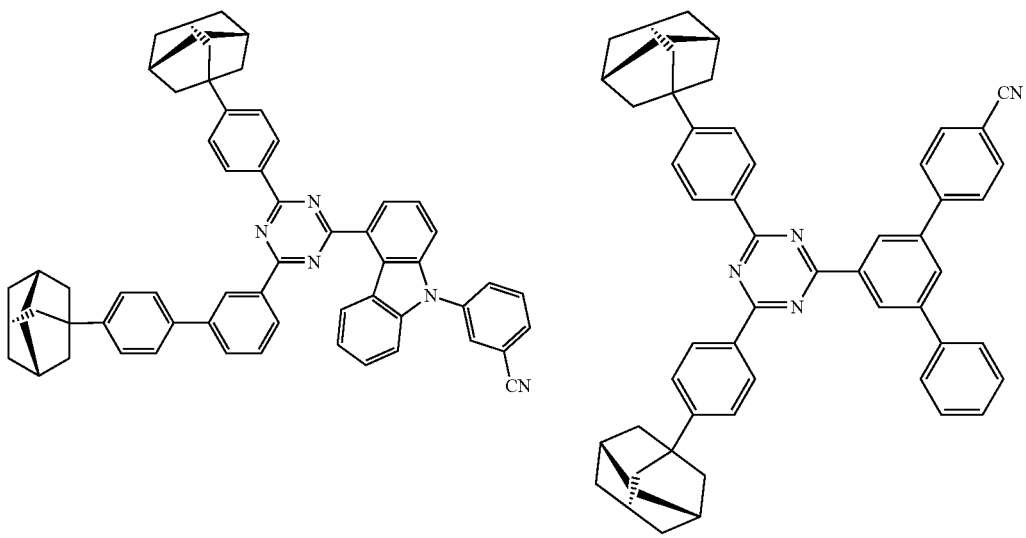
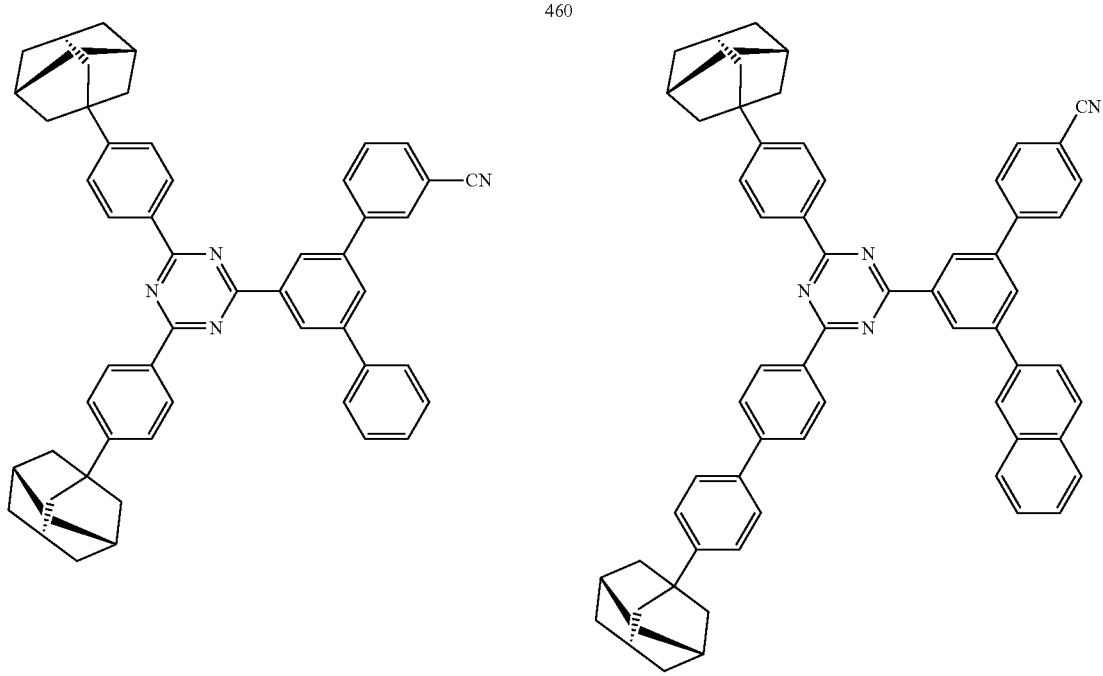

471 472
-continued
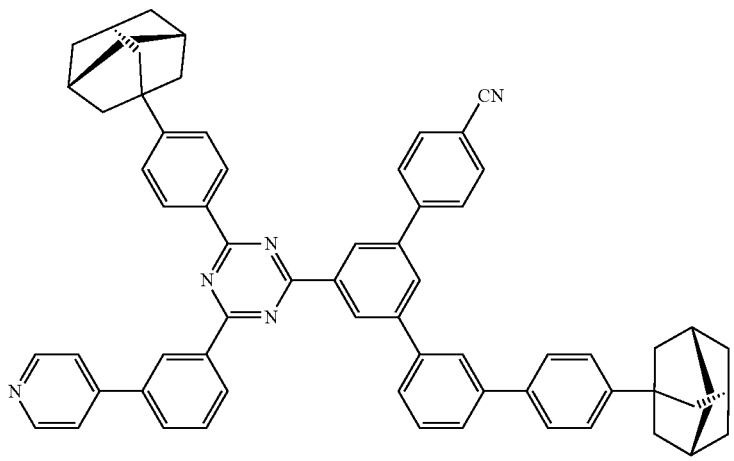
462
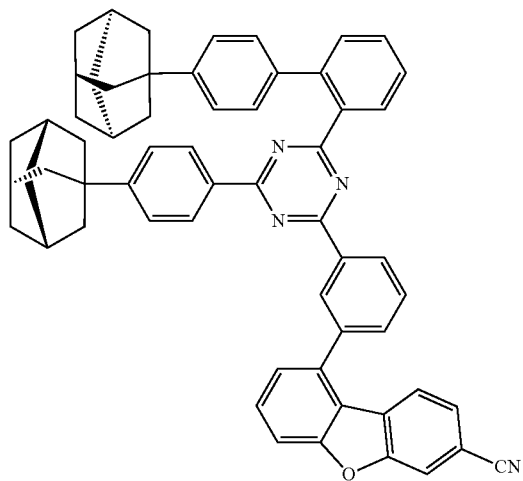
463
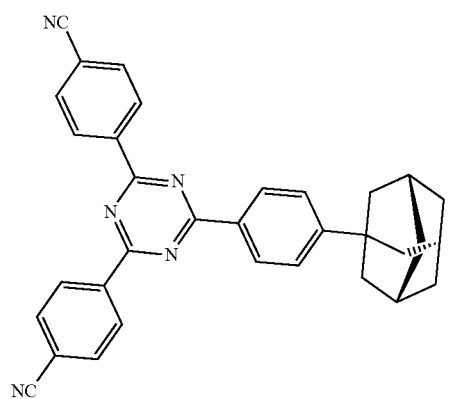
464
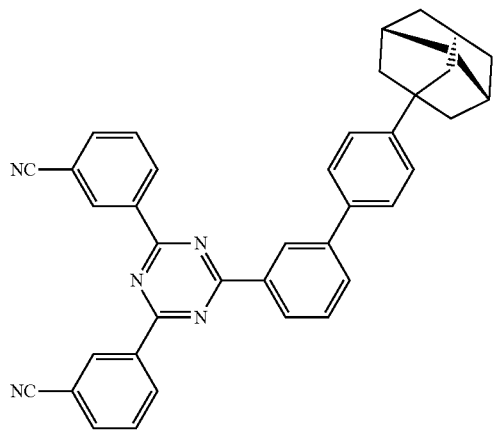
465
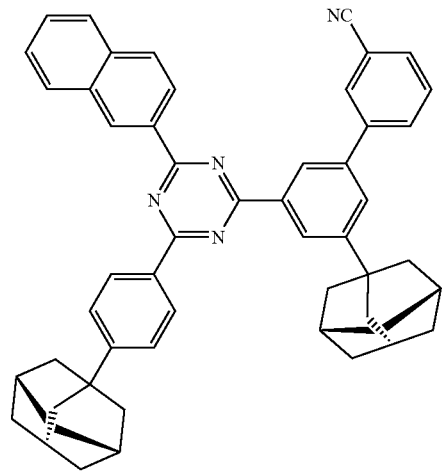
466

473 474
467 468
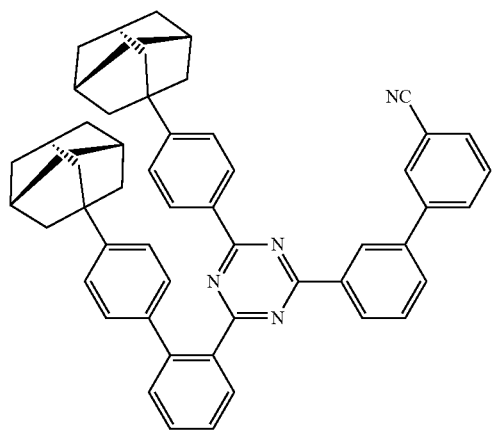
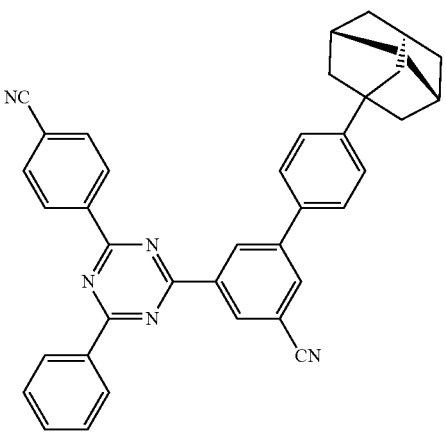
469 470
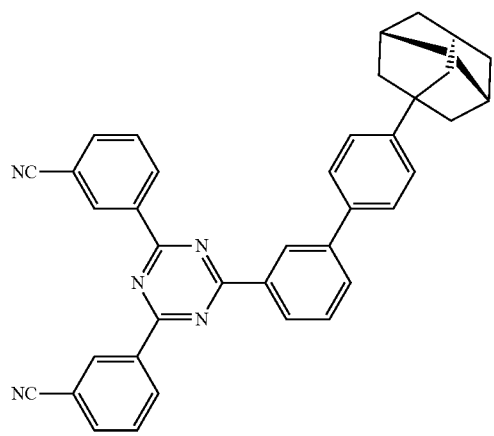
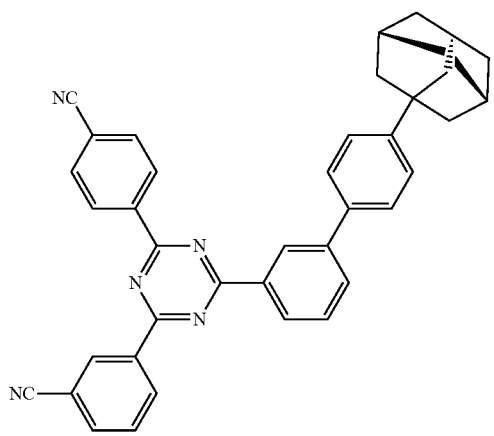
471 472
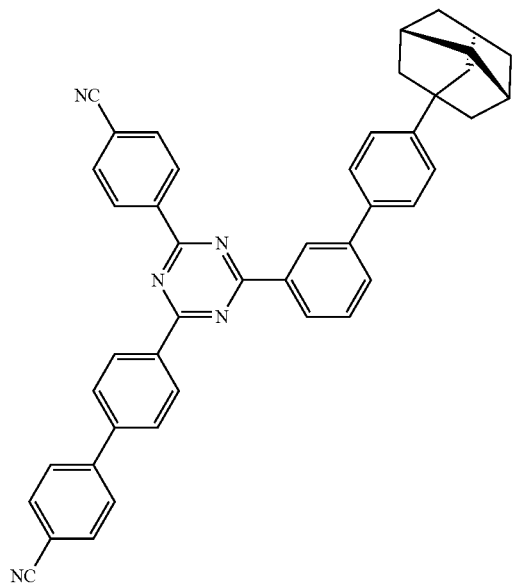
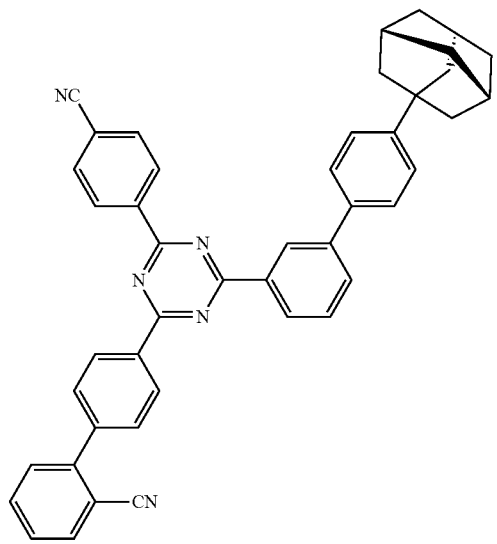

-continued
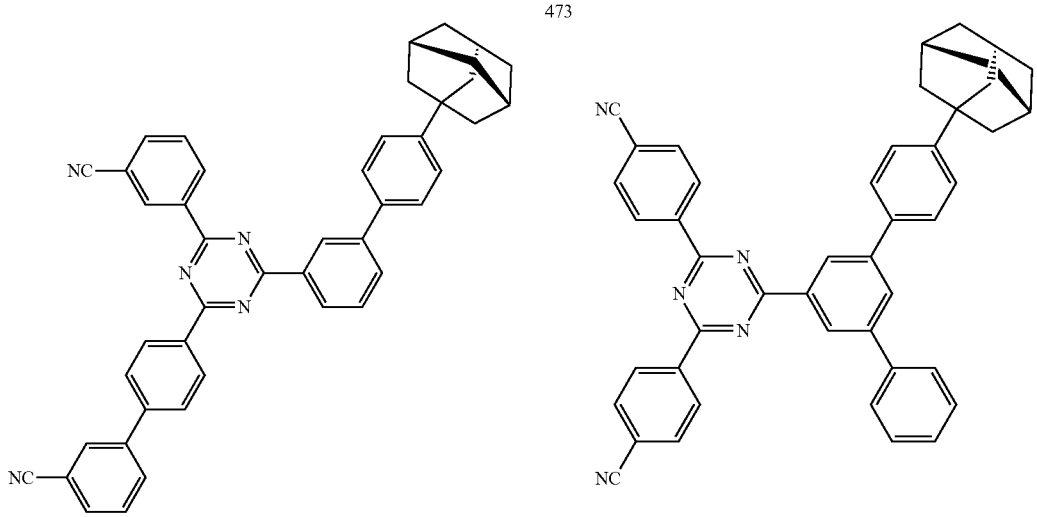
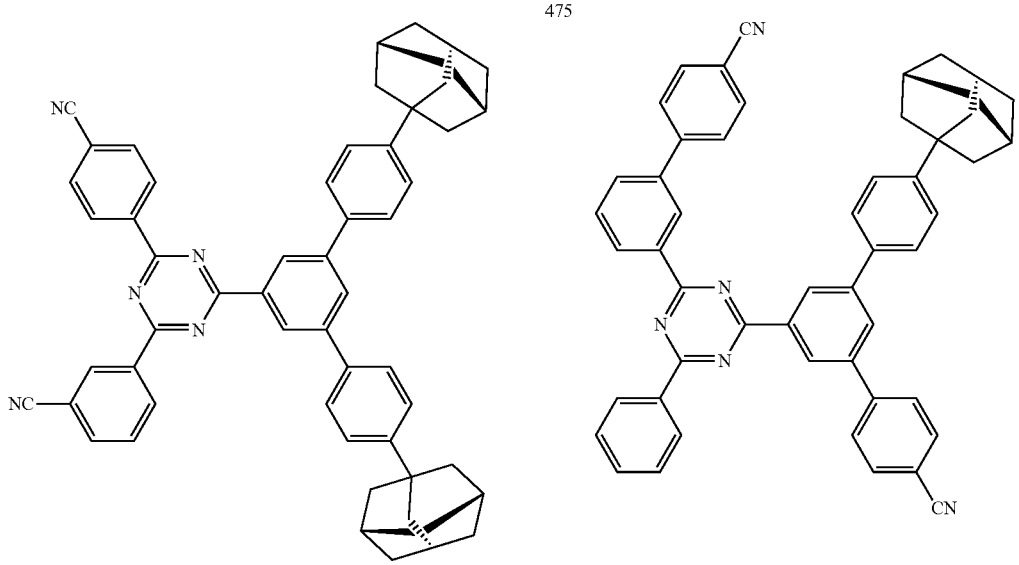
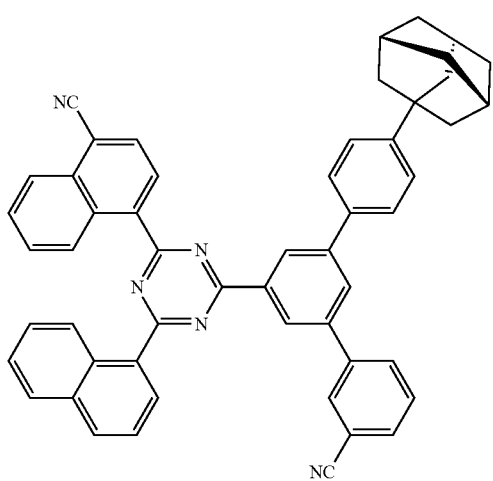

-continued
477
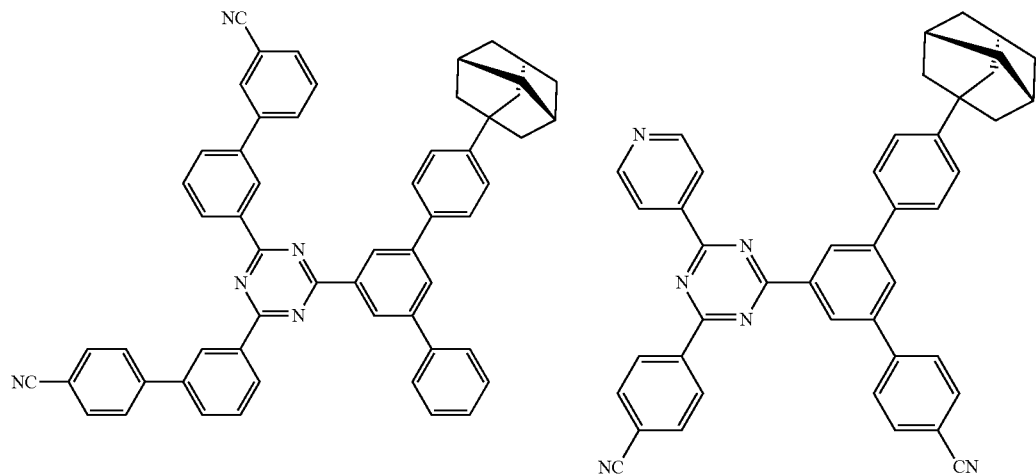
478
478
479
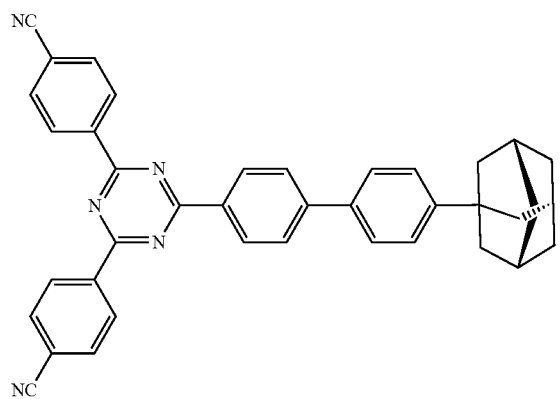
480
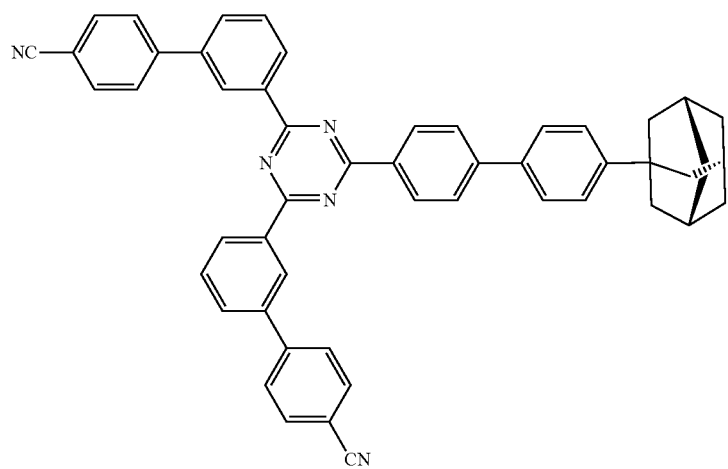
481

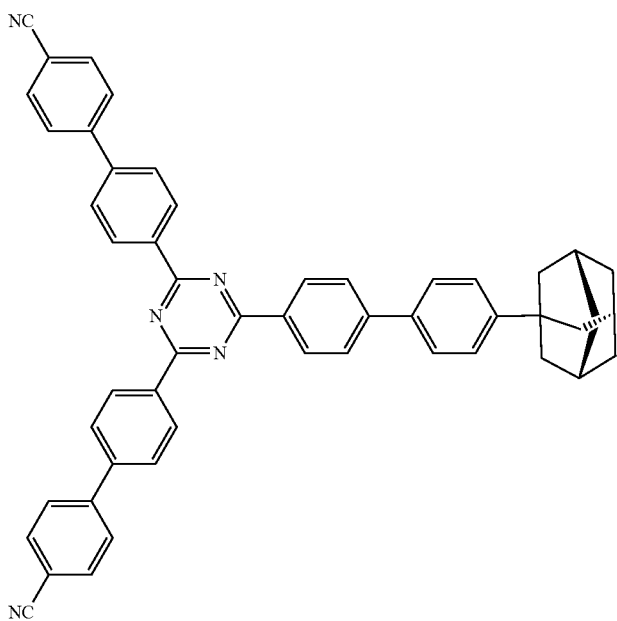
482
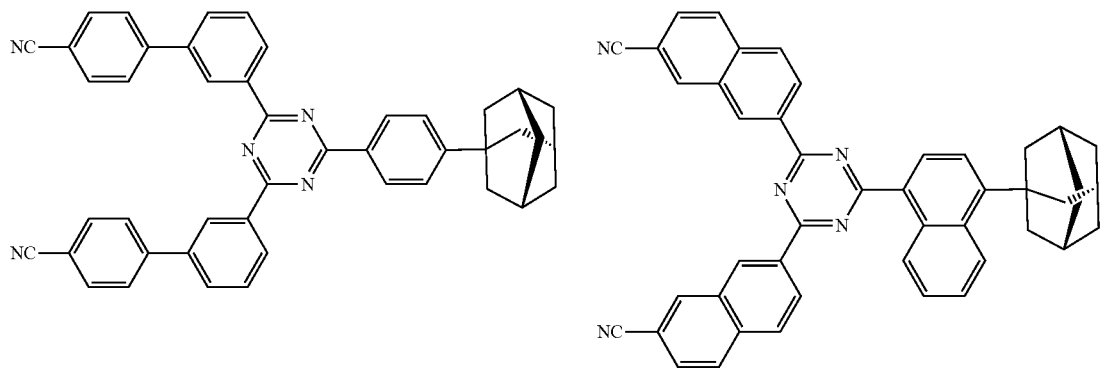
483
484
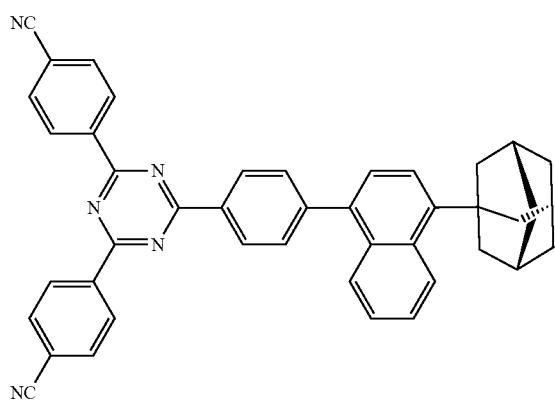
485

-continued
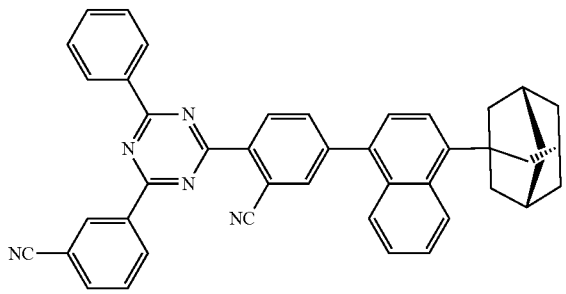
486
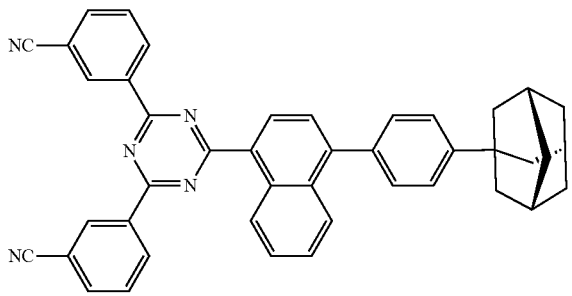
487
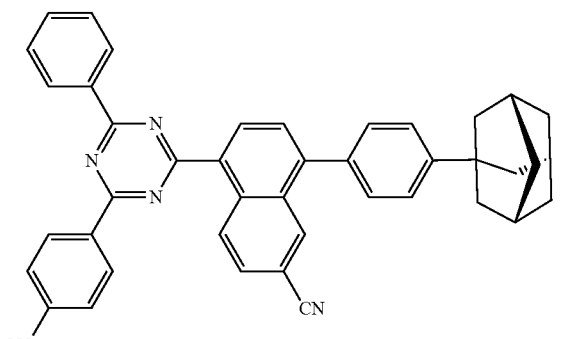
488
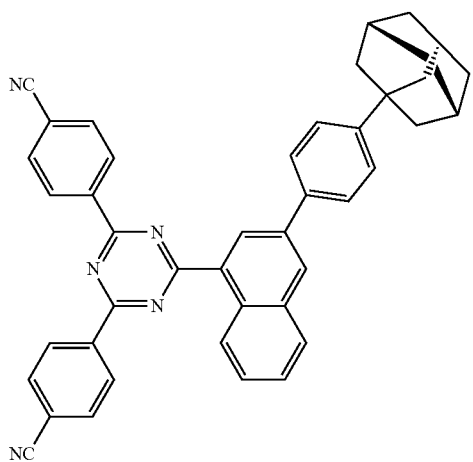
489
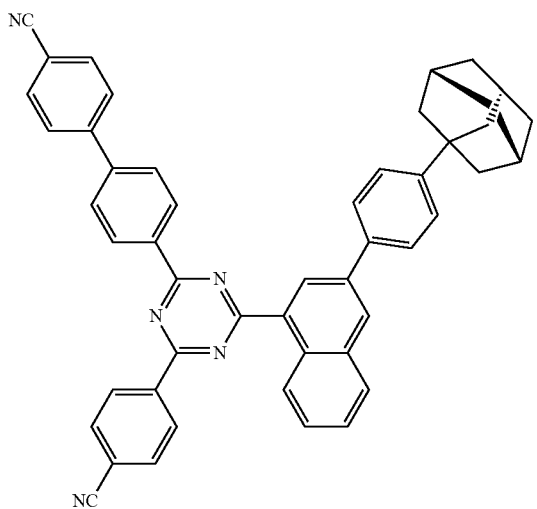
490

491
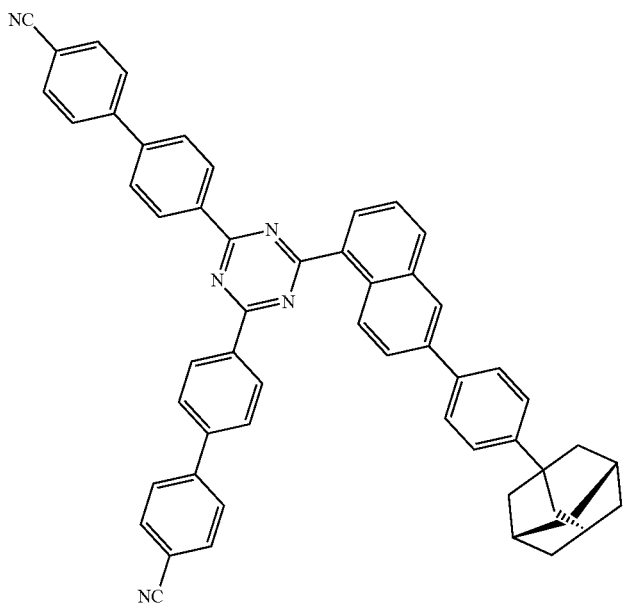
492
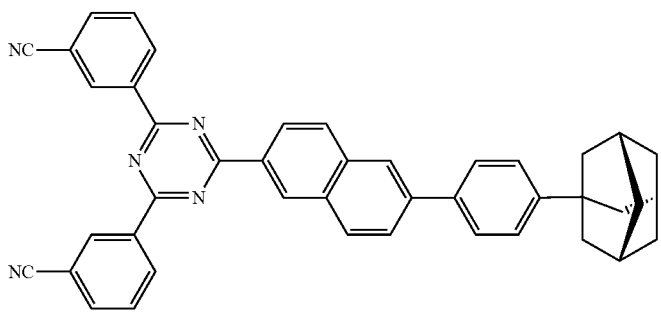
493
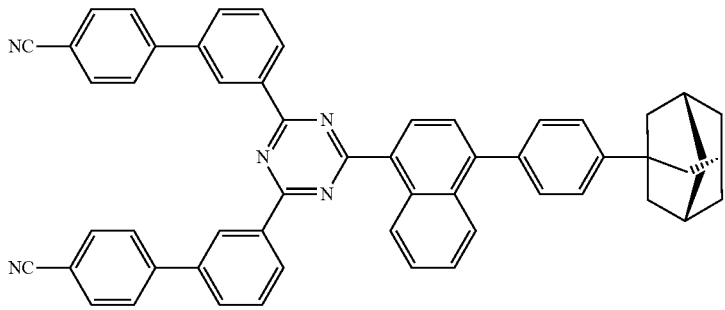
494
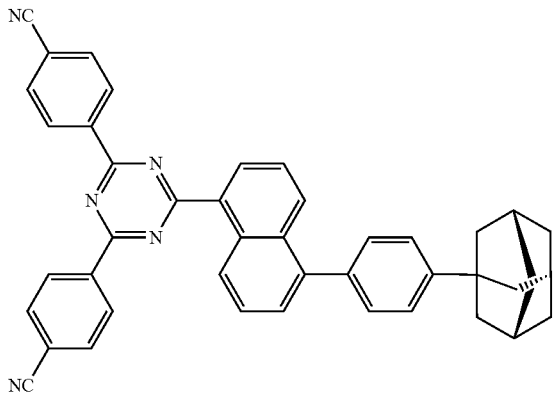

485 486
-continued
| 495 | 496 |
|---|---|
| 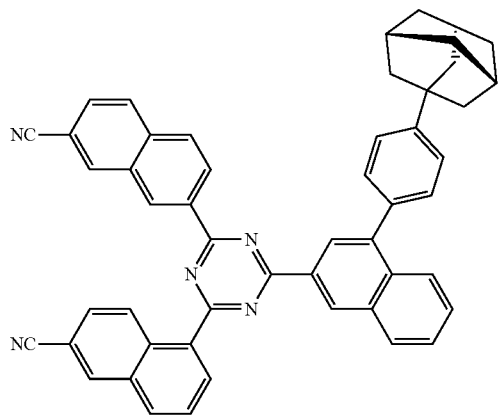 | 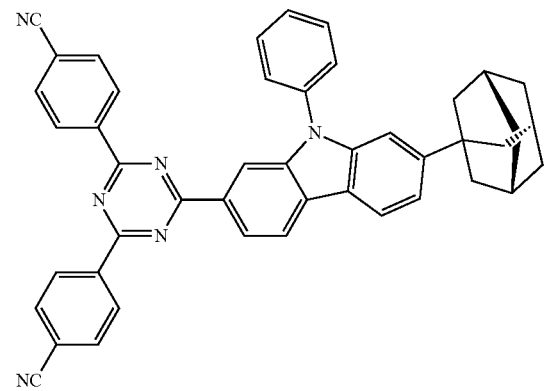 |
| 497 | 498 |
| 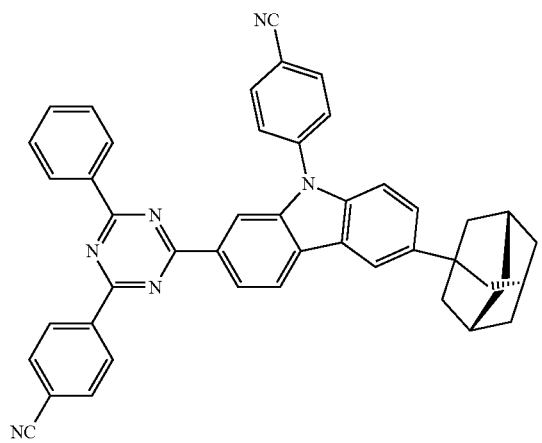 | 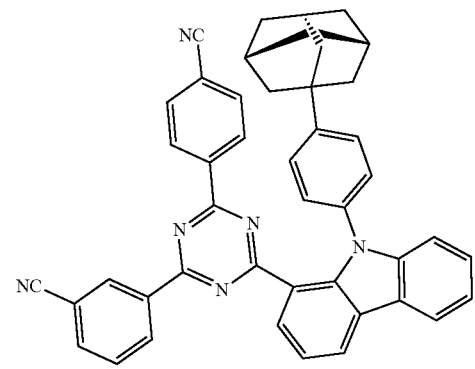 |
| 499 | 500 |
| 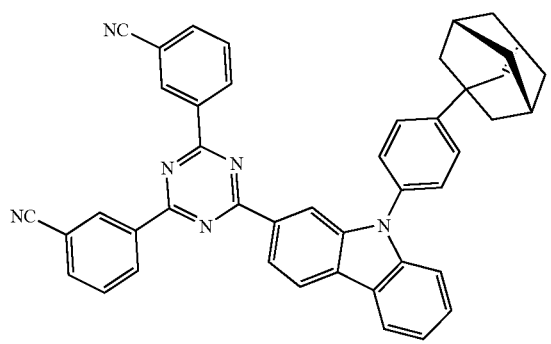 | 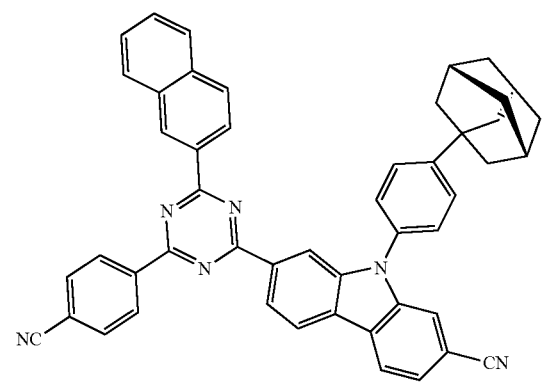 |

501
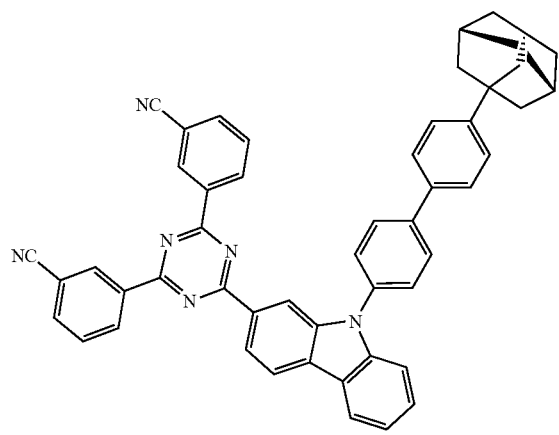
502
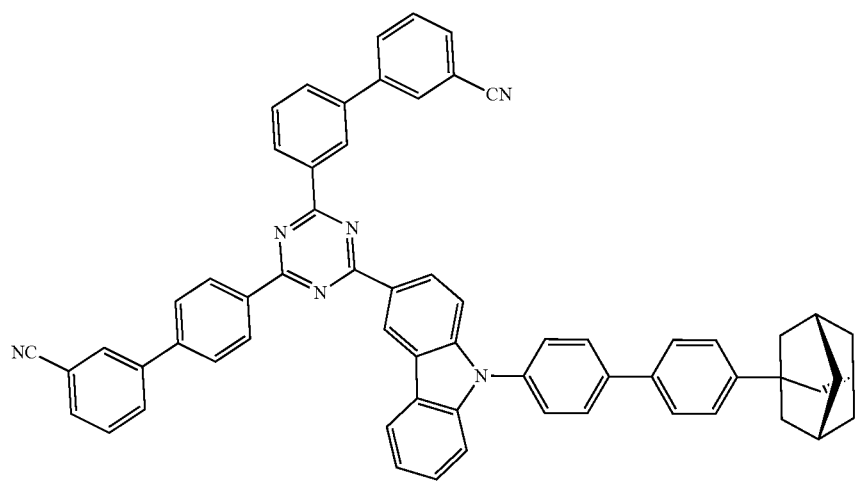
503
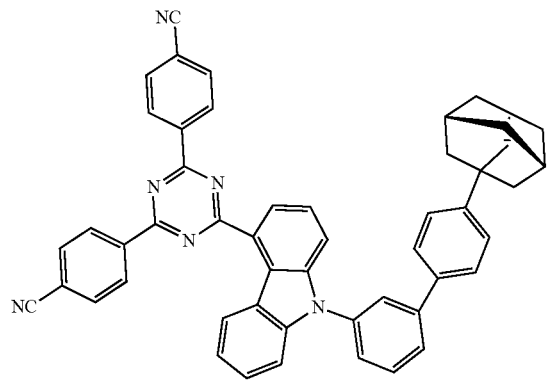

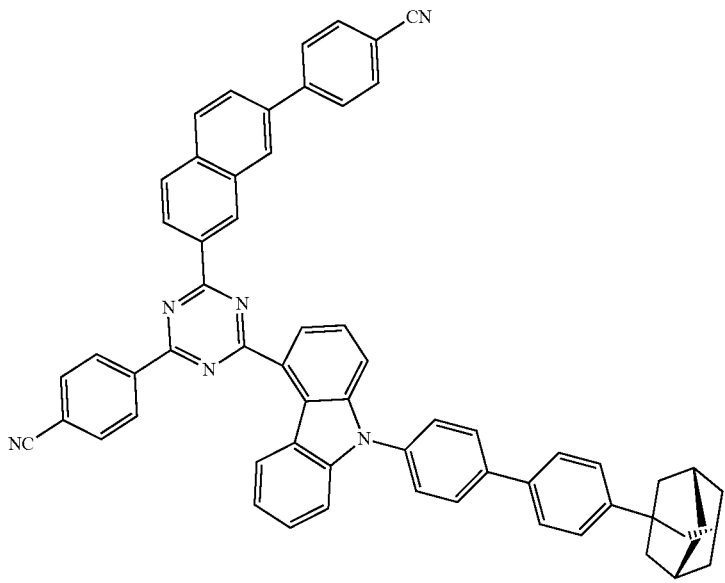
504
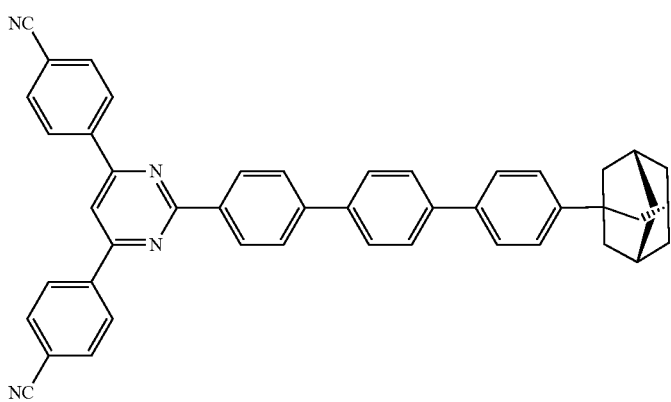
505
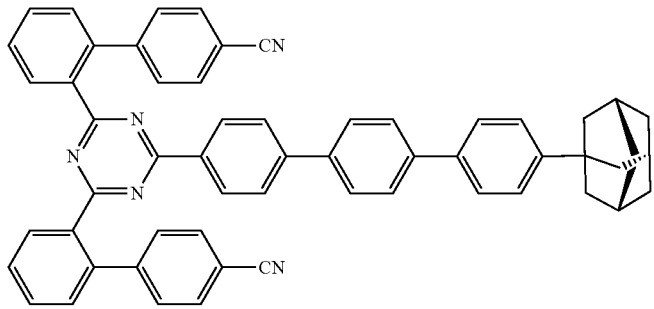
506
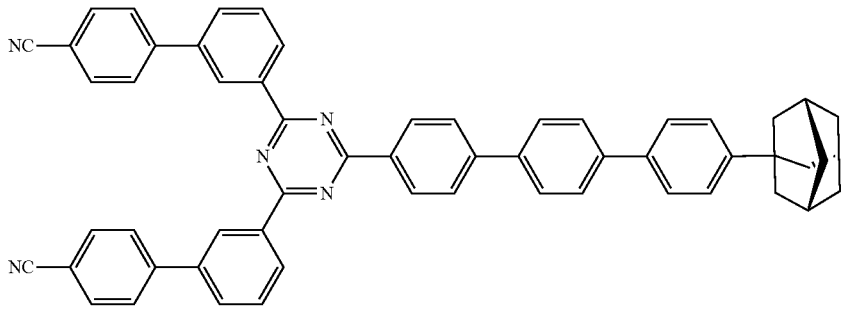
507

491 492
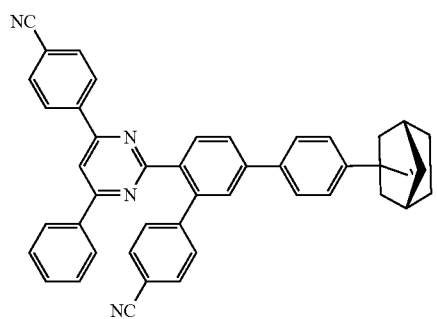
508
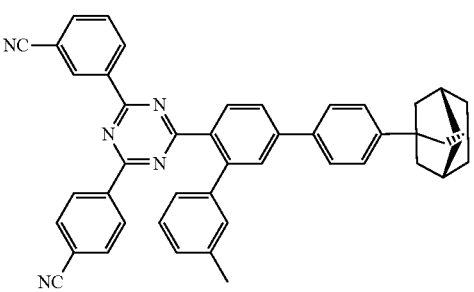
509
-continued
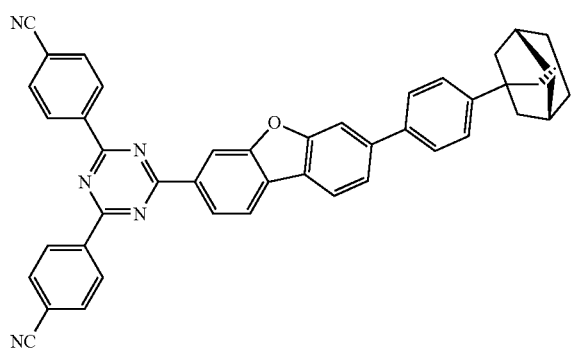
510
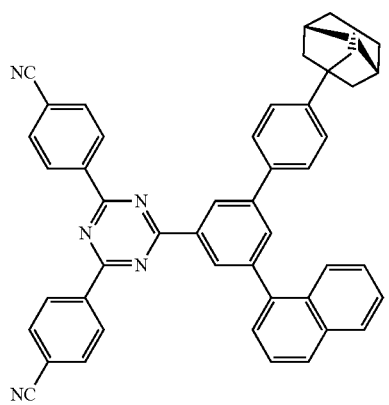
512
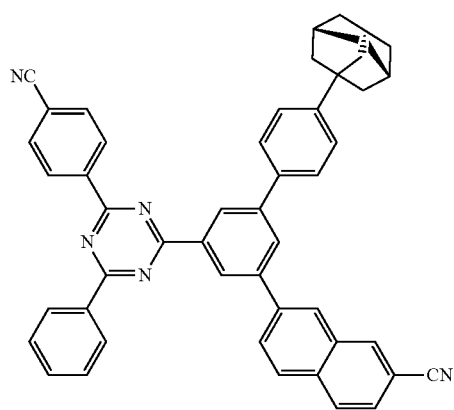
513
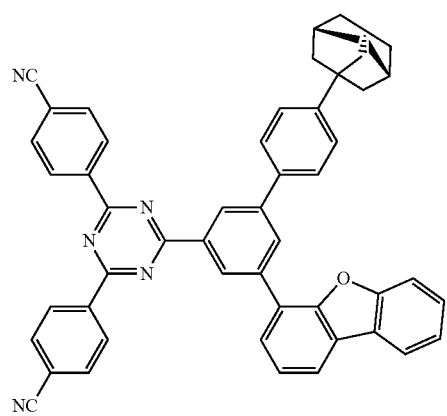
514

-continued
493 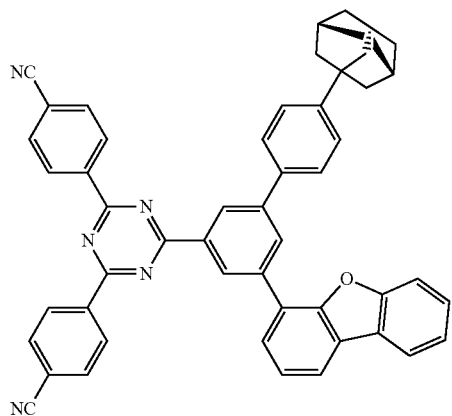 515
494 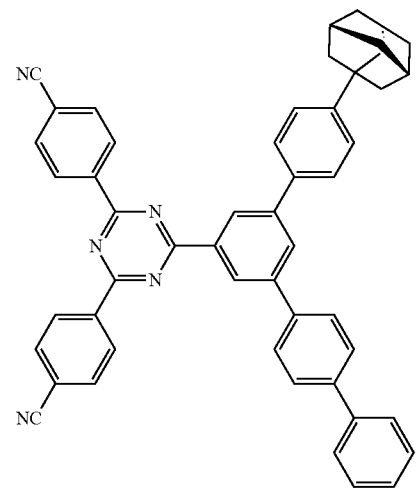 516
517 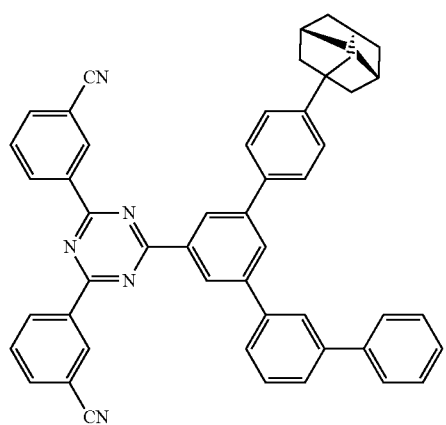
518 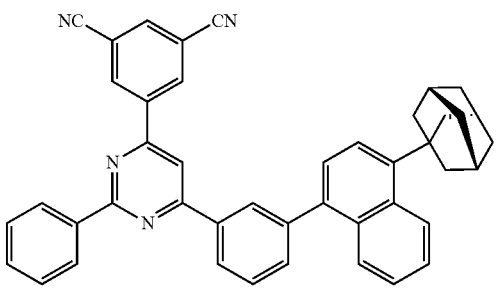
519 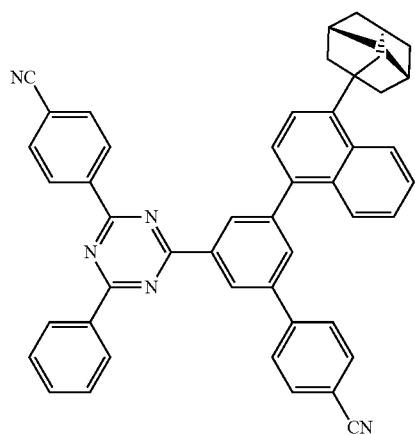
520 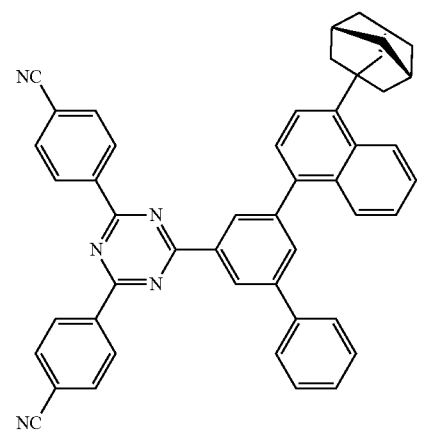

-continued
495
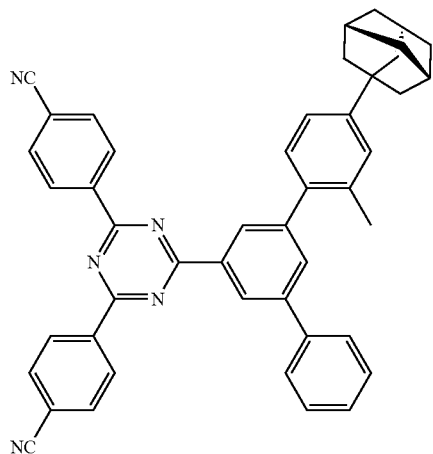
521
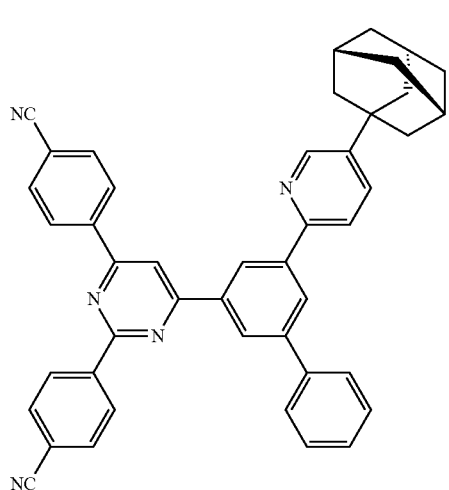
522
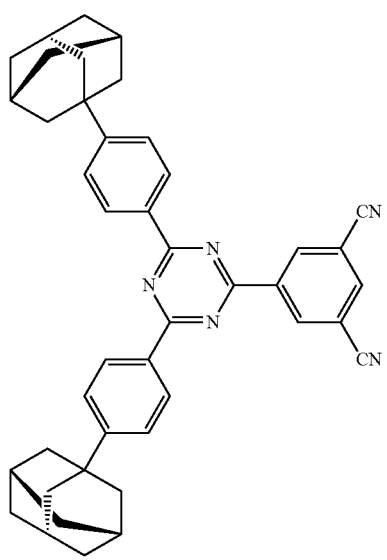
523
-continued
496
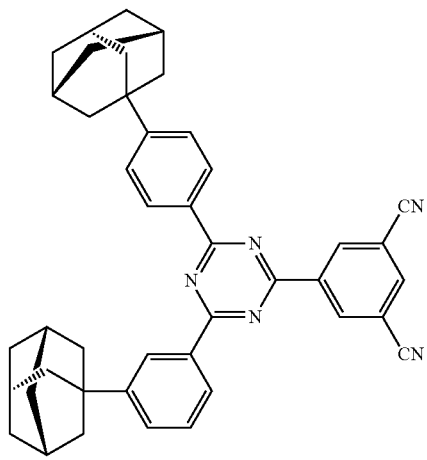
524
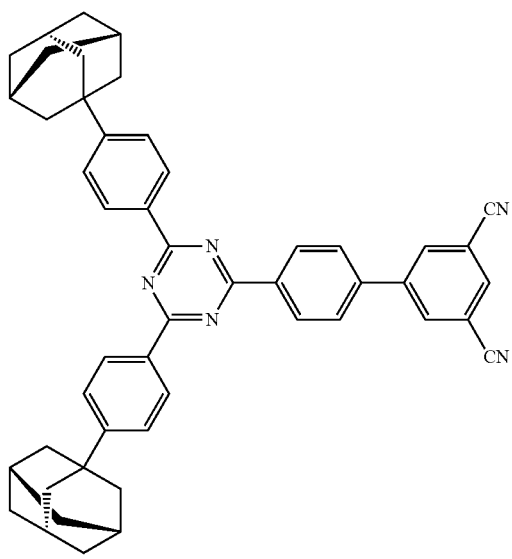
525

497
-continued
498
-continued
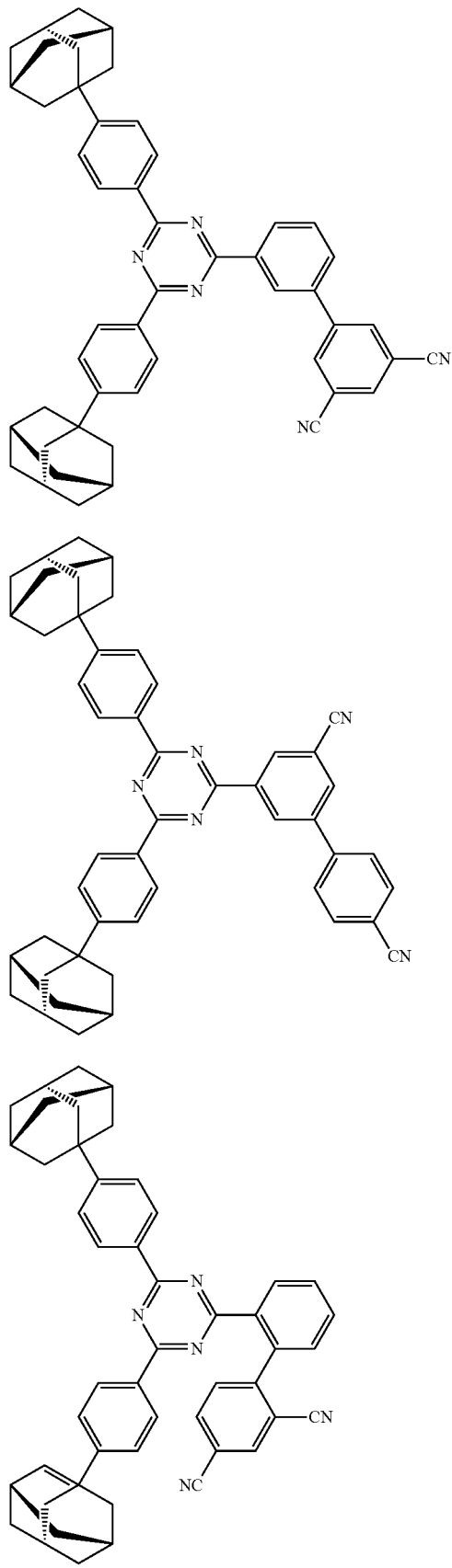
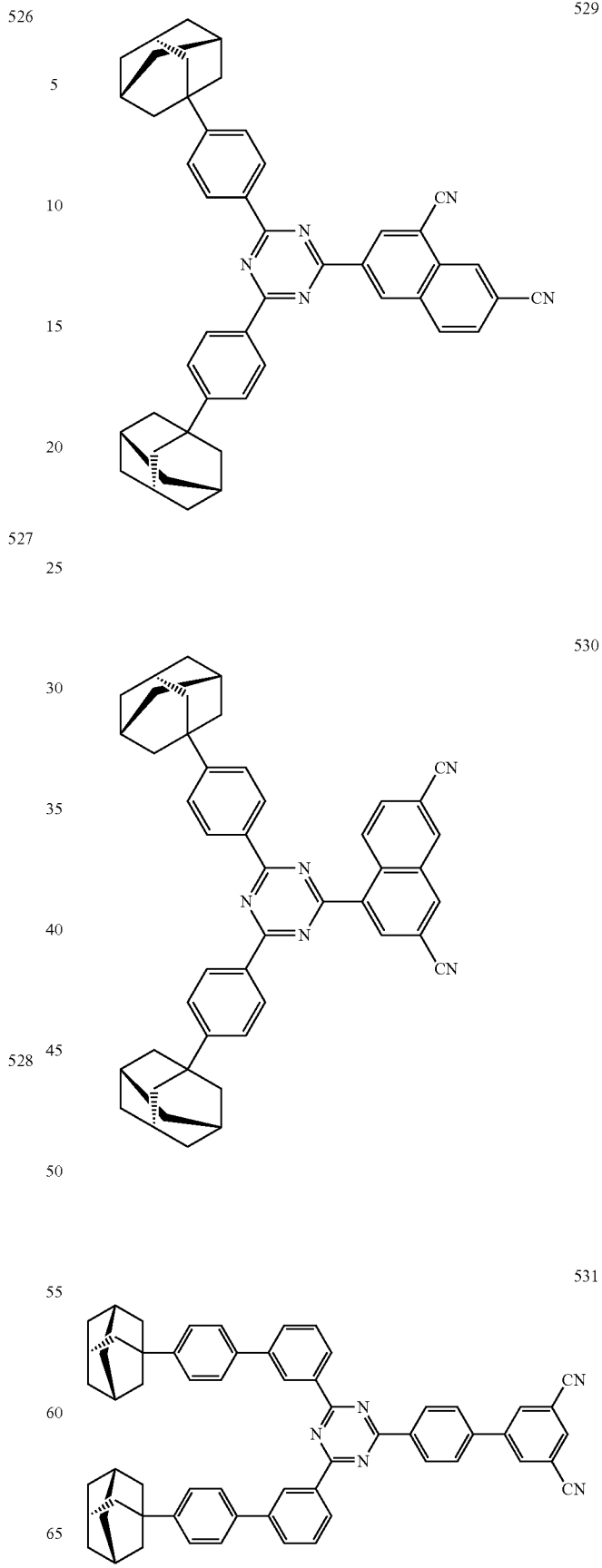

499
-continued
532
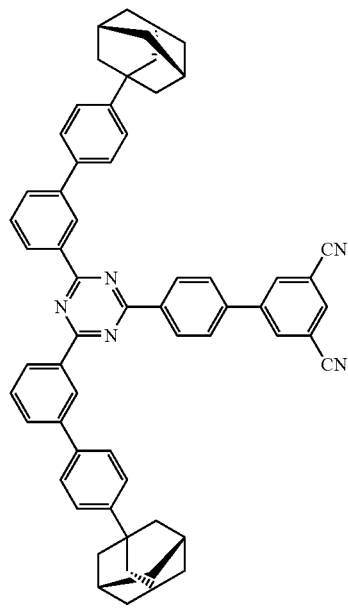
533
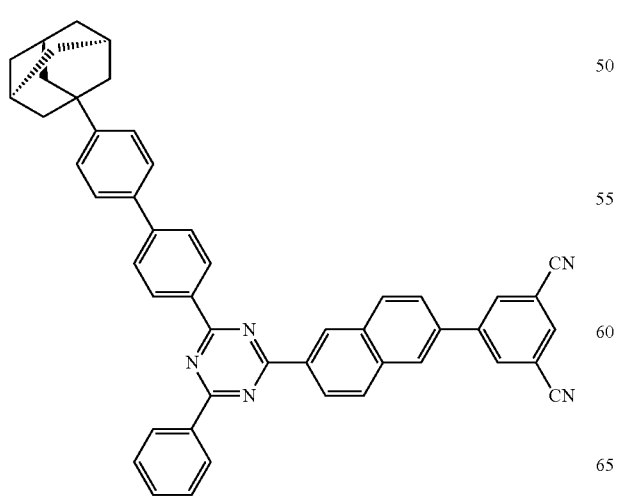
500
-continued
534
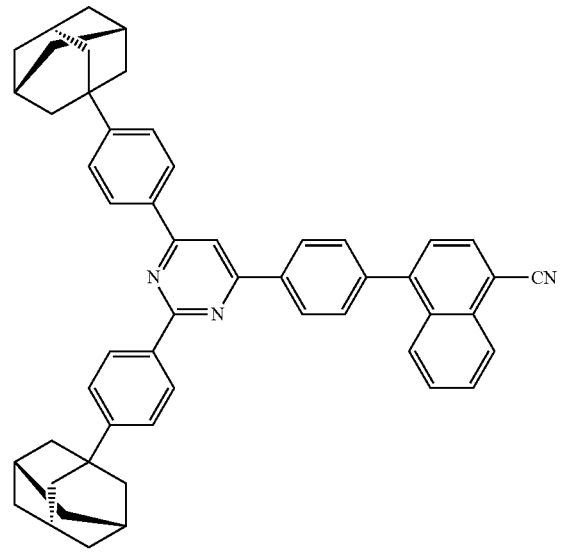
538
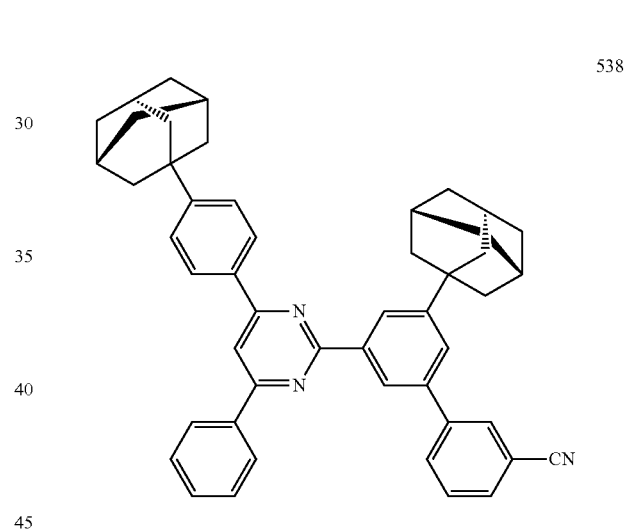
539
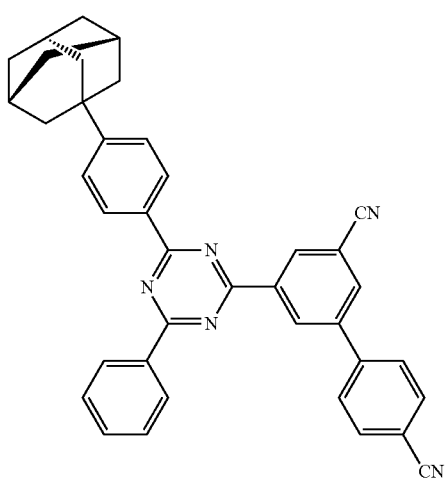

501 -continued
552
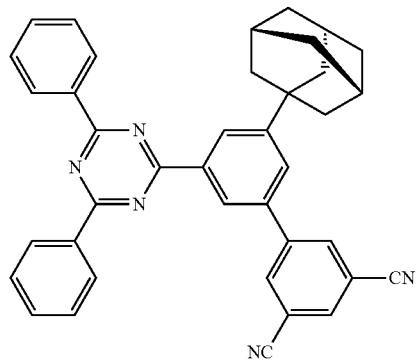
553
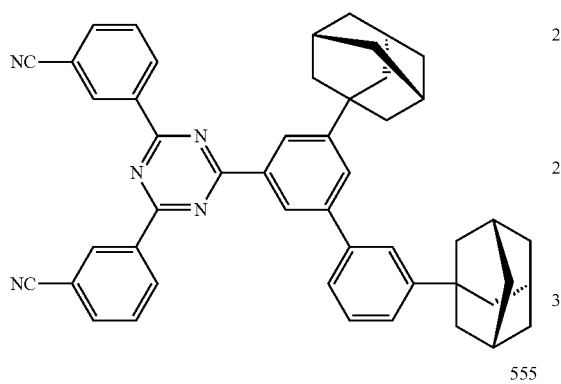
555
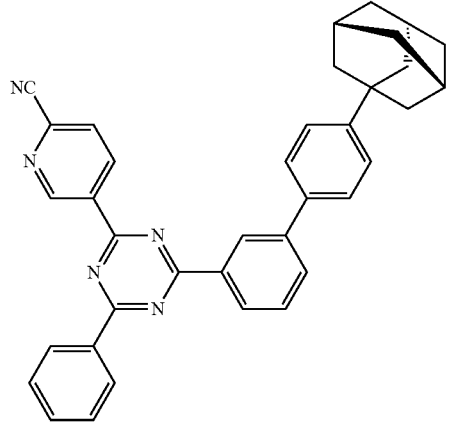
556
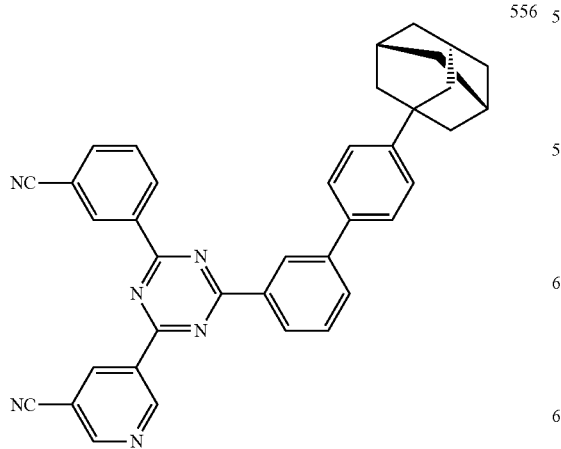
502 -continued
557
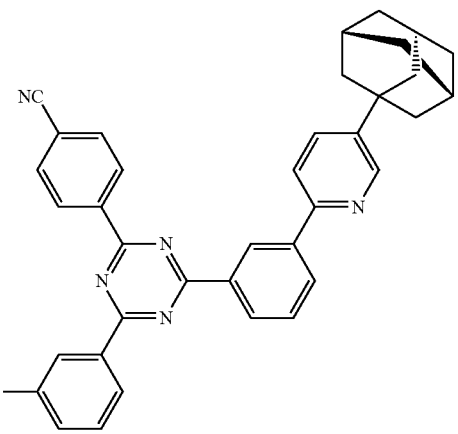
558
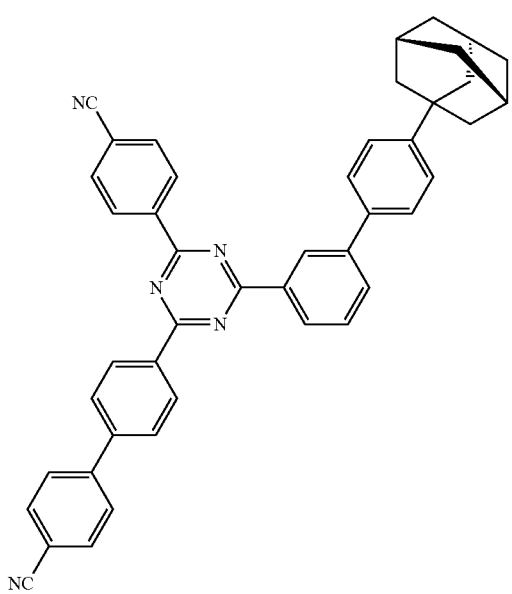
559
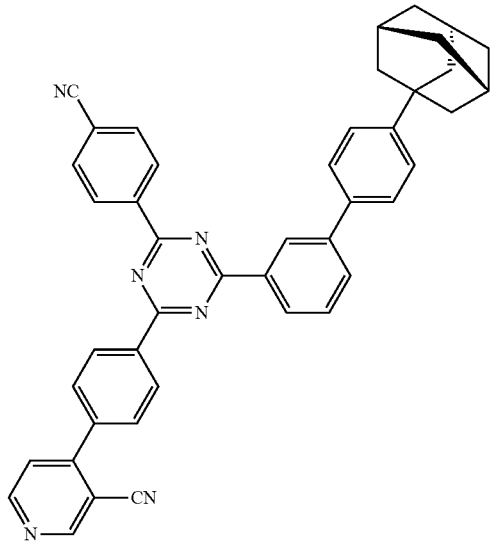

-continued
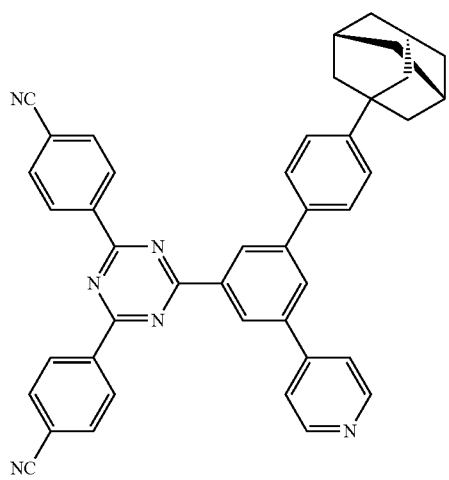
560
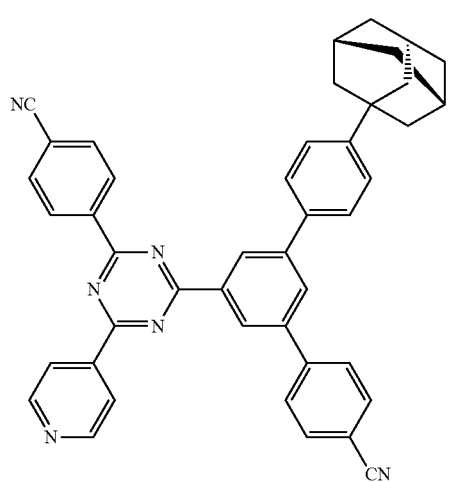
561
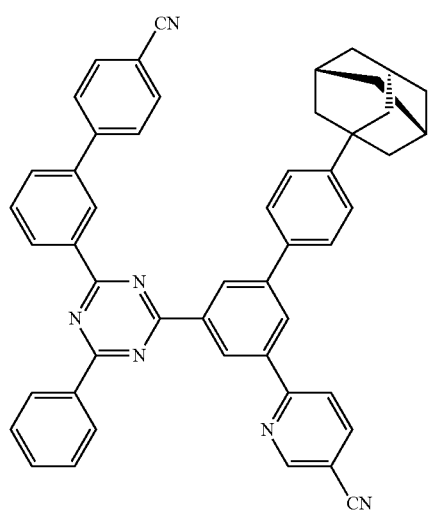
562
-continued
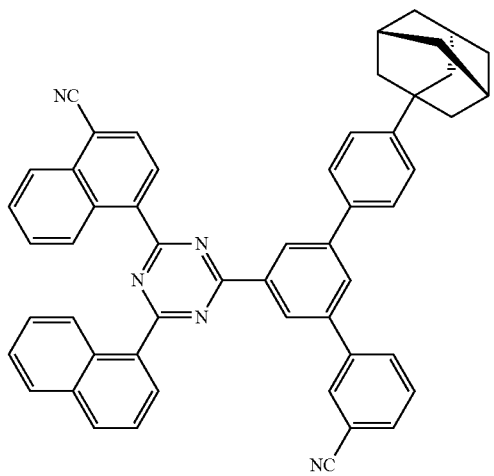
563
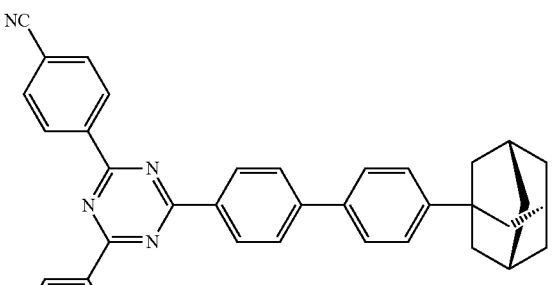
564
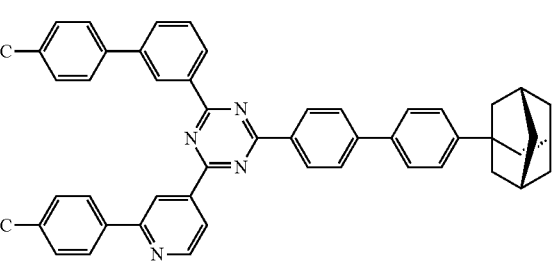
568
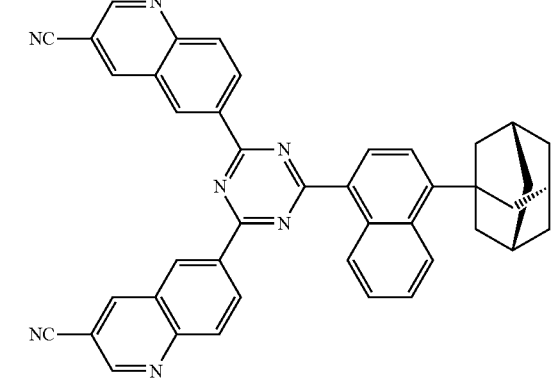
569

505
-continued
570
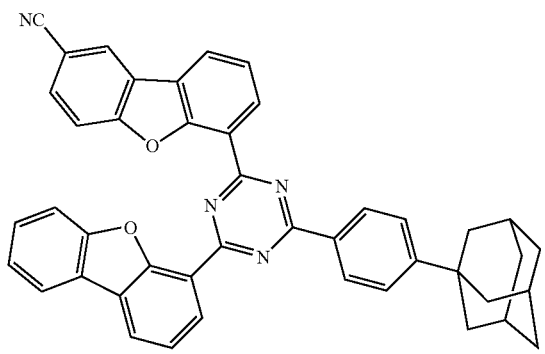
571
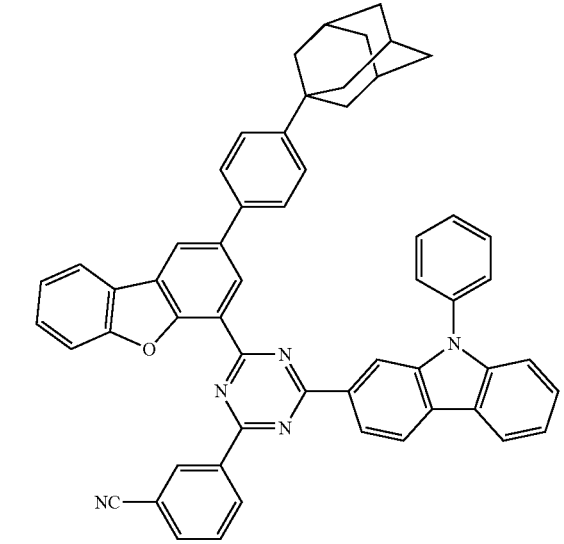
572
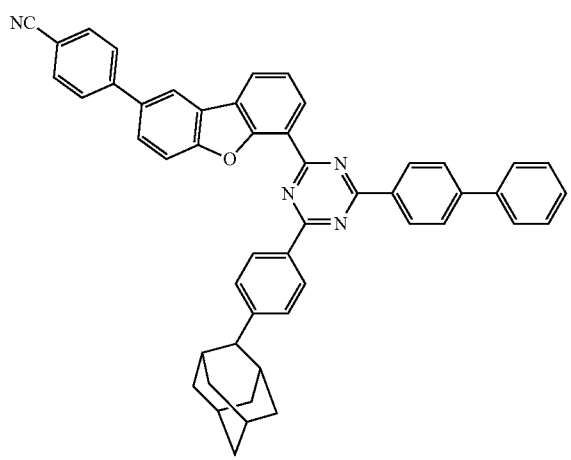
506
-continued
573
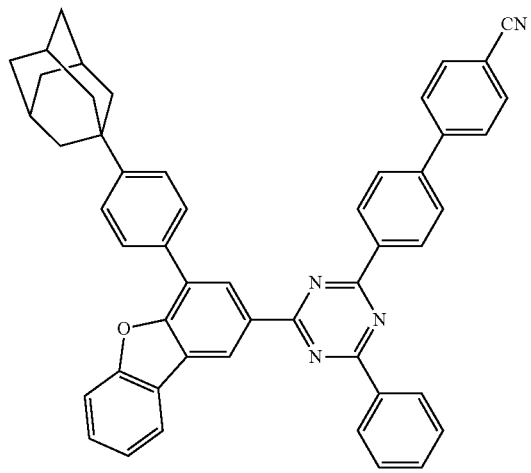
574
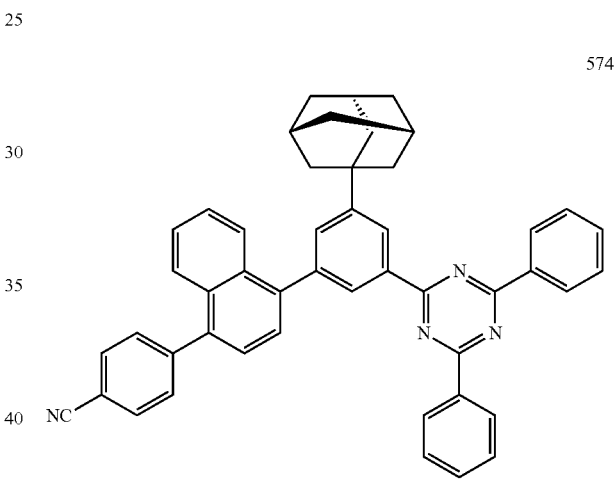
575
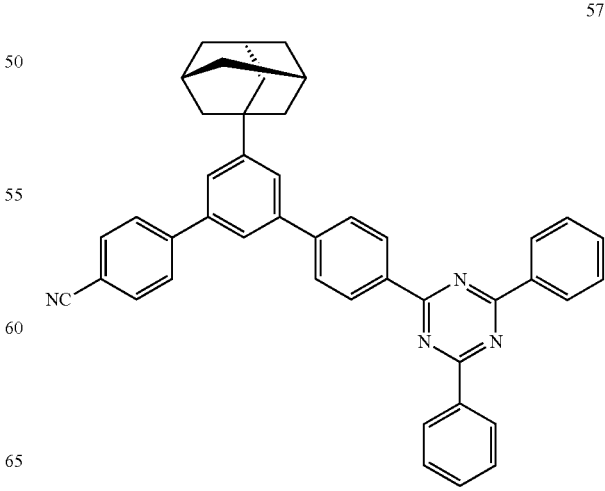

507
-continued
575
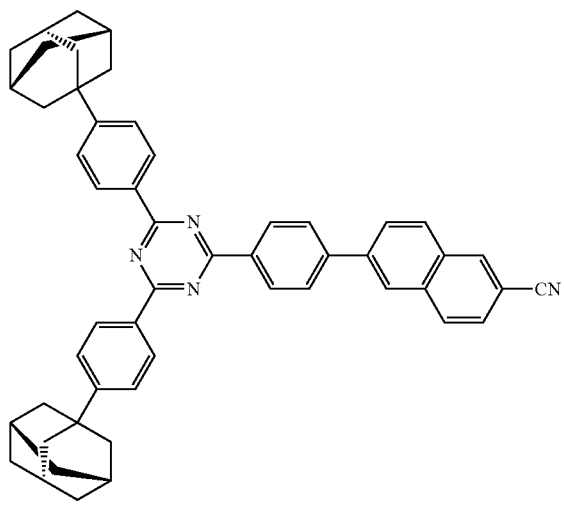
576
577
580
508
-continued
581
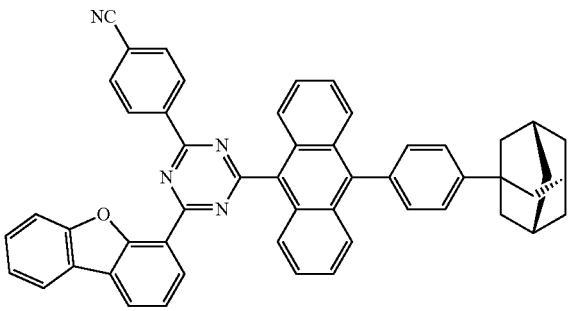
582
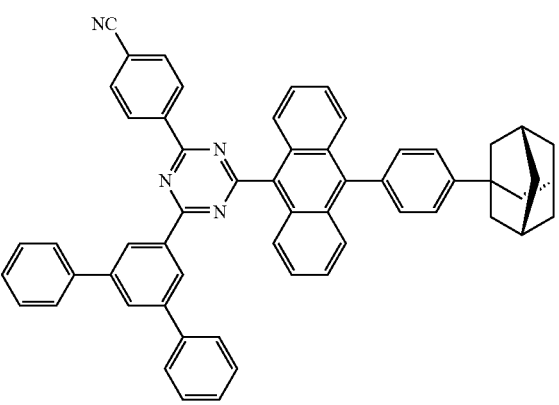
583
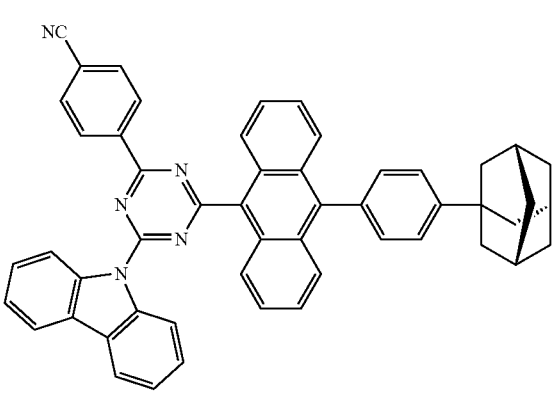
584
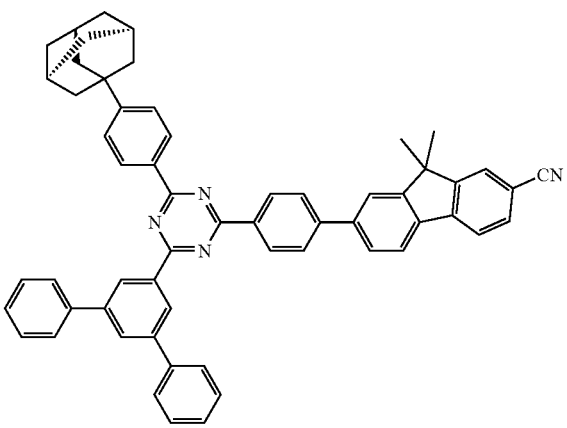

509
-continued
585
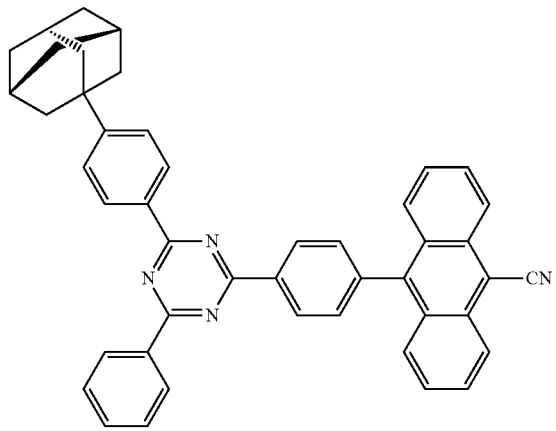
586
587
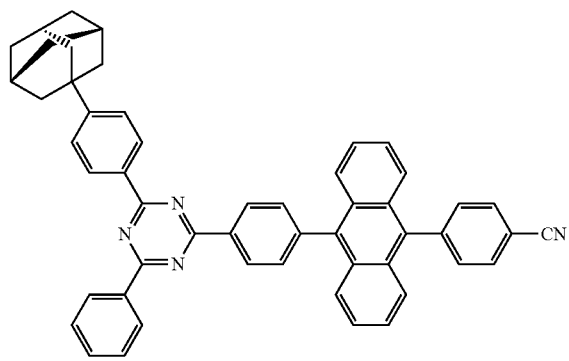
510
-continued
588
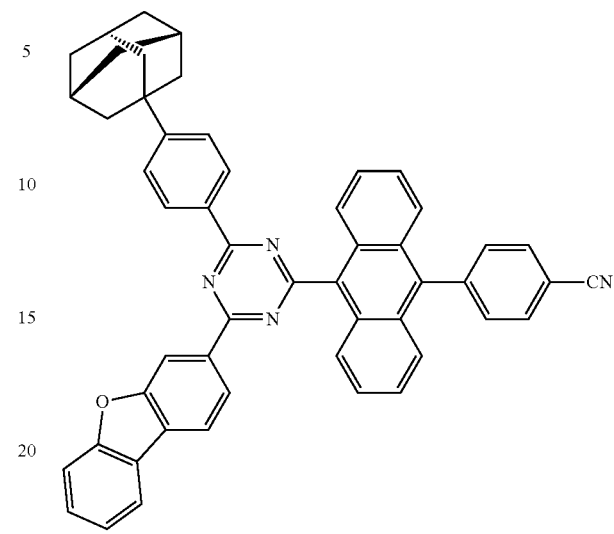
589
590
591
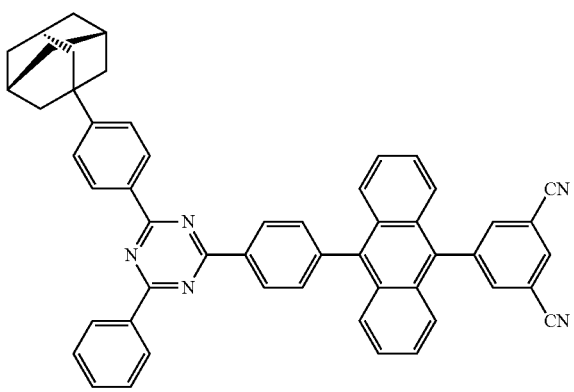
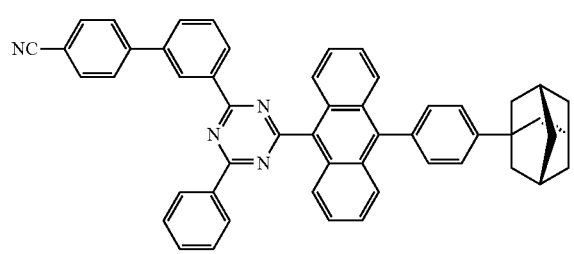

511
-continued
595
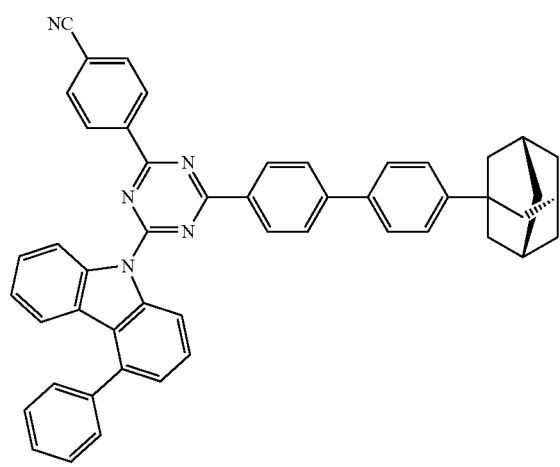
597
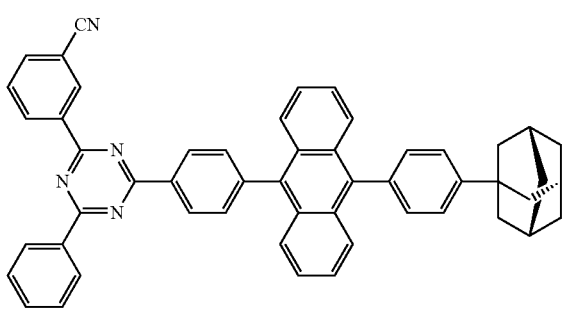
598
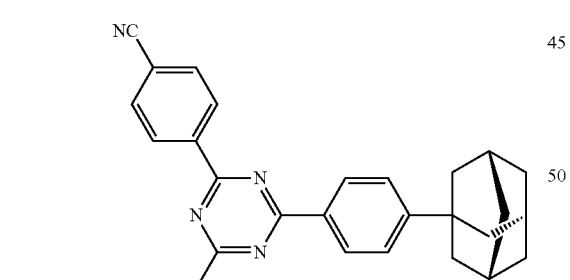
512
-continued
599
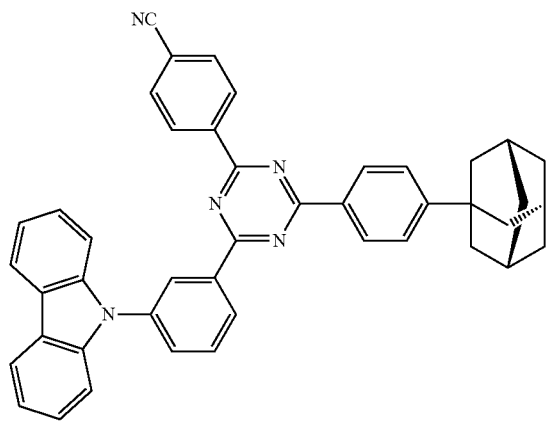
600
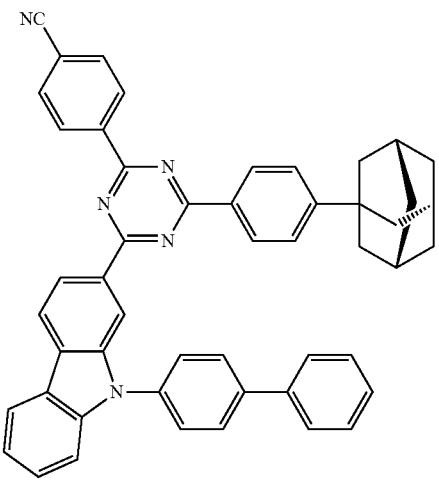
603
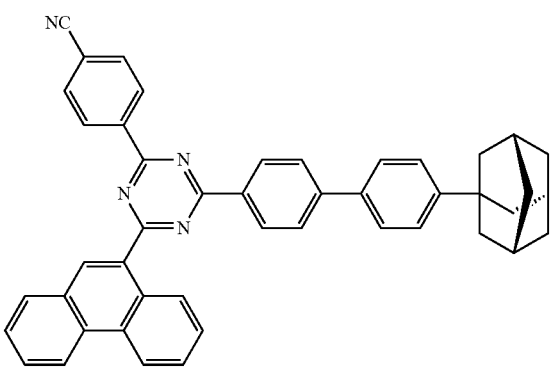

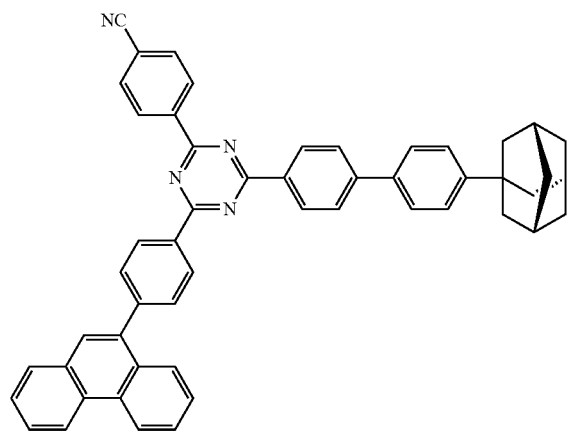
604
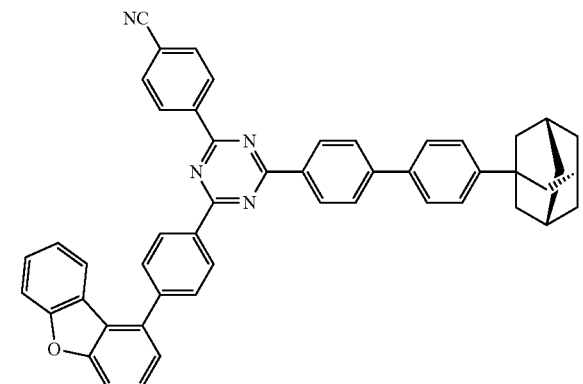
608
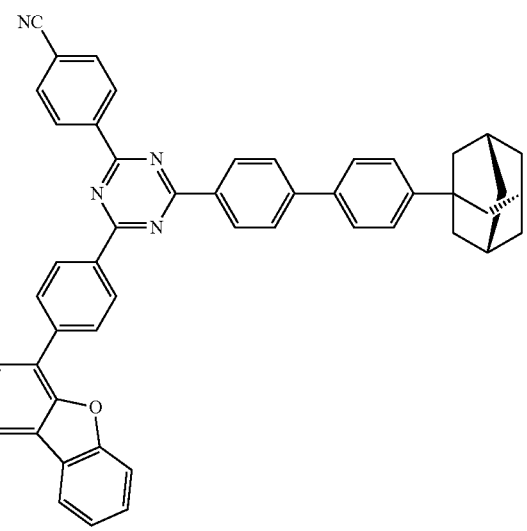
609
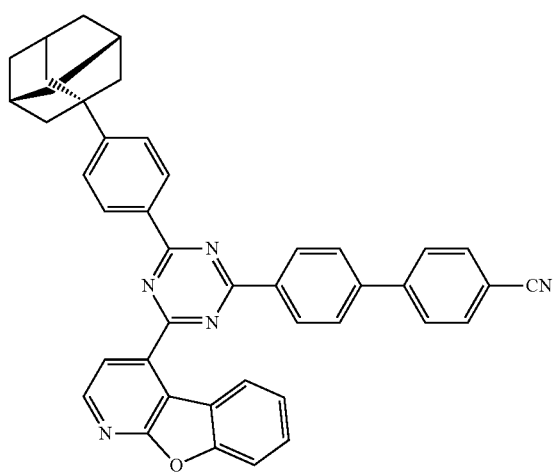
606
607
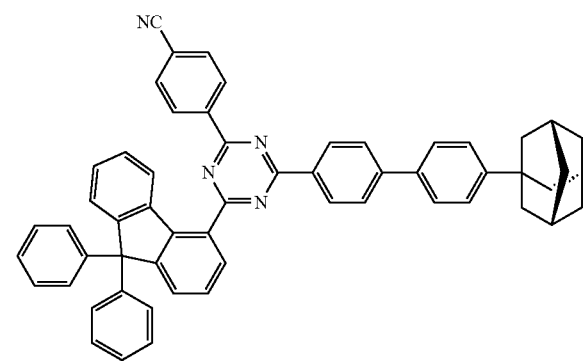
610

515
-continued
612
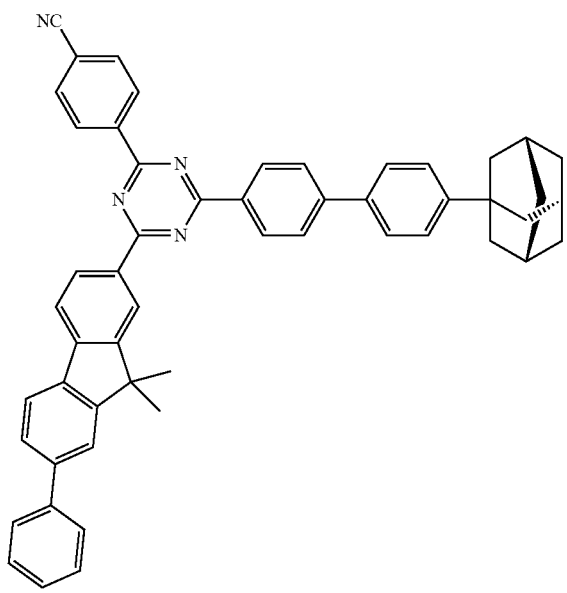
613
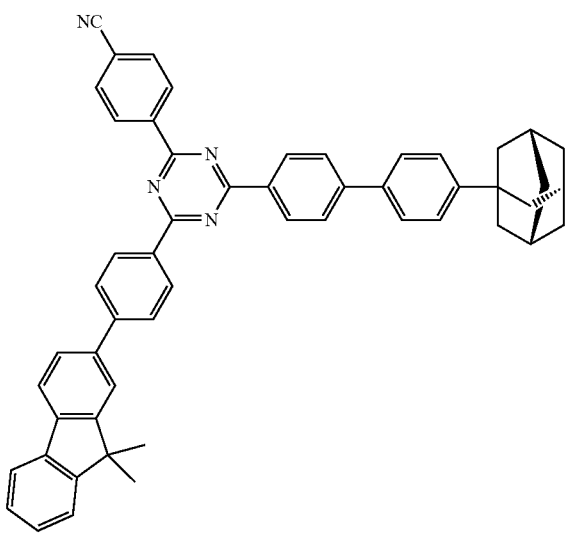
614
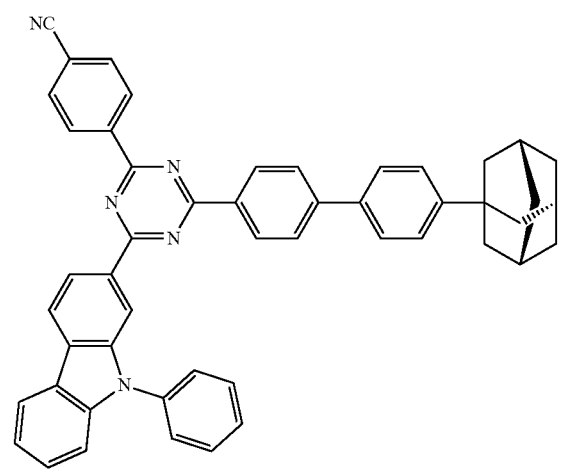
516
-continued
615
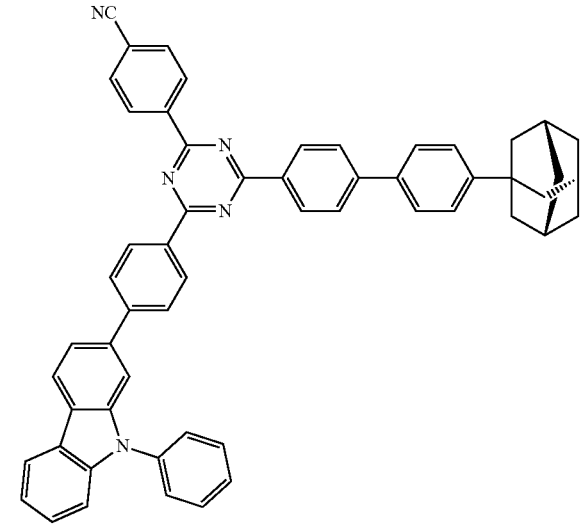
616
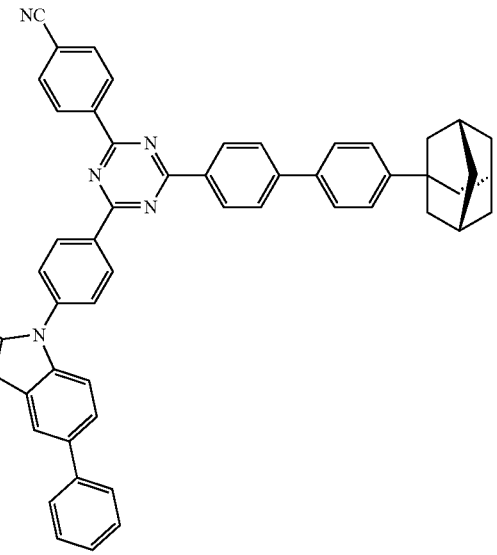
617
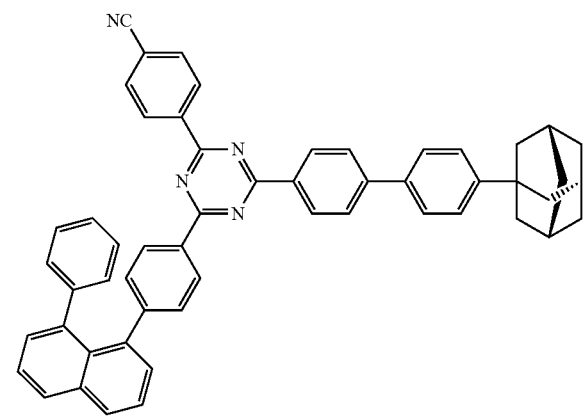

517
-continued

618
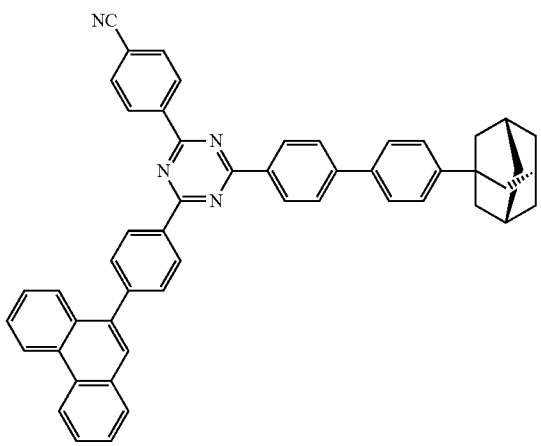

619
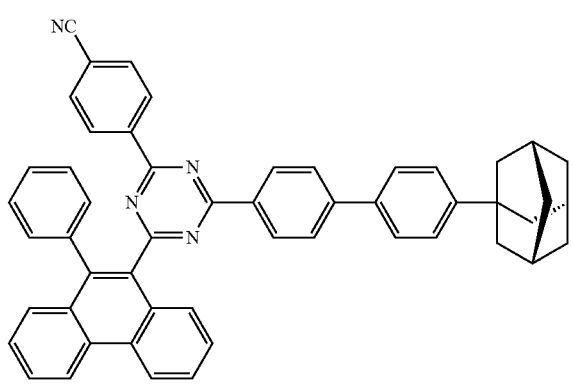

621
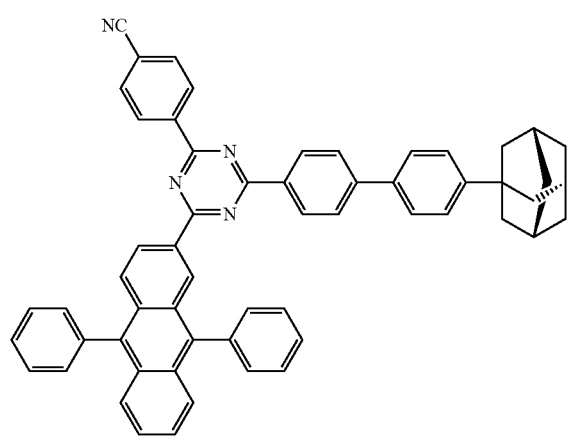

518
-continued

623
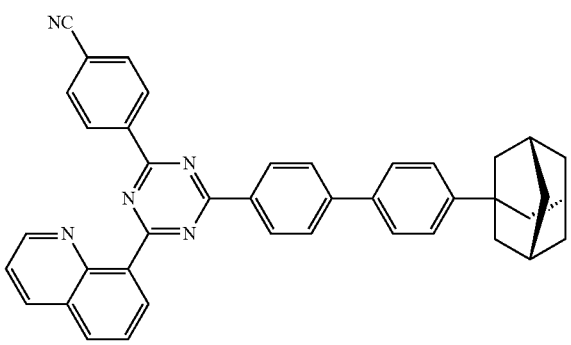

624
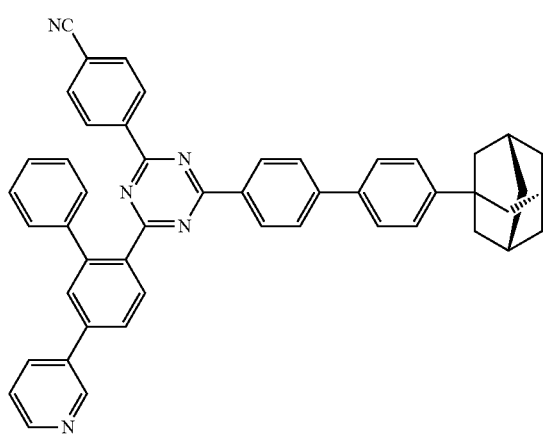

8. An electronic element, comprising an anode and a cathode which are oppositely disposed, and a functional layer disposed between the anode and the cathode; wherein the functional layer comprises an electron transport layer, and the electron transport layer comprises the nitrogen-containing compound according to claim 1.

9. The electronic element according to claim 8, wherein the electronic element is an organic electroluminescent device or a photoelectric conversion device.

10. An electronic device, comprising the electronic element according to claim 8.

* * * * *

UNITED STATES PATENT AND TRADEMARK OFFICE
CERTIFICATE OF CORRECTION

PATENT NO. : 11,746,093 B2
APPLICATION NO. : 18/010241
DATED : September 5, 2023
INVENTOR(S) : Kongyan Zhang, Tiantian Ma and Jiamei Cao Page 1 of 6

It is certified that error appears in the above-identified patent and that said Letters Patent is hereby corrected as shown below:

In the Specification

Column 104, Lines 20-34, compound 169, " 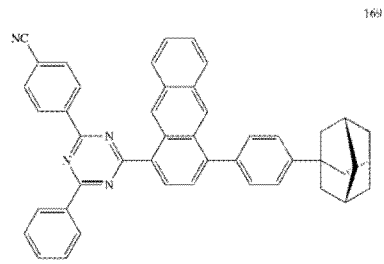 " should be 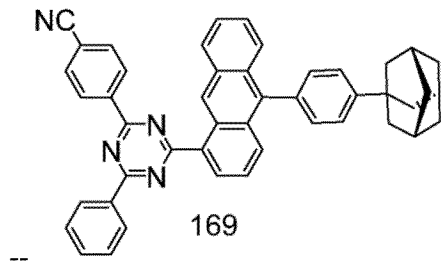 --.

Column 168, compound number "359" should be --358--.

Column 180, compound 398, " 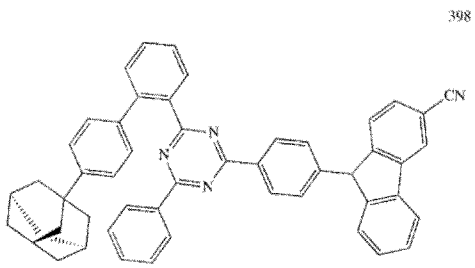 " should be

Signed and Sealed this
Seventeenth Day of September, 2024

*Katherine Kelly Vidal*
Katherine Kelly Vidal
*Director of the United States Patent and Trademark Office*

CERTIFICATE OF CORRECTION (continued)
U.S. Pat. No. 11,746,093 B2

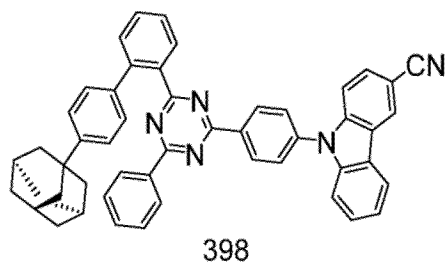

-- 398 --.

Table 3, Column 285, compound sub 1-A14, " 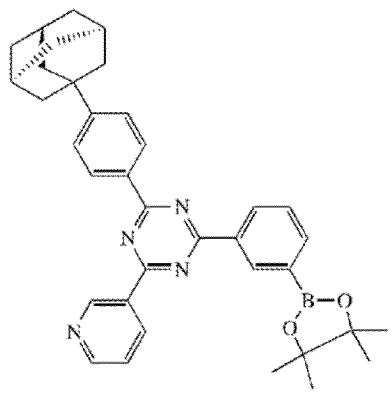 sub 1-A14 " should be

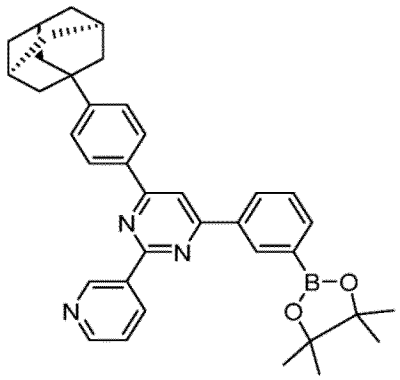

-- sub 1-A14 --.

Table 3, Column 286, compound 348, " 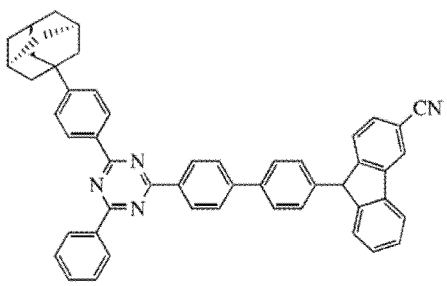 348 " should be

CERTIFICATE OF CORRECTION (continued)
U.S. Pat. No. 11,746,093 B2

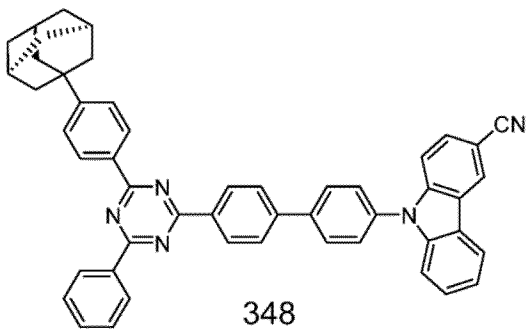

Table 3, Column 286, compound 318, " 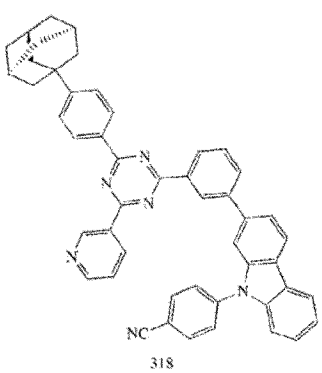 " should be

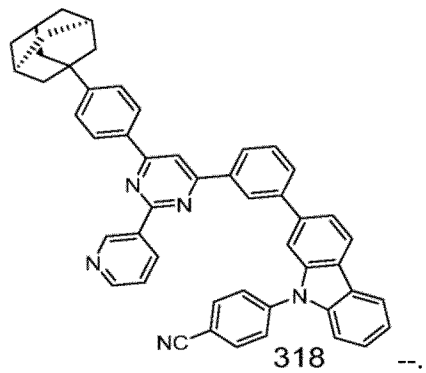

In the Claims

Claim 3 at Column 313, Lines 11-14, " 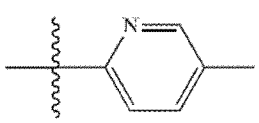 " should be -- 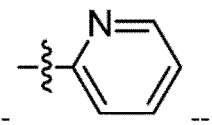 --.

CERTIFICATE OF CORRECTION (continued)
U.S. Pat. No. 11,746,093 B2

Claim 7 at Column 406, compound 297, " 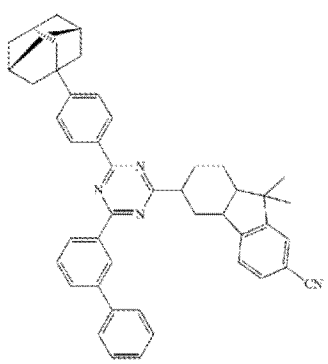 " should be

-- 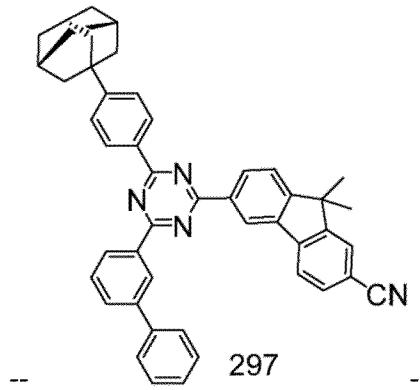 --.

Claim 7 at Column 491, compound 512, " 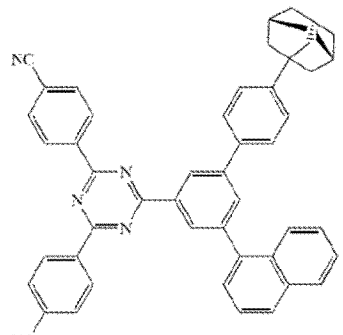 " should be

-- 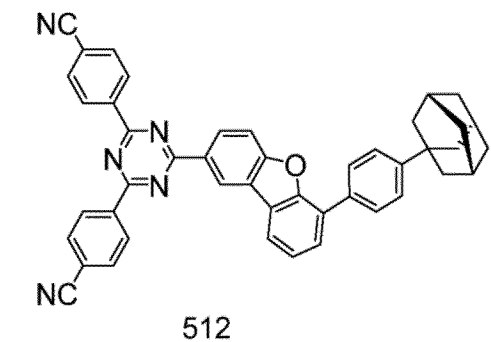 --.

CERTIFICATE OF CORRECTION (continued)
U.S. Pat. No. 11,746,093 B2

Claim 7 at Column 491, compound 513, " 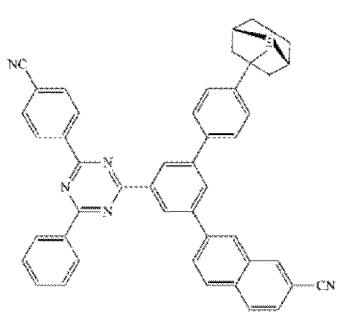 " should be

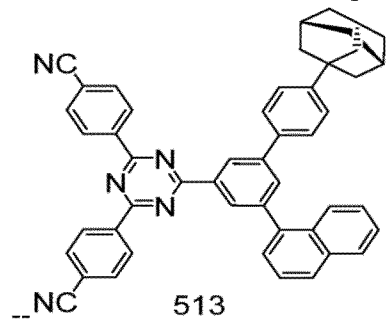

--.

Claim 7 at Column 492, compound 514, " 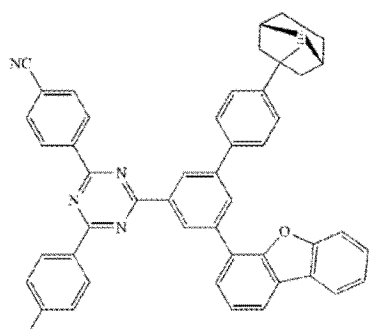 " should be

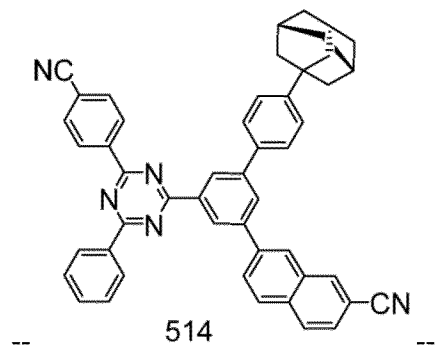

--.

CERTIFICATE OF CORRECTION (continued)
U.S. Pat. No. 11,746,093 B2

Claim 7 at Column 495, compound 522, " 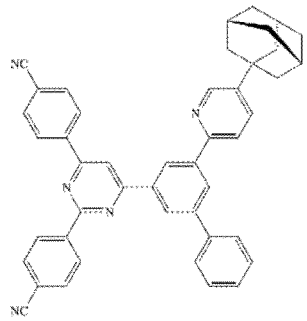 " should be

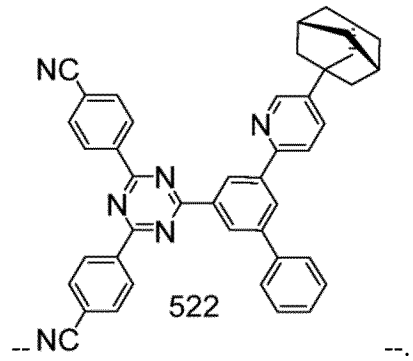

--.